United States Patent
Su et al.

(10) Patent No.: US 9,434,726 B2
(45) Date of Patent: Sep. 6, 2016

(54) SUBSTITUTED PYRIDO[3,4-B]PYRAZINES AS SYK INHIBITORS

(75) Inventors: Wei-Guo Su, Shanghai (CN); Wei Deng, Shanghai (CN); Jianguo Ji, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 198 days.

(21) Appl. No.: 14/124,325

(22) PCT Filed: Jun. 7, 2012

(86) PCT No.: PCT/CN2012/076576
§ 371 (c)(1),
(2), (4) Date: Dec. 6, 2013

(87) PCT Pub. No.: WO2012/167733
PCT Pub. Date: Dec. 13, 2012

(65) Prior Publication Data
US 2014/0121200 A1    May 1, 2014

(30) Foreign Application Priority Data

Jun. 8, 2011 (WO) ................. PCT/CN2011/075431

(51) Int. Cl.
| | | |
|---|---|---|
| A61K 31/4985 | (2006.01) | |
| C07D 241/38 | (2006.01) | |
| C07D 471/04 | (2006.01) | |
| C07D 519/00 | (2006.01) | |

(52) U.S. Cl.
CPC .......... *C07D 471/04* (2013.01); *C07D 519/00* (2013.01)

(58) Field of Classification Search
CPC ........................ A61K 31/4985; C07D 241/38
USPC ........... 514/249; 540/544, 575; 544/61, 117, 544/333, 350, 362; 546/199, 268.1; 548/335.1, 361.1, 373.1, 453, 518; 549/356, 429, 464, 471, 505, 510
See application file for complete search history.

(56) References Cited

U.S. PATENT DOCUMENTS

2011/0201608 A1    8/2011    Hoffmann et al.

FOREIGN PATENT DOCUMENTS

| WO | 0183485 A1 | 11/2001 |
|---|---|---|
| WO | 03057695 A1 | 7/2003 |
| WO | 03057695 B1 | 7/2003 |
| WO | 03063794 A2 | 8/2003 |
| WO | 2004005472 A2 | 1/2004 |
| WO | 2006078846 A1 | 7/2006 |
| WO | 2007124221 A1 | 11/2007 |
| WO | 2009099801 A1 | 8/2009 |
| WO | 2011014795 A2 | 2/2011 |
| WO | 2011092128 A1 | 8/2011 |
| WO | 2011134971 A1 | 11/2011 |
| WO | 2012123312 A1 | 9/2012 |
| WO | 2013014060 A1 | 1/2013 |

OTHER PUBLICATIONS

Jordan, V. C. Nature Reviews: Drug Discovery, 2, 2003, 205.*
Hackam, et al. JAMA, 296(14), 2006, 1731-1732.*
Braselmann, S et al., R406, an Orally Available Spleen Tyrosine Kinase Inhibitor Blocks Fc Receptor Signaling and Reduces Immune Complex-Mediated Inflammation, 2006, J. Pharmacol. and Experimental Therapeutics, 319 (3):998-1008.
Chen, D et al., Computational selection of inhibitors of Abeta aggregation and neuronal toxicity, 2009, Bioorganic & Medicinal Chemistry 17:5189-5197.
Coffey, G et al., Specific Inhibition of Spleen Tyrosine Kinase Suppresses Leukocyte Immune Function and Inflammation in Animal Models of Rheumatoid Arthritis, 2012, J Pharmacol Experiment Therapeutics, 340:350-359.
Elliott, et al., The Isomeric Pyridopyrazines from the Reaction of Some Tetraaminopyridines with Pyruvaldehyde and Benzil, 1968, J Org Chem 33(6):2393-2397.
Elliott, R et al., Potential Folic Acid Antagonists. VI. The Syntheses of 1- and 3-Deazamethotrexate, 1971, J. Org. Chem. 36(10):2818-2823.
Hoffmann, C et al., Comparative Effects of Selected Antifolates on Transforming Human Lymphocytes and on Established Human Lymphoblastic Cell Lines, 1976, Biochemical Pharmacology 25:1947-1954.
Nisius, B et al., Development of a Fingerprint Reduction Approach for Bayesian Similarity Searching Based on Kullback-Leibler Divergence Analysis, 2009, J. Chem. Inf. Model. 49:1347-1358.
Spurgeon, S et al., The Selective Syk Inhibitor P505-15 (PRT062607) Inhibits B Cell Signaling and Function In Vitro and In Vivo and Aguments the Activity of Fludarabine in Chronic Lymphocytic Leukemia, 2013, J Pharmacol Experiment Therapeutics, Feb. 2013, 344:378-387.
Temple, C et al., 1,2-Dihydropyrido[3,4-b]pyrazines: Structure-Activity Relationships, 1983, J. Med. Chem. 26:91-95.
Wheeler, G et al., Biolgoical Effects and Structure-Activity Relationships of 1,2-Dihydropyrido[3,4-b]pyrazines, Aug. 1993, Cancer Res 43:3567-3575.
Williams, J et al., The Inhibition of Dihydrofolate Reductase by Folate Analogues: Structural Requirements for Slow- and Tight-Binding Inhibition,1980, Biochemical Pharmacology, 29:589-595.

(Continued)

*Primary Examiner* — Douglas M Willis
(74) *Attorney, Agent, or Firm* — Gorman IP Law, APC

(57) ABSTRACT

Provided are pyridopyrazine compounds of formula (I), pharmaceutical compositions thereof and methods of use therefore, wherein $R^1$, $R^2$, $R^3$, $R^4$ and m are as defined in the specification.

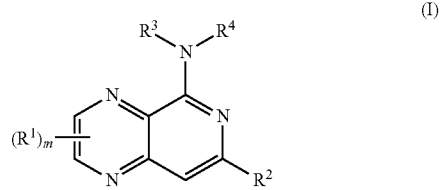

28 Claims, No Drawings

(56) References Cited

OTHER PUBLICATIONS

Yamamoto, N et al., The Orally Available Spleen Tyrosine Kinase Inhibitor 2-[7-(3,4-Dimethoxyphenyl)-imidao[1,2-c] pyrimidin-5-ylamino]-nicotinamide Dihydrochloride (BAY 61-3606) Blocks Antigen-Induced Airway Inflammation in Rodents, 2003, J Pharmacol Exp Ther, 306 (3): 1174-1181.

Efremov, Dimitar & Laurenti, Luca, The Syk kinase as a therapeutic target in leukemia and lymphoma, Expert Opin. Investig. Drugs 2011, 20(5): 623-636, Informa UK, Ltd.

Friedberg, Jonathan et al, Inhibition of Syk with fostamatinib disodium has significant clinical activity in non-Hodgkin lymphoma and chronic lymphocytic leukemia, Blood, Apr. 2010, 115(13): 2578-2585.

Pamuk, Omer N. et al, Spleen tyrosine kinase inhibition in the treatment of autoimmune, allergic and autoinflammatory diseases, Arthritis Research & Therapy, 2010, 12(222): 1-11, BioMed Central.

Wong, Brian R. et al., Targeting Syk as a treatment for allergic and autoimmune disorders, Expert Opin. Investig. Drugs 2004, 13(7): 743-762, Ashley Publications Ltd.

* cited by examiner

SUBSTITUTED PYRIDO[3,4-B]PYRAZINES AS SYK INHIBITORS

This application is a National Phase entry of PCT Application No. PCT/CN2012/076576 filed on Jun. 7, 2012, which claims priority under 35 U.S.C. §§119, 120 and/or 365 to PCT Patent Application No. PCT/CN2011/075431 filed on Jun. 8, 2011, the entire contents of each of which are hereby incorporated by reference in their entirety.

TECHNICAL FIELD

The present invention relates to novel pyridopyrazine compounds, pharmaceutical compositions thereof and methods of use therefore.

BACKGROUND OF THE INVENTION

Protein kinases, the largest family of human enzymes, encompass well over 500 proteins. Spleen Tyrosine Kinase (Syk) is a member of the Syk family of tyrosine kinases, and is a regulator of early B-cell development as well as mature B-cell activation, signaling, and survival.

Syk is a non-receptor tyrosine kinase that plays critical roles in immunoreceptor- and integrin-mediated signaling in a variety of cell types, including B cells, macrophages, monocytes, mast cells, eosinophils, basophils, neutrophils, dendritic cells, T cells, natural killer cells, platelets, and osteoclasts. Immunoreceptors as described herein include classical immunoreceptors and immunoreceptor-like molecules. Classical immunoreceptors include B-cell and T-cell antigen receptors as well as various immunoglobulin receptors (Fc receptors). Immunoreceptor-like molecules are either structurally related to immunoreceptors or participate in similar signal transduction pathways, and are primarily involved in non-adaptive immune functions, including, for example, neutrophil activation, natural killer cell recognition, and osteoclast activity. Integrins are cell surface receptors that play key roles in the control of leukocyte adhesion and activation in both innate and adaptive immunity.

Ligand binding leads to activation of both immunoreceptors and integrins, which results in Src family kinases being activated, and phosphorylation of immunoreceptor tyrosine-based activation motifs (ITAMs) in the cytoplasmic face of receptor-associated transmembrane adaptors. Syk binds to the phosphorylated ITAM motifs of the adaptors, leading to activation of Syk and subsequent phosphorylation and activation of downstream signaling pathways.

Syk is essential for B-cell activation through B-cell receptor (BCR) signaling. SYK becomes activated upon binding to phosphorylated BCR and thus initiates the early signaling events following BCR activation. B-cell signaling through BCR can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mice lacking Syk show impaired maturation of B-cells, diminished immunoglobulin production, compromised T-cell-independent immune responses, and marked attenuation of the sustained calcium sign upon BCR stimulation.

A large body of evidence supports the role of B-cells and the humoral immune system in the pathogenesis of autoimmune and/or inflammatory diseases. Protein-based therapeutics (such as Rituxan) developed to deplete B-cells represent an approach to the treatment of a number of autoimmune and inflammatory diseases. Auto-antibodies and their resulting immune complexes are known to play pathogenic roles in autoimmune disease and/or inflammatory disease. The pathogenic response to these antibodies is dependent on signaling through Fc Receptors, which is, in turn, dependent upon Syk. Because of Syk's role in B-cell activation, as well as FcR dependent signaling, inhibitors of Syk can be useful as inhibitors of B-cell mediated pathogenic activity, including autoantibody production. Therefore, inhibition of Syk enzymatic activity in cells is proposed as a treatment for autoimmune disease through its effects on autoantibody production.

Syk also plays a key role in FCεRI mediated mast cell degranulation and eosinophil activation. Thus, Syk is implicated in allergic disorders including asthma. Syk binds to the phosphorylated gamma chain of FCεRI via its SH2 domains and is essential for downstream signaling. Syk deficient mast cells demonstrate defective degranulation, and arachidonic acid and cytokine secretion. This also has been shown for pharmacologic agents that inhibit Syk activity in mast cells. Syk antisense oligonucleotides inhibit antigen-induced infiltration of eosinophils and neutrophils in an animal model of asthma. Syk deficient eosinophils also show impaired activation in response to FCεRI stimulation. Therefore, small molecule inhibitors of Syk may be useful for treatment of allergy-induced inflammatory diseases including asthma.

Syk is also expressed in mast cells and monocytes and has been shown to be important for the function of these cells. For example, Syk deficiency in mice is associated with impaired IgE-mediated mast cell activation, which causes marked diminution of TNF-alpha and other inflammatory cytokine release. Additionally, Syk inhibitors have been shown to inhibit antigen-induced passive cutaneous anaphylaxsis, bronchoconstriction and bronchial edema in rats.

Thus, the inhibition of Syk activity can be useful for the treatment of allergic disorders, autoimmune diseases, and inflammatory diseases, such as: SLE, rheumatoid arthritis, multiple vasculitides, idiopathic thrombocytopenic purpura (ITP), myasthenia gravis, allergic rhinitis, chronic obstructive pulmonary disease (COPD), adult respiratory distress syndrome (ARDs) and asthma. In addition, Syk has been reported to play an important role in ligand-independent tonic signaling through the B-cell receptor, known to be an important survival signal in B-cells. Thus, inhibition of Syk activity may be useful in treating certain types of cancer, including B-cell lymphoma and leukemia.

SUMMARY OF THE INVENTION

Provided is at least one compound of formula (I):

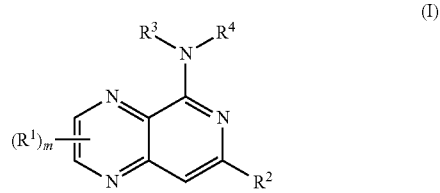

and/or its racemic mixture, enantiomers, diastereomers, tautomers, or mixtures of optional ratio, or at least one pharmaceutically acceptable salt thereof, wherein $R^1$ is independently chosen from hydrogen, halo, —CN, hydroxyl, optionally substituted $C_1$-$C_6$ alkyl, optionally substituted $C_3$-$C_6$ cycloalkyl, optionally substituted amino, and optionally substituted $C_1$-$C_6$ alkoxy, $R^2$ is —$NR^5R^6$, —$OR^7$, —$S(O)_nR^8$, —$C(O)R^9$, —$C(O)OR^7$, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$S(O)_nNR^5R^6$, optionally substituted lower alkyl, optionally substituted alkenyl, and optionally substituted alkynyl;

or is cycloalkyl, heterocycle, aryl, heteroaryl, which is optionally substituted by one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, $R^3$ and $R^4$ are independently selected from hydrogen, alkyl, cycloalkyl, aryl, heteroaryl, and heterocycle, each of which except for hydrogen, is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, or $R^3$ and $R^4$, together with the N atom to which they are attached, can form a 4-12 membered mono-cyclic, fused bicyclic or spirocyclic ring optionally containing an additional 1-3 hetero-atoms chosen from N, O and S, which is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, m is 0, 1 or 2, n is 1 or 2, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

wherein each optionally substituted group above for which the substituent(s) is (are) not specifically designated, can be unsubstituted or independently substituted with, for example, one or more, such as one, two, or three, substituents independently chosen from $C_1$-$C_4$ alkyl, cycloalkyl, aryl, heterocycle, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo, —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —NHC(O)(phenyl), —$N(C_1$-$C_4$ alkyl)C(O)($C_1$-$C_4$ alkyl), —$N(C_1$-$C_4$ alkyl)C(O)(phenyl), —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl), in which each of phenyl, aryl, heterocycle, and heteroaryl is optionally substituted by one or more groups chosen from halo, cycloalkyl, heterocycle, $C_1$-$C_4$ alkyl, $C_1$-$C_4$ haloalkyl-, —$OC_1$-$C_4$ alkyl, $C_1$-$C_4$ alkyl-OH, —$C_1$-$C_4$ alkyl-O—$C_1$-$C_4$ alkyl, —$OC_1$-$C_4$ haloalkyl, cyano, nitro, —$NH_2$, —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$N(C_1$-$C_4$ alkyl)C(O)($C_1$-$C_4$ alkyl), —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

Also provided is a pharmaceutical composition comprising at least one compound and/or at least one pharmaceutically acceptable salt thereof described herein and at least one pharmaceutically acceptable carrier.

Also provided is a method of inhibiting the activity of Syk kinase comprising inhibiting said activity with an effective amount of at least one compound and/or at least one pharmaceutically acceptable salt thereof described herein.

Also provided is a method of treating a subject with a recognized inflammatory disease responsive to inhibition of Syk comprising administering to said subject in recognized need thereof an effective amount to treat said disease of at least one compound and/or at least one pharmaceutically acceptable salt thereof described herein.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —$CONH_2$ is attached through the carbon atom.

The term "alkyl" herein refers to a straight or branched hydrocarbon, containing 1-18, preferably 1-12, more preferably 1-6 carbon atoms. Examples of alkyl groups include, but are not limited to, methyl, ethyl, n-propyl, i-propyl, n-butyl, i-butyl, and t-butyl. "Lower alkyl" refers to a straight or branched hydrocarbon, containing 1-6, preferably 1-4 carbon atoms.

By "alkoxy" is meant a straight or branched alkyl group containing 1-18, preferably 1-12, more preferably 1-6 carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to a straight or branched alkoxy, wherein the alkyl portion contains 1-6, preferably 1-4 carbon atoms.

The term "alkenyl" herein refers to a straight or branched hydrocarbon, containing one or more C=C double bonds and 2-10, preferably 2-6 carbon atoms. Examples of alkenyl groups include, but are not limited to, vinyl, 2-propenyl, and 2

The term "alkynyl" herein refers to a straight or branched hydrocarbon, containing one or more C≡O triple bonds and 2-10, preferably 2-6 carbon atoms. Examples of alkynyl groups include, but are not limited to, ethynyl, 2-propynyl, and 2

The term "cycloalkyl" refers to saturated and partially unsaturated cyclic hydrocarbon groups having 3 to 12, preferably 3 to 8 carbon atoms. Examples of cycloalkyl groups include, but are not limited to, cyclopropyl, cyclobutyl, cyclopentyl, cyclopentenyl, cyclohexyl, cyclohexenyl, cycloheptyl, and cyclooctyl. The ring may be saturated or have one or more double bonds (i.e. partially unsaturated), but not fully conjugated, and not aryl, as defined herein.

"Aryl" encompasses:

5- and 6-membered carbocyclic aromatic rings, for example, benzene;
  bicyclic ring systems wherein at least one ring is carbocyclic and aromatic, for example, naphthalene, indane, and 1,2,3,4-tetrahydroquinoline; and
  tricyclic ring systems wherein at least one ring is carbocyclic and aromatic, for example, fluorene.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

The term "heteroaryl" refers to
  5- to 8-membered aromatic, monocyclic rings containing one or more, for example, from 1 to 4, or, in some embodiments, from 1 to 3, heteroatoms selected from N, O, and S, with the remaining ring atoms being carbon;
  8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and
  11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

For example, heteroaryl includes a 5- to 7-membered heterocyclic aromatic ring fused to a 5- to 7-membered cycloalkyl ring. For such fused, bicyclic heteroaryl ring systems wherein only one of the rings contains one or more heteroatoms, the point of attachment is at the heteroaromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O⁻) substituents, such as pyridinyl N-oxides.

By "heterocycle" is meant a 4- to 12-membered monocyclic, bicyclic or tricyclic saturated or partially unsaturated ring containing at least 2 carbon atoms in addition to 1-3 heteroatoms independently selected from oxygen, sulfur, and nitrogen. "Heterocycle" also refers to 5- to 7-membered heterocyclic ring containing one or more heteroatoms selected from N, O, and S fused with 5-, 6-, and/or 7-membered cycloalkyl, heterocyclic, carbocyclic aromatic or heteroaromatic ring, provided that the point of attachment is at the heterocyclic ring. "Heterocycle" also refers to an aliphatic spirocyclic ring containing one or more heteroatoms selected from N, O, and S, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring. A heterocyle is not a heteroaryl as defined herein.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, and 2,5 Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1

By "optional" or "optionally" is meant that the subsequently described event or circumstance may or may not occur, and that the description includes instances where the event or circumstance occurs and instances in which it does not. For example, "optionally substituted alkyl" encompasses both "unsubstituted alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

In some embodiments, "substituted with one or more groups" refers to two hydrogens on the designated atom or group being independently replaced with two selections from the indicated group of substituents. In some embodiments, "substituted with one or more groups" refers to three hydrogens on the designated atom or group being independently replaced with three selections from the indicated group of substituents. In some embodiments, "substituted with one or more groups" refers to four hydrogens on the designated atom or group being independently replaced with four selections from the indicated group of substituents.

Compounds described herein include, but are not limited to, when possible, to the extent that they can be made by one of ordinary skill without undue experimentation, their regioisomers, their N-oxide derivatives, their optical isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of enantiomers or diastereomers. Resolution of the racemates or mixtures of diastereomers, if possible, can be accomplished, for example, by conventional methods such as crystallization in the presence of a resolving agent, or chromatography, using, for example a chiral high-pressure liquid chromatography (HPLC) column. In addition, when possible, such compounds include Z- and E-forms (or cis- and trans-forms) of compounds with carbon-carbon double bonds. Where compounds described herein exist in various tautomeric forms, the term "compound" is intended to include, to the extent they can be made without undue experimentation, all tautomeric forms of the compound. Such compounds also include crystal forms including polymorphs and clathrates, to the extent they can be made by one of ordinary skill in the art without undue experimentation. Similarly, the term "salt" is intended to include all isomers, racemates, other mixtures, Z- and E-forms, tautomeric forms and crystal forms of the salt of the compound, to the extent they can be made by one of ordinary skill in the art without undue experimentation.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, salts with $HOOC-(CH_2)_n-COOH$ where n is 0-4, and like salts. Similarly, pharmaceutically acceptable cations include, but are not limited to sodium, potassium, calcium, aluminum, lithium, and ammonium.

In addition, if a compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

A "solvate," such as a "hydrate," is formed by the interaction of a solvent and a compound. The term "compound" is intended to include solvates, including hydrates, of compounds, to the extent they can be made by one of ordinary skill in the art by routine experimentation. Similarly, "salts" includes solvates, such as hydrates, of salts, to the extent they can be made by one of ordinary skill in the art by routine experimentation. Suitable solvates are pharmaceutically acceptable solvates, such as hydrates, including monohydrates and hemi-hydrates, to the extent they can be made by one of ordinary skill in the art by routine experimentation.

A "chelate" is formed by the coordination of a compound to a metal ion at two (or more) points. The term "compound" is intended to include chelates of compounds to the extent they can be made by one of ordinary skill in the art by routine experimentation. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound" to the extent they can be made by one of ordinary skill in the art by routine experimentation.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

As used herein the terms "group", "radical" or "fragment" are synonymous and are intended to indicate functional groups or fragments of molecules attachable to a bond or other fragments of molecules.

The term "active agent" is used to indicate a chemical substance which has biological activity. In some embodiments, an "active agent" is a chemical substance having pharmaceutical utility.

"Treating," "treat," or "treatment" or "alleviation" refers to administering at least one compound and/or at least one pharmaceutically acceptable salt thereof described herein to a subject that has a disease or disorder, or has a symptom of a disease or disorder, or has a predisposition toward a disease or disorder, with the purpose to cure, heal, alleviate, relieve, alter, remedy, ameliorate, improve, or affect cancer, the symptoms of the disease or disorder, or the predisposition toward the disease or disorder. In some embodiments, the disease or disorder may be cancer. In some embodiments, the disease or disorder may be an inflammatory disease.

The term "effective amount" refers to an amount of at least one compound and/or at least one pharmaceutically acceptable salt thereof described herein effective to "treat", as defined above, a disease or disorder in a subject responsive to the inhibition of Syk. The effective amount may cause any of the changes observable or measurable in a subject as described in the definition of "treating," "treat," "treatment" and "alleviation" above. For example, in the case of cancer, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of Syk kinase The term "effective amount" may also refer to an amount of at least one compound and/or at least one pharmaceutically acceptable salt described herein effective to inhibit the activity of Syk in a subject responsive to the inhibition of Syk.

The term "inhibition" indicates a decrease in the baseline activity of a biological activity or process. "Inhibition of Syk" refers to a decrease in the activity of Syk kinase as a direct or indirect response to the presence of at least one compound and/or at least one pharmaceutically acceptable salt thereof described herein, relative to the activity of Syk kinase in the absence of the at least one compound and/or the at least one pharmaceutically acceptable salt thereof. The decrease in activity may be due to the direct interaction of the at least one compound and/or at least one pharmaceutically acceptable salt thereof described herein with the Syk kinase, or due to the interaction of the at least one compound and/or at least one pharmaceutically acceptable salt thereof described herein, with one or more other factors that in turn affect the at least one kinase activity. For example, the presence of at least one compound and/or at least one pharmaceutically acceptable salt thereof described herein, may decrease the at least one kinase activity by directly binding to the Syk kinase, by causing (directly or indirectly) another factor to decrease the at least one kinase activity, or by (directly or indirectly) decreasing the amount of the at least one kinase present in the cell or organism.

DETAILED DESCRIPTION OF THE INVENTION

Provided is at least one compound of formula (I):

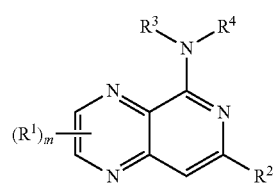

and/or its racemic mixture, enantiomers, diastereomers, tautomers, or mixtures of optional ratio, or at least one pharmaceutically acceptable salt thereof, wherein $R^1$ is independently chosen from hydrogen, halo, —CN, hydroxyl, optionally substituted $C_1$-$C_6$ alkyl, optionally substituted $C_3$-$C_6$ cycloalkyl, optionally substituted amino, and optionally substituted $C_1$-$C_6$ alkoxy, $R^2$ is —$NR^5R^6$, —$OR^7$, —$S(O)_nR^8$, —$C(O)R^9$, —$C(O)OR^7$, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$S(O)_nNR^5R^6$, optionally substituted lower alkyl, optionally substituted alkenyl, and optionally substituted alkynyl;

or is cycloalkyl, heterocycle, aryl, heteroaryl, which is optionally substituted by one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, $R^3$ and $R^4$ are independently selected from hydrogen, alkyl, cycloalkyl, aryl, heteroaryl, and heterocycle, each of which except for hydrogen, is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, or $R^3$ and $R^4$, together with the N atom to which they are attached, can form a 4-12 membered mono-cyclic, fused bicyclic or spirocyclic ring optionally containing an additional 1-3 hetero-atoms chosen from N, O and S, which is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, m is 0, 1 or 2, n is 1 or 2, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

wherein each optionally substituted group above for which the substituent(s) is (are) not specifically designated, can be unsubstituted or independently substituted with, for example, one or more, such as one, two, or three, substituents independently chosen from $C_1$-$C_4$ alkyl, cycloalkyl, aryl, heterocycle, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl), in which each of phenyl, aryl, heterocycle, and heteroaryl is optionally substituted by one or more groups chosen from halo, cycloalkyl, heterocycle, $C_1$-$C_4$ alkyl, $C_1$-$C_4$ haloalkyl-, —O$C_1$-$C_4$ alkyl, $C_1$-$C_4$ alkyl-OH, —$C_1$-$C_4$ alkyl-O—$C_1$-$C_4$ alkyl, —O$C_1$-$C_4$ haloalkyl, cyano, nitro, —NH$_2$, —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —N($C_1$-$C_4$ alkyl)C(O)($C_1$-$C_4$ alkyl), —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

In some embodiments, $R^1$ is independently chosen from hydrogen, halo, hydroxyl, —CN, optionally substituted $C_1$-$C_6$ alkyl, optionally substituted $C_3$-$C_6$ cycloalkyl, optionally substituted amino, and optionally substituted $C_1$-$C_6$ alkoxy.

In some embodiments, $R^1$ is independently chosen from hydrogen, halo, —CN, hydroxyl; or is chosen from methyl, ethyl, n-propyl, i-propyl, cyclopropyl, cyclobutyl, cyclopentyl, cyclopentenyl, cyclohexyl, N-methylamino, N-ethylamino, N-n-propylamino, N-i-propylamino, methoxy, ethoxy, propoxy, isopropoxy, each of which is optionally substituted.

In some embodiments, $R^1$ is independently chosen from hydrogen, hydroxyl, and alkyl.

In some embodiments, m is 1.

In some embodiments, $R^2$ is $C_5$-$C_{10}$aryl, 3-8 membered heterocycle, or 5-10 membered heteroaryl, which is optionally substituted by one or more groups selected from halo, —NR$^5$R$^6$, —OR$^7$, —S(O)$_n$R$^8$, —C(O)R$^9$, —C(O)OR$^7$, —CN, —C(O)NR$^5$R$^6$, —NR$^5$C(O)R$^9$, —NR$^5$S(O)$_n$R$^8$, —NR$^5$S(O)$_n$NR$^{10}$R$^{11}$, —NR$^5$C(O)OR$^7$, —NR$^5$C(O)NR$^{10}$R$^{11}$, —NO$_2$, —S(O)$_n$NR$^5$R$^6$, optionally substituted $C_1$-$C_6$ alkyl, optionally substituted $C_3$-$C_8$ cycloalkyl, optionally substituted 3-8 membered heterocycle, optionally substituted 5-10 membered heteroaryl, optionally substituted $C_5$-$C_{10}$ aryl, optionally substituted $C_2$-$C_6$ alkenyl, and optionally substituted $C_2$-$C_6$ alkynyl, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, $R^2$ is independently chosen from phenyl, naphthyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, pyrrolidinyl, tetrahydrofuryl, piperidinyl, piperazinyl, morpholinyl, homomorpholinyl, thiomorpholinyl, diazepanyl, oxazepanyl, which is optionally substituted by one or more groups selected from halo, —NR$^5$R$^6$, —OR$^7$, —S(O)$_n$R$^8$, —C(O)R$^9$, —C(O)OR$^7$, —CN, —C(O)NR$^5$R$^6$, —NR$^5$C(O)R$^9$, —NR$^5$S(O)$_n$R$^8$, —NR$^5$S(O)$_n$NR$^{10}$R$^{11}$, —NR$^5$C(O)OR$^7$, —NR$^5$C(O)NR$^{10}$R$^{11}$, —NO$_2$, —S(O)$_n$NR$^5$R$^6$; or selected from methyl, ethyl, n-propyl, i-propyl, n-butyl, i-butyl, and t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, naphthyl, each of which is optionally substituted by one or more groups selected from halo, —NR$^5$R$^6$, —OR$^7$, —S(O)$_n$R$^8$, —C(O)R$^9$, —C(O)OR$^7$, —CN, —C(O)NR$^5$R$^6$, —NR$^5$C(O)R$^9$, —NR$^5$S(O)$_n$R$^8$, —NR$^5$S(O)$_n$NR$^{10}$R$^{11}$, —NR$^5$C(O)OR$^7$, —NR$^5$C(O)NR$^{10}$R$^{11}$, —NO$_2$, —S(O)$_n$NR$^5$R$^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl.

$R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, R² is chosen from

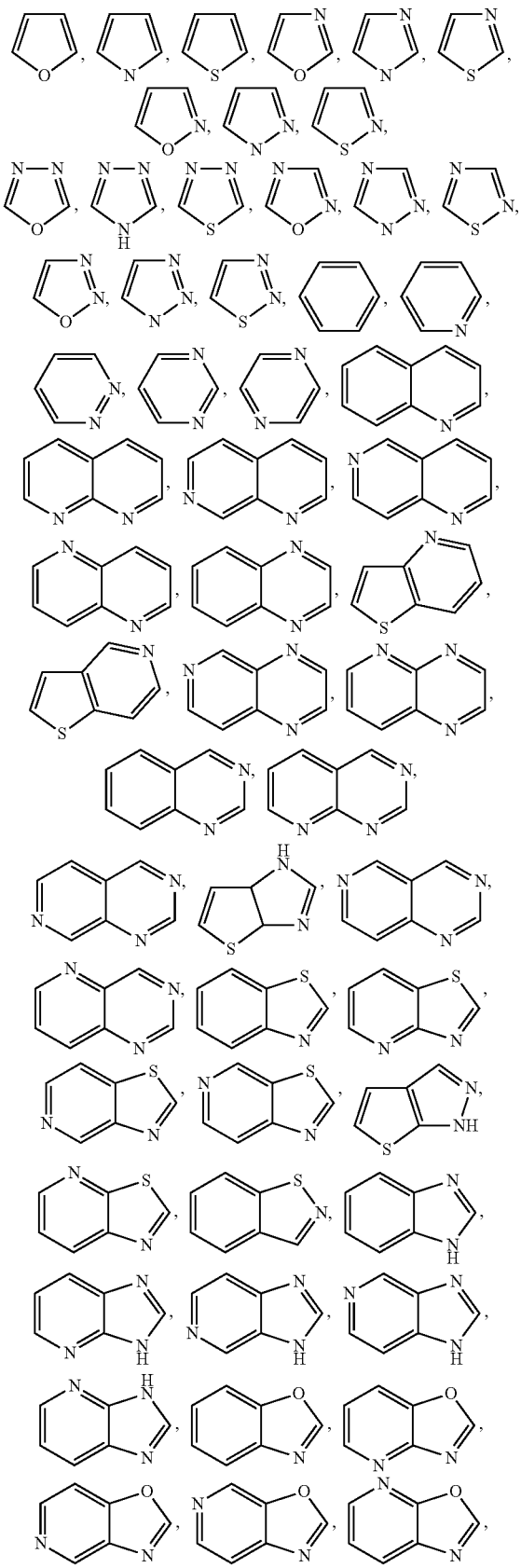
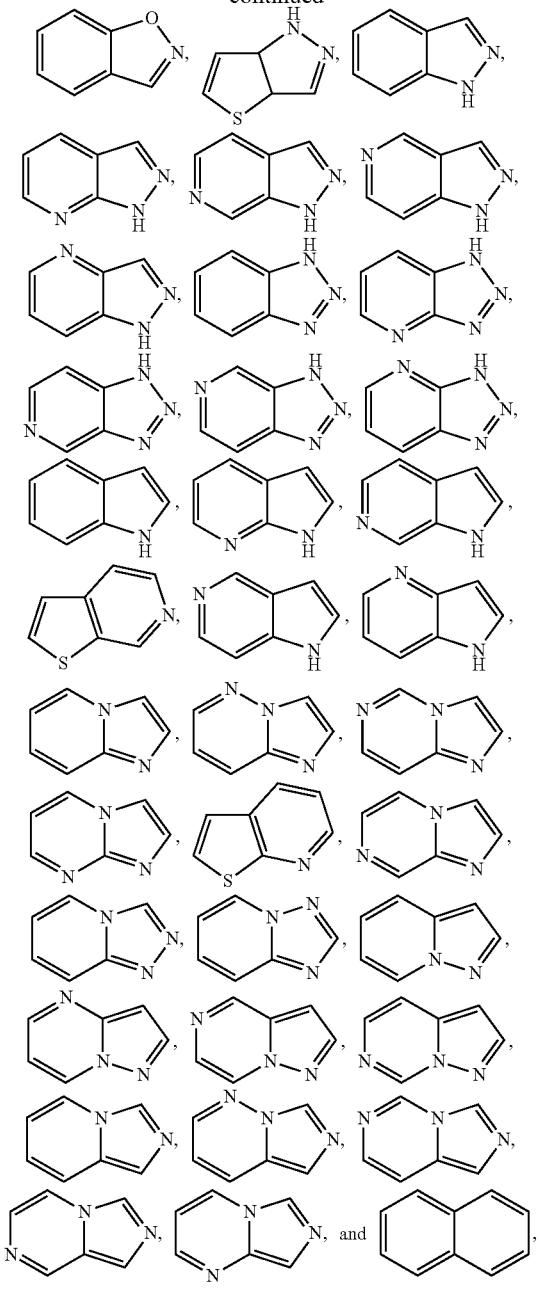

which is optionally substituted by one or more groups selected from halo, —NR⁵R⁶, —OR⁷, —S(O)$_n$R⁸, —C(O)R⁹, —C(O)OR⁷, —CN, —C(O)NR⁵R⁶, —NR⁵C(O)R⁹, —NR⁵S(O)$_n$R⁸, —NR⁵S(O)$_n$NR¹⁰R¹¹, —NR⁵C(O)OR⁷, —NR⁵C(O)NR¹⁰R¹¹, —NO₂, —S(O)$_n$NR⁵R⁶; or selected from methyl, ethyl, n-propyl, i-propyl, n-butyl, i-butyl, and t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, naphthyl, each of which is optionally substituted by one or more groups selected from halo, —NR⁵R⁶, —OR⁷, —S(O)$_n$R⁸, —C(O)R⁹, —C(O)OR⁷, —CN, —C(O)NR⁵R⁶, —NR⁵C(O)

R⁹, —NR⁵S(O)ₙR⁸, —NR⁵S(O)ₙNR¹⁰R¹¹, —NR⁵C(O)OR⁷, —NR⁵C(O)NR¹⁰R¹¹, —NO₂, —S(O)ₙNR⁵R⁶, optionally substituted lower alkyl, optionally substituted cycloalkyl, optionally substituted heterocycle, optionally substituted heteroaryl, optionally substituted aryl, optionally substituted alkenyl, and optionally substituted alkynyl.

R⁵, R⁶, R⁷, R⁸, R⁹, R¹⁰, and R¹¹ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or R⁵ and R⁶, R⁵ and R⁷, R⁵ and R⁸, R⁵ and R⁹, and R⁵ and R¹⁰ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, R² is chosen from

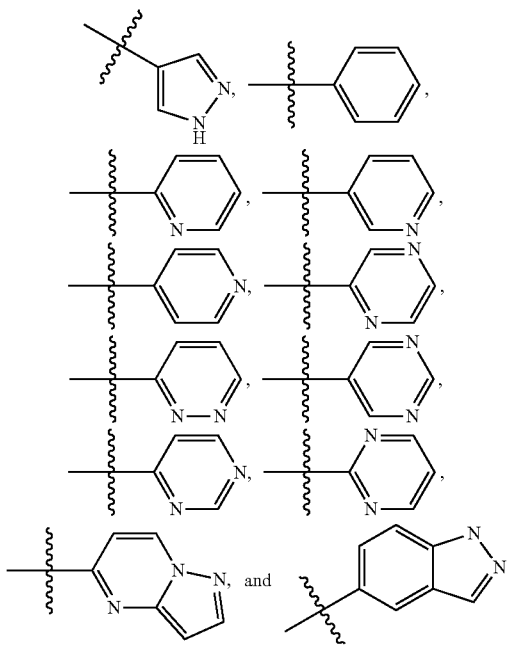

which is optionally substituted by one or more groups selected from halo, —NR⁵R⁶, —OR⁷, —S(O)ₙR⁸, —C(O)R⁹, —C(O)OR⁷, —CN, —C(O)NR⁵R⁶, —NR⁵C(O)R⁹, —NR⁵S(O)ₙR⁸, —NR⁵S(O)ₙNR¹⁰R¹¹, —NR⁵C(O)OR⁷, —NR⁵C(O)NR¹⁰R¹¹, —NO₂, —S(O)ₙNR⁵R⁶; or selected from methyl, ethyl, n-propyl, i-propyl, n-butyl, i-butyl, and t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, naphthyl, each of which is optionally substituted by one or more groups selected from halo, —NR⁵R⁶, —OR⁷, —S(O)ₙR⁸, —C(O)R⁹, —C(O)OR⁷, —CN, —C(O)NR⁵R⁶, —NR⁵C(O)R⁹, —NR⁵S(O)ₙR⁸, —NR⁵S(O)ₙNR¹⁰R¹¹, —NR⁵C(O)OR⁷, —NR⁵C(O)NR¹⁰R¹¹, —NO₂, —S(O)ₙNR⁵R⁶, optionally substituted lower alkyl, optionally substituted cycloalkyl, optionally substituted heterocycle, optionally substituted heteroaryl, optionally substituted aryl, optionally substituted alkenyl, and optionally substituted alkynyl.

R⁵, R⁶, R⁷, R⁸, R⁹, R¹⁰, and R¹¹ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or R⁵ and R⁶, R⁵ and R⁷, R⁵ and R⁸, R⁵ and R⁹, and R⁵ and R¹⁰ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, R² is

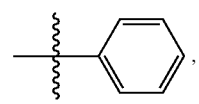

which is optionally substituted by one or more groups selected from halo, —NR⁵R⁶, —OR⁷, —S(O)ₙR⁸, —C(O)R⁹, —C(O)OR⁷, —CN, —C(O)NR⁵R⁶, —NR⁵C(O)R⁹, —NR⁵S(O)ₙR⁸, —NR⁵S(O)ₙNR¹⁰R¹¹, —NR⁵C(O)OR⁷, —NR⁵C(O)NR¹⁰R¹¹, —NO₂, —S(O)ₙNR⁵R⁶; or selected from methyl, ethyl, n-propyl, i-propyl, n-butyl, i-butyl, and t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, naphthyl, each of which is optionally substituted by one or more groups selected from halo, —NR⁵R⁶, —OR⁷, —S(O)ₙR⁸, —C(O)R⁹, —C(O)OR⁷, —CN, —C(O)NR⁵R⁶, —NR⁵C(O)R⁹, —NR⁵S(O)ₙR⁸, —NR⁵S(O)ₙNR¹⁰R¹¹, —NR⁵C(O)OR⁷, —NR⁵C(O)NR¹⁰R¹¹, —NO₂, —S(O)ₙNR⁵R⁶, optionally substituted lower alkyl, optionally substituted cycloalkyl, optionally substituted heterocycle, optionally substituted heteroaryl, optionally substituted aryl, optionally substituted alkenyl, and optionally substituted alkynyl.

R⁵, R⁶, R⁷, R⁸, R⁹, R¹⁰, and R¹¹ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, $R^2$ is

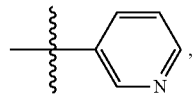

which is optionally substituted by one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$; or selected from methyl, ethyl, n-propyl, i-propyl, n-butyl, i-butyl, and t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, naphthyl, each of which is optionally substituted by one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl.

$R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, $R^3$ and $R^4$ are independently selected from hydrogen, $C_1$-$C_6$ alkyl, $C_3$-$C_8$ cycloalkyl, $C_5$-$C_{10}$ aryl, 5-10 membered heteroaryl, and 3-8 membered heterocycle, each of which except for hydrogen, is optionally substituted with one or more groups selected from halo, —$NR^5R^6$, —$OR^7$, —$S(O)_nR^8$, —$C(O)R^9$, —$C(O)OR'$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted $C_1$-$C_6$ alkyl, optionally substituted $C_3$-$C_8$ cycloalkyl, optionally substituted 3-8 membered heterocycle, optionally substituted 5-10 membered heteroaryl, optionally substituted $C_5$-$C_{10}$ aryl, optionally substituted $C_2$-$C_6$ alkenyl, and optionally substituted $C_2$-$C_6$ alkynyl, or $R^3$ and $R^4$, together with the N atom to which they are attached, can form a 4-12 membered mono-cyclic, fused bicyclic or spirocyclic ring optionally containing an additional 1-3 hetero-atoms chosen from N, O and S, which is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted $C_1$-$C_6$ alkyl, optionally substituted $C_3$-$C_8$ cycloalkyl, optionally substituted 3-8 membered heterocycle, optionally substituted 5-10 membered heteroaryl, optionally substituted $C_5$-$C_{10}$ aryl, optionally substituted $C_2$-$C_6$ alkenyl, and optionally substituted $C_2$-$C_6$ alkynyl, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, $R^3$ and $R^4$ are independently selected from hydrogen, methyl, ethyl, n-propyl, i-propyl, n-butyl, i-butyl, and t-butyl, cyclopropyl, cyclobutyl, cyclopentyl, cyclopentenyl, cyclohexyl, cyclohexenyl, phenyl, naphthyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, and pyrrolidinyl, tetrahydrofuryl, piperidinyl, piperazinyl, morpholinyl, homomorpholinyl, thiomorpholinyl, diazepanyl, oxazepanyl, each of which except for hydrogen, is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$; or selected from methyl, ethyl, n-propyl, i-propyl, n-butyl, i-butyl, and t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, naphthyl, $C_2$-$C_6$ alkenyl, $C_2$-$C_6$ alkynyl, each of which is optional substituted, or $R^3$ and $R^4$, together with the N atom to which they are attached, can form a 4-12 membered mono-cyclic, fused bicyclic or spirocyclic ring optionally containing an additional 1-3 hetero-atoms chosen from N, O and S, which is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$; or selected from methyl, ethyl, n-propyl, i-propyl, n-butyl, i-butyl, and t-butyl, optionally substituted cyclopropyl, cyclobutyl, cyclopentyl, cyclopentenyl, cyclohexyl, cyclohexenyl, optionally substituted pyrrolidinyl, tetrahydrofuryl, piperidinyl, piperazinyl, morpholinyl, homomorpholinyl, thiomorpholinyl, diazepanyl, oxazepanyl, optionally substituted pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, optionally substituted phenyl, naphthyl, optionally substituted $C_2$-$C_6$ alkenyl, and optionally substituted $C_2$-$C_6$ alkynyl, each of which is optional substituted, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, $R^4$ is H and $R^3$ is lower alkyl, which is optionally substituted with one or more groups selected from alkyl, cycloalkyl, heterocycle and heteroaryl, each of which is optionally substituted by one or more groups chosen from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, $R^3$ and $R^4$, together with the N atom to which they are attached can form a 4-12 membered mono-cyclic ring optionally containing an additional 1-3 hetero-atoms chosen from N, O and N, which is optionally substituted with one or more groups selected from halo, —$NR^5R^6$, —$OR^7$, —$S(O)_nR^8$, —$C(O)R^9$, —$C(O)OR'$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, $R^3$ and $R^4$, together with the N atom to which they are attached can form a 7-14 membered fused bicyclic ring optionally containing an additional 1-3 hetero-atoms chosen from N, O and N, which is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, $R^3$ and $R^4$, together with the N atom to which they are attached can form a 7-14 membered spirocyclic ring optionally containing an additional 1-3 hetero-atoms chosen from N, O and N, which is optionally substituted with one or more groups selected from halo, $-NR^5R^6$, $-OR^7$, $-S(O)_nR^8$, $-C(O)R^9$, $-C(O)OR'$, $-CN$, $-C(O)NR^5R^6$, $-NR^5C(O)R^9$, $-NR^5S(O)_nR^8$, $-NR^5S(O)_nNR^{10}R^{11}$, $-NR^5C(O)OR^7$, $-NR^5C(O)NR^{10}R^{11}$, $-NO_2$, $-S(O)_nNR^5R^6$, optionally substituted lower alkyl, optionally substituted cycloalkyl, optionally substituted heterocycle, optionally substituted heteroaryl, optionally substituted aryl, optionally substituted alkenyl, and optionally substituted alkynyl, $R^5$, $R^6$, $R^7$, $R^8$, $R^9$, $R^{10}$, and $R^{11}$ are independently selected from hydrogen, alkyl, cycloalkyl, aryl, heteroaryl, and heterocycle, each of which except for hydrogen, is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxyl, cyano, optionally substituted lower alkyl, optionally substituted lower alkoxyl, optionally substituted lower alkylsulfonyl, optionally substituted lower alkylacyl, optionally substituted cycloalkyl, optionally substituted heterocycle, optionally substituted amino, and optionally substituted amide, optionally substituted sulfonamide.

In some embodiments, the optionally substituted lower alkyl is chosen from $CF_3$, $CF_2H$, aminoalkyl, hydroxyalkyl, alkoxyalkyl, and haloalkyl.

Also provided is at least one compound chosen from compounds 1 to 516 and/or at least one pharmaceutically acceptable salt thereof.

The compounds described herein, and/or the pharmaceutically acceptable salts thereof, can be synthesized from commercially available starting materials by methods well known in the art, taken together with the disclosure in this patent application. The following schemes illustrate methods for preparation of most of the compounds disclosed herein.

Scheme I

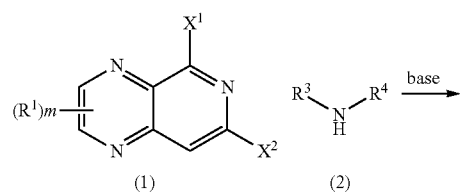

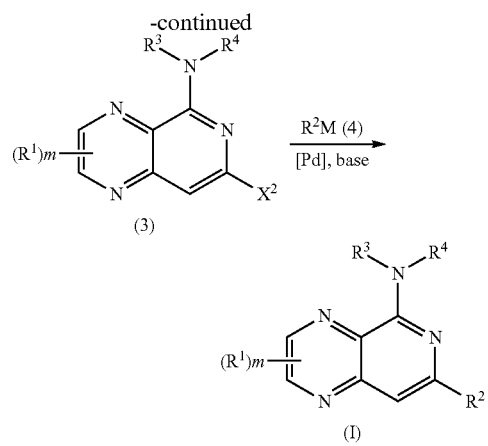

As shown in Scheme I, compounds of formula (1), can react with compounds of formula (2), wherein n, $R^1$, $R^2$ and $R^3$ are as defined herein, $X^1$ and $X^2$ are halo chosen from Cl, Br or I, in the presence of a base, such as but not limited to $K_2CO_3$, $Na_2CO_3$, NaH, $Et_3N$ or diisopropylethylamine (DIPEA), to give compounds of formula (3) that can react with compounds of formula (4), wherein $R^2$ is as defined herein, M is chosen from boronic acid/ester or a tin substituted with $C_1$-$C_4$ alkyl groups, under the catalysis of a palladium reagent, such as but not limited to $PdCl_2$, $Pd(OAc)_2Pd_2(dba)_3$ or $Pd(PPh_3)_4$, and a ligand, such as but not limited to $Ph_3P$, $^tBu_3P$, 2,2'-bis(diphenylphosphino)-1,1'-binaphthalene (BINAP), 1,1'-bis(diphenylphosphino)ferrocene (dppf) or 1,3-bis(2,6-dipropylphenyl)-1H-imidazol-3-ium chloride, in the presence of a base, such as but not limited to $K_2CO_3$, $Na_2CO_3$, $Cs_2CO_3$, NaH, t-BuONa, t-BuOK, $Et_3N$, or diisopropylethylamine (DIPEA), to give the compound of formula (I).

The compounds thus obtained can be further modified at their peripheral positions to provide the desired compounds. Synthetic chemistry transformations are described, for example, in R. Larock, *Comprehensive Organic Transformations,* VCH Publishers (1989); T. W. Greene and P. G. M. Wuts, *Protective Groups in Organic Synthesis,* 3$^{rd}$ Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995) and subsequent editions thereof.

Before use, the at least one compound and/or at least one pharmaceutically acceptable salt described herein, can be purified by column chromatography, high performance liquid chromatography, crystallization, or other suitable methods.

Also provided is a composition comprising at least one compound and/or at least one pharmaceutically acceptable salt described herein, and at least one pharmaceutically acceptable carrier.

A composition comprising at least one compound and/or at least one pharmaceutically acceptable salt described herein, can be administered in various known manners, such as orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable Intermediate can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the Intermediate of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the at least one compound and/or at least one pharmaceutically acceptable salt described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10.

Suitable in vitro assays can be used to preliminarily evaluate the efficacy of the at least one compound and/or at least one pharmaceutically acceptable salt described herein, in inhibiting the activity of Syk kinase. The at least one compound and/or at least one pharmaceutically acceptable salt described herein, can further be examined for efficacy in treating inflammatory disease by in vivo assays. For example, the compounds described herein, and/or the pharmaceutically acceptable salts thereof, can be administered to an animal (e.g., a mouse model) having inflammatory disease and its therapeutic effects can be accessed. Based on the results, an appropriate dosage range and administration route for animals, such as humans, can also be determined.

Also provided is a method of inhibiting the activity of Syk kinase. The method comprises contacting the at least one kinase with an amount of at least one compound and/or at least one pharmaceutically acceptable salt described herein effective to inhibit the activity of the Syk kinase.

The at least one compound and/or at least one pharmaceutically acceptable salt described herein can be used to achieve a beneficial therapeutic or prophylactic effect, for example, in subjects with an inflammatory disease or inflammatory disorder. The term "inflammatory disease" or "inflammatory disorder" refers to pathological states resulting in inflammation, typically caused by neutrophil chemotaxis. Examples of such disorders include inflammatory skin diseases including psoriasis and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc. The preferred indications include, without limitation, chronic inflammation, autoimmune diabetes, rheumatoid arthritis (RA), rheumatoid spondylitis, gouty arthritis and other arthritic conditions, multiple sclerosis (MS), asthma, systhemic lupus erythrematosus, adult respiratory distress syndrome, Behcet's disease, psoriasis, chronic pulmonary inflammatory disease, graft versus host reaction, Crohn's Disease, ulcerative colitis, inflammatory bowel disease (IBD), Alzheimer's disease, and pyresis, along with any disease or disorder that relates to inflammation and related disorders.

The at least one compound and/or at least one pharmaceutically acceptable salt described herein can be used to achieve a beneficial therapeutic or prophylactic effect, for example, in subjects with an autoimmune disease. The term "autoimmune disease" refers to a disease or disorder arising from and/or directed against an individual's own tissues or organs, or a co-segregate or manifestation thereof, or resulting condition therefrom. Examples of autoimmune diseases include, but are not limited to, lupus, myasthenia gravis, multiple sclerosis (MS), rheumatoid arthritis (RA), psoriasis, inflammatory bowel disease, asthma and idiopathic thrombocytopenic purpura, and myeloid proliferative disorder, such as myelofibrosis, PV/ET (Post-Polycythemia/Essential Thrombocythemia Myelofibrosis).

In some embodiments, the at least one compound and/or at least one pharmaceutically acceptable salt described herein, is administered in conjunction with another therapeutic agent. In some embodiments, the other therapeutic agent is one that is normally administered to patients with the disease or condition being treated. For example, the other therapeutic agent may be an anti-inflammatory agent or an anti-neoplastic agent, depending on the disease or condition being treated. The at least one compound and/or at least one pharmaceutically acceptable salt described herein, may be administered with the other therapeutic agent in a single dosage form or as a separate dosage form. When administered as a separate dosage form, the other therapeutic agent may be administered prior to, at the same time as, or following administration of the at least one compound and/or at least one pharmaceutically acceptable salt described herein.

In some embodiments, the at least one compound and/or at least one pharmaceutically acceptable salt described herein, is administered in conjunction with an anti-inflammatory agent. Nonlimiting examples of anti-inflammatory agents include corticosteroids (e.g., fluticasone propionate, beclomethasone dipropionate, mometasone furoate, triamcinolone acetonide or budesonide), disease-modifying agents (e.g., antimalarials, methotrexate, sulfasalazine, mesalamine, azathioprine, 6 metronidazole, injectable and oral gold, or D-penicillamine), non-steroidal antiinflammatory drugs (e.g., acetominophen, aspirin, sodium salicylate, sodium cromoglycate, magnesium salicylate, choline magnesium salicylate, salicylsalicylic acid, ibuprofen, naproxen, diclofenac, diflunisal, etodolac, fenoprofen calcium, fluriprofen, piroxicam, indomethacin, ketoprofen, ketorolac tromethamine, meclofenamate, meclofenamate sodium, mefenamic acid, nabumetone, oxaprozin, phenyl butyl nitrone (PBN), sulindac, or tolmetin), COX-2 inhibitors, inhibitors of cytokine synthesis/release (e.g., anti-cytokine antibodies, anti-cytokine receptor antibodies, and the like).

EXAMPLES

The examples below are intended to be purely exemplary and should not be considered to be limiting in any way. Efforts have been made to ensure accuracy with respect to numbers used (for example, amounts, temperature, etc.) but some experimental errors and deviations should be accounted for. Unless indicated otherwise, parts are parts by weight, temperature is in degrees of Centigrade, and pressure is at or near atmospheric. All MS data were checked by Agilent 6120 and/or Agilent 1100. All reagents, except intermediates, used in this invention are commercially available. All compound names except the reagents were generated by Chemdraw 8.0.

In the following examples, the abbreviations below are used:
Boc tert-butoxycarbonyl
Boc$_2$O di-t-butyl-dicarbonate
CU N,N'-Carbonyldiimidazole
DAST Diethylaminosulfur trifluoride
DCM dichloromethane
DMF N,N-dimethylformamide
DMAP 4-dimethylaminopyridine
DIPEA N,N-Diisopropylethylamine
EDCl 1-(3-Dimethylaminopropyl)-3-ethylcarbodiimide Hydrochloride
EtOAc/EA ethyl acetate
Et$_3$N triethylamine
HATU O-(7-azabenzotriazol-1-yl)-N,N,N',N'-tetra-methyl-uronium hexafluorophosphate
HOAc acetic acid
HOBt Hydroxybenzotriazole
mL milliliter(s)
min minute(s)
MeOH methanol
MsCl methanesulfonyl chloride
NaH Sodium hydride
PE petroleum ether
Pd(dppf)Cl$_2$ 1,1'-Bis(diphenylphosphino)ferrocene-palladium(II)dichloride
Pd$_2$(dba)$_3$ tris(dibenzylideneacetone)dipalladium(0)
Pd(PPh$_3$)$_4$ tetrakis(triphenylphosphine)palladium(0)
PPh$_3$ triphenylphosphine
TBDMSCl tert-Butyldimethylsilyl chloride
TMSNCO trimethylsilyl isocyanate
THF tetrahydrofuran Intermediate 1

5,7-dichloropyrido[4,3-b]pyrazine

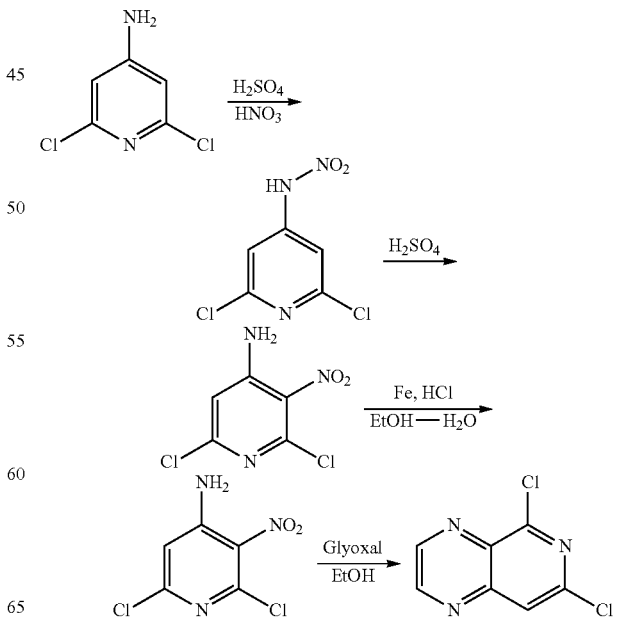

(A) N-(2,6-dichloropyridin-4-yl)nitramide 2,6-dichloropyridine-4-ylamine (10.0 g, 61 mmol) was slowly added in concentrated sulfuric acid (64 mL) at the rate to keep the internal reaction temperature <10° C. The mixture was then cooled to −5° C. and nitric acid (90%, 30 mL) was added dropwise to keep the reaction temperature below 0° C. over a period of 40 minutes. The reaction mixture was stirred at 0° C. for 2 hours and then poured into ice-water (500 mL). The title compound was isolated by filtration and dried in vacuo for the next step.

(B) 2,6-dichloro-3-nitropyridin-4-amine

N-(2,6-dichloropyridin-4-yl)nitramide from the previous step was slowly added into concentrated sulfuric acid (64 mL) at a rate sufficient to keep the internal reaction temperature <40° C. The reaction mixture was then stirred at 100° C. for 1 hour, and poured into ice-water (300 mL), and basified with 6 M of NaOH solution (about 190 mL) to reach a pH=9.5. The precipitates were collected by filtration and dried in vacuo to give the title compound.

(C) 2,6-dichloropyridine-3,4-diamine

To a solution of 2,6-dichloro-3-nitropyridin-4-amine in ethanol (150 mL) was added iron powder (14.3 g, 0.255 mol), water (46 mL), and then concentrated HCl (28 mL). The reaction mixture was then stirred at 95° C. for 16 hours, cooled to room temperature, and neutralized. The precipitates were collected by filtration and dried in vacuo. The crude product was then treated with water (200 mL) and extracted with EtOAc (3×200 mL). The combined extracts were dried over anhydrous $Na_2SO_4$, filtered, and concentrated to afford 7.85 g of the title compound (86.5% yield).

(D) 5,7-dichloropyrido[4,3-b]pyrazine

A mixture of the solution of 2,6-dichloropyridine-3,4-diamine (7.85 g, 0.044 mol) in ethanol and 40% glyoxal solution in water (26 g, 0.178 mol) was refluxed overnight. It was then cooled to ambient temperature, and the precipitates were collected, washed with EtOH, and dried in vacuo to give the title compound (7.32 g, 83% yield).

Intermediate 2

N,N-dimethyl-1-(4-(4,4,5,5-tetramethyl-1,3,2-dioxaborolan-2-yl)phenyl)methanamine

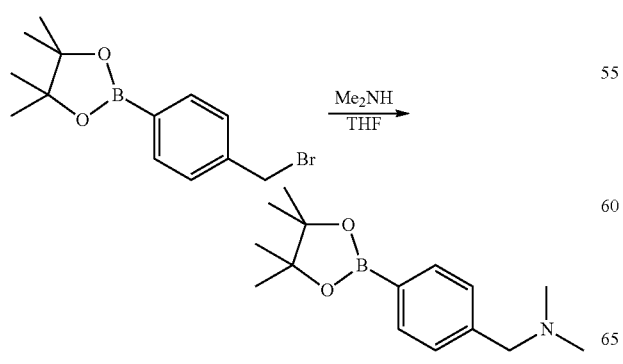

A mixture of 2-(4-(bromomethyl)phenyl)-4,4,5,5-tetramethyl-1,3,2-dioxaborolane (200 mg, 0.673 mmol) and aqueous $Me_2NH$ (4 mL) in THF (10 mL) was stirred at room temperature overnight. It was then concentrated under reduced pressure to give the title compound. MS (m/z): 262 $(M+H)^+$.

Intermediate 3

Morpholino(4-(4,4,5,5-tetramethyl-1,3,2-dioxaborolan-2-yl)phenyl)methanone

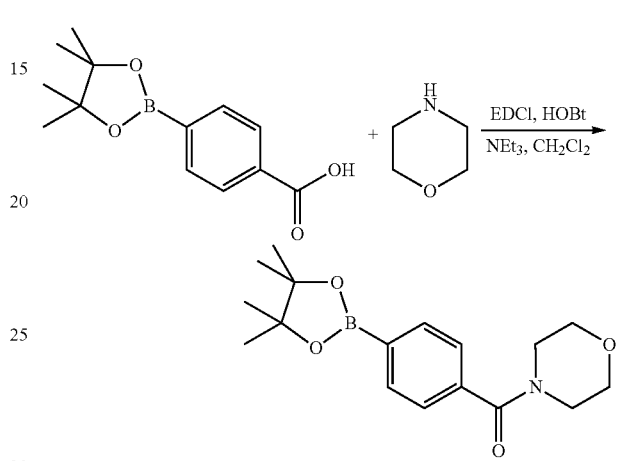

To a solution of 4-(4,4,5,5-tetramethyl-1,3,2-dioxaborolan-2-yl)benzoic acid (200 mg, 0.806 mmol) in $CH_2Cl_2$ (10 mL) was subsequently added EDCl (232 mg, 1.21 mmol), HOBt (163 mg, 1.21 mmol), morpholine (0.11 mL, 1.21 mmol), and $Et_3N$ (0.22 mL, 1.61 mmol). The mixture was stirred at room temperature overnight, treated with EtOAc/$H_2O$, and extracted with EtOAc. The combined extracts were washed with brine, dried over anhydrous $Na_2SO_4$, filtered, and concentrated. The residue was purified by flash chromatography to give the title compound (207 mg, 81% yield). MS (m/z): 318 $(M+H)^+$ Intermediate 4

N-ethyl-4-(4,4,5,5-tetramethyl-1,3,2-dioxaborolan-2-yl)benzamide

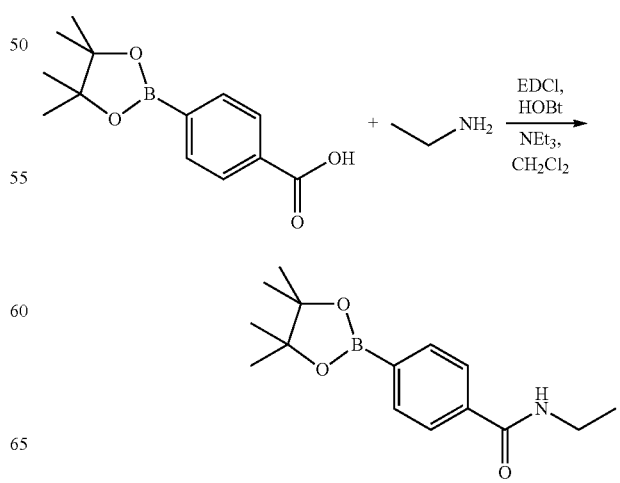

The title compound was prepared according to the procedures of Intermediate 3 using instead 4-(4,4,5,5-tetramethyl-1,3,2-dioxaborolan-2-yl)benzoic acid and ethylamine. MS (m/z): 276 (M+H)+

Intermediate 5

2-(4-(2-methoxyethoxy)phenyl)-4,4,5,5-tetramethyl-1,3,2-dioxaborolane

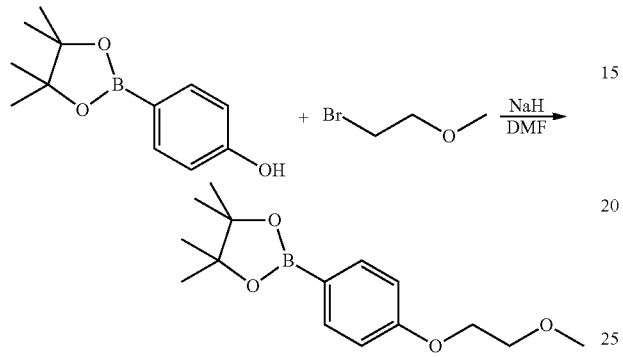

To a solution of 4-(4,4,5,5-tetramethyl-1,3,2-dioxaborolan-2-yl)phenol (150 mg, 0.682 mmol) in DMF (5 mL) was added 60% NaH (136 mg, 3.41 mmol) and 2-bromoethyl methyl ether (0.13 mL, 1.363 mmol). The resulting solution was stirred at 50° C. overnight, cooled to ambient temperature, quenched with water, and extracted with EtOAc. The combined extracts were washed with brine, dried over anhydrous Na$_2$SO$_4$, filtered, and concentrated. The residue was purified by flash chromatography to give the title compound (114 mg, 60% yield).

Intermediate 6

N,N-dimethyl-2-(4-(4,4,5,5-tetramethyl-1,3,2-dioxaborolan-2-yl)phenoxy)ethanamine

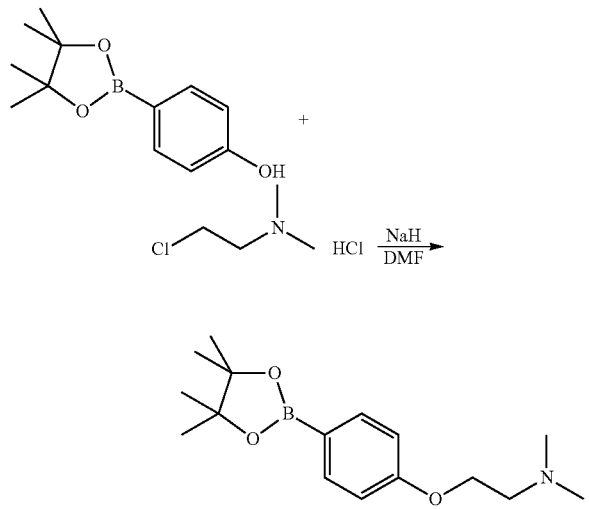

To a solution of 4-(4,4,5,5-tetramethyl-1,3,2-dioxaborolan-2-yl)phenol (258 mg, 0.509 mmol) in DMF (10 mL) was added 60% NaH (204 mg, 5.09 mmol) and 2-chloro-N,N-dimethylethylamine (220 mg, 1.527 mmol). The resulting solution was stirred at 60° C. overnight, cooled to the ambient temperature, quenched with aqueous NH$_4$Cl, and extracted with EtOAc. The combined extracts were washed with brine, dried over anhydrous Na$_2$SO$_4$, filtered, and concentrated. The residue was purified by flash chromatography to give the title compound (100 mg, 29% yield).

Intermediate 7 tert-butyl piperidin-4-ylmethylcarbamate

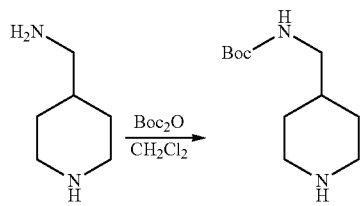

A solution of 4-aminomethylpiperidine (242 mg, 2.12 mmol) and di-tert-butyl dicarbonate (Boc$_2$O) (463 mg, 2.12 mmol) in CH$_2$Cl$_2$ (5 mL) was stirred at room temperature overnight. The solution was then diluted with CH$_2$Cl$_2$, washed with brine, dried over anhydrous Na$_2$SO$_4$, filtered, and concentrated under reduced pressure to give the title compound.

Intermediate 8

N-methyl-5-(4,4,5,5-tetramethyl-1,3,2-dioxaborolan-2-yl)pyridin-2-amine

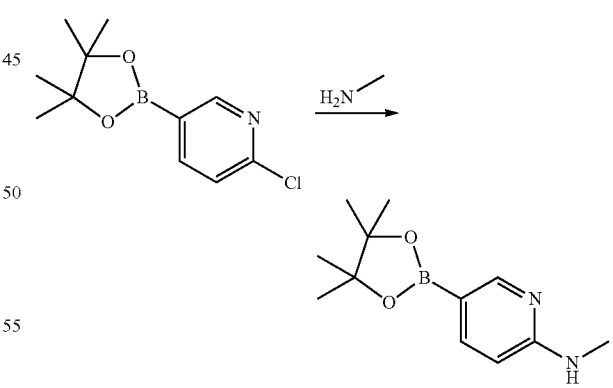

A mixture of 2-chloro-5-(4,4,5,5-tetramethyl-1,3,2-dioxaborolan-2-yl)pyridine (200 mg, 0.84 mmol), methanamine (277 mg, 8.4 mmol), and DIPEA (0.35 mL, 2.01 mmol) in dioxane (5 mL) was stirred at room temperature for 16 hours. It was then concentrated under reduced pressure, and the residue was treated in EtOAc. The insoluble solid was removed by filtration, and the organic solution was concentrated under reduced pressure to give the title compound.

Intermediate 9

N,N-dimethyl-5-(4,4,5,5-tetramethyl-1,3,2-dioxaborolan-2-yl)pyridin-2-amine

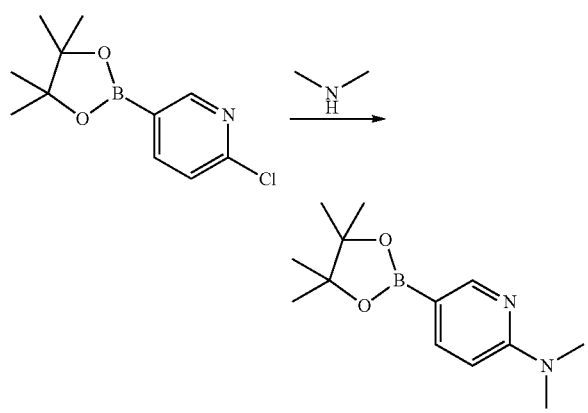

The title compound was prepared according to the procedures of intermediate 8 except using 2-chloro-5-(4,4,5,5-tetramethyl-1,3,2-dioxaborolan-2-yl)pyridine and dimethyl amine.

Intermediate 10

N,N-diethyl-4-(4,4,5,5-tetramethyl-1,3,2-dioxaborolan-2-yl)benzenamine

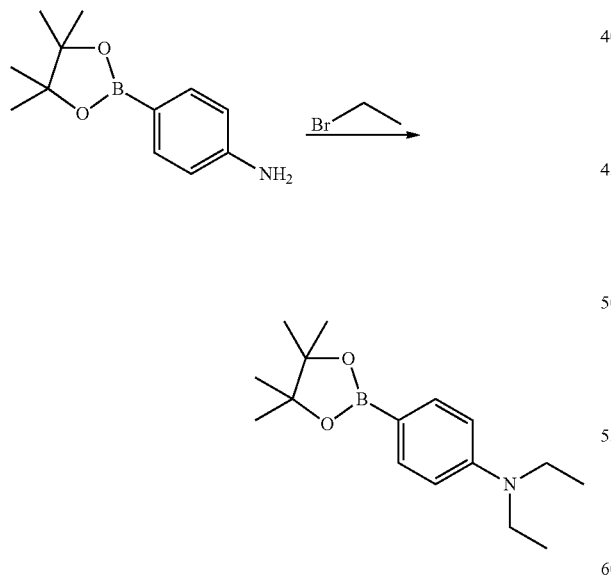

A mixture of 4-(4,4,5,5-tetramethyl-1,3,2-dioxaborolan-2-yl)benzenamine (100 mg, 0.45 mmol) and bromoethane (200 mg, 1.8 mmol), NaH (100 mg, 1.8 mmol) in THF was stirred at room temperature overnight, and concentrated in vacuo to give the crude title compound used for the next step. MS (m/z): 276 (M+H)$^+$.

Intermediate 11

1-(2-methoxyethyl)-4-(4,4,5,5-tetramethyl-1,3,2-dioxaborolan-2-yl)-1H-pyrazole

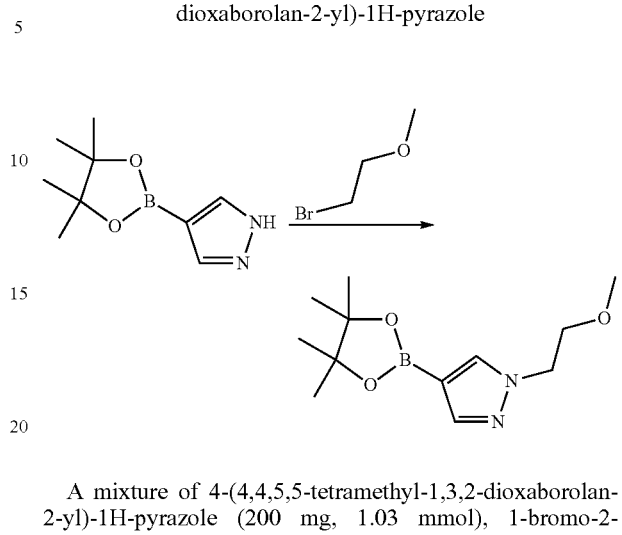

A mixture of 4-(4,4,5,5-tetramethyl-1,3,2-dioxaborolan-2-yl)-1H-pyrazole (200 mg, 1.03 mmol), 1-bromo-2-methoxyethane (280 mg, 2.01 mmol), and NaH (200 mg, 4 mmol) in THF (15 mL) was stirred at reflux for 24 hours, cooled to the ambient temperature, and concentrated in vacuo. The residue was treated with HCl(aq) and extracted with EtOAc. The insoluble solid was removed by filtration, and the organic solution was concentrated to give the title compound. MS (m/z): 253 (M+H)$^+$.

Intermediate 12

6-(dimethylamino)pyridin-3-ylboronic acid

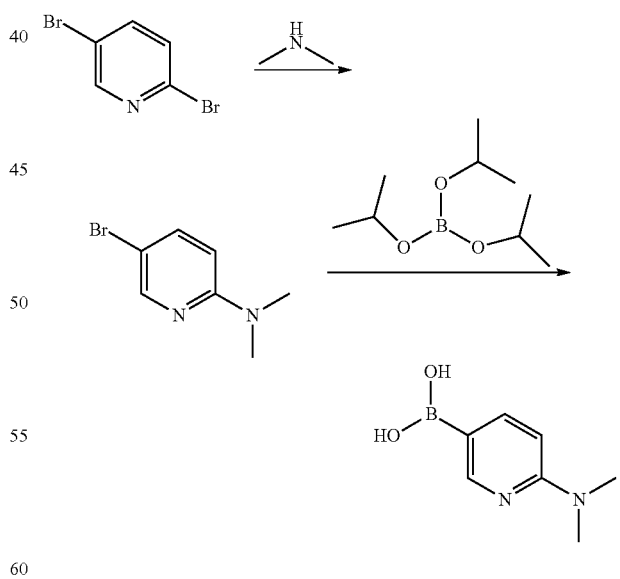

(A) 5-bromo-N,N-dimethylpyridin-2-amine

A solution of 2,5-dibromopyridine (10 g, 42.3 mmol) in aqueous dimethylamine (50 mL) was refluxed overnight. The volatiles were removed in vacuo, and the residue was treated with EtOAc/PE. The precipitates were collected by filtration and dried to give the title compound. MS (m/z): 201 (M+H)+, 203 (M+H)+.

(B) 6-(dimethylamino)pyridin-3-ylboronic acid

A solution of 5-bromo-N,N-dimethylpyridin-2-amine (500 mg, 2.5 mmol) in THF (10 mL) was treated with n-BuLi (1.2 mL, 3 mmol) at −72° C. for 2 hours. Triisopropyl borate (705 mg, 3.75 mmol) was then added dropwise. After the completion of the addition, the mixture was stirred at −72° C. for an additional 1 hour and slowly warmed up and stirred at the ambient temperature overnight. MeOH was carefully added, and the volatiles were removed under reduced pressure to give the title compound. MS (m/z): 167 (M+H)+.

Intermediate 13

6-(pyrrolidin-1-yl)pyridin-3-ylboronic acid

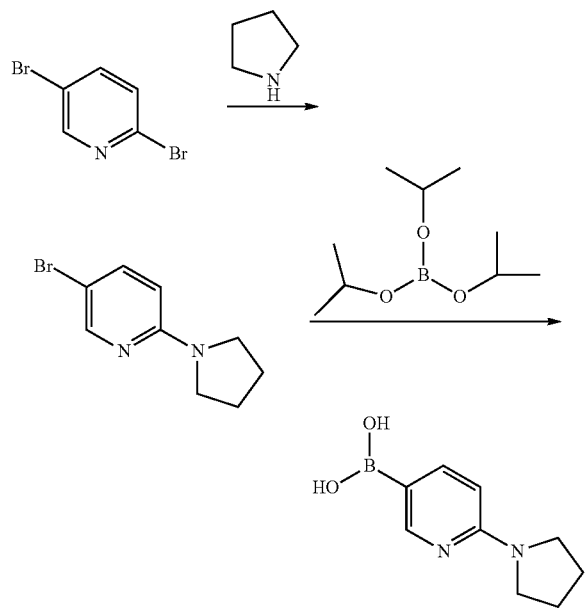

The title compound was prepared according to the procedures of intermediate 12 using the corresponding reagents under appropriate conditions that will be recognized by one skilled in the art. MS (m/z): 193 (M+H)+.

Intermediate 14

4-(3-(4,4,5,5-tetramethyl-1,3,2-dioxaborolan-2-yl)phenyl)morpholine

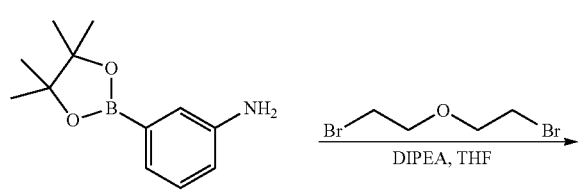

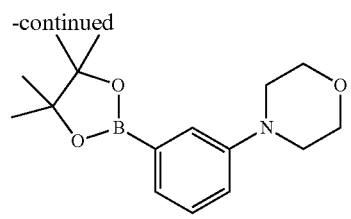

A solution of 3-(4,4,5,5-tetramethyl-1,3,2-dioxaborolan-2-yl)benzenamine (164 mg, 0.75 mmol), 1-bromo-2-(2-bromoethoxy)ethane (418 mg, 1.8 mmol), and DIPEA (0.64 mL, 3.6 mmol) in THF (2 mL) was stirred at reflux overnight. The mixture was concentrated, diluted with water, and extracted with EtOAc. The combined extracts were dried over Na$_2$SO$_4$, filtered, and concentrated. The residue was purified by preparative thin-layer chromatography to give the title compound. MS (m/z): 290 (M+H)+.

Intermediate 15

N-methyl-2-(3-(4,4,5,5-tetramethyl-1,3,2-dioxaborolan-2-yl)phenoxy)acetamide

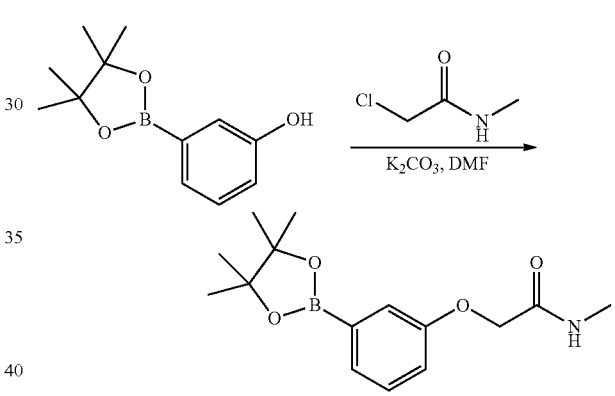

A mixture of 3-(4,4,5,5-tetramethyl-1,3,2-dioxaborolan-2-yl)phenol (220 mg, 1.0 mmol), 2-chloro-N-methylacetamide (129 mg, 1.2 mmol), and K$_2$CO$_3$ (207 mg, 1.5 mmol) in DMF (1.5 mL) was stirred at 80° C. overnight. The mixture was poured into water and extracted with EtOAc. The combined extracts were dried over Na$_2$SO$_4$, filtered, and concentrated. The residue was purified by chromatography to give the title compound in the yield of 72%. MS (m/z): 292 (M+H)+.

Intermediate 16

N-methyl-2-(4-(4,4,5,5-tetramethyl-1,3,2-dioxaborolan-2-yl)phenoxy)acetamide

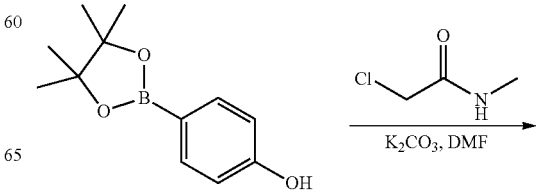

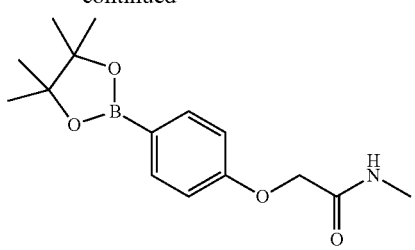

The title compound was prepared according to the procedures of intermediate 15 using the corresponding reagents under appropriate conditions that will be recognized by one skilled in the art. MS (m/z): 292 (M+H)$^+$.

Intermediate 17

3-methoxy-4-(2-morpholinoethoxy)phenylboronic acid

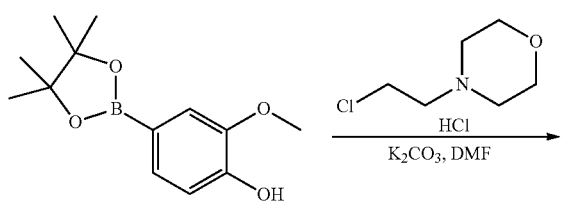

The title compound was prepared according to the procedures of Intermediate 15 using the corresponding reagents under appropriate conditions that will be recognized by one skilled in the art. MS (m/z): 364 (M+H)$^+$.

Intermediate 18 tert-butyl methyl(4-(4,4,5,5-tetramethyl-1,3,2-dioxaborolan-2-yl)phenyl)carbamate

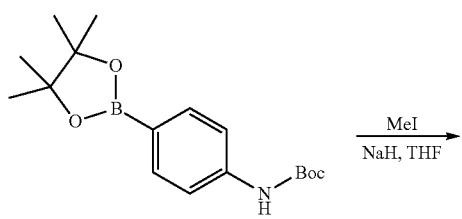

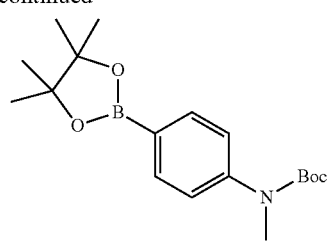

Under N$_2$, to a solution of tert-butyl 4-(4,4,5,5-tetramethyl-1,3,2-dioxaborolan-2-yl)phenylcarbamate (500 mg, 1.57 mmol) in anhydrous THF (4 mL), was slowly added sodium hydride (94 mg, 2.35 mmol) at 0° C. The mixture was stirred at room temperature for 20 minutes, then cooled to 0° C. CH$_3$I (445 mg, 3.13 mmol) was slowly added. After the completion of the addition, the reaction mixture was stirred at room temperature overnight, quenched with H$_2$O, and extracted with EtOAc. The combined extracts were concentrated, and the residue was purified by flash chromatography to give the title compound. MS (m/z): 278 (M−56)$^+$.

Intermediate 19

1-(4-(4,4,5,5-tetramethyl-1,3,2-dioxaborolan-2-yl)phenyl)pyrrolidin-2-one

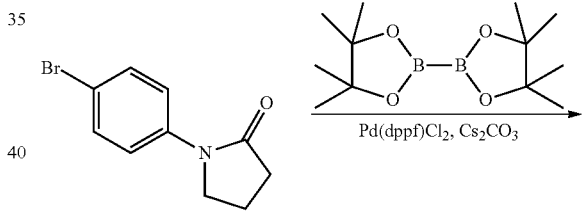

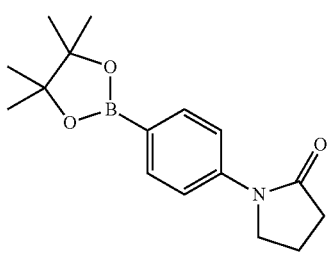

Under N$_2$, to a solution of 1-(4-bromophenyl)pyrrolidin-2-one (300 mg, 1.25 mmol) and 4,4,5,5-tetramethyl-2-(4,4,5,5-tetramethyl-1,3,2-dioxaborolan-2-yl)-1,3,2 (381 mg, 1.50 mmol) in dioxane/H$_2$O (10:1, 5 mL), was added Pd(dppf)Cl$_2$.CH$_2$Cl$_2$ complex (102 mg, 0.125 mmol) and cesium carbonate (489 mg, 1.5 mmol). The reaction mixture was stirred at reflux for 24 hours. It was then concentrated, and the residue was purified by chromatography to give the title compound in 86% yield. MS (m/z): 288 (M+H)$^+$.

Intermediate 20 tert-butyl 2-fluoro-4-(4,4,5,5-tetramethyl-1,3,2-dioxaborolan-2-yl)phenyl(methyl) carbamate

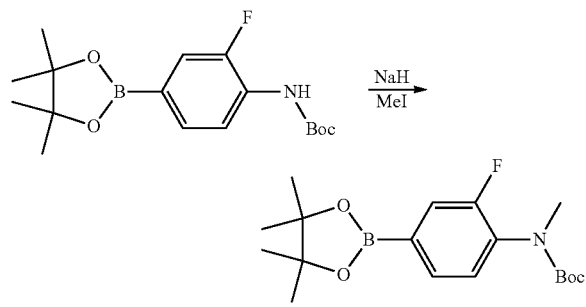

The title compound was prepared according to the procedures of Intermediate 18 using tert-butyl 2-fluoro-4-(4,4,5,5-tetramethyl-1,3,2-dioxaborolan-2 MS (m/z): 296 (M−56)$^+$.

Intermediate 21

2-fluoro-N,N-dimethyl-4-(4,4,5,5-tetramethyl-1,3,2-dioxaborolan-2-yl)aniline

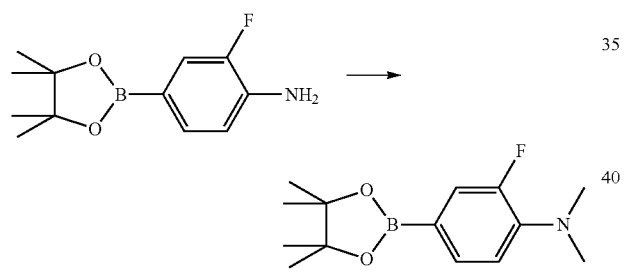

The mixture of 2-fluoro-4-(4,4,5,5-tetramethyl-1,3,2-dioxaborolan-2-yl)aniline (474 mg, 2 mmol), K$_2$CO$_3$ (828 mg, 6 mmol), and MeI (710 mg, 5 mmol) in DMF (10 mL), was stirred at 100° C. overnight. Then it was cooled and extracted by EA/H$_2$O, the organic layer was combined, washed by brine, dried over anhydrous Na$_2$SO$_4$, and concentrated to give the crude compound in 93% yield. MS (m/z): 266 (M+H)$^+$.

Intermediate 22

2-(4-(difluoromethoxy)phenyl)-4,4,5,5-tetramethyl-1,3,2-dioxaborolane

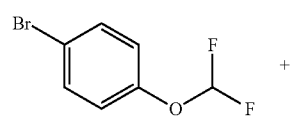 +

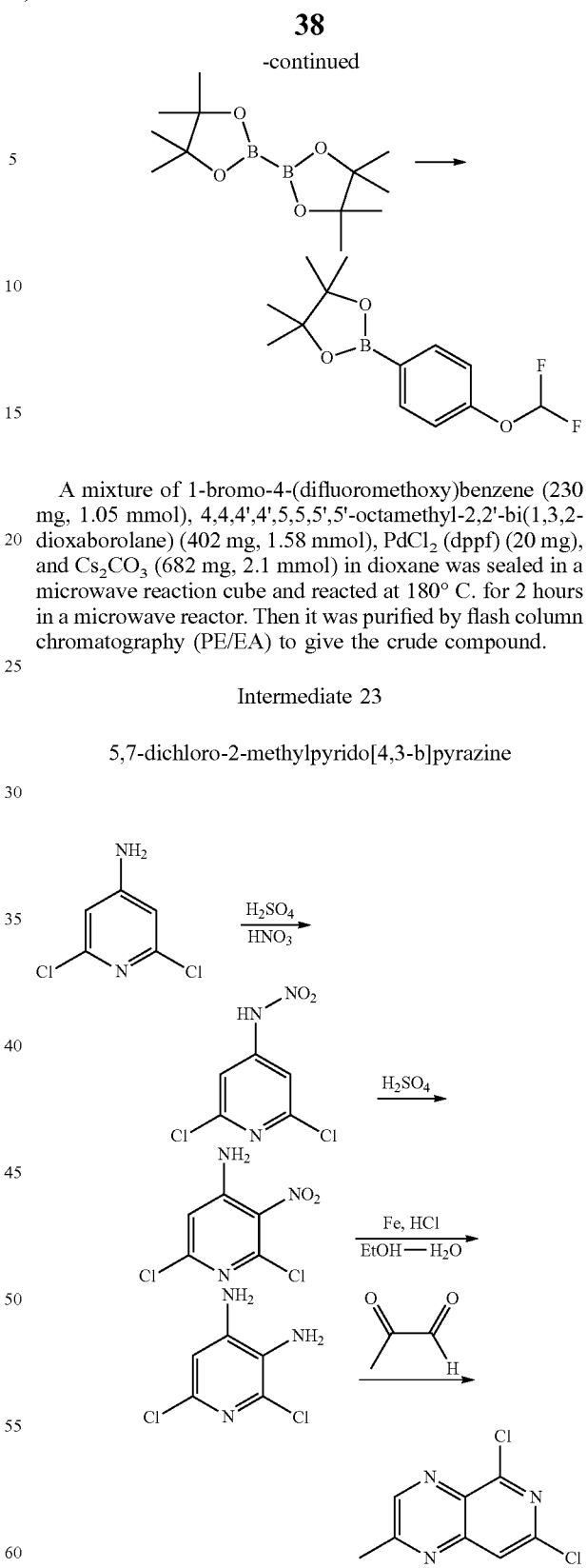

A mixture of 1-bromo-4-(difluoromethoxy)benzene (230 mg, 1.05 mmol), 4,4,4',4',5,5,5',5'-octamethyl-2,2'-bi(1,3,2-dioxaborolane) (402 mg, 1.58 mmol), PdCl$_2$ (dppf) (20 mg), and Cs$_2$CO$_3$ (682 mg, 2.1 mmol) in dioxane was sealed in a microwave reaction cube and reacted at 180° C. for 2 hours in a microwave reactor. Then it was purified by flash column chromatography (PE/EA) to give the crude compound.

Intermediate 23

5,7-dichloro-2-methylpyrido[4,3-b]pyrazine (A) 2,6-dichloropyridine-3,4-diamine

The title compound was prepared according to the procedures of Intermediate 1.

(B) 5,7-dichloro-2-methylpyrido[4,3-b]pyrazine

The title compound was prepared according to the procedure of reference (*HETEROCYCLES*, Vol. 60, No. 4, 2003, pp. 925-932) using the corresponding reagents under appropriate conditions that can be recognized by one skilled in the art. MS (m/z): 214 (M+H)+, 216 (M+H)+.

Intermediate 24 tert-butyl 3-((7-chloropyrido[4,3-b]pyrazin-5-ylamino)methyl)-5-hydroxypiperidine-1-carboxylate

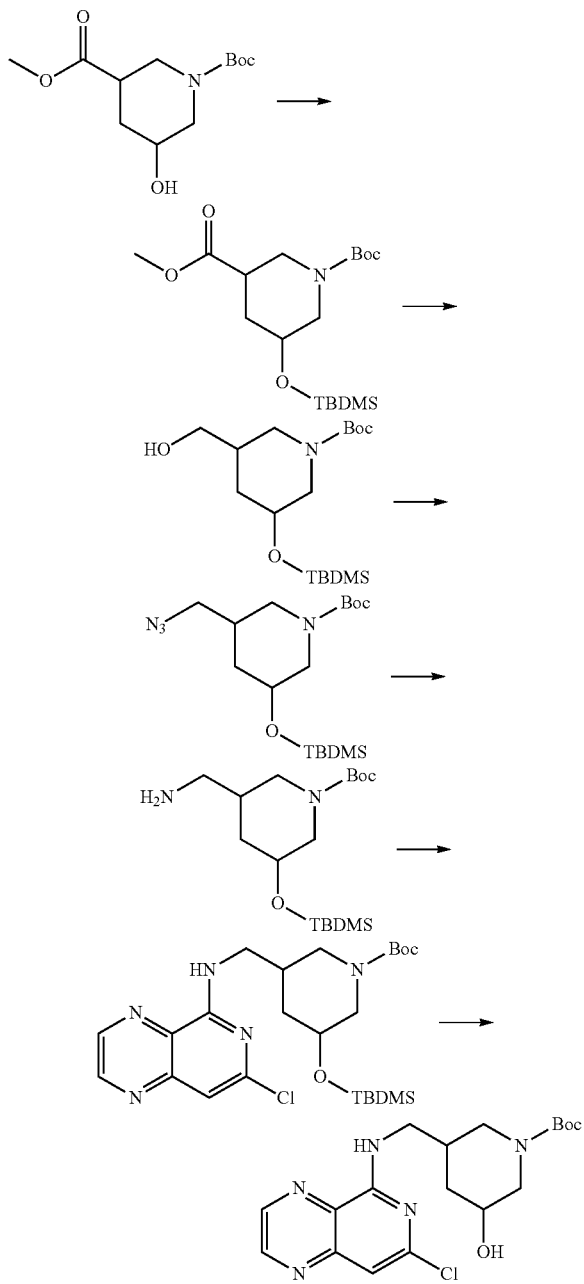

(A) 1-tert-butyl 3-methyl 5-(tert-butyldimethylsilyloxy)piperidine-1,3 dicarboxylate To a solution of 1-tert-butyl 3-methyl 5-hydroxypiperidine-1,3-dicarboxylate (4.00 g, 15.4 mmol) in dichloromethane (40 mL) was subsequently added imidazole (1.26 g, 18.5 mmol), DMAP (0.38 g, 3.1 mmol), and TBDMS-Cl (2.79 g, 18.5 mmol). The reaction was stirred at room temperature for 40 h. The mixture was washed with HCl solution (1N), saturated sodium bicarbonate, and brine sequentially and dried over anhydrous sodium sulfate, filtrated, and concentrated to give the title compound. MS (m/z): 274 (M-Boc+H)+.

(B) tert-butyl 3-(tert-butyldimethylsilyloxy)-5-(hydroxymethyl)piperidine-1-carboxylate A solution of 1-tert-butyl 3-methyl 5-(tert-butyldimethylsilyloxy)piperidine-1,3 from step A in THF (100 mL) was treated with LiBH4 (0.84 g, 38.5 mmol) at 0° C. stirring for 2 hours, warmed to room temperature, and then treated with citric acid (1M) till pH=4. The volatiles were removed in vacuo, and the residue was dissolved in ethyl acetate, washed with water and brine, dried over anhydrous sodium sulfate, filtered, and concentrated to give the title compound. MS (m/z): 246 (M-Boc+H)+.

(C) tert-butyl 3-(azidomethyl)-5-(tert-butyldimethylsilyloxy)piperidine-1-carboxylate To a solution of tert-butyl 3-(tert-butyldimethylsilyloxy)-5-(hydroxymethyl)piperidine-1-carboxylate from step B in dichloromethane (50 mL) was added triethylamine (4.67 g, 46.2 mmol) and methanesulfonyl chloride (2.65 g, 23.1 mmol) at 0° C. The reaction mixture was stirred at room temperature for 1.5 hours, then diluted with diethyl ether, washed with saturated sodium bicarbonate solution and brine, dried over anhydrous sodium sulfate, filtered, and concentrated in vacuo. The crude residue was dissolved in NMP. Sodium azide (3.00 g, 46.2 mmol) was added, and the resulting suspension was stirred at 80° C. overnight. The reaction mixture was diluted with EtOAc/hexane, washed with brine, then dried over anhydrous sodium sulfate, filtered, and concentrated to give the title compound. MS (m/z): 271 (M-Boc+H)+.

(D) tert-butyl 3-(aminomethyl)-5-(tert-butyldimethylsilyloxy)piperidine-1-carboxylate A solution of tert-butyl 3-(tert-butyldimethylsilyloxy)-5-((methylsulfonyloxy)methyl) piperidine-1-carboxylate from step C in EtOAc was hydrogenated under hydrogen atmosphere with 10% Pd/C (500 mg) overnight. The catalyst was removed by filtration, and the filtrate was concentrated under reduced pressure to give the title compound. MS (m/z): 345 (M+H)+.

(E) tert-butyl 3-(tert-butyldimethylsilyloxy)-5-((7-chloropyrido[4,3-b]pyrazin-5-ylamino)methyl)piperidine-1-carboxylate A solution of tert-butyl 3-(aminomethyl)-5-(tert-butyldimethylsilyloxy)piperidine-1-carboxylate (4.74 g, 13.7 mmol), 5,7-dichloropyrido[4,3-b]pyrazine (2.75 g, 13.7 mmol) and DIPEA (2.12 g, 16.4 mmol) in THF (20 mL) was stirred at room temperature for 48 hours. The volatiles were removed under reduced pressure and the residue was treated with ethyl acetate, washed with brine, dried over Na₂SO₄, filtered, and concentrated to give the title compound.

(F) tert-butyl 3-((7-chloropyrido[4,3-b]pyrazin-5-ylamino)methyl)-5-hydroxypiperidine-1-carboxylate A solution of tert-butyl 3-(tert-butyldimethylsilyloxy)-5-(7-chloropyrido[4,3-b]pyrazin-5-ylamino)methyl)piperidine-1-carboxylate from step E in THF (16 mL) was treated with TBAF (5.17 g, 16.4 mmol) at room temperature for 2 hours, then diluted with ethyl acetate, washed with brine, dried over Na₂SO₄, filtered, and concentrated. The residue was purified by chromatography to give the title compound. MS (m/z): 394 (M+H)⁺.

Intermediate 25 tert-butyl 3-((7-chloropyrido[4,3-b]pyrazin-5-ylamino)methyl)-5-fluoropiperidine-1-carboxylate

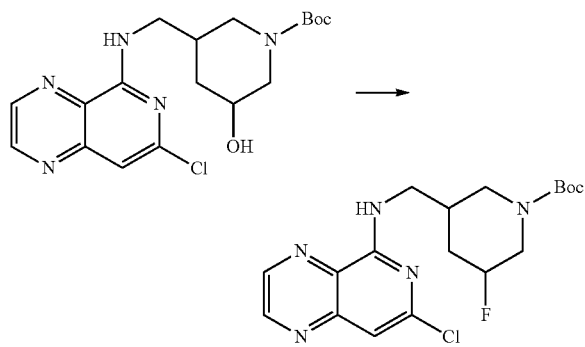

To a solution of tert-butyl 3-((7-chloropyrido[4,3-b]pyrazin-5-ylamino)methyl)-5-hydroxypiperidine-1-carboxylate (1.97 g, 5.0 mmol) in dichloromethane was added DAST (4.03 g, 25 mmol). The reaction mixture was stirred at room temperature for 2 hours, then diluted with ethyl acetate, washed with brine, dried over anhydrous sodium sulfate, filtered, and concentrated in vacuo. The crude residue was purified by chromatography to give the title compound. MS (m/z): 396 (M+H)⁺.

Intermediate 26 tert-butyl 5-((7-chloropyrido[4,3-b]pyrazin-5-ylamino)methyl)-3,3 difluoropiperidine-1-carboxylate

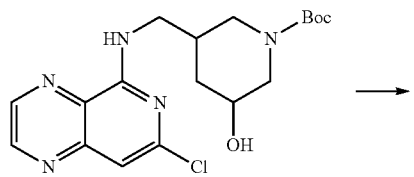

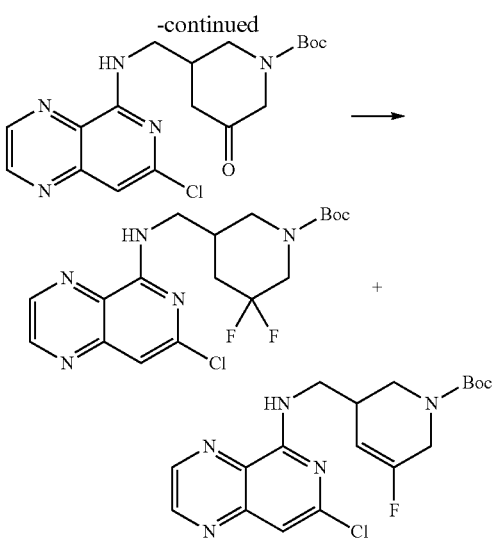

(A) tert-butyl 3-((7-chloropyrido[4,3-b]pyrazin-5-ylamino)methyl)-5-oxopiperidine-1-carboxylate To a solution of tert-butyl 3-((7-chloropyrido[4,3-b]pyrazin-5-ylamino)methyl)-5-hydroxypiperidine-1-carboxylate (1.97 g, 5.0 mmol) in dichloromethane was added Dess-Martin periodinane (2.54 g, 6.0 mmol) at room temperature. The reaction mixture was stirred at room temperature overnight, then diluted with ethyl acetate, washed with brine, dried over anhydrous sodium sulfate, filtered, and concentrated in vacuo to give the title compound.

(B) tert-butyl 5-((7-chloropyrido[4,3-b]pyrazin-5-ylamino)methyl)-3,3-difluoropiperidine-1-carboxylate To a solution of tert-butyl 3-((7-chloropyrido[4,3-b]pyrazin-5-ylamino)methyl)-5-oxopiperidine-1-carboxylate from step A in dichloromethane was added DAST (8.06 g, 50 mmol). The reaction mixture was stirred at room temperature for 2 hours, then was diluted with ethyl acetate, washed with brine, then dried over anhydrous sodium sulfate, filtered, and concentrated in vacuo. The crude residue was purified by chromatography to give the title compound (866 mg), MS (m/z): 414 (M+H)⁺.

Intermediate 27 tert-butyl 5-((7-chloropyrido[4,3-b]pyrazin-5-ylamino)methyl)-3-fluoro-5,6 dihydropyridine-1-(2H)-carboxylate

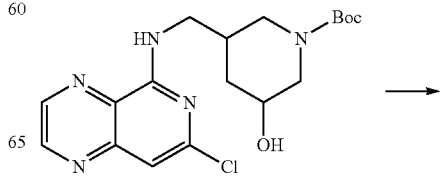

43

-continued

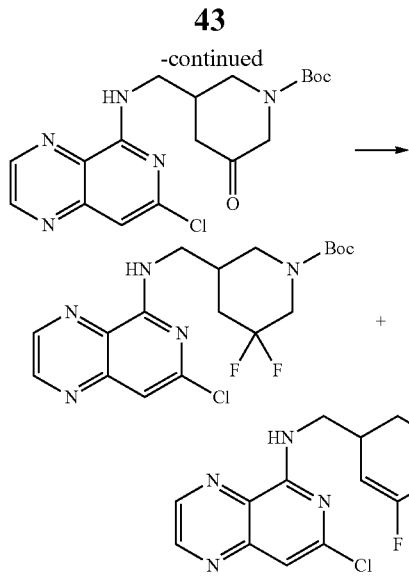

The title compound was obtained by the chromatographic purification of the crude residue from the reaction of Intermediate 26 (B) (214 mg), MS (m/z): 394 (M+H)$^+$.

Intermediate 28

(R)-1-(pyrrolidin-3-yl)urea

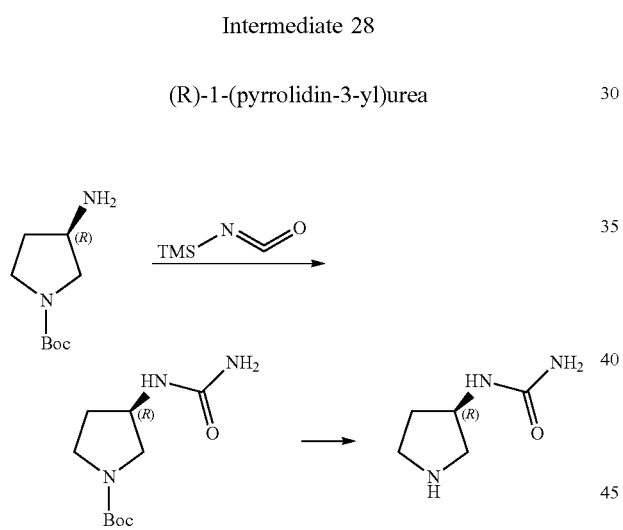

(A) (R)-tert-butyl 3-ureidopyrrolidine-1-carboxylate

To a solution of (R)-tert-butyl 3-aminopyrrolidine-1-carboxylate (180 mg, 1 mmol) in dichloromethane was added TMS-NCO (1 g, 8.7 mmol) and DIPEA (1.2 g, 10 mmol). The mixture was stirred at room temperature overnight, then was concentrated in vacuo. The residue was treated with EtOAc/H$_2$O, the organic layer was combined, washed with brine, dried over anhydrous sodium sulfate, filtered, and concentrated to give the crude title compound.

(B) (R)-1-(pyrrolidin-3-yl)urea (R)-tert-butyl 3-ureidopyrrolidine-1-carboxylate from step A was treated with HCl solution (in EtOAc, 30 mL) for 2 hours. The mixture was concentrated in vacuo to give the crude title compound. MS (m/z): 130 (M+H)$^+$.

44

Intermediate 29 tert-butyl 3-((7-chloropyrido[4,3-b]pyrazin-5-ylamino)methyl)-4,4 difluoropiperidine-1-carboxylate

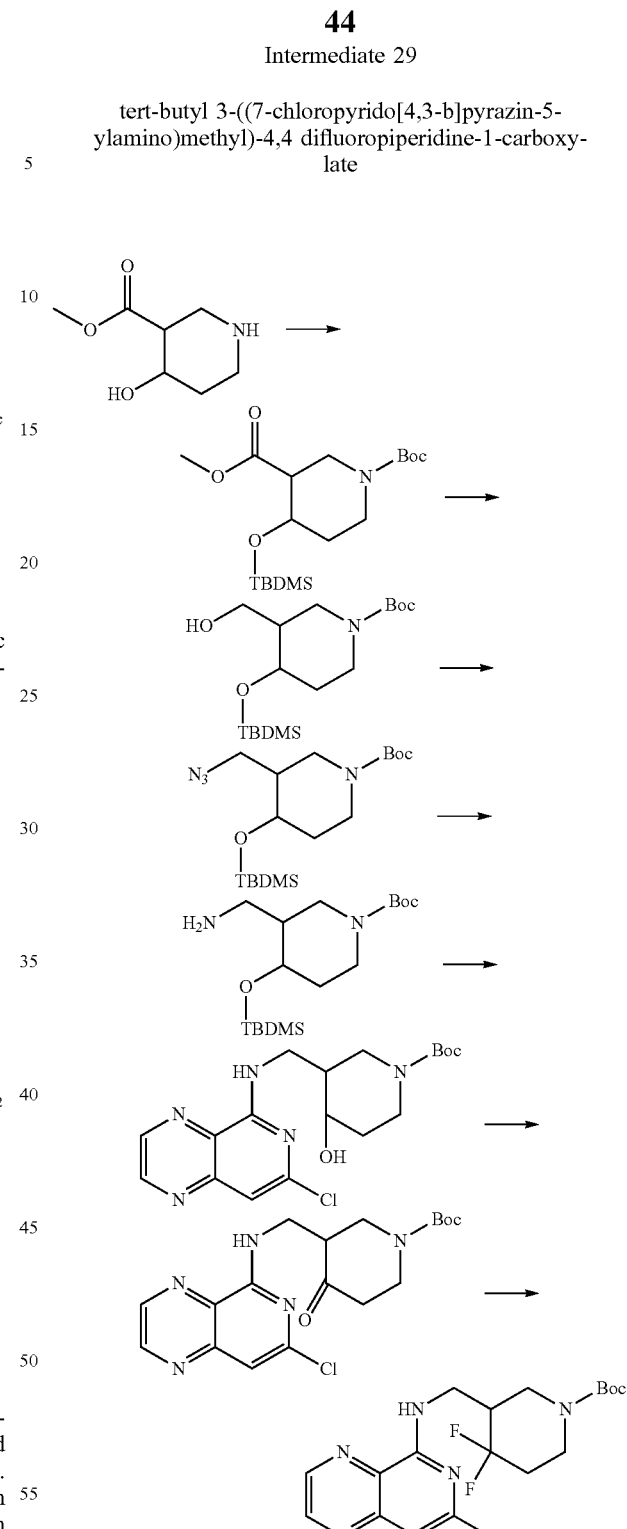

(A) 1-tert-butyl 3-methyl 4-(tert-butyldimethylsilyloxy)piperidine-1,3 dicarboxylate A mixture of methyl 4-hydroxypiperidine-3-carboxylate (3.18 g, 20 mmol), aqueous sodium hydrogen carbonate (30 mL, 1M), di-tert-butyl dicarbonate (4.37 g, 20 mmol) and dichloromethane (30 mL) was stirred for 15 hours. The phases were separated and dichloromethane phase was dried over anhydrous sodium sulfate and filtrated. The filtrate was diluted to 200 mL. To the resulted solution was added imidazole (1.64 g, 24 mmol), DMAP (0.488 g, 4 mmol), and TBDMSCl (3.62 g, 24 mmol) sequentially. The reaction mixture was stirred at room temperature for 40 hours. The mixture was washed with 1N HCl solution, NaHCO$_3$ solution and brine sequentially and dried over anhydrous sodium sulfate. Filtration and concentration gave the crude compound which was used directly in the next step. MS (m/z): 274 (M-Boc+H)$^+$.

(B) tert-butyl 4-(tert-butyldimethylsilyloxy)-3-(hydroxymethyl)piperidine-1-carboxylate A solution of 1-tert-butyl 3-methyl 4-(tert-butyldimethylsilyloxy)piperidine-1,3 dicarboxylate from step A in THF (100 mL) was cooled at 0° C. and then LiBH$_4$ (1.10 g, 50 mmol) was added in. After stirring for 2 hours as the solution was warmed to room temperature, the pH value was adjusted to 4 with 1M citric acid. After removal of the volatiles in vacuo, the product was extracted in ethyl acetate, washed with water and brine, dried over anhydrous sodium sulfate. Upon filtering and removal of the volatiles in vacuo, tert-butyl 4-(tert-butyldimethylsilyloxy)-3 (hydroxymethyl)piperidine-1-carboxylate was obtained (8.82 g, 100% yield), which was used directly in the next step. MS (m/z): 246 (M-Boc+H)$^+$.

(C) tert-butyl 3-(azidomethyl)-4-(tert-butyldimethylsilyloxy)piperidine-1-carboxylate To a solution of tert-butyl 4-(tert-butyldimethylsilyloxy)-3-(hydroxymethyl)piperidine-1-carboxylate from step B in dichloromethane (50 mL) was added triethylamine (6.06 g, 60 mmol) and methanesulfonyl chloride (3.43 g, 30 mmol) at 0° C. The reaction mixture was allowed to stir at room temperature for 1.5 hours. The crude mixture was diluted with diethyl ether, washed with sat. aq. sodium bicarbonate, brine, then dried over anhydrous sodium sulfate, filtered, and concentrated in vacuo. The crude residue was dissolved in NMP (30 mL). Sodium azide (3.90 g, 60 mmol) was added in and the resulting suspension was stirred at 80° C. overnight. The reaction mixture was diluted with EtOAc and hexanes, washed with water, brine, then dried over anhydrous sodium sulfate, filtered, concentrated to give the crude compound. MS (m/z): 271 (M-Boc+H)$^+$.

(D) tert-butyl 3-(aminomethyl)-4-(tert-butyldimethylsilyloxy)piperidine-1-carboxylate The solution of tert-butyl 3-(azidomethyl)-4-(tert-butyldimethylsilyloxy)piperidine-1-carboxylate in ethyl acetate from step C was hydrogenated under hydrogen atmosphere with 10% Pd/C (500 mg) overnight. The catalyst was filtered and the filtrate was concentrated under reduced pressure to give the title compound (6.2 g, 90% yield). MS (m/z): 345 (M+H)$^+$.

(E) tert-butyl 3-((7-chloropyrido[4,3-b]pyrazin-5-ylamino)methyl)-4-hydroxypiperidine-1-carboxylate 5,7-dichloropyrido[4,3-b]pyrazine (3.6 g, 18 mmol) and DIPEA (2.8 g, 21.6 mmol) was added to a solution of tert-butyl tert-butyl 3-(aminomethyl)-4-(tert-butyldimethylsilyloxy)piperidine-1-carboxylate (6.2 g, 18 mmol) in THF (20 mL) and the mixture was refluxed overnight. The volatile components were evaporated and the residue was extracted with ethyl acetate. Ethyl acetate was washed with brine and dried. The solvent was removed and the residue was re-dissolved in THF (16 mL) and TBAF was added in. The reaction mixture was stirred at room temperature for 2 hours. The mixture was diluted with ethyl acetate, washed with brine, then dried, filtered, and concentrated in vacuo. The crude residue was purified by flash chromatography to give the title compound (3.35 g, 47% yield). MS (m/z): 394 (M+H)$^+$.

(F) tert-butyl 3-((7-chloropyrido[4,3-b]pyrazin-5-ylamino)methyl)-4-oxopiperidine-1-carboxylate To a solution of tert-butyl 3-((7-chloropyrido[4,3-b]pyrazin-5-ylamino)methyl)-5-hydroxypiperidine-1-carboxylate (3.35 g, 8.5 mmol) in dichloromethane (50 mL) was added Dess-Martin periodinane (4.33 g, 10.2 mmol) at room temperature. The reaction mixture was stirred at that temperature overnight. The mixture was diluted with ethyl acetate, washed with brine, then dried over anhydrous sodium sulfate, filtered, and concentrated in vacuo. The residue was used directly in the next step. MS (m/z): 392 (M+H)$^+$.

(G) tert-butyl 3-((7-chloropyrido[4,3-b]pyrazin-5-ylamino)methyl)-4,4-difluoropiperidine-1-carboxylate To a solution of tert-butyl 3-((7-chloropyrido[4,3-b]pyrazin-5-ylamino)methyl)-4-oxopiperidine-1-carboxylate from step F in dichloromethane (30 mL) was added DAST (13.7 g, 85 mmol). The reaction mixture was stirred at room temperature for 2 hours. The mixture was diluted with ethyl acetate, washed with brine, then dried over anhydrous sodium sulfate, filtered, and concentrated in vacuo. The crude residue was purified by flash chromatography (ethyl acetate/petro ether) to give the title compound (497 mg, 14% yield). MS (m/z): 414 (M+H)$^+$.

Intermediate 30 and 31

(S)-tert-butyl 3-((7-chloropyrido[4,3-b]pyrazin-5-ylamino)methyl)-4,4-difluoropiperidine-1-carboxylate and (R)-tert-butyl 3-((7-chloropyrido[4,3-b]pyrazin-5-ylamino)methyl)-4,4-difluoropiperidine-1-carboxylate

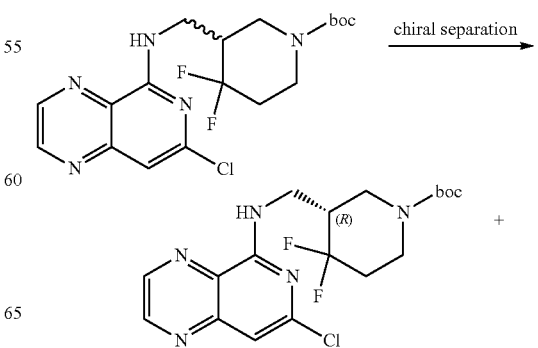

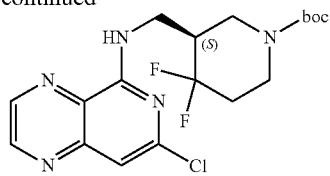

The racemic intermediate 29 was resolved by chiral HPLC to provide the optically pure enantiomers Intermediate 30 and 31 (HPLC conditions: column: CHIRALCEL AD-H 0.46×15 cm; mobile phase: $CO_2$/MeOH=85/15; flow rate=2 mL/min; detector: UV 254 nm). The first eluent (intermediate 30, Rf=6.79 min) was 98% ee, MS (m/z): 414 $(M+H)^+$. and the second eluent (intermediate 31, Rf=7.06 min) was 98.7% ee, MS (m/z): 414 $(M+H)^+$.

Intermediate 32

2-(tetrahydro-2H-pyran-4-yloxy)-5-(4,4,5,5-tetramethyl-1,3,2-dioxaborolan-2-yl)pyridine

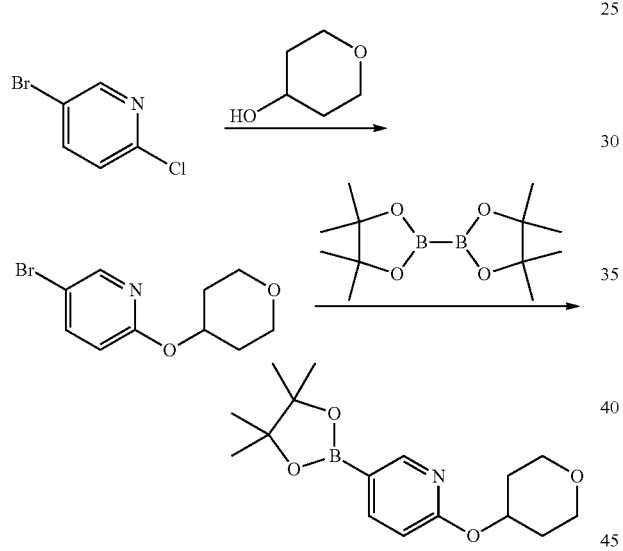

(A) 5-bromo-2-(tetrahydro-2H-pyran-4-yloxy)pyridine tetrahydro-2H-pyran-4-ol (850 mg, 8.32 mmol) was dissolved in DMF (10 mL), cooled to 0° C., NaH (500 mg, 10.4 mmol) was added and stirred for 45 minutes at room temperature, then 5-bromo-2-chloropyridine (2 g, 10.4 mmol) was added and the mixture was stirred overnight at 60° C. The mixture was poured into water, extracted by EA, the organic layer was washed by brine, dried over $Na_2SO_4$, concentrated and purified by flash chromatography, gave 1.7 g white solid. MS: (m/z): 258 $(M-H)^+$, 260 $(M+H)^+$ (B) 2-(tetrahydro-2H-pyran-4-yloxy)-5-(4,4,5,5-tetramethyl-1,3,2-dioxaborolan-2-yl)pyridine 5-bromo-2-(tetrahydro-2H-pyran-4-yloxy)pyridine (500 mg, 1.93 mmol) and 4,4,4',4',5,5,5',5'-octamethyl-2,2'-bi(1,3,2-dioxaborolane) (600 mg, 2.32 mmol) were dissolved in dioxane (100 mL), $Cs_2CO_3$ (941 mg, 2.90 mmol) and dppf($PdCl_2$) (10 mg) were added in, then the mixture was charged with $N_2$, stirred at 80° C. overnight. The solvent was removed in vacuum and the residue was used directly in the next step. MS (m/z): 306 $(M+H)^+$ Intermediate 33

6-((tetrahydro-2H-pyran-4-yl)methoxy)pyridin-3-ylboronic acid

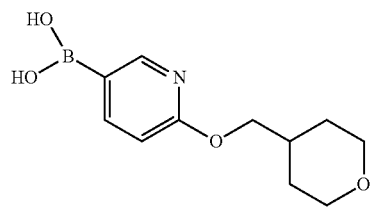 [SMILES: OB(O)c1ccc(OCC2CCOCC2)nc1]

The title compound was prepared according to the procedures of Intermediate 32 using 5-bromo-2-chloropyridine. MS (m/z): 238 $(M+H)^+$ Intermediate 34

4-(2-(5-(4,4,5,5-tetramethyl-1,3,2-dioxaborolan-2-yl)pyridin-2-yloxy)ethyl)morpholine

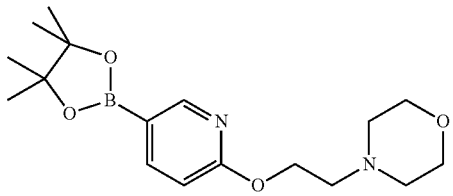 [SMILES: CC1(C)OB(c2ccc(OCCN3CCOCC3)nc2)OC1(C)C]

The title compound was prepared according to the procedures of Intermediate 32 using 5-bromo-2-chloropyridine.

Intermediate 35

6-(3-hydroxypyrrolidin-1-yl)pyridin-3-ylboronic acid

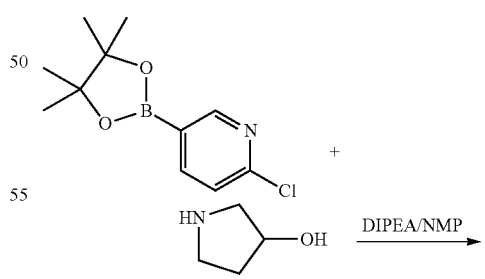

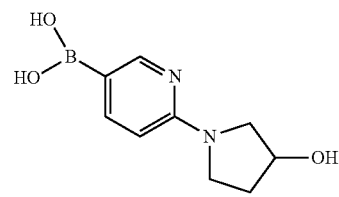

6-(3-hydroxypyrrolidin-1-yl)pyridin-3-ylboronic acid

To a solution of 2-chloro-5-(4,4,5,5-tetramethyl-1,3,2-dioxaborolan-2-yl)pyridine (239 mg, 1 mmol) in NMP (2 mL) was added pyrrolidin-3-ol (174 mg, 2 mmol) and DIPEA (500 uL, 3 mmol), then the mixture was sealed in a microwave tube and heated in microwave reactor at 180° C. for 1.5 hours. TLC and LC-Ms showed the reaction had completed and the desired compound was detected. The reaction mixture was poured into 30 mL of H$_2$O, and extracted with n-BuOH, washed with water and brine, concentrated and purified on TLC(CH$_2$Cl$_2$:MeOH=10:1) to give a white solid. MS (m/z): 209 (M+H)$^+$ Intermediate 36

2-methyl-5-(5-(4,4,5,5-tetramethyl-1,3,2-dioxaborolan-2-yl)pyridin-2-yl)-octahydropyrrolo[3,4-c]pyrrole

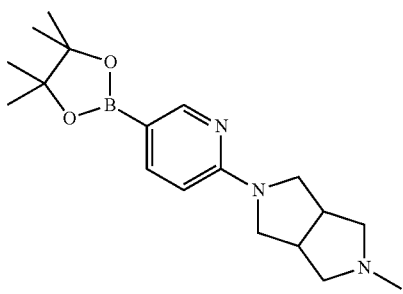

The title compound was prepared according to the procedures of Intermediate 35 using 2-chloro-5-(4,4,5,5-tetramethyl-1,3,2-dioxaborolan-2-yl)pyridine. MS (m/z): 248 (M+H)$^+$ Intermediate 37

6-((2S,6R)-2,6-dimethylmorpholino)pyridin-3-ylboronic acid

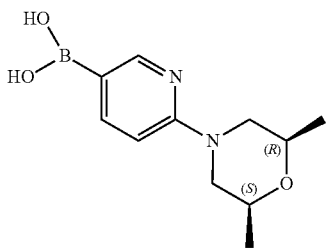

The title compound was prepared according to the procedures of Intermediate 35 using 2-chloro-5-(4,4,5,5-tetramethyl-1,3,2-dioxaborolan-2-yl)pyridine. MS (m/z): 237 (M+H)$^+$ Intermediate 38

N-methyl-N-(tetrahydro-2H-pyran-4-yl)-5-(4,4,5,5-tetramethyl-1,3,2 dioxaborolan-2-yl)pyridin-2-amine

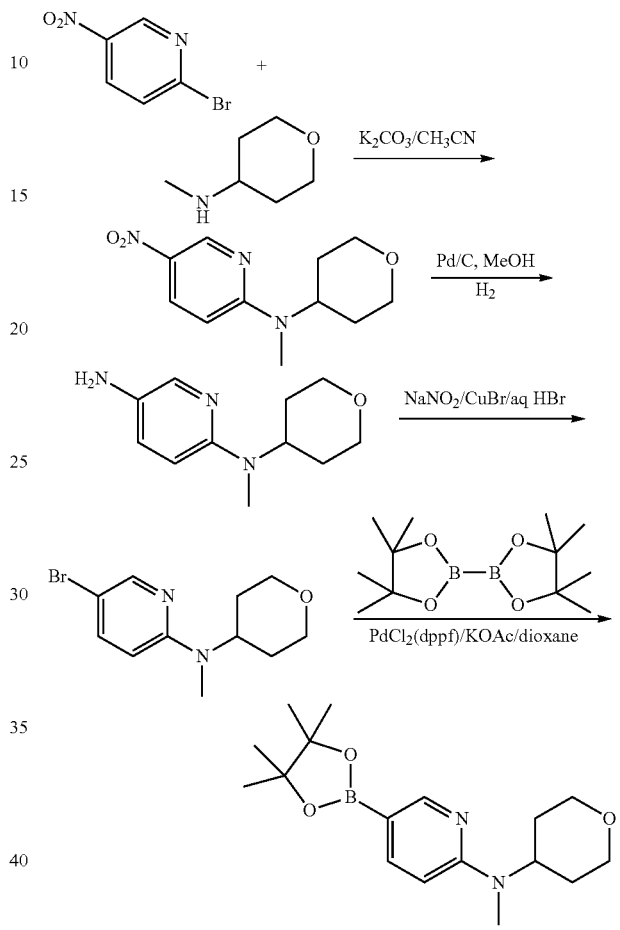

(A) N-methyl-5-nitro-N-(tetrahydro-2H-pyran-4-yl)pyridin-2-amine

To a solution of N-methyltetrahydro-2H-pyran-4-amine (172.5 mg, 1.5 mmol) in CH$_3$CN (5 mL) was added K$_2$CO$_3$ (207 mg, 1.5 mmol) and 2-bromo-5-nitropyridine (203 mg, 1 mmol). The reaction was stirred at 80° C. for 16 hours. TLC and LC-Ms showed the reaction had completed and the reaction was poured into water, extracted with EA, washed with water and brine, dried and concentrated to give a yellow solid. MS (m/z): 238 (M+H)$^+$ (B) N$^2$-methyl-N$^2$-(tetrahydro-2H-pyran-4-yl)pyridine-2,5-diamine To a solution of N-methyl-5-nitro-N-(tetrahydro-2H-pyran-4-yl)pyridin-2-amine (217 mg, 0.92 mmol) in MeOH (30 mL) was added Pd/C (0.5 g). The mixture was stirred for 3 hours at 20° C. under 1 atm. H$_2$. The reaction was filtered and concentrated to give dark red oil. MS (m/z): 208 (M+H)$^+$

(C) 5-bromo-N-methyl-N-(tetrahydro-2H-pyran-4-yl)pyridin-2-amine

To a solution of $N^2$-methyl-$N^2$-(tetrahydro-2H-pyran-4-yl)pyridine-2,5-diamine (150 mg, 0.73 mmol) in 2 mL of aq HBr was added a solution of $NaNO_2$ (55 mg, 0.80 mmol) in 1 mL of $H_2O$ at 0° C. Then the mixture was stirred at 0° C. for 40 minutes. After that, the mixture was poured into a solution of CuBr (220 mg, 1.53 mmol) in 2 mL aq HBr at 0° C., the reaction was heated to 60° C. and stirred for 2 hours. After cooling, the mixture was based with 2M NaOH to pH=8-9 and extracted with EA, washed with $H_2O$ and brine, dried and concentrated, purified on TLC (EA:PE=1:1) to give white solid. MS (m/z): 273 (M+H)$^+$

(D) N-methyl-N-(tetrahydro-2H-pyran-4-yl)-5-(4,4,5,5-tetramethyl-1,3,2-dioxaborolan-2-yl)pyridin-2-amine To a solution of 5-bromo-N-methyl-N-(tetrahydro-2H-pyran-4-yl)pyridin-2-amine (125 mg, 0.46 mmol) in dioxane (5 mL) was added KOAc (135 mg, 1.38 mmol), Pd Cl$_2$(dppf) (50.5 mg, 0.069 mmol) and 4,4,4',4',5,5,5',5'-octamethyl-2,2'-bi(1,3,2-dioxaborolane) (234 mg, 0.92 mmol). The mixture was stirred at 80° C. overnight. The reaction was filtered and concentrated to give crude product. The crude product was purified on TLC (EA:PE=1:1) to give white solid. MS (m/z): 319 (M+H)$^+$

Intermediate 39

2-methyl-1-(4-(4,4,5,5-tetramethyl-1,3,2-dioxaborolan-2-yl)phenoxy)propan-2-ol

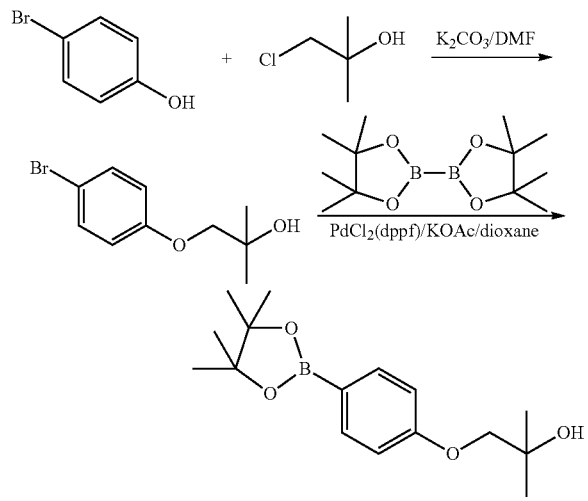

(A) 1-(4-bromophenoxy)-2-methylpropan-2-ol

To a solution of 1-chloro-2-methylpropan-2-ol (434.4 mg, 4 mmol) in DMF (10 mL) was added $K_2CO_3$ (552 mg, 4 mmol) and 4-bromophenol (346 mg, 2 mmol), the reaction was stirred at 140° C. for 48 hours. About of 10% 4-bromophenol was remained and the reaction was poured into 30 mL of water, extracted with EA (20 mL×3), washed with 30 mL of water and brine, concentrated and purified on TLC (EA:PE=1:3) to give yellow solid. MS (m/z): 196 (M−50)$^+$

(B) 2-methyl-1-(4-(4,4,5,5-tetramethyl-1,3,2-dioxaborolan-2-yl)phenoxy) propan-2-ol To a solution of 1-(4-bromophenoxy)-2-methylpropan-2-ol (437 mg, 1.78 mmol) in dioxane (15 mL) was added KOAc (526 mg, 5.35 mmol), PdCl$_2$(dppf) (196 mg, 0.27 mmol) and 4,4,4',4',5,5,5',5'-octamethyl-2,2'-bi(1,3,2-dioxaborolane) (906 mg, 3.57 mmol). The mixture was stirred at 100° C. overnight. The reaction was filtered and concentrated to give crude product. The crude product was purified on TLC (EA:PE=1:4) to give white solid. MS (m/z): 292 (M)$^+$

Intermediate 40

N-methyl-N-(1-(4-(4,4,5,5-tetramethyl-1,3,2-dioxaborolan-2-yl)phenyl)piperidin-4-yl)acetamide

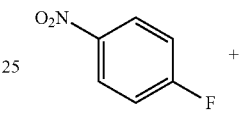

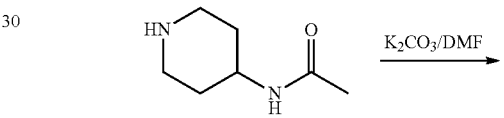

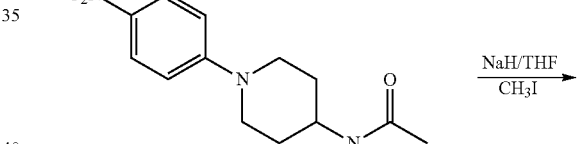

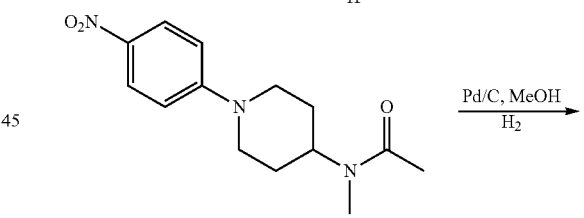

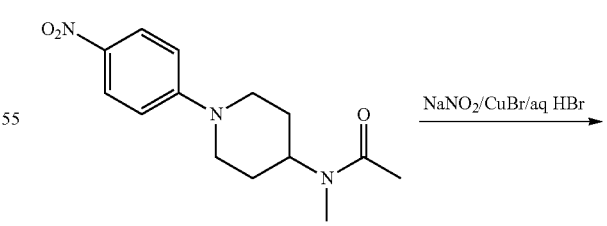

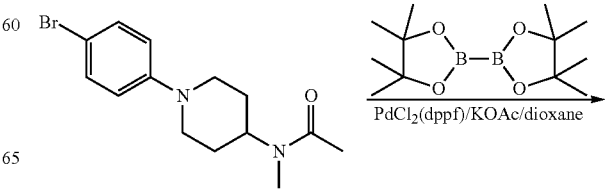

-continued

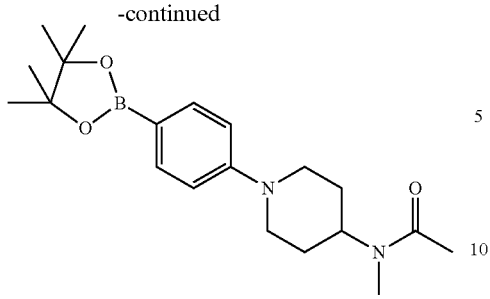

(A) N-(1-(4-nitrophenyl)piperidin-4-yl)acetamide

To a solution of N-(piperidin-4-yl)acetamide (341 mg, 2.4 mmol) in DMF (15 mL) was added $K_2CO_3$ (331 mg, 2.4 mmol) and 1-fluoro-4-nitrobenzene (282 mg, 2 mmol) at room temperature. The reaction was stirred at 80° C. for 24 hours. After that, the reaction was poured into 50 mL of water and extracted with EA (3×25 mL), washed with $H_2O$ (25 mL) and brine (25 mL), dried over $Na_2SO_4$ and concentrated to give yellow solid. MS (m/z): 264 (M+H)$^+$

(B) N-methyl-N-(1-(4-nitrophenyl)piperidin-4-yl)acetamide

To a solution of N-(1-(4-nitrophenyl)piperidin-4-yl)acetamide (568 mg, 2 mmol) in THF (15 mL) was added NaH (60%, 200 mg, 5 mmol) at room temperature. The reaction was stirred at 20° C. for 15 minutes. After that, iodomethane (300 mg, 4 mmol) was dropped into the reaction and stirred at 60° C. for 18 hours. The reaction was treated with sat. $NH_4Cl$ solution and extracted with n-BuOH, washed with brine, dried over $Na_2SO_4$ and concentrated to give yellow solid. MS (m/z): 278 (M+H)$^+$

(C) N-(1-(4-aminophenyl)piperidin-4-yl)-N-methylacetamide

To a solution of N-methyl-N-(1-(4-nitrophenyl)piperidin-4-yl)acetamide (2 mmol) in MeOH (30 mL) was added Pd/C (0.5 g), then the mixture was stirred for 4 hours at 20° C. under 1 atm. $H_2$. The reaction was filtered and concentrated to give gray yellow oil. MS (m/z): 248 (M+H)$^+$

(D) N-(1-(4-bromophenyl)piperidin-4-yl)-N-methylacetamide

To a solution of N-(1-(4-aminophenyl)piperidin-4-yl)-N-methylacetamide (479.7 mg, 1.94 mmol) in 6 mL of aq HBr was added a solution of $NaNO_2$ (147 mg, 2.13 mmol) in 2 mL of $H_2O$ at 0° C., then the mixture was stirred at 0° C. for 40 minutes. After that, the mixture was poured into a solution of CuBr (584 mg, 4.07 mmol) in 6 mL aq HBr at 0° C., the reaction was heated to 60° C. and stirred for 2 hours. After cooling, the mixture was based with 2M NaOH to pH=8-9 and extracted with EA, washed with $H_2O$ and brine, dried and concentrated to give black solid. MS (m/z): 313 (M+H)$^+$

(E) N-methyl-N-(1-(4-(4,4,5,5-tetramethyl-1,3,2-dioxaborolan-2-yl)phenyl) piperidin-4-yl)acetamide To a solution of N-(1-(4-bromophenyl)piperidin-4-yl)-N-methylacetamide (~40%, 160 mg, 0.63 mmol) in dioxane (15 mL) was added KOAc (185 mg, 1.89 mmol), $PdCl_2$(dppf) (69 mg, 0.095 mmol) and 4,4,4',4',5,5,5',5'-octamethyl-2,2'-bi(1,3,2-dioxaborolane) (320 mg, 1.26 mmol). The mixture was stirred at 110° C. overnight. The reaction was filtered and concentrated to give crude product. The crude product was purified on TLC($CH_2Cl_2$:MeOH=50:1) to give white solid. MS (m/z): 359 (M+H)$^+$ Intermediate 41

1-(2-fluoro-4-(4,4,5,5-tetramethyl-1,3,2-dioxaborolan-2-yl)phenyl)piperazine

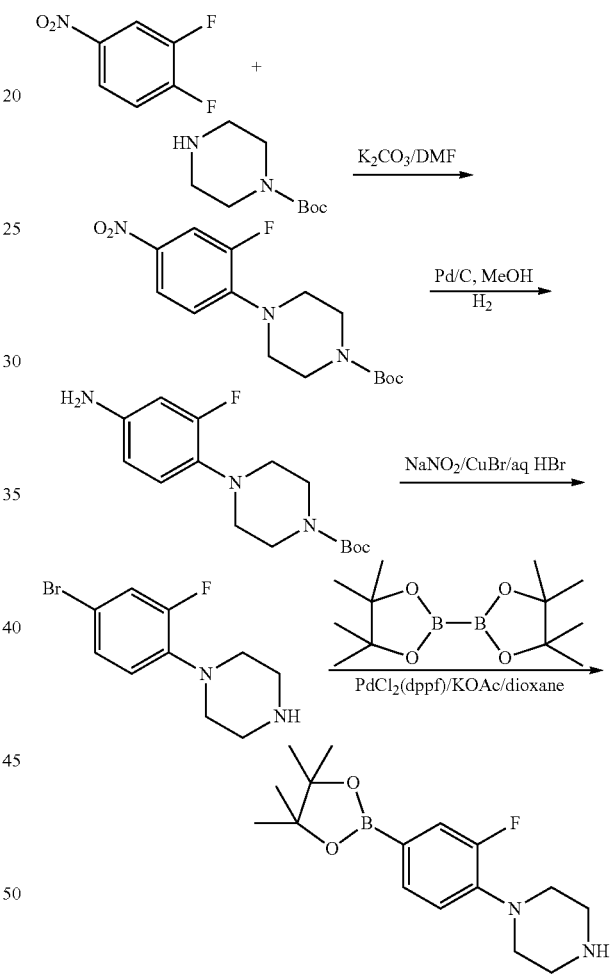

(A) tert-butyl 4-(2-fluoro-4-nitrophenyl)piperazine-1-carboxylate

To a solution of tert-butyl piperazine-1-carboxylate (1120 mg, 6 mmol) in DMF (25 mL) was added $K_2CO_3$ (828 mg, 6 mmol) and 1,2-difluoro-4-nitrobenzene (795 mg, 5 mmol) at room temperature. The reaction was stirred at 80° C. for 24 hours. After that, the reaction was poured into 50 mL of water and extracted with EA (3×25 mL), washed with $H_2O$ (25 mL) and brine (25 mL), dried over $Na_2SO_4$ and concentrated to give yellow solid. MS (m/z): 226 (M−99)$^+$

(B) tert-butyl 4-(4-amino-2-fluorophenyl)piperazine-1-carboxylate

To a solution of tert-butyl 4-(2-fluoro-4-nitrophenyl)piperazine-1-carboxylate (5 mmol) in MeOH (30 mL) was added Pd/C (1 g), then the mixture was stirred for 18 hours at 20° C. under 1 atm. $H_2$. The reaction was filtered and concentrated to give gray yellow oil. MS (m/z): 296 $(M+H)^+$

(C) 1-(4-bromo-2-fluorophenyl)piperazine

To a solution of tert-butyl 4-(4-amino-2-fluorophenyl)piperazine-1-carboxylate (885 mg, 3 mmol) in 8 mL of aq HBr was added a solution of $NaNO_2$ (228 mg, 3.3 mmol) in 2 mL of $H_2O$ at 0° C., then the mixture was stirred at 0° C. for 40 minutes. After that, the mixture was poured into a solution of CuBr (905 mg, 6.3 mmol) in 8 mL aq HBr at 0° C. The reaction was heated to 60° C. and stirred for 2 hours. After cooling, the mixture was based with 2M NaOH to pH=8-9 and extracted with EA, washed with $H_2O$ and brine, dried and concentrated to give black solid. MS (m/z): 261 $(M+H)^+$

(D) 1-(2-fluoro-4-(4,4,5,5-tetramethyl-1,3,2-dioxaborolan-2-yl)phenyl)piperazine To a solution of 1-(4-bromo-2-fluorophenyl)piperazine (309 mg, 1.2 mmol) in dioxane (15 mL) was added KOAc (353 mg, 3.6 mmol), $PdCl_2(dppf)$ (132 mg, 0.18 mmol) and 4,4,4',4',5,5,5',5'-octamethyl-2,2'-bi(1,3,2-dioxaborolane) (610 mg, 2.4 mmol). The mixture was stirred at 80° C. overnight. The reaction was filtered and concentrated to give crude product. The crude product was purified on TLC ($CH_2Cl_2$:MeOH=20:1) to give black solid. MS (m/z): 307 $(M+H)^+$

Intermediate 42

2-methyl-4-(4-(4,4,5,5-tetramethyl-1,3,2-dioxaborolan-2-yl)phenyl)morpholine

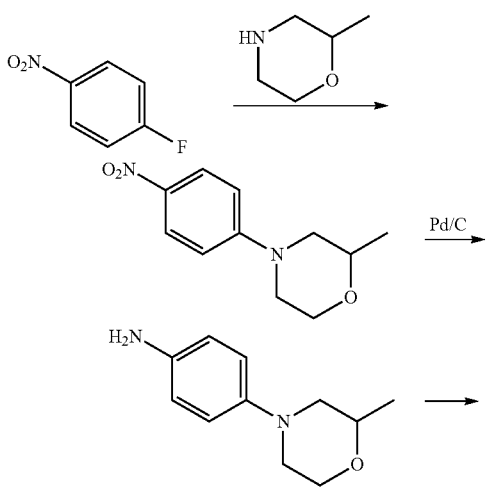

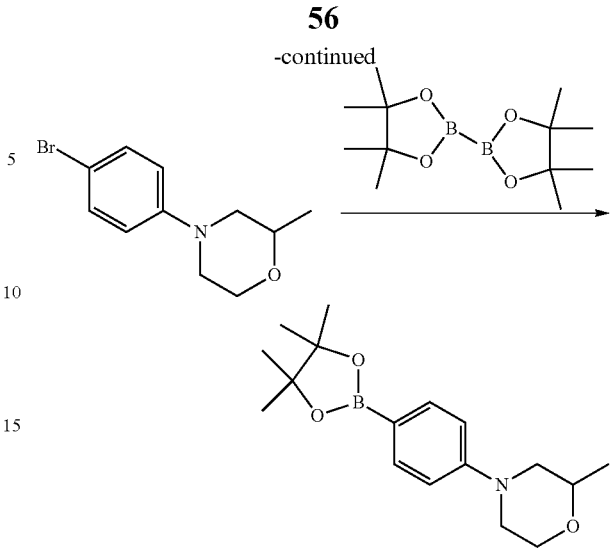

(A) 4-(2-methylmorpholino)aniline

To a mixture of 1-fluoro-4-nitrobenzene (5.64 g, 40.0 mmol) and potassium carbonate (11.1 g, 80.0 mmol) in DMSO (30 mL) was added 2-methylmorpholine (4.05 g, 40.0 mmol), then the mixture was heated at 100° C. for 4 hours. This solution was poured on to water (300 mL) and extracted with EA (3×100 mL). The combined organic phase was washed with brine and dried. Filtered and Pd/C (1.0 g) was added to the filtrate, charged with $H_2$, and stirred at room temperature overnight. The catalyst was filtered and the filtrate was concentrated to give product as a light red solid. MS (m/z): 193 $(M+H)^+$.

(B) 4-(4-bromophenyl)-2-methylmorpholine

To a solution of 4-(2-methylmorpholino)aniline (7.21 g, 37.5 mmol) in 100 mL HBr in water (40%), a solution of $NaNO_2$ (2.59 g, 37.5 mmol) in 15 mL water was added slowly at −10° C.~0° C. The mixture was stirred for 30 minutes and was added dropwise to a solution of CuBr (2.96 g, 20.6 mmol) in 30 mL HBr in water (40%). The resulting mixture was stirred and heated at 60° C. for 2 hours. Then the reaction solution was adjusted by 2N NaOH solution to pH>7. Extracted by EA, the combined organic phase was washed with brine, dried and concentrated to give crude product as black oil. MS (m/z): 256 $(M+H)^+$; 258 $(M+3)^+$.

(C) 2-methyl-4-(4-(4,4,5,5-tetramethyl-1,3,2-dioxaborolan-2-yl)phenyl)morpholine A solution of 4-(4-bromophenyl)-2-methylmorpholine (8.0 g, <31 mmol), 4,4,4',4',5,5,5',5'-octamethyl-2,2'-bi(1,3,2-dioxaborolane) (10.3 g, 40.6 mmol), [1,1'-Bis(diphenylphosphino)ferrocene]palladium(II) chloride (2.26 g, 3.1 mmol) and potassium acetate (4.6 g, 46.5 mmol) in DMSO (80 mmol) was heated at 70° C. under $N_2$ for 4 hours. After cooling the reaction was partitioned at EA and water. The combined organic phase was dried and concentrated. Purification over silica gel chromatography, eluting with EA/PE=5/1, to give product as a light yellow solid. MS (m/z): 304 $(M+H)^+$.

Intermediate 43

4-(2-fluoro-4-(4,4,5,5-tetramethyl-1,3,2-dioxaborolan-2-yl)phenyl)-2-methylmorpholine

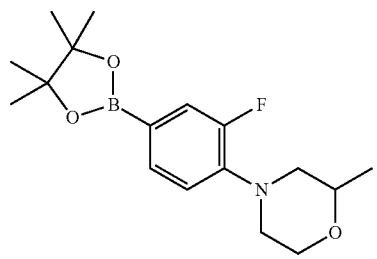

The title compound was prepared according to the procedures of Intermediate 42 using 1,2-difluoro-4-nitrobenzene. MS (m/z): 322 (M+H)+.

Intermediate 44

1-(4-(2-fluoro-4-(4,4,5,5-tetramethyl-1,3,2-dioxaborolan-2-yl)phenyl)piperazin-1-yl)ethanone

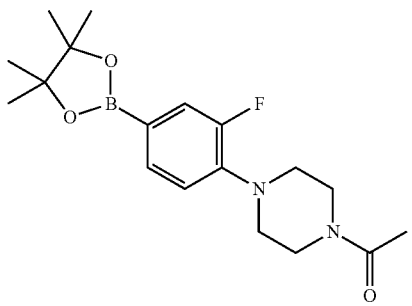 [SMILES: CC(=O)N1CCN(c2ccc(B3OC(C)(C)C(C)(C)O3)cc2F)CC1]

The title compound was prepared according to the procedures of Intermediate 42 using 1,2-difluoro-4-nitrobenzene. MS (m/z): 349 (M+H)+.

Intermediate 45

1-(ethylsulfonyl)-4-(2-fluoro-4-(4,4,5,5-tetramethyl-1,3,2-dioxaborolan-2-yl)phenyl)piperazine

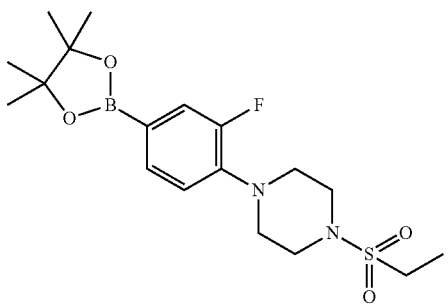 [SMILES: CCS(=O)(=O)N1CCN(c2ccc(B3OC(C)(C)C(C)(C)O3)cc2F)CC1]

The title compound was prepared according to the procedures of Intermediate 42 using 1,2-difluoro-4-nitrobenzene. MS (m/z): 399 (M+H)+.

Intermediate 46

(2S,6R)-4-(2-fluoro-4-(4,4,5,5-tetramethyl-1,3,2-dioxaborolan-2-yl)phenyl)-2,6-dimethylmorpholine

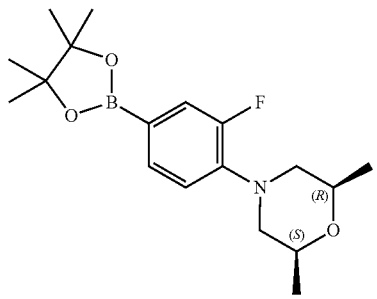

The title compound was prepared according to the procedures of Intermediate 42 using 1,2-difluoro-4-nitrobenzene. MS (m/z): 336 (M+H)+.

Intermediate 47

1-(4-(4,4,5,5-tetramethyl-1,3,2-dioxaborolan-2-yl)phenyl)-1H-imidazole

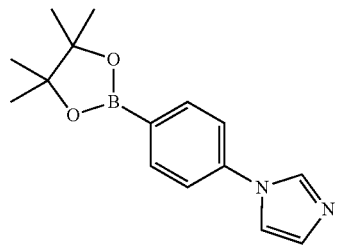 [SMILES: CC1(C)OB(c2ccc(-n3ccnc3)cc2)OC1(C)C]

The title compound was prepared according to the procedures of Intermediate 42 using 1-fluoro-4-nitrobenzene. MS (m/z): 271 (M+H)+.

Intermediate 48

N-methyl-N-(4-(4,4,5,5-tetramethyl-1,3,2-dioxaborolan-2-yl)phenyl)-tetrahydro-2H-pyran-4-amine

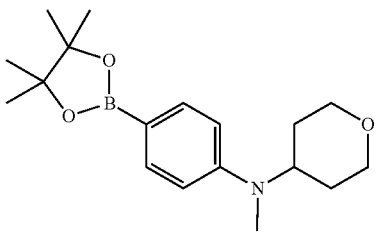 [SMILES: CN(c1ccc(B2OC(C)(C)C(C)(C)O2)cc1)C1CCOCC1]

The title compound was prepared according to the procedures of Intermediate 42 using 1-fluoro-4-nitrobenzene. MS (m/z): 318 (M+H)⁺.

Intermediate 49

1-(2-fluoro-4-(4,4,5,5-tetramethyl-1,3,2-dioxaborolan-2-yl)phenyl)-4-methylpiperazine

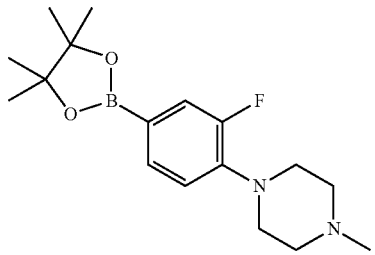

The title compound was prepared according to the procedures of Intermediate 42 using 1,2-difluoro-4-nitrobenzene.

Intermediate 50

4-(4-(4,4,5,5-tetramethyl-1,3,2-dioxaborolan-2-yl)phenylsulfonyl)morpholine

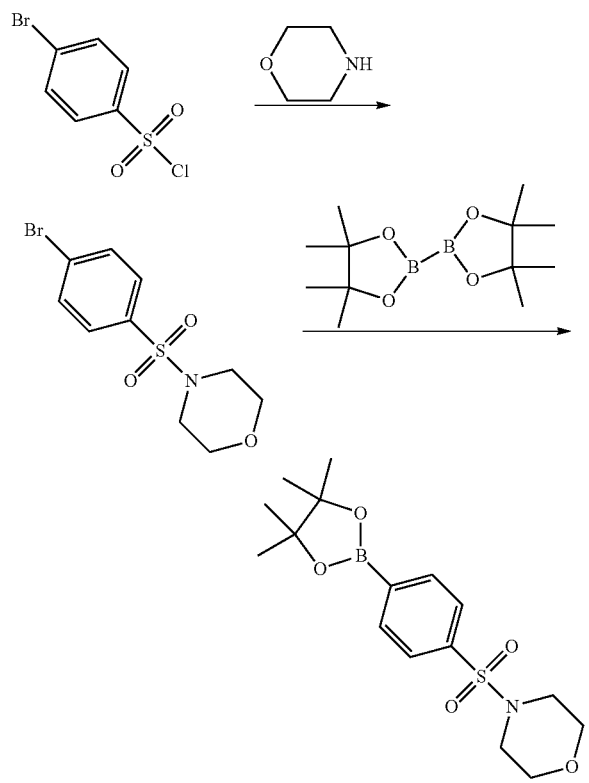

(A) 4-(4-bromophenylsulfonyl)morpholine

To a solution of 4-bromobenzene-1-sulfonyl chloride (2.56 g, 10.0 mmol) and triethylamine (1.82 mL, 13 mmol) in DCM (50 mL) was added morpholine (960 mg, 11.0 mmol) dropwise and the mixture was stirred for 30 minutes at room temperature. Then the mixture was concentrated and extracted with EA, washed with 0.1M HCl water solution (2×100 mL), NaHCO₃ solution (2×100 mL) and brine, dried and concentrated to give product as a white solid.

(B) 4-(4-(4,4,5,5-tetramethyl-1,3,2-dioxaborolan-2-yl)phenylsulfonyl)morpholine

To a solution of 4-(4-bromophenylsulfonyl)morpholine (3.06 g, 10 mmol) in DMSO (20 mL) was added 4,4,4',4',5,5,5',5'-octamethyl-2,2'-bi(1,3,2-dioxaborolane) (3.3 g, 13.0 mmol), [1,1'-Bis(diphenylphosphino)ferrocene]palladium(II) chloride (730 mg, 1.0 mmol) and potassium acetate (1.47 g, 15 mmol). Then the mixture was heated to 70° C. for 4 hours. After cooling the mixture was extracted with EA, wash with brine, dried and purified by silica gel chromatography, eluting with PE/EA=1/1 to give product as a yellow solid. MS (m/z): 354 (M+H)⁺.

Intermediate 51

N-methyl-4-(4,4,5,5-tetramethyl-1,3,2-dioxaborolan-2-yl)benzenesulfonamide

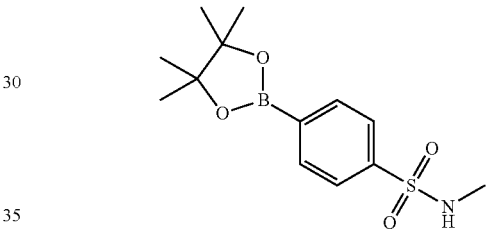

The title compound was prepared according to the procedures of Intermediate 50 using 4-bromobenzene-1-sulfonyl chloride. MS (m/z): 298 (M+H)⁺.

Intermediate 52

2-(4-(4-(4,4,5,5-tetramethyl-1,3,2-dioxaborolan-2-yl)phenyl)piperazin-1-yl)ethanol

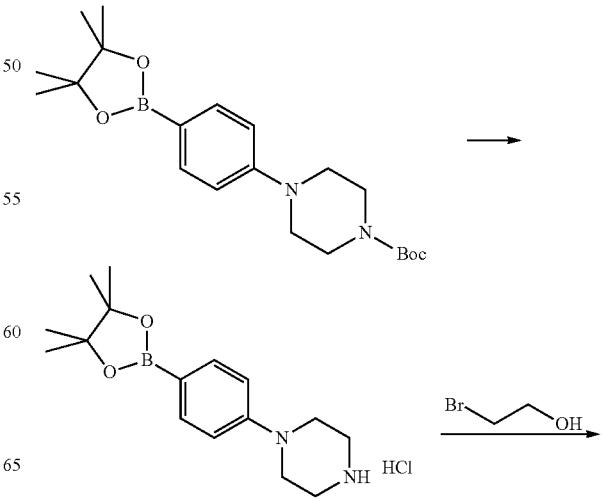

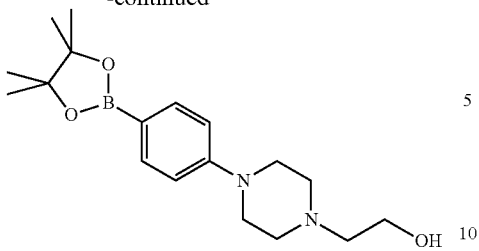

(A) 1-(4-(4,4,5,5-tetramethyl-1,3,2-dioxaborolan-2-yl)phenyl)piperazine hydrochloride A solution of tert-butyl 4-(4-(4,4,5,5-tetramethyl-1,3,2-dioxaborolan-2-yl)phenyl)piperazine-1-carboxylate (5.0 g, 12.9 mmol) in 5N HCl in EA (30 mL) was stirred at room temperature overnight, then concentrated to give product as a off-white solid, which was used for next step directly.

(B) 2-(4-(4-(4,4,5,5-tetramethyl-1,3,2-dioxaborolan-2-yl)phenyl)piperazin-1-yl)ethanol To a solution of 1-(4-(4,4,5,5-tetramethyl-1,3,2-dioxaborolan-2-yl)phenyl)piperazine hydrochloride (500 mg, 1.54 mmol) and potassium carbonate (430 mg, 3.1 mmol) in acetonitrile (20 mL) was added 2-bromoethanol (388 mg, 3.1 mmol), then the mixture was heated at 60° C. overnight under an atmosphere of nitrogen. Then the mixture was filtered over celite and washed with DCM, concentrated to give product as a light brown solid. MS (m/z): 333 (M+H)$^+$.

Intermediate 53

2-(4-(4,4,5,5-tetramethyl-1,3,2-dioxaborolan-2-yl)-1H-pyrazol-1-yl)ethanol

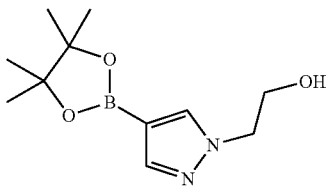 [SMILES: CC1(C)OB(c2cnn(CCO)c2)OC1(C)C]

The title compound was prepared according to the procedures of Intermediate 52 using 4-(4,4,5,5-tetramethyl-1,3,2-dioxaborolan-2-yl)-1H-pyrazole. MS (m/z): 239 (M+H)$^+$.

Intermediate 54

1-(4-(4-(4,4,5,5-tetramethyl-1,3,2-dioxaborolan-2-yl)phenyl)piperazin-1-yl)ethanone

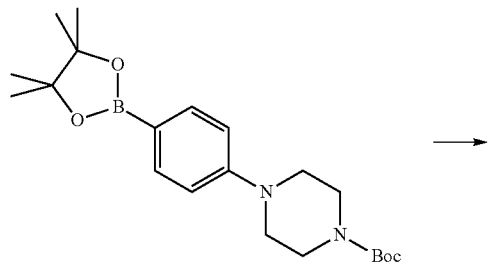

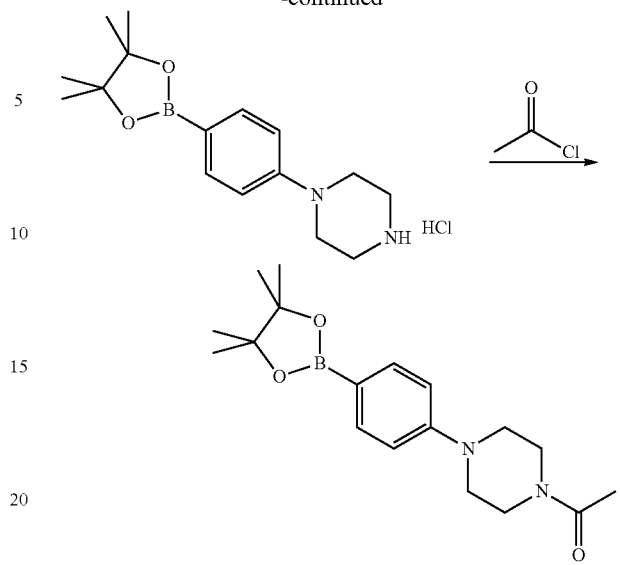

(A) 1-(4-(4,4,5,5-tetramethyl-1,3,2-dioxaborolan-2-yl)phenyl)piperazine hydrochloride A solution of tert-butyl 4-(4-(4,4,5,5-tetramethyl-1,3,2-dioxaborolan-2-yl)phenyl)piperazine-1-carboxylate (500 mg, 1.29 mmol) in 5N HCl in EA (20 mL) was stirred at room temperature for 2 hours, then concentrated to give curd product as a white solid.

(B) 1-(4-(4-(4,4,5,5-tetramethyl-1,3,2-dioxaborolan-2-yl)phenyl)piperazin-1-yl)ethanone To a solution of 1-(4-(4,4,5,5-tetramethyl-1,3,2-dioxaborolan-2-yl)phenyl) piperazine hydrochloride (419 mg, 1.29 mmol) and cesiumcarbonate (1.27 g, 3.9 mmol) in THF (30 mL) was added acetyl chloride (0.5 mL, 6.5 mmol). Then the mixture was stirred at room temperature overnight, extracted with EA, washed with NaHCO$_3$ solution and brine. The organic solution was concentrated and purified by flash column chromatography, eluting with PE/EA, to give product as a white solid. MS (m/z): 331 (M+H)$^+$.

Intermediate 55

1-(4-(4-(4,4,5,5-tetramethyl-1,3,2-dioxaborolan-2-yl)phenyl)piperazin-1-yl)propan-1-one

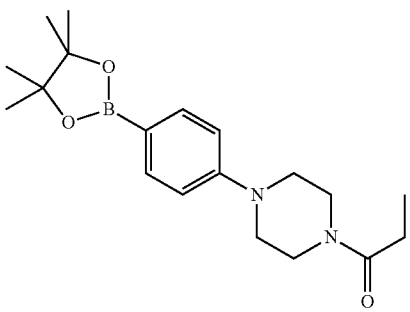 [SMILES: CCC(=O)N1CCN(c2ccc(B3OC(C)(C)C(C)(C)O3)cc2)CC1]

The title compound was prepared according to the procedures of Intermediate 54 using 1-(4-(4,4,5,5-tetramethyl-1,3,2-dioxaborolan-2-yl)phenyl)piperazine. MS (m/z): 345 (M+H)$^+$.

Intermediate 56

2-(methylsulfonyl)-1-(4-(4-(4,4,5,5-tetramethyl-1,3,2-dioxaborolan-2-yl)phenyl)piperazin-1-yl)ethanone

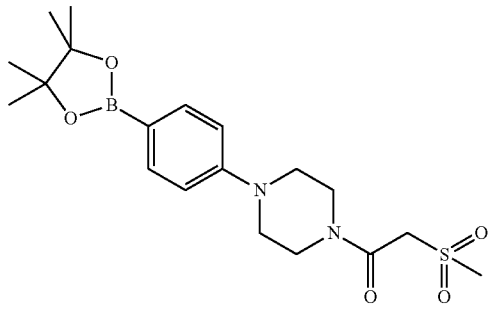

The title compound was prepared according to the procedures of Intermediate 54 using 1-(4-(4,4,5,5-tetramethyl-1,3,2-dioxaborolan-2-yl)phenyl)piperazine. MS (m/z): 409 (M+H)⁺.

Intermediate 57

2-methoxy-1-(4-(4-(4,4,5,5-tetramethyl-1,3,2-dioxaborolan-2-yl)phenyl)piperazin-1-yl)ethanone

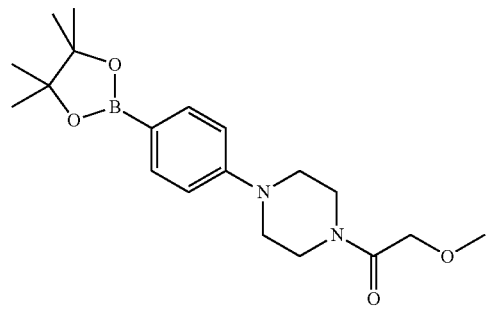

The title compound was prepared according to the procedures of Intermediate 54 using 1-(4-(4,4,5,5-tetramethyl-1,3,2-dioxaborolan-2-yl)phenyl)piperazine. MS (m/z): 361 (M+H)⁺.

Intermediate 58

2-hydroxy-1-(4-(4-(4,4,5,5-tetramethyl-1,3,2-dioxaborolan-2-yl)phenyl)piperazin-1-yl)ethanone

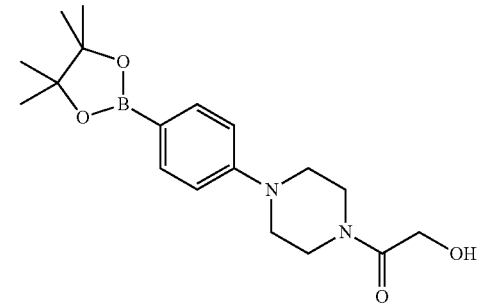 [SMILES: CC1(C)OB(c2ccc(N3CCN(C(=O)CO)CC3)cc2)OC1(C)C]

The title compound was prepared according to the procedures of Intermediate 54 using 1-(4-(4,4,5,5-tetramethyl-1,3,2-dioxaborolan-2-yl)phenyl)piperazine. MS (m/z): 347 (M+H)⁺.

Intermediate 59

Cyclopropyl(4-(4-(4,4,5,5-tetramethyl-1,3,2-dioxaborolan-2-yl)phenyl)piperazin-1-yl)methanone

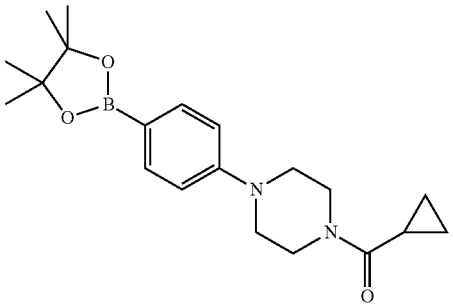 [SMILES: CC1(C)OB(c2ccc(N3CCN(C(=O)C4CC4)CC3)cc2)OC1(C)C]

The title compound was prepared according to the procedures of Intermediate 54 using 1-(4-(4,4,5,5-tetramethyl-1,3,2-dioxaborolan-2-yl)phenyl)piperazine. MS (m/z): 357 (M+H)⁺.

Intermediate 60

1-(methylsulfonyl)-4-(4-(4,4,5,5-tetramethyl-1,3,2-dioxaborolan-2-yl)phenyl)piperazine

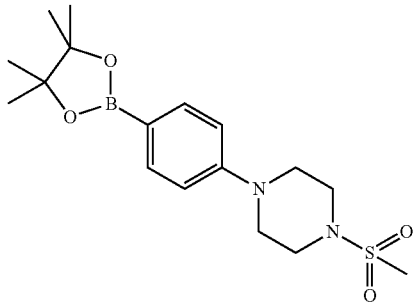

The title compound was prepared according to the procedures of Intermediate 54 using 1-(4-(4,4,5,5-tetramethyl-1,3,2-dioxaborolan-2-yl)phenyl)piperazine. MS (m/z): 367 (M+H)⁺.

Intermediate 61

1-(methylsulfonyl)-4-(4-(4,4,5,5-tetramethyl-1,3,2-dioxaborolan-2-yl)-1H-pyrazol-1-yl)piperidine

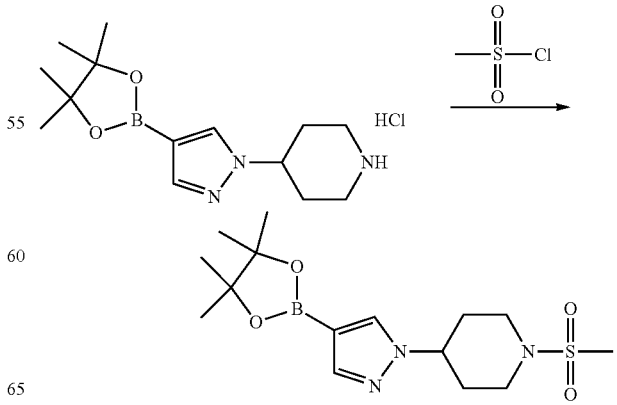

1-(methylsulfonyl)-4-(4-(4,4,5,5-tetramethyl-1,3,2-dioxaborolan-2-yl)-1H-pyrazol-1-yl)piperidine To a solution of 4-(4-(4,4,5,5-tetramethyl-1,3,2-dioxaborolan-2-yl)-1H-pyrazol-1-yl)piperidine hydrochloride (315 mg, 1.0 mmol) and triethylamine (303 mg, 3.0 mmol) in DCM (15 mL) was added methanesulfonyl chloride (230 mg, 2.0 mmol) dropwise, the mixture was stirred at room temperature for 1 hour. Then the mixture was extracted with EA, wash with brine, dried and purified by flash column chromatography, eluting with EA/MeOH, to give product as light yellow solid. MS (m/z): 356 (M+H)$^+$.

Intermediate 62

1-(4-(4-(4,4,5,5-tetramethyl-1,3,2-dioxaborolan-2-yl)-1H-pyrazol-1-yl)piperidin-1-yl)ethanone

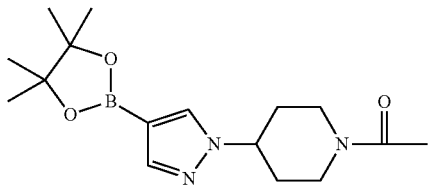 [SMILES: CC(=O)N1CCC(n2cc(B3OC(C)(C)C(C)(C)O3)cn2)CC1]

The title compound was prepared according to the procedures of Intermediate 51 using 4-(4-(4,4,5,5-tetramethyl-1,3,2-dioxaborolan-2-yl)-1H-pyrazol-1-yl)piperidine MS (m/z): 320 (M+H)$^+$.

Intermediate 63

6-(4-acetylpiperazin-1-yl)pyridin-3-ylboronic acid

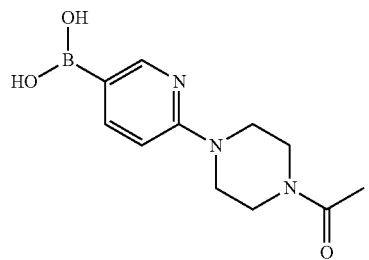 [SMILES: CC(=O)N1CCN(c2ccc(B(O)O)cn2)CC1]

The title compound was prepared according to the procedures of Intermediate 35 using 2-chloro-5-(4,4,5,5-tetramethyl-1,3,2-dioxaborolan-2-yl)pyridine MS (m/z): 250 (M+H)$^+$.

Intermediate 64

6-(4-methylpiperazin-1-yl)pyridin-3-ylboronic acid

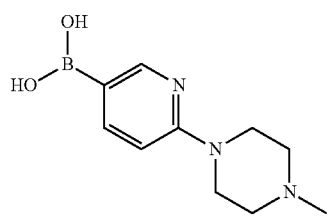 [SMILES: CN1CCN(c2ccc(B(O)O)cn2)CC1]

The title compound was prepared according to the procedures of Intermediate 35 using 2-chloro-5-(4,4,5,5-tetramethyl-1,3,2-dioxaborolan-2-yl)pyridine Intermediate 65

6-(4-methyl-1,4-diazepan-1-yl)pyridin-3-ylboronic acid

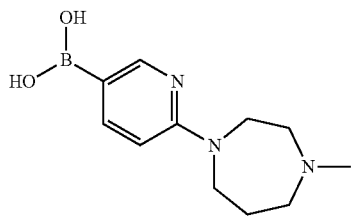 [SMILES: CN1CCCN(c2ccc(B(O)O)cn2)CC1]

The title compound was prepared according to the procedures of Intermediate 35 using 2-chloro-5-(4,4,5,5-tetramethyl-1,3,2-dioxaborolan-2-yl)pyridine Intermediate 66

N-methyl-N-(4-(4,4,5,5-tetramethyl-1,3,2-dioxaborolan-2-yl)phenyl)methanesulfonamide

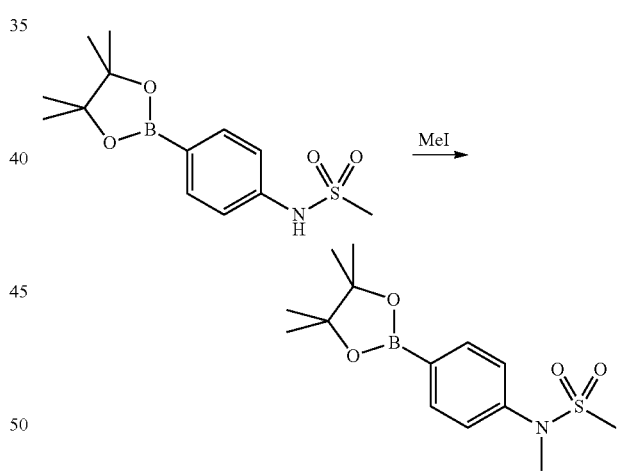

N-methyl-N-(4-(4,4,5,5-tetramethyl-1,3,2-dioxaborolan-2-yl)phenyl)methanesulfonamide To a suspension of N-(4-(4,4,5,5-tetramethyl-1,3,2-dioxaborolan-2-yl)phenyl)methanesulfonamide (0.5 g, 1.7 mmol) and potassium carbonate (0.28 g, 2.0 mmol) in acetone (10 mL) was added methyl iodide (0.12 mL, 2.0 mmol). The mixture was stirred at room temperature for 18 hours under atmosphere of nitrogen, then diluted with CH$_2$Cl$_2$ (20 mL), filtered through a plug of diatomaceous earth, rinsed with CH$_2$Cl$_2$ and evaporated to give product as a off-white solid. MS (m/z): 312 (M+H)$^+$.

67

Intermediate 67

1-ethyl-4-(4-(4,4,5,5-tetramethyl-1,3,2-dioxaborolan-2-yl)phenyl)piperidine

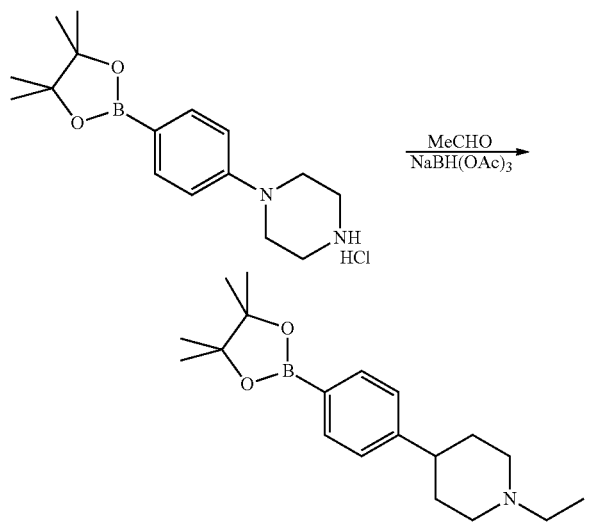

1-ethyl-4-(4-(4,4,5,5-tetramethyl-1,3,2-dioxaborolan-2-yl)phenyl)piperidine

To a solution of 4-(4-(4,4,5,5-tetramethyl-1,3,2-dioxaborolan-2-yl)phenyl)piperidine in THF was added MeCHO (40%, 0.17 mL, 1.48 mmol) and AcOH (45 mg, 0.74 mmol), the mixture was stirred at room temperature for 20 minutes. Then the NaBH(OAc)$_3$ (157 mg, 0.74 mmol) was added and stirred overnight. The reaction solution was poured to NaHCO$_3$, extracted with EA, dried and concentrated to give product as white solid. MS (m/z): 316 (M+H)$^+$.

Intermediate 68

1-methyl-4-(4-(4,4,5,5-tetramethyl-1,3,2-dioxaborolan-2-yl)-1H-pyrazol-1-yl)piperidine

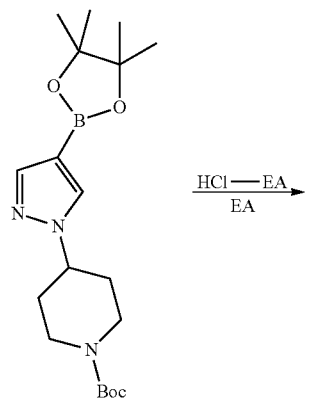

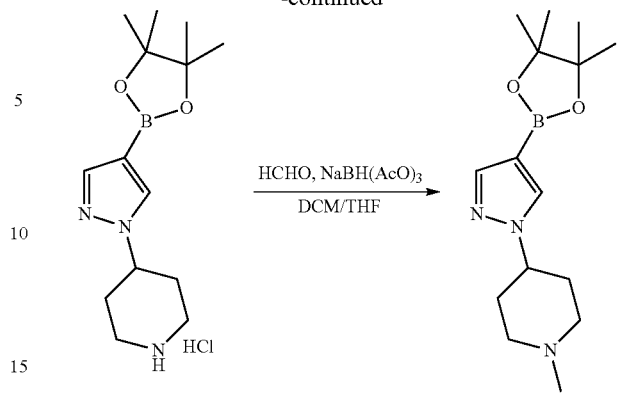

(A) 4-(4-(4,4,5,5-tetramethyl-1,3,2-dioxaborolan-2-yl)-1H-pyrazol-1-yl)piperidine hydrochloride A solution of tert-butyl 4-(4-(4,4,5,5-tetramethyl-1,3,2-dioxaborolan-2-yl)-1H-pyrazol-1-yl)piperidine-1-carboxylate (8.2 g, 21.73 mmol) and 30 mL of HCl-EA (5.0 N) in 15 mL of EA was stirred at room temperature for 2 hours. The volatiles were removed in vacuo to give 7.3 g of title compound.

(B) 1-methyl-4-(4-(4,4,5,5-tetramethyl-1,3,2-dioxaborolan-2-yl)-1H-pyrazol-1-yl)piperidine A solution of 4-(4,4,5,5-tetramethyl-1,3,2-dioxaborolan-2-yl)-1H-pyrazole hydrochloride (740 mg, 2.36 mmol) and Formalin (1.0 g, 11.80 mmol) in 10 mL of DCM and 2 mL of THF, under N$_2$, was stirred at room temperature for 1 hour. Then the NaBH(AcO)$_3$ (1.0 g, 4.72 mmol) was added to the mixture at 0° C. The mixture was stirred at room temperature overnight. The volatiles were removed in vacuo, and the residue was purified by chromatography with MeOH/H2O (1:20~10:1) to give 620 mg of title compound. MS (m/z)=292 (M+H)$^+$.

Intermediate 69

6-(1,4-oxazepan-4-yl)pyridin-3-ylboronic acid

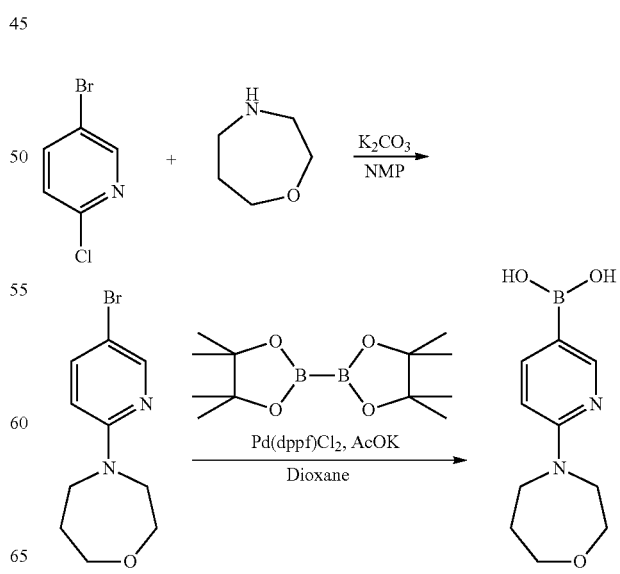

(A) 4-(5-bromopyridin-2-yl)-1,4-oxazepane

The solution of 5-bromo-2-chloropyridine (1.5 g, 7.8 mmol), 1,4-oxazepane (1.29 g, 9.36 mmol) and $K_2CO_3$ in 15 mL of NMP was stirred at 120° C. overnight. The mixture was added to 150 mL of water, washed with EA, dried over $Na_2SO_4$, and the volatiles were removed in vacuo to give 1.86 g of 4-(5-bromopyridin-2-yl)-1,4-oxazepane. MS(m/z)= 259 (M+H)$^+$.

(B) 6-(1,4-oxazepan-4-yl)pyridin-3-ylboronic acid

A solution of 4-(5-bromopyridin-2-yl)-1,4-oxazepane (600 mg, 2.33 mmol), 4,4,5,5-tetramethyl-2-(4,4,5,5-tetramethyl-1,3,2-dioxaborolan-2-yl)-1,3,2-dioxaborolane (1.18 g, 4.67 mmol), Pd(dppf)Cl$_2$ (286 mg, 0.35 mmol) and KOAc (687 mg, 6.99 mmol) in 30 ml of dioxane, under $N_2$, was stirred at 110° C. for 3 hours. The volatiles were removed in vacuo, and the residue was purified by chromatography with EA/MeOH (20:1~5:1) to give 165 mg of 6-(1,4-oxazepan-4-yl)pyridin-3-ylboronic acid. MS (m/z)=223 (M+H)$^+$.

Intermediate 70

N,N-di methyl-1-(4-(4,4,5,5-tetramethyl-1,3,2-dioxaborolan-2-yl)phenyl)piperidine-4-carboxamide

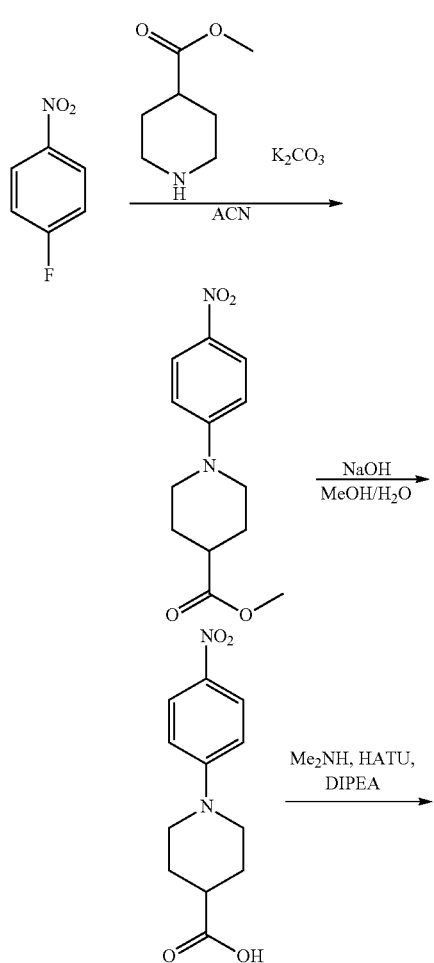

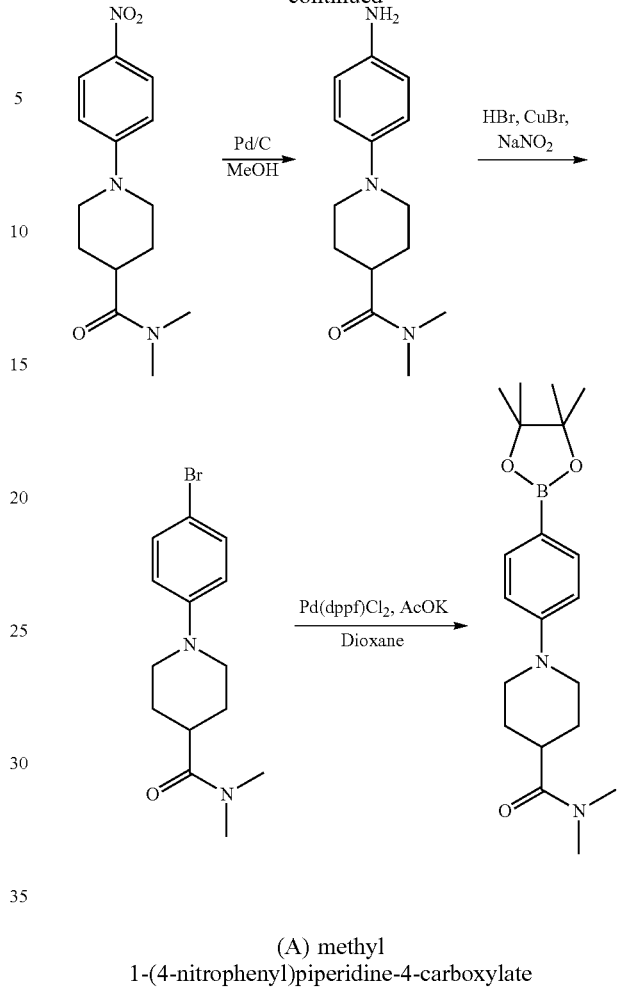

(A) methyl 1-(4-nitrophenyl)piperidine-4-carboxylate

A solution of 1-fluoro-4-nitrobenzene (3.5 g, 24.81 mmol), methyl piperidine-4-carboxylate (4.26 g, 29.77 mmol) and $K_2CO_3$ in 40 mL of ACN, was stirred at reflux overnight. The mixture was added to 150 mL of water, extracted with EA, dried over $Na_2SO_4$. The volatiles were removed in vacuo, and the residue was purified by chromatography with PE/EA (10:1~2:1) to give 3.84 g of methyl 1-(4-nitrophenyl)piperidine-4-carboxylate.

(B) N,N-dimethyl-1-(4-nitrophenyl)piperidine-4-carboxamide

A solution of methyl 1-(4-nitrophenyl)piperidine-4-carboxylate (3.84 g, 14.53 mmol) and NaOH (0.87 g, 21.79 mmol) in 15 mL of MeOH and 5 mL of water was stirred at room temperature for 3 hours. The volatiles were removed in vacuo to give 1-(4-nitrophenyl)piperidine-4-carboxylic acid.

A solution of 1-(4-nitrophenyl)piperidine-4-carboxylic acid, (CH$_3$)$_2$NH (2.37 g, 29.06 mmol), HATU (11.05 g, 29.06 mmol) and DIPEA (7.51 g, 58.12 mmol) in 30 mL of THF, was stirred at room temperature overnight. The mixture was added to 20 mL of water, extracted with EA, washed with water and brine, dried over $Na_2SO_4$. The volatiles were removed in vacuo to give 4.2 g of N,N-dimethyl-1-(4-nitrophenyl)piperidine-4-carboxamide. MS (m/z)=278 (M+H)$^+$.

(C) 1-(4-aminophenyl)-N,N-dimethylpiperidine-4-carboxamide

A solution of N,N-dimethyl-1-(4-nitrophenyl)piperidine-4-carboxamide (2.5 g, 9.01 mmol) and 0.3 g of Pd/C in 20 mL of MeOH, under $H_2$, was stirred at room temperature for 5 hours. The mixture was filtered, and the volatiles were removed in vacuo to give 1.9 g of 1-(4-aminophenyl)-N,N-dimethylpiperidine-4-carboxamide.

(D) 1-(4-bromophenyl)-N,N-dimethylpiperidine-4-carboxamide

A solution of 1-(4-aminophenyl)-N,N-dimethylpiperidine-4-carboxamide (4.2 g, 16.98 mmol) in 25 mL HBr in 20 mL of water was added a solution of $NaNO_2$ (1.17 g, 16.98 mmol) in water (2 mL) slowly. The mixture was stirred at −10° C.~0° C. for 30 minutes, and added dropwise to a solution of CuBr (1.34 g, 9.34 mmol) in 12 mL HBr in water (10 mL). Then the mixture was stirred at reflux for 2 hours. The mixture was partitioned between 2N NaOH and EA, washed with EA, dried over $Na_2SO_4$. The volatiles were removed in vacuo, and the residue was purified by chromatography with PE/EA (15:1~2:1) to give 2.5 g of 1-(4-bromophenyl)-N,N-dimethylpiperidine-4-carboxamide.

(E) N,N-dimethyl-1-(4-(4,4,5,5-tetramethyl-1,3,2-dioxaborolan-2-yl)phenyl)piperidine-4-carboxamide A solution of 1-(4-bromophenyl)-N,N-dimethylpiperidine-4-carboxamide (500 mg, 1.61 mmol), 4,4,5,5-tetramethyl-2-(4,4,5,5-tetramethyl-1,3,2-dioxaborolan-2-yl)-1,3,2-dioxaborolane (916 mg, 3.21 mmol), $Pd(dppf)Cl_2$ (177 mg, 0.24 mmol) and KOAc (475 mg, 4.83 mmol) in 20 mL of dioxane, under $N_2$, was stirred at 110° C. overnight. The volatiles were removed in vacuo, and the residue was purified by chromatography with PE/EA (10:1~1:4) to give 326 mg of N,N-dimethyl-1-(4-(4,4,5,5-tetramethyl-1,3,2-dioxaborolan-2-yl)phenyl)piperidine-4-carboxamide. MS (m/z)=359 (M+H)$^+$.

Intermediate 71

4,4,5,5-tetramethyl-2-(4-(tetrahydro-2H-pyran-4-yl)phenyl)-1,3,2-dioxaborolane

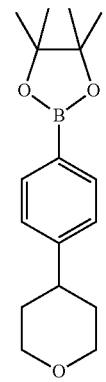

(A) 4-(4-bromophenyl)-tetrahydro-2H-pyran

A solution of 4-(tetrahydro-2H-pyran-4-yl)benzenamine (1.79 g, 10.10 mmol) in 15 mL of HBr and 5 mL of water was stirred at 0° C. for 10 minutes, then 0.77 g of $NaNO_2$ was added to the mixture at −5° C.~0° C. The mixture was stirred at −5° C. for 30 minutes. Then the solution of CuBr in 3 mL of HBr was added to the mixture, after that the mixture was heated at 100° C. for 2 hours. The mixture was cooled to room temperature, partitioned between 2N NaOH and EA, washed with water and aqueous NaCl, dried over $Na_2SO_4$. The volatiles were removed in vacuo, and the residue was purified by chromatography with PE/EA (10:1~4:1) to give 1.11 g of title compound.

(B) 4,4,5,5-tetramethyl-2-(4-(tetrahydro-2H-pyran-4-yl)phenyl)-1,3,2-dioxaborolane A solution of 4-(4-bromophenyl)-tetrahydro-2H-pyran (500 mg, 2.07 mmol), 4,4,5,5-tetramethyl-2-(4,4,5,5-tetramethyl-1,3,2-dioxaborolan-2-yl)-1,3,2-dioxaborolane (842 mg, 3.32 mmol), $Pd(dppf)Cl_2$ (303 mg, 0.41 mmol) and KOAc (610 mg, 6.21 mmol) in 20 mL of DMSO, under $N_2$, was stirred at 90° C. overnight. The mixture was added to 100 mL of water, extracted with EA, dried over $Na_2SO_4$, The volatiles were removed in vacuo, and the residues was purified by chromatography with PE/EA (30:1~5:1) to give 57 mg of title compound.

Intermediate 72

4-(4-(4,4,5,5-tetramethyl-1,3,2-dioxaborolan-2-yl)phenyl)piperidine hydrochloride

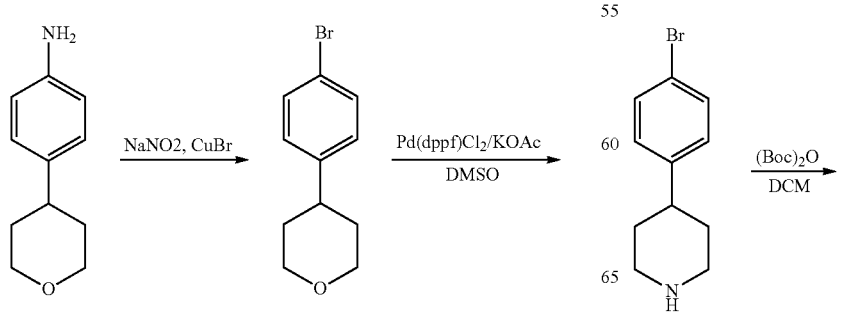

Intermediate 73 tert-butyl 4-(4-(4,4,5,5-tetramethyl-1,3,2-dioxaborolan-2-yl)-1H-pyrazol-1-yl)piperidine-1-carboxylate

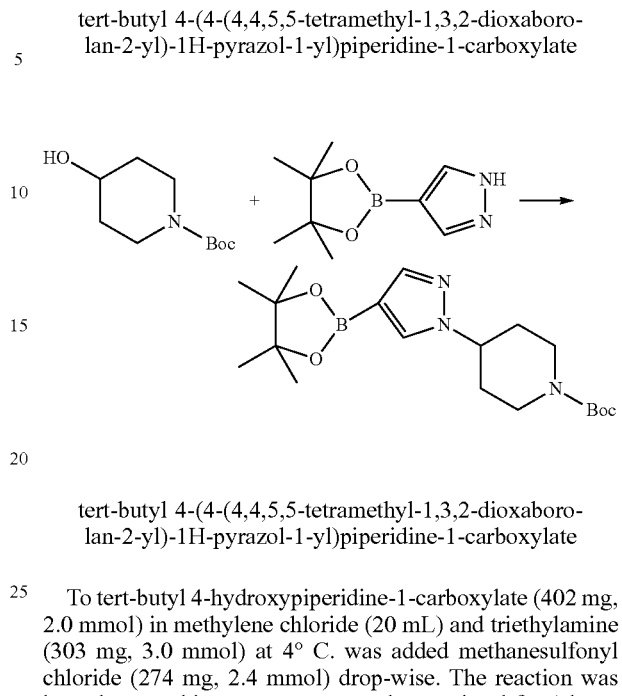

tert-butyl 4-(4-(4,4,5,5-tetramethyl-1,3,2-dioxaborolan-2-yl)-1H-pyrazol-1-yl)piperidine-1-carboxylate To tert-butyl 4-hydroxypiperidine-1-carboxylate (402 mg, 2.0 mmol) in methylene chloride (20 mL) and triethylamine (303 mg, 3.0 mmol) at 4° C. was added methanesulfonyl chloride (274 mg, 2.4 mmol) drop-wise. The reaction was brought to ambient temperature and was stirred for 1 hour. The reaction mixture was concentrated in vacuo and diluted in diethyl ether (20 mL). The solution was washed with 1N hydrochloric acid (3 mL), water (3 mL), and saturated sodium bicarbonate (3 mL). The organics were dried (sodium sulfate) and concentrated in vacuo to afford tert-butyl4-(methylsulfonyloxy)piperidine-1-carboxylate in quantitative yield. The product was used directly in the next step without further purification. A mixture of 4-(4,4,5,5-tetramethyl-1,3,2-dioxaborolan-2-yl)-1H-pyrazole (427 mg, 2.2 mmol), tert-butyl4-(methylsulfonyloxy)piperidine-1-carboxylate (2.0 mmol), and cesium carbonate (847 mg, 2.6 mmol) in DMF (5 mL) was stirred at 100° C. overnight. The mixture was diluted with saturated aqueous $NaHCO_3$ and extracted with EtOAc (3×). The combined organic layers were dried over $Na_2SO_4$, filtered and concentrated to provide crude pale yellow oil 884 mg. MS (m/z): 378 (M+H)+.

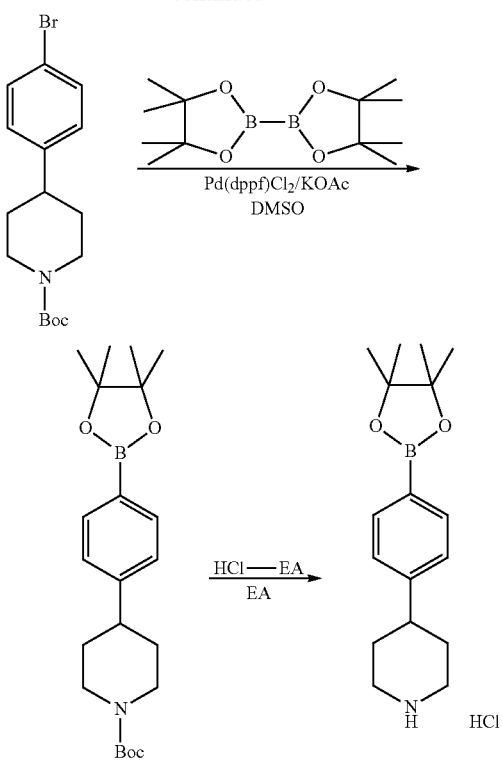

(A) tert-butyl 4-(4-bromophenyl)piperidine-1-carboxylate

A solution of 4-(4-bromophenyl)piperidine (2.7 g, 11.25 mmol) and di-tert-butyl dicarbonate (2.5 g, 11.47 mmol) in 20 mL of DCM was stirred at room temperature for 2 hours. The volatiles were removed in vacuo to give 4.6 g of tert-butyl 4-(4-bromophenyl)piperidine-1-carboxylate.

(B) tert-butyl 4-(4-(4,4,5,5-tetramethyl-1,3,2-dioxaborolan-2-yl)phenyl)piperidine-1-carboxylate A solution of tert-butyl 4-(4-bromophenyl)piperidine-1-carboxylate (3.38 g, 11.25 mmol), 4,4,5,5-tetramethyl-2-(4,4,5,5-tetramethyl-1,3,2-dioxaborolan-2-yl)-1,3,2-dioxaborolane (4.57 g, 18 mmol), Pd(dppf)Cl₂ (2.47 g, 3.38 mmol) and KOAc (3.32 g, 33.75 mmol) in 60 mL of DMSO, under N₂, was stirred at 80° C. overnight. The volatiles were removed in vacuo, and the residue was purified by chromatography with PE/EA (40:1~1:1) to give 3.81 g of title compound.

(C) 4-(4-(4,4,5,5-tetramethyl-1,3,2-dioxaborolan-2-yl)phenyl)piperidine hydrochloride A solution of tert-butyl 4-(4-(4,4,5,5-tetramethyl-1,3,2-dioxaborolan-2-yl)phenyl)piperidine-1-carboxylate (3.0 g, 7.75 mmol) and 10 mL of HCl-EA (5.0 N) in 20 mL of EA was stirred at room temperature for 2 hours. The volatiles were removed in vacuo to give 2.6 g of title compound. MS (m/z)=288 (M+H)+.

Intermediate 74

1-cyclopentyl-4-(4,4,5,5-tetramethyl-1,3,2-dioxaborolan-2-yl)-1H-pyrazole

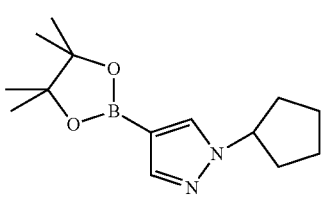 [SMILES: CC1(C)OB(c2cnn(C3CCCC3)c2)OC1(C)C]

The title compound was prepared according to the procedures of Intermediate 73 using 4-(4,4,5,5-tetramethyl-1,3,2-dioxaborolan-2-yl)-1H-pyrazole. MS (m/z): 263 (M+H)+.

Intermediate 75

1-(tetrahydro-2H-pyran-4-yl)-4-(4,4,5,5-tetramethyl-1,3,2-dioxaborolan-2-yl)-1H-pyrazole

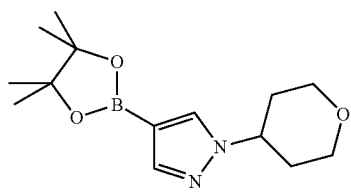 [SMILES: CC1(C)OB(c2cnn(C3CCOCC3)c2)OC1(C)C]

The title compound was prepared according to the procedures of Intermediate 73 using 4-(4,4,5,5-tetramethyl-1,3,2-dioxaborolan-2-yl)-1H-pyrazole. MS (m/z): 279 (M+H)$^+$.

Intermediate 76 tert-butyl 3-((7-chloropyrido[3,4-b]pyrazin-5-ylamino)methyl)-3-fluoropiperidine-1-carboxylate

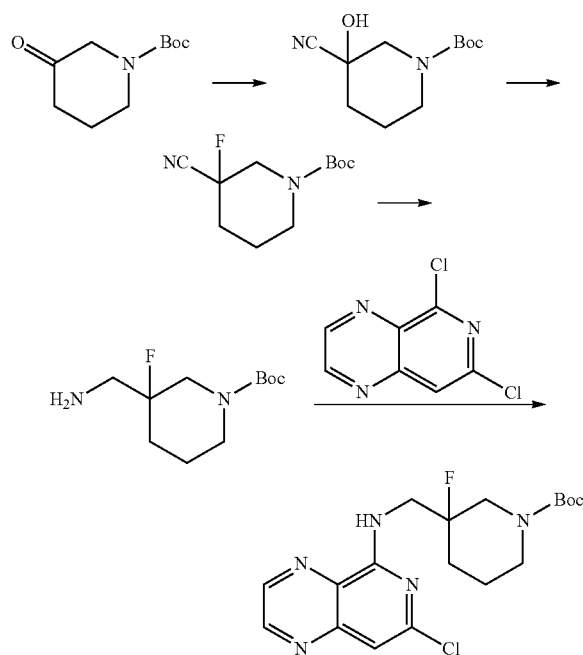

(A) tert-butyl 3-cyano-3-hydroxypiperidine-1-carboxylate

To a solution of N-Boc-3-piperidone (5.00 g, 25.1 mmol) and THF (15 mL) was added KCN (2.34 g, 37.6 mmol) and H$_2$O (15 mL) and the resulting solution was cooled to 0° C. To the resulting homogeneous orange solution was added a solution of NaHSO$_3$ (1.25 g, 37.6 mmol) and H$_2$O (15 mL). The resulting solution was stirred at 0° C. for 1 hour. The solution was twice extracted DCM and the combined extracts were dried by Na$_2$SO$_4$, filtered and evaporated to afford title compound 5.7 g as white solid. MS (m/z): 127 (M+H-Boc)$^+$

(B) tert-butyl 3-cyano-3-fluoropiperidine-1-carboxylate

To a solution of tert-butyl 3-cyano-3-hydroxypiperidine-1-carboxylate (5.7 g, 25.1 mmol) in DCM (50 mL) cooled to −78° C., DAST (4.85 g, 30.1 mmol) was added drop-wise and the resulting solution stirred at −78° C. for 1 hour. The reaction was warmed to 0° C. and stirred for an additional 1 hour. The reaction mixture was diluted with DCM and quenched with sat. aq. NaHCO$_3$. The combined extracts were dried by Na$_2$SO$_4$, filtered and concentrated in vacuo to afford crude title compound as a pale yellow oil 5.5 g. MS (m/z): 129 (M+H-Boc)$^+$

(C) tert-butyl 3-(aminomethyl)-3-fluoropiperidine-1-carboxylate

To a stirred and cooled (0° C.) suspension of lithium aluminium hydride (1.02 g, 26.8 mmol) in dry THF (50 mL) was added drop-wise a solution of tert-butyl 3-cyano-3-fluoropiperidine-1-carboxylate (5.50 g, 24.0 mmol) in dry THF (30 mL). The reaction was stirred at 0° C. for 1 hour then at room temperature for 3 hours. The mixture was quenched with water (1.0 mL) at 0° C., and stirred at room temperature for 20 minutes. Then 15% sodium hydroxide aqueous solution (2.0 mL) was added, and stirred at room temperature for 20 minutes. Finally, water (1.0 mL) was added, and stirred at room temperature for 20 minutes. The mixture was filtered through Celite pad washing with tetrahydrofuran (25 mL). The filtrate was concentrated to afford the title product as pale yellow oil 3.86 g. MS (m/z): 233 (M+H)$^+$

(D) tert-butyl 3-((7-chloropyrido[3,4-b]pyrazin-5-ylamino)methyl)-3-fluoropiperidine-1-carboxylate tert-butyl 3-(aminomethyl)-3-fluoropiperidine-1-carboxylate (3.86 g, 16.6 mmol) and DIPEA (3.22 g, 24.9 mmol) were added to a solution of 5,7-dichloropyrido[3,4-b]pyrazine (3.32 g, 16.6 mmol) in THF (60 mL) and the mixture was refluxed overnight. The volatile components were evaporated and the residue was extracted with ethyl acetate. Ethyl acetate was washed with brine and dried. The solvent was removed in vacuo The crude residue was purified by silica-gel chromatography eluting with Hexane-50% EtOAc/Hexane (gradient) then C$_{18}$ column to afford the subtitled compound as pale yellow solid 1.76 g. MS (m/z): 396 (M+H)$^+$

Intermediate 77 tert-butyl 2-(aminomethyl)thiomorpholine-4-carboxylate

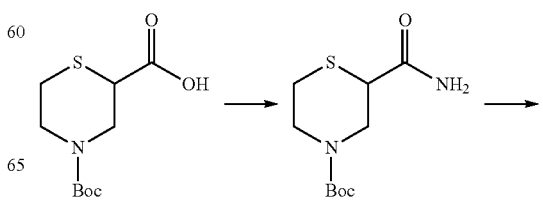

(A) tert-butyl 2-carbamoylthiomorpholine-4-carboxylate

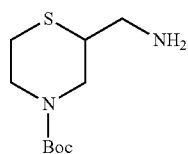

4-(tert-butoxycarbonyl)thiomorpholine-2-carboxylic acid (2.47 g, 10 mmol) and HOBt (1.62 g, 12 mmol) were dissolved in DMF (20 mL), and EDCl (2.11 g, 11 mmol) was added. The reaction mixture was stirred for 1 hour, and 25% aqueous ammonia (5 mL) was added, and the reaction was stirred for another 2 hours. The reaction was then diluted with EtOAc (200 mL) and partitioned with water (100 mL). The organic layer was washed with saturated aq. NaHCO$_3$ (2×100 mL), and then dried with Na$_2$SO$_4$. The solvent was removed in vacuo to afford title compound as white solid 2.46 g. MS (m/z): 147 (M+H-Boc)$^+$

(B) tert-butyl 2-(aminomethyl)thiomorpholine-4-carboxylate

A solution of tert-butyl 2-carbamoylthiomorpholine-4-carboxylate (2.46 g, 10 mmol) in THF (80 mL) was cooled to 0° C. A solution of borane in THF (1.0 M, 40 mL, 40 mmol) was added over 15 minutes via addition funnel and the mixture was stirred at ambient temperature for 72 hours. The reaction was quenched by dropwise addition of methanol/acetic acid (18 mL, 9:1 v/v). The solvent was removed under reduced pressure and the residue partitioned between ethyl acetate and sat. aqueous Na$_2$CO$_3$. The aqueous layer was extracted with ethyl acetate and combined extracts were washed with water, brine and dried over sodium sulfate. Removal of the solvent under reduced pressure afforded the crude desired material 2.11 g, which was used directly in the next step. MS (m/z): 233 (M+H)$^+$

Intermediate 78

(2S)-tert-butyl 2-(1-(7-chloropyrido[3,4-b]pyrazin-5-ylamino)ethyl)morpholine-4-carboxylate

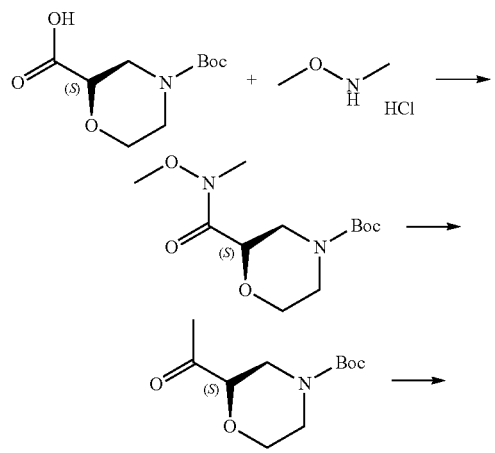

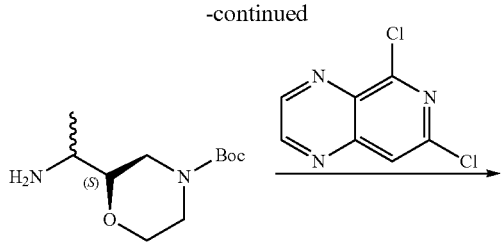

(A) (S)-tert-butyl 2-(methoxy(methyl)carbamoyl)morpholine-4-carboxylate

A mixture of (S)-4-(tert-butoxycarbonyl)morpholine-2-carboxylic acid (3.46 g, 15 mmol), DIPEA (7.75 g, 60 mmol), and N,O-dimethylhydroxylamine HCl (4.39 g, 45 mmol) in DCM (100 mL) was treated with EDCl (9.63 g, 45 mmol) at room temperature. The reaction mixture was stirred for 16 hours and then poured into saturated aqueous sodium bicarbonate solution and extracted with CH$_2$Cl$_2$. The combined extracts were dried over MgSO$_4$, filtered, and concentrated to provide light yellow oil 3.5 g. MS (m/z): 175 (M+H-Boc)$^+$

(B) (S)-tert-butyl 2-acetylmorpholine-4-carboxylate (S)-tert-butyl 2-(methoxy(methyl)carbamoyl)morpholine-4-carboxylate obtained above was dissolved in THF (60 mL) at room temperature under nitrogen and cooled to 0° C. Methylmagnesium bromide (3.0 M solution in diethyl ether, 15 mL, 45 mmol) was added in portions. The reaction mixture was stirred at 0° C. for 1 hour, allowed to warm to room temperature and then stirred for 16 hours. The mixture was again cooled to 0° C. and saturated aqueous ammonium chloride solution was slowly added. The mixture was extracted with EtOAc, and the extracts were washed with brine, dried over MgSO$_4$, filtered and concentrated to provide 2.29 g of crude (S)-tert-butyl 2-acetylmorpholine-4-carboxylate as yellow oil that was used without further purification. MS (m/z): 130 (M+H-Boc)$^+$

(C) (2S)-tert-butyl 2-(1-(7-chloropyrido[3,4-b]pyrazin-5-ylamino)ethyl)morpholine-4-carboxylate A mixture of (S)-tert-butyl 2-acetylmorpholine-4-carboxylate (2.29 g, 10.0 mmol), ammonium acetate (7.70 g, 100 mmol), sodium cyanoborohydride (0.94 g, 15.0 mmol), and 5 angstrom molecular sieves (10 g) in methanol (50 mL) was stirred at room temperature under nitrogen for 16 hours. The sieves were removed by filtration and the filtrate was concentrated. A solution of 1 N NaOH was added until the pH reached 12. The mixture was extracted with CH$_2$Cl$_2$ and the combined extracts were dried over MgSO$_4$, filtered and concentrated. The resulting light yellow oil (2.17 g) was dissolved in THF (40 mL) and 5,7-dichloropyrido[3,4-b]pyrazine (2.00 g, 10.0 mmol) and DIPEA (1.94 g, 15.0 mmol) were added. The mixture was heated to reflux for 48 hours. The volatile components were evaporated and the residue was extracted with ethyl acetate. Ethyl acetate was washed with brine and dried. The solvent was removed in vacuo. The crude residue was purified by silica-gel chromatography eluting with Hexane-50% EtOAc/Hexane (gradient) then $C_{18}$ column to afford the subtitled compound as brown oil 450 mg. MS (m/z): 394 (M+H)$^+$ Intermediate 79

2-(1-(4-(4,4,5,5-tetramethyl-1,3,2-dioxaborolan-2-yl)phenyl)piperidin-4-yl)propan-2-ol

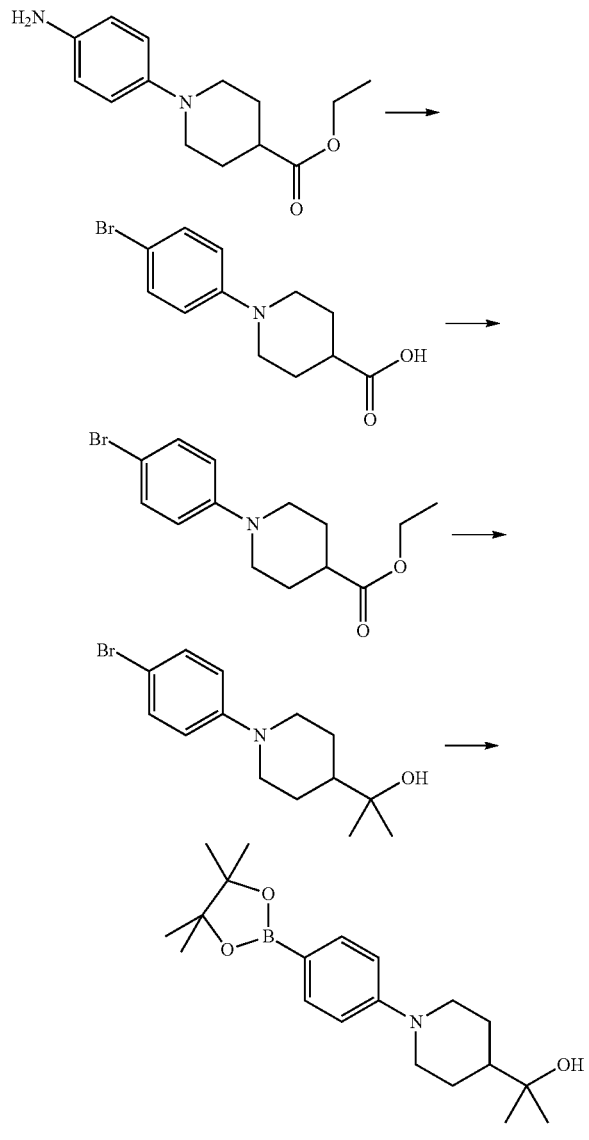

(A) 1-(4-bromophenyl)piperidine-4-carboxylic acid

To a solution of ethyl 1-(4-aminophenyl)piperidine-4-carboxylate (2.48 g, 10 mmol) in 40 mL of HBr 40%, a solution of NaNO$_2$ (0.69 g, 10 mmol) in 7 mL of water was slowly added at 0° C. The mixture was stirred for 15 minutes and added to a solution of CuBr (0.79 g, 5.5 mmol) in 30 mL of HBr 40%. The resulting mixture was stirred and refluxed for 2 hours. The suspension thus obtained was partitioned between 2N NaOH and ethyl acetate. The organic layer was washed with aqueous NaCl, dried over Na$_2$SO$_4$ and concentrated to afford crude title compound 1.56 g. MS (m/z): 286 (M+2)$^+$ (B) ethyl 1-(4-bromophenyl)piperidine-4-carboxylate To a stirred solution of 1-(4-bromophenyl)piperidine-4-carboxylic acid (1.56 g, 5.5 mmol) in absolute ethanol (30 mL) was cooled to 0° C. and SOCl$_2$ (1.18 g, 10 mmol) added drop-wise. The mixture was stirred to room temperature and heated to reflux for 3 hours. The reaction mixture was evaporated in vacuo and the residue dissolved in saturated aqueous solution of NaHCO$_3$ (50 mL). The aqueous solution was extracted with EtOAc (3×30 mL). The organic extracts was dried over Na$_2$SO$_4$, filtered and evaporated in vacuo. The residue was purified by silica gel column chromatography (eluent; ethyl acetate: hexane=1:1) to yield the title compound pale brown oil 1.08 g. MS (m/z): 314 (M+2)$^+$ (C) 2-(1-(4-bromophenyl)piperidin-4-yl)propan-2-ol Ethyl 1-(4-bromophenyl)piperidine-4-carboxylate (1.08 g, 3.5 mmol) was dissolved in THF (20 mL) under nitrogen atmosphere; methyl magnesium bromide (3.0 M solution in diethyl ether, 3.5 mL, 10.5 mmol) was added drop-wise while cooled with an ice water bath; and the reaction mixture was stirred at room temperature overnight. The reaction mixture was partitioned between ethyl acetate and the saturated aqueous solution of ammonium chloride. The organic layer was washed with brine and dried over anhydrous sodium sulfate. The solvent was removed in vacuo to yield the desired compound (1.0 g) as white solid. MS (m/z): 300 (M+2)$^+$ (D) 2-(1-(4-(4,4,5,5-tetramethyl-1,3,2-dioxaborolan-2-yl)phenyl)piperidin-4-yl)propan-2-ol To a solution of 2-(1-(4-bromophenyl)piperidin-4-yl)propan-2-ol (1.0 g, 3.3 mmol) in DMSO (20 mL) was added bis-pinacolatodiboron (1.15 g, 4.5 mmol) and KOAc (515 mg, 5.3 mmol). The reaction was degassed under vacuum for 30 minutes. then the flask was flushed N$_2$. Pd(dppf)Cl$_2$ (292 mg, 0.4 mmol) was added, then the reaction was heated to 70° C. for 20 hours. After cooling, the reaction mixture was partitioned between ethyl acetate and water. The aqueous layer was extracted with additional ethyl acetate. The organic layers were combined, dried, filtered, and concentrated in vacuo. The residue was purified by silica-gel column to afford title compound as pale yellow solid 590 mg. MS (m/z): 346 (M+H)$^+$ Intermediate 80

2-(1-(4-(4,4,5,5-tetramethyl-1,3,2-dioxaborolan-2-yl)phenyl)piperidin-4-yloxy)ethanol

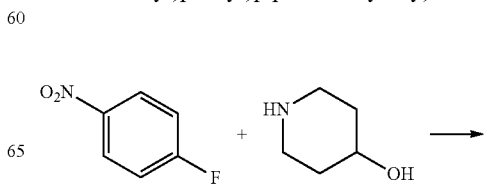

-continued

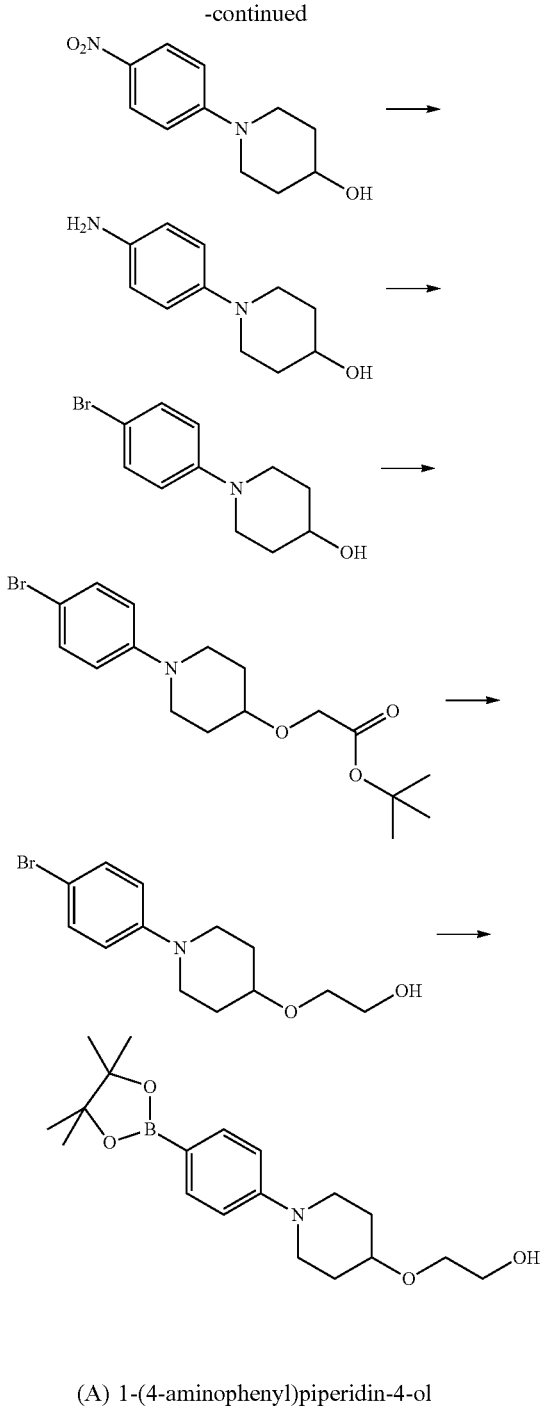

(A) 1-(4-aminophenyl)piperidin-4-ol

To a mixture of 1-fluoro-4-nitrobenzene (2.82 g, 20 mmol) and $K_2CO_3$ (6.92 g, 50 mmol) in dimethyl sulfoxide (20 mL) was added piperidin-4-ol (2.22 g, 22 mmol) and the reaction was heated to 100° C. for 4 hours. This solution was poured into 200 ml of water and extracted with ethyl acetate (30 mL×3). The organic phase was combined and washed with saturated brine and dried over anhydrous sodium sulfate. The solid was filtered and the filtrate, 10% Pd/C (100 mg) was added and the mixture was stirred under hydrogen atmosphere at ambient temperature overnight. The catalyst was filtered, and the filtrate was concentrated to afford tan solid 3.7 g. MS (m/z): 193 $(M+H)^+$ (B) 1-(4-bromophenyl)piperidin-4-ol To a solution of 1-(4-aminophenyl)piperidin-4-ol (3.7 g, 319 mmol) in 60 mL of HBr 48%, a solution of $NaNO_2$ (1.38 g, 20 mmol) in 15 mL of water was slowly added at 0° C. The mixture was stirred for 30 minutes and added to a solution of CuBr (1.57 g, 11 mmol) in 50 mL of HBr 48%. The resulting mixture was stirred and refluxed for 2 hours. The suspension thus obtained was partitioned between 2N NaOH and ethyl acetate. The organic layer was washed with aqueous NaCl, dried over $Na_2SO_4$ and concentrated to afford crude compound as grey solid 4.6 g. MS (m/z): 256 $(M)^+$ (C) tert-butyl 2-(1-(4-bromophenyl)piperidin-4-yloxy)acetate Tetrabutylammonium bromide (1.06 g, 3.3 mmol) is added to a solution of 1-(4-bromophenyl)piperidin-4-ol (2.56 g, 10 mmol) in toluene (30 mL). The reaction mixture was cooled to 0° C. and aq. 35% sodium hydroxide (30 mL) was added followed by a drop-wise addition of tert-butyl bromoacetate (2.92 g, 15 mmol). The mixture was then allowed to reach room temperature and was stirred for 17 hours at this temperature. The layers were separated and the organic layer was washed twice with water (4 mL), dried over sodium sulfate, concentrated under vacuum and co-evaporated with petroleum ether. Purification of the crude material by flash column chromatography on silica gel (0-20% ethyl acetate in petroleum ether) yielded the desired pure material 3.08 g as pale yellow solid. MS (m/z): 372 $(M+2)^+$ (D) 2-(1-(4-bromophenyl)piperidin-4-yloxy)ethanol To a stirred solution of tert-butyl 2-(1-(4-bromophenyl) piperidin-4-yloxy)acetate (3.08 g, 8.3 mmol) in THF (20 mL) at −10° C. under nitrogen was added lithium aluminum hydride (0.57 g, 15 mmol). After 2 hours, the reaction mixture was quenched by sequential addition of water (0.6 mL), 15 percent aqueous sodium hydroxide solution (1.8 mL) and water (0.6 mL). The resulting mixture was filtered and concentrated under vacuum to provide the crude 2-(1-(4-bromophenyl) piperidin-4-yloxy)ethanol 2.16 g. MS (m/z): 302 $(M+2)^+$ (E) 2-(1-(4-(4,4,5,5-tetramethyl-1,3,2-dioxaborolan-2-yl)phenyl)piperidin-4-yloxy)ethanol To a solution of 2-(1-(4-bromophenyl)piperidin-4-yloxy) ethanol (2.16 g, 7.2 mmol) in DMSO (50 mL) was added bis-pinacolatodiboron (2.54 g, 10 mmol) and KOAc (1.17 g, 12 mmol). The reaction was degassed under vacuum for 30 minutes. then the flask was flushed $N_2$. $Pd(dppf)C_2$ (732 mg, 1.0 mmol) was added, then the reaction was heated to 70° C. for 20 hours. After cooling, the reaction mixture was partitioned between ethyl acetate and water. The aqueous layer was extracted with additional ethyl acetate. The organic layers were combined, dried, filtered, and concentrated in vacuo. The residue was purified by silica-gel column (0-70% ethyl acetate in petroleum ether) to afford title compound as pale yellow solid 920 mg. MS (m/z): 348 $(M+H)^+$

83

Intermediate 81

(R)-1-(2-((7-chloropyrido[4,3-b]pyrazin-5-ylamino)methyl)morpholino)-2,2-difluoroethanone

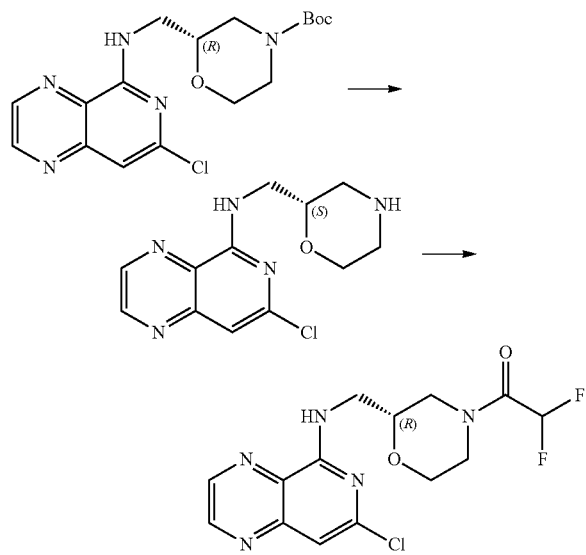

(R)-1-(2-((7-chloropyrido[4,3-b]pyrazin-5-ylamino)methyl)morpholino)-2,2-difluoroethanone The (R)-tert-butyl 2-((7-chloropyrido[4,3-b]pyrazin-5-ylamino)methyl)morpholine-4-carboxylate (3.00 g, 8.0 mmol) was dissolved in the solution of HCl in ethyl acetate (20 mL), and the mixture was stirred at room temperature for 2 hours until TLC indicated Boc group was removed. The volatile materials were removed in vacuo and the residues were dissolved in dichloromethane. To the solution, difluoroacetic acid (1.15 g, 12 mmol), HATU (7.60 g, 20.0 mmol) and DIPEA (6.20 g, 48.0 mmol) were added subsequently and stirred at room temperature overnight. The mixture was purified by $C_{18}$ column chromatography to give the desired amide as yellow solid (2.1 g). MS (m/z): 358 (M+H)+

Intermediate 82

(R)-7-chloro-N-((4-(methylsulfonyl)morpholin-2-yl)methyl)pyrido[4,3-b]pyrazin-5-amine

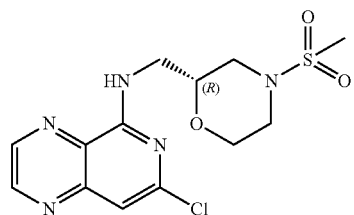

The title compound was prepared according to the procedures of Intermediate 81 using the same starting material. MS (m/z): 358 (M+H)+.

84

Intermediate 83

6-((7-chloro pyrido[4,3-b]pyrazin-5-ylamino)methyl)morpholin-3-one

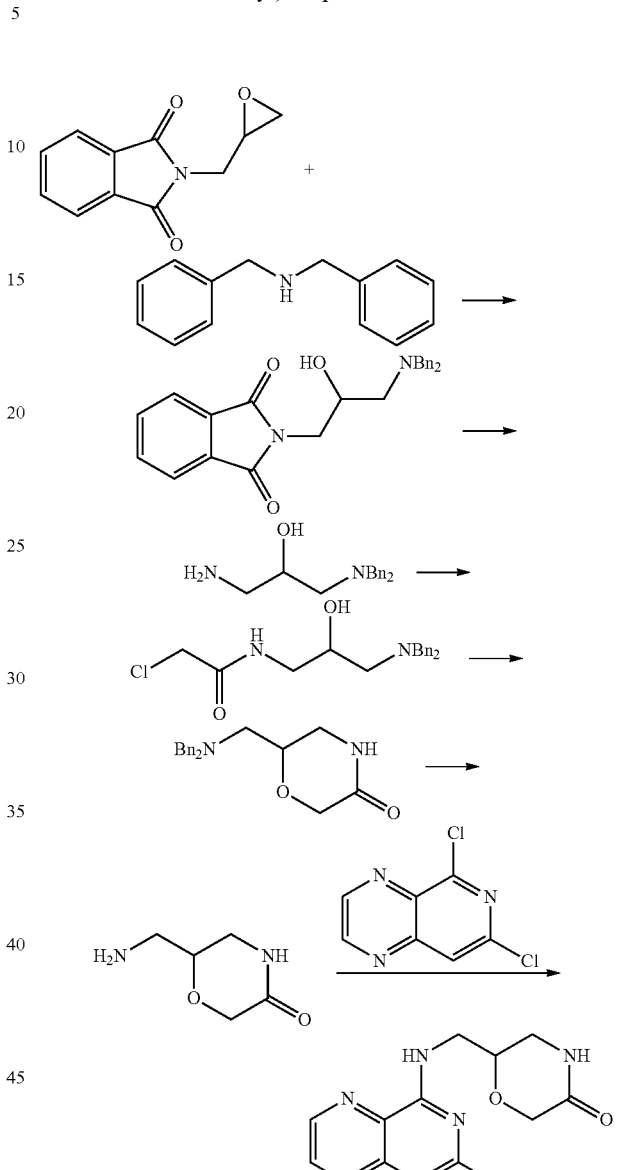

(A) 2-(3-(dibenzylamino)-2-hydroxypropyl)isoindoline-1,3-dione

A mixture of 2-(oxiran-2-ylmethyl)isoindoline-1,3-dione (4.06 g, 20.0 mmol) and dibenzylamine (5.0 g, 25.4 mmol) was stirred at 80° C. overnight. EtOH (50 mL) was added, and stirred at room temperature. The mixture was filtered to give white solid (4.5 g).

(B) 1-amino-3-(dibenzylamino)propan-2-ol

A solution of 2-(3-(dibenzylamino)-2-hydroxypropyl)isoindoline-1,3-dione (4.5 g, 11.25 mmol) in conc. HCl (50 mL) was stirred at 120° C. overnight. After cooling to room temperature, the mixture was filtered. And the filtrate was extracted with CHCl₃. The aqueous layer was added aq. 30% NaOH until pH was above 7, then the solution was extracted with CH₂Cl₂, dried over Na₂SO₄ and concentrated to give yellow solid (3.0 g).

(C) 2-chloro-N-(3-(dibenzylamino)-2-hydroxypropyl)acetamide

A solution of 2-chloroacetyl chloride (1.25 g, 10.96 mmol) in CHCl₃ was added to the solution of 1-amino-3-(dibenzylamino)propan-2-ol (2.5 g, 9.26 mmol) in CHCl₃ (50 mL) in ice-bath. The mixture was stirred for 1 hour, then stirred at room temperature for 2 hours. The organic layer concentrated, the residue was purified by column to give white solid.

(D) 6-((dibenzylamino)methyl)morpholin-3-one

A solution of 2-chloro-N-(3-(dibenzylamino)-2-hydroxypropyl)acetamide (1.0 g, 2.49 mmol), t-BuOK (0.39 g, 3.57 mmol) in t-BuOH (30 mL) was stirred at reflux overnight. After concentration, the residue was purified by column chromatography to give product as white solid.

(E) 6-(aminomethyl)morpholin-3-one

A solution of 6-((dibenzylamino)methyl)morpholin-3-one (340 mg, 1.09 mmol), Pd(OH)₂/C (170 mg) in EtOH (30 mL) was stirred equipped under H₂ balloon overnight. The solution was filtered and concentrated to give white oil. The crude product was used directly for next step without purification.

(F) 6-((7-chloropyrido[4,3-b]pyrazin-5-ylamino)methyl)morpholin-3-one

A solution of 6-(aminomethyl)morpholin-3-one (130 mg, 1 mmol), 5,7-dichloropyrido[4,3-b]pyrazine (200 mg, 1 mmol) and DIEA (260 mg, 2 mmol) in THF (20 mL) was stirred at reflux overnight. After concentration, the residue was purified by column chromatography to give product as yellow solid (100 mg).

Example 1

Synthesis of Compounds 1-516

Compound 1

((R)-7-(4-morpholinophenyl)-N-(piperidin-3-yl methyl)pyrido[4,3-b]pyrazin-5-amine

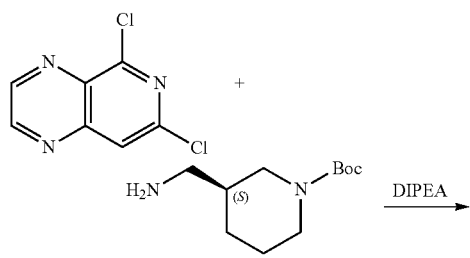

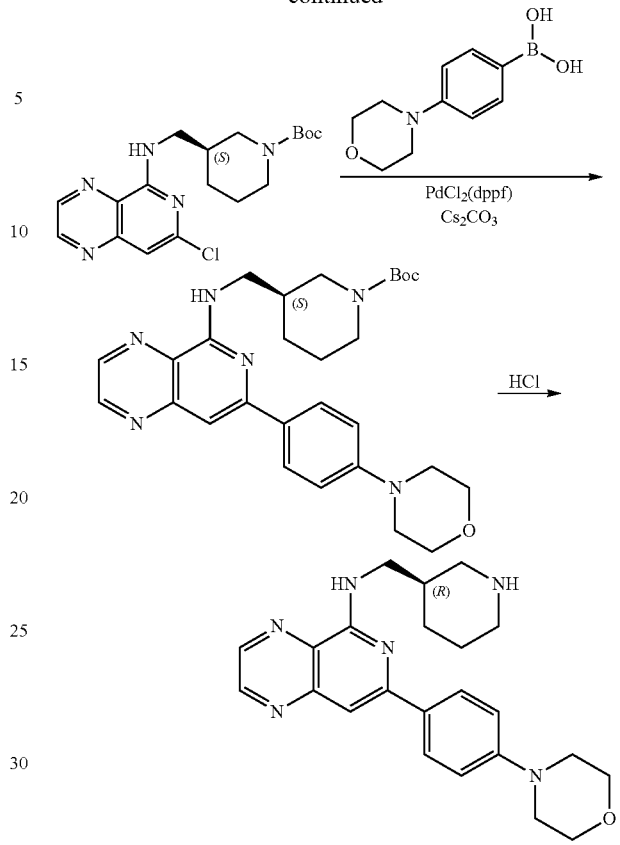

(A) (S)-tert-butyl 3-((7-chloropyrido[4,3-b]pyrazin-5-ylamino)methyl)piperidine-1-carboxylate A solution of (S)-tert-butyl 3-(aminomethyl)piperidine-1-carboxylate (100 mg, 0.5 mmol), 5,7-dichloropyrido[4,3-b]pyrazine (100 mg, 0.5 mmol) and DIPEA (77 mg, 0.6 mmol) in THF (5 mL) was stirred at room temperature for 4 hours. The volatiles were removed under reduced pressure, and the residue was treated with ethyl acetate, with brine, and concentrated to give the crude title compound.

(B) (S)-tert-butyl 3-((7-(4-morpholinophenyl)pyrido[4,3-b]pyrazin-5-ylamino)methyl)piperidine-1-carboxylate A mixture of (S)-tert-butyl 3-((7-chloropyrido[4,3-b]pyrazin-5-ylamino)methyl)piperidine-1-carboxylate (0.15 mmol), 4-morpholinophenylboronic acid (0.23 mmol), PdCl₂ (dppf) (0.015 mmol) and Cs₂CO₃ (0.30 mmol) in dimethoxyethane/ethanol was sealed in a microwave reaction and stirred at 160° C. for 45 minutes in a microwave reactor. The mixture was cooled to room temperature, concentrated, and purified by chromatography to afford the title compound (73% yield). MS (m/z): 505 (M+H)⁺.

(C) ((R)-7-(4-morpholinophenyl)-N-(piperidin-3-ylmethyl)pyrido[4,3-b]pyrazin-5-amine (S)-tert-butyl 3-((7-(4-morpholinophenyl)pyrido[4,3-b]pyrazin-5-ylamino)methyl)piperidine-1-carboxylate (0.11 mmol) was treated with HCl solution (in EtOAc, 4 N, 3 mL)

at room temperature until the reaction was completed. The precipitates were collected by filtration and further purified by chromatography to afford the title compound. MS (m/z): 405 (M+H)$^+$.

The following compounds were prepared according to the procedures of Compound 1 using the corresponding intermediates and reagents under appropriate conditions that will be recognized by one skilled in the art.

| Compound | Structure | MS (M + H)$^+$ |
|---|---|---|
| 2 | 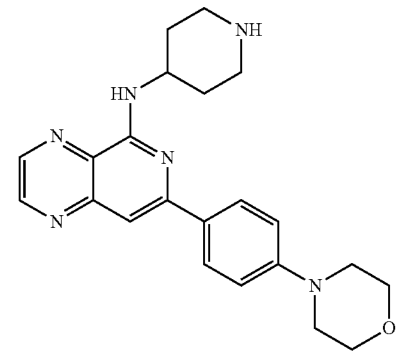 [SMILES: c1cnc2c(NC3CCNCC3)nc(-c3ccc(N4CCOCC4)cc3)cc2n1] | 391 |
| 3 | 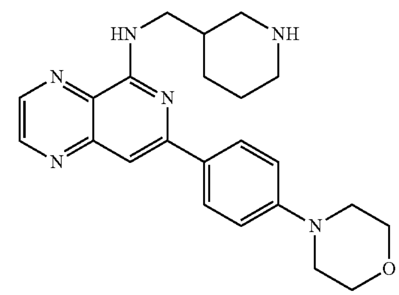 | 405 |
| 4 | 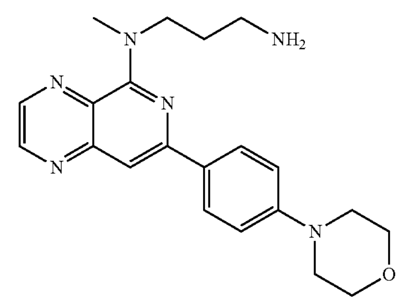 [SMILES: CN(CCCN)c1nc(-c2ccc(N3CCOCC3)cc2)cc2nccnc12] | 379 |
| 5 | 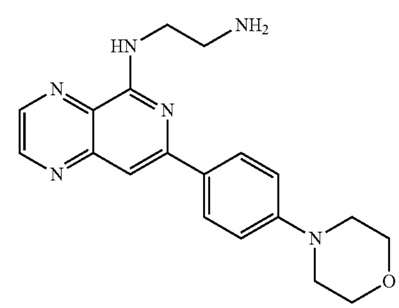 [SMILES: NCCNc1nc(-c2ccc(N3CCOCC3)cc2)cc2nccnc12] | 351 |

-continued

| Compound | Structure | MS (M + H)+ |
|---|---|---|
| 6 | 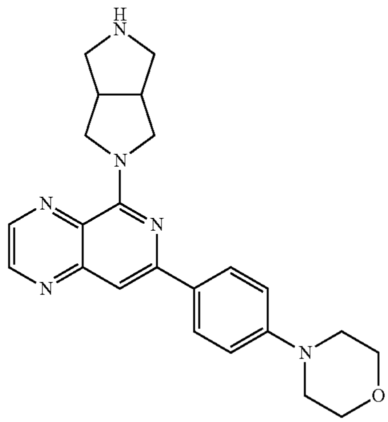 [SMILES: c1cnc2c(N3CC4CNCC4C3)nc(-c3ccc(N4CCOCC4)cc3)cc2n1] | 403 |
| 7 | 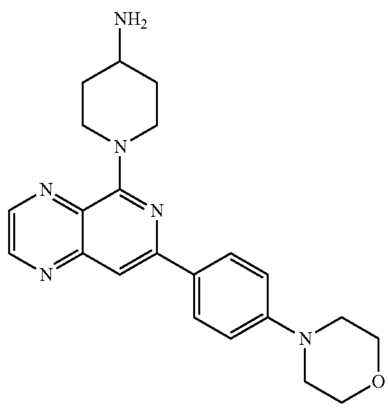 [SMILES: NC1CCN(c2nc(-c3ccc(N4CCOCC4)cc3)cc3nccnc23)CC1] | 391 |
| 8 | 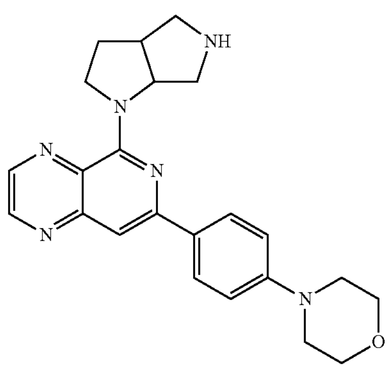 [SMILES: c1cnc2c(N3CCC4CNCC43)nc(-c3ccc(N4CCOCC4)cc3)cc2n1] | 403 |
| 9 | 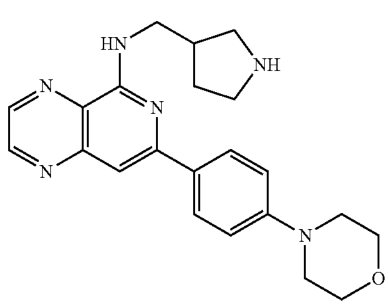 [SMILES: c1cnc2c(NCC3CCNC3)nc(-c3ccc(N4CCOCC4)cc3)cc2n1] | 391 |

-continued
| Compound | Structure | MS (M + H)+ |
|---|---|---|
| 10 | 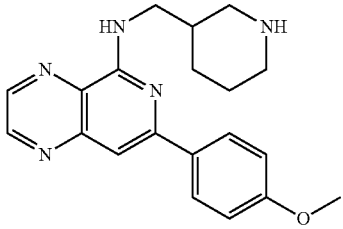 [SMILES: COc1ccc(-c2cc3nccnc3c(NCC3CCCNC3)n2)cc1] | 350 |
| 11 | 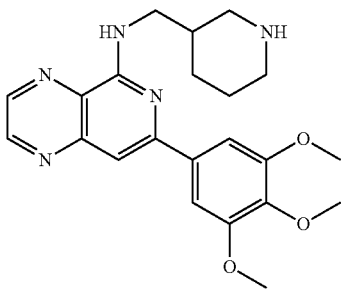 [SMILES: COc1cc(-c2cc3nccnc3c(NCC3CCCNC3)n2)cc(OC)c1OC] | 410 |
| 12 | 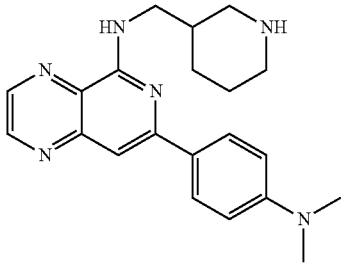 [SMILES: CN(C)c1ccc(-c2cc3nccnc3c(NCC3CCCNC3)n2)cc1] | 363 |
| 13 | 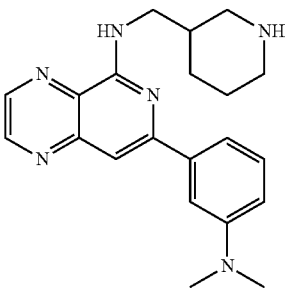 [SMILES: CN(C)c1cccc(-c2cc3nccnc3c(NCC3CCCNC3)n2)c1] | 363 |
| 14 | 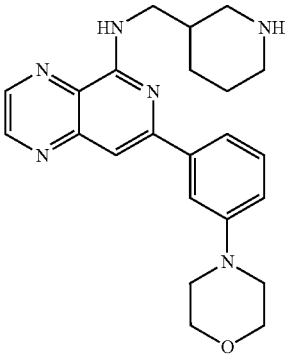 | 405 |

-continued

| Compound | Structure | MS (M + H)+ |
|---|---|---|
| 15 | pyrido[3,4-b]pyrazine with 5-(piperidin-3-ylmethylamino) and 7-(3,5-dimethoxyphenyl) | 380 |
| 16 | pyrido[3,4-b]pyrazine with 5-(piperidin-3-ylmethylamino) and 7-(2-methoxyphenyl) | 350 |
| 17 | pyrido[3,4-b]pyrazine with 5-(piperidin-3-ylmethylamino) and 7-(3-methoxyphenyl) | 350 |
| 18 | pyrido[3,4-b]pyrazine with 5-(piperidin-3-ylmethylamino) and 7-(1-methyl-1H-pyrazol-4-yl) | 324 |
| 19 | pyrido[3,4-b]pyrazine with 5-(piperidin-3-ylmethylamino) and 7-(3-fluoro-4-methoxyphenyl) | 368 |
| 20 | pyrido[3,4-b]pyrazine with 5-(piperidin-3-ylmethylamino) and 7-(3-chloro-4-fluorophenyl) | 372<br>374 |

| Compound | Structure | MS (M + H)+ |
|---|---|---|
| 21 | 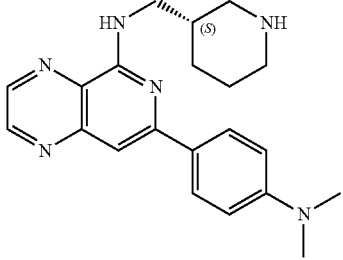 | 363 |
| 22 | 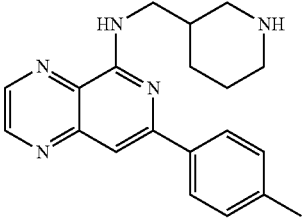 [SMILES: Cc1ccc(-c2cc3nccnc3c(NCC3CCCNC3)n2)cc1] | 334 |
| 23 | 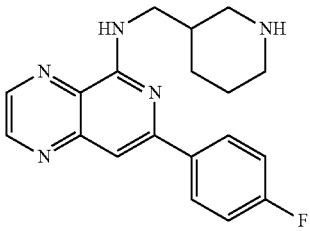 [SMILES: Fc1ccc(-c2cc3nccnc3c(NCC3CCCNC3)n2)cc1] | 338 |
| 24 | 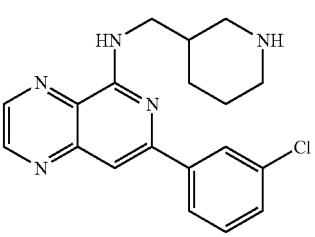 [SMILES: Clc1cccc(-c2cc3nccnc3c(NCC3CCCNC3)n2)c1] | 354<br>356 |
| 25 | 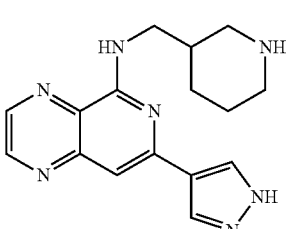 | 310 |
| 26 | 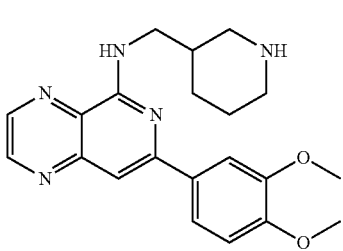 [SMILES: COc1ccc(-c2cc3nccnc3c(NCC3CCCNC3)n2)cc1OC] | 380 |

-continued

| Compound | Structure | MS (M + H)+ |
|---|---|---|
| 27 | 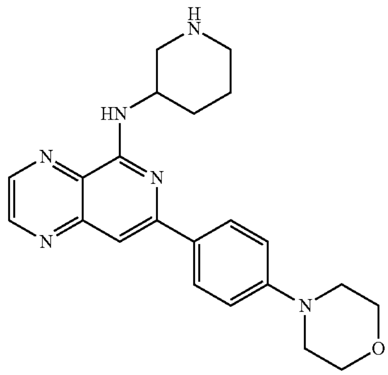 [SMILES: c1cnc2c(NC3CCCNC3)nc(-c3ccc(N4CCOCC4)cc3)cc2n1] | 391 |
| 28 | 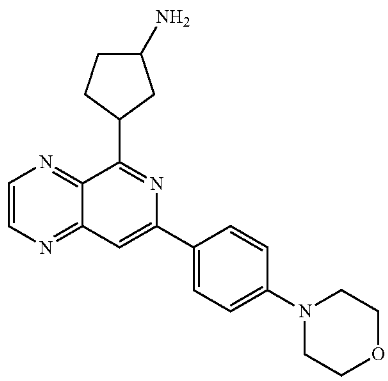 | 377 |
| 29 | 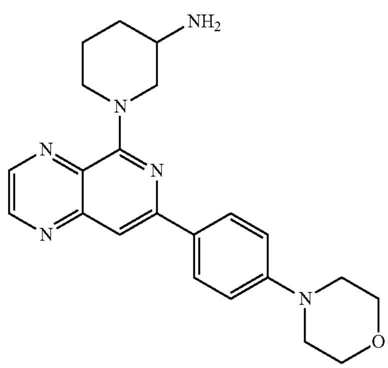 [SMILES: NC1CCCN(c2nc(-c3ccc(N4CCOCC4)cc3)cc3nccnc23)C1] | 390 |
| 30 | 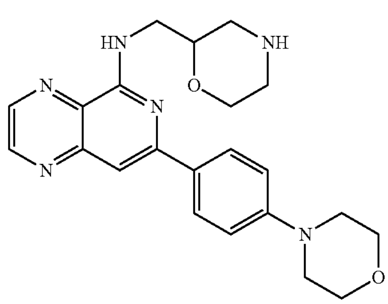 | 407 |

-continued

| Compound | Structure | MS (M + H)+ |
|---|---|---|
| 31 | 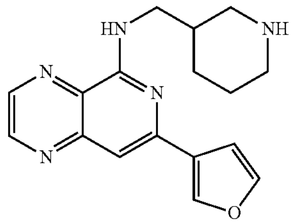 [SMILES: c1cnc2c(NCC3CCCNC3)nc(-c3ccoc3)cc2n1] | 310 |
| 32 | 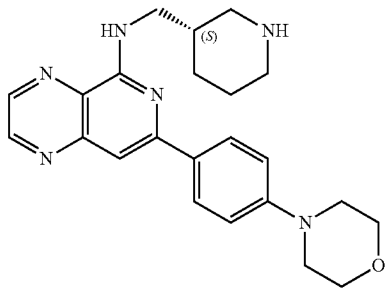 | 405 |
| 33 | 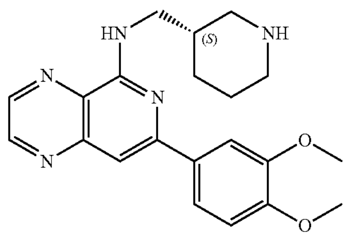 | 380 |
| 34 | 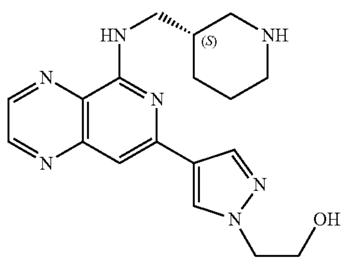 | 354 |
| 35 | 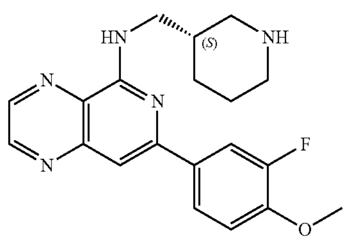 | 368 |
| 36 | 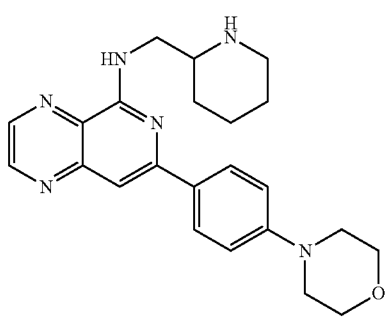 [SMILES: c1cnc2c(NCC3CCCCN3)nc(-c3ccc(N4CCOCC4)cc3)cc2n1] | 405 |

-continued

| Compound | Structure | MS (M + H)+ |
|---|---|---|
| 37 | 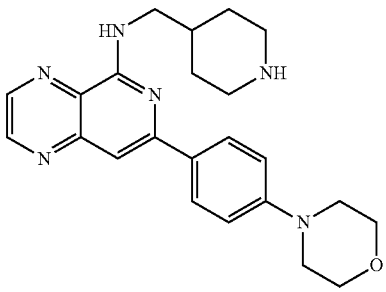 [SMILES: c1cnc2c(NCC3CCNCC3)nc(-c3ccc(N4CCOCC4)cc3)cc2n1] | 405 |
| 38 | 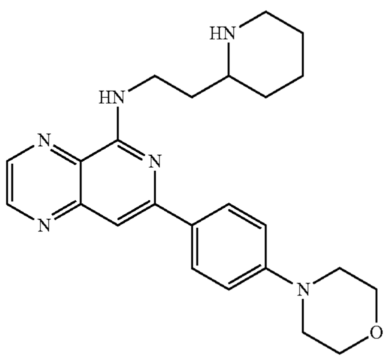 [SMILES: c1cnc2c(NCCC3CCCCN3)nc(-c3ccc(N4CCOCC4)cc3)cc2n1] | 415 |
| 39 | 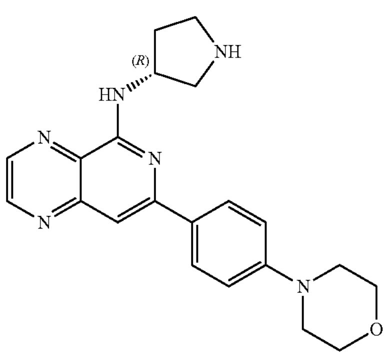 | 377 |
| 40 | 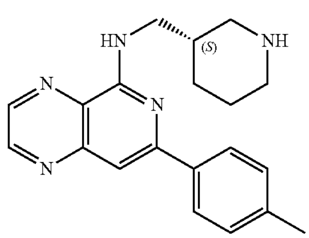 | 334 |
| 41 | 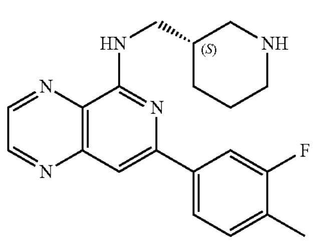 | 352 |

-continued

| Compound | Structure | MS (M + H)+ |
|---|---|---|
| 42 | 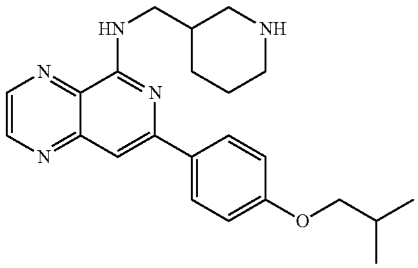 [SMILES: CC(C)COc1ccc(-c2cc3nccnc3c(NCC3CCCNC3)n2)cc1] | 392 |
| 43 | 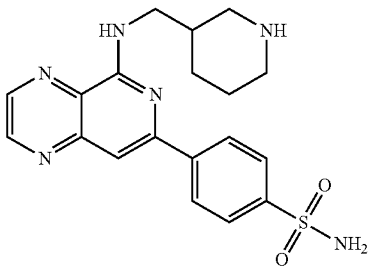 [SMILES: NS(=O)(=O)c1ccc(-c2cc3nccnc3c(NCC3CCCNC3)n2)cc1] | 399 |
| 44 | 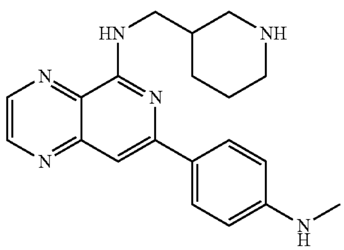 | 349 |
| 45 | 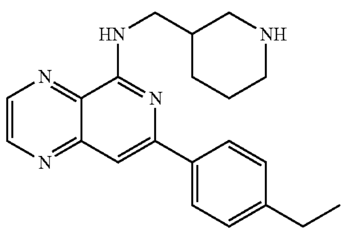 [SMILES: CCc1ccc(-c2cc3nccnc3c(NCC3CCCNC3)n2)cc1] | 348 |
| 46 | 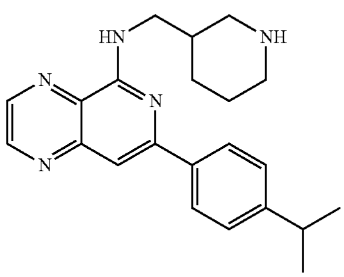 | 362 |
| 47 | 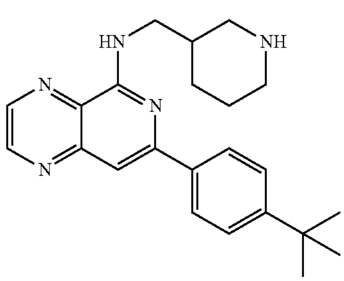 [SMILES: CC(C)(C)c1ccc(-c2cc3nccnc3c(NCC3CCCNC3)n2)cc1] | 376 |

-continued

| Compound | Structure | MS (M + H)+ |
|---|---|---|
| 48 | (structure) | 407 |
| 49 | (structure) | 407 |
| 50 | (structure) | 321 |
| 51 | (structure) | 321 |
| 52 | (structure) | 396 |
| 53 | (structure) | 413 |

| Compound | Structure | MS (M + H)+ |
|---|---|---|
| 54 | 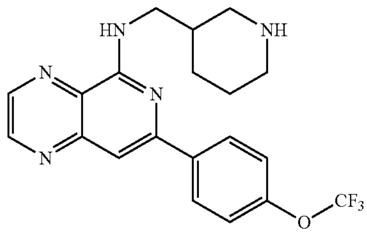 [SMILES: FC(F)(F)Oc1ccc(-c2cc3nccnc3c(NCC3CCCNC3)n2)cc1] | 404 |
| 55 | 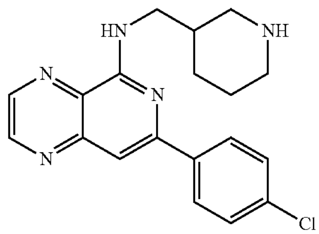 [SMILES: Clc1ccc(-c2cc3nccnc3c(NCC3CCCNC3)n2)cc1] | 354<br>356 |
| 56 | 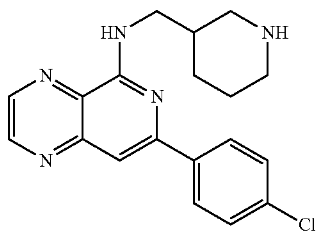 | 351 |
| 57 | 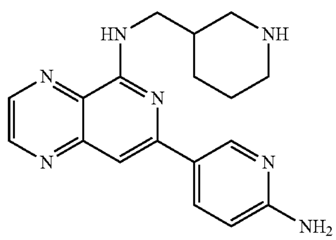 | 336 |
| 58 | 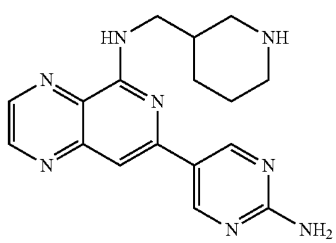 | 337 |
| 59 | 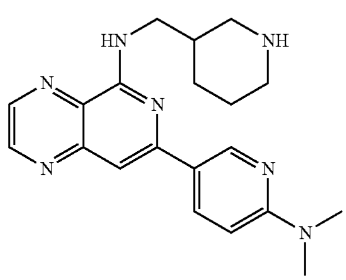 [SMILES: CN(C)c1ccc(-c2cc3nccnc3c(NCC3CCCNC3)n2)cn1] | 364 |

-continued

| Compound | Structure | MS (M + H)+ |
|---|---|---|
| 60 | 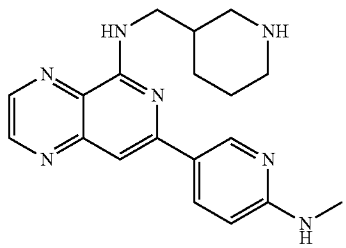 [SMILES: CNc1ccc(-c2cc3nccnc3c(NCC3CCCNC3)n2)cn1] | 350 |
| 61 | 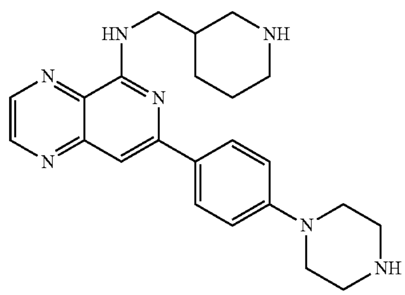 [SMILES: c1cnc2c(NCC3CCCNC3)nc(-c3ccc(N4CCNCC4)cc3)cc2n1] | 404 |
| 62 | 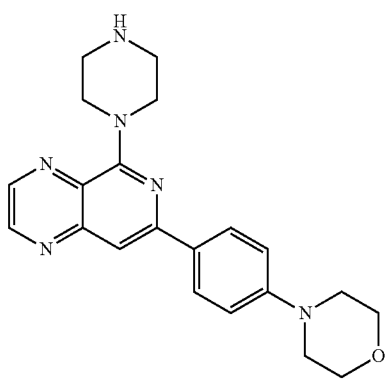 [SMILES: c1cnc2c(N3CCNCC3)nc(-c3ccc(N4CCOCC4)cc3)cc2n1] | 377 |
| 63 | 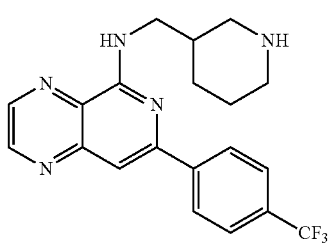 [SMILES: FC(F)(F)c1ccc(-c2cc3nccnc3c(NCC3CCCNC3)n2)cc1] | 388 |
| 64 | 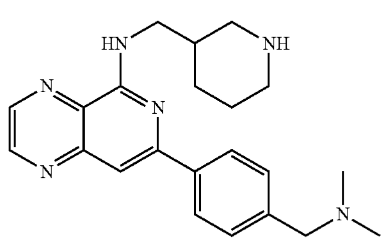 [SMILES: CN(C)Cc1ccc(-c2cc3nccnc3c(NCC3CCCNC3)n2)cc1] | 377 |

-continued

| Compound | Structure | MS (M + H)+ |
|---|---|---|
| 65 | 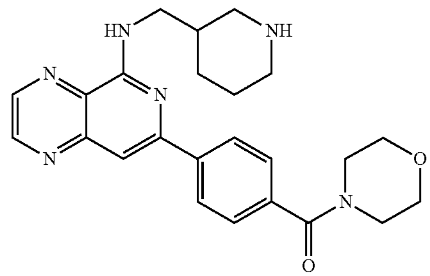 [SMILES: O=C(c1ccc(-c2cc3nccnc3c(NCC3CCCNC3)n2)cc1)N1CCOCC1] | 433 |
| 66 | 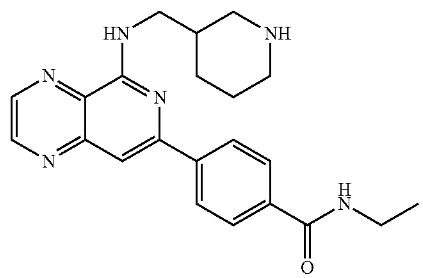 [SMILES: CCNC(=O)c1ccc(-c2cc3nccnc3c(NCC3CCCNC3)n2)cc1] | 391 |
| 67 | 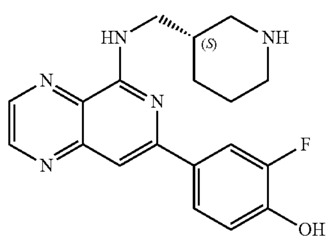 | 354 |
| 68 | 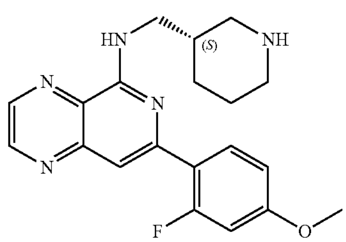 | 368 |
| 69 | 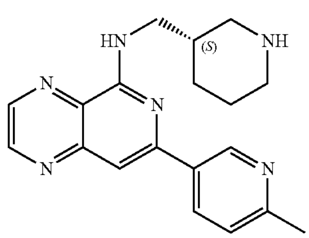 | 335 |
| 70 | 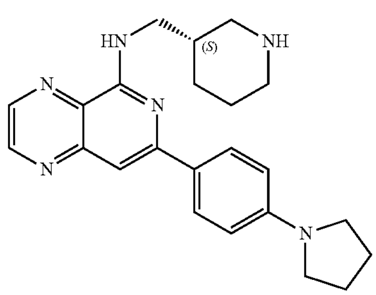 | 389 |

-continued

| Compound | Structure | MS (M + H)+ |
|---|---|---|
| 71 | 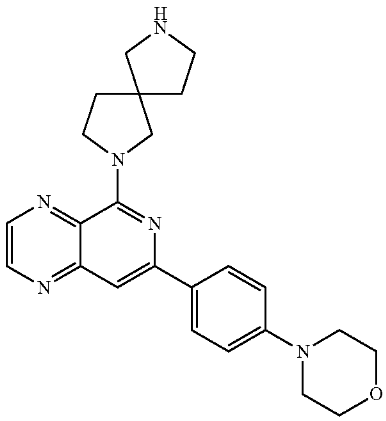 [SMILES: c1cnc2c(N3CCC4(CCNC4)C3)nc(-c3ccc(N4CCOCC4)cc3)cc2n1] | 417 |
| 72 | 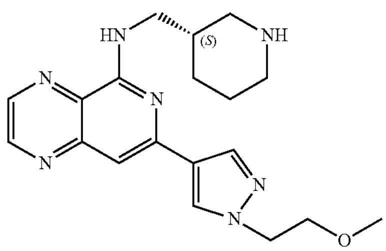 | 368 |
| 73 | 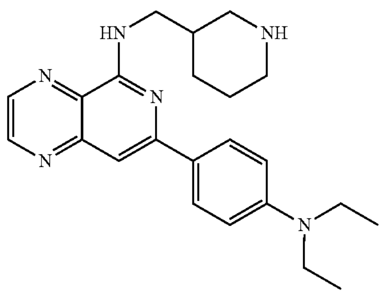 [SMILES: CCN(CC)c1ccc(-c2cc3nccnc3c(NCC3CCCNC3)n2)cc1] | 391 |
| 74 | 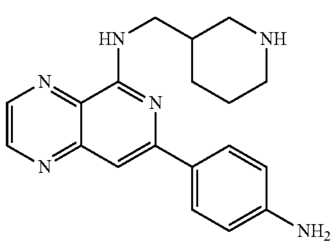 [SMILES: Nc1ccc(-c2cc3nccnc3c(NCC3CCCNC3)n2)cc1] | 335 |
| 75 | 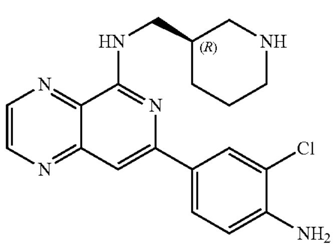 | 369<br>371 |

-continued

| Compound | Structure | MS (M + H)+ |
|---|---|---|
| 76 | 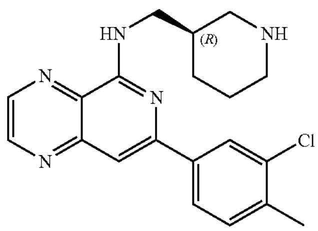 | 368 370 |
| 77 | 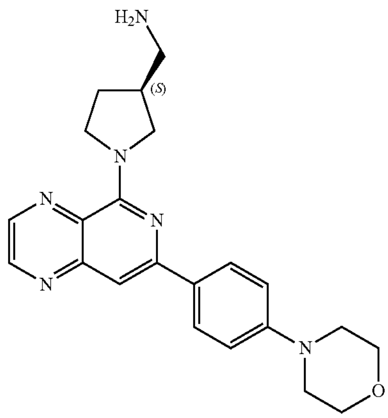 | 391 |
| 78 | 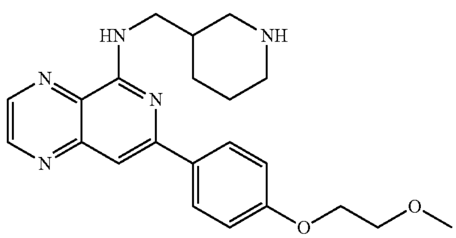 [SMILES: COCCOc1ccc(-c2cc3nccnc3c(NCC3CCCNC3)n2)cc1] | 394 |
| 79 | 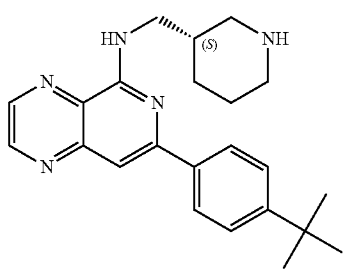 | 376 |
| 80 | 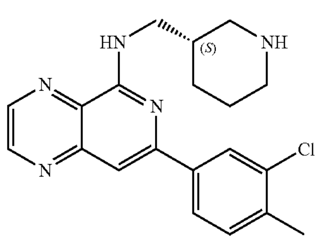 | 368 370 |

-continued

| Compound | Structure | MS (M + H)+ |
|---|---|---|
| 81 | 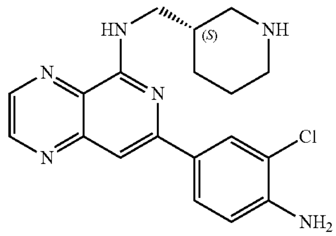 | 369, 371 |
| 82 | 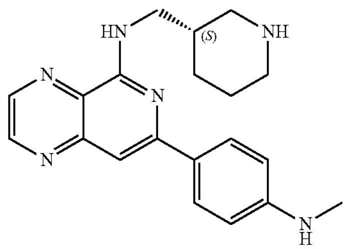 | 349 |
| 83 | 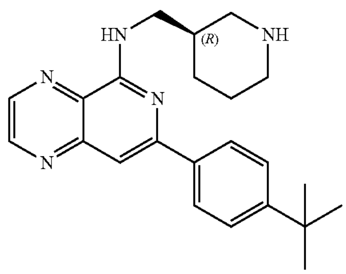 | 376 |
| 84 | 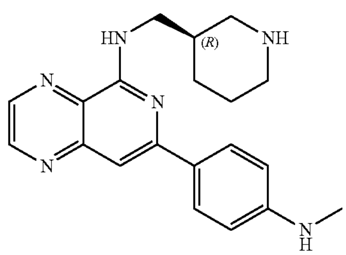 | 349 |
| 85 | 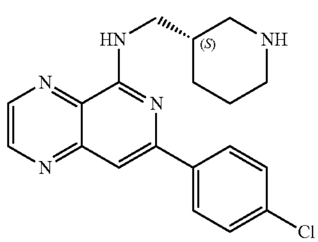 | 354, 356 |
| 86 | 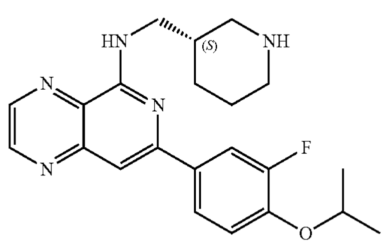 | 396 |

-continued

| Compound | Structure | MS (M + H)+ |
|---|---|---|
| 87 | 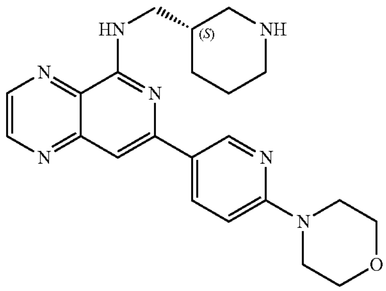 | 406 |
| 88 | 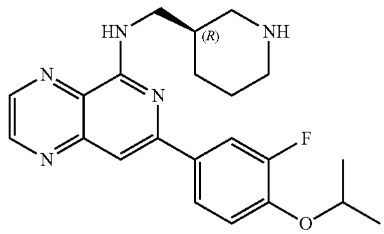 | 396 |
| 89 | 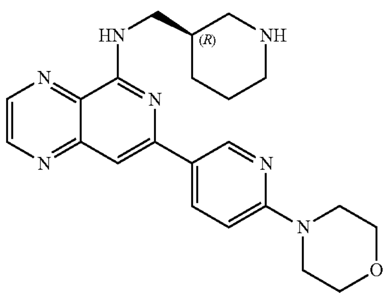 | 406 |
| 90 | 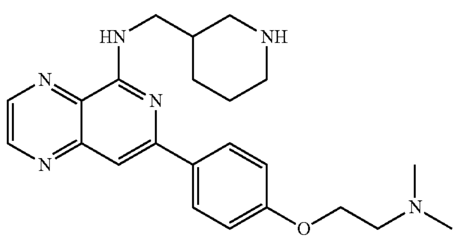 [SMILES: CN(C)CCOc1ccc(-c2cc3nccnc3c(NCC3CCCNC3)n2)cc1] | 407 |
| 91 | 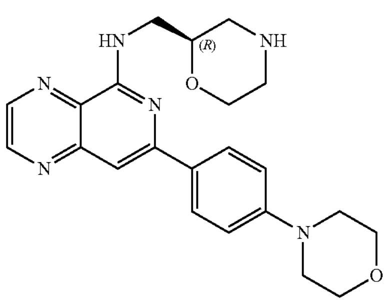 | 407 |

-continued

| Compound | Structure | MS (M + H)+ |
|---|---|---|
| 92 | 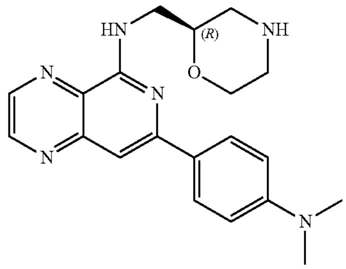 | 365 |
| 93 | 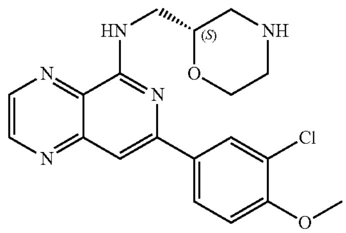 | 384<br>386 |
| 94 | 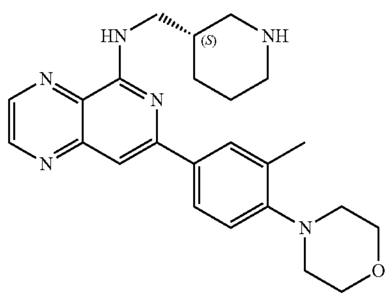 | 419 |
| 95 | 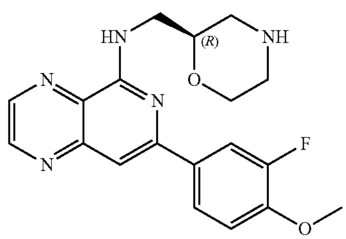 | 370 |
| 96 | 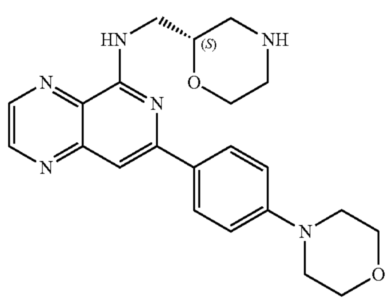 | 407 |

-continued

| Compound | Structure | MS (M + H)+ |
|---|---|---|
| 97 | 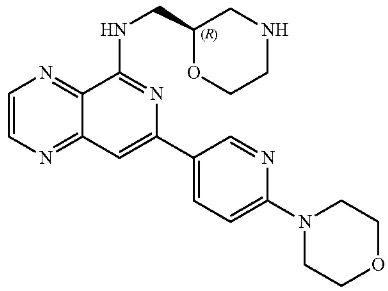 | 408 |
| 98 | 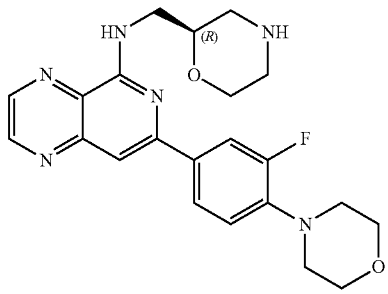 | 425 |
| 99 | 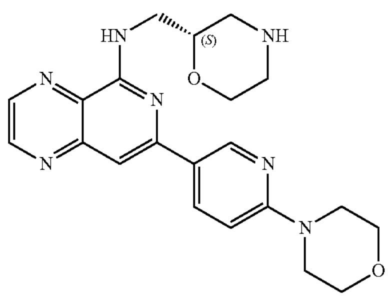 | 408 |
| 100 | 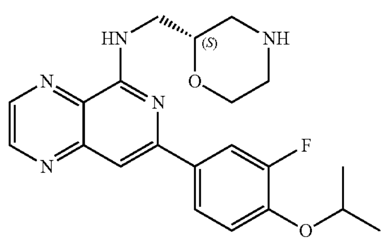 | 396 |
| 101 | 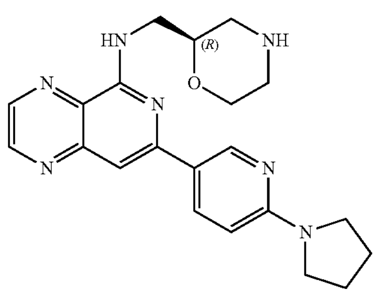 | 392 |

-continued

| Compound | Structure | MS (M + H)+ |
|---|---|---|
| 102 | 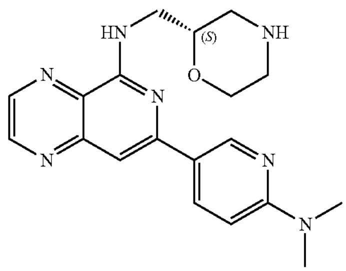 | 366 |
| 103 | 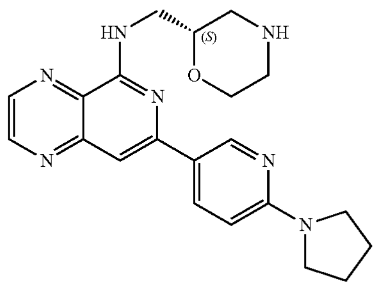 | 392 |
| 104 | 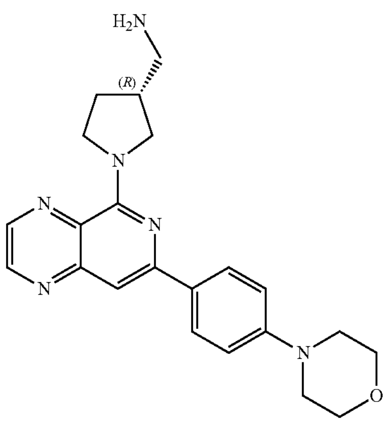 | 391 |
| 105 | 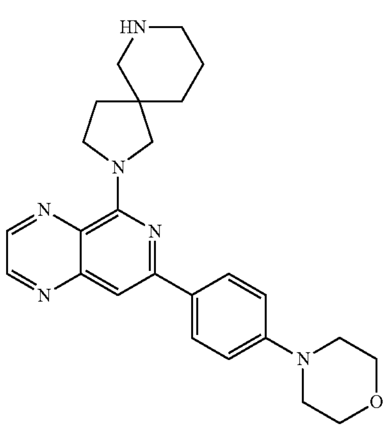 [SMILES: c1cnc2c(N3CCC4(CCCNC4)C3)nc(-c3ccc(N4CCOCC4)cc3)cc2n1] | 431 |

-continued

| Compound | Structure | MS (M + H)+ |
|---|---|---|
| 106 | 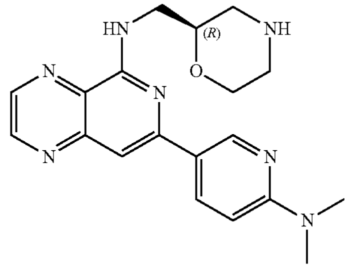 | 366 |
| 107 | 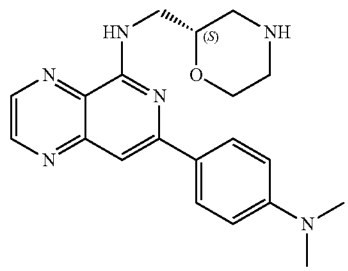 | 365 |
| 108 | 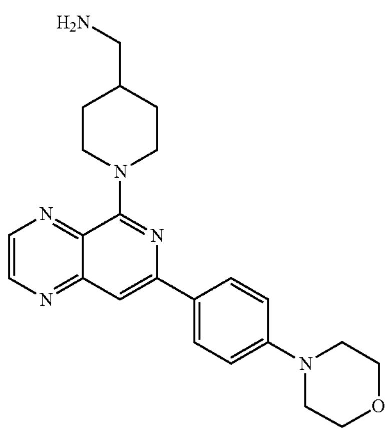 [SMILES: NCC1CCN(c2nc(-c3ccc(N4CCOCC4)cc3)cc3nccnc23)CC1] | 405 |
| 109 | 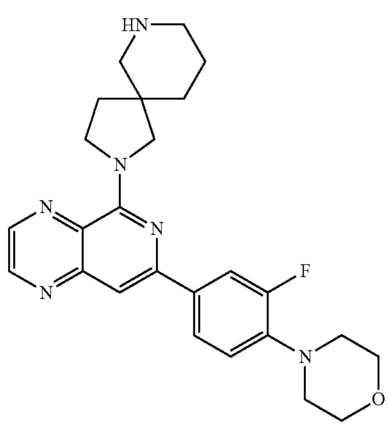 [SMILES: Fc1cc(-c2cc3nccnc3c(N3CCC4(CCCNC4)C3)n2)ccc1N1CCOCC1] | 449 |

-continued
| Compound | Structure | MS (M + H)+ |
|---|---|---|
| 110 | 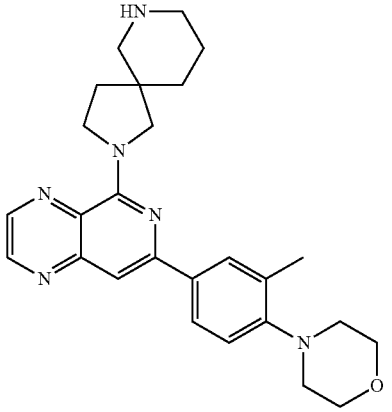 [SMILES: Cc1cc(-c2cc3nccnc3c(N3CCC4(CCCNC4)C3)n2)ccc1N1CCOCC1] | 445 |
| 111 | 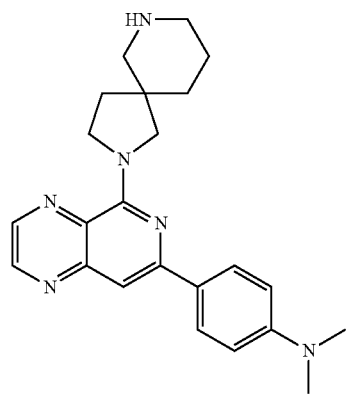 [SMILES: CN(C)c1ccc(-c2cc3nccnc3c(N3CCC4(CCCNC4)C3)n2)cc1] | 389 |
| 112 | 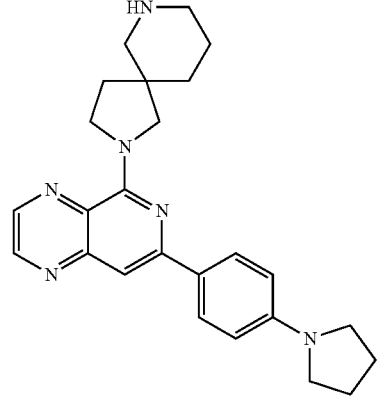 [SMILES: c1cnc2c(N3CCC4(CCCNC4)C3)nc(-c3ccc(N4CCCC4)cc3)cc2n1] | 415 |
| 113 | 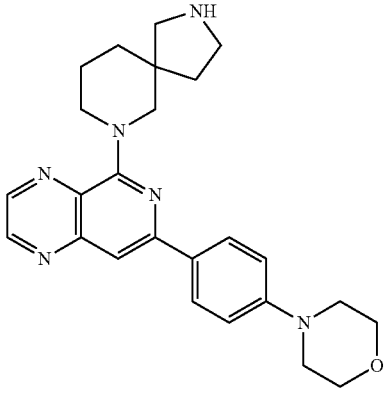 [SMILES: c1cnc2c(N3CCCC4(CCNC4)C3)nc(-c3ccc(N4CCOCC4)cc3)cc2n1] | 431 |

-continued

| Compound | Structure | MS (M + H)+ |
|---|---|---|
| 114 | 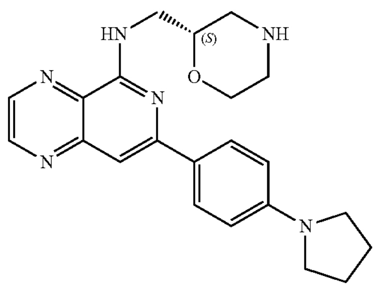 | 391 |
| 115 | 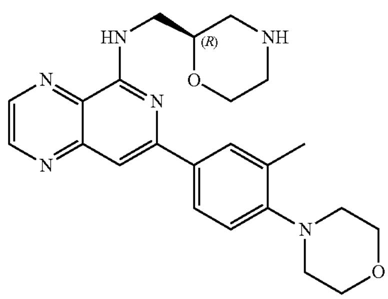 | 421 |
| 116 | 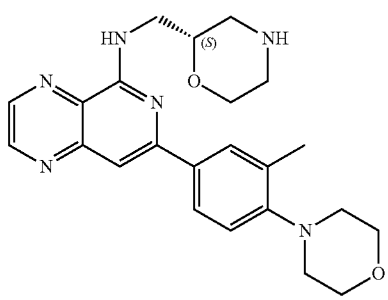 | 421 |
| 117 | 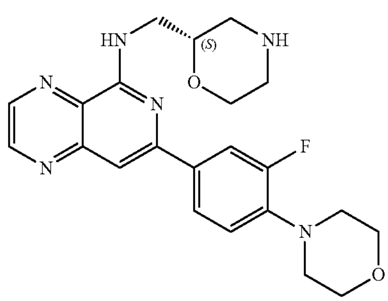 | 425 |
| 118 | 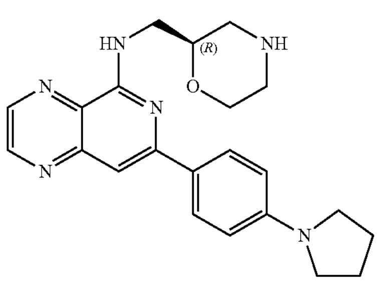 | 391 |

-continued

| Compound | Structure | MS (M + H)+ |
|---|---|---|
| 119 | 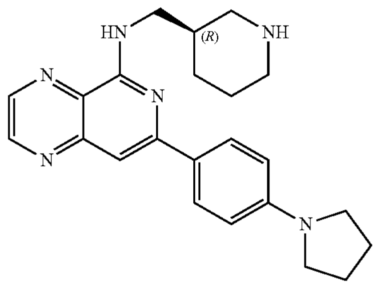 | 389 |
| 120 | 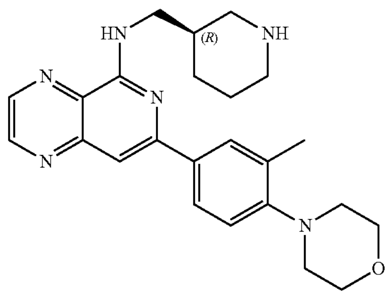 | 419 |
| 121 | 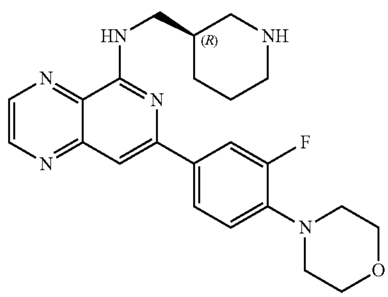 | 423 |
| 122 | 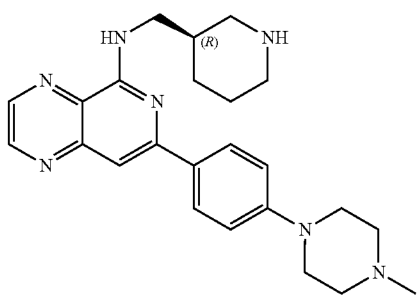 | 418 |
| 123 | 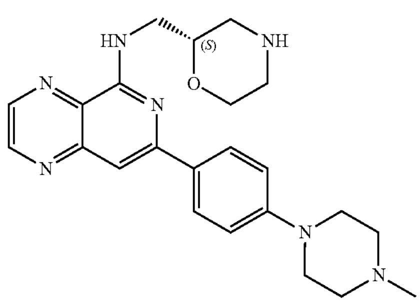 | 420 |

| Compound | Structure | MS (M + H)+ |
|---|---|---|
| 124 | 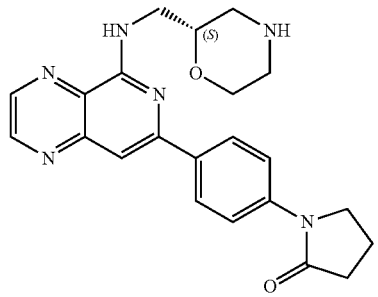 | 405 |
| 125 | 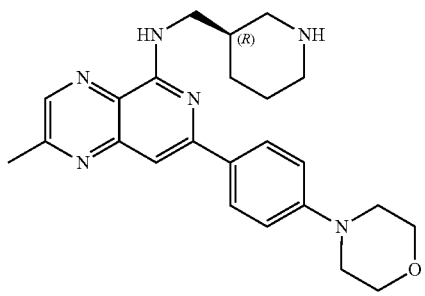 | 419 |
| 126 | 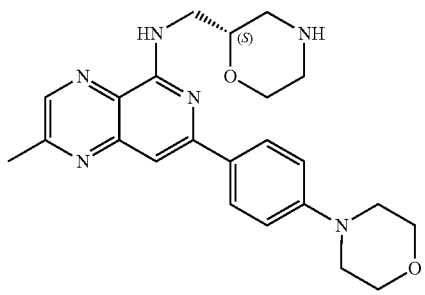 | 421 |
| 127 | 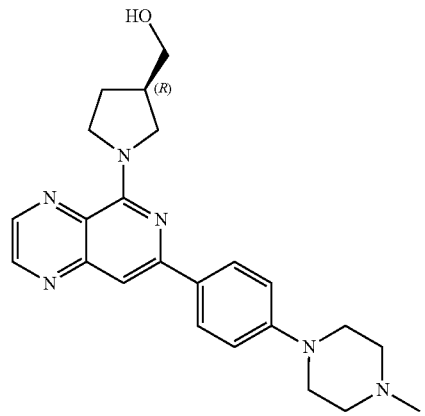 | 405 |

-continued
| Compound | Structure | MS (M + H)+ |
|---|---|---|
| 128 | 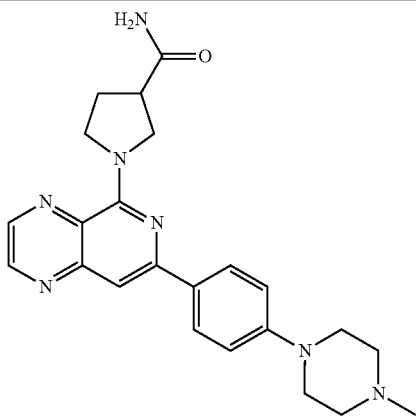 [SMILES: CN1CCN(c2ccc(-c3cc4nccnc4c(N4CCC(C(N)=O)C4)n3)cc2)CC1] | 418 |
| 129 | 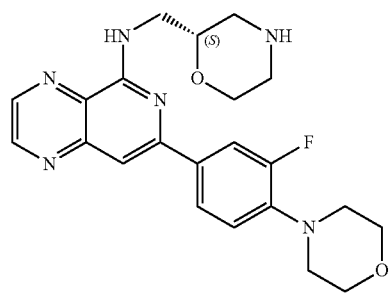 | 423 |
| 130 | 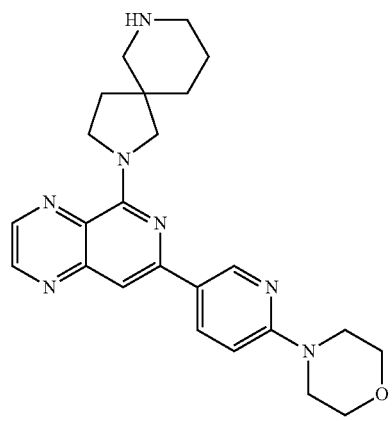 [SMILES: c1cnc2c(N3CCC4(CCCNC4)C3)nc(-c3ccc(N4CCOCC4)nc3)cc2n1] | 432 |
| 131 | 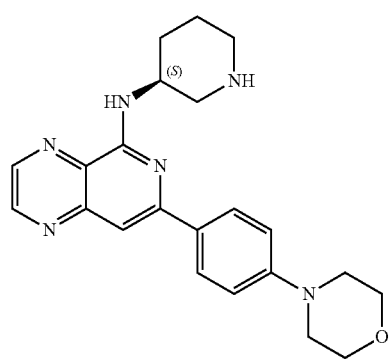 | 391 |

-continued

| Compound | Structure | MS (M + H)+ |
|---|---|---|
| 132 | 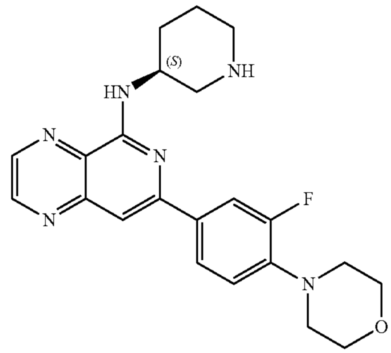 | 409 |
| 133 | 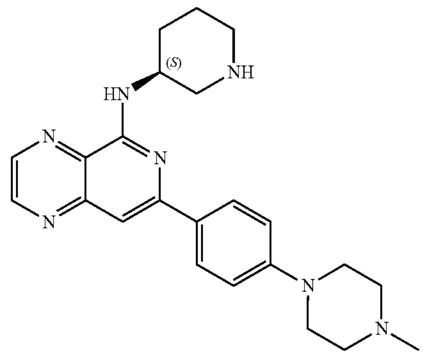 | 404 |
| 134 | 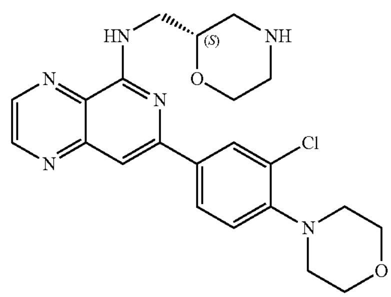 | 442<br>444 |
| 135 | 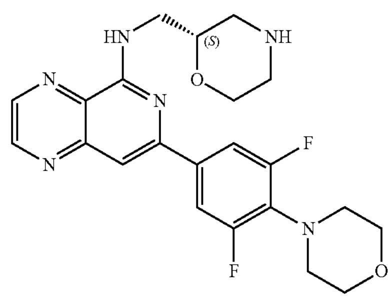 | 443 |
| 136 | 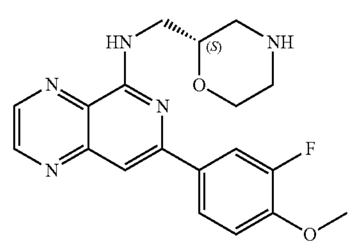 | 370 |

-continued

| Compound | Structure | MS (M + H)+ |
|---|---|---|
| 137 | 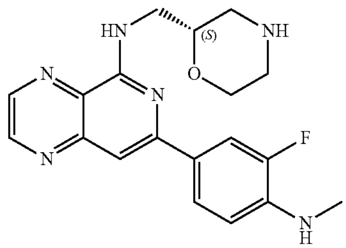 | 369 |
| 138 | 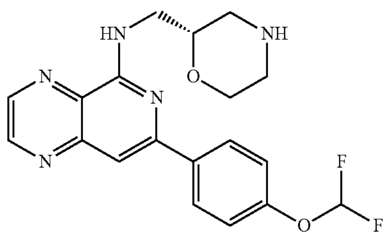 [SMILES: FC(F)Oc1ccc(-c2cc3nccnc3c(NC[C@@H]3CNCCO3)n2)cc1] | 388 |
| 139 | 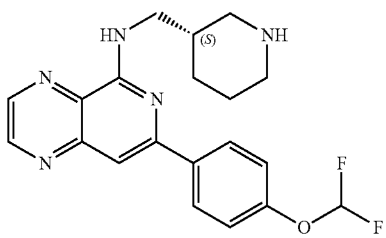 | 386 |
| 140 | 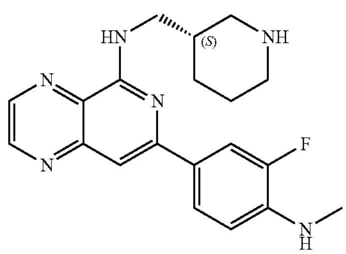 | 367 |
| 141 | 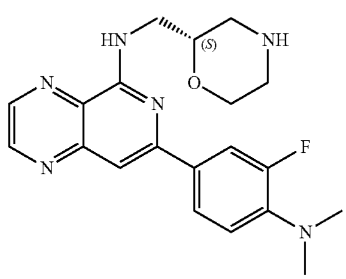 | 383 |
| 142 | 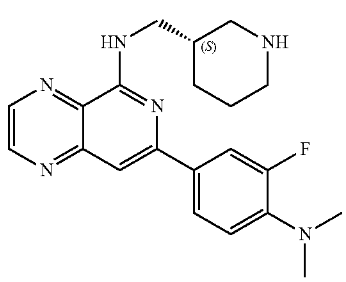 | 381 |

-continued

| Compound | Structure | MS (M + H)+ |
|---|---|---|
| 143 | 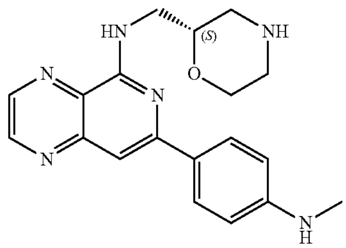 | 351 |
| 144 | 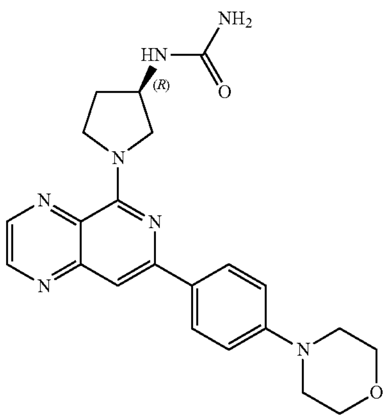 | 420 |
| 208 | 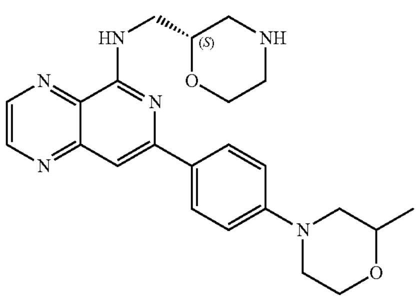 | 421 |
| 209 | 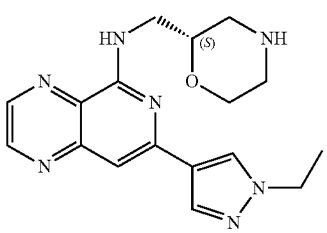 | 340 |
| 210 | 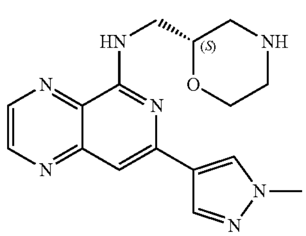 | 326 |

-continued

| Compound | Structure | MS (M + H)+ |
|---|---|---|
| 211 | 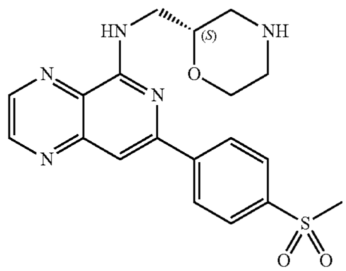 | 400 |
| 212 | 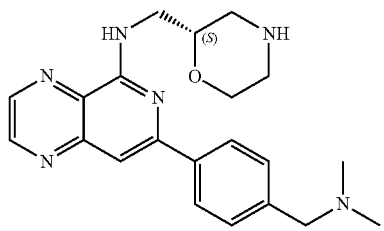 | 379 |
| 213 | 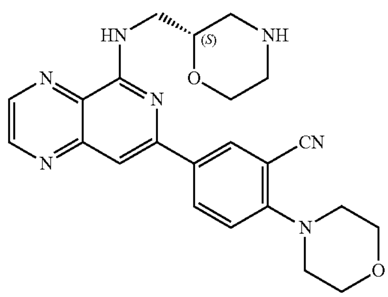 | 432 |
| 214 | 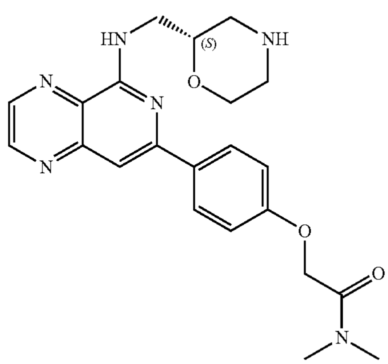 | 423 |
| 215 | 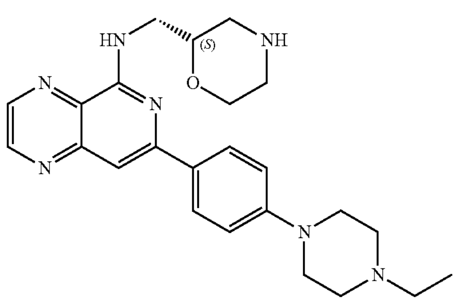 | 434 |

-continued

| Compound | Structure | MS (M + H)+ |
|---|---|---|
| 216 | 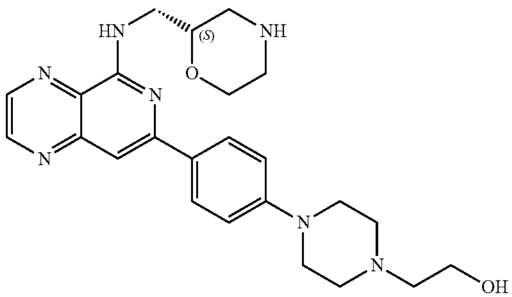 | 450 |
| 217 | 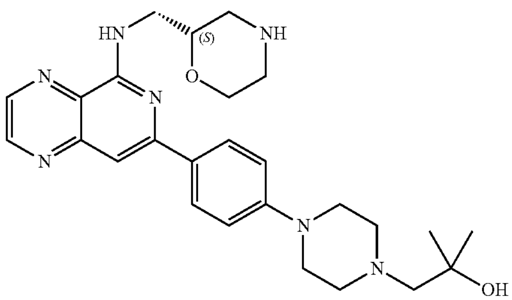 | 478 |
| 218 | 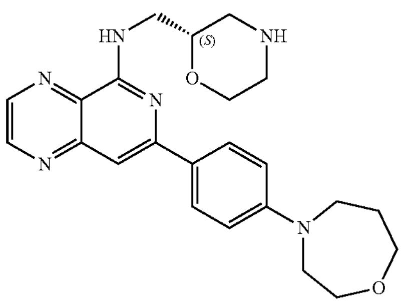 | 421 |
| 219 | 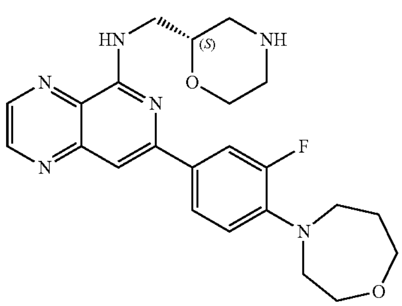 | 439 |
| 220 | 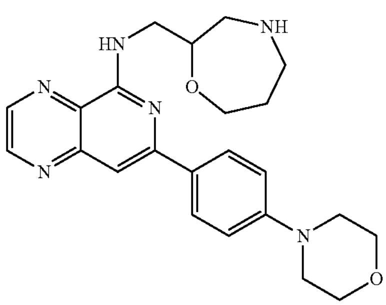 [SMILES: c1cnc2c(NCC3CNCCCO3)nc(-c3ccc(N4CCOCC4)cc3)cc2n1] | 421 |

-continued

| Compound | Structure | MS (M + H)+ |
|---|---|---|
| 221 | 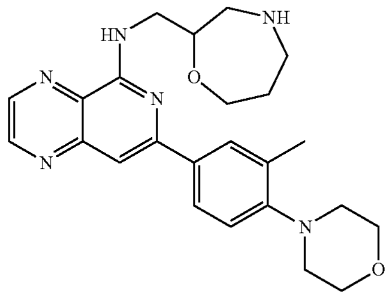 [SMILES: Cc1cc(-c2cc3nccnc3c(NCC3CNCCCO3)n2)ccc1N1CCOCC1] | 435 |
| 222 | 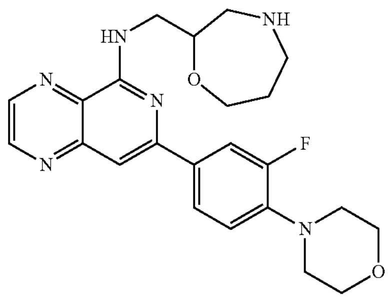 | 439 |
| 223 | 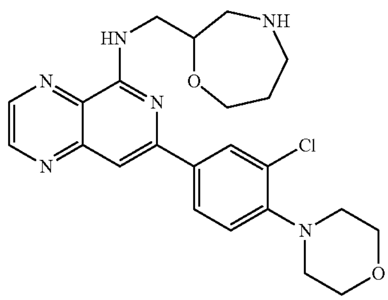 | 455 |
| 224 | 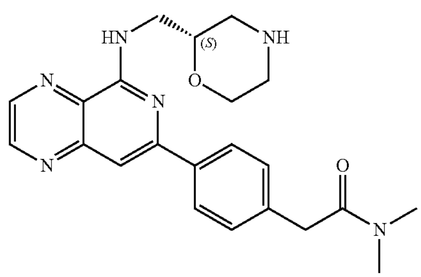 | 407 |
| 225 | 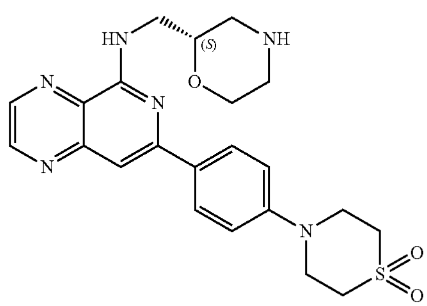 | 455 |

| Compound | Structure | MS (M + H)+ |
|---|---|---|
| 226 | 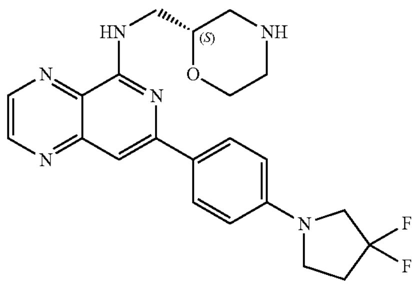 | 427 |
| 227 | 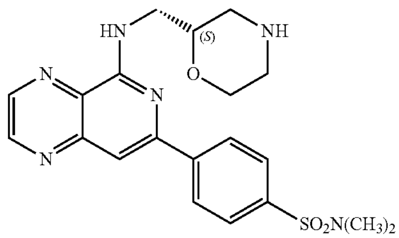 | 429 |
| 228 | 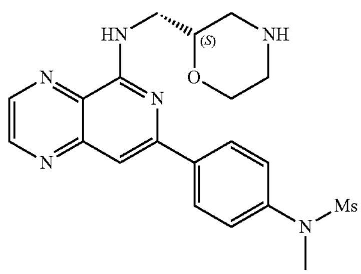 | 429 |
| 229 | 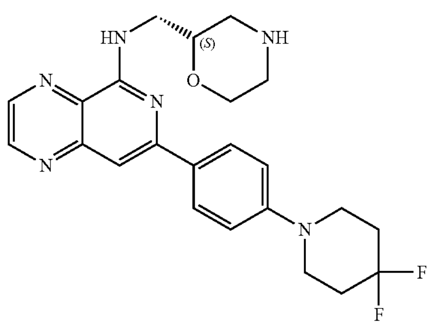 | 441 |
| 230 | 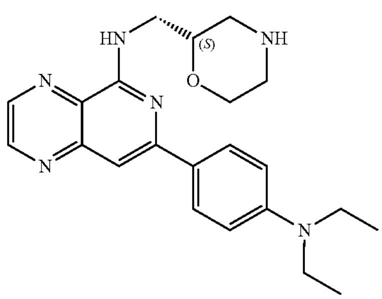 | 394 |

-continued

| Compound | Structure | MS (M + H)+ |
|---|---|---|
| 231 | 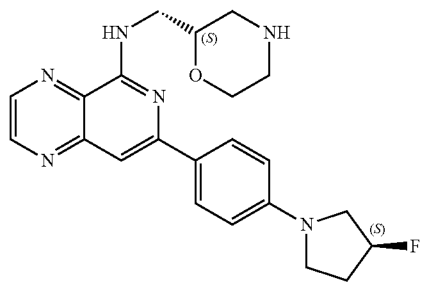 | 409 |
| 234 | 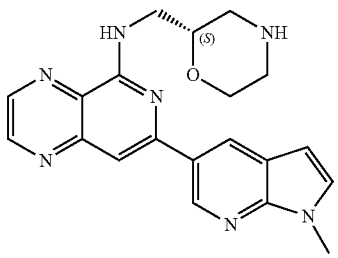 | 376 |
| 235 | 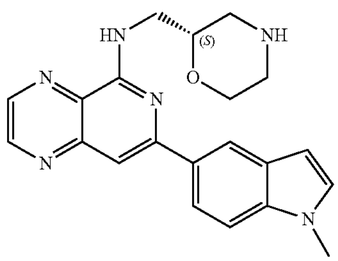 | 375 |
| 236 | 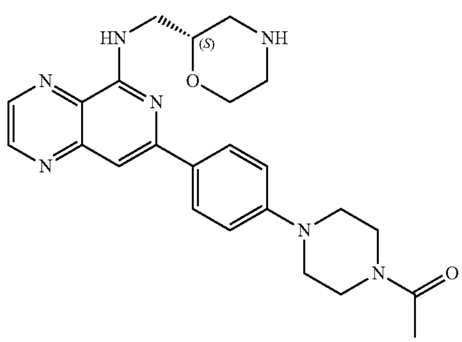 | 448 |
| 237 | 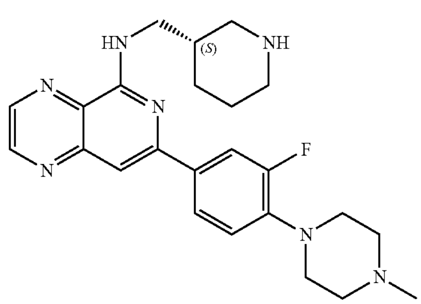 | 436 |

-continued
| Compound | Structure | MS (M + H)+ |
|---|---|---|
| 238 | 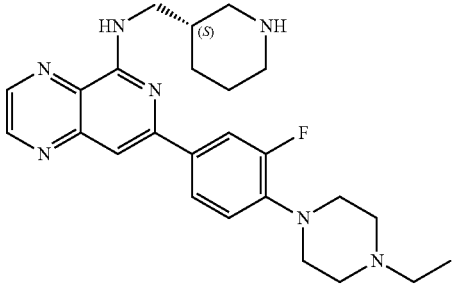 | 450 |
| 239 | 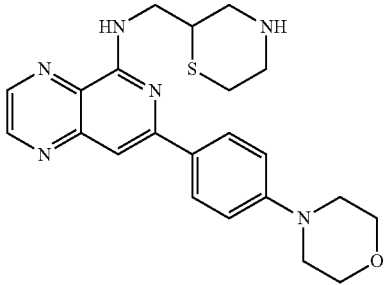 | 423 |
| 240 | 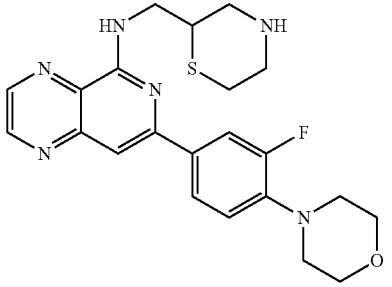 [SMILES: Fc1cc(-c2cc3nccnc3c(NCC3CNCCS3)n2)ccc1N1CCOCC1] | 441 |
| 241 | 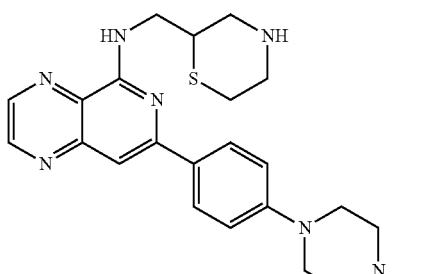 | 436 |
| 242 | 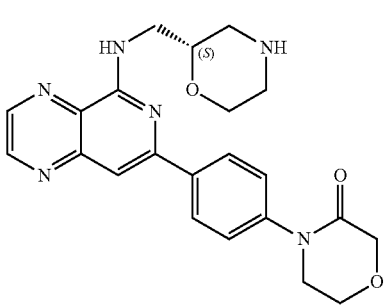 | 421 |

-continued

| Compound | Structure | MS (M + H)+ |
|---|---|---|
| 243 | 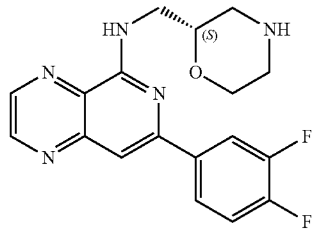 | 358 |
| 244 | 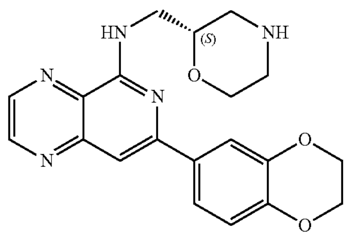 | 380 |
| 245 | 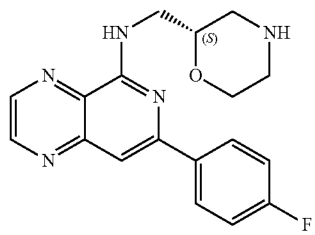 | 340 |
| 246 | 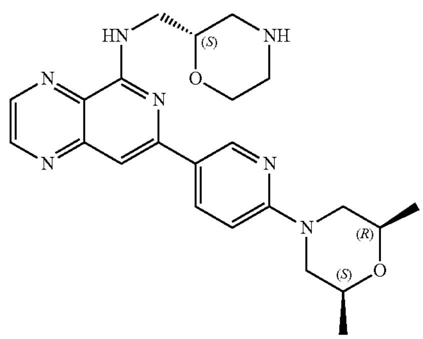 | 436 |
| 247 | 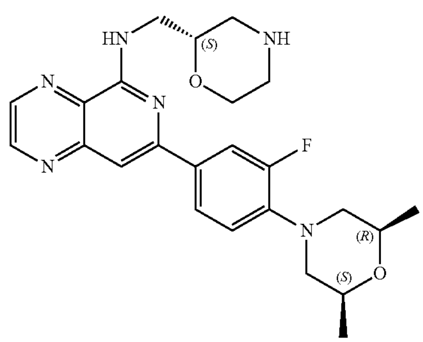 | 453 |

-continued

| Compound | Structure | MS (M + H)+ |
|---|---|---|
| 248 | 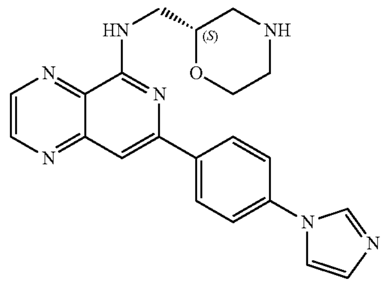 | 388 |
| 249 | 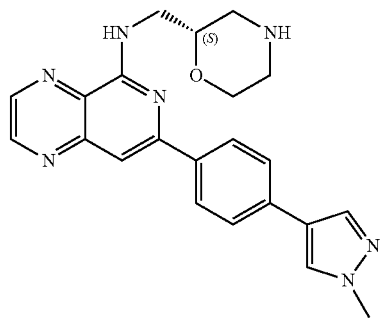 | 402 |
| 250 | 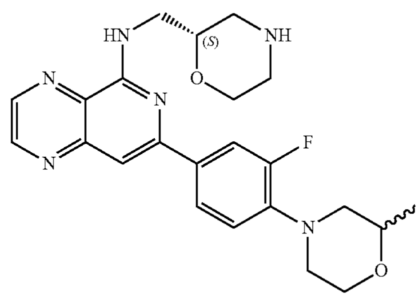 | 439 |
| 251 | 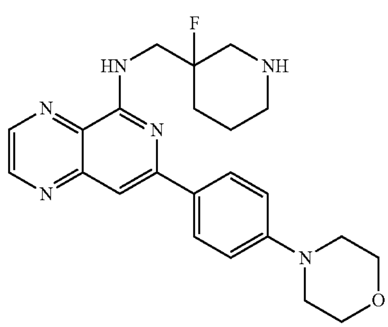 [SMILES: FC1(CNc2nc(-c3ccc(N4CCOCC4)cc3)cc3nccnc23)CCCNC1] | 423 |
| 252 | 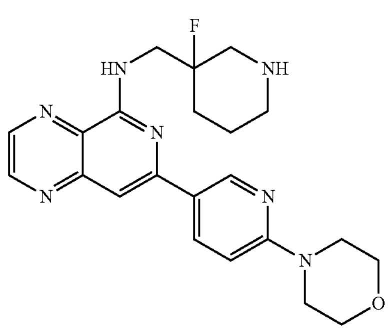 [SMILES: FC1(CNc2nc(-c3ccc(N4CCOCC4)nc3)cc3nccnc23)CCCNC1] | 424 |

-continued

| Compound | Structure | MS (M + H)+ |
|---|---|---|
| 253 | 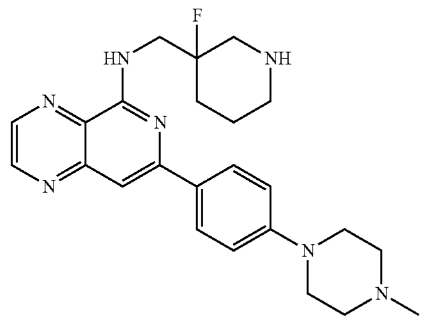 [SMILES: CN1CCN(c2ccc(-c3cc4nccnc4c(NCC4(F)CCCNC4)n3)cc2)CC1] | 436 |
| 254 | 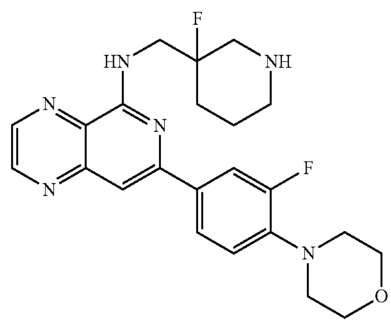 [SMILES: Fc1cc(-c2cc3nccnc3c(NCC3(F)CCCNC3)n2)ccc1N1CCOCC1] | 441 |
| 255 | 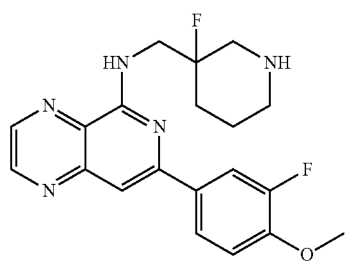 [SMILES: COc1ccc(-c2cc3nccnc3c(NCC3(F)CCCNC3)n2)cc1F] | 386 |
| 256 | 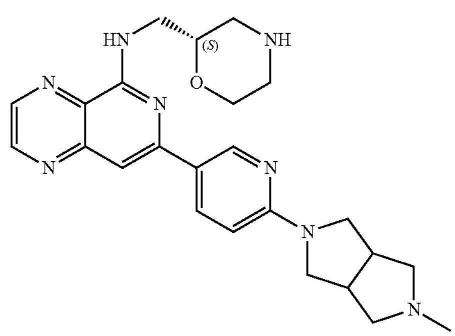 | 447 |
| 257 | 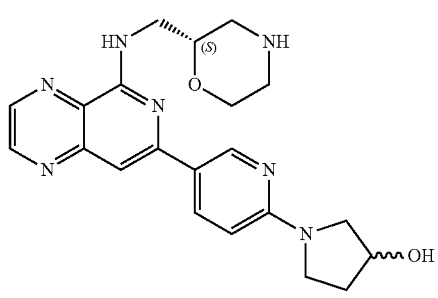 | 408 |

| Compound | Structure | MS (M + H)+ |
|---|---|---|
| 258 | 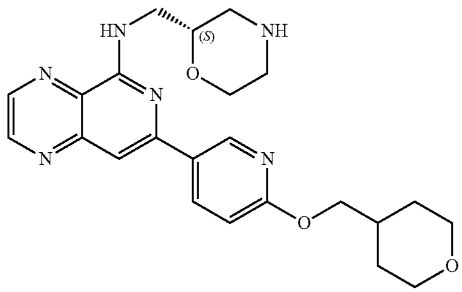 | 437 |
| 259 | 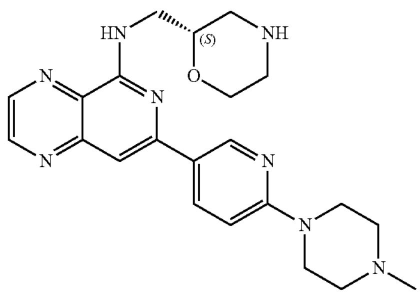 | 421 |
| 260 | 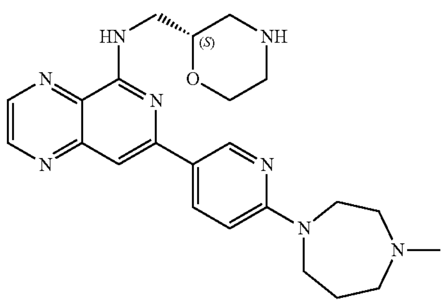 | 435 |
| 261 | 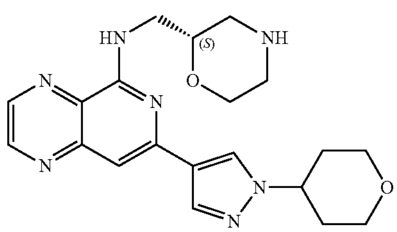 | 395 |
| 262 | 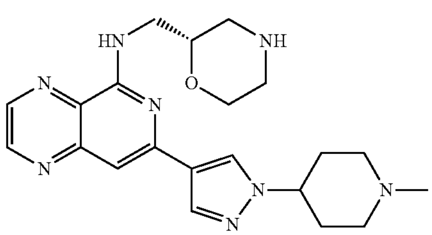 [SMILES: CN1CCC(n2cc(-c3cc4nccnc4c(NC[C@@H]4CNCCO4)n3)cn2)CC1] | 409 |
| 263 | 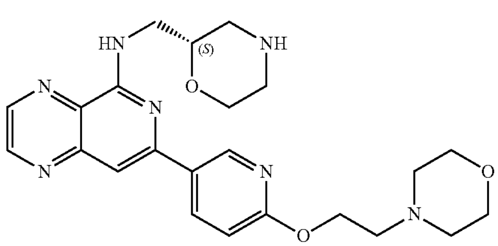 | 452 |

-continued

| Compound | Structure | MS (M + H)+ |
|----------|-----------|-------------|
| 264 | 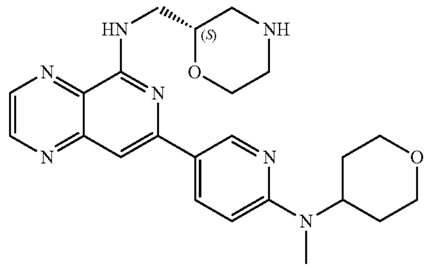 | 436 |
| 265 | 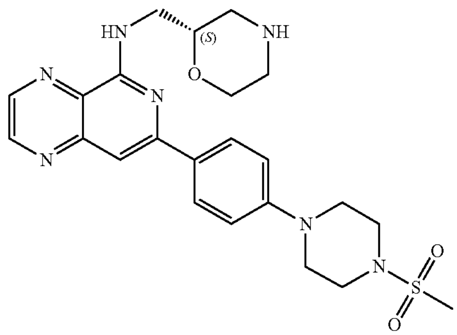 | 484 |
| 266 | 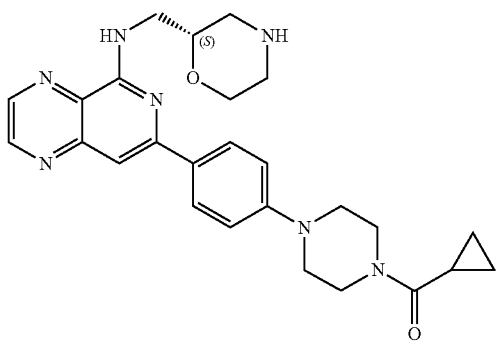 | 474 |
| 267 | 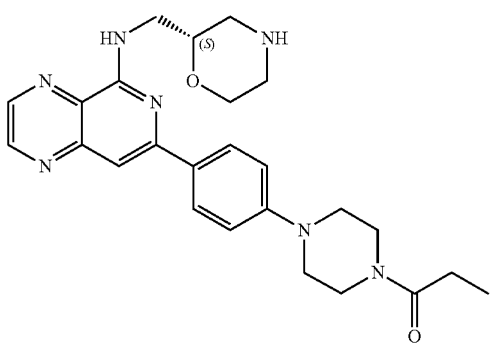 | 462 |
| 268 | 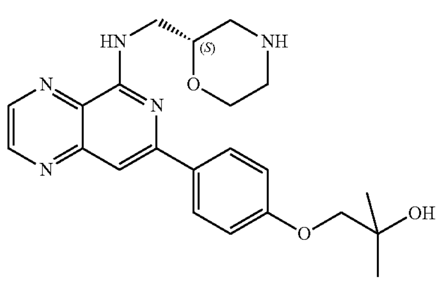 | 410 |

-continued

| Compound | Structure | MS (M + H)+ |
|---|---|---|
| 269 | 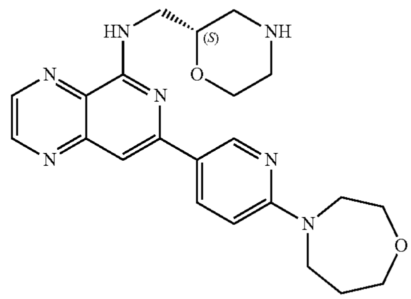 | 422 |
| 270 | 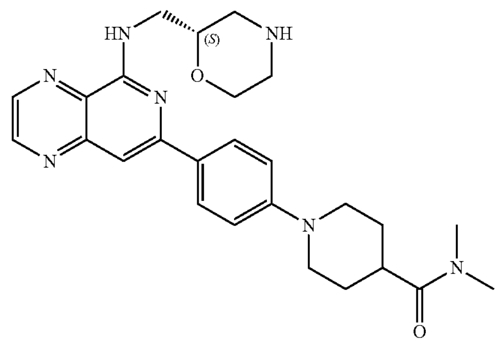 | 476 |
| 271 | 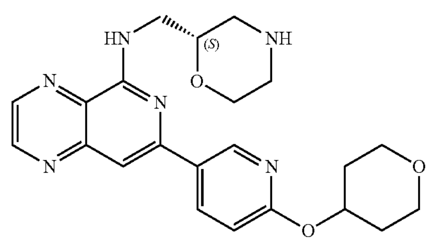 | 423 |
| 272 | 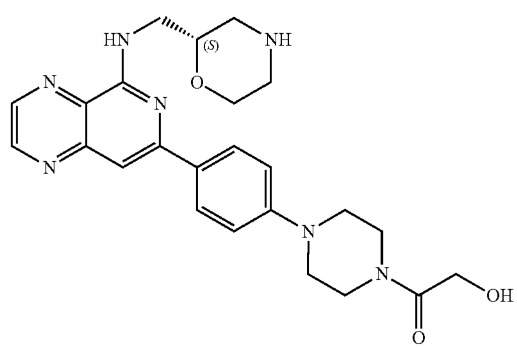 | 464 |
| 273 | 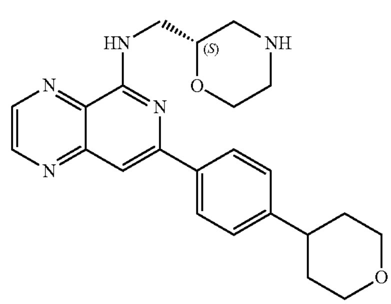 | 406 |

-continued
| Compound | Structure | MS (M + H)+ |
|---|---|---|
| 274 | 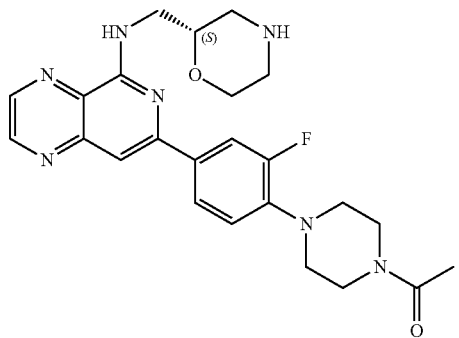 | 466 |
| 275 | 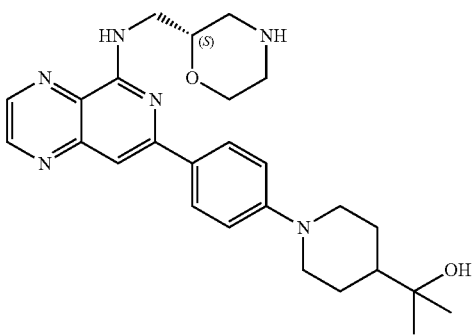 | 463 |
| 276 | 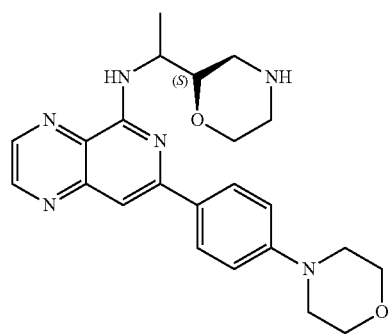 | 421 |
| 277 | 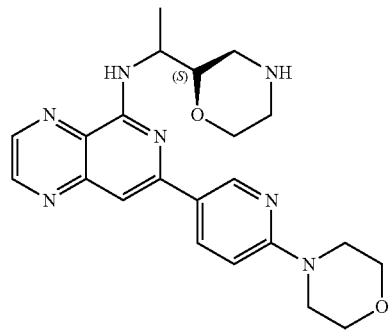 | 422 |

-continued

| Compound | Structure | MS (M + H)+ |
|---|---|---|
| 278 | 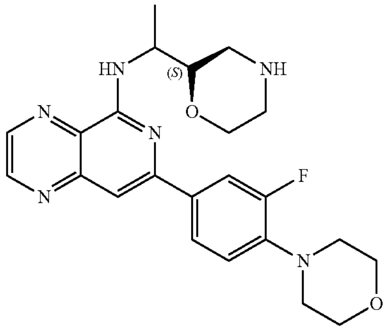 | 439 |
| 279 | 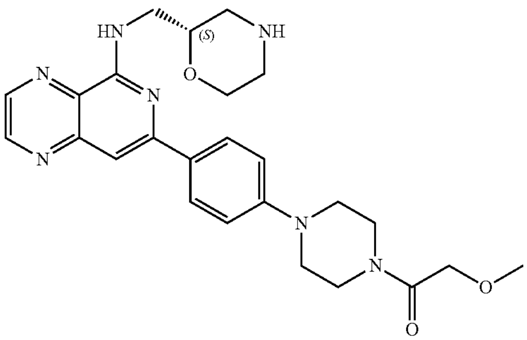 | 478 |
| 280 | 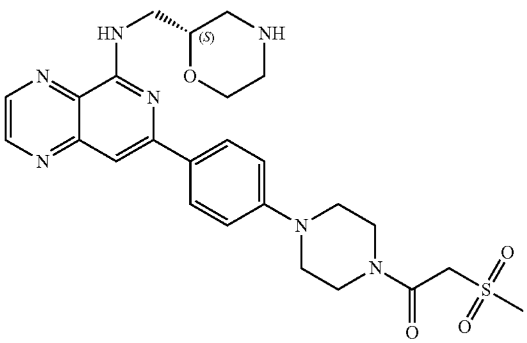 | 526 |
| 281 | 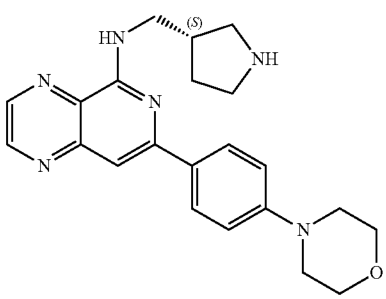 | 391 |
| 282 | 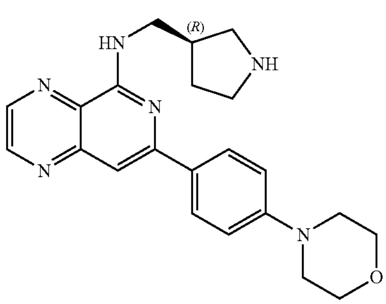 | 391 |

-continued
| Compound | Structure | MS (M + H)+ |
|---|---|---|
| 283 | 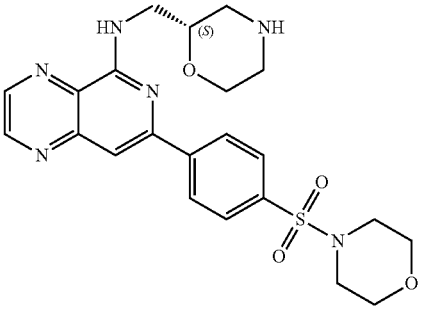 | 471 |
| 284 | 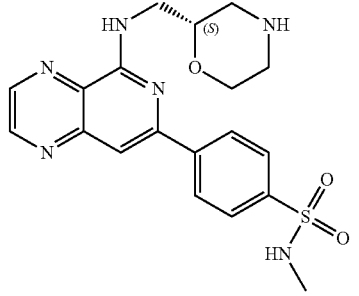 | 415 |
| 285 | 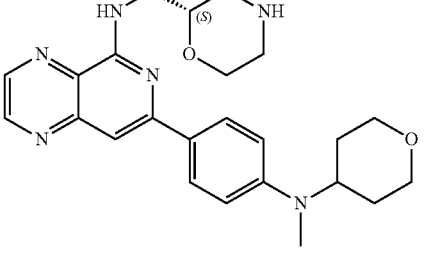 | 435 |
| 286 | 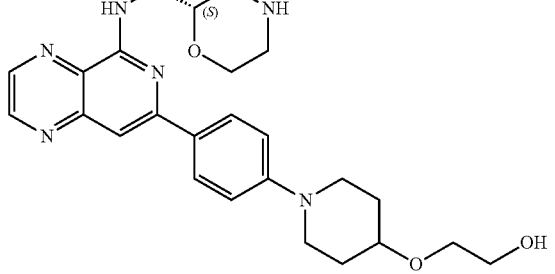 | 465 |
| 287 | 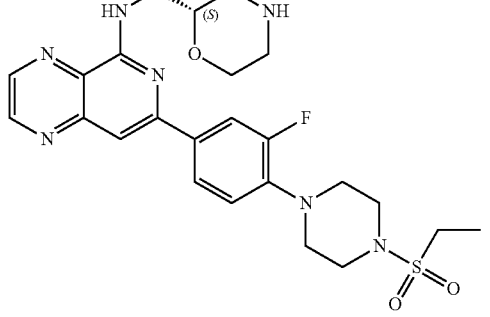 | 516 |

-continued

| Compound | Structure | MS (M + H)+ |
|---|---|---|
| 288 | 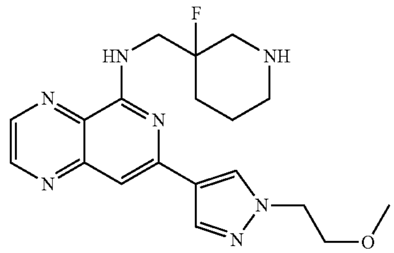 [SMILES: COCCn1cc(-c2cc3nccnc3c(NCC3(F)CCCNC3)n2)cn1] | 386 |
| 289 | 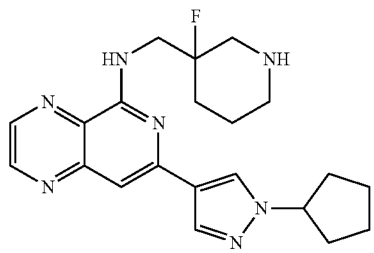 [SMILES: FC1(CNc2nc(-c3cnn(C4CCCC4)c3)cc3nccnc23)CCCNC1] | 396 |
| 290 | 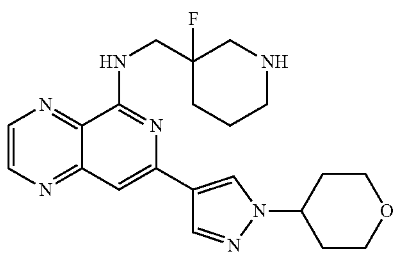 [SMILES: FC1(CNc2nc(-c3cnn(C4CCOCC4)c3)cc3nccnc23)CCCNC1] | 412 |
| 500 | 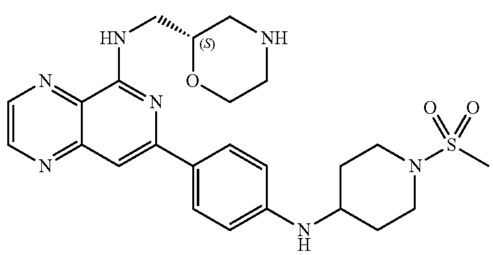 | 498 |
| 502 | 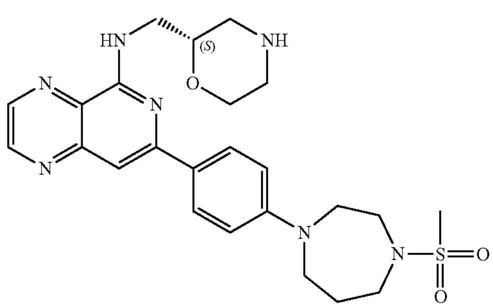 | 498 |
| 503 | 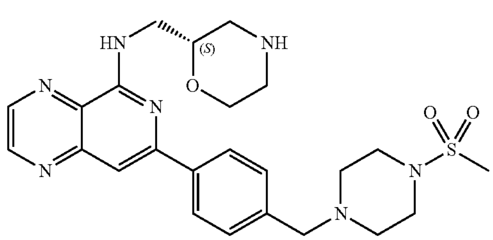 | 498 |

| Compound | Structure | MS (M + H)+ |
|---|---|---|
| 513 | 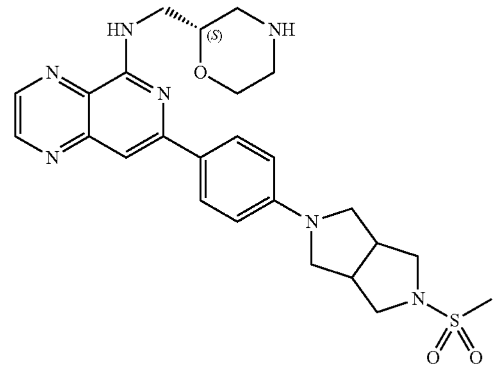 | 510 |
| 515 | 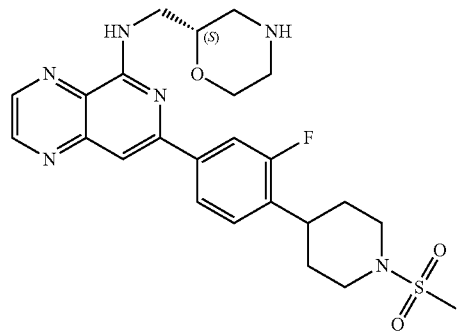 | 501 |
| 516 | 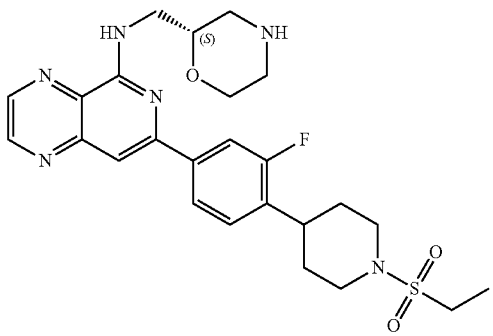 | 515 |
Compound 145
4-(4-(5-(hexahydropyrrolo[3,4-b]pyrrol-5(1H)-yl)pyrido[4,3-b]pyrazin-7-yl)phenyl)morpholine
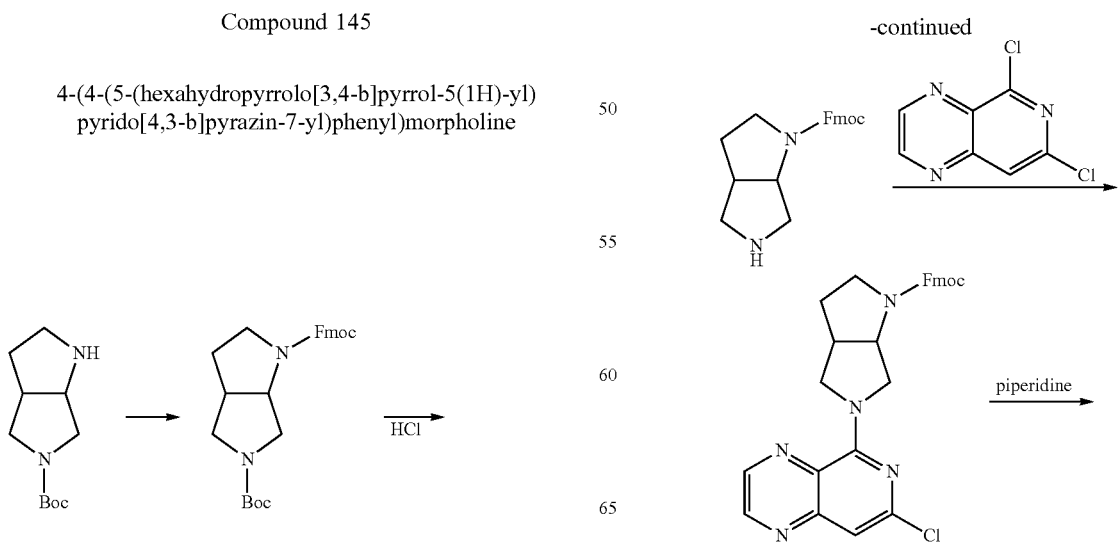

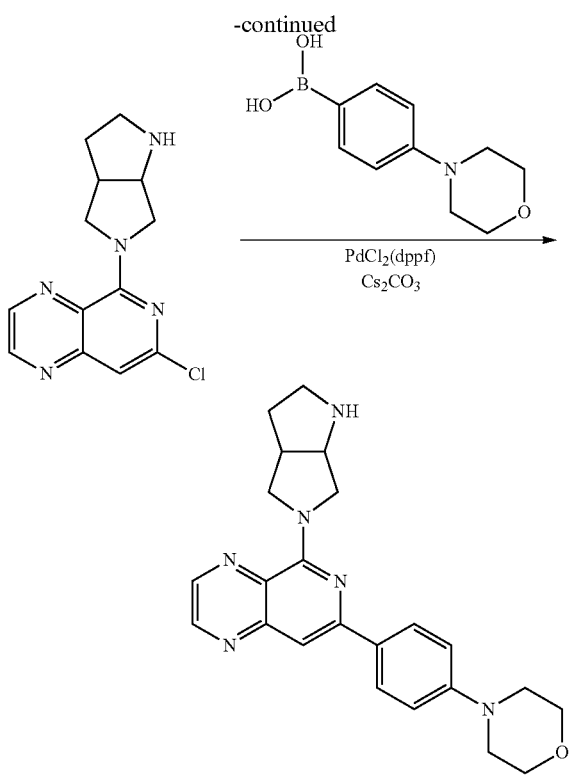

(A) 1-(9H-fluoren-9-yl)methyl 5-tert-butyl hexahydropyrrolo[3,4-b]pyrrole-1,5-dicarboxylate A solution of tert-butyl hexahydropyrrolo[3,4-b]pyrrole-5(1H)-carboxylate (424 mg, 2 mmol), N-(9-fluorenylmethoxycarbonyloxy) succinimide (600 mg, 1.8 mmol) and DIPEA (310 mg, 2.4 mmol) in dioxane (20 mL) was stirred at room temperature overnight and then concentrated in vacuo. The residue was treated with EtOAc/H$_2$O, separated, and the aqueous layer was extracted with EtOAc. The combined extracts were washed with brine, dried over Na$_2$SO$_4$, filtered, and concentrated to give the title compound. MS (m/z): 355 (M-boc+H)$^+$.

(B) (9H-fluoren-9-yl)methyl hexahydropyrrolo[3,4-b]pyrrole-1 (2H)-carboxylate hydrochloric acid 1-(9H-fluoren-9-yl)methyl 5-tert-butyl hexahydropyrrolo[3,4-b]pyrrole-1,5-dicarboxylate (810 mg, 1.86 mmol) was treated with HCl in MeOH (5 mL) for 2 hours and then concentrated in vacuo to afford the title compound.

(C) (9H-fluoren-9-yl)methyl 5-(7-chloropyrido[4,3-b]pyrazin-5-yl)hexahydropyrrolo[3,4-b]pyrrole-1 (2H)-carboxylate The mixture of (9H-fluoren-9-yl)methyl hexahydropyrrolo[3,4-b]pyrrole-1(2H)-carboxylate (100 mg, 0.5 mmol) and 5,7-dichloropyrido[4,3-b]pyrazine (600 mg, 1.8 mmol) in dioxane was stirred at 0° C. for 30 minutes and then at room temperature for 4 hours. The mixture was concentrated, and the residue was purified by chromatography to give the title compound. MS (m/z): 498 (M+H)$^+$.

(D) 7-chloro-5-(hexahydropyrrolo[3,4-b]pyrrol-5 (1H)-yl)pyrido[4,3-b]pyrazine

A solution of (9H-fluoren-9-yl)methyl 5-(7-chloropyrido[4,3-b]pyrazin-5-yl)hexahydropyrrolo[3,4-b]pyrrole-1 (2H)-carboxylate (140 mg) and piperidine (2 mL) in CH$_2$Cl$_2$ (8 mL) was stirred at room temperature for 3 hours. The volatiles were removed under reduced pressure. The residue was treated with EtOAc/H$_2$O, separated, and the aqueous solution was extracted with EtOAc. The combined extracts were washed with brine, dried over Na$_2$SO$_4$, filtered, and concentrated. The residue was purified by chromatography to afford the title compound. MS (m/z): 276 (M+H)$^+$.

(E) 4-(4-(5-(hexahydropyrrolo[3,4-b]pyrrol-5(1H)-yl)pyrido[4,3-b]pyrazin-7-yl)phenyl)morpholine A mixture of 7-chloro-5-(hexahydropyrrolo[3,4-b]pyrrol-5(1H)-yl)pyrido[4,3-b]pyrazine (47 mg, 0.17 mmol), 4-morpholinophenylboronic acid (105 mg, 0.51 mmol), and PdCl$_2$ (dppf) (10 mg), Cs$_2$CO$_3$ (130 mg, 0.51 mmol) in dioxane (5 mL) was sealed in a microwave reaction cube, stirred at 180° C. for 60 minutes in a microwave reactor, cooled to ambient temperature, concentrated under reduced pressure, and the residue was purified by chromatography to give the title compound. MS (m/z): 403 (M+H)$^+$.

The following compound was prepared according to the procedures of Compound 145 using the corresponding intermediates and reagents under appropriate conditions that will be recognized by one skilled in the art.

| Compound | Structure | MS (M + H)$^+$ |
|---|---|---|
| 146 | 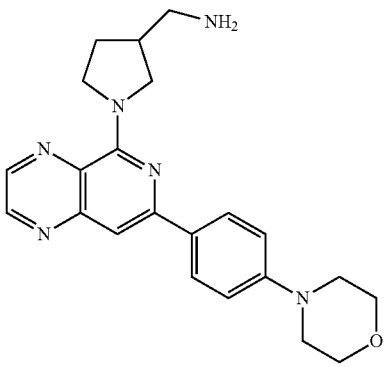 [SMILES: NCC1CCN(c2nc(-c3ccc(N4CCOCC4)cc3)cc3nccnc23)C1] | 391 |

Compound 147

(S)—N-methyl (1-(7-(4-morpholinophenyl)pyrido[4,3-b]pyrazin-5-yl)pyrrolidin-3-yl) methanamine

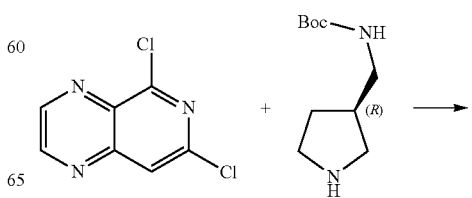

181
-continued

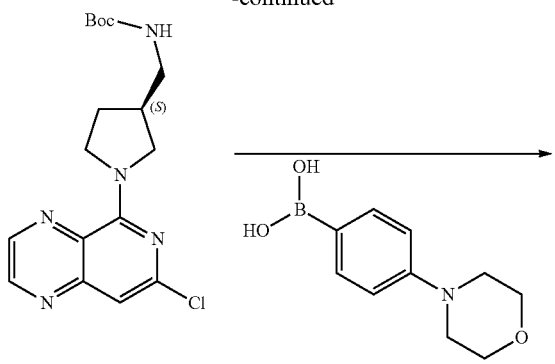

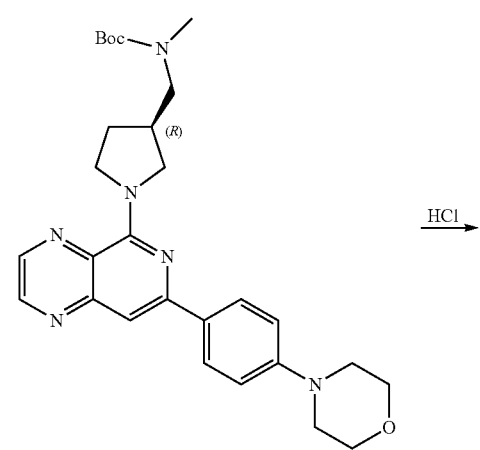

182
-continued

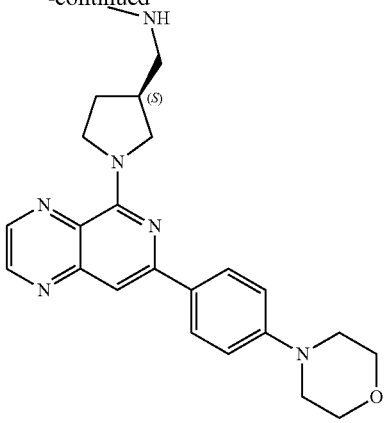

(A) (S)-tert-butyl(1-(7-chloropyrido[4,3-b]pyrazin-5-yl)pyrrolidin-3-yl)methylcarbamate The title compound was prepared according to the procedure of Compound 1 (A) using (R)-tert-butyl pyrrolidin-3-ylmethylcarbamate. MS (m/z): 364 (M+H)⁺.

(B) (S)-tert-butyl(1-(7-(4-morpholinophenyl)pyrido[4,3-b]pyrazin-5-yl)pyrrolidin-3-yl)methylcarbamate The title compound was prepared according to the procedure of Compound 1 (B) using (S)-tert-butyl(1-(7-chloropyrido[4,3-b]pyrazin-5-yl)pyrrolidin-3-yl)methylcarbamate. MS (m/z): 491 (M+H)⁺.

(C) (R)-tert-butyl methyl((1-(7-(4-morpholinophenyl)pyrido[4,3-b]pyrazin-5-yl)pyrrolidin-3-yl)methyl)carbamate Under $N_2$, to a solution of (S)-tert-butyl(1-(7-(4-morpholinophenyl)pyrido[4,3-b]pyrazin-5-yl)pyrrolidin-3-yl)methylcarbamate (150 mg, 0.31 mmol) in anhydrous THF (10 mL) was slowly added sodium hydride (49 mg, 1.22 mmol) at 0° C. The mixture was warmed up and stirred at room temperature for 0.5 h. The reaction mixture was then cooled to 0° C., and $CH_3I$ (174 mg, 1.22 mmol) was added slowly. After the completion of the addition, the reaction mixture was stirred at reflux for 4 hours, cooled to ambient temperature, quenched with $H_2O$, and extracted with EtOAc. The combined extracts were dried and concentrated to give the title compound. MS (m/z): 505 (M+H)⁺.

(D) (S)—N-methyl(1-(7-(4-morpholinophenyl)pyrido[4,3-b]pyrazin-5-yl)pyrrolidin-3-yl)methanamine The title compounds was prepared according to the procedure of Compound 1 (C) using (R)-tert-butyl methyl((1-(7-(4-morpholinophenyl)pyrido[4,3-b]pyrazin-5-yl)pyrrolidin-3-yl) methyl)carbamate. MS (m/z): 405 (M+H)⁺.

The following compound 148 was were prepared according to the procedures of Compound 147 using the corresponding intermediates and reagents under appropriate conditions that will be recognized by one skilled in the art.

| Compound | Structure | MS (M + H)+ |
|---|---|---|
| 148 | 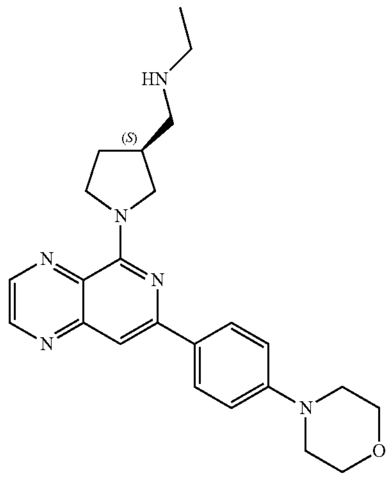 | 419 |

Compound 149

(R)—N-((1-(7-(4-morpholinophenyl)pyrido[4,3-b]pyrazin-5-yl)pyrrolidin-3-yl)methyl)methanesulfonamide

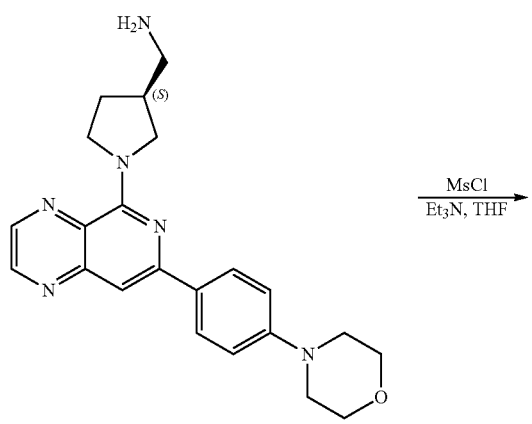

((R)—N-((1-(7-(4-morpholinophenyl)pyrido[4,3-b]pyrazin-5-yl)pyrrolidin-3-yl)methyl)methanesulfonamide

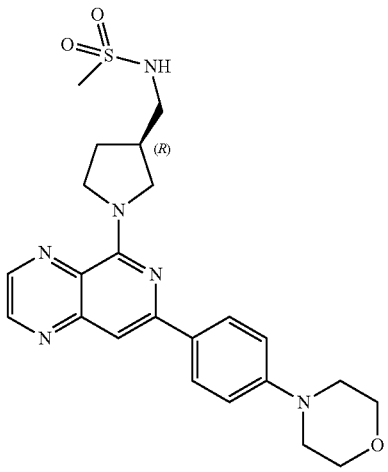

Under N$_2$, to a solution of (S)-(1-(7-(4-morpholinophenyl)pyrido[4,3-b]pyrazin-5-yl)pyrrolidin-3-yl)methanamine (Compound 77, 51 mg, 0.13 mmol) and Et$_3$N (0.04 mL, 0.26 mmol) in anhydrous THF (3 mL) was added MsCl (30 mg, 0.26 mmol) at 0° C. The reaction mixture was stirred at ambient temperature for 0.5 hour, then quenched with H$_2$O and extracted with EtOAc. The combined extracts were dried over Na$_2$SO$_4$, filtered, and concentrated under reduced pressure. The residue was purified by preparative thin-layer chromatography to afford the title compound. MS (m/z): 469 (M+H)+.

The following compounds were prepared according to the procedures of Compound 149 using the corresponding intermediates and reagents under appropriate conditions that will be recognized by one skilled in the art.

| Compound | Structure | MS (M + H)+ |
|---|---|---|
| 322 | 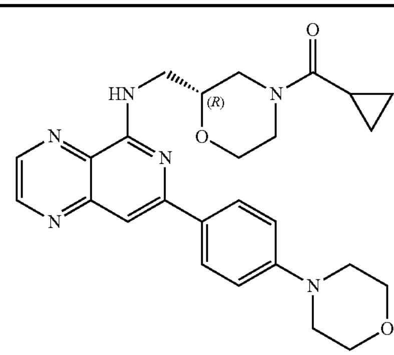 | 475 |

-continued
| Compound | Structure | MS (M + H)+ |
|---|---|---|
| 323 | 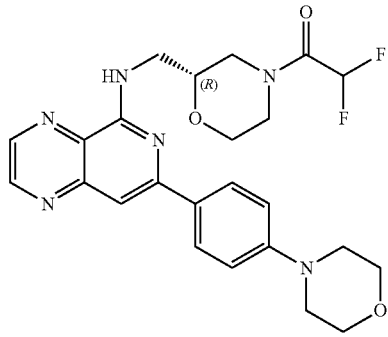 | 485 |
| 324 | 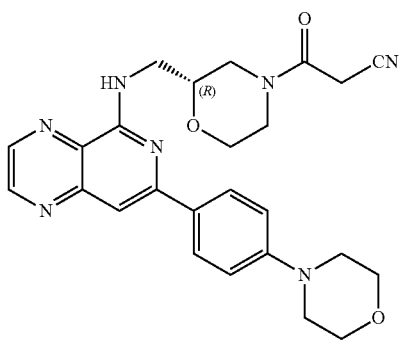 | 474 |
| 325 | 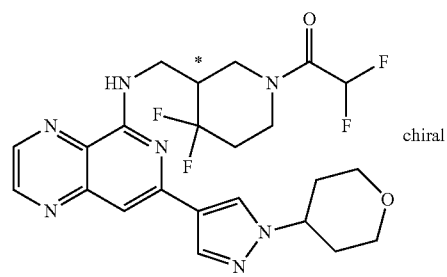 [SMILES: O=C(C(F)F)N1CCC(F)(F)C(CNc2nc(-c3cnn(C4CCOCC4)c3)cc3nccnc23)C1] chiral | 508 |
| 326 | 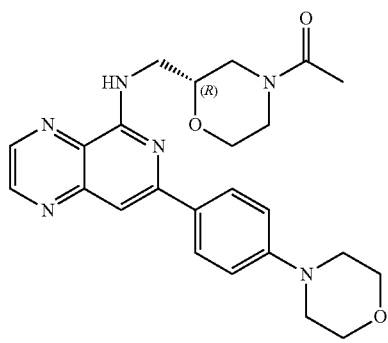 | 449 |

-continued
| Compound | Structure | MS (M + H)+ |
|---|---|---|
| 327 | 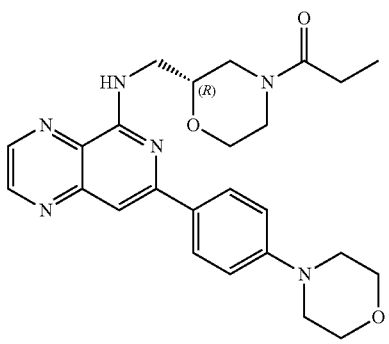 | 463 |
| 328 | 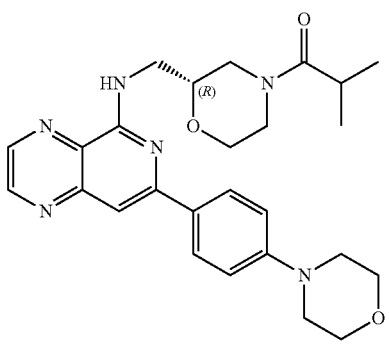 | 477 |
| 329 | 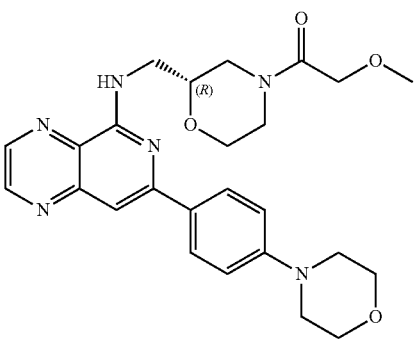 | 479 |
| 330 | 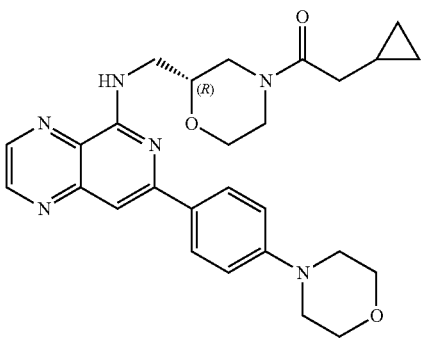 | 489 |

-continued

| Compound | Structure | MS (M + H)+ |
|---|---|---|
| 331 | 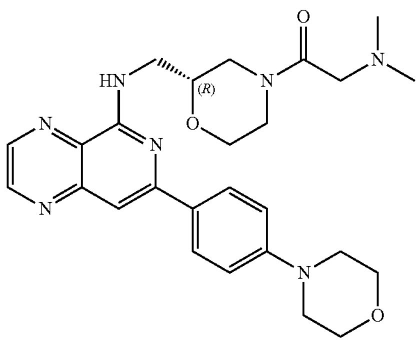 | 492 |
| 332 | 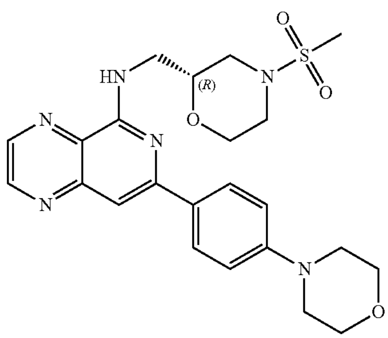 | 485 |
| 333 | 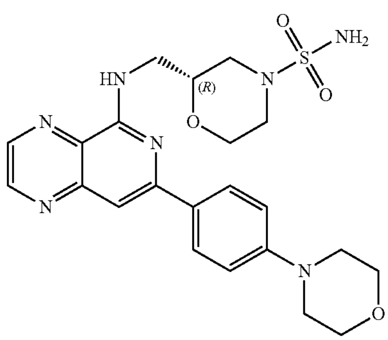 | 486 |
| 334 | 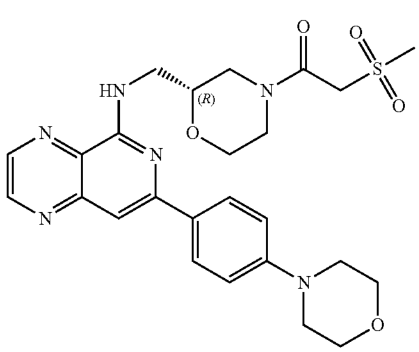 | 527 |

-continued

| Compound | Structure | MS (M + H)+ |
|---|---|---|
| 335 | 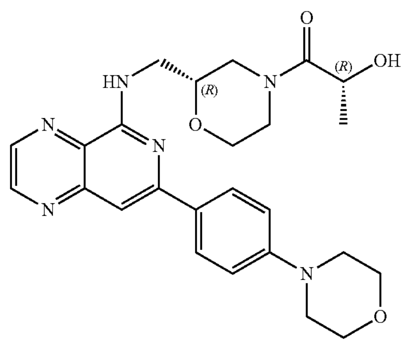 | 479 |
| 336 | 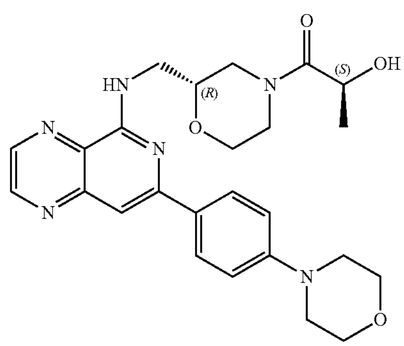 | 479 |
| 337 | 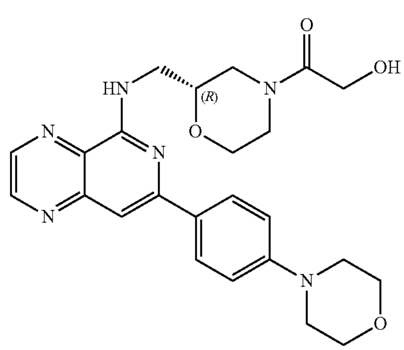 | 465 |
| 338 | 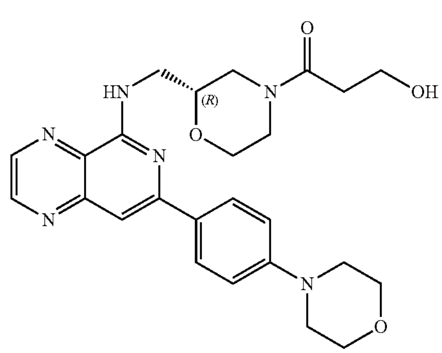 | 479 |

| Compound | Structure | MS (M + H)+ |
|---|---|---|
| 339 | 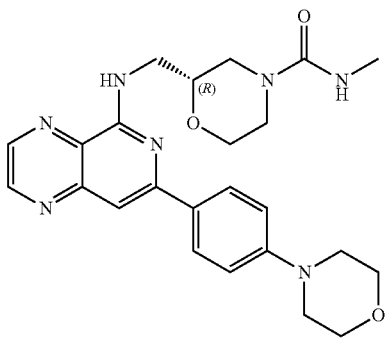 | 464 |
| 340 | 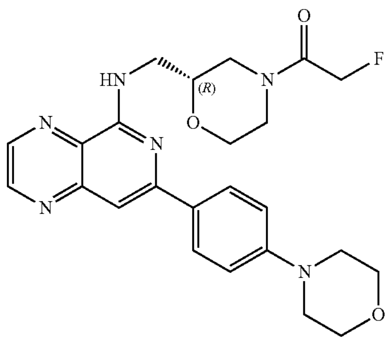 | 467 |
| 341 | 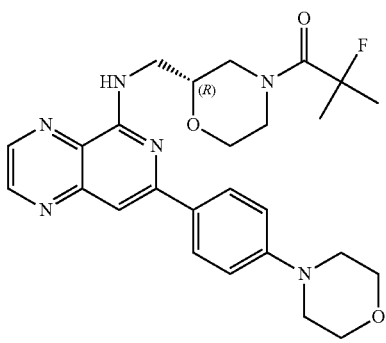 | 495 |
| 342 | 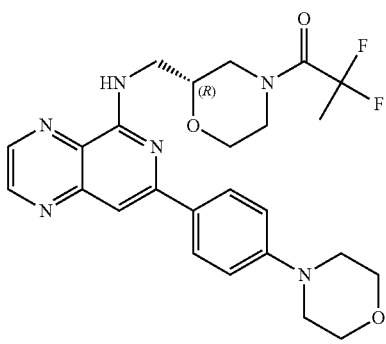 | 499 |

-continued
| Compound | Structure | MS (M + H)+ |
|---|---|---|
| 343 | 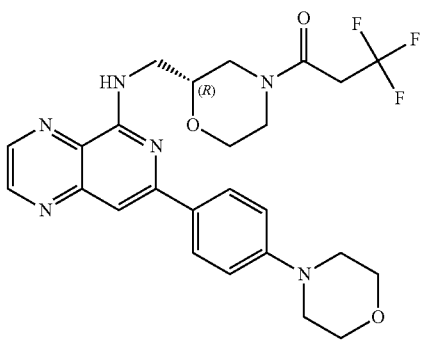 | 517 |
| 344 | 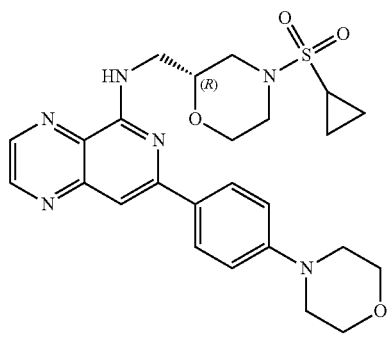 | 511 |
| 345 | 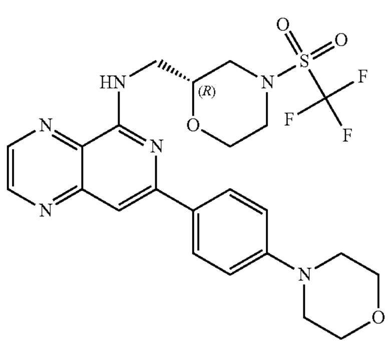 | 539 |
| 346 | 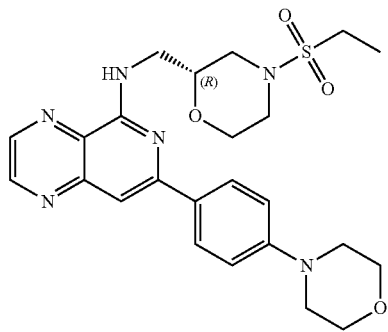 | 499 |

| Compound | Structure | MS (M + H)+ |
|---|---|---|
| 465 | 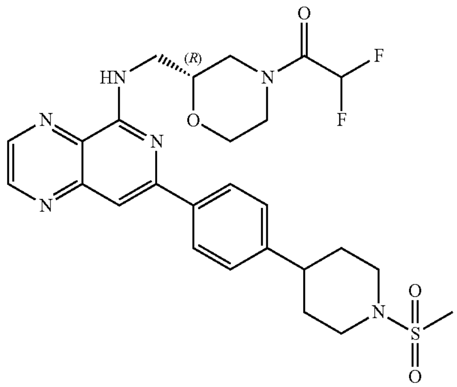 | 561 |
| 510 | 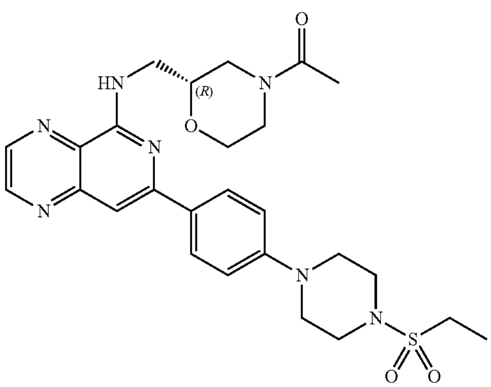 | 541 |

Compound 150

(S)-1-((1-(7-(4-morpholinophenyl)pyrido[4,3-b]pyrazin-5-yl)pyrrolidin-3-yl)methyl)urea

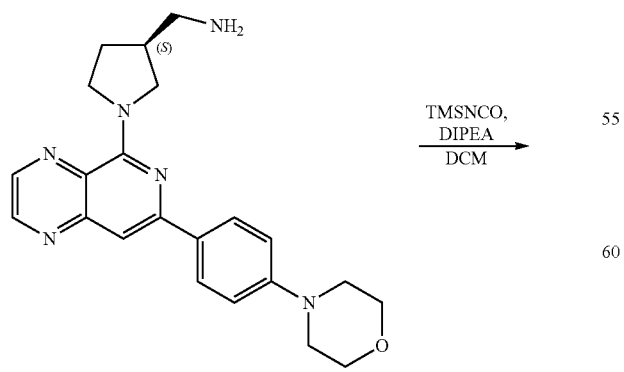

TMSNCO, DIPEA / DCM →

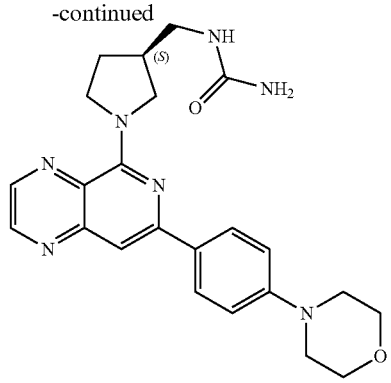

A solution of (S)-(1-(7-(4-morpholinophenyl)pyrido[4,3-b]pyrazin-5-yl)pyrrolidin-3-yl)methanamine (Compound 77, 0.16 mmol), DIPEA (207 mg, 1.6 mmol) and TMSNCO (184 mg, 1.6 mmol) in anhydrous $CH_2Cl_2$ (5 mL) was stirred at room temperature for 70 hours. The reaction mixture was poured into saturated $NaHCO_3$ aqueous and extracted with $CH_2Cl_2$. The combined extracts were dried over $Na_2SO_4$, filtered, and concentrated under reduced pressure. The residue was purified by chromatography to afford the title compound. MS (m/z): 434 (M+H)+.

The following compounds were prepared according to the procedures of Compound 150 using the corresponding intermediates and reagents under appropriate conditions that will be recognized by one skilled in the art.

| Compound | Structure | MS (M + H)+ |
|---|---|---|
| 151 | 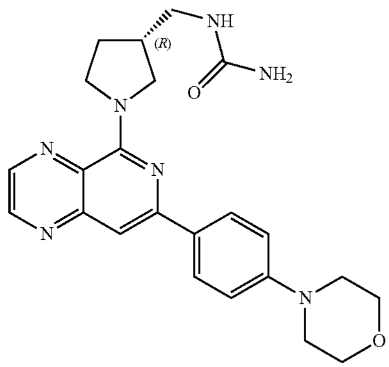 | 434 |
| 347 | 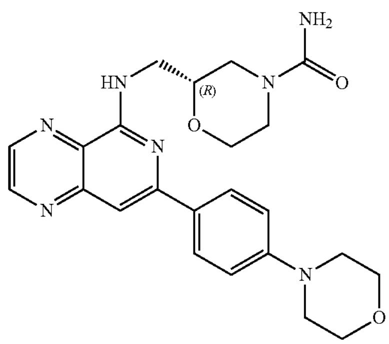 | 450 |
| 348 | 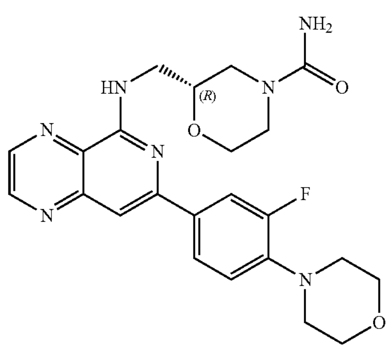 | 468 |
| 349 | 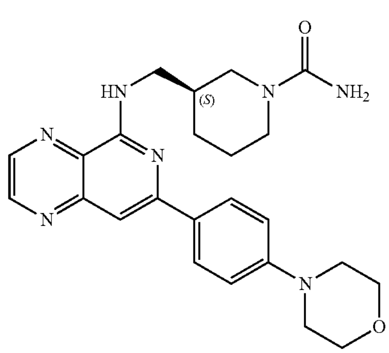 | 448 |
| 350 | | 448 |
| 351 | | 434 |
| 352 | | 434 |
| 353 | | 448 |

-continued

| Compound | Structure | MS (M + H)+ |
|---|---|---|
| 354 | 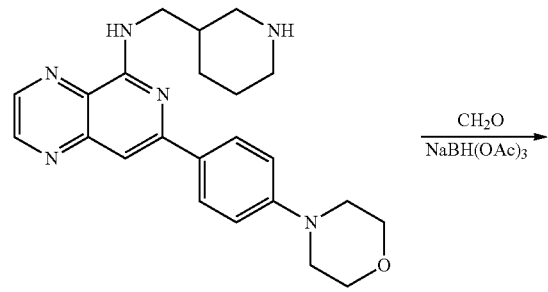 | 448 |
| 355 | 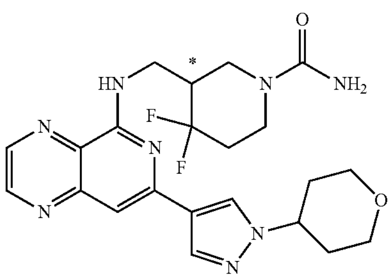 [SMILES: NC(=O)N1CCC(F)(F)C(CNc2nc(-c3cnn(C4CCOCC4)c3)cc3nccnc23)C1] | 473 |
| 356 | 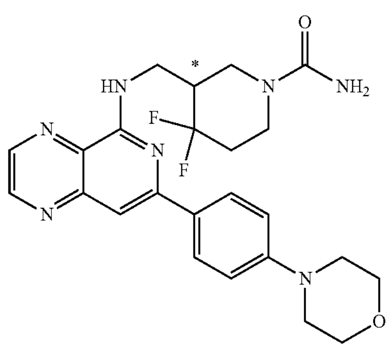 [SMILES: NC(=O)N1CCC(F)(F)C(CNc2nc(-c3ccc(N4CCOCC4)cc3)cc3nccnc23)C1] | 484 |

Compound 152

N-((1-methylpiperidin-3-yl)methyl)-7-(4-morpholinophenyl)pyrido[4,3-b]pyrazin-5-amine -continued

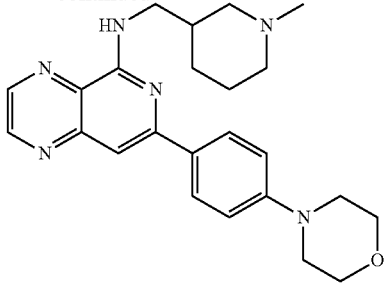

A solution of 7-(4-morpholinophenyl)-N-(piperidin-3-yl-methyl)pyrido[4,3-b]pyrazin-5-amine (Compound 3, 40 mg, 0.1 mmol) and formaldehyde (60 mg, 2.0 mmol), NaBH(OAc)₃ (25 mg, 0.15 mmol) in THF (20 mL) was stirred at ambient temperature overnight, then concentrated under reduced pressure. The residue was purified by chromatography to afford the title compound. MS (m/z): 419 (M+H)+.

Compound 153

N-methyl-7-(4-morpholinophenyl)-N-(piperidin-3-yl methyl)pyrido[4,3-b]pyrazin-5-amine

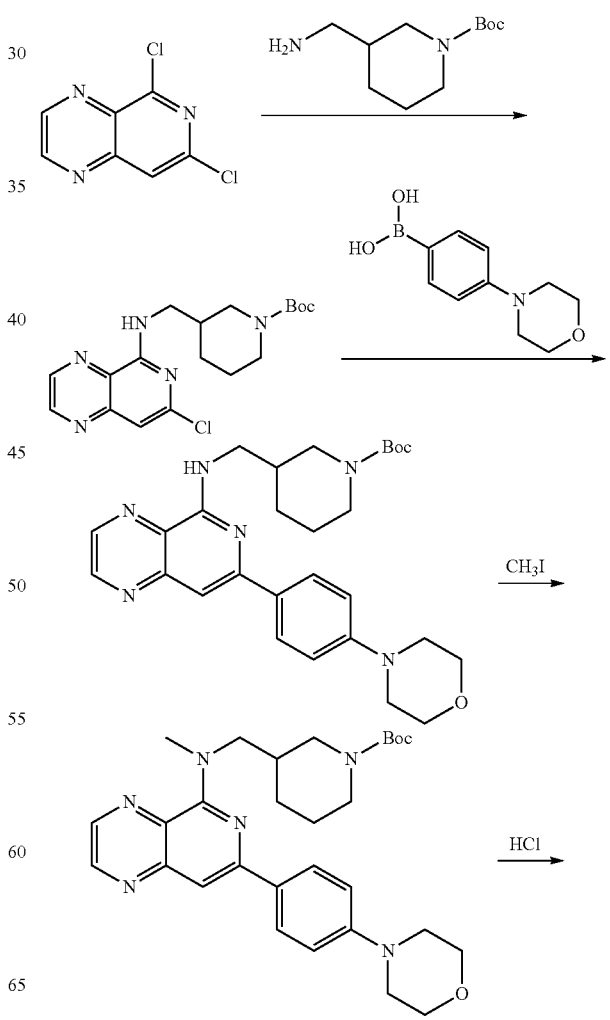

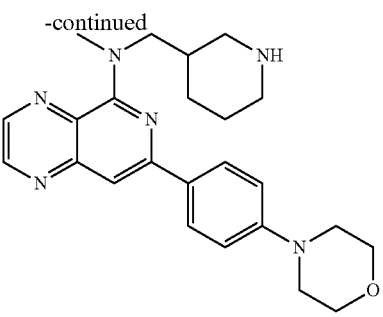

(A) tert-butyl 3-((7-chloropyrido[4,3-b]pyrazin-5-ylamino)methyl)piperidine-1-carboxylate The title compound was prepared according to the procedure of Compound 1 (A) using tert-butyl 3-(aminomethyl)piperidine-1-carboxylate. MS (m/z): 378 (M+H)⁺.

(B) tert-butyl 3-((7-(4-morpholinophenyl)pyrido[4,3-b]pyrazin-5-ylamino) methyl)piperidine-1-carboxylate The title compound was prepared according to the procedure of Compound 1 (B). MS (m/z): 505 (M+H)⁺.

(C) tert-butyl 3-((methyl(7-(4-morpholinophenyl)pyrido[4,3-b]pyrazin-5-yl)amino)methyl)piperidine-1-carboxylate To a solution of tert-butyl 3-((7-(4-morpholinophenyl)pyrido[4,3-b]pyrazin-5-ylamino) methyl)piperidine-1-carboxylate (100 mg, 0.2 mmol) in THF (20 mL) was added NaH (30 mg, 0.6 mmol). The mixture was stirred for 2-3 hours at 0° C., and iodomethane (142 mg, 1 mmol) was then added dropwise. The reaction mixture was stirred at room temperature overnight, quenched with water and concentrated under reduced pressure. The residue was purified by chromatography to afford the title compound.

(D) N-methyl-7-(4-morpholinophenyl)-N-(piperidin-3-ylmethyl)pyrido[4,3-b]pyrazin-5-amine The title compounds was prepared according to the procedure of Compound 1 (C) using tert-butyl 3-((methyl(7-(4-morpholinophenyl)pyrido[4,3-b]pyrazin-5-yl)amino)methyl)piperidine-1-carboxylate. MS (m/z): 419 (M+H)⁺.

The following compound 154 was prepared according to the procedures of Compound 153 using the corresponding intermediates and reagents under appropriate conditions that will be recognized by one skilled in the art.

| Compound | Structure | MS (M + H)⁺ |
|---|---|---|
| 154 | 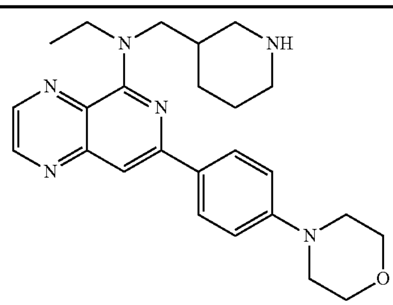 | 433 |

Compound 155

N-((5,5-difluoropiperidin-3-yl)methyl)-7-(4-morpholinophenyl)pyrido[4,3-b]pyrazin-5-amine

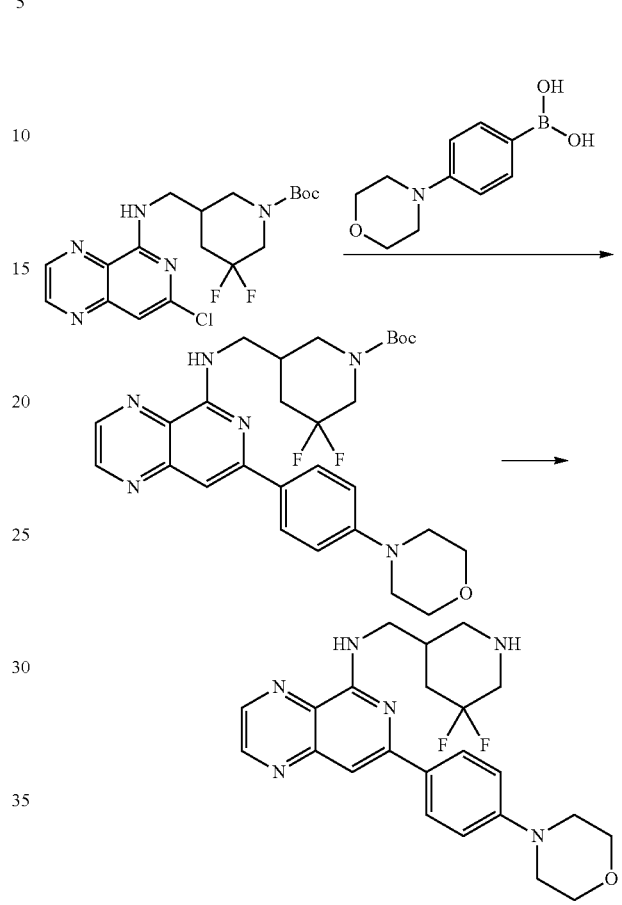

(A) tert-butyl 3,3-difluoro-5-((7-(4-morpholinophenyl)pyrido[4,3-b]pyrazin-5-ylamino)methyl)piperidine-1-carboxylate A mixture of tert-butyl 5-((7-chloropyrido[4,3-b]pyrazin-5-ylamino)methyl)-3,3-difluoropiperidine-1-carboxylate (206 mg, 0.5 mmol), 4-morpholinophenylboronic acid (207 mg, 1.0 mmol), tri(cyclohexyl)phosphine (56 mg, 0.2 mmol), Pd₂(dba)₃ (91 mg, 0.1 mmol) and Cs₂CO₃ (325 mg, 2.0 mmol) in dimethoxyethane/H₂O was sealed in a microwave reaction tube and stirred at 160° C. for 80 minutes in a microwave reactor. The mixture was cooled to room temperature, concentrated under reduced pressure, and the residue was purified by chromatography to give the title compound. MS (m/z): 541 (M+H)⁺.

(B) N-((5,5-difluoropiperidin-3-yl)methyl)-7-(4-morpholinophenyl)pyrido[4,3-b]pyrazin-5-amine tert-Butyl 3,3-difluoro-5-((7-(4-morpholinophenyl)pyrido[4,3-b]pyrazin-5-ylamino)methyl)piperidine-1-carboxylate from step A (227 mg, 0.42 mmol) was treated with HCl solution (in EtOAc, 5 N) at room temperature until the reaction was finished. The volatiles were removed under reduced pressure, dissolved in dichloromethane (5 mL), and neutralized with ammonium hydroxide. The dichloromethane phase was concentrated to afford N-((5,5-difluoropiperidin-3-yl)methyl)-7-(4-morpholinophenyl)pyrido[4,3-b]pyrazin-5-amine. MS (m/z): 441 (M+H)+.

The following compounds were prepared according to the procedures of Compound 155 using the corresponding intermediates and reagents under appropriate conditions that will be recognized by one skilled in the art.

| Compound | Structure | MS (M + H)+ |
|---|---|---|
| 156 | 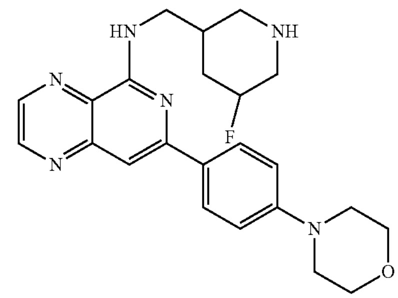 [SMILES: FC1CNCC(CNc2nc(-c3ccc(N4CCOCC4)cc3)cc3nccnc23)C1] | 423 |
| 157 | 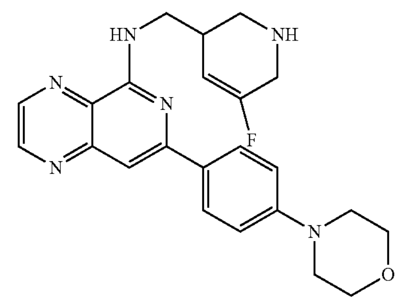 [SMILES: FC1=CC(CNc2nc(-c3ccc(N4CCOCC4)cc3)cc3nccnc23)CNC1] | 421 |
| 200 | 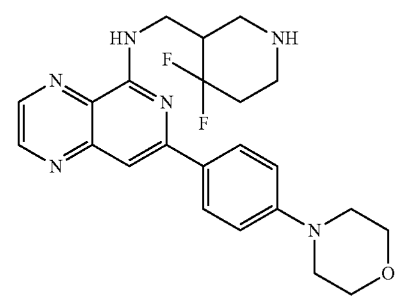 [SMILES: FC1(F)CCNCC1CNc1nc(-c2ccc(N3CCOCC3)cc2)cc2nccnc12] | 441 |
| 201 | 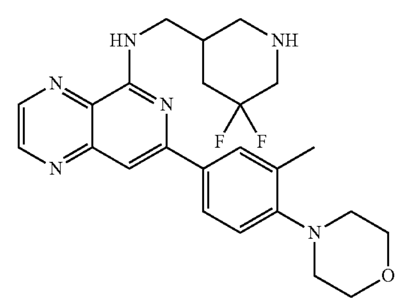 [SMILES: Cc1cc(-c2cc3nccnc3c(NCC3CNCC(F)(F)C3)n2)ccc1N1CCOCC1] | 455 |
| 202 | 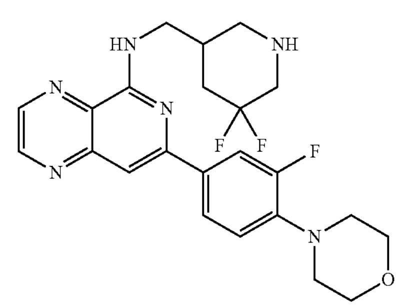 | 459 |

-continued
| Compound | Structure | MS (M + H)+ |
|---|---|---|
| 203 | 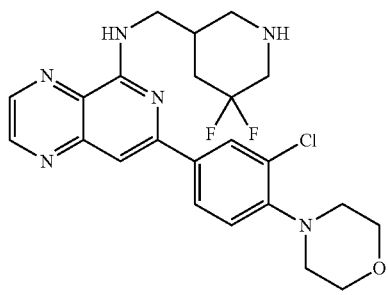 | 475 |
| 204 | 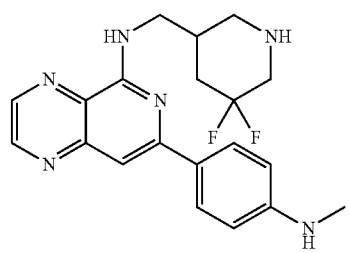 [SMILES: CNc1ccc(-c2cc3nccnc3c(NCC3CNCC(F)(F)C3)n2)cc1] | 385 |
| 205 | 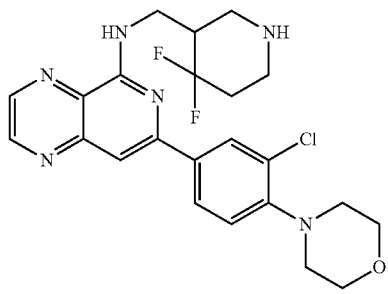 [SMILES: FC1(F)CCNCC1CNc1nc(-c2ccc(N3CCOCC3)c(Cl)c2)cc2nccnc12] | 475 |
| 206 | 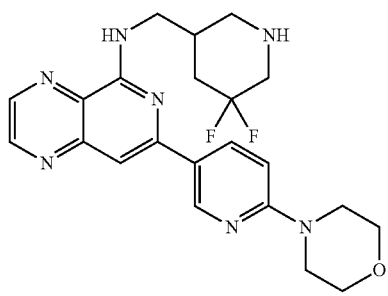 [SMILES: FC1(F)CNCC(CNc2nc(-c3ccc(N4CCOCC4)nc3)cc3nccnc23)C1] | 442 |
| 207 | 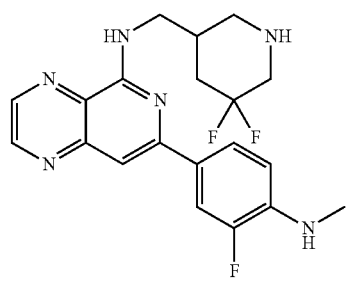 [SMILES: CNc1ccc(-c2cc3nccnc3c(NCC3CNCC(F)(F)C3)n2)cc1F] | 403 |

| Compound | Structure | MS (M + H)+ |
|---|---|---|
| 291 | 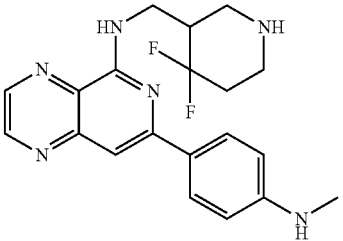 [SMILES: CNc1ccc(-c2cc3nccnc3c(NCC3CNCCC3(F)F)n2)cc1] | 385 |
| 292 | 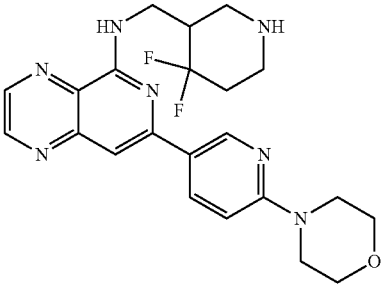 [SMILES: FC1(F)CCNCC1CNc1nc(-c2ccc(N3CCOCC3)nc2)cc2nccnc12] | 442 |
| 293 | 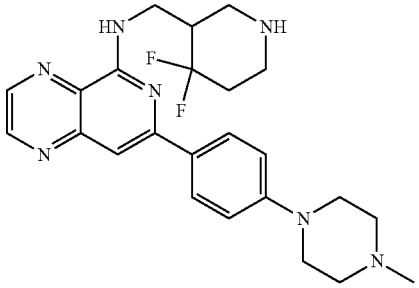 [SMILES: CN1CCN(c2ccc(-c3cc4nccnc4c(NCC4CNCCC4(F)F)n3)cc2)CC1] | 454 |
| 294 | 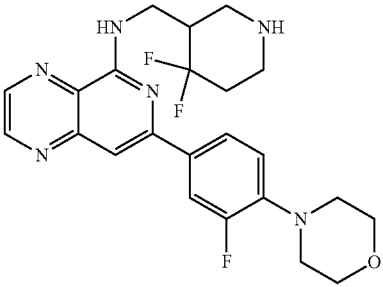 [SMILES: Fc1cc(-c2cc3nccnc3c(NCC3CNCCC3(F)F)n2)ccc1N1CCOCC1] | 459 |
| 295 | 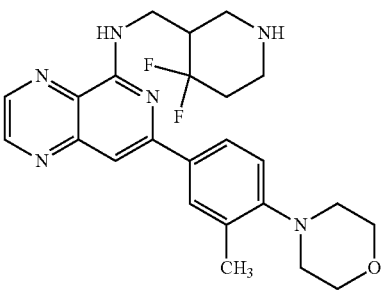 [SMILES: Cc1cc(-c2cc3nccnc3c(NCC3CNCCC3(F)F)n2)ccc1N1CCOCC1] | 455 |

-continued

| Compound | Structure | MS (M + H)+ |
|---|---|---|
| 296 | 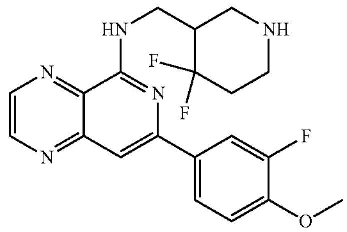 [SMILES: COc1ccc(-c2cc3nccnc3c(NCC3CNCCC3(F)F)n2)cc1F] | 404 |
| 297 | 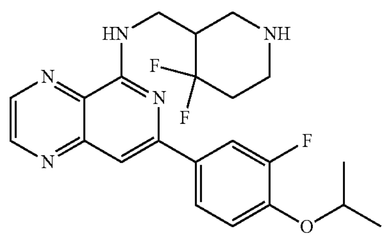 [SMILES: CC(C)Oc1ccc(-c2cc3nccnc3c(NCC3CNCCC3(F)F)n2)cc1F] | 432 |
| 298 | 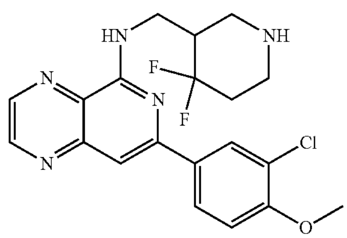 [SMILES: COc1ccc(-c2cc3nccnc3c(NCC3CNCCC3(F)F)n2)cc1Cl] | 420
422 |
| 299 | | 387 |
| 300 | | 403 |
| 301 | | 417 |

-continued

| Compound | Structure | MS (M + H)+ |
|---|---|---|
| 302 | 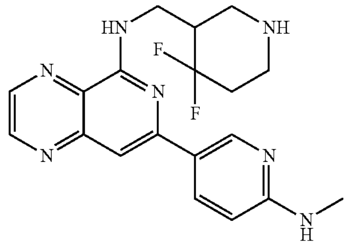 [SMILES: CNc1ccc(-c2cc3nccnc3c(NCC3CNCCC3(F)F)n2)cn1] | 386 |
| 303 | 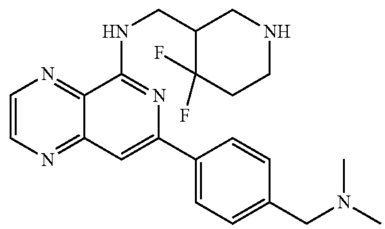 [SMILES: CN(C)Cc1ccc(-c2cc3nccnc3c(NCC3CNCCC3(F)F)n2)cc1] | 413 |
| 304 | 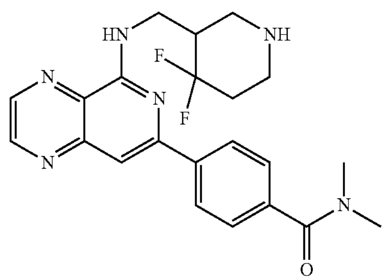 [SMILES: CN(C)C(=O)c1ccc(-c2cc3nccnc3c(NCC3CNCCC3(F)F)n2)cc1] | 427 |
| 305 | 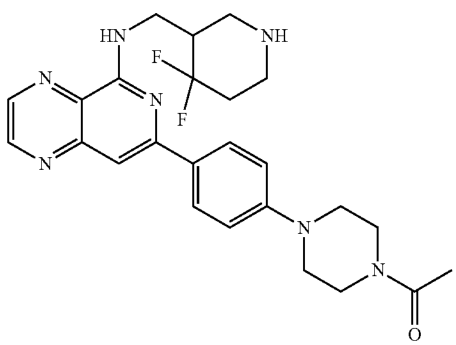 [SMILES: CC(=O)N1CCN(c2ccc(-c3cc4nccnc4c(NCC4CNCCC4(F)F)n3)cc2)CC1] | 482 |
| 306 | 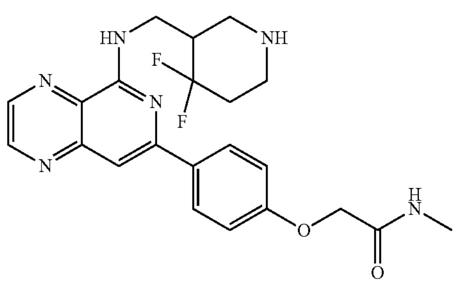 [SMILES: CNC(=O)COc1ccc(-c2cc3nccnc3c(NCC3CNCCC3(F)F)n2)cc1] | 443 |

-continued

| Compound | Structure | MS (M + H)+ |
|---|---|---|
| 307 | 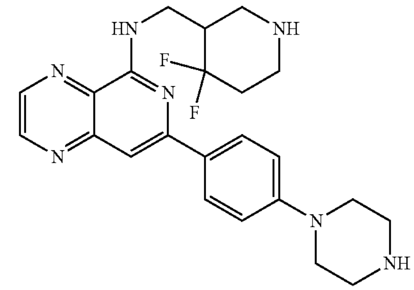 [SMILES: FC1(F)CCNCC1CNc1nc(-c2ccc(N3CCNCC3)cc2)cc2nccnc12] | 440 |
| 308 | 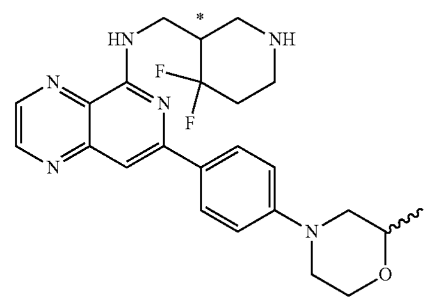 [SMILES: CC1CN(c2ccc(-c3cc4nccnc4c(NCC4CNCCC4(F)F)n3)cc2)CCO1] | 455 |
| 309 | | 455 |
| 310 | 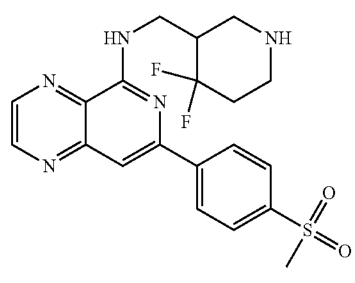 [SMILES: CS(=O)(=O)c1ccc(-c2cc3nccnc3c(NCC3CNCCC3(F)F)n2)cc1] | 434 |
| 311 | 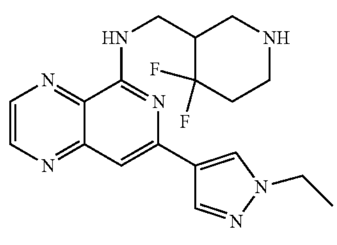 [SMILES: CCn1cc(-c2cc3nccnc3c(NCC3CNCCC3(F)F)n2)cn1] | 374 |

-continued

| Compound | Structure | MS (M + H)+ |
|---|---|---|
| 312 | 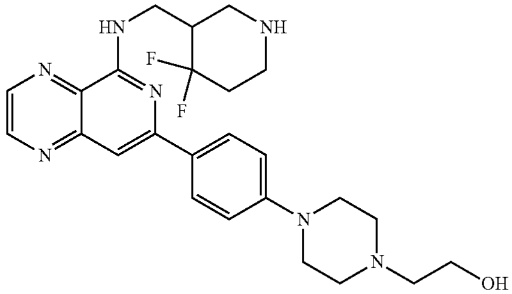 [SMILES: OCCN1CCN(c2ccc(-c3cc4nccnc4c(NCC4CNCCC4(F)F)n3)cc2)CC1] | 484 |
| 313 | 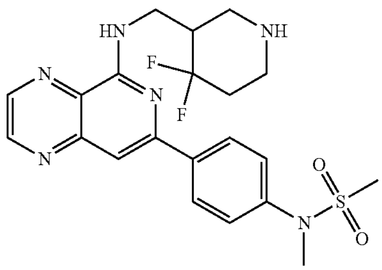 [SMILES: CN(c1ccc(-c2cc3nccnc3c(NCC3CNCCC3(F)F)n2)cc1)S(C)(=O)=O] | 463 |
| 314 | 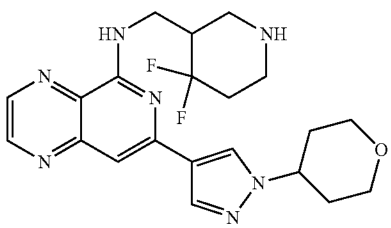 [SMILES: FC1(F)CCNCC1CNc1nc(-c2cnn(C3CCOCC3)c2)cc2nccnc12] | 430 |
| 315 | 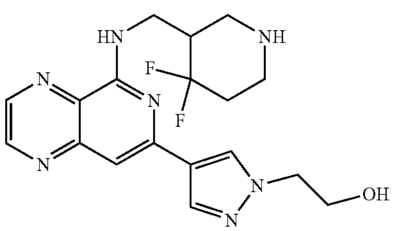 [SMILES: OCCn1cc(-c2cc3nccnc3c(NCC3CNCCC3(F)F)n2)cn1] | 390 |
| 316 | chiral | 483 |

-continued
| Compound | Structure | MS (M + H)+ |
|---|---|---|
| 317 | chiral 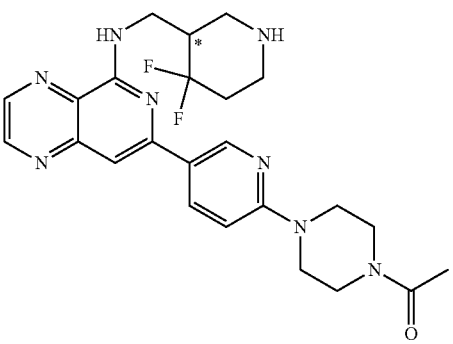 | 483 |
| 318 | chiral 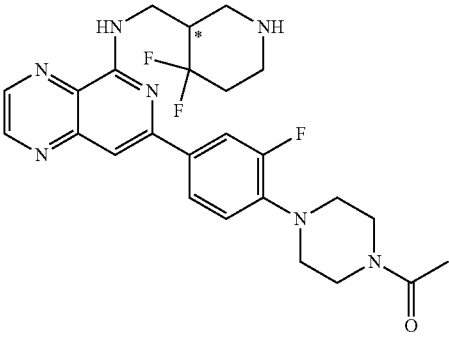 | 500 |
| 319 | chiral 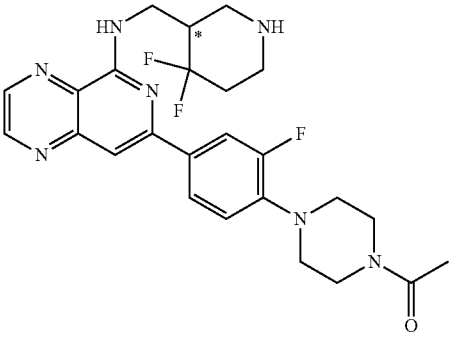 | 500 |
| 320 | chiral 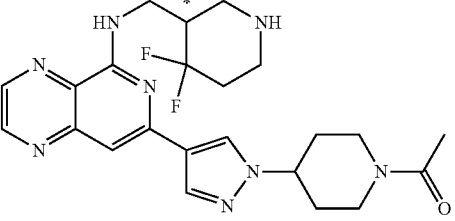 | 471 |

-continued

| Compound | Structure | MS (M + H)+ |
|---|---|---|
| 321 | chiral | 507 |

Compound 158

5-((7-(4-morpholinophenyl)pyrido[4,3-b]pyrazin-5-ylamino)methyl)piperidin-3-ol

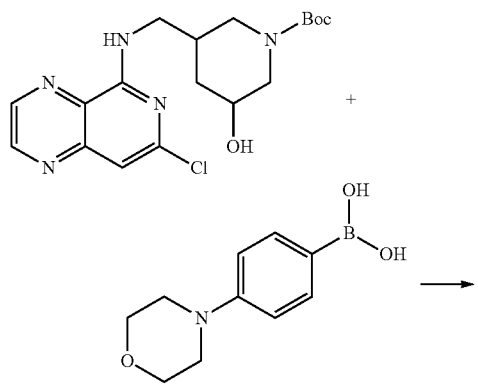

(A) tert-butyl 3-hydroxy-5-((7-(4-morpholinophenyl)pyrido[4,3-b]pyrazin-5-ylamino)methyl)piperidine-1-carboxylate The title compound was prepared according to the procedures of Compound 1 (B) using tert-butyl 3-((7-chloropyrido[4,3-b]pyrazin-5-ylamino)methyl)-5-hydroxypiperidine-1-carboxylate and 4-morpholinophenylboronic acid. MS (m/z): 521 (M+H)+.

(B) 5-((7-(4-morpholinophenyl)pyrido[4,3-b]pyrazin-5-ylamino)methyl)piperidin-3-ol The title compound was prepared according to the procedures of Compound 155 (B) using tert-butyl 3-hydroxy-5-((7-(4-morpholinophenyl)pyrido[4,3-b]pyrazin-5-ylamino)methyl)piperidine-1-carboxylate MS (m/.z): 421 (M+H)+.

Compound 159

(R)-(1-(7-(4-morpholinophenyl)pyrido[4,3-b]pyrazin-5-yl)pyrrolidin-3-yl)methanol

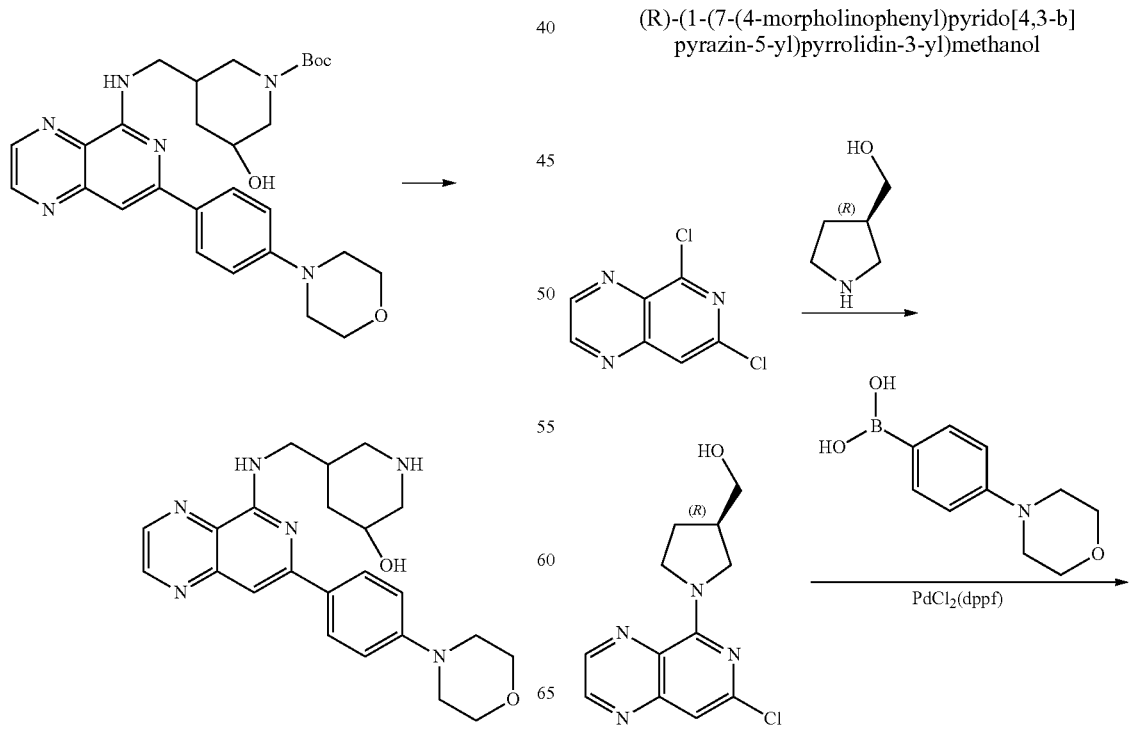

-continued

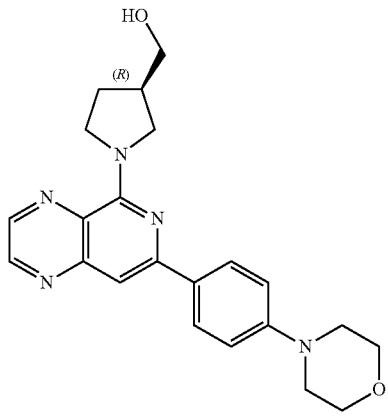

(A) (R)-(1-(7-chloropyrido[4,3-b]pyrazin-5-yl)pyrrolidin-3-yl)methanol

The title compound was prepared according to the procedure of Compound 1 (A) using (R)-pyrrolidin-3-ylmethanol and 5,7-dichloropyrido[4,3-b]pyrazine. MS (m/z): 265 (M+H)$^+$.

(B) (R)-(1-(7-(4-morpholinophenyl)pyrido[4,3-b]pyrazin-5-yl)pyrrolidin-3-yl)methanol The title compound was prepared according to the procedure of Compound 145 (E) using (R)-(1-(7-chloropyrido[4,3-b]pyrazin-5-yl)pyrrolidin-3-yl)methanol. MS (m/z): 392 (M+H)$^+$.

The following compounds were prepared according to the procedures of Compound 159 using the corresponding intermediates and reagents under appropriate conditions that will be recognized by one skilled in the art.

| Compound | Structure | MS (M + H)$^+$ |
|---|---|---|
| 160 | 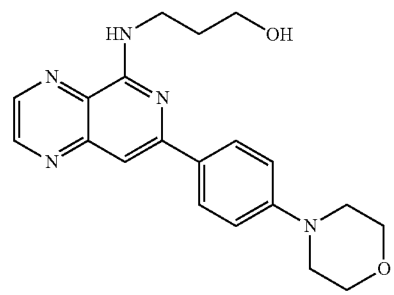 [SMILES: OCCCNc1nc(-c2ccc(N3CCOCC3)cc2)cc2nccnc12] | 366 |
| 161 | 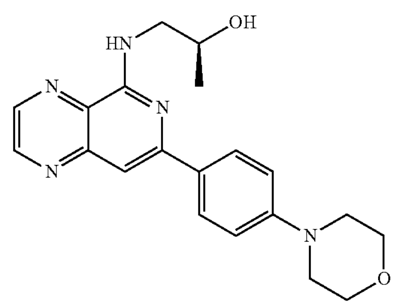 [SMILES: C[C@H](O)CNc1nc(-c2ccc(N3CCOCC3)cc2)cc2nccnc12] | 366 |
| 162 | 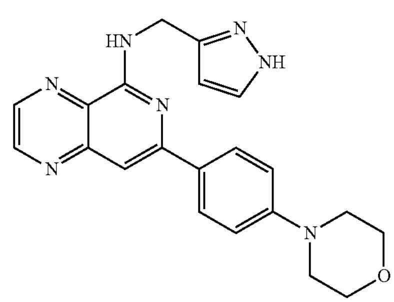 [SMILES: c1cnc2c(NCc3cc[nH]n3)nc(-c3ccc(N4CCOCC4)cc3)cc2n1] | 388 |

-continued

| Compound | Structure | MS (M + H)+ |
|---|---|---|
| 163 | 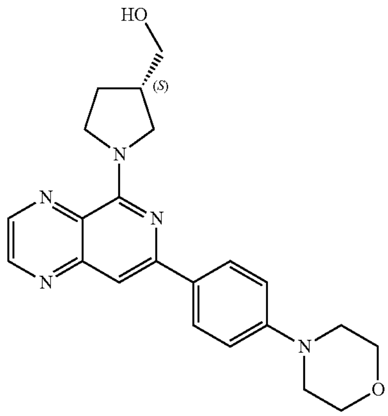 | 392 |
| 164 | 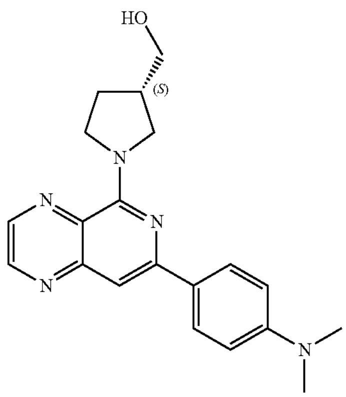 | 350 |
| 165 | 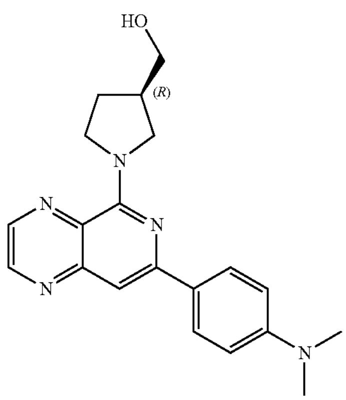 | 350 |
| 166 | 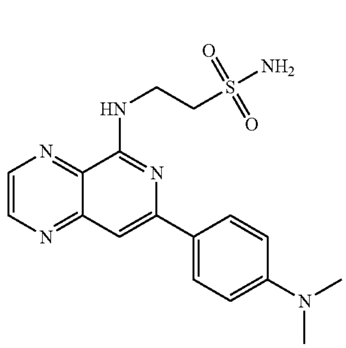 [SMILES: CN(C)c1ccc(-c2cc3nccnc3c(NCCS(N)(=O)=O)n2)cc1] | 373 |

-continued
| Compound | Structure | MS (M + H)+ |
|---|---|---|
| 167 | 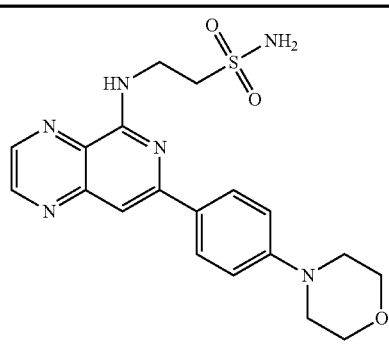 | 415 |
| 168 | 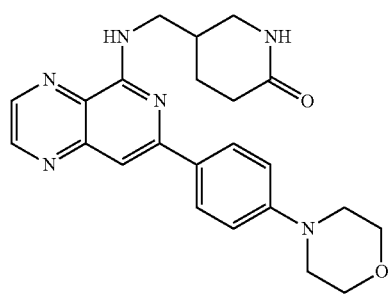 [SMILES: O=C1CCC(CNc2nc(-c3ccc(N4CCOCC4)cc3)cc3nccnc23)CN1] | 419 |
| 169 | 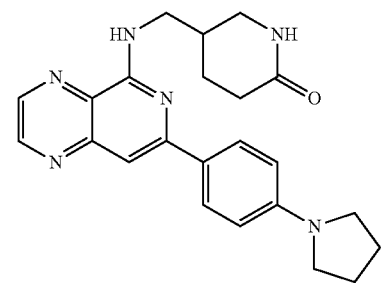 [SMILES: O=C1CCC(CNc2nc(-c3ccc(N4CCCC4)cc3)cc3nccnc23)CN1] | 403 |
| 170 | 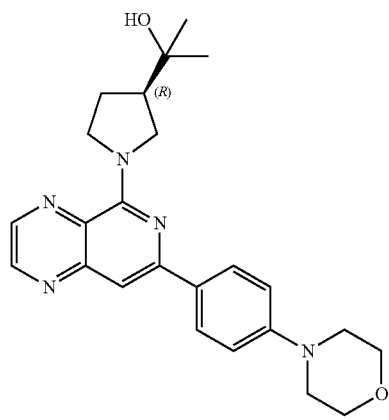 | 420 |

-continued
| Compound | Structure | MS (M + H)+ |
|---|---|---|
| 171 | 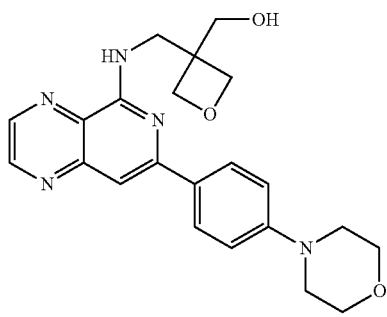 [SMILES: OCC1(CNc2nc(-c3ccc(N4CCOCC4)cc3)cc3nccnc23)COC1] | 408 |
| 172 | 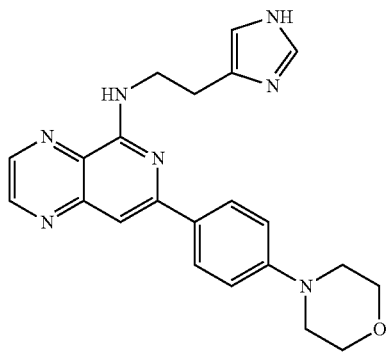 [SMILES: c1cnc2c(NCCc3c[nH]cn3)nc(-c3ccc(N4CCOCC4)cc3)cc2n1] | 402 |
| 357 | 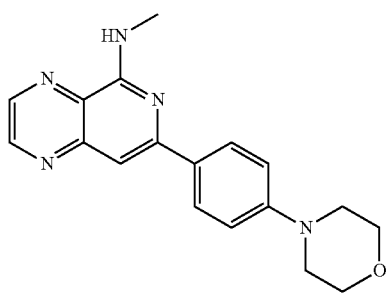 [SMILES: CNc1nc(-c2ccc(N3CCOCC3)cc2)cc2nccnc12] | 322 |
| 358 | 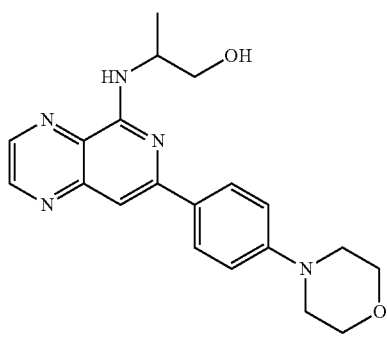 [SMILES: CC(CO)Nc1nc(-c2ccc(N3CCOCC3)cc2)cc2nccnc12] | 366 |

-continued

| Compound | Structure | MS (M + H)+ |
|---|---|---|
| 359 | 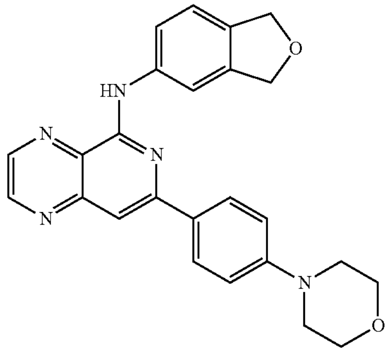 [SMILES: c1cnc2c(Nc3ccc4c(c3)COC4)nc(-c3ccc(N4CCOCC4)cc3)cc2n1] | 426 |
| 360 | 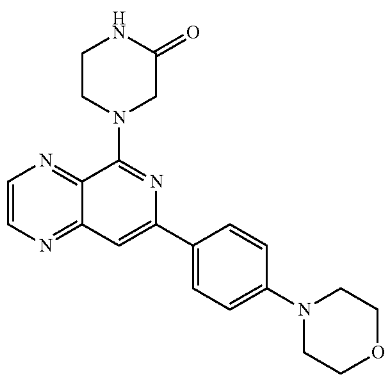 [SMILES: O=C1CN(c2nc(-c3ccc(N4CCOCC4)cc3)cc3nccnc23)CCN1] | 391 |
| 361 | 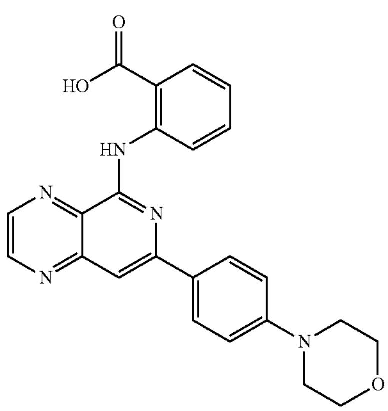 [SMILES: O=C(O)c1ccccc1Nc1nc(-c2ccc(N3CCOCC3)cc2)cc2nccnc12] | 428 |
| 362 | 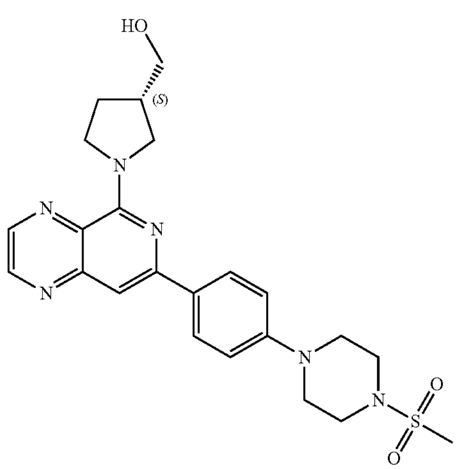 | 469 |

-continued
| Compound | Structure | MS (M + H)+ |
|---|---|---|
| 363 | 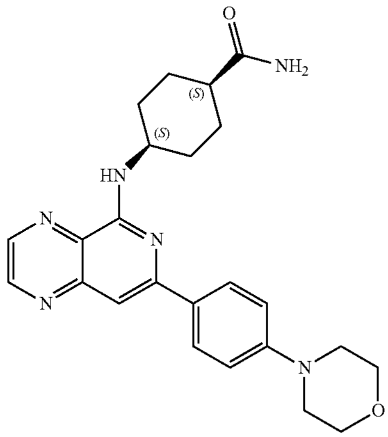 | 433 |
| 364 | 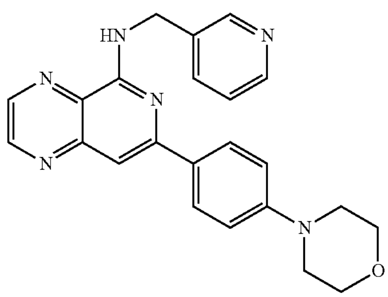 [SMILES: c1cncc(CNc2nc(-c3ccc(N4CCOCC4)cc3)cc3nccnc23)c1] | 399 |
Compound 173
(R)—N-methyl (1-(7-(4-morpholinophenyl)pyrido[4,3-b]pyrazin-5-yl)pyrrolidin-3-yl)methanamine
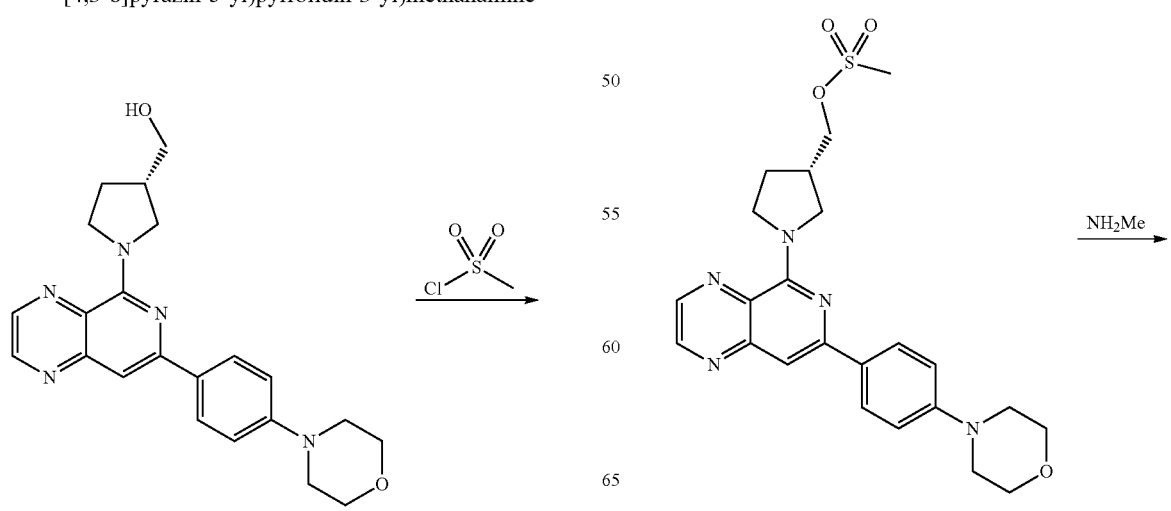
-continued

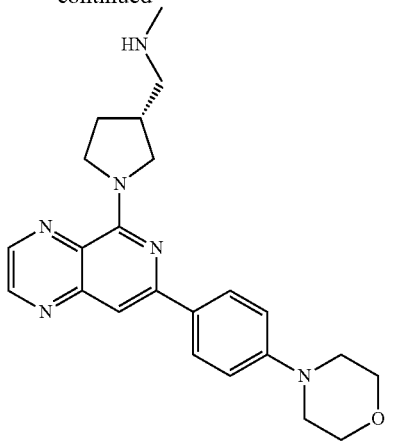

(A) (S)-(1-(7-(4-morpholinophenyl)pyrido[4,3-b]pyrazin-5-yl)pyrrolidin-3-yl)methyl methanesulfonate To a solution of (S)-(1-(7-(4-morpholinophenyl)pyrido[4,3-b]pyrazin-5-yl)pyrrolidin-3-yl)methanol (compound 163, 500 mg, 1.27 mmol) in THF (15 mL) were added MsCl (200 mg, 1.6 mmol) and TEA (370 mg, 3.7 mmol). The mixture was stirred for 4 hours at room temperature and concentrated in vacuo. The residue was washed by H$_2$O and EtOAc to give the title compound. MS (m/z): 470 (M+H)$^+$

(B) (R)—N-methyl(1-(7-(4-morpholinophenyl)pyrido[4,3-b]pyrazin-5-yl)pyrrolidin-3-yl)methanamine The mixture of (S)-(1-(7-(4-morpholinophenyl)pyrido[4,3-b]pyrazin-5-yl)pyrrolidin-3-yl)methyl methanesulfonate (100 mg, 0.21 mmol) and MeNH$_2$ solution (33% in water, 5 mL) was refluxed overnight, concentrated, and purified by chromatography to give the title compound. MS (m/z): 405 (M+H)$^+$

Compound 174

(S)-1-(1-(7-(4-morpholinophenyl)pyrido[4,3-b]pyrazin-5-yl)pyrrolidin-3-yl)ethanol

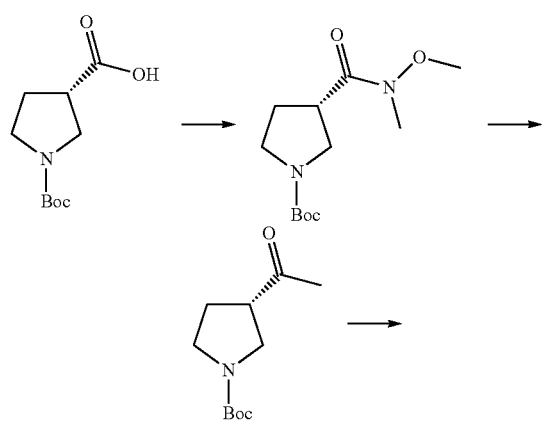

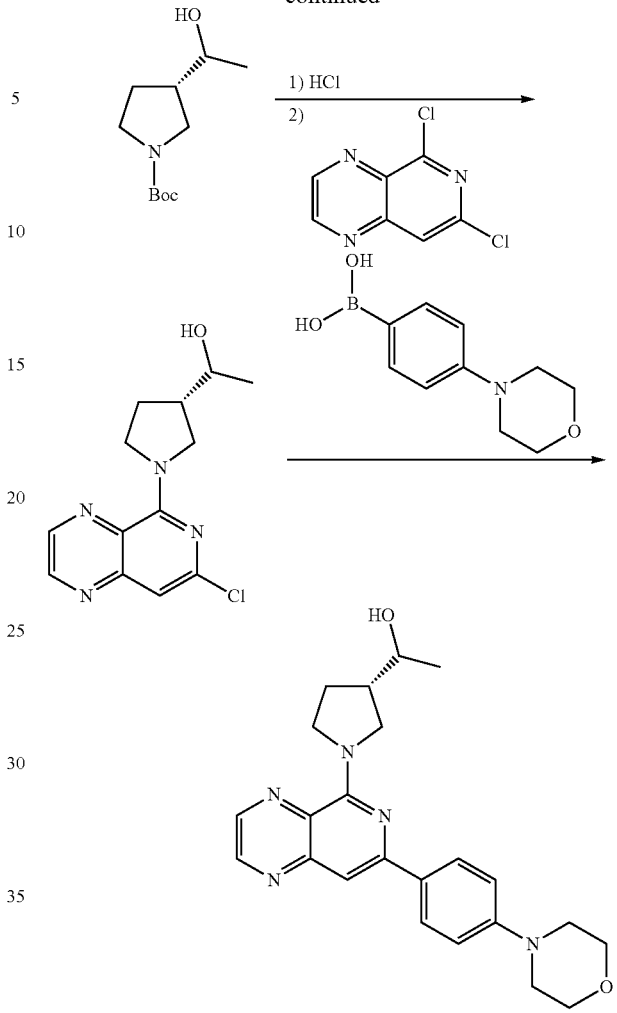

(A) (S)-tert-butyl 3-(methoxy(methyl)carbamoyl)pyrrolidine-1-carboxylate

To a solution of (S)-1-(tert-butoxycarbonyl)pyrrolidine-3-carboxylic acid (430 mg, 2.0 mmol) in CH$_2$Cl$_2$ (20 mL) was added CDI (356 mg, 2.2 mmol). The mixture was stirred at room temperature for 20 minutes, N,O-dimethylhydroxylamine hydrochloride (234 mg, 2.4 mmol) and DIPEA (258 mg, 2.6 mmol) were then added subsequently at 0° C. The mixture was stirred at 0° C. for 0.5 hour, then warmed up and stirred at ambient temperature overnight. The mixture was washed with HCl (1 N), saturated aqueous NaHCO$_3$ and water, dried over Na$_2$SO$_4$, filtered, and concentrated under reduced pressure to give the title compound for the next step.

(B) (S)-tert-butyl 3-acetylpyrrolidine-1-carboxylate

To a solution of (S)-tert-butyl 3-(methoxy(methyl)carbamoyl)pyrrolidine-1-carboxylate in THF (18 mL) was added methylmagnesium bromide (in ether, 3 M, 2.7 mL) at 0° C. The mixture was stirred at 0° C. for 2 hours, then quenched with saturated aqueous NH$_4$Cl, and extracted with Et$_2$O. The combined extracts were washed with saturated aqueous NaHCO$_3$, dried over Na$_2$SO$_4$, filtered, and concentrated to give the tile compound for the next step.

(C) (S)-tert-butyl 3-(1-hydroxyethyl)pyrrolidine-1-carboxylate

To a solution of (S)-tert-butyl 3-acetylpyrrolidine-1-carboxylate in methanol (10 mL) was added sodium borohydride (114 mg, 3.0 mmol) at 0° C. The reaction mixture was stirred at ambient temperature for 2 hours then quenched with saturated ammonium chloride solution and extracted with dichloromethane. The combined extracts were dried over magnesium sulfate, filtered, and concentrated to give the title compound for the next step.

(D) (S)-1-(1-(7-chloropyrido[4,3-b]pyrazin-5-yl)pyrrolidin-3-yl)ethanol (S)-tert-butyl 3-(1-hydroxyethyl)pyrrolidine-1-carboxylate was treated with HCl solution (in EtOAc, 5 mL) at room temperature for 2 hours. The volatiles were removed under reduced pressure, and the residue was dissolved in anhydrous THF (10 mL). To the resulted THF solution, DIPEA (570 mg, 4.4 mmol) and 5,7-dichloropyrido[4,3-b]pyrazine (400 mg, 2.0 mmol) were added, and the reaction was stirred at room temperature overnight. The volatiles were removed under reduced pressure, and the residue was dissolved in ethyl acetate, washed with brine and dried over $Na_2SO_4$, filtered, and concentrated. The residue was purified by chromatography to afford the title compound. MS (m/z): 279 (M+H)$^+$.

(E) (S)-1-(1-(7-(4-morpholinophenyl)pyrido[4,3-b]pyrazin-5-yl)pyrrolidin-3-yl)ethanol The title compound was prepared according to the procedure of Compound 1 (B) using (S)-1-(1-(7-chloropyrido[4,3-b]pyrazin-5-yl)pyrrolidin-3-yl)ethanol and 4-morpholinophenylboronic acid. MS (m/z): 406 (M+H)$^+$.

Compound 175

3-(7-(4-(di methylamino)phenyl)pyrido[4,3-b]pyrazin-5-ylamino)propanamide

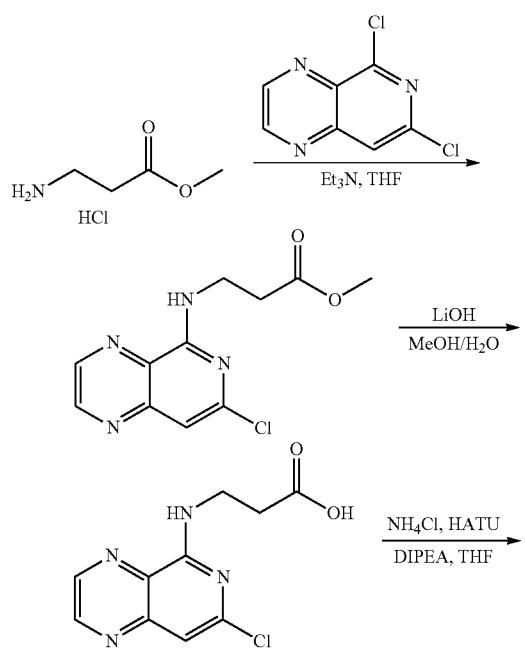

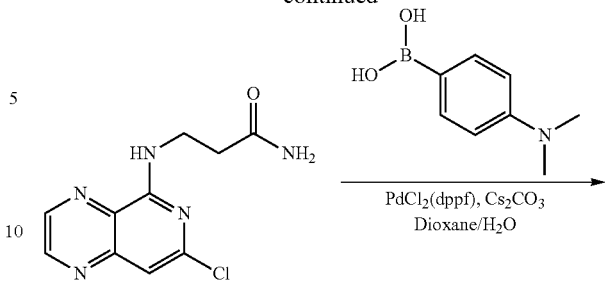

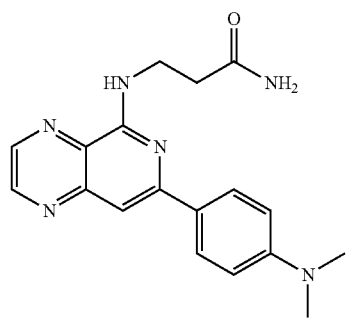

(A) methyl 3-(7-chloropyrido[4,3-b]pyrazin-5-ylamino)propanoate

A solution of methyl 3-aminopropanoate hydrochloride (4.88 mmol), Et$_3$N (6.50 mmol) and 5,7-dichloropyrido[4,3-b]pyrazine (3.25 mmol) in THF (10 mL) was stirred at room temperature overnight. Volatiles were removed under reduced pressure, and the residue was treated with water and extracted with EtOAc. The combined extracts were dried over Na$_2$SO$_4$, filtered, and concentrated. The residue was purified by chromatography to afford the title compound. MS (m/z): 267 (M+H)$^+$.

(B) 3-(7-chloropyrido[4,3-b]pyrazin-5-ylamino)propanoic acid

A solution of methyl 3-(7-chloropyrido[4,3-b]pyrazin-5-ylamino)propanoate (545 mg, 2.04 mmol) and LiOH.H$_2$O (172 mg, 4.09 mmol) in MeOH/H$_2$O (v. 20:1, 40 mL/2 mL) was stirred at room temperature for 20 hours. The volatiles were removed under reduced pressure, and the residue was acidified with HCl solution (1 N) till pH=2~3. The precipitates were collected by filtration and dried to afford the title compound. MS (m/z): 253 (M+H)$^+$.

(C) 3-(7-chloropyrido[4,3-b]pyrazin-5-ylamino)propanamide

A solution of 3-(7-chloropyrido[4,3-b]pyrazin-5-ylamino)propanoic acid (2.22 mmol), HATU (2.66 mmol), DIPEA (6.65 mmol) and NH$_4$Cl (4.43 mmol) in THF (10 mL) was stirred at room temperature overnight. The volatiles were removed under reduced pressure and the residue was treated with water. The precipitates were collected by filtration and dried to give the title compound. MS (m/z): 252 (M+H)$^+$.

(D) 3-(7-(4-(dimethylamino)phenyl)pyrido[4,3-b]pyrazin-5-ylamino)propanamide The title compound was prepared according to the procedure of Compound 1 (B) using 3-(7-chloropyrido[4,3-b]

pyrazin-5-ylamino)propanamide prepared above and 4-(dimethylamino)phenylboronic acid. MS (m/z): 337 (M+H)+.

The following compounds 176 to 178 were prepared according to the procedures of Compound 175 using the corresponding intermediates and reagents under appropriate conditions that will be recognized by one skilled in the art.

| Compound | Structure | MS (M + H)+ |
|---|---|---|
| 176 | 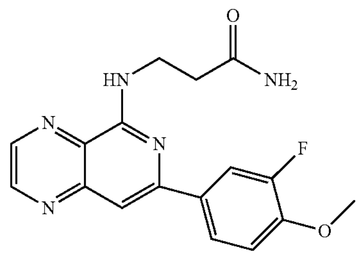 [SMILES: COc1ccc(-c2cc3nccnc3c(NCCC(N)=O)n2)cc1F] | 342 |
| 177 | 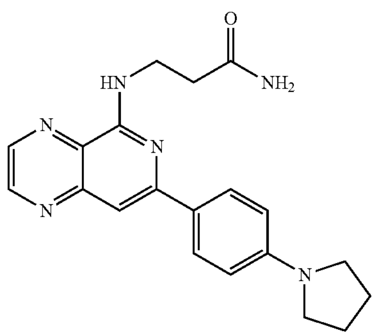 [SMILES: NC(=O)CCNc1nc(-c2ccc(N3CCCC3)cc2)cc2nccnc12] | 363 |
| 178 | 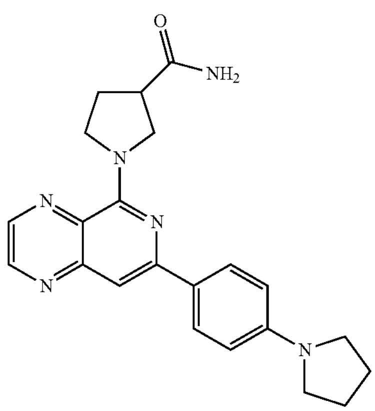 [SMILES: NC(=O)C1CCN(c2nc(-c3ccc(N4CCCC4)cc3)cc3nccnc23)C1] | 389 |
| 179 | 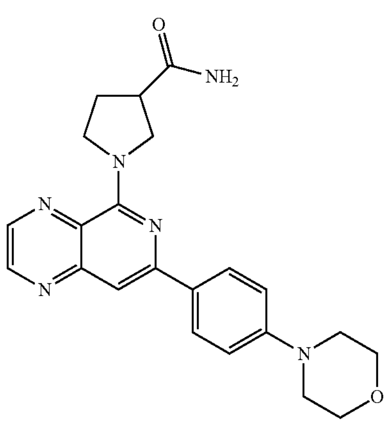 [SMILES: NC(=O)C1CCN(c2nc(-c3ccc(N4CCOCC4)cc3)cc3nccnc23)C1] | 405 |
| 365 | | 380 |
| 366 | | 406 |
| 367 | | 406 |

Compound 180

N-(3-aminopropyl)-7-(4-morpholinophenyl)pyrido[4,3-b]pyrazin-5-amine

-continued

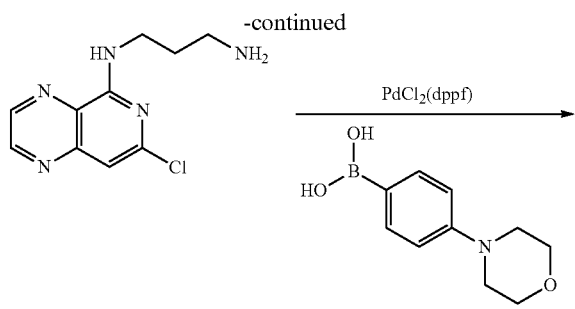

(A) N-(3-aminopropyl)-7-chloropyrido[4,3-b]pyrazin-5-amine

A solution of propane-1,3-diamine (890 mg, 12 mmol) and 5,7-dichloropyrido[4,3-b]pyrazine (600 mg, 3 mmol) in methanol (10 mL) was stirred at room temperature for 4 hours. The volatiles were evaporated, and the residue was purified by chromatography to afford the title compound. MS (m/z): 238 (M+H)$^+$.

(B) N-(3-aminopropyl)-7-(4-morpholinophenyl)pyrido[4,3-b]pyrazin-5-amine

The title compound was prepared according to the procedure of Compound 145 (E) using N-(3-aminopropyl)-7-chloropyrido[4,3-b]pyrazin-5-amine prepared above. MS (m/z): 365 (M+H)$^+$.

The following compounds 181-199 were prepared according to the procedures of Compound 180 using the corresponding intermediates and reagents under appropriate conditions that will be recognized by one skilled in the art.

| Compound | Structure | MS (M + H)$^+$ |
|---|---|---|
| 181 | 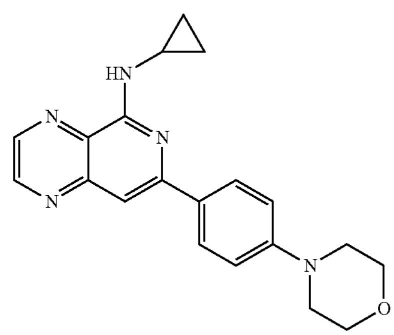 [SMILES: c1cnc2c(NC3CC3)nc(-c3ccc(N4CCOCC4)cc3)cc2n1] | 348 |
| 182 | 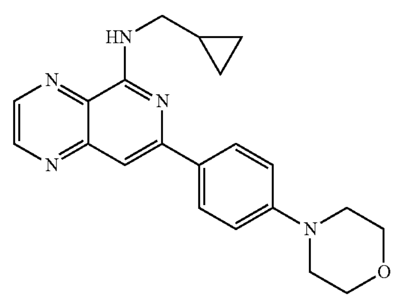 [SMILES: c1cnc2c(NCC3CC3)nc(-c3ccc(N4CCOCC4)cc3)cc2n1] | 362 |
| 183 | 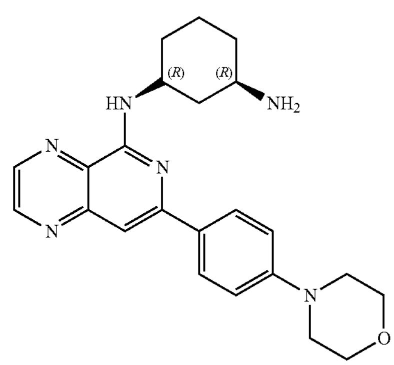 | 405 |

-continued

| Compound | Structure | MS (M + H)⁺ |
|---|---|---|
| 184 | *5-[(pyridin-4-ylmethyl)amino]-7-[4-(morpholin-4-yl)phenyl]pyrido[3,4-b]pyrazine* | 399 |
| 185 | *5-[(3-aminopropyl)amino]-7-[4-(dimethylamino)phenyl]pyrido[3,4-b]pyrazine* | 323 |
| 186 | *5-[(3-aminopropyl)amino]-7-[4-(4-methylpiperazin-1-yl)phenyl]pyrido[3,4-b]pyrazine* | 378 |
| 187 | *5-[(2-cyanoethyl)amino]-7-[4-(morpholin-4-yl)phenyl]pyrido[3,4-b]pyrazine* | 361 |
| 188 | *5-[(3-amino-3-oxopropyl)amino]-7-[4-(morpholin-4-yl)phenyl]pyrido[3,4-b]pyrazine* | 379 |

-continued
| Compound | Structure | MS (M + H)+ |
|---|---|---|
| 189 | 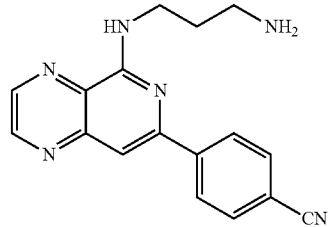 [SMILES: N#Cc1ccc(-c2cc3nccnc3c(NCCCN)n2)cc1] | 305 |
| 190 | 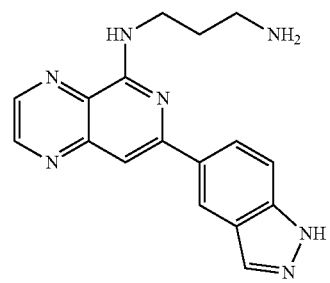 [SMILES: NCCCNc1nc(-c2ccc3[nH]ncc3c2)cc2nccnc12] | 320 |
| 191 | 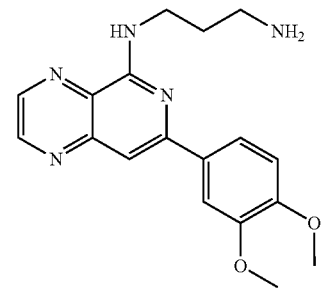 [SMILES: COc1ccc(-c2cc3nccnc3c(NCCCN)n2)cc1OC] | 340 |
| 192 | 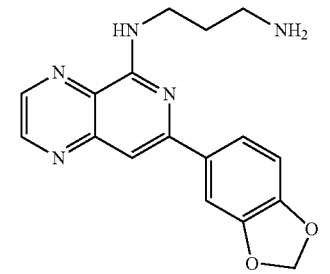 [SMILES: NCCCNc1nc(-c2ccc3c(c2)OCO3)cc2nccnc12] | 324 |
| 193 | 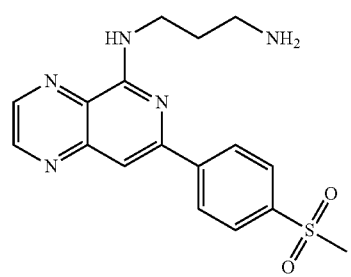 [SMILES: CS(=O)(=O)c1ccc(-c2cc3nccnc3c(NCCCN)n2)cc1] | 358 |

-continued

| Compound | Structure | MS (M + H)+ |
|---|---|---|
| 194 | 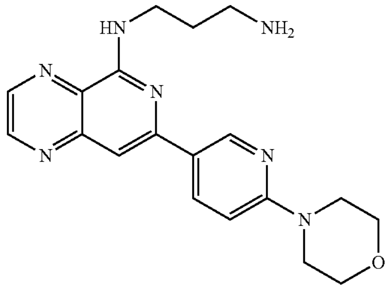 [SMILES: NCCCNc1nc(-c2ccc(N3CCOCC3)nc2)cc2nccnc12] | 366 |
| 195 | 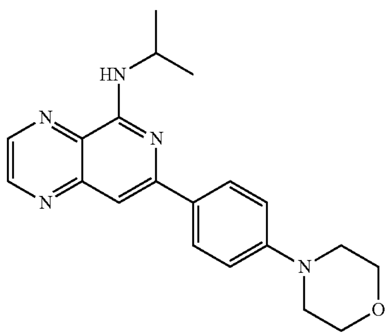 [SMILES: CC(C)Nc1nc(-c2ccc(N3CCOCC3)cc2)cc2nccnc12] | 350 |
| 196 | 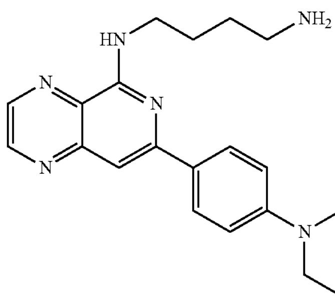 | 379 |
| 197 | 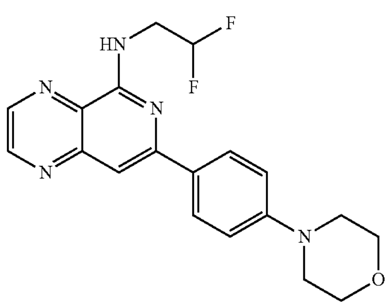 [SMILES: FC(F)CNc1nc(-c2ccc(N3CCOCC3)cc2)cc2nccnc12] | 372 |
| 198 | 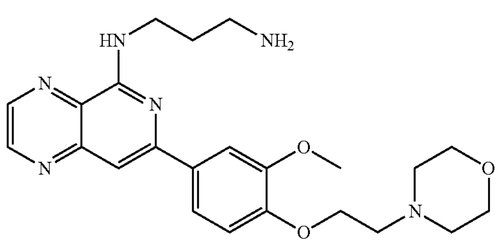 [SMILES: COc1cc(-c2cc3nccnc3c(NCCCN)n2)ccc1OCCN1CCOCC1] | 439 |

-continued

| Compound | Structure | MS (M + H)+ |
|---|---|---|
| 199 | 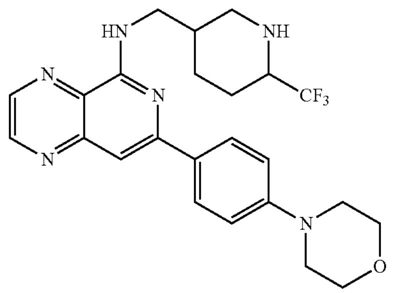 [SMILES: FC(F)(F)C1CCC(CNc2nc(-c3ccc(N4CCOCC4)cc3)cc3nccnc23)CN1] | 473 |
| 509 | 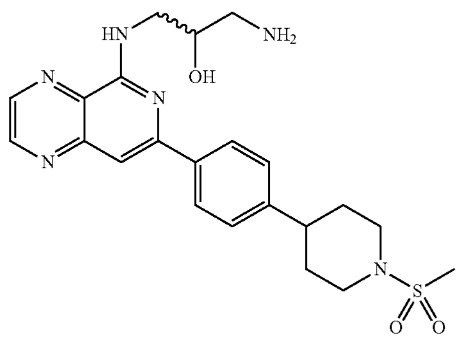 [SMILES: CS(=O)(=O)N1CCC(c2ccc(-c3cc4nccnc4c(NCC(O)CN)n3)cc2)CC1] | 457 |

Compound 232 and 233

(S)—N-((4,4-difluoropiperidin-3-yl)methyl)-7-(4-morpholinophenyl)pyrido[4,3-b]pyrazin-5-amine and (R)—N-((4,4-difluoropiperidin-3-yl)methyl)-7-(4-morpholinophenyl)pyrido[4,3-b]pyrazin-5-amine

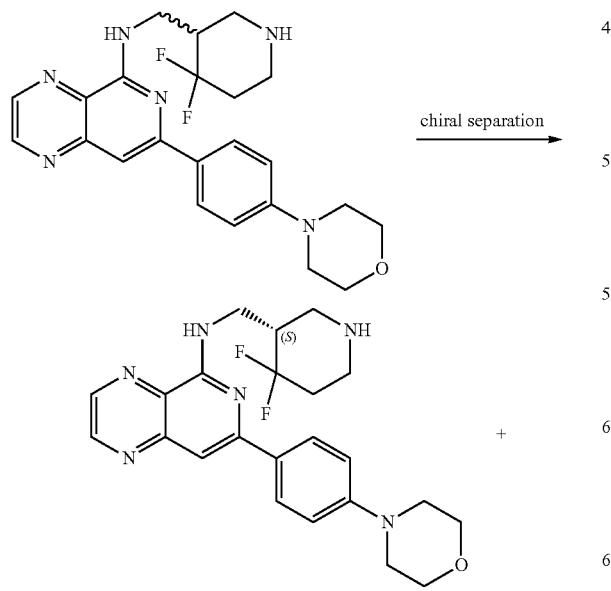

chiral separation →

-continued

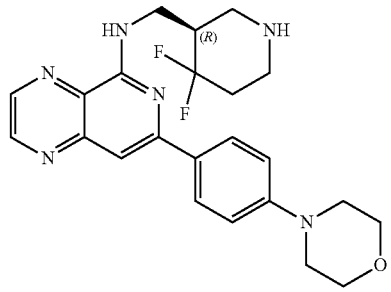

The racemic compound 200 was resolved by chiral HPLC to provide the optically pure enantiomers Compound 232 and 233 (HPLC conditions: column: CHIRALPAK IA 20×250 mm; mobile phase: CH$_3$CN/MeOH/DEA=9/1/0.01; flow rate=10 mL/min; detector: UV 254 nm). The first eluent (compound 232, Rf=9.62 min) was 99% ee, MS (m/z): 441 (M+H)+. and the second eluent (compound 233, Rf=13.60 min) was 95.5% ee, MS (m/z): 441 (M+H)+.

251

Compound 368 and 369

(S)—N-((4,4-difluoropiperidin-3-yl)methyl)-7-(3-fluoro-4-morpholinophenyl) pyrido[4,3-b]pyrazin-5-amine and (R)—N-((4,4-difluoropiperidin-3-yl)methyl)-7-(3-fluoro-4-morpholinophenyl)pyrido[4,3-b]pyrazin-5-amine

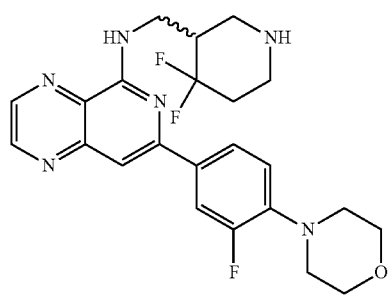

→

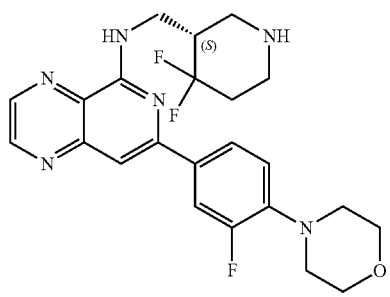

+

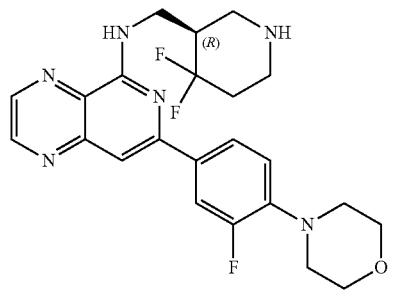

The racemic compound 294 was resolved by chiral HPLC to provide the optically pure enantiomers Compound 368 and 369 (HPLC conditions: column: CHIRALPAK IA 0.46× 15 cm; mobile phase: CH$_3$CN/MeOH/DEA=9/1/0.01; flow rate=1.0 mL/min; detector: UV 220 nm). The first eluent (compound 368, Rf=11.36 min) was 100% ee, MS (m/z): 459 (M+H)$^+$. and the second eluent (compound 369, Rf=14.72 min) was 100% ee, MS (m/z): 459 (M+H)$^+$.

252

Compound 370 and 371

(S)—N-((4,4-difluoropiperidin-3-yl)methyl)-7-(3-methyl-4-morpholinophenyl) pyrido[4,3-b]pyrazin-5-amine and (R)—N-((4,4-difluoropiperidin-3-yl)methyl)-7-(3-methyl-4-morpholinophenyl)pyrido[4,3-b]pyrazin-5-amine

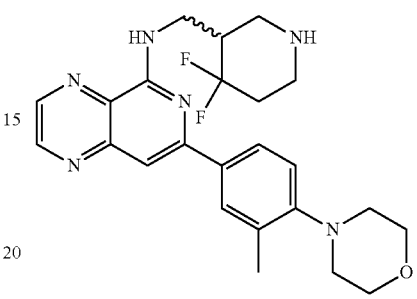

→

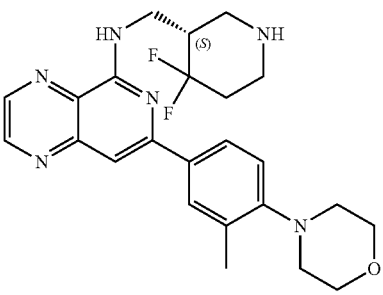

+

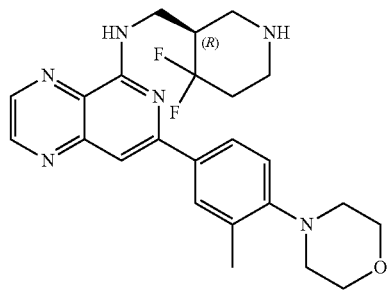

The racemic compound 295 was resolved by chiral HPLC to provide the optically pure enantiomers Compound 370 and 371 (HPLC conditions: column: CHIRALCEL OJH 0.46×15 cm; mobile phase: EtOH/DEA=100/0.001; flow rate=1.0 mL/min; detector: UV 254 nm). The first eluent (compound 370, Rf=6.20 min) was 100% ee, MS (m/z): 455 (M+H)$^+$. and the second eluent (compound 371, Rf=6.32 min) was 100% ee, MS (m/z): 455 (M+H)$^+$.

253

Compound 372 and 373

(S)—N-((4,4-difluoropiperidin-3-yl)methyl)-7-(4-(4-methylpiperazin-1-yl)phenyl)pyrido[4,3-b]pyrazin-5-amine and (R)—N-((4,4-difluoropiperidin-3-yl)methyl)-7-(4-(4-methyl piperazin-1-yl)phenyl)pyrido[4,3-b]pyrazin-5-amine

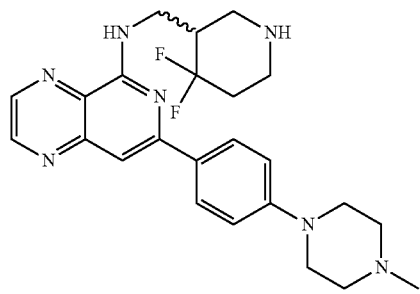

→

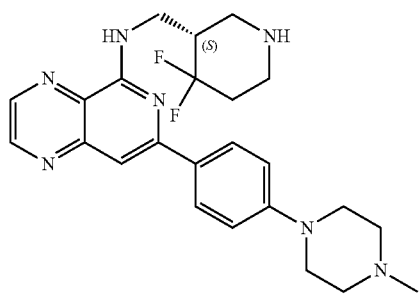

+

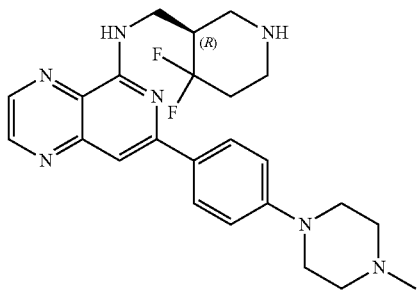

254

Compound 374 and 375

(S)—N-((4,4-difluoropiperidin-3-yl)methyl)-7-(6-morpholinopyridin-3-yl)pyrido[4,3-b]pyrazin-5-amine and (R)—N-((4,4-difluoropiperidin-3-yl)methyl)-7-(6-morpholinopyridin-3-yl)pyrido[4,3-b]pyrazin-5-amine

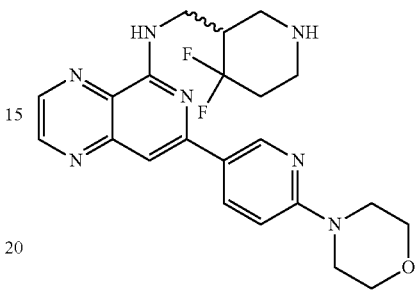

→

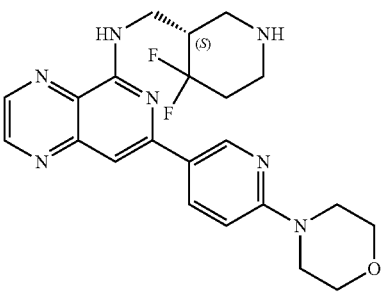

+

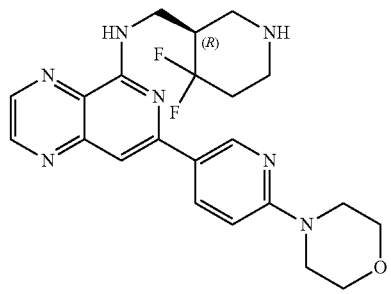

The racemic compound 293 was resolved by chiral HPLC to provide the optically pure enantiomers Compound 372 and 373 (HPLC conditions: column: CHIRALPAK IA 0.46×15 cm; mobile phase: MeOH/EtOH/DEA=50/50/0.1; flow rate=1.0 mL/min; detector: UV 220 nm). The first eluent (compound 372, Rf=10.89 min) was 100% ee, MS (m/z): 454 (M+H)$^+$. and the second eluent (compound 373, Rf=14.23 min) was 100% ee, MS (m/z): 454 (M+H)$^+$.

The racemic compound 292 was resolved by chiral HPLC to provide the optically pure enantiomers Compound 374 and 375 (HPLC conditions: column: CHIRALCEL OJH 0.46×15 cm; mobile phase: EtOH/DEA=100/0.001; flow rate=1 mL/min; detector: UV 254 nm). The first eluent (compound 374, Rf=8.60 min) was 100% ee, MS (m/z): 442 (M+H)$^+$. and the second eluent (compound 375, Rf=12.10 min) was 97.37% ee, MS (m/z): 442 (M+H)$^+$.

Compound 376 and 377

(S)—N-((3-fluoropiperidin-3-yl)methyl)-7-(4-morpholinophenyl)pyrido[4,3-b]pyrazin-5-amine and (R)—N-((3-fluoropiperidin-3-yl)methyl)-7-(4-morpholinophenyl)pyrido[4,3-b]pyrazin-5-amine

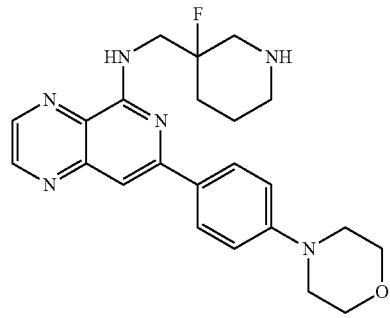

→

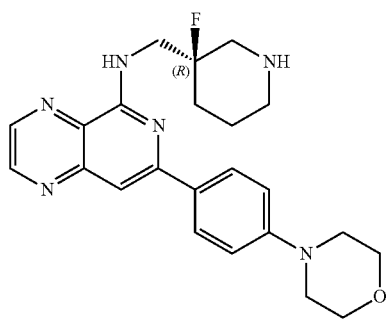

+

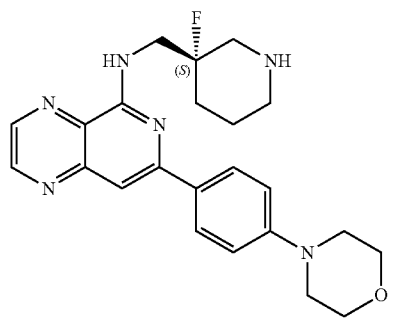

The racemic compound 251 was resolved by chiral HPLC to provide the optically pure enantiomers Compound 376 and 377 (HPLC conditions: column: CHIRALPAK IA 0.46×15 cm; mobile phase: CH$_3$CN/EtOH/DEA=90/10/0.1; flow rate=10.0 mL/min; detector: UV 254 nm). The first eluent (compound 376, Rf=7.45 min) was 100% ee, MS (m/z): 423 (M+H)$^+$. and the second eluent (compound 377, Rf=14.97 min) was 96.07% ee, MS (m/z): 423 (M+H)$^+$.

Compound 378 and 379

(S)—N-((3-fluoropiperidin-3-yl)methyl)-7-(6-morpholinopyridin-3-yl)pyrido[4,3-b]pyrazin-5-amine and (R)—N-((3-fluoropiperidin-3-yl)methyl)-7-(6-morpholinopyridin-3-yl)pyrido[4,3-b]pyrazin-5-amine

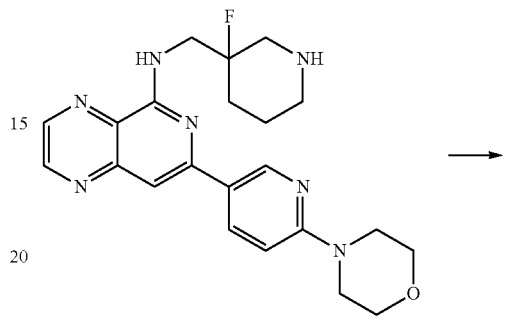

→

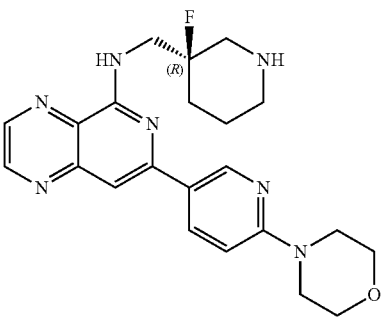

+

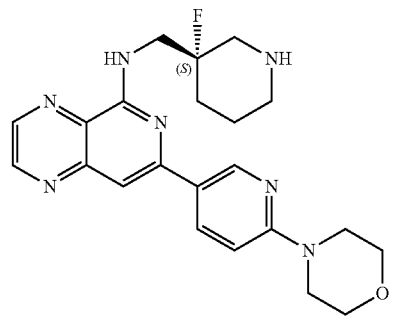

The racemic compound 252 was resolved by chiral HPLC to provide the optically pure enantiomers Compound 378 and 379 (HPLC conditions: column: CHIRALPAK IA 0.46×15 cm; mobile phase: CH$_3$CN/EtOH/DEA=90/10/0.1; flow rate=10.0 mL/min; detector: UV 254 nm). The first eluent (compound 378, Rf=9.17 min) was 100% ee, MS (m/z): 424 (M+H)$^+$. and the second eluent (compound 379, Rf=16.65 min) was 92.59% ee, MS (m/z): 424 (M+H)$^+$.

257
Compound 380 and 381

(S)—N-((3-fluoropiperidin-3-yl)methyl)-7-(4-(4-methylpiperazin-1-yl)phenyl)pyrido[4,3-b]pyrazin-5-amine and (R)—N-((3-fluoropiperidin-3-yl)methyl)-7-(4-(4-methyl piperazin-1-yl)phenyl)pyrido[4,3-b]pyrazin-5-amine

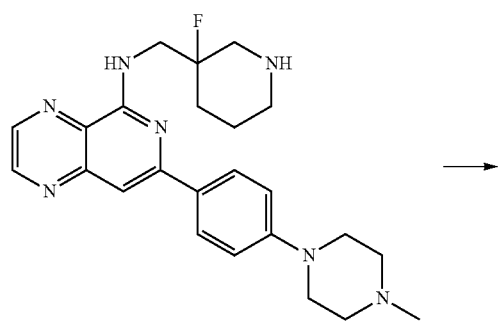

→

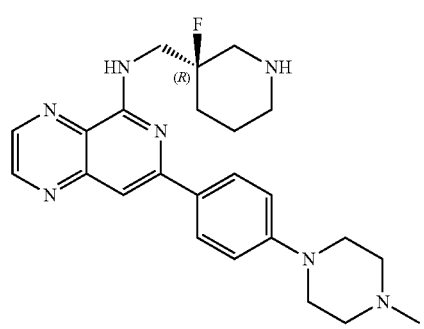

+

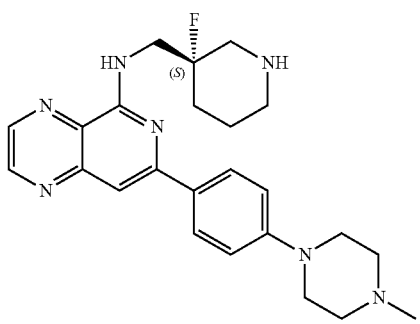

258
Compound 382 and 383

(S)-7-(3-fluoro-4-morpholinophenyl)-N-((3-fluoropiperidin-3-yl)methyl)pyrido[4,3-b]pyrazin-5-amine and (R)-7-(3-fluoro-4-morpholinophenyl)-N-((3-fluoropiperidin-3-yl)methyl)pyrido[4,3-b]pyrazin-5-amine

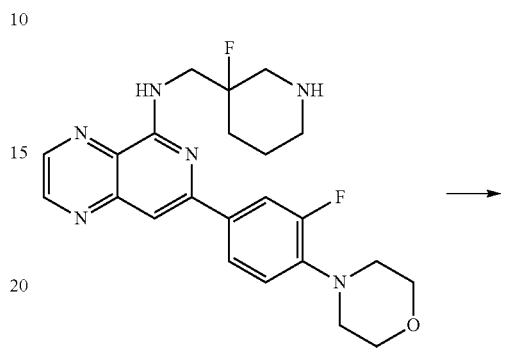

→

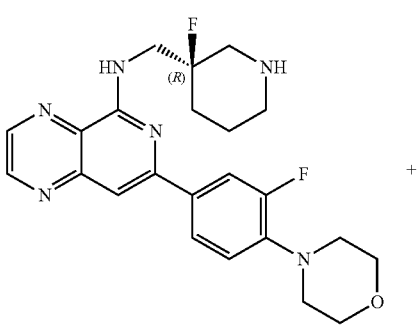

+

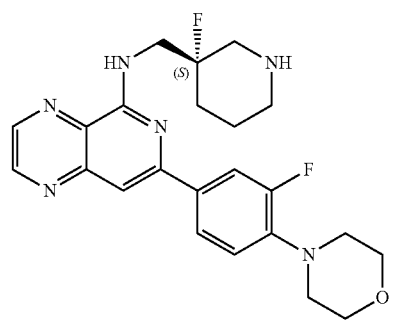

The racemic compound 253 was resolved by chiral HPLC to provide the optically pure enantiomers Compound 380 and 381 (HPLC conditions: column: CHIRALPAK IA 0.46× 15 cm; mobile phase: CH$_3$CN/EtOH/DEA=90/10/0.1; flow rate=10.0 mL/min; detector: UV 254 nm). The first eluent (compound 380, Rf=10.46 min) was 100% ee, MS (m/z): 436 (M+H)$^+$. and the second eluent (compound 381, Rf=20.42 min) was 94.93% ee, MS (m/z): 436 (M+H)$^+$.

The racemic compound 254 was resolved by chiral HPLC to provide the optically pure enantiomers Compound 382 and 383 (HPLC conditions: column: CHIRALPAK IA 0.46× 15 cm; mobile phase: CH$_3$CN/EtOH/DEA=90/10/0.1; flow rate=10.0 mL/min; detector: UV 254 nm). The first eluent (compound 382, Rf=7.14 min) was 98.75% ee, MS (m/z): 441 (M+H)$^+$. and the second eluent (compound 383, Rf=14.97 min) was 96.07% ee, MS (m/z): 441 (M+H)$^+$.

259
Compound 384 and 385

(S)-1-(4-(4-(5-((4,4-difluoropiperidin-3-yl)methyl-amino)pyrido[4,3-b]pyrazin-7-yl)phenyl)piperazin-1-yl)ethanone and (R)-1-(4-(4-(5-((4,4-difluoropiperidin-3-yl)methyl amino)pyrido[4,3-b]pyrazin-7-yl)phenyl)piperazin-1-yl)ethanone

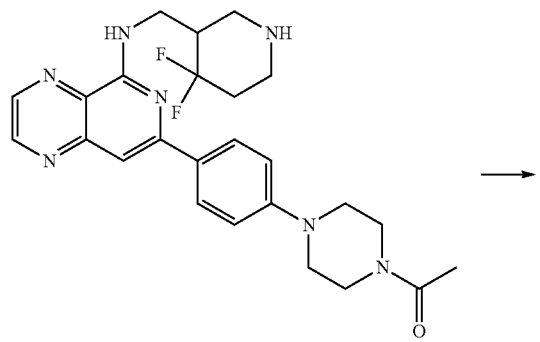

+

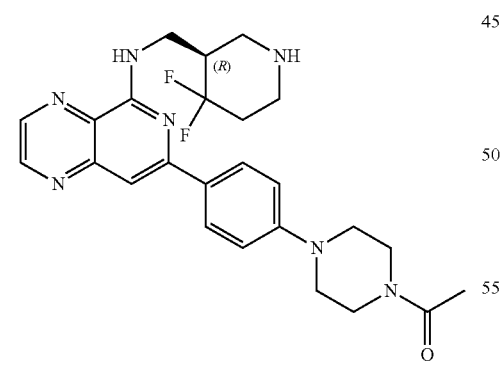

260
Compound 386 and 387

7-(3-fluoro-4-((S)-2-methylmorpholino)phenyl)-N—((S)-morpholin-2-ylmethyl)pyrido[4,3-b]pyrazin-5-amine and 7-(3-fluoro-4-((R)-2-methylmorpholino)phenyl)-N—((S)-morpholin-2-ylmethyl)pyrido[4,3-b]pyrazin-5-amine

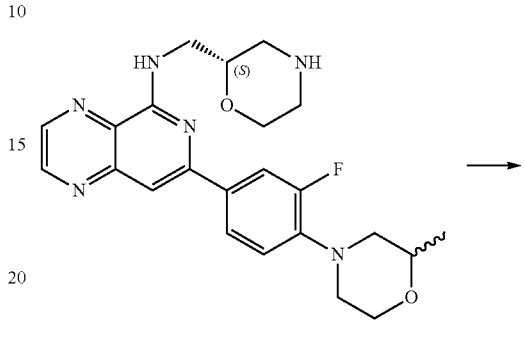

+

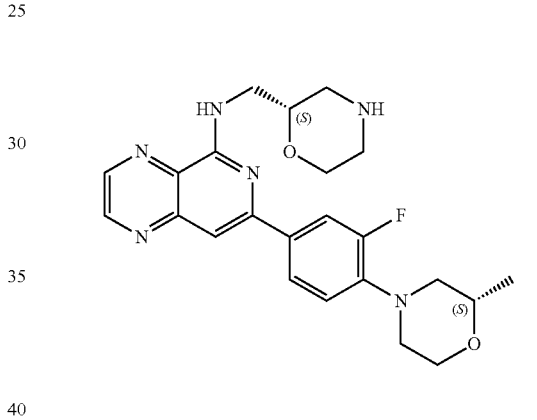

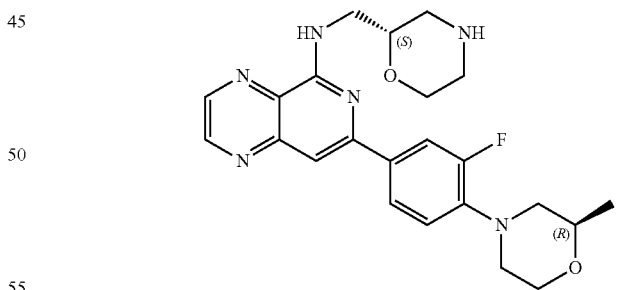

The racemic compound 305 was resolved by chiral HPLC to provide the optically pure enantiomers Compound 384 and 385 (HPLC conditions: column: CHIRALPAK IA 0.46× 25 cm; mobile phase: CAN/DEA=100/0.1; flow rate=1.0 mL/min; detector: UV 365 nm). The first eluent (compound 384, Rf=10.09 min) was 98% ee, MS (m/z): 482 (M+H)+. and the second eluent (compound 385, Rf=13.39 min) was 98% ee, MS (m/z): 482 (M+H)+.

The racemic compound 250 was resolved by chiral HPLC to provide the optically pure isomers Compound 386 and 387 (HPLC conditions: column: CHIRALPAK AD-H 0.46× 15 cm; mobile phase: EtOH/ACN/DEA=95/5/0.1; flow rate=0.5 mL/min; detector: UV 254 nm). The first eluent (compound 386, Rf=13.40 min) was 99.83% ee, MS (m/z): 439 (M+H)+. and the second eluent (compound 387, Rf=16.30 min) was 98.9% ee, MS (m/z): 439 (M+H)+.

261
Compound 388 and 389

(S)-2-(4-(5-((4,4-difluoropiperidin-3-yl)methyl-amino)pyrido[4,3-b]pyrazin-7-yl)phenoxy)-N-methylacetamide and (R)-2-(4-(5-((4,4-difluoropiperidin-3-yl)methylamino)pyrido[4,3-b]pyrazin-7-yl)phenoxy)-N-methylacetamide

262
Compound 390 and 391

(S)—N-((4,4-difluoropiperidin-3-yl)methyl)-7-(4-(methylsulfonyl)phenyl)pyrido[4,3-b]pyrazin-5-amine and (R)—N-((4,4-difluoropiperidin-3-yl)methyl)-7-(4-(methylsulfonyl)phenyl)pyrido[4,3-b]pyrazin-5-amine

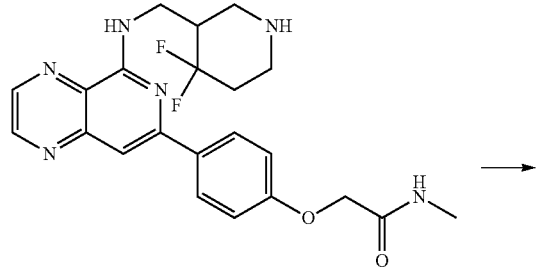

The racemic compound 306 was resolved by chiral HPLC to provide the optically pure enantiomers Compound 388 and 389 (HPLC conditions: column: CHIRALPAK IAs 0.46×15 cm; mobile phase: ACN/DEA=100/0.1; flow rate=10 mL/min; detector: UV 254 nm). The first eluent (compound 388, Rf=12.58 min) was 100% ee, MS (m/z): 443 (M+H)$^+$. and the second eluent (compound 389, Rf=23.88 min) was 93.9% ee, MS (m/z): 443 (M+H)$^+$.

The racemic compound 310 was resolved by chiral HPLC to provide the optically pure enantiomers Compound 390 and 391 (HPLC conditions: column: CHIRALPAK IAs 0.46×15 cm; mobile phase: ACN/DEA=100/0.1; flow rate=10 mL/min; detector: UV 254 nm). The first eluent (compound 390, Rf=12.05 min) was 98.17% ee, MS (m/z): 434 (M+H)$^+$. and the second eluent (compound 391, Rf=13.11 min) was 97.51% ee, MS (m/z): 434 (M+H)$^+$.

Compound 392 and 393

(S)—N-((4,4-difluoropiperidin-3-yl)methyl)-7-(1-ethyl-1H-pyrazol-4-yl)pyrido[4,3-b]pyrazin-5-amine and (R)—N-((4,4-difluoropiperidin-3-yl)methyl)-7-(1-ethyl-1H-pyrazol-4-yl)pyrido[4,3-b]pyrazin-5-amine

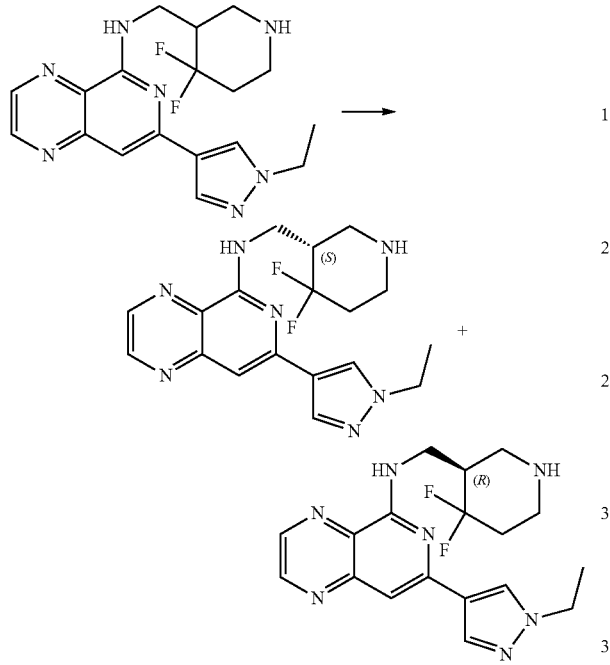

The racemic compound 311 was resolved by chiral HPLC to provide the optically pure enantiomers Compound 392 and 393 (HPLC conditions: column: CHIRALPAK IAs 0.46×15 cm; mobile phase: ACN/DEA=100/0.1; flow rate=10 mL/min; detector: UV 254 nm). The first eluent (compound 392, Rf=7.64 min) was 100% ee, MS (m/z): 374 (M+H)$^+$. and the second eluent (compound 393, Rf=13.11 min) was 97.47% ee, MS (m/z): 374 (M+H)$^+$.

Compound 394 and 395

(S)—N-(4-(5-((4,4-difluoropiperidin-3-yl)methylamino)pyrido[4,3-b]pyrazin-7-yl)phenyl)-N-methylmethanesulfonamide and (R)—N-(4-(5-((4,4-difluoropiperidin-3-yl)methylamino)pyrido[4,3-b]pyrazin-7-yl)phenyl)-N-methylmethanesulfonamide

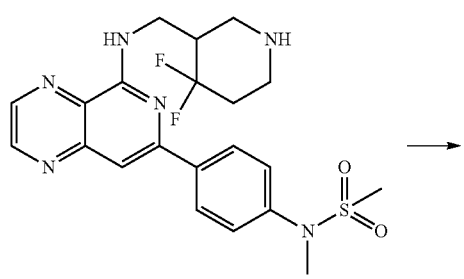

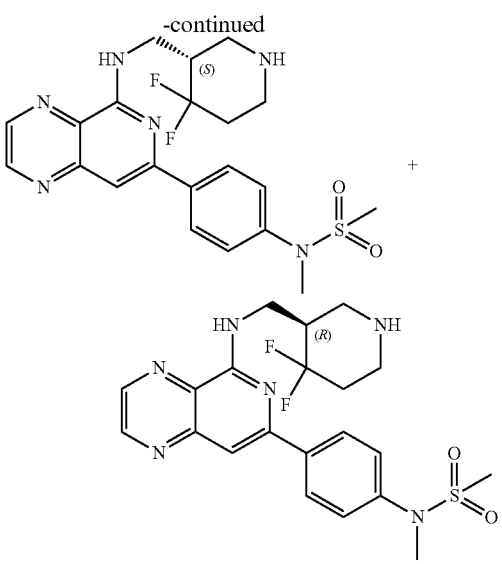

The racemic compound 313 was resolved by chiral HPLC to provide the optically pure enantiomers Compound 394 and 395 (HPLC conditions: column: CHIRALPAK IAs 0.46×15 cm; mobile phase: ACN/DEA=100/0.1; flow rate=10 mL/min; detector: UV 254 nm). The first eluent (compound 394, Rf=8.03 min) was 100% ee, MS (m/z): 463 (M+H)$^+$. and the second eluent (compound 395, Rf=11.54 min) was 95.7% ee, MS (m/z): 463 (M+H)$^+$.

Compound 396 and 397

N-((4,4-difluoropiperidin-3-yl)methyl)-7-(4-((S)-2-methyl morpholino)phenyl) pyrido[4,3-b]pyrazin-5-amine and (R)—N-((4,4-difluoropiperidin-3-yl)methyl)-7-(4-((S)-2-methyl morpholino)phenyl) pyrido[4,3-b]pyrazin-5-amine

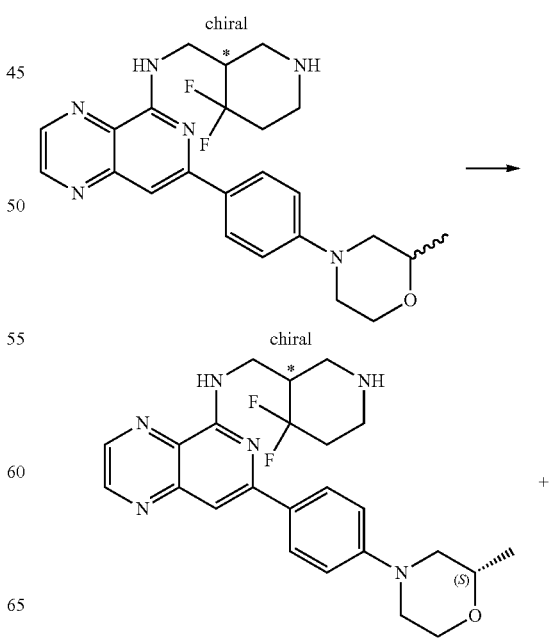

-continued

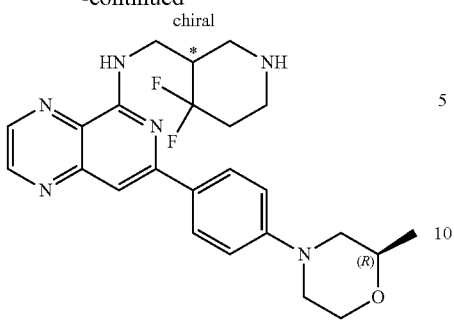

The racemic compound 309 was resolved by chiral HPLC to provide the optically pure isomers Compound 396 and 397 (HPLC conditions: column: CHIRALPAK AD-H 0.46×15 cm; mobile phase: MeOH/DEA=100/0.1; flow rate=1.0 mL/min; detector: UV 254 nm). The first eluent (compound 396, Rf=11.37 min) was 99.44% ee, MS (m/z): 455 (M+H)$^+$. and the second eluent (compound 397, Rf=14.69 min) was 98.36% ee, MS (m/z): 455 (M+H)$^+$.

Compound 398 and 399

(S)—N-((4,4-difluoropiperidin-3-yl)methyl)-7-(1-(tetrahydro-2H-pyran-4-yl)-1H-pyrazol-4-yl)pyrido[4,3-b]pyrazin-5-amine and (R)—N-((4,4-difluoropiperidin-3-yl)methyl)-7-(1-(tetrahydro-2H-pyran-4-yl)-1H-pyrazol-4-yl)pyrido[4,3-b]pyrazin-5-amine

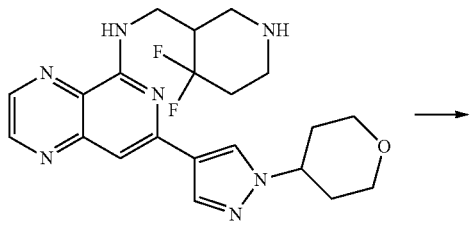

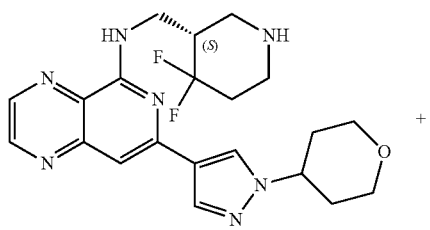

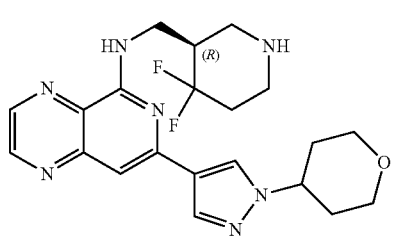

The racemic compound 314 was resolved by chiral HPLC to provide the optically pure enantiomers Compound 398 and 399 (HPLC conditions: column: CHIRALPAK IAs 0.46×15 cm; mobile phase: CAN/EtOH/DEA=100/10/0.1; flow rate=10 mL/min; detector: UV 254 nm). The first eluent (compound 398, Rf=7.42 min) was 100% ee, MS (m/z): 430 (M+H)$^+$. and the second eluent (compound 399, Rf=10.74 min) was 93.0% ee, MS (m/z): 430 (M+H)$^+$.

Compound 400

(S)-7-(4-(4-(cyclopropylsulfonyl)piperazin-1-yl)phenyl)-N-(morpholin-2-ylmethyl)pyrido[4,3-b]pyrazin-5-amine

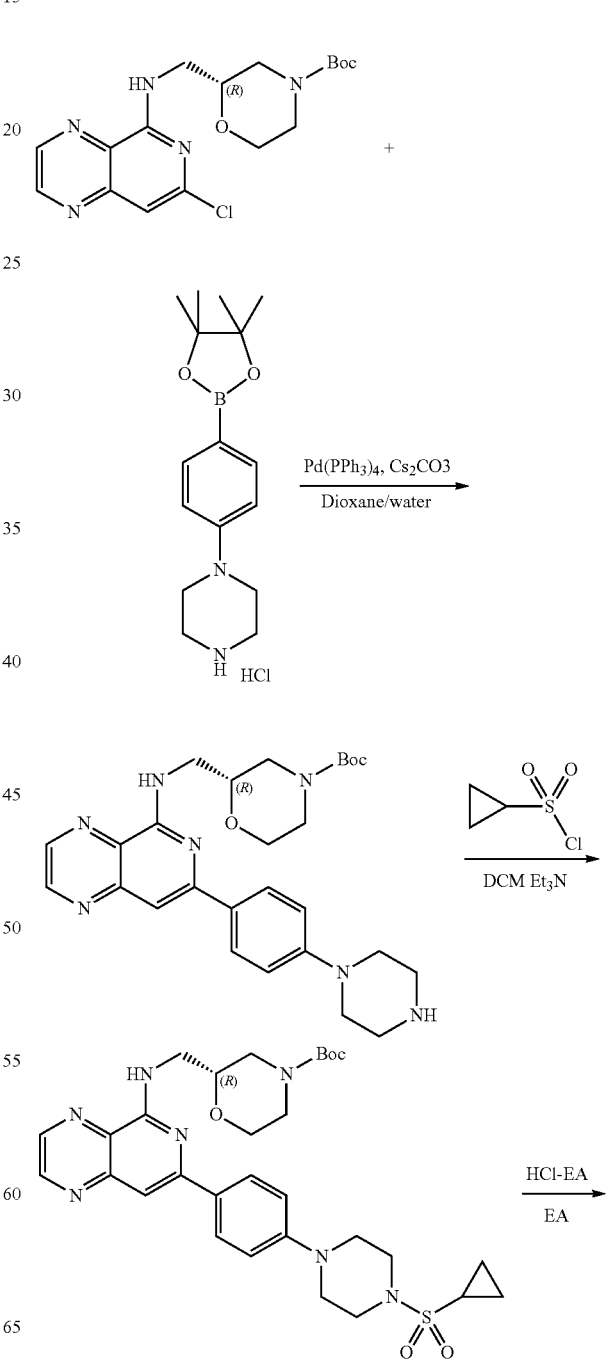

-continued

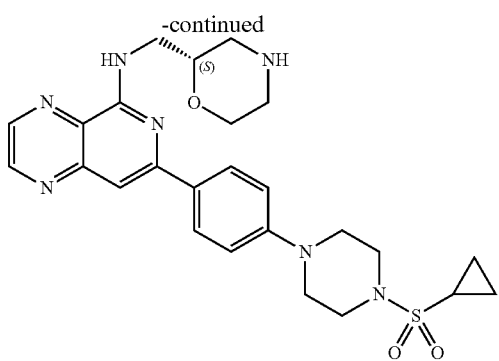

(A) (S)-tert-butyl 2-((7-(4-(piperazin-1-yl)phenyl)pyrido[4,3-b]pyrazin-5-ylamino)methyl)morpholine-4-carboxylate A solution of (S)-tert-butyl 2-((7-chloropyrido[4,3-b]pyrazin-5-ylamino)methyl)morpholine-4-carboxylate (3.96 g, 10.43 mmol), 1-(4-(4,4,5,5-tetramethyl-1,3,2-dioxaborolan-2-yl)phenyl)piperazine hydrochloride (4.4 g, 13.55 mmol), Pd(PPh$_3$)$_4$ (2.41 g, 2.09 mmol) and Cs$_2$CO$_3$ (10.19 g, 31.29 mmol) in 150 mL of dioxane and 3 mL of water, under N$_2$, was stirred at 110° C. overnight. The volatiles were removed in vacuo, and the residues was purified by chromatography with MeOH/H2O (1:20-5:1) to give 4.747 g of title compound. MS (m/z)=506 (M+H)$^+$.

(B) (S)-tert-butyl 2-((7-(4-(4-(cyclopropylsulfonyl)piperazin-1-yl)phenyl)pyrido[4,3-b]pyrazin-5-ylamino)methyl)morpholine-4-carboxylate A solution of (S)-tert-butyl 2-((7-(4-(piperazin-1-yl)phenyl)pyrido[4,3-b]pyrazin-5-ylamino)methyl)morpholine-4-carboxylate (100 mg, 0.20 mmol), cyclopropanesulfonyl chloride (33 mg, 0.24 mmol) and Et$_3$N (41 mg, 0.40 mmol) in 5 mL of DCM at 0° C. was stirred at room temperature for 1 hour. The volatiles were removed in vacuo, and the residues was purified by chromatography with PE/EA (1:2~1:10) to give 52 mg of title compound.

(C) (S)-7-(4-(4-(cyclopropylsulfonyl)piperazin-1-yl)phenyl)-N-(morpholin-2-yl methyl)pyrido[4,3-b]pyrazin-5-amine A solution of (S)-tert-butyl 2-((7-(4-(4-(cyclopropylsulfonyl)piperazin-1-yl)phenyl)pyrido[4,3-b]pyrazin-5-ylamino)methyl)morpholine-4-carboxylate (52 mg, 0.09 mmol) and 2 mL of HCl-EA (5.0 N) in 5 mL of EA, was stirred at room temperature for 1 hour. The volatiles were removed in vacuo, and the residue was added to 5 mL of MeOH and 0.5 mL of NH$_3$.H$_2$O, was stirred at room temperature for 10 minutes. The volatiles were removed in vacuo, and the residue was purified by chromatography with MeOH/H$_2$O (1:6~5:1) to give 18 mg title compound. MS (m/z)=510 (M+H)$^+$.

The following compounds were prepared according to the procedures of Compound 400 using the corresponding intermediates and reagents under appropriate conditions that will be recognized by one skilled in the art.

| Compound | Structure | MS (M + H)$^+$ |
|---|---|---|
| 401 | 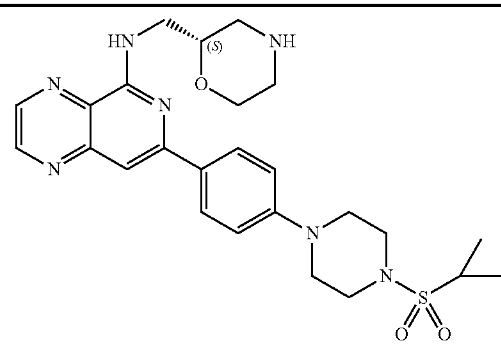 | 512 |
| 402 | 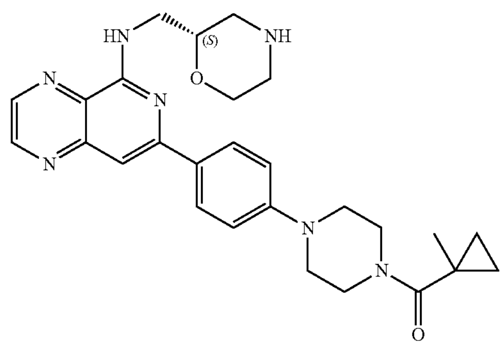 | 488 |

-continued
| Compound | Structure | MS (M + H)+ |
|---|---|---|
| 403 | 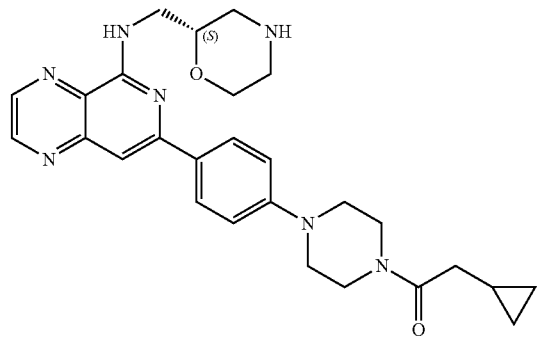 | 488 |
| 404 | 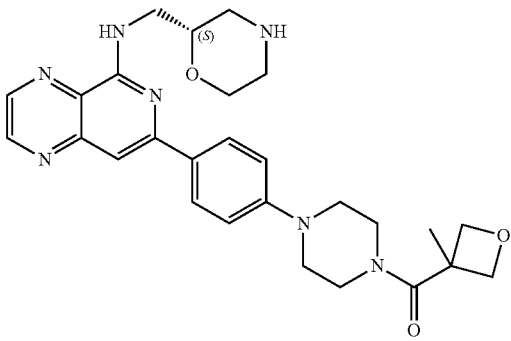 | 504 |
| 405 | 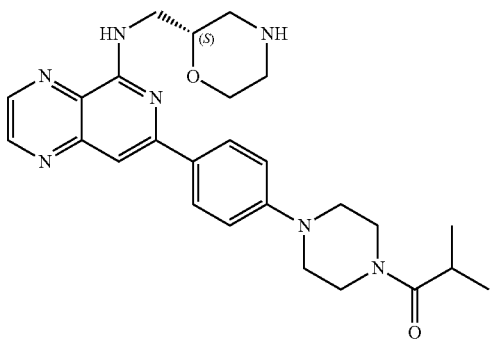 | 476 |
| 406 | 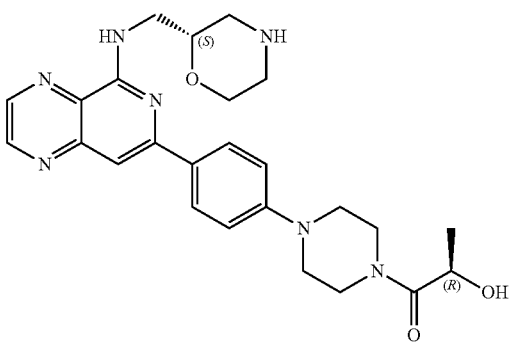 | 478 |

-continued
| Compound | Structure | MS (M + H)+ |
|---|---|---|
| 407 | 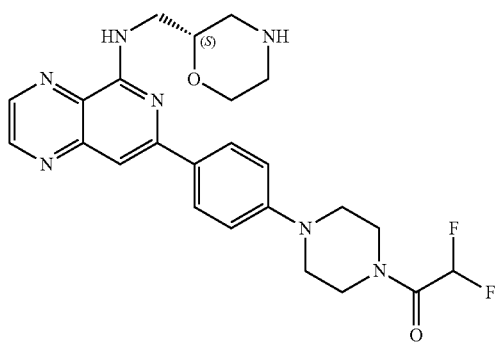 | 484 |
| 408 | 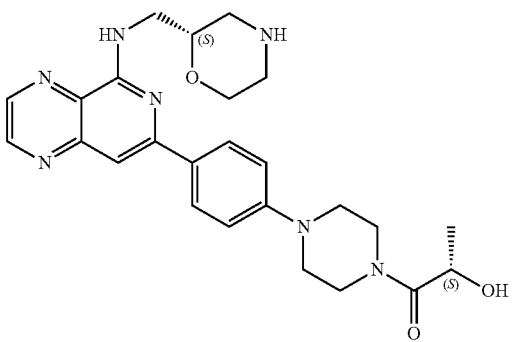 | 478 |
| 409 | 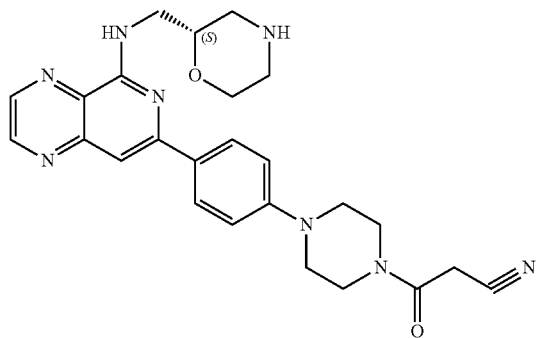 | 473 |
| 410 | 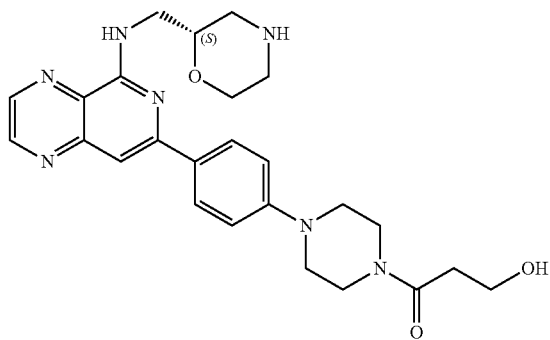 | 478 |

-continued
| Compound | Structure | MS (M + H)+ |
|---|---|---|
| 411 | 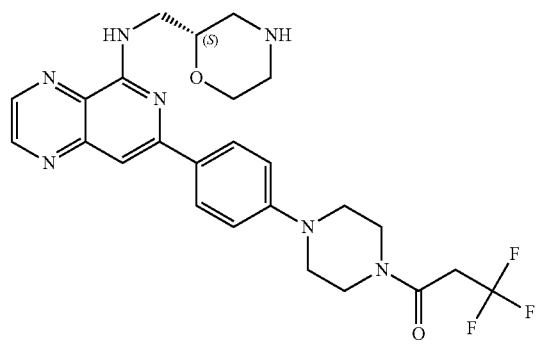 | 516 |
| 412 | 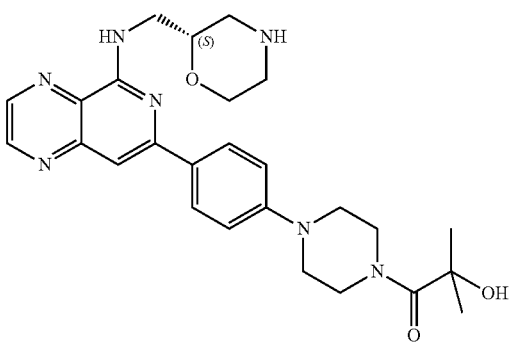 | 492 |
| 413 | 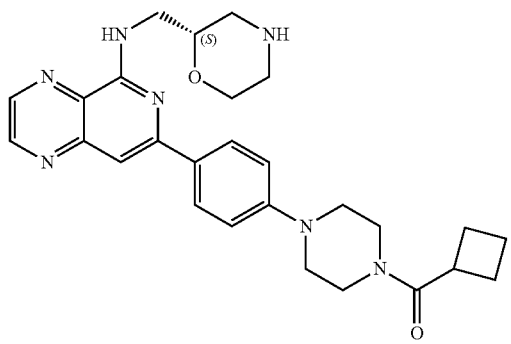 | 488 |
| 414 | 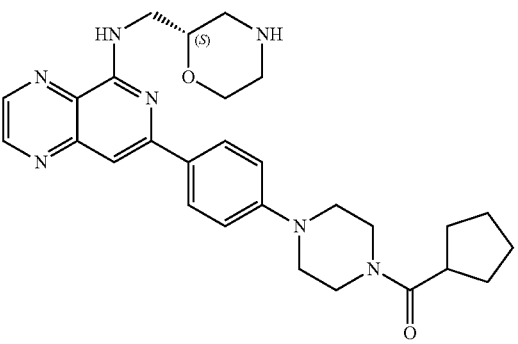 | 502 |

-continued
| Compound | Structure | MS (M + H)+ |
|---|---|---|
| 415 | 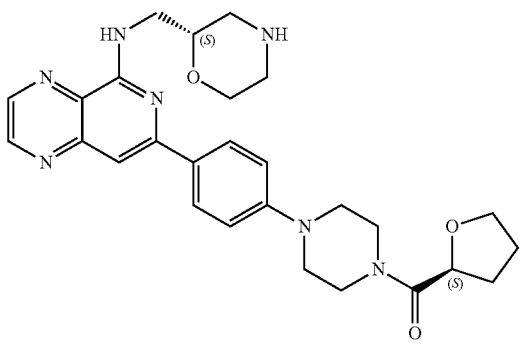 | 504 |
| 416 | 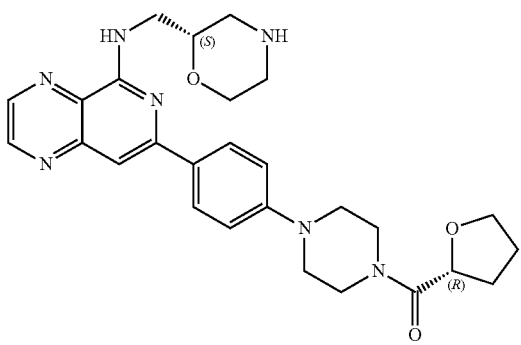 | 504 |
| 417 | 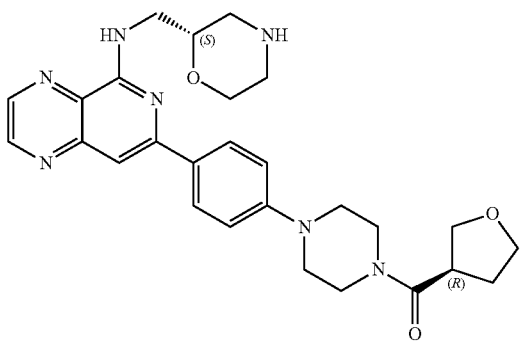 | 504 |
| 418 | 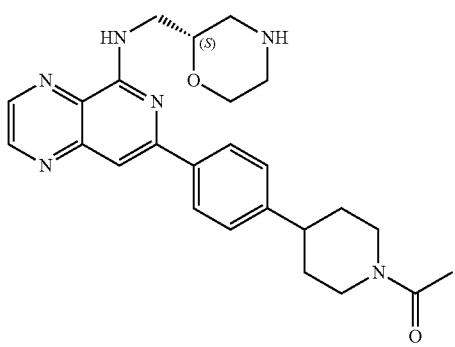 | 447 |

-continued
| Compound | Structure | MS (M + H)+ |
|---|---|---|
| 419 | 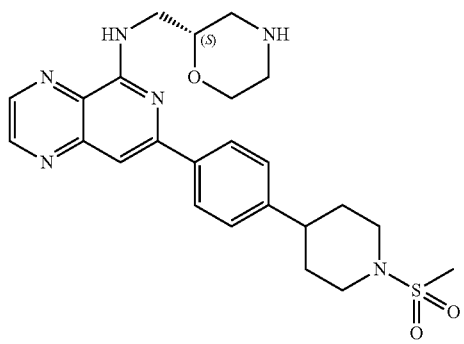 | 483 |
| 420 | 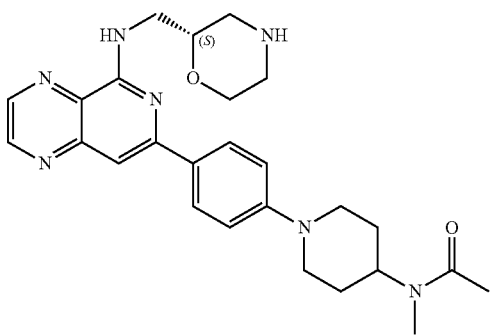 | 476 |
| 421 | 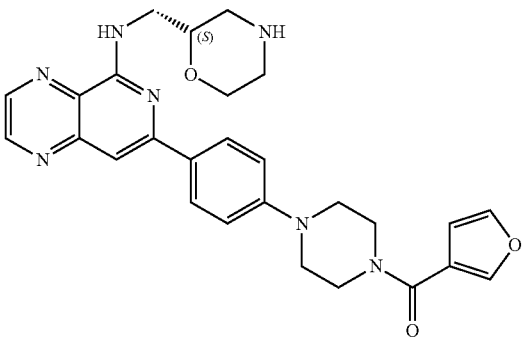 | 500 |
| 422 | 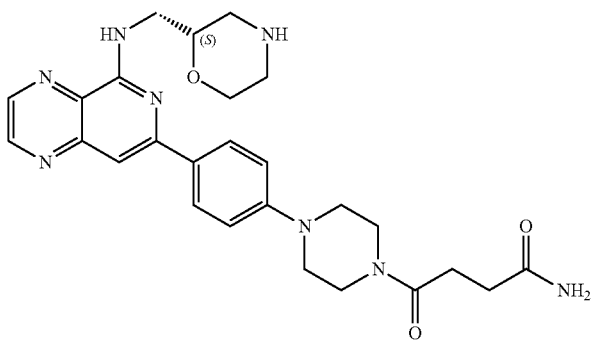 | 505 |

-continued

| Compound | Structure | MS (M + H)⁺ |
|---|---|---|
| 423 | 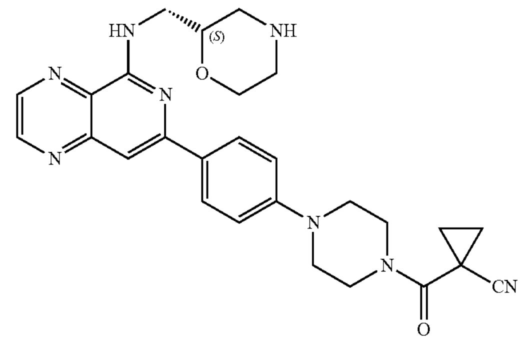 | 499 |
| 424 | 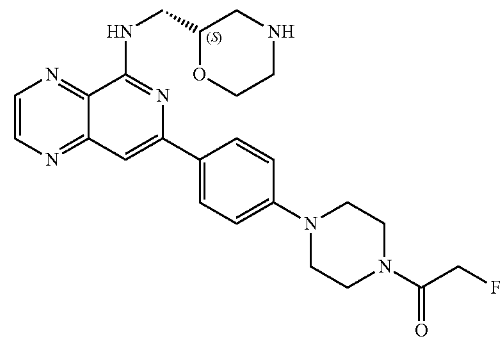 | 466 |
| 425 | 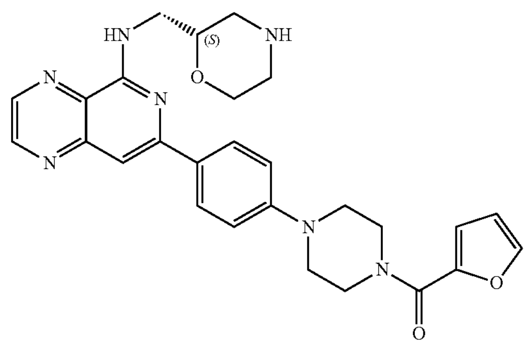 | 500 |
| 426 | 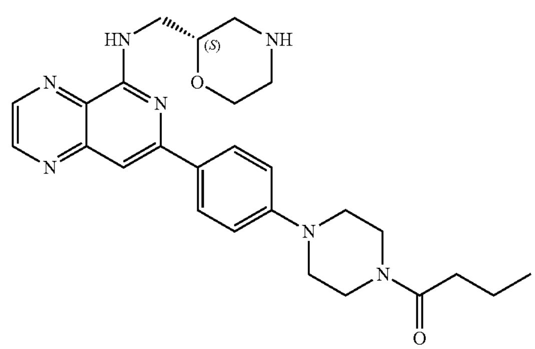 | 476 |

-continued

| Compound | Structure | MS (M + H)+ |
|---|---|---|
| 427 | 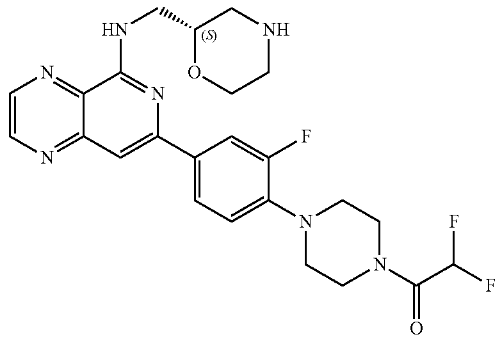 | 502 |
| 428 | 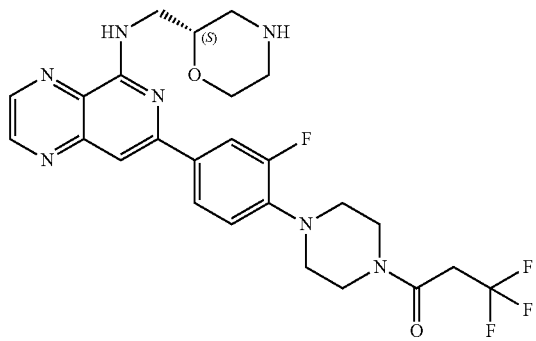 | 534 |
| 429 | 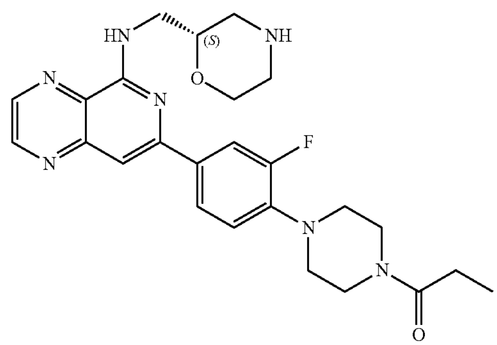 | 480 |
| 430 | 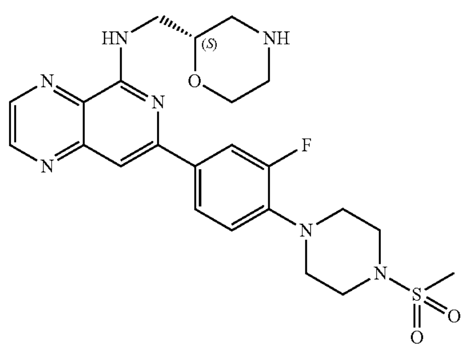 | 502 |
| 431 | 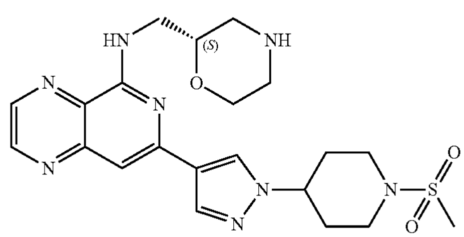 | 473 |

-continued
| Compound | Structure | MS (M + H)+ |
|---|---|---|
| 432 | 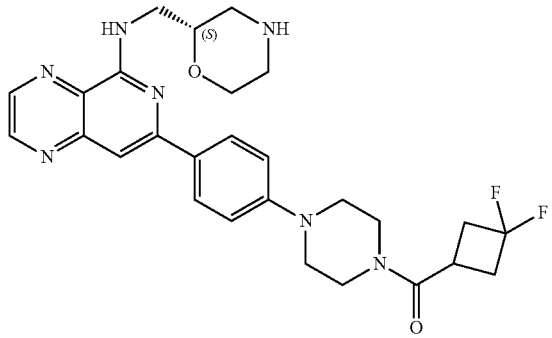 | 524 |
| 433 | 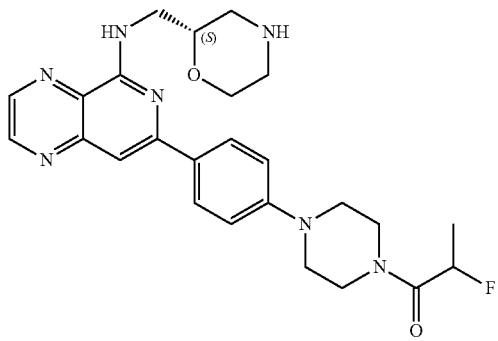 | 480 |
| 434 | 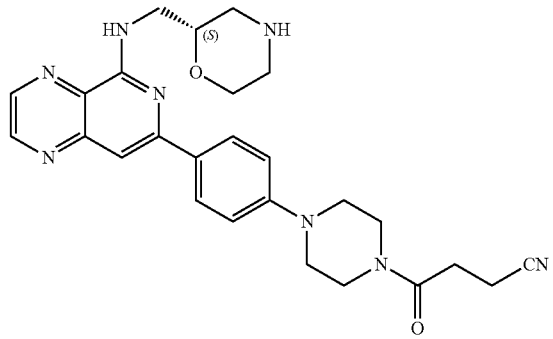 | 487 |
| 435 | 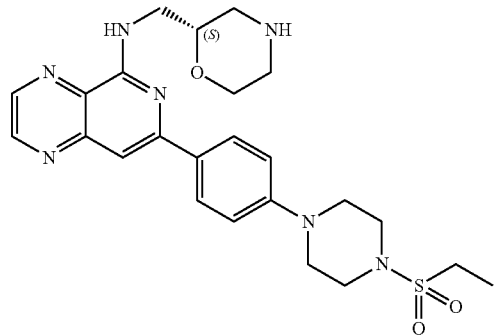 | 498 |

| Compound | Structure | MS (M + H)+ |
|---|---|---|
| 436 | 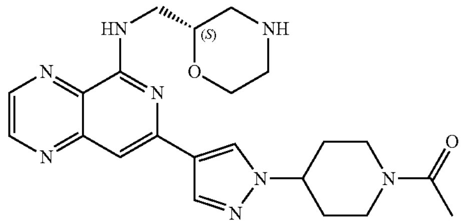 | 437 |
| 437 | 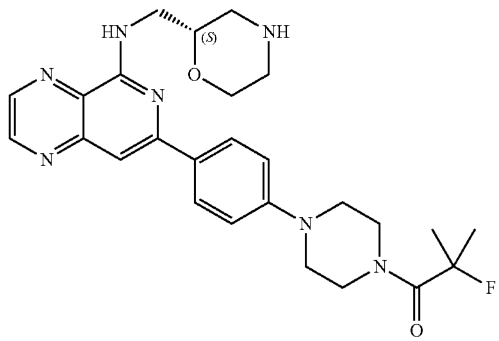 | 494 |
| 438 | 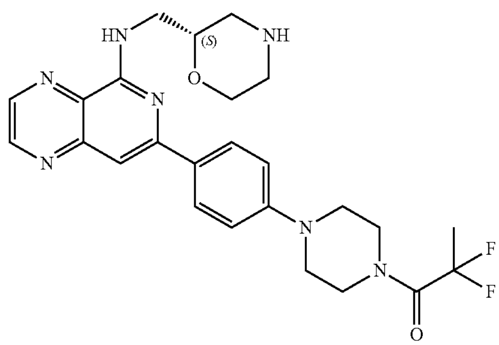 | 498 |
| 439 | 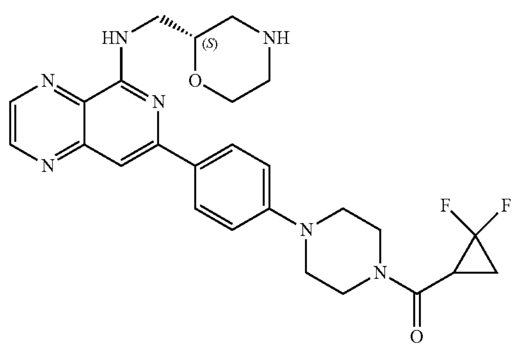 | 510 |
| 440 | 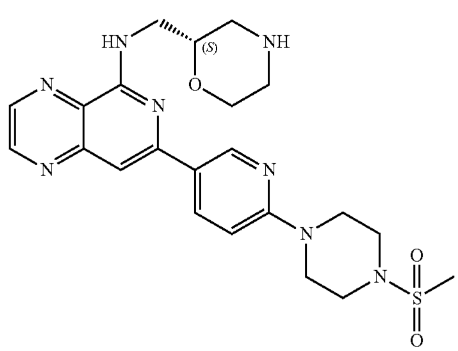 | 485 |

-continued
| Compound | Structure | MS (M + H)+ |
|---|---|---|
| 441 | 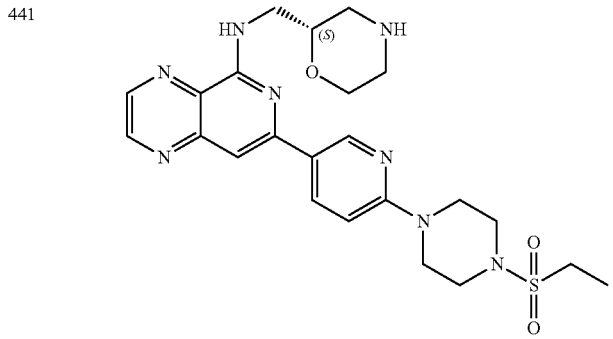 | 499 |
| 442 | 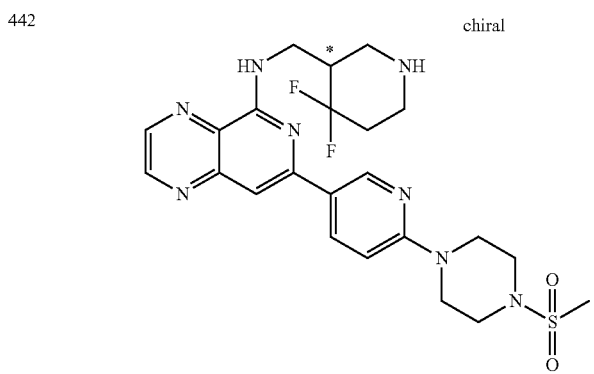 chiral | 519 |
| 443 | 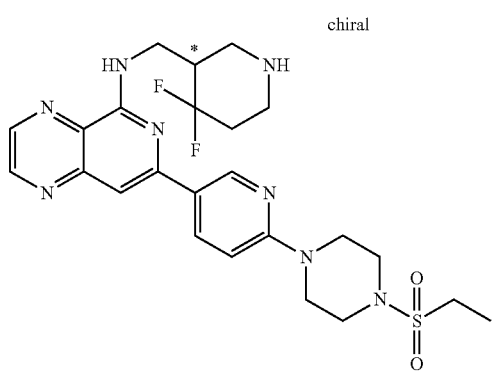 [SMILES: CCS(=O)(=O)N1CCN(c2ccc(-c3cc4nccnc4c(NCC4CNCCC4(F)F)n3)cn2)CC1] chiral | 533 |
| 444 | 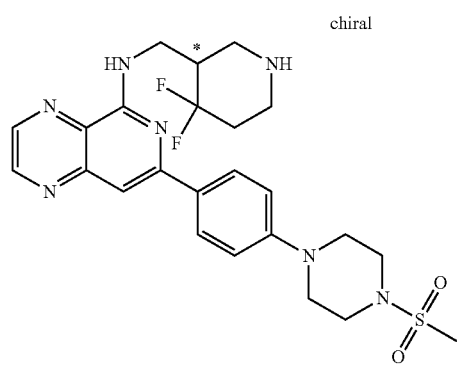 [SMILES: CS(=O)(=O)N1CCN(c2ccc(-c3cc4nccnc4c(NCC4CNCCC4(F)F)n3)cc2)CC1] chiral | 518 |

-continued
| Compound | Structure | MS (M + H)+ |
|---|---|---|
| 445 | chiral 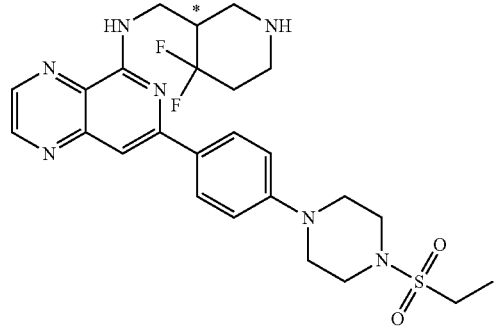 | 532 |
| 446 | 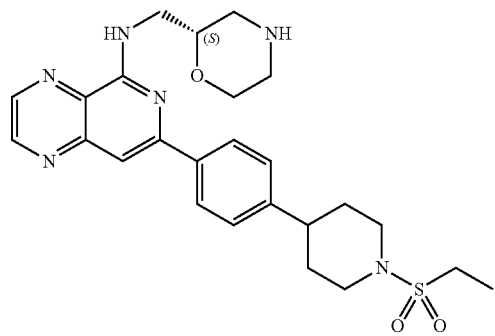 | 497 |
| 447 | chiral 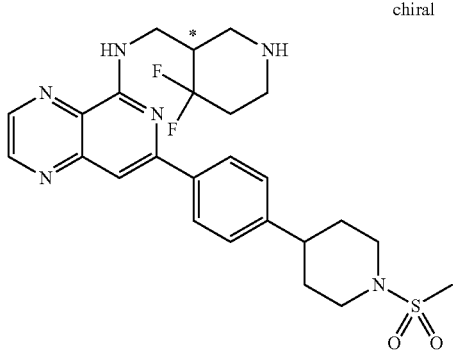 [SMILES: CS(=O)(=O)N1CCC(c2ccc(-c3cc4nccnc4c(NCC4CNCCC4(F)F)n3)cc2)CC1] | 517 |
| 448 | chiral 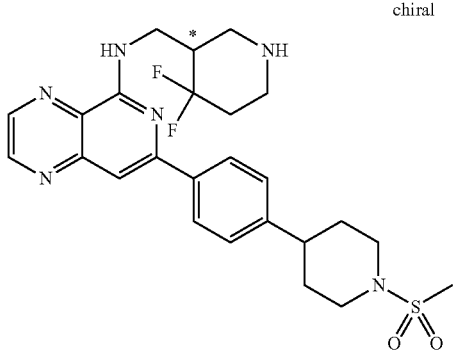 [SMILES: CS(=O)(=O)N1CCC(c2ccc(-c3cc4nccnc4c(NCC4CNCCC4(F)F)n3)cc2)CC1] | 517 |

-continued
| Compound | Structure | MS (M + H)+ |
|---|---|---|
| 495 | 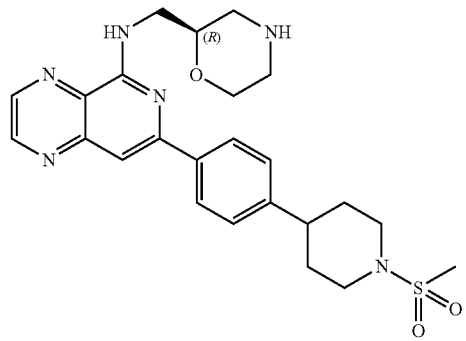 | 483 |
| 497 | 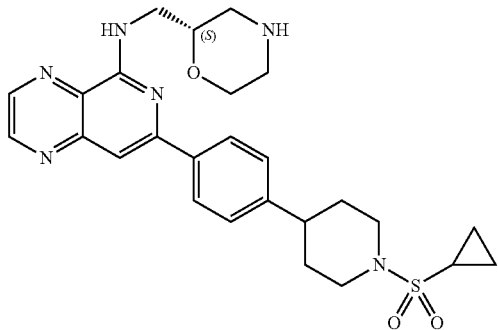 | 509 |
| 498 | 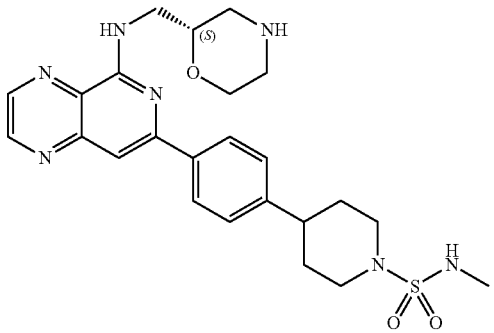 | 498 |
| 499 | 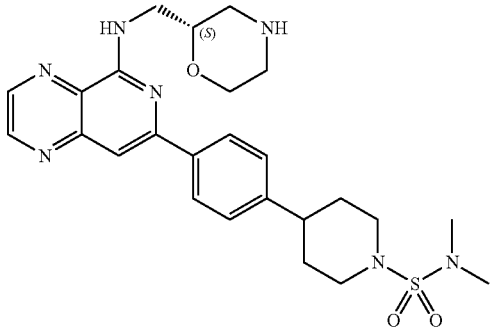 | 512 |

-continued

| Compound | Structure | MS (M + H)+ |
|---|---|---|
| 504 | 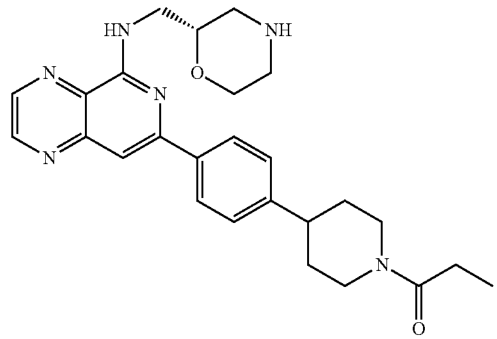 [SMILES: CCC(=O)N1CCC(c2ccc(-c3cc4nccnc4c(NC[C@@H]4CNCCO4)n3)cc2)CC1] | 461 |
| 505 | 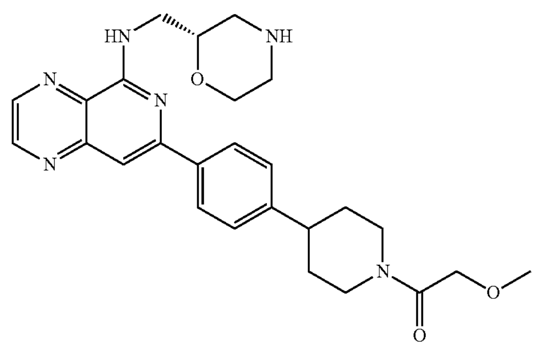 [SMILES: COCC(=O)N1CCC(c2ccc(-c3cc4nccnc4c(NC[C@@H]4CNCCO4)n3)cc2)CC1] | 477 |
| 506 | 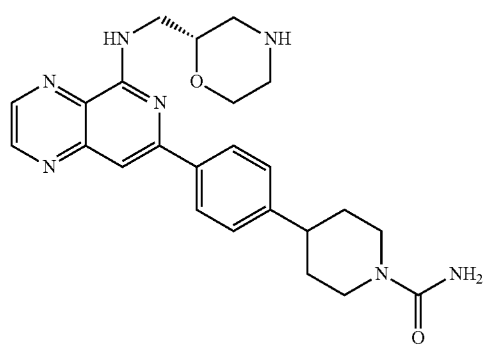 [SMILES: NC(=O)N1CCC(c2ccc(-c3cc4nccnc4c(NC[C@@H]4CNCCO4)n3)cc2)CC1] | 448 |
| 511 | 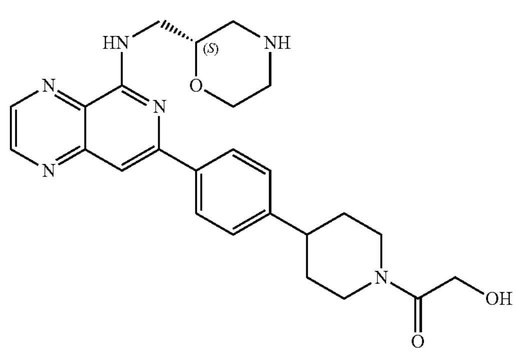 | 463 |

| Compound | Structure | MS (M + H)+ |
|---|---|---|
| 512 | 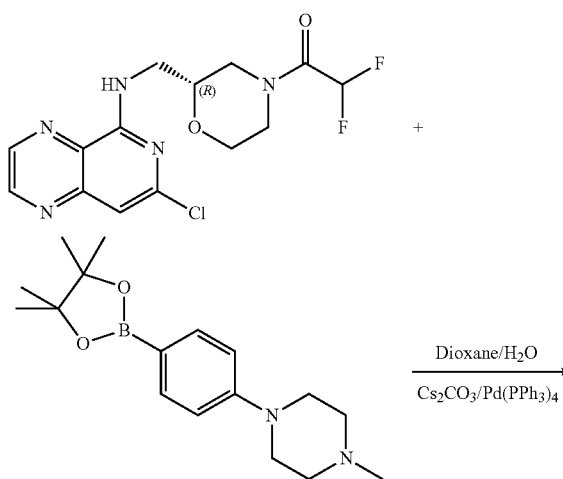 | 477 |

Compound 449

(R)-2,2-difluoro-1-(2-((7-(4-(4-methyl piperazin-1-yl)phenyl)pyrido[4,3-b]pyrazin-5-ylamino)methyl)morpholino)ethanone

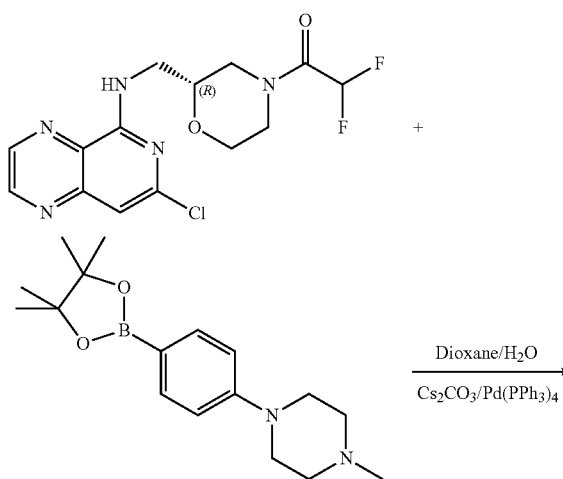

(R)-2,2-difluoro-1-(2-((7-(4-(4-methylpiperazin-1-yl)phenyl)pyrido[4,3-b]pyrazin-5-ylamino)methyl)morpholino)ethanone To a solution of (R)-1-(2-((7-chloropyrido[4,3-b]pyrazin-5-ylamino)methyl)morpholino)-2,2-difluoroethanone (72 mg, 0.2 mmol) in dioxane/H$_2$O (5 mL/0.5 mL) was added Cs$_2$CO$_3$ (98 mg, 0.3 mmol), Pd (PPh$_3$)$_4$ (46.2 mg, 0.04 mmol) and 1-methyl-4-(4-(4,4,5,5-tetramethyl-1,3,2-dioxaborolan-2-yl)phenyl)piperazine (72.5 mg, 0.24 mmol). The mixture was stirred at 110° C. for 24 hours under N$_2$. The reaction was filtered, concentrated and purified on column (CH$_2$Cl$_2$:MeOH=20:1) to give yellow solid. MS (m/z): 498 (M+H)+

The following compounds were prepared according to the procedures of Compound 449 using the corresponding intermediates and reagents under appropriate conditions that will be recognized by one skilled in the art.

| Compound | Structure | MS (M + H)+ |
|---|---|---|
| 450 | 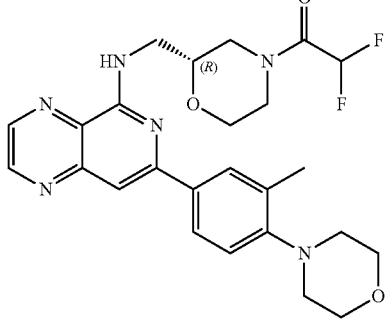 | 499 |

| Compound | Structure | MS (M + H)+ |
|---|---|---|
| 451 | 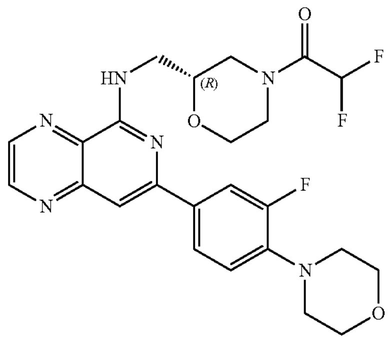 | 503 |
| 452 | 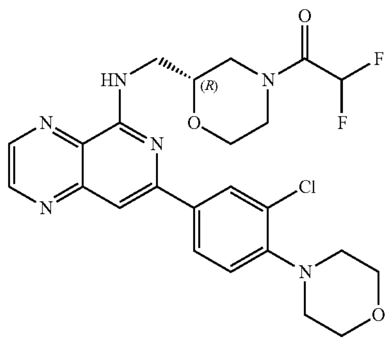 | 519<br>521 |
| 453 | 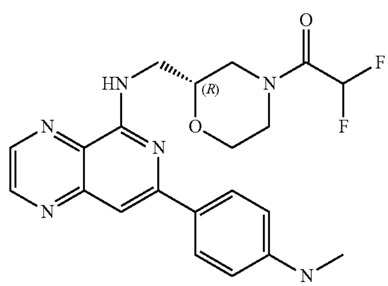 | 429 |
| 454 | 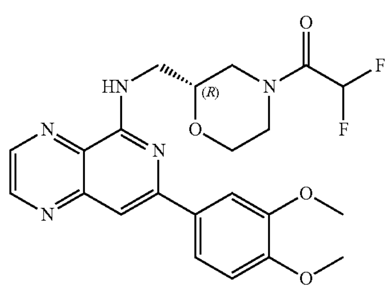 | 460 |
| 455 | 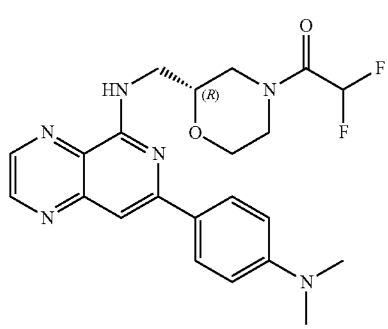 | 443 |

| Compound | Structure | MS (M + H)+ |
|---|---|---|
| 456 | 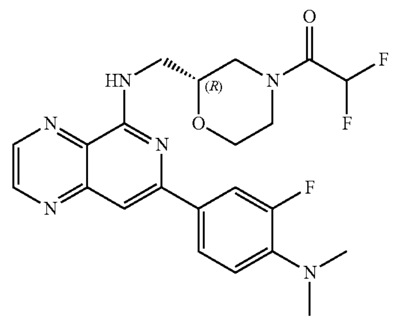 | 461 |
| 457 | 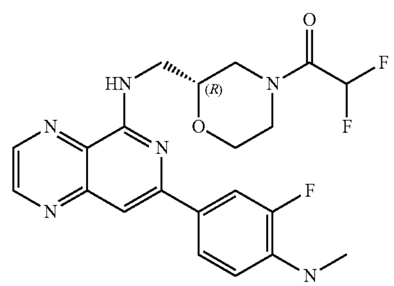 | 447 |
| 458 | 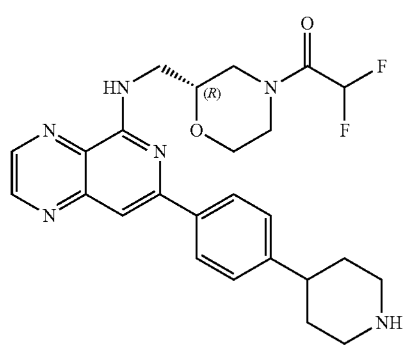 | 483 |
| 459 | 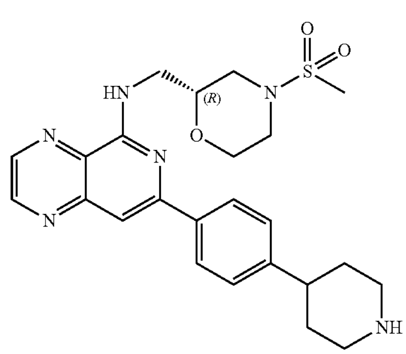 | 483 |

| Compound | Structure | MS (M + H)+ |
|---|---|---|
| 460 | 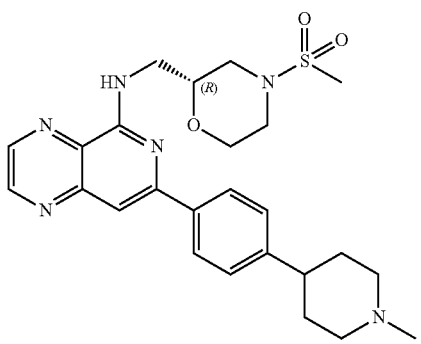 | 497 |
| 461 | 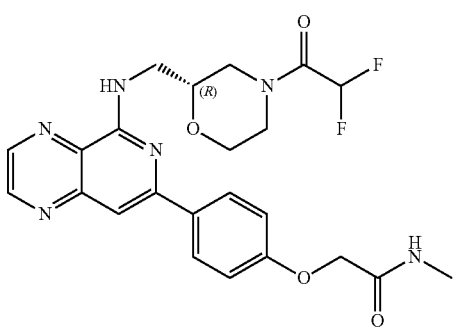 | 487 |
| 462 | 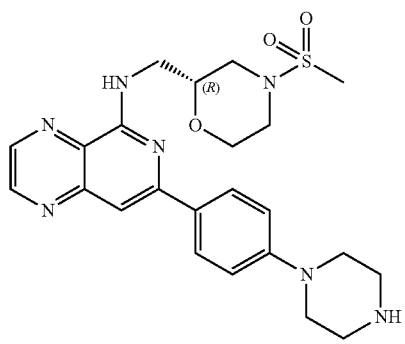 | 484 |
| 463 | 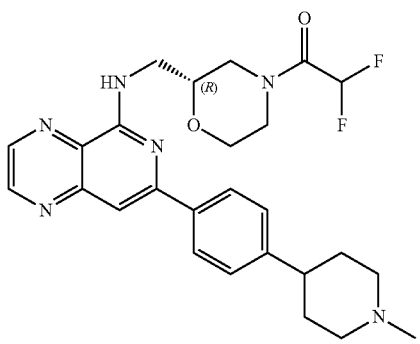 | 497 |

-continued

| Compound | Structure | MS (M + H)+ |
|---|---|---|
| 464 | 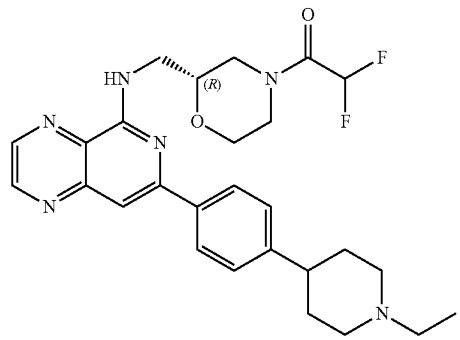 | 511 |
| 471 | 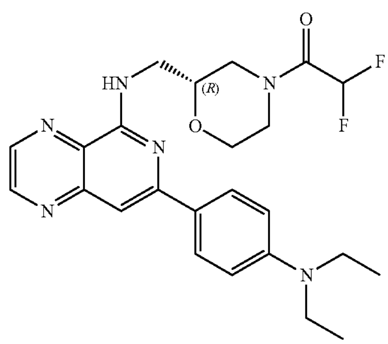 | 471 |
| 488 | 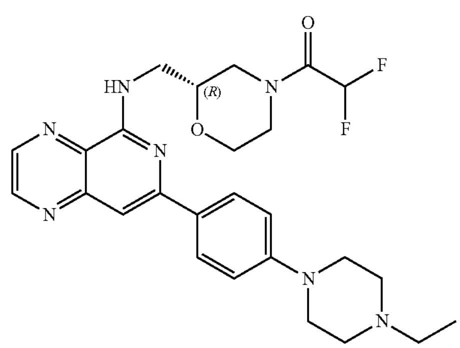 | 512 |
| 489 | 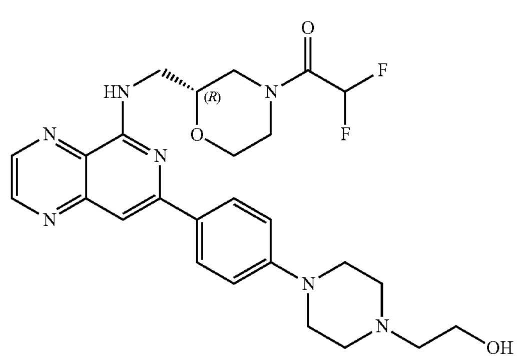 | 528 |

-continued
| Compound | Structure | MS (M + H)+ |
|---|---|---|
| 490 | 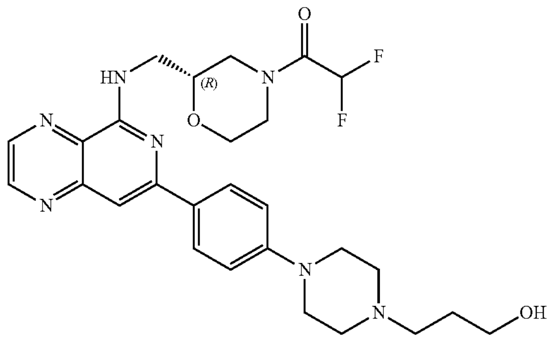 | 542 |
| 501 | 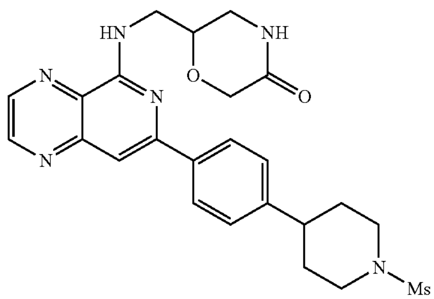 [SMILES: CS(=O)(=O)N1CCC(c2ccc(-c3cc4nccnc4c(NCC4CNC(=O)CO4)n3)cc2)CC1] | 497 |
| 514 | 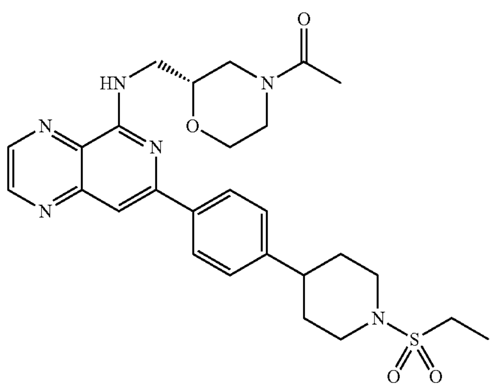 [SMILES: CCS(=O)(=O)N1CCC(c2ccc(-c3cc4nccnc4c(NC[C@@H]4CN(C(C)=O)CCO4)n3)cc2)CC1] | 539 |
Compound 466
(S)-1-(2-((7-(4-phenylpiperazin-1-yl)ethanone[4,3-b]pyrazin-5-ylamino)methyl)morpholino)-2,2-difluoroethanone
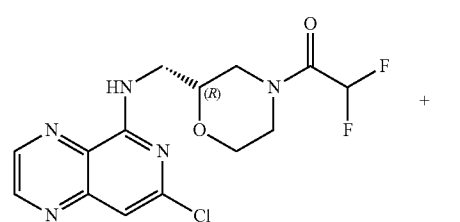
+
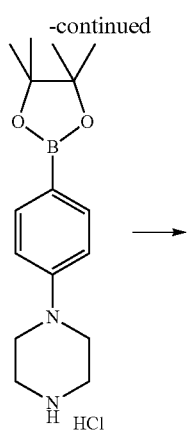
-continued 307
-continued

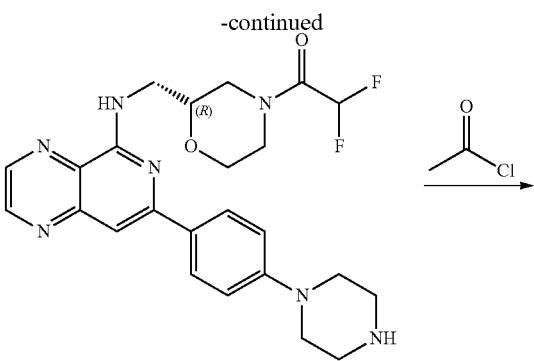

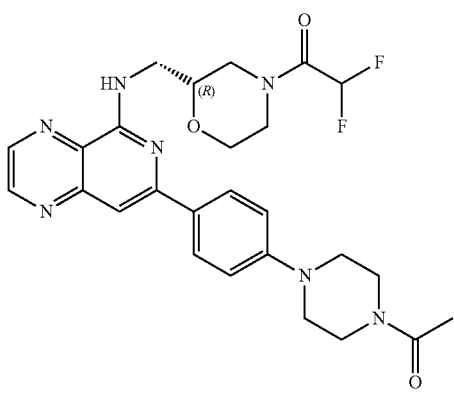

(A) (S)-2,2-difluoro-1-(2-((7-(4-(piperazin-1-yl)phenyl)pyrido[4,3-b]pyrazin-5-ylamino)methyl)morpholino)ethanone A solution of (S)-1-(2-((7-chloropyrido[4,3-b]pyrazin-5-ylamino)methyl)morpholino)-2,2-difluoroethanone (70 mg, 0.19 mmol), 1-(4-(4,4,5,5-tetramethyl-1,3,2-dioxaborolan-2-yl)phenyl)piperazine hydrochloride (96 mg, 0.29 mmol), Pd(PPh$_3$)$_4$ (45 mg, 0.04 mmol) and Cs$_2$CO$_3$ (191 mg, 0.59 mmol) in 8 mL of dioxane and 0.1 mL of water, under N$_2$, was stirred at 110° C. overnight. The volatiles were removed in vacuo, and the residue was purified by chromatography with MeOH/H$_2$O (1:10~8:1) to give 100 mg of title compound.

(B) (S)-1-(2-((7-(4-phenylpiperazin-1-yl)ethanone[4,3-b]pyrazin-5-ylamino)methyl)morpholino)-2,2-difluoroethanone A solution of (S)-2,2-difluoro-1-(2-((7-(4-(piperazin-1-yl)phenyl)pyrido[4,3-b]pyrazin-5-ylamino)methyl)morpholino)ethanone (50 mg, 0.10 mmol), acetyl chloride (12 mg, 0.16 mmol) and Et$_3$N (31 mg, 0.3 mmol) in 5 mL of DCM, was stirred at room temperature for 1 hour. The volatiles were removed in vacuo, and the residue was purified by chromatography with MeOH/H$_2$O (1:10-10:1) to give 24 mg of title compound. MS (m/z)=526 (M+H)$^+$.

The following compounds were prepared according to the procedures of Compound 466 using the corresponding intermediates and reagents under appropriate conditions that will be recognized by one skilled in the art.

| Compound | Structure | MS (M + H)$^+$ |
|---|---|---|
| 467 | 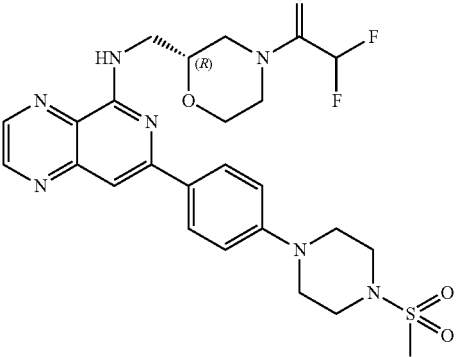 | 562 |
| 468 | 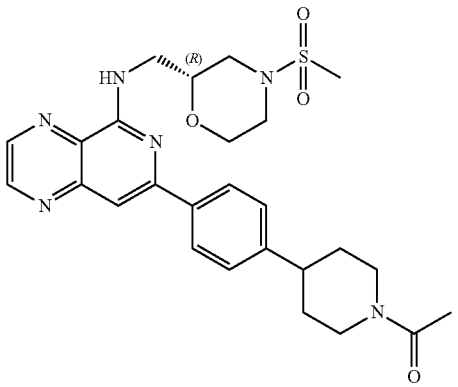 | 525 |

-continued

| Compound | Structure | MS (M + H)+ |
|---|---|---|
| 469 | 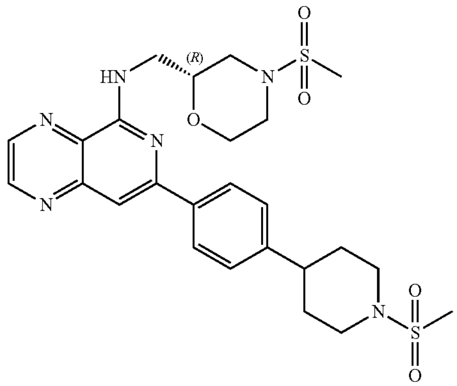 | 561 |
| 470 | 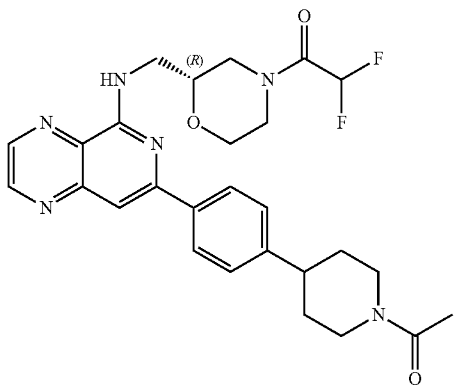 | 525 |
| 491 | 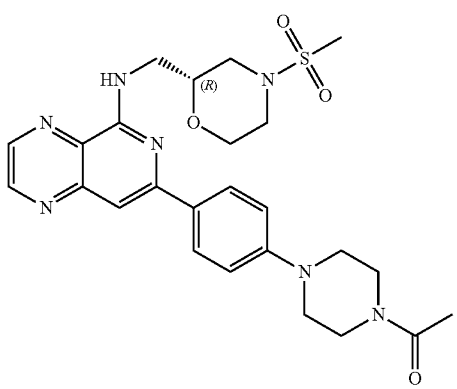 | 526 |
| 492 | 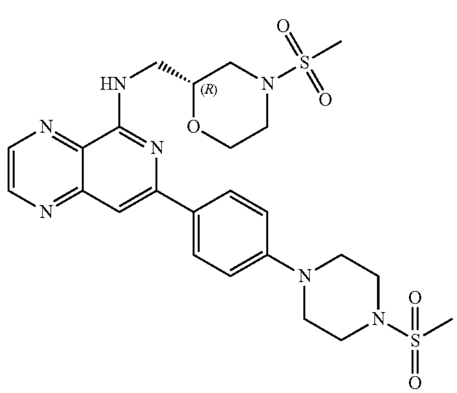 | 562 |

311

Compound 472

(S)-2-(methyl(4-(5-(morpholin-2-yl methylamino)
pyrido[4,3-b]pyrazin-7-yl)phenyl)amino)ethanol

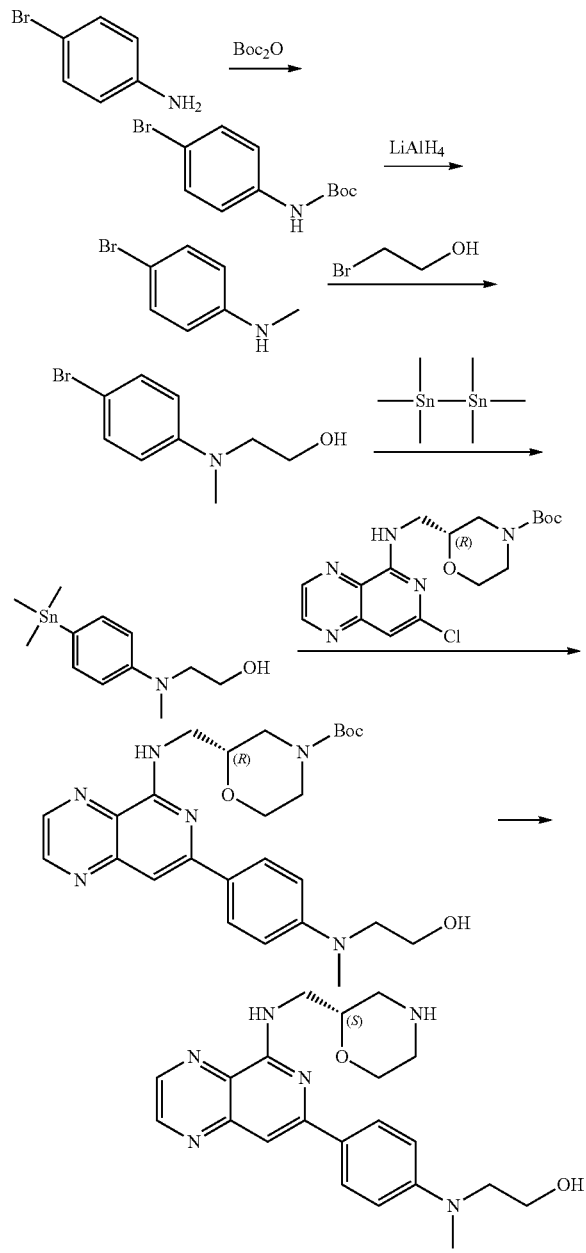

(A) tert-butyl 4-bromophenylcarbamate 4-bromoaniline (4.0 g, 23.25 mmol) was dissolved in CH$_2$Cl$_2$ (100 mL), DMAP (0.284 g), Et$_3$N (6.5 mL), Boc$_2$O (8.0 mL) were added in, the mixture was stirred at room temperature overnight. Extracted by CH$_2$Cl$_2$ and water, the mixture was then washed by water, dried over Na$_2$SO$_4$, concentrated and purified by flash chromatography (PE: EA=10:1) to give 5.5 g white solid.

312

(B) 4-bromo-N-methylaniline

Tert-butyl 4-bromophenylcarbamate (5.5 g, 20.21 mmol) was dissolved in THF, Lithium aluminum hydride (2.301 g, 60.63 mmol) was added and it was stirred at 60° C. overnight. Then it was quenched by EA, followed by H$_2$O, concentrated and CH$_2$Cl$_2$ and 1M NaOH was added in, washed with CH$_2$Cl$_2$, extracted with CH$_2$Cl$_2$, dried over Na$_2$SO$_4$, concentrated, purified by flash chromatography (PE: EA=40:3) to give 2.1 g yellow oil.

(C) 2-((4-bromophenyl)(methyl)amino)ethanol 4-bromo-N-methylaniline (700 mg, 3.76 mmol) was dissolved in DMF (20 mL), K$_2$CO$_3$ (1.56 g, 11.29 mmol) and 2-bromoethanol (1.41 g, 11.29 mmol) were added in. The mixture was reacted at 100° C. for 2 days. Then it was extracted by EA and brine, washed by brine, dried over Na$_2$SO$_4$, concentrated and purified by flash chromatography, (PE: EA=10:1 to 3:1) to give 164 mg brown oil.

(D)
2-(methyl(4-(trimethylstannyl)phenyl)amino)ethanol 2-((4-bromophenyl)(methyl)amino)ethanol (164 mg, 0.713 mmol) was dissolved in toluene, Tetrakis(triphenylphosphine)palladium (164 mg, 0.143 mmol) and 1,1,1,2,2,2-hexamethyldistannane (377 mg, 1.07 mmol) was added and reacted at 100° C. for 3.5 hours. Then it was directly used in the next step.

(E) (R)-tert-butyl 2-((7-(4-((2-hydroxyethyl)(methyl)amino)phenyl)pyrido[4,3-b]pyrazin-5-ylamino)methyl)morpholine-4-carboxylate 2-(methyl(4-(trimethylstannyl)phenyl)amino)ethanol (223 mg, 0.713 mmol), (R)-tert-butyl 2-((7-chloropyrido[4,3-b]pyrazin-5-ylamino)methyl)morpholine-4-carboxylate (246 mg, 0.648 mmol), tetrakis(triphenylphosphine)palladium (150 mg, 0.13 mmol) was mixed in toluene, reacted at 100° C. overnight. Then it was filtrated and concentrated, purified by flash chromatography (PE: EA=2:1 to 1:1) to give crude product as a reddish-brown oil. And it was used without further purification.

(F) (S)-2-(methyl(4-(5-(morpholin-2-ylmethylamino)pyrido[4,3-b]pyrazin-7-yl)phenyl)amino)ethanol (R)-tert-butyl 2-((7-(4-((2-hydroxyethyl)(methyl)amino)phenyl)pyrido[4,3-b]pyrazin-5-ylamino)methyl)morpholine-4-carboxylate was dissolved in EA (20 mL), 5M HCl in EA (10 mL) was added, the mixture was stirred at room temperature overnight. It was concentrated, treated with NH$_3$.H$_2$O, concentrated, purified by preparative TLC to give 10 mg reddish-brown solid. MS (m/z): 395 (M+H)$^+$ The following compounds were prepared according to the procedures of Compound 472 using the corresponding intermediates and reagents under appropriate conditions that will be recognized by one skilled in the art.

| Compound | Structure | MS (M + H)+ |
|---|---|---|
| 473 | 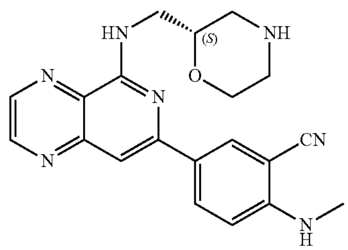 | 376 |
| 474 | 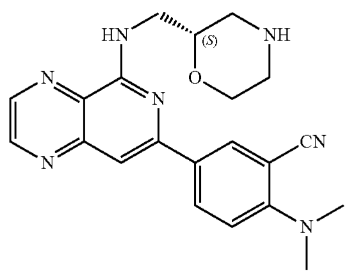 | 390 |

Compound 475

(S)-1-(4-(5-(morpholin-2-yl methylamino)pyrido[4,3-b]pyrazin-7-yl)phenyl)piperidin-4-ol

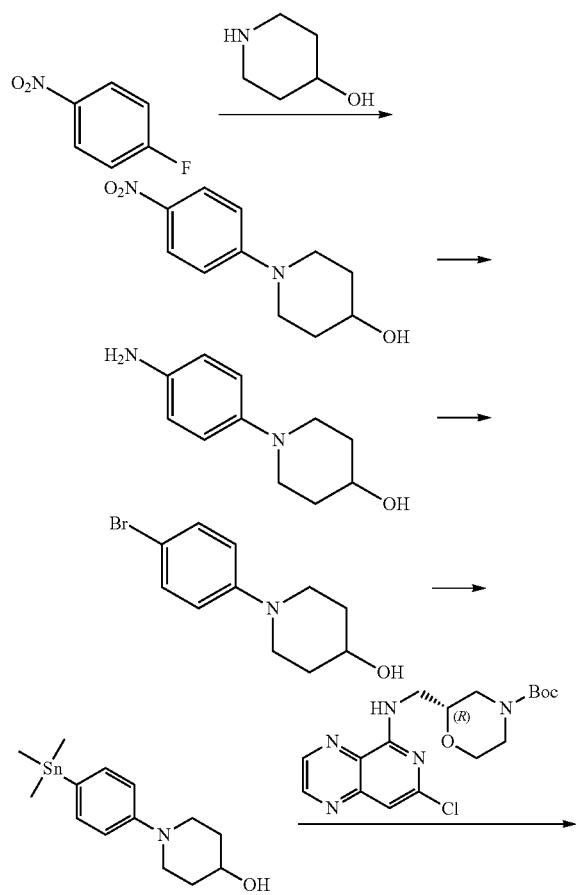

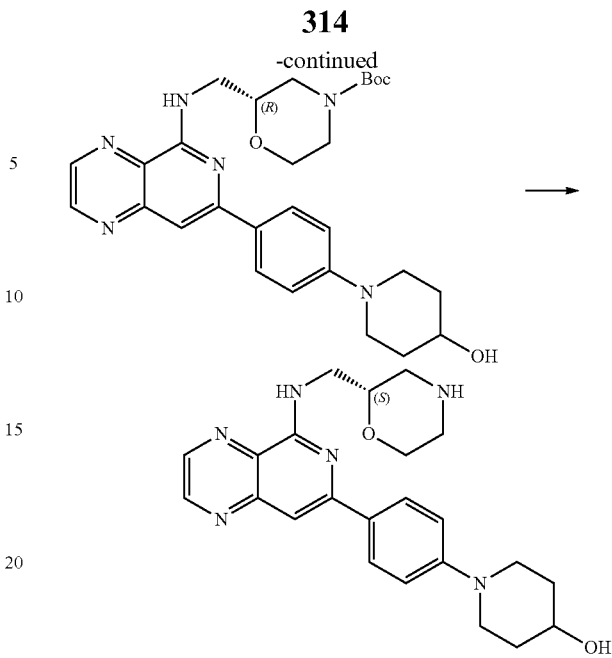

(A) 1-(4-nitrophenyl)piperidin-4-ol 1-fluoro-4-nitrobenzene (3.0 g 21.26 mmol), piperidin-4-ol (2.26 g, 22.32 mmol), K₂CO₃ (4.4 g, 31.89 mmol) was mixed in 20 mL DMF, reacted at 80° C. for 2.5 hours. Then the mixture was extracted by EA and brine, washed by brine and then water, dried over Na₂SO₄, concentrated. The crude product was used directly in the next step without further purification.

(B) 1-(4-aminophenyl)piperidin-4-ol 1-(4-nitrophenyl)piperidin-4-ol (4.725 g, 21.26 mmol), Fe (11.87 g, 212.6 mmol), NH₄Cl (11.41 g, 212.6 mmol), EtOH (100 mL) and water (50 mL) were mixed. The mixture was stirred at 100° C. overnight. Then Fe (5.9 g, 106.3 mmol) was added and reacted at 100° C. for 7 hours. Filtrated and the liquid was concentrated, purified by flash chromatography to give 1.8 g yellow solid.

(C) 1-(4-bromophenyl)piperidin-4-ol 1-(4-aminophenyl)piperidin-4-ol (600 mg, 3.12 mmol), HBr (14 mL, 48%), was mixed and cooled to 0° C., the solution of NaNO₂ (215 mg, 3.12 mmol) in 2.3 mL water was added in. the mixture was stirred for 15 minutes, the solution of CuBr (246 mg, 1.72 mmol) in HBr (4.4 mL 4.8%) was added and reacted at 100° C. for 3 hours. 2M NaOH solution was added, extracted by EA, washed by 2M NaOH, dried over Na₂SO₄, concentrated and purified by flash chromatography. (PE:EA=3:1) to give 520 mg pale brown solid.

(D) 1-(4-(trimethylstannyl)phenyl)piperidin-4-ol 1-(4-bromophenyl)piperidin-4-ol (300 mg, 1.17 mmol), tetrakis(triphenylphosphine)palladium (270 mg, 0.23 mmol), 1,1,1,2,2,2-hexamethyldistannane (499 mg, 1.52 mmol) were mixed in toluene (20 mL), reacted at 100° C. for 5 hours. The mixture was used directly in the next step.

(E) (R)-tert-butyl 2-((7-(4-(4-hydroxypiperidin-1-yl) phenyl)pyrido[4,3-b]pyrazin-5-ylamino)methyl)morpholine-4-carboxylate 1-(4-(trimethylstannyl)phenyl)piperidin-4-ol (398 mg, 1.17 mmol), (R)-tert-butyl 2-((7-chloropyrido[4,3-b]pyrazin-5-ylamino)methyl)morpholine-4-carboxylate (297 mg, 0.78 mmol), tetrakis(triphenylphosphine)palladium (180 mg, 0.15 mmol) were mixed in 5 mL toluene. The mixture was reacted at 100° C. overnight. Filtrated and concentrated, purified by flash chromatography (PE:EA=1:2) to give 112 mg reddish solid.

(F) (S)-1-(4-(5-(morpholin-2-ylmethylamino)pyrido[4,3-b]pyrazin-7-yl)phenyl)piperidin-4-ol (R)-tert-butyl 2-((7-(4-(4-hydroxypiperidin-1-yl)phenyl) pyrido[4,3-b]pyrazin-5-ylamino)methyl)morpholine-4-carboxylate (112 mg, 0.21 mmol) was dissolved in 20 mL EA, then 15 mL 5M HCl in EA was added in. The mixture was stirred at room temperature overnight, concentrated, treated with ammonia, purified by preparative TLC to give 40 mg reddish solid. MS: (m/z): 421 (M+H)$^+$

Compound 476 and 477

(S)-3-(4-(5-(morpholin-2-yl methylamino)pyrido[4,3-b]pyrazin-7-yl)phenoxy)propan-1-ol and (S)-3-(4-(5-(morpholin-2-ylmethylamino)pyrido[4,3-b]pyrazin-7-yl)phenoxy)propyl acetate

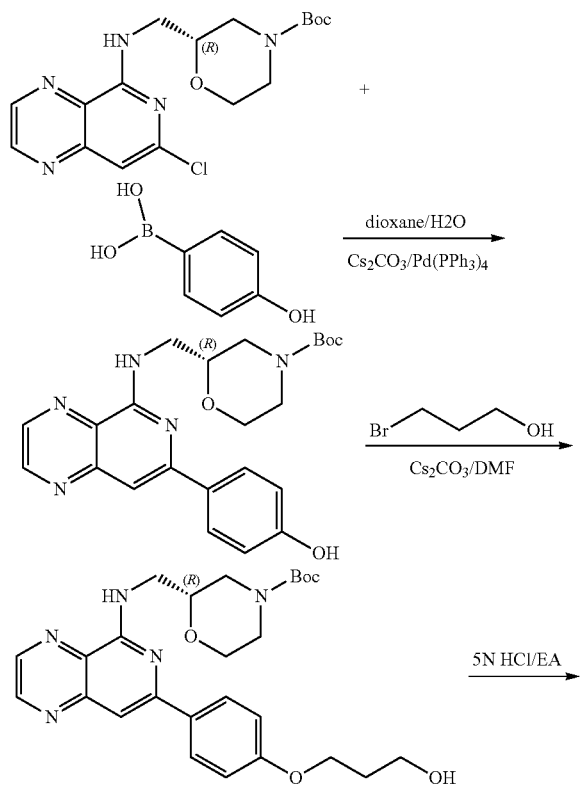

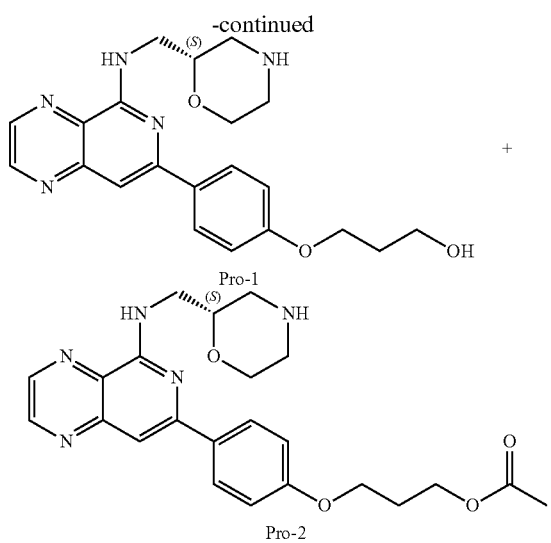

(A) (R)-tert-butyl 2-((7-(4-hydroxyphenyl)pyrido[4,3-b]pyrazin-5-ylamino)methyl) morpholine-4-carboxylate To a solution of (R)-tert-butyl 2-((7-chloropyrido[4,3-b] pyrazin-5-ylamino)methyl) morpholine-4-carboxylate (380 mg, 1 mmol) in dioxane/H$_2$O (20 mL/2 mL) was added Cs$_2$CO$_3$ (652 mg, 2 mmol), Pd (PPh$_3$)$_4$ (231 mg, 0.2 mmol) and 4-hydroxyphenyl boron-ic acid (207 mg, 1.5 mmol). The mixture was sealed in a tube and heated in microwave reactor at 160° C. for 1.5 hours under N$_2$. (R)-tert-butyl 2-((7-chloropyrido[4,3-b]pyrazin-5-ylamino)methyl) morpholine-4-carboxylate was consumed and the reaction was filtered, concentrated and purified on TLC (CH$_2$Cl$_2$:MeOH=30:1) to give yellow solid. MS (m/z): 438 (M+H)$^+$

(B) (R)-tert-butyl 2-((7-(4-(3-hydroxypropoxy)phenyl)pyrido[4,3-b]pyrazin-5-ylamino)methyl)morpholine-4-carboxylate To a solution of (R)-tert-butyl 2-((7-(4-hydroxyphenyl) pyrido[4,3-b]pyrazin-5-ylamino)methyl)morpholine-4-carboxylate (115 mg, 0.26 mmol) in DMF (5 mL) was added Cs$_2$CO$_3$ (128 mg, 0.39 mmol) and 3-bromopropan-1-ol (55 mg, 0.39 mmol). The reaction was stirred at 80° C. for 0.5 hours. TLC and LC-Ms showed the reaction had completed and the reaction was poured into water, extracted with EA, washed with water and brine, dried and concentrated, purified on TLC (CH$_2$Cl$_2$:MeOH=30:1) to give yellow solid. MS (m/z): 496 (M+H)$^+$

(C) (S)-3-(4-(5-(morpholin-2-ylmethylamino)pyrido[4,3-b]pyrazin-7-yl)phen oxy)propan-1-ol and (S)-3-(4-(5-(morpholin-2-ylmethylamino)pyrido[4,3-b]pyrazin-7-yl)phenoxy)propyl acetate (R)-tert-butyl 2-((7-(4-(3-hydroxypropoxy)phenyl)pyrido [4,3-b]pyrazin-5-ylamino)methyl)morpholine-4-carboxylate (98 mg, 0.20 mmol) was dissolved in a solution of HCl/EA (5 N, 5 mL) and stirred for 4 hours at 20° C. The reaction was concentrated and washed with sat. NaHCO$_3$, water and brine, concentrated and purified on TLC (CH$_2$Cl$_2$:MeOH=5:1) to give two yellow solids. Pro-1 is (S)-3-(4-(5-(morpholin-2-ylmethylamino)pyrido[4,3-b]pyrazin-7-yl)

phenoxy)propan-1-ol, MS (m/z): 396 (M+H)⁺. Pro-2 is (S)-3-(4-(5-(morpholin-2-ylmethylamino)pyrido[4,3-b]pyrazin-7-yl)phenoxy)propyl acetate, MS (m/z): 438 (M+H)⁺.

Compound 478

(S)-7-(4-(2-(methylsulfonyl)ethoxy)phenyl)-N-(morpholin-2-yl methyl)pyrido[4,3-b]pyrazin-5-amine

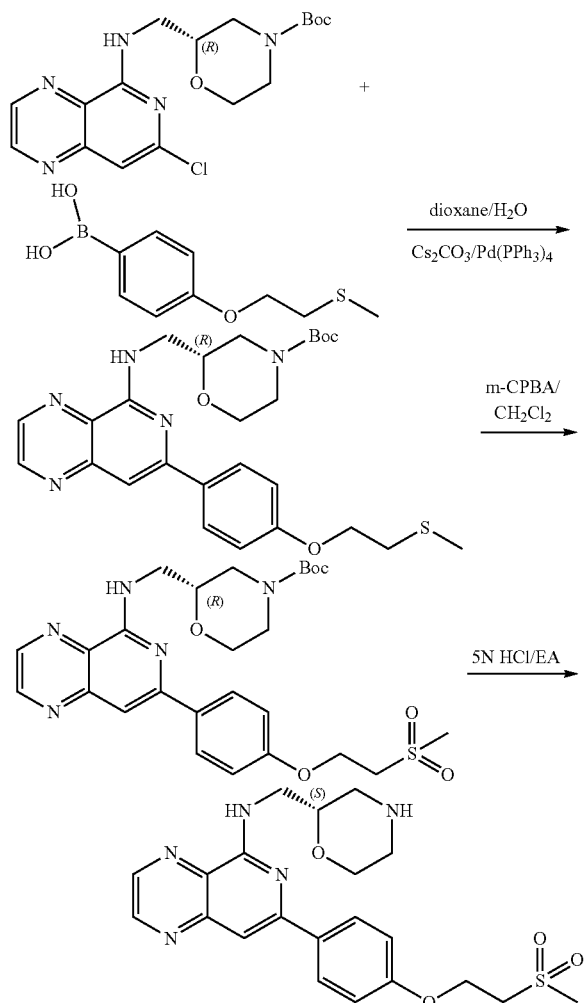

(A) (R)-tert-butyl 2-((7-(4-(2-(methylthio)ethoxy)phenyl)pyrido[4,3-b]pyrazin-5-ylamino)methyl)morpholine-4-carboxylate To a solution of (R)-tert-butyl 2-((7-chloropyrido[4,3-b]pyrazin-5-ylamino)methyl) morpholine-4-carboxylate (114 mg, 0.3 mmol) in dioxane/$H_2O$ (5 mL/1 mL) was added $Cs_2CO_3$ (195 mg, 0.6 mmol), Pd (PPh$_3$)$_4$ (69 mg, 0.06 mmol) and 4-(2-(methylthio)ethoxy)phenylboronic acid (127 mg, 0.6 mmol). The mixture was sealed in a tube and heated in microwave reactor at 160° C. for 1.5 hours under $N_2$. (R)-tert-butyl 2-((7-chloropyrido[4,3-b]pyrazin-5-ylamino)methyl) morpholine-4-carboxylate was consumed and the reaction was filtered, concentrated and purified on TLC (EA:PE=1:1) to give yellow solid. MS (m/z): 512 (M+H)

(B) (R)-tert-butyl 2-((7-(4-(2-(methylsulfonyl)ethoxy)phenyl)pyrido[4,3-b]pyrazin-5-ylamino)methyl)morpholine-4-carboxylate To a solution of (R)-tert-butyl 2-((7-(4-(2-(methylthio)ethoxy)phenyl)pyrido[4,3-b]pyrazin-5-ylamino)methyl) morpholine-4-carboxylate (150 mg, 0.29 mmol) in $CH_2Cl_2$ (5 mL) was added m-CPBA (125 mg, 0.73 mmol) at 0° C. After that the reaction was stirred at room temperature for 24 hours. TLC and LC-Ms showed the reaction had completed and the reaction was washed with sat. $Na_2S_2O_3$, sat. $NaHCO_3$, water and brine, concentrated and purified on TLC ($CH_2Cl_2$:MeOH=30:1) to give yellow solid. MS (m/z): 544 (M+H)⁺

(C) (S)-7-(4-(2-(methylsulfonyl)ethoxy)phenyl)-N-(morpholin-2-yl methyl)pyrido[4,3-b]pyrazin-5-amine (R)-tert-butyl 2-((7-(4-(2-(methylsulfonyl)ethoxy)phenyl)pyrido[4,3-b]pyrazin-5-ylamino)methyl)morpholine-4-carboxylate (76 mg, 0.14 mmol) was dissolved in a solution of HCl/EA (5 N, 5 mL) and stirred for 4 hours at 20° C. The reaction was concentrated and washed with sat. $NaHCO_3$, water and brine, concentrated and purified on TLC ($CH_2Cl_2$:MeOH=5:1) to give yellow solid. MS (m/z): 444 (M+H)⁺

Compound 479

(R)-7-(4-(1-ethylpiperidin-4-yl)phenyl)-N-((4-(methylsulfonyl)morpholin-2-yl)methyl)pyrido[4,3-b]pyrazin-5-amine

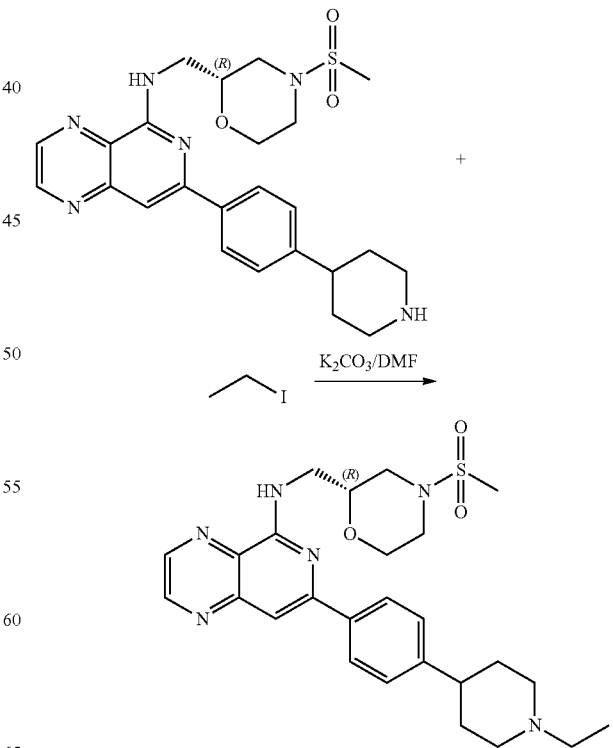

319

(R)-7-(4-(1-ethylpiperidin-4-yl)phenyl)-N-((4-(methylsulfonyl)morpholin-2-yl)methyl)pyrido[4,3-b]pyrazin-5-amine To a solution of (R)—N-((4-(methylsulfonyl)morpholin-2-yl)methyl)-7-(4-(piperidin-4-yl)phenyl)pyrido[4,3-b]pyrazin-5-amine in (39.5 mg, 0.082 mmol) in DMF (5 mL) was added $K_2CO_3$ (22.6 mg, 0.164 mmol) and iodoethane (25.5 mg, 0.164 mmol) at room temperature. The reaction was stirred at 100° C. for 18 hours. After that, the reaction was dissolved in 50 mL of EA, washed with $H_2O$ (25 mL) and brine (25 mL), dried over $Na_2SO_4$ and concentrated, purified on TLC ($CH_2Cl_2$:MeOH=20:1) to give yellow solid. MS (m/z): 511 (M+H)$^+$ The following compounds were prepared according to the procedures of Compound 479 using the corresponding intermediates and reagents under appropriate conditions that will be recognized by one skilled in the art.

| Compound | Structure | MS (M + H)$^+$ |
|---|---|---|
| 493 | (structure) | 527 |
| 494 | (structure) | 541 |

Compound 480

(R)-4-(4-(5-((4-(2,2-difluoroacetyl)morpholin-2-yl)methylamino)pyrido[4,3-b]pyrazin-7-yl)phenyl)-1,1-diethylpiperidinium iodide

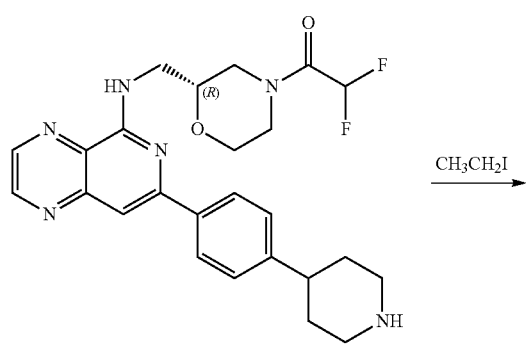

CH₃CH₂I →

320

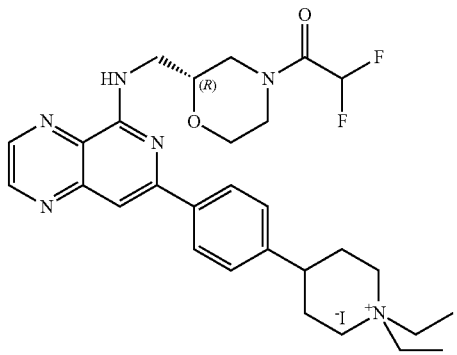

(R)-4-(4-(5-((4-(2,2-difluoroacetyl)morpholin-2-yl)methylamino)pyrido[4,3-b]pyrazin-7-yl)phenyl)-1,1-diethylpiperidinium iodide A solution of (R)-2,2-difluoro-1-(2-((7-(4-(piperidin-4-yl)phenyl)pyrido[4,3-b]pyrazin-5-ylamino)methyl)morpholino)ethanone (85 mg, 0.175 mmol), iodoethane (82 mg, 0.52 mmol) and potassium carbonate (97 mg, 0.70 mmol) in DMF (15 mL) was heated in a sealed tube at 100° C. for 4 hours. Then the mixture was extracted with DCM, washed brine, dried and purified by pre-TLC (DCM/MeOH=10/1) to give product as yellow solid. MS (m/z): 539 (M+H−1⁻)$^+$.

Compound 481

(R)-7-(4-morpholinophenyl)-N-((4-(pyrimidin-2-yl)morpholin-2-yl)methyl)pyrido[4,3-b]pyrazin-5-amine

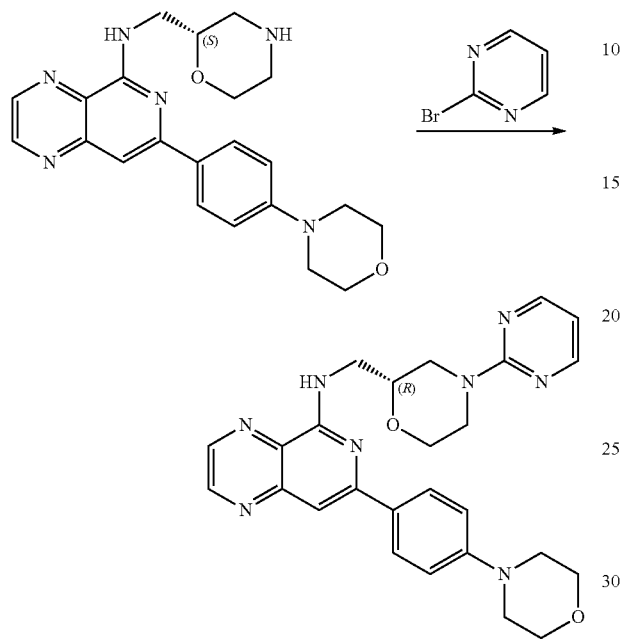

(R)-7-(4-morpholinophenyl)-N-((4-(pyrimidin-2-yl)morpholin-2-yl)methyl)pyrido[4,3-b]pyrazin-5-amine A solution of (S)—N-(morpholin-2-ylmethyl)-7-(4-morpholinophenyl)pyrido[4,3-b]pyrazin-5-amine (100 mg, 0.246 mmol), 2-bromopyrimidine (59 mg, 0.37 mmol) and cesiumcarbonate (193 mg, 0.592 mmol) in DMF (2 mL) was heated at 100° C. in a sealed tube for overnight. Then the mixture was extracted with EA, washed with brine, concentrated and purified by flash column chromatography, eluting with DCM/MeOH to give product as light yellow solid. MS (m/z): 485 (M+H)+

Compound 482

7-(4-morpholinophenyl)-N-(1,1-dioxo-thiomorpholin-2-ylmethyl)pyrido[4,3-b]pyrazin-5-amine

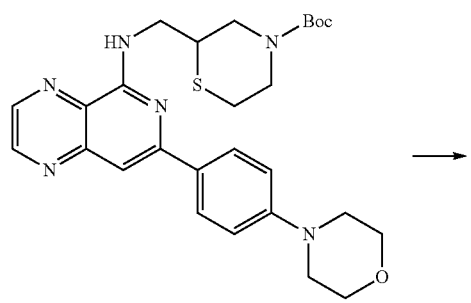

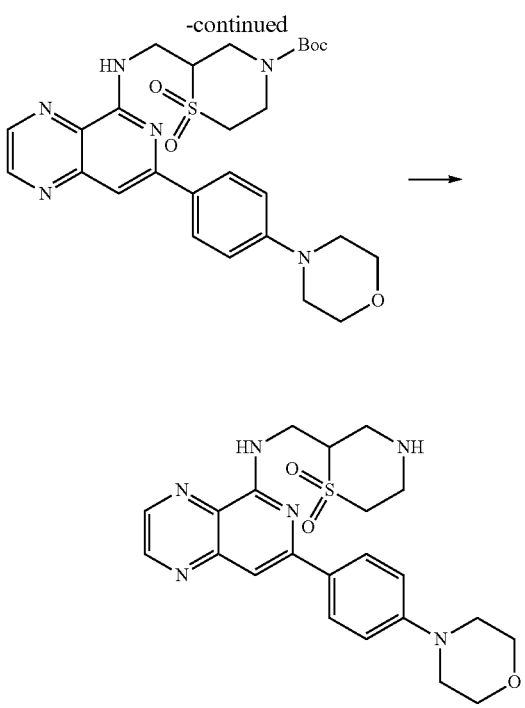

(A) tert-butyl 2-((7-(4-morpholinophenyl)pyrido[4,3-b]pyrazin-5-ylamino)methyl)-1,1-dioxo-thiomorpholine-4-carboxylate To a solution of tert-butyl 2-((7-(4-morpholinophenyl)pyrido[4,3-b]pyrazin-5-ylamino)methyl)thiomorpholine-4-carboxylate (178 mg, 0.34 mmol) in $CH_2Cl_2$ (5 mL) was added 3-chloroperoxybenzoic acid (70%, 251 mg, 1.02 mmol) at 0° C. The resulting mixture was stirred at room temperature for 3 hours, and subsequently, a saturated aqueous sodium thiosulfate solution was added and the mixture was stirred for another 30 minutes. The layers were separated and the aqueous layer was extracted twice with EtOAc. The combined EtOAc layers were washed twice with an aqueous $Na_2CO_3$ solution. The combined organic layers were dried ($Na_2SO_4$), filtered and concentrated in vacuo to afford title compound 52 mg. MS (m/z): 555 (M+H)+

(B) 7-(4-morpholinophenyl)-N-(1,1-dioxo-thiomorpholin-2-ylmethyl)pyrido[4,3-b]pyrazin-5-amine The tert-butyl 2-((7-(4-morpholinophenyl)pyrido[4,3-b]pyrazin-5-ylamino)methyl)-1,1-dioxo-thiomorpholine-4-carboxylate (52 mg, 0.094 mmol) was dissolved in the solution of HCl in ethyl acetate (3 mL), and the mixture was stirred at room temperature for 2 hours until TLC indicated Boc group was removed. The volatile materials was removed, the residue was neutralized with ammonium hydroxide (25%, 1 mL) and purified by $C_{18}$ column to afford yellow solid 33 mg. MS (m/z): 455 (M+H)+

The following compounds were prepared according to the procedures of Compound 482 using the corresponding intermediates and reagents under appropriate conditions that will be recognized by one skilled in the art.

| Compound | Structure | MS (M + H)+ |
|---|---|---|
| 483 | 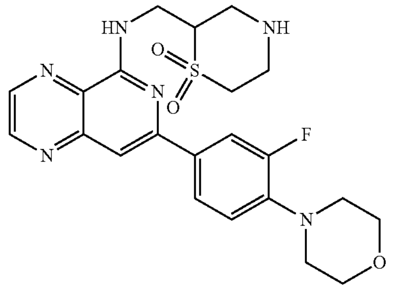 [SMILES: O=S1(=O)CCNCC1CNc1nc(-c2ccc(N3CCOCC3)c(F)c2)cc2nccnc12] | 473 |
| 484 | 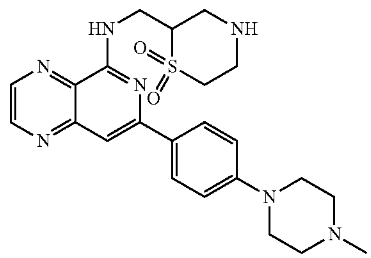 [SMILES: CN1CCN(c2ccc(-c3cc4nccnc4c(NCC4CNCCS4(=O)=O)n3)cc2)CC1] | 468 |

Compound 485

2-((4-(5-((4,4-difluoropiperidin-3-yl)methylamino)pyrido[4,3-b]pyrazin-7-yl)phenyl)(methyl)amino)ethanol

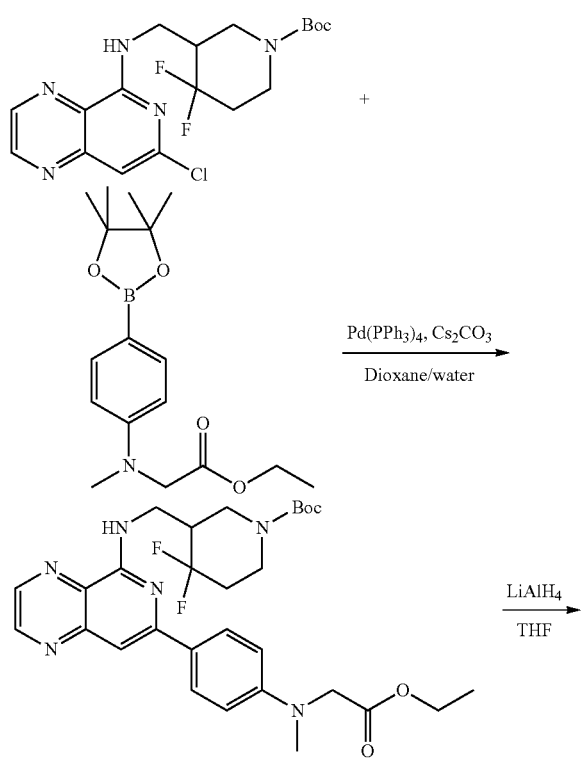

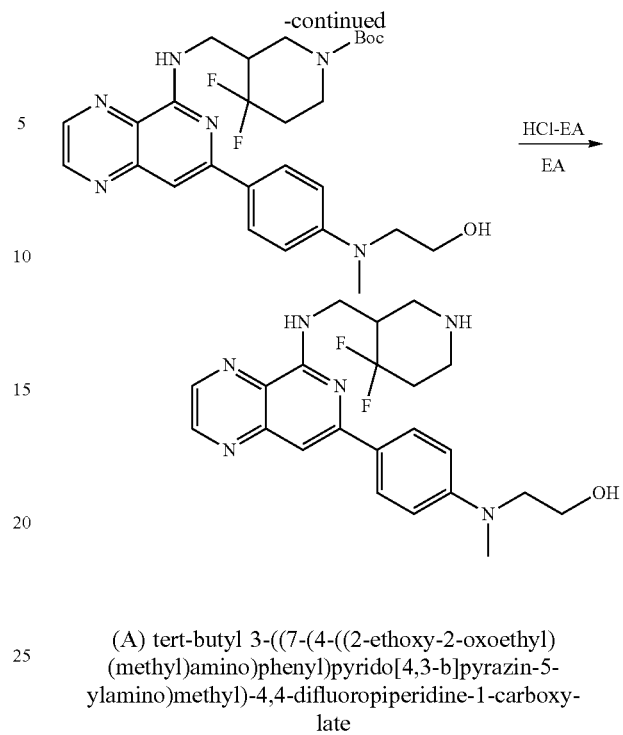

(A) tert-butyl 3-((7-(4-((2-ethoxy-2-oxoethyl)(methyl)amino)phenyl)pyrido[4,3-b]pyrazin-5-ylamino)methyl)-4,4-difluoropiperidine-1-carboxylate A solution of tert-butyl 3-((7-chloropyrido[4,3-b]pyrazin-5-ylamino)methyl)-4,4-difluoropiperidine-1-carboxylate (173 mg, 0.42 mmol), ethyl 2-(methyl(4-(4,4,5,5-tetramethyl-1,3,2-dioxaborolan-2-yl)phenyl)amino)acetate (200 mg, 0.63 mmol), Pd(PPh$_3$)$_4$ and Cs$_2$CO$_3$ in 4 mL of dioxane and 0.5 mL of water was stirred at 160° C. for 1 hour. The volatiles were removed in vacuo, and the residue was purified by chromatography with MeOH/H$_2$O (1:8~5:1) to give 373 mg of title compound.

(B) tert-butyl 4,4-difluoro-3-((7-(4-((2-hydroxyethyl)(methyl)amino)phenyl)pyrido[4,3-b]pyrazin-5-ylamino)methyl)piperidine-1-carboxylate A solution of tert-butyl 3-((7-(4-((2-ethoxy-2-oxoethyl)(methyl)amino)phenyl)pyrido[4,3-b]pyrazin-5-ylamino)methyl)-4,4-difluoropiperidine-1-carboxylate (120 mg, 0.21 mmol) and LiAlH$_4$ (10 mg, 0.25 mmol) in 5 mL of THF at 0° C., under N$_2$, was stirred at 0° C. for 1 hour. The volatiles were removed in vacuo, and the residue was purified by chromatography with MeOH/H$_2$O (1:8~5:1) to give 25 mg of title compound.

(C) 2-((4-(5-((4,4-difluoropiperidin-3-yl)methylamino)pyrido[4,3-b]pyrazin-7-yl)phenyl)(methyl)amino)ethanol A solution of tert-butyl 4,4-difluoro-3-((7-(4-((2-hydroxyethyl)(methyl)amino)phenyl) pyrido[4,3-b]pyrazin-5-ylamino)methyl)piperidine-1-carboxylate (25 mg, 0.05 mmol) and 2 mL of HCl-EA (5.0 N) in 4 mL of EA was stirred at room temperature for 1.5 hours. The volatiles were removed in vacuo, and the residue was added to 5 mL of MeOH and 0.5 mL of NH$_3$.H$_2$O. The volatiles were removed in vacuo, and the residue was purified by chromatography with MeOH/H$_2$O (1:10-5:1) to give 14 mg of title compound. MS (m/z)=429 (M+H)+.

Compound 486

(S)-7-(4-(4-methyl piperazin-1-yl)phenyl)-N-((4-(methylsulfonyl)morpholin-2-yl)methyl)pyrido[4,3-b]pyrazin-5-amine

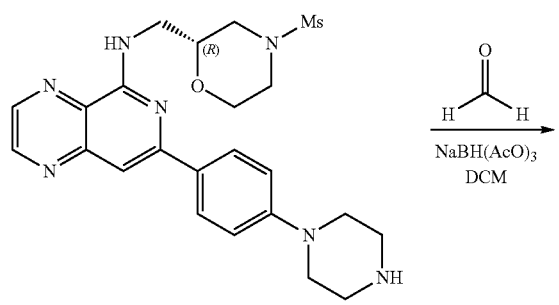
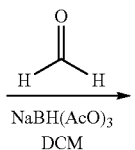

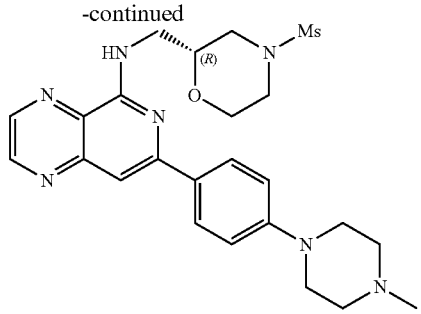

A solution of (S)—N-((4-(methylsulfonyl)morpholin-2-yl)methyl)-7-(4-(piperazin-1-yl)phenyl)pyrido[4,3-b]pyrazin-5-amine (60 mg, 0.12 mmol), Formalin (48 mg, 0.48 mmol) and NaBH(AcO)$_3$ in 5 mL of DCM, was stirred at room temperature for 2 hours. The volatiles were removed in vacuo, and the residue was purified by chromatography with MeOH/H$_2$O (1:10~10:1) to give 46 mg of title compound. MS (m/z)=498 (M+H)$^+$.

The following compound was prepared according to the procedures of Compound 486 using the corresponding intermediates and reagents under appropriate conditions that will be recognized by one skilled in the art.

| Compound | Structure | MS (M + H)$^+$ |
|---|---|---|
| 487 | 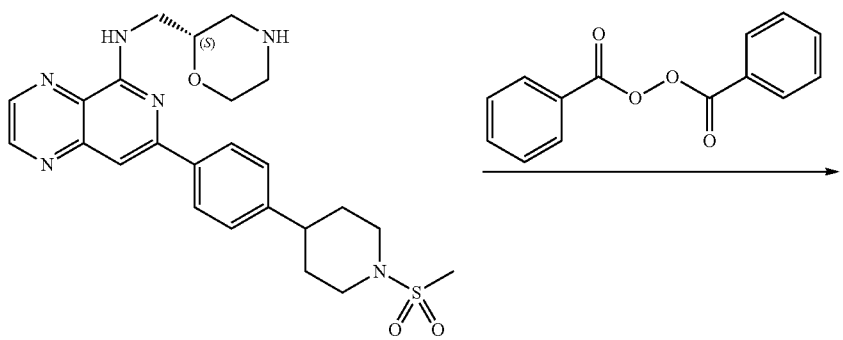 | 512 |

Compound 496

(R)-2-((7-(4-(1-(methylsulfonyl)piperidin-4-yl)phenyl)pyrido[4,3-b]pyrazin-5-ylamino)methyl)morpholin-4-ol

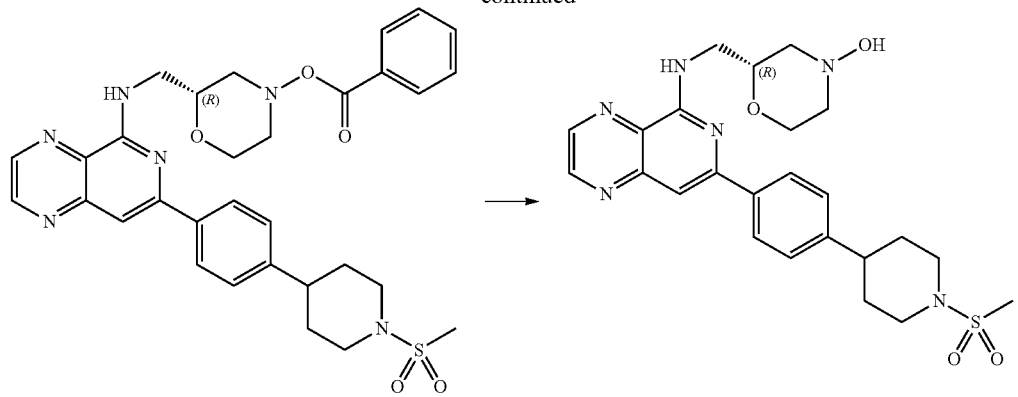

To a solution of benzoyl peroxide (430 mg, 1.78 mmol) in DMF at −5° C. was added K$_2$HPO$_4$ (360 mg, 2.07 mmol), then was added the solution of compound 419 (833 mg, 1.73 mmol) in DMF. The mixture was stirred at room temperature overnight. The reaction solution was poured into ice-water, filter, the filter cake was washed with water and PE, dried to afford the crude product as yellow solid. The crude product was dissolved in methanol and THF, cooled to −5° C., LiOH (15 mL) was added dropwise, the mixture was stirred for 1 hour. 100 mL water was added into the reaction solution, extracted with DCM (50 mL×4), washed with brine, dried with anhydrous Na$_2$SO$_4$. The solvent was removed to get crude product. The crude product was purified by column chromatograph (DCM:MeOH=100:1~50:1), washed by 5 mL EA and 1 mL methanol to afford the title compound as yellow solid (145 mg). MS (m/z)=499 (M+H)$^+$.

Compound 507 and 508

(S)-6-((7-(4-(1-(methylsulfonyl)piperidin-4-yl)phenyl)pyrido[4,3-b]pyrazin-5-ylamino)methyl)morpholin-3-one and (R)-6-((7-(4-(1-(methylsulfonyl)piperidin-4-yl)phenyl)pyrido[4,3-b]pyrazin-5-ylamino)methyl)morpholin-3-one

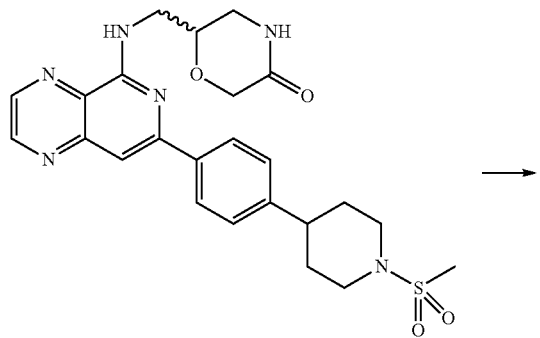

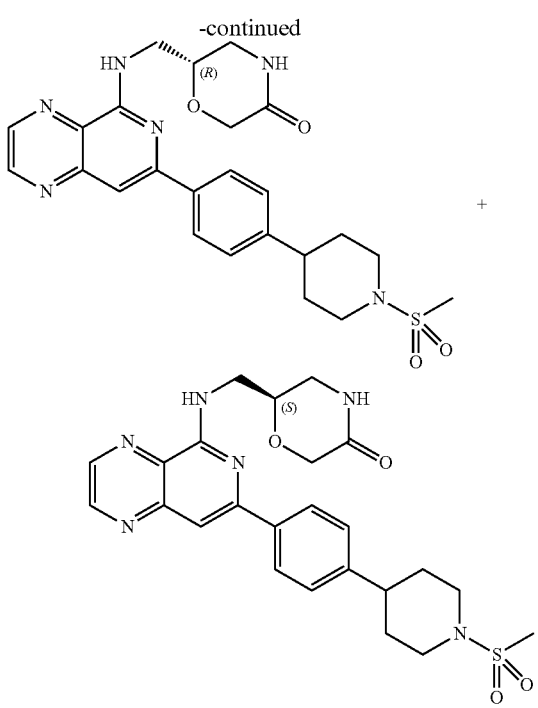

The racemic compound 501 was resolved by chiral HPLC to provide the optically pure enantiomers Compound 507 and 508 (HPLC conditions: column: CHIRALPAK IA 0.20× 25 cm; mobile phase: CH$_3$CN/EtOH=90/10; flow rate=10.0 mL/min; detector: UV 254 nm). The first eluent (compound 507, Rf=9.759 min) was 100% ee, MS (m/z): 497 (M+H)$^+$. and the second eluent (compound 508, Rf=10.916 min) was 100% ee, MS (m/z): 497 (M+H)$^+$.

Example 2

Enzymatic Assay

Syk kinase assay are performed in vitro using Kit-Tyr 2 Peptide (Invitrogen, Cat. No. PV3191) and in a 384-well assay plate. All reactions (40 μL) are started by adding 0.8 μL of the testing compound in 100% DMSO solution, 10 μL of Kinase/Peptide substrate mixture or Phospho-Peptide solution (Invitrogen, Cat. No. PV3192, diluted with 1.33× Kinase Buffer), 5 μL ATP solution (100 μM) or 1.33× kinase buffer (Invitrogen, Cat. No. PV3189, 5× diluted with distilled water), 4.2 µL distilled water. The 384-well assay plate (Corning, Cat. No. 3575) is mixed and incubated at room temperature for 1 hour. 10 µL of the Development Solution (prepared by diluting Development Reagent A (Cat. No. PV3297) to ⅟32 with Development Buffer (Cat. No. PV3127)) is then added to each well, mixed and incubated at room temperature for another 1 hour. The reactions are then stopped by adding 10 µL of the Stop Reagent (Invitrogen, Cat. No. PV3094), and the plate is read with Wallac 1420 VICTOR³ Multilabel Counter (PerkinElmer™) at 445 nm and 520 nm fluorescence. All compounds are tested at 8 concentrations (1 µM down to 0.0003 µM) using a 1:3 serial dilution scheme.

Below are the $IC_{50}$ values of some compounds.

$IC_{50}$: enzymatic activity $IC_{50}$ values of compounds 1, 3, 9, 10, 12, 19, 21, 22, 26, 30, 32, 33, 34, 35, 40, 41,42, 44, 46, 47, 48, 52, 53, 54, 55, 59, 60, 61,63, 64, 67, 70, 71,73, 74, 77, 78, 79, 80, 81,82, 83, 85, 86, 87, 90, 93, 94, 96, 99, 102, 103, 104, 105, 107, 109, 110, 111, 112, 114, 116, 117, 119, 120, 121,122, 123, 127, 128, 129, 130, 134, 136, 137, 139, 140, 141,142, 143, 146, 156, 157, 158, 173, 179, 185, 186, 200, 205, 208, 213, 215, 216, 217, 218, 219, 221, 225, 226, 228, 229, 230, 231, 232, 233, 235, 236, 237, 238, 239, 240, 241, 251, 253, 254, 264, 265, 266, 267, 269, 270, 272, 273, 274, 275, 276, 278, 279, 280, 281, 285, 286, 287, 289, 290, 291, 292, 293, 294, 295, 296, 297, 298, 300, 301, 302, 305, 306, 307, 308, 309, 310, 311,312, 313, 314, 315, 316, 317, 318, 319, 320, 321, 322, 323, 324, 332, 333, 340, 346, 347, 362, 368, 370, 371, 372, 374, 376, 377, 380, 381, 382, 383, 384, 385, 386, 387, 388, 389, 390, 392, 394, 396, 397, 398, 399, 400, 401, 402, 403, 404, 405, 406, 407, 408, 409, 410, 411,412, 413, 414, 415, 416, 417, 418, 419, 420, 421, 422, 423, 424, 425, 426, 427, 428, 429, 430, 431, 432, 433, 434, 435, 437, 438, 439, 440, 441, 442, 443, 444, 445, 446, 447, 448, 449, 450, 451, 455, 456, 458, 459, 460, 462, 463, 464, 465, 466, 467, 468, 469, 470, 473, 474, 475, 476, 479, 480, 485, 486, 487, 488, 489, 490, 493, 494, 497, 498, 499, 500, 501, 502, 503, 504, 505, 506, 510, 511, 512 are in the range of 0.001 to less than 0.1 uM.

$IC_{50}$ values of compounds 4, 6, 7, 8, 11, 13, 14, 15, 17, 18, 20, 23, 24, 25, 27, 28, 31,37, 39, 43, 45, 49, 57, 65, 66, 68, 69, 72, 75, 76, 84, 88, 89, 91,92, 95, 97, 98, 100, 101,106, 108, 115, 124, 135, 138, 144, 145, 147, 148, 149, 150, 151, 154, 155, 159, 161,162, 163, 164, 165, 166, 167, 168, 172, 174, 175, 176, 177, 180, 188, 191, 194, 195, 196, 198, 201,202,203, 204,206, 207, 209, 210, 211,212, 214, 220, 222, 223, 224, 227, 234, 242, 244, 245, 246, 247, 248, 249, 250, 252, 255, 256, 257, 258, 259, 260, 261, 262, 263, 268, 271, 277, 283, 284, 288, 299, 303, 304, 325, 326, 327, 328, 337, 339, 341, 342, 343, 344, 348, 349, 350, 353, 354, 355, 356, 357, 358, 360, 361, 363, 364, 369, 373, 375, 378, 379, 391, 393, 395, 452, 453, 454, 457, 461, 471, 472, 477, 478, 482, 483, 484, 491, 492, 495, 496, 509 are from 0.1 uM to less than 1 uM.

Example 3

Cellular Assays

For the determination of IgE-induced Beta-hexosaminidase secretion, RBL-2H3 cells (SIBS) are seeded in 96 well plates at 4×10⁴ cells per well and incubated in MEM media with 15% FBS and Glutamine (2 nM) for 4 hours and sensitized with 0.5 ug/ml of SPE-7 overnight. Cells are washed 3 times with Tyrode's buffer and incubated in the presence or absence of various concentrations of the testing compound for 20 min at 37° C., 5% $CO_2$. Cells are stimulated by adding 10 uL of DNP-BSA solution (150 ng/mL) to each well and incubating for 45 minutes at 37° C., 5% $CO_2$. Then, 45 µL of the supernatant is taken and incubated with 100 µL of 1 mM 4-Nitrophenyl N-acetyl-β-D-glucosaminide (Sigma, Cat. No. N9376), which is diluted in 0.05 M citrate buffer (pH 4.5), for 1.5 hr at 37° C. The reactions are quenched by adding 185 µL of 0.05 M sodium carbonate buffer (pH 10.0). Plates are read at 405 nm on Multiskan (MK 3).

$IC_{50}$ values of compounds 1,3, 12, 19, 21, 22, 30, 32, 35, 44, 70, 77, 82, 93, 96, 99, 102, 104, 105, 107, 109, 110, 111,114, 115, 116, 117, 123, 129, 130, 134, 136, 137, 139, 140, 141,142, 143, 146, 155, 156, 157, 159, 163, 165, 173, 177, 188, 196, 200, 205, 208, 213, 215, 216, 217, 218, 219, 221, 226, 229, 230, 231, 232, 233, 235, 236, 237, 239, 240, 247, 250, 251, 254, 255, 264, 265, 266, 267, 269, 272, 273, 274, 275, 276, 278, 279, 285, 286, 287, 289, 290, 291, 292, 294, 295, 296, 297, 298, 300, 301, 302, 304, 305, 306, 307, 308, 309, 310, 311, 312, 313, 314, 315, 316, 317, 318, 319, 320, 321, 323, 324, 332, 333, 340, 346, 347, 362, 368, 370, 371, 374, 376, 377, 380, 382, 383, 384, 385, 387, 388, 389, 390, 392, 393, 394, 395, 396, 397, 398, 399, 400, 402, 405, 407, 411,413, 414, 415, 416, 418, 419, 421, 423, 424, 425, 426, 427, 428, 429, 430, 432, 433, 435, 437, 438, 439, 442, 443, 444, 445, 446, 447, 448, 449, 450, 451, 455, 456, 460, 465, 466, 467, 469, 470, 473, 474, 476, 477, 479, 485, 486, 488, 489, 490, 497, 498, 499, 501, 504, 505, 511 are in the range of 0.001 to less than 0.1 uM.

$IC_{50}$ values of compounds 4, 9, 10, 13, 15, 17, 18, 23, 24, 25, 26, 28, 33, 37, 39, 40, 41,42, 45, 46, 47, 52, 54, 55, 60, 63, 67, 68, 69, 71, 73, 74, 75, 76, 78, 79, 80, 81,83, 84, 85, 86, 87, 88, 89, 91, 92, 94, 95, 97, 98, 100, 103, 106, 108, 112, 119, 120, 121, 122, 124, 127, 128, 135, 138, 144, 147, 148, 149, 150, 151, 158, 160, 161, 162, 164, 166, 167, 168, 170, 171,172, 174, 175, 176, 179, 180, 181, 184, 185, 186, 187, 194, 197, 199, 220, 222, 223, 225, 228, 234, 238, 241, 253, 259, 260, 261, 270, 280, 281, 293, 303, 322, 372, 373, 381, 386, 401, 403, 404, 406, 408, 409, 410, 412, 417, 420, 434, 440, 441, 458, 462, 463, 464, 468, 475, 487, 493, 494, 500, 502, 503, 506, 510, 512 are from 0.1 uM to less than 1 uM.

For the determination of IgE-induced LAT phosphorylation, Bone marrow mast cells (BMMCs) are isolated from the femur of female BALB/C mice (6-8 weeks old) and cultured in RPMI 1640 medium with 10% FBS, L-Glutamine (2 nM) and IL-3 (10 ng/ml) for 4 to 6 weeks. BMMCs are starved in RPMI 1640 with 10% FBS, L-Glutamine (2 nM) and without IL-3 overnight. Cells are sensitized with 1 µg/mL of SPE-7 (1×10⁷ cell/ml) for 4 hours. Cells are washed 3 times with Tyrode's buffer and seeded in 96-well plates (3×10⁵/well). Then the cells are incubated in the presence or absence of various concentrations of testing compound for 20 min at 37° C., 5% $CO_2$. The cells are stimulated by adding 10 uL of DNP-BSA solution (100 ng/mL) to each well and incubating for 5 minutes at 37° C., 5% $CO_2$. The plates are centrifuged and medium removed. Then 80 µL of 1× cell lysis buffer is added to each well in the plates, which are frozen at −80° C., overnight. 100 µl of 1 ug/ml anti-LAT polyclonal antibody (Abcam, diluted in PBS) is added to each well of new 96-well plates and incubated at RT overnight. After washing with 200 µL/well wash solution, the plates are blocked by adding 200 μL of PBS containing 1.0% BSA to each well and incubating at room temperature for 2 hrs. 50 μL of cell lysate diluted by 50 μL of sample diluents is added into the plates and incubated at room temperature for 2 hrs. After washing, anti-phosphotyrosine-HRP detection antibody (R&D, diluted in PBS with 0.1% BSA, 1:2000) is added and the plates are incubated at room temperature for 1 hr. After washing, 100 μL TMB is added to each well and the plates stand for 20 min in the dark. The reaction is stopped by adding 100 μL stop buffer. Plates are read at 450 nm and 570 nM on Multiskan (MK3).

$IC_{50}$ values of compounds 1, 3, 10, 12, 32, 35, 44, 70, 71, 77, 81, 82, 93, 94, 96, 99, 104, 105, 107, 116, 117, 134, 137, 140, 156, 159, 160, 161,163, 181,184, 185, 188, are from 0.1 uM to less than 1 uM.

What is claimed is:

1. A compound of formula (I):

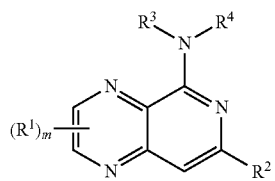

(I)

and/or a pharmaceutically acceptable salt thereof, wherein
$R^1$ is independently chosen from hydrogen and $C_1$-$C_6$ alkyl;
$R^2$ is aryl, or heteroaryl, which is optionally substituted by one or more groups (i) selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, or —$S(O)_nNR^5R^6$, or (ii) selected from $C_{1-6}$ alkyl, cycloalkyl, heterocycyl, heteroaryl, and aryl, wherein each of (ii) is optionally substituted with one or more groups selected from halo, hydroxy, —$C_1$-$C_4$ alkyl, —$C_1$-$C_4$ haloalkyl, —O—$C_1$-$C_4$ alkyl, —$C_1$-$C_4$ alkyl-OH, —$NH_2$, —$N(C_1$-$C_4$ alkyl)($C_1$-$C_4$ alkyl), —$NH(C_1$-$C_4$ alkyl), —$CON(C_1$-$C_4$ alkyl)($C_1$-$C_4$ alkyl), —$CONH(C_1$-$C_4$ alkyl), —$CONH_2$, —$N(C_1$-$C_4$ alkyl)$C(O)(C_1$-$C_4$ alkyl), —$C(O)$ $C_1$-$C_4$ alkyl, —$C(O)$ $C_1$-$C_4$ haloalkyl, —$SO_2(C_1$-$C_4$ alkyl), —$SO_2(C_1$-$C_4$ haloalkyl), —$SO_2NH_2$, —$SO_2NH(C_1$-$C_4$ alkyl), —$NHSO_2(C_1$-$C_4$ alkyl), and heterocyclyl optionally substituted by —$SO_2(C_1$-$C_4$ alkyl),
$R^3$ and $R^4$ are independently selected from hydrogen, alkyl, cycloalkyl, aryl, heteroaryl, and heterocyclyl, each of which, except for hydrogen, is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, $C_{1-6}$ alkyl, cycloalkyl, heterocyclyl, heteroaryl, aryl, alkenyl, and alkynyl, wherein the heterocyclyl is optionally substituted by one or more groups selected from —$C_1$-$C_4$ alkyl, —$C_1$-$C_4$ haloalkyl, —$C_1$-$C_4$ alkyl-OH, halo, hydroxy, —$CON(C_1$-$C_4$ alkyl)($C_1$-$C_4$ alkyl), —$CONH(C_1$-$C_4$ alkyl), —$CONH_2$, —$C(O)C_1$-$C_4$ alkyl, —$C(O)$ $C_1$-$C_4$ haloalkyl, —$SO_2(C_1$-$C_4$ alkyl), —$SO_2(C_1$-$C_4$ haloalkyl), —$SO_2NH_2$, and heteroaryl,
or $R^3$ and $R^4$, together with the N atom to which they are attached, can form a 4-12 membered monocyclic, fused bicyclic or spirocyclic ring optionally containing an additional 1-3 heteroatoms chosen from N and O, which is optionally substituted with one or more groups selected from halo, —$NR^5R^6$, —$OR^7$, —$S(O)_nR_8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, —$S(O)_nNR^5R^6$, $C_{1-6}$ alkyl, cycloalkyl, heterocyclyl, heteroaryl, aryl, alkenyl, and alkynyl, wherein the $C_{1-6}$ alkyl is optionally substituted by one or more groups selected from hydroxy, —$NH_2$, —$N(C_1$-$C_4$ alkyl)($C_1$-$C_4$ alkyl), —$NH(C_1$-$C_4$ alkyl), and —$NHSO_2(C_1$-$C_4$ alkyl),
m is 0, 1 or 2,
n is 1 or 2,
$R^5$, $R^6$, $R^7$, $R^8$, $R^9$, $R^{10}$, and $R^{11}$ are independently selected from hydrogen, alkyl, cycloalkyl, aryl, heteroaryl, and heterocyclyl, each of which, except for hydrogen, is optionally substituted with one or more groups selected from halo, hydroxy, $C_{1-6}$ alkyl, cycloalkyl, heterocyclyl, amino, and amide, wherein the amino is optionally substituted by one or two —$C_1$-$C_4$ alkyl,
or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxy, $C_1$-6 alkyl, cycloalkyl, heterocycyl, amino, and amide.

2. The compound of claim 1, and/or a pharmaceutically acceptable salt thereof, wherein
$R^1$ is independently chosen from hydrogen, and $C_1$-$C_6$ alkyl;
$R^2$ is $C_5$-$C_{10}$aryl or 5-10 membered heteroaryl, which is optionally substituted by one or more groups (i) selected from halo, —$NR^5R^6$, —$OR^7$, —$S(O)_nR^8$, —$C(O)R^9$, —CN, —$C(O)NR^5R^6$, —$NR^5C(O)R^9$, —$NR^5S(O)_nR^8$, —$NO_2$, or —$S(O)_nNR^5R^6$, or (ii) selected from $C_1$-$C_6$ alkyl, $C_3$-$C_8$ cycloalkyl, 3-8 membered heterocyclyl, 5-10 membered heteroaryl, or $C_5$-$C_{10}$ aryl, wherein each of (ii) is optionally substituted with one or more groups selected from halo, hydroxy, —$C_1$-$C_4$ alkyl, —$C_1$-$C_4$ haloalkyl, —O—$C_1$-$C_4$ alkyl, —$C_1$-$C_4$ alkyl-OH, —$NH_2$, —$N(C_1$-$C_4$ alkyl)($C_1$-$C_4$ alkyl), —$NH(C_1$-$C_4$ alkyl), $CON(C_1$-$C_4$ alkyl)($C_1$-$C_4$ alkyl), —$CONH(C_1$-$C_4$ alkyl), —$CONH_2$, —$N(C_1$-$C_4$ alkyl)$C(O)(C_1$-$C_4$ alkyl), —$C(O)$ $C_1$-$C_4$ alkyl, —$C(O)$—$C_1$-$C_4$ haloalkyl, —$SO_2(C_1$-$C_4$ alkyl), —$SO_2(C_1$-$C_4$ haloalkyl), —$SO_2NH_2$, —$SO_2NH(C_1$-$C_4$ alkyl), —$NHSO_2(C_1$-$C_4$ alkyl), and heterocyclyl optionally substituted by —$SO_2(C_1$-$C_4$ alkyl),
$R^3$ and $R^4$ are independently selected from hydrogen, $C_1$-$C_6$ alkyl, $C_3$-$C_8$ cycloalkyl, and 3-8 membered heterocyclyl, each of which, except for hydrogen, is optionally substituted with one or more groups selected from halo, —$NR^5R^6$, —$OR^7$, —$C(O)OR^7$, —CN, —$C(O)NR^5R^6$, —$S(O)_nNR^5R^6$, $C_1$-$C_6$ alkyl, $C_3$-$C_8$ cycloalkyl, 3-8 membered heterocyclyl, 5-10 membered heteroaryl, and $C_5$-$C_{10}$ aryl, wherein the 3-8 membered heterocyclyl is optionally substituted by one or more groups selected from —$C_1$-$C_4$ alkyl, —$C_1$-$C_4$ haloalkyl, —$C_1$-$C_4$ alkyl-OH, halo, -hydroxy, —$CON(C_1$-$C_4$ alkyl)($C_1$-$C_4$ alkyl), —$CONH(C_1$-$C_4$ alkyl), —$CONH_2$, —$C(O)C_1$-$C_4$ alkyl, —$C(O)C_1$-$C_4$ haloalkyl, —SO$_2$(C$_1$-C$_4$ alkyl), —SO$_2$(C$_1$-C$_4$ haloalkyl), —SO$_2$NH$_2$, and heteroaryl, or R$^3$ and R$^4$, together with the N atom to which they are attached, can form a 4-12 membered monocyclic, fused bicyclic or spirocyclic ring optionally containing an additional 1-3 heteroatoms chosen from N and O, which is optionally substituted with one or more groups selected from —NR$^5$R$^6$, —OR$^7$, —C(O)OR$^7$, —C(O)NR$^5$R$^6$, —NR$^5$S(O)$_n$NR$^{10}$R$^{11}$, —NR$^5$C(O)NR$^{10}$R$^{11}$, —S(O)$_n$NR$^5$R$^6$, C$_1$-C$_6$ alkyl, C$_3$-C$_8$ cycloalkyl, 3-8 membered heterocyclyl, 5-10 membered heteroaryl, and C$_5$-C$_{10}$ aryl, wherein the C$_{1-6}$ alkyl is optionally substituted by one or more groups selected from hydroxy, —NH$_2$, —N(C$_1$-C$_4$ alkyl)(C$_1$-C$_4$ alkyl), —NH(C$_1$-C$_4$ alkyl), and —NHSO$_2$(C$_1$-C$_4$ alkyl), m is 0 or 1, n is 2, R$^5$, R$^6$, R$^7$, R$^8$, R$^9$, R$^{10}$, and R$^{11}$ are independently selected from hydrogen, alkyl, cycloalkyl, aryl, heteroaryl, and heterocyclyl, each of which, except for hydrogen, is optionally substituted with one or more groups selected from halo, hydroxy, C$_{1-6}$ alkyl, cycloalkyl, heterocyclyl, amino, and amide, wherein the amino is optionally substituted by one or two —C$_1$-C$_4$ alkyl, or R$^5$ and R$^6$, R$^5$ and R$^7$, R$^5$ and R$^8$, R$^5$ and R$^9$, and R$^5$ and R$^{10}$ together with the atom(s) to which they are attached can form a ring.

3. The compound of claim 1, and/or a pharmaceutically acceptable salt thereof, wherein R$^1$ is independently chosen from hydrogen and methyl;

R$^2$ is independently selected from phenyl, pyridyl, pyrimidinyl, pyrazolyl, furyl, and indolyl, which is optionally substituted by one or more groups (i) selected from halo, —NR$^5$R$^6$, —OR$^7$, —S(O)$_n$R$^8$, —CN, —C(O)NR$^5$R$^6$, —NR$^5$S(O)$_n$R$^8$, or —S(O)$_n$NR$^5$R$^6$; or (ii) selected from methyl, ethyl, i-propyl, t-butyl, cyclopentyl, pyrrolidinyl, tetrahydrofuryl, piperidinyl, piperazinyl, morpholinyl, thiomorpholinyl, diazepanyl, oxazepanyl, pyrazolyl, imidazolinyl, and phenyl, wherein each of (ii) is optionally substituted by one or more groups selected from halo, hydroxy, —C$_1$-C$_4$ alkyl, —C$_1$-C$_4$ haloalkyl, —O—C$_1$-C$_4$ alkyl, —C$_1$-C$_4$ alkyl-OH, —NH$_2$, —N(C$_1$-C$_4$ alkyl)(C$_1$-C$_4$ alkyl), —NH(C$_1$-C$_4$ alkyl), CON(C$_1$-C$_4$ alkyl)(C$_1$-C$_4$ alkyl), —CONH(C$_1$-C$_4$ alkyl), —CONH$_2$, —N(C$_1$-C$_4$ alkyl)C(O)(C$_1$-C$_4$ alkyl), —C(O)—C$_1$-C$_4$ alkyl, —C(O)—C$_1$-C$_4$ haloalkyl, —SO$_2$(C$_1$-C$_4$ alkyl), —SO$_2$(C$_1$-C$_4$ haloalkyl), —SO$_2$NH$_2$, —SO$_2$NH(C$_1$-C$_4$ alkyl), —NHSO$_2$(C$_1$-C$_4$ alkyl), and heterocycyl optionally substituted by —SO$_2$(C$_1$-C$_4$ alkyl), R$^3$ and R$^4$ are independently selected from hydrogen, methyl, ethyl, n-propyl, i-propyl, n-butyl, i-butyl, t-butyl, cyclopropyl, cyclohexyl, phenyl, pyrrolidinyl, and pipericnyl, each of which, except for hydrogen, is optionally substituted with one or more groups (i) selected from halo, —NR$^5$R$^6$, —OR$^7$, —C(O)OR$^7$, —CN, —C(O)NR$^5$R$^6$, —S(O)$_n$NR$^5$R$^6$; or (ii) selected from cyclopropyl, pyrrolidinyl, tetrahydrofuryl, piperidinyl, piperazinyl, morpholinyl, thiomorpholinyl, diazepanyl, oxazepanyl, pyridyl, pyrazolyl, and imidazolinyl, each of said piperidinyl, morpholinyl, and thiomorpholinyl is optionally substituted by one or more groups selected from —C$_1$-C$_4$ alkyl, —C$_1$-C$_4$ haloalkyl, —C$_1$-C$_4$ alkyl-OH, halo, hydroxy, —CON(C$_1$-C$_4$ alkyl)(C$_1$-C$_4$ alkyl), —CONH(C$_1$-C$_4$ alkyl), —CONH$_2$, —C(O)C$_1$-C$_4$ alkyl, —C(O)C$_1$-C$_4$ haloalkyl, —SO$_2$(C$_1$-C$_4$ alkyl), —SO$_2$(C$_1$-C$_4$ haloalkyl), —SO$_2$NH$_2$, and heteroaryl, or R$^3$ and R$^4$, together with the N atom to which they are attached, can form a 4-12 membered monocyclic, fused bicyclic or spirocyclic ring optionally containing an additional 1-3 heteroatoms chosen from N and O, which is optionally substituted with one or more groups (i) selected from —NR$^5$R$^6$, —OR$^7$, —C(O)NR$^5$R$^6$, —NR$^5$S(O)$_n$NR$^{10}$R$^{11}$, —NRC(O)NR$^{10}$R$^{10}$, and —S(O)$_n$R$^5$R$^6$; or (ii) selected from methyl, ethyl, n-propyl, i-propyl, n-butyl, i-butyl, and t-butyl, wherein each of (ii) is optionally substituted by one or more groups selected from hydroxy, —NH$_2$, —N(C$_1$-C$_4$ alkyl)(C$_1$-C$_4$ alkyl), —NH(C$_1$-C$_4$ alkyl), and —NHSO$_2$(C$_1$-C$_4$ alkyl), m is 0 or 1, n is 2, R$^5$, R$^6$, R$^7$, R$^8$, R$^9$, R$^{10}$, and R$^{11}$ are independently selected from hydrogen, methyl, ethyl, n-propyl, i-propyl, n-butyl, i-butyl, t-butyl, pyrrolidinyl, tetrahydrofuryl, and piperidinyl, each of which, except for hydrogen, is optionally substituted with one or more groups selected from halo, methoxy, ethoxy, n-propoxy, i-propoxy, pyrrolidinyl, tetrahydrofuryl, piperidinyl, morpholinyl, amino, and amide, wherein amino is optionally substituted by one or two —C$_1$-C$_4$ alkyl, or R$^5$ an R$^6$, R$^5$ and R$^7$, R$^5$ and R$^8$, R$^5$ and R$^9$, and R$^5$ an R$^{10}$ together with the atom(s) to which they are attached can form a ring.

4. The compound of claim 1, and/or a pharmaceutically acceptable salt thereof, wherein R$^1$ is independently selected from hydrogen, methyl, ethyl, n-propyl, and i-propyl;

R$^2$ is independently selected from phenyl, naphthyl, pyridyl, pyrimidinyl, pyrazinyl, pyridazinyl, pyrazolyl, imidazolinyl, oxazolyl, and quinolinyl, which is optionally substituted by one or more groups selected from halo, —NR$^5$R$^6$, —OR$^7$, —S(O)$_n$R$^8$, —C(O)R$^9$, —C(O)OR$^7$, —CN, —C(O)NR$^5$R$^6$, —NR$^5$C(O)R$^9$, —NR$^5$S(O)$_n$R$^8$, —NR$^5$S(O)$_n$NR$^{10}$R$^{11}$, —NR$^5$C(O)OR$^7$, —NR$^5$C(O)NR$^{10}$R$^{11}$, —NO$_2$, and —S(O)$_n$R$^5$R$^6$;

R$^3$ and R$^4$ are independently selected from hydrogen, methyl, ethyl, n-propyl, i-propyl, n-butyl, i-butyl, t-butyl, cyclopropyl, cyclobutyl, cyclopentyl, cyclopentenyl, cyclohexyl, cyclohexenyl, phenyl, naphthyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, pyrrolidinyl, tetrahydrofuryl, piperidinyl, piperazinyl, morpholinyl, homomorpholinyl, thiomorpholinyl, diazepanyl, and oxazepanyl, each of which, except for hydrogen, is optionally substituted with one or more groups selected from halo, —NR$^5$R$^6$, —OR$^7$, —S(O)$_n$R$^8$, —C(O)R$^9$, —C(O)OR$^7$, —CN, —C(O)NR$^5$R$^6$, —NR$^5$C(O)R$^9$, —NR$^5$S(O)$_n$R$^8$, —NR$^5$S(O)$_n$NR$^{10}$R$^{11}$, —NR$^5$C(O)OR$^7$, —NR$^5$C(O)NR$^{10}$R$^{11}$, —NO$_2$, and —S(O)$_n$R$^5$R$^6$;

or R$^3$ and R$^4$, together with the N atom to which they are attached, form a 4-12 membered monocyclic, fused bicyclic or spirocyclic ring optionally containing an additional 1-3 heteroatoms chosen from N and O, which is optionally substituted with one or more groups selected from (i) halo, —NR$^5$R$^6$, —OR$^7$, —S(O)$_n$R$^8$, —C(O)R$^9$, —C(O)OR$^7$, —CN, —C(O)NR$^5$R$^6$, —NR$^5$C(O)R$^9$, —NR$^5$S(O)$_n$R$^8$, —NR$^5$S(O)$_n$NR$^{10}$R$^{11}$, —NR$^5$C(O)OR$^7$, —NR$^5$C(O)NR$^{10}$R$^{11}$, —NO$_2$, and —S(O)$_n$R$^5$R$^6$; or (ii) selected from methyl, ethyl, n-propyl, i-propyl, n-butyl, i-butyl, t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, naphthyl, and $C_2$-$C_6$ alkynyl;

m is 0, 1 or 2;

n is 1 or 2;

$R^5$, $R^6$, $R^7$, $R^8$, $R^9$, $R^{10}$, and $R^{11}$ are independently selected from hydrogen, methyl, ethyl, n-propyl, i-propyl, n-butyl, i-butyl, t-butyl, cyclopropyl, cyclobutyl, cyclopentyl, cyclopentenyl, cyclohexyl, cyclohexenyl, phenyl, naphthyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, pyrrolidinyl, tetrahydrofuryl, piperidinyl, piperazinyl, morpholinyl, homomorpholinyl, thiomorpholinyl, diazepanyl, and oxazepanyl;

or $R^5$ and $R^6$, $R^5$ and $R^7$, $R^5$ and $R^8$, $R^5$ and $R^9$, and $R^5$ and $R^{10}$ together with the atom(s) to which they are attached form a ring, which is optionally substituted with one or more groups selected from (i) halo and hydroxy; or (ii) selected from methyl, ethyl, n-propyl, i-propyl, n-butyl, i-butyl, t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, amino, and amide.

5. The compound of claim 1, and/or a pharmaceutically acceptable salt thereof, wherein $R^1$ is independently chosen from hydrogen, methyl, ethyl, n-propyl, or i-propyl.

6. The compound of claim 1, and/or a pharmaceutically acceptable salt thereof, wherein $R^1$ is hydrogen.

7. The compound of claim 1, and/or a pharmaceutically acceptable salt thereof, wherein $R^2$ is $C_5$-$C_{10}$aryl, or 5-10 membered heteroaryl, which is optionally substituted by one or more groups (i) selected from halo, $-NR^5R^6$, $-OR^7$, $-S(O)_nR^8$, $-C(O)R^9$, $-C(O)OR^7$, $-CN$, $-C(O)NR^5R^6$, $-NR^5C(O)R^9$, $-NR^5S(O)_nR^8$, $-NR^5C(O)R^9$, $-NR^5S(O)_nNR^{10}R^{11}$, $-NR^5C(O)OR^7$, $-NR^5C(O)NR^{10}R^{11}$, $-NO_2$, or $-S(O)_nNR^5R^6$, or (ii) selected from $C_1$-$C_6$ alkyl, $C_3$-$C_8$ cycloalkyl, 3-8 membered heterocyclyl, 5-10 membered heteroaryl, and $C_5$-$C_{10}$ aryl, wherein each of (ii) is optionally substituted with one or more groups selected from halo, hydroxy, $-C_1$-$C_4$ alkyl, $-C_1$-$C_4$ haloalkyl, $-O-C_1$-$C_4$ alkyl, $-C_1$-$C_4$ alkyl-OH, $-NH_2$, $-N(C_1$-$C_4$ alkyl)($C_1$-$C_4$ alkyl), $-NH(C_1$-$C_4$ alkyl), $-CON(C_1$-$C_4$ alkyl)($C_1$-$C_4$ alkyl), $-CONH(C_1$-$C_4$ alkyl), $-CONH_2$, $-N(C_1$-$C_4$ alkyl)C(O)($C_1$-$C_4$ alkyl), $-C(O)$ $C_1$-$C_4$ alkyl, $-C(O)C_1$-$C_4$ haloalkyl, $-SO_2$($C_1$-$C_4$ alkyl), $-SO_2(C_1$-$C_4$ haloalkyl), $-SO_2NH_2$, $SO_2NH$($C_1$-$C_4$ alkyl), $-NHSO_2(C_1$-$C_4$ alkyl), and heterocyclyl optionally substituted by $-SO_2(C_1$-$C_4$ alkyl), $R^5$, $R^6$, $R^7$, $R^8$, $R^9$, $R^{10}$, and $R^{11}$ are independently selected from hydrogen, alkyl, cycloalkyl, aryl, heteroaryl, and heterocyclyl, each of which, except for hydrogen, is optionally substituted with one or more groups selected from halo, hydroxy, $C_{1-6}$ alkyl, cycloalkyl, amino, and amide, wherein the amino is optionally substituted by one or two $-C_1$-$C_4$ alkyl, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxy, $C_{1-6}$ alkyl, cycloalkyl, amino, and amide.

8. The compound of claim 1, and/or a pharmaceutically acceptable salt thereof, wherein $R^2$ is independently selected from phenyl-naphtyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, or quinolinyl, which is optionally substituted by one or more groups (i) selected from halo, $-NR^5R^6$, $-OR^7$, $-S(O)_nR^8$, $-C(O)R^9$, $-C(O)OR^7$, $-CN$, $-C(O)NR^5R^6$, $-NR^5C(O)R^9$, $-NR^5S(O)_nR^8$, $-NR^5S(O)_nNR^{10}R^{11}$, $-NR^5C(O)OR^7$, $-NR^5C(O)NR^{10}R^{11}$, $-NO_2$, or $-S(O)_nNR^5R^6$; or (ii) selected from methyl, ethyl, n-propyl, i-propyl, n-butyl, i-butyl, and t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, or naphthyl, wherein each of (ii) is optionally substituted with one or more groups selected from halo, hydroxy, $-C_1$-$C_4$ alkyl, $-C_1$-$C_4$ haloalkyl, $-O-C_1$-$C_4$ alkyl, $-C_1$-$C_4$ alkyl-OH, $-NH_2$, $-N(C_1$-$C_4$ alkyl)($C_1$-$C_4$ alkyl), $-NH(C_1$-$C_4$ alkyl), $CON(C_1$-$C_4$ alkyl)($C_1$-$C_4$ alkyl), $-CONH(C_1$-$C_4$ alkyl), $-CONH_2$, $-N(C_1$-$C_4$ alkyl)C(O)($C_1$-$C_4$ alkyl), $-C(O)-$ $C_1$-$C_4$ alkyl, $-C(O)-C_1$-$C_4$ haloalkyl, $-SO_2(C_1$-$C_4$ alkyl), $-SO_2(C_1$-$C_4$ haloalkyl), $-SO_2NH_2$, $-SO_2NH(C_1$-$C_4$ alkyl), $-NHSO_2(C_1$-$C_4$ alkyl), and heterocyclyl optionally substituted by $-SO_2(C_1$-$C_4$ alkyl), $R^5$, $R^6$, $R^7$, $R^8$, $R^9$, $R^{10}$, and $R^{11}$ are independently selected from hydrogen alkyl, cycloalkyl, aryl, heteroaryl, and heterocyclyl, each of which, except for hydrogen, is optionally substituted with one or more groups selected from halo, hydroxy, $C_{1-6}$ alkyl, cycloalkyl, amino, and amide, wherein the amino is optionally substituted by one or two $-C_1$-$C_4$ alkyl, or $R^5$ and $R^6$, $R^5$ and $R^7$, $R^5$ and $R^8$, $R^5$ and $R^9$, and $R^5$ and $R^{10}$ together with the atom(s) to which they are attached can form a ring, which is optionally substituted with one or more groups selected from halo, hydroxy, $C_{1-6}$ alkyl, cycloalkyl, amino, or and amide.

9. The compound of claim 1, and/or a pharmaceutically acceptable salt thereof, wherein $R^2$ is independently selected from

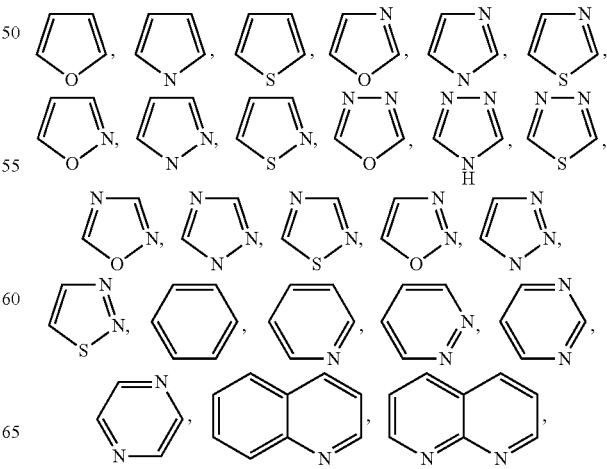

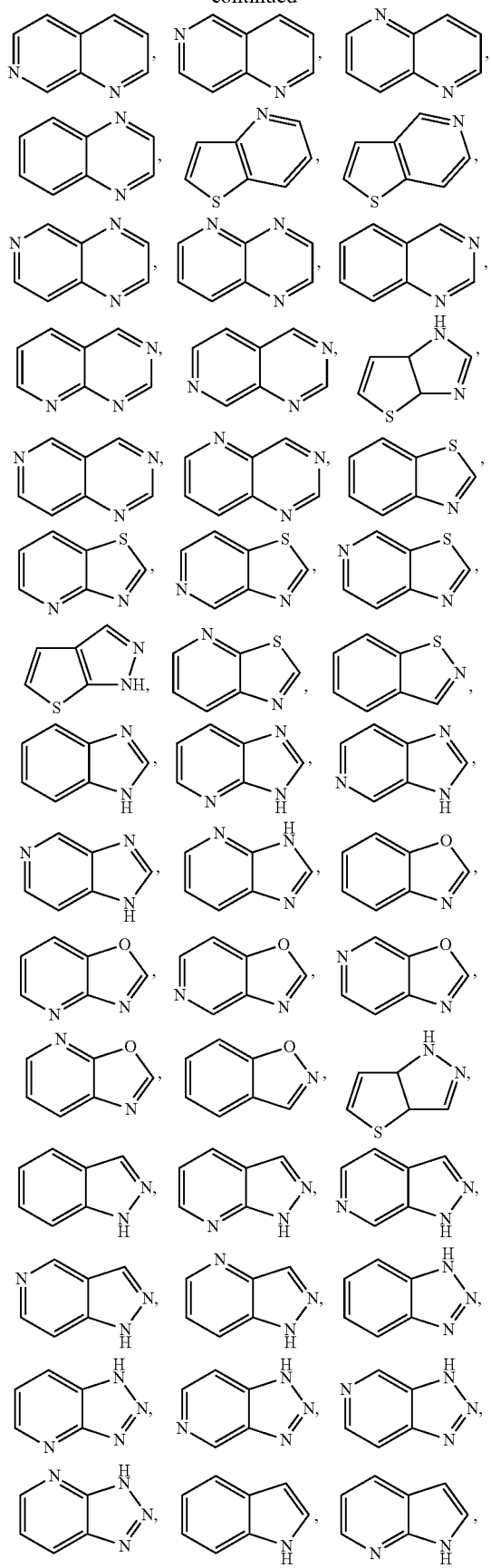
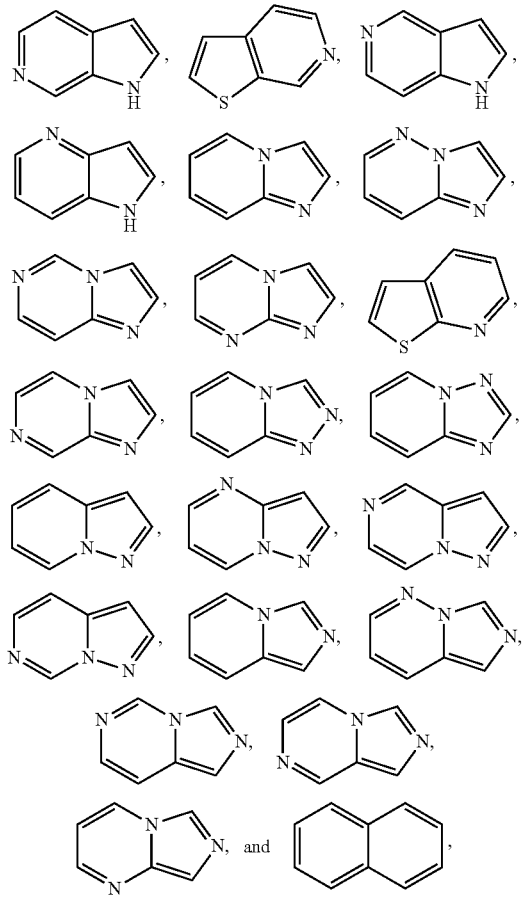

each of which is optionally substituted by one or more groups (i) selected from halo, —NR$^5$R$^6$, —OR$^7$, —S(O)$_n$R$^8$, —C(O)R$^9$, —C(O)OR$^7$, —CN, —C(O)NR$^5$R$^6$, —NR$^5$C(O)R$^9$, —NR$^5$S(O)$_n$R$^8$, —NR$^5$S(O)$_n$NR$^{10}$R$^{11}$, —NR$^5$C(O)OR$^7$, —NR$^5$C(O)NR$^{10}$R$^{11}$, —NO$_2$, or —S(O)$_n$NR$^5$R$^6$, or (ii) selected from C$_{1-6}$ alkyl, cycloalkyl, heterocyclyl, heteroaryl, and aryl, wherein each of (ii) is optionally substituted with one or more groups selected from halo, hydroxy, —C$_1$-C$_4$ alkyl, —C$_1$-C$_4$ haloalkyl, —O—C$_1$-C$_4$ alkyl, —C$_1$-C$_4$ alkyl-OH, —NH$_2$, —N(C$_1$-C$_4$ alkyl)(C$_1$-C$_4$ alkyl), —NH(C$_1$-C$_4$ alkyl), —CON(C$_1$-C$_4$ alkyl)(C$_1$-C$_4$ alkyl), —CONH(C$_1$-C$_4$ alkyl), —CONH$_2$, —N(C$_1$-C$_4$ alkyl)C(O)(C$_1$-C$_4$ alkyl), —C(O)—C$_1$-C$_4$ alkyl, —C(O)—C$_1$-C$_4$ haloalkyl, —SO$_2$(C$_1$-C$_4$ alkyl), —SO$_2$(C$_1$-C$_4$ haloalkyl), —SO$_2$NH$_2$, —SO$_2$NH(C$_1$-C$_4$ alkyl), —NHSO$_2$(C$_1$-C$_4$ alkyl), and heterocyclyl optionally substituted by —SO$_2$(C$_1$-C$_4$ alkyl), R$^5$, R$^6$, R$^7$, R$^8$, R$^9$, R$^{10}$, and R$^{11}$ are independently selected from hydrogen, alkyl, cycloalkyl, aryl, heteroaryl, and heterocyclyl, each of which, except for hydrogen, is optionally substituted with one or more groups selected from halo, hydroxy, C$_{1-6}$ alkyl, cycloalkyl, amino, and amide, wherein the amino is optionally substituted by one or two —C$_1$-C$_4$ alkyl, or R$^5$ and R$^6$, R$^5$ and R$^7$, R$^5$ and R$^8$, R$^5$ and R$^9$, and R$^5$ and R$^{10}$ together with the atom(s) to which they are attached can form a ring, which is optionally substituted with one or more groups selected from halo, hydroxy, C$_{1-6}$ alkyl, cycloalkyl, amino, and amide.

10. The compound of claim 1, and/or a pharmaceutically acceptable salt thereof, wherein $R^2$ is

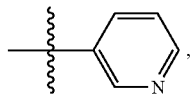

which is optionally substituted by one or more groups (i) selected from halo, $-NR^5R^6$, $-OR^7$, $-S(O)_nR^8$, $-CN$, $-C(O)NR^5R^6$, $-NR^5S(O)_nR^8$, or $-S(O)_nNR^5R^6$, or (ii) selected from $C_{1-6}$ alkyl, cycloalkyl, heterocyclyl, heteroaryl, aryl, wherein each of (ii) is optionally substituted with one or more groups selected from halo, hydroxy, $-C_1$-$C_4$ alkyl, $-C_1$-$C_4$ haloalkyl, $-O-C_1$-$C_4$ alkyl, $-NH_2$, $-C(O)-C_1$-$C_4$ alkyl, $-C(O)-C_1$-$C_4$ haloalkyl, $-SO_2(C_1$-$C_4$ alkyl), and $-SO_2(C_1$-$C_4$ haloalkyl), $R^5$, $R^6$, $R^7$, and $R^8$ are independently selected from hydrogen, alkyl, cycloalkyl, aryl, heteroaryl, and heterocyclyl, each of which, except for hydrogen, is optionally substituted with one or more groups selected from halo, hydroxy, $C_{1-6}$ alkyl, cycloalkyl, amino, and amide, or $R^5$ and $R^6$, $R^5$ and $R^7$, and $R^5$ and $R^8$ together with the atom(s) to which they are attached can form a ring.

11. The compound of claim 1, and/or a pharmaceutically acceptable salt thereof, wherein $R^2$ is

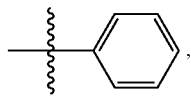

which is optionally substituted by one or more groups (i) selected from halo, $-NR^5R^6$, $-OR^7$, $-S(O)_nR^8$, $-C(O)R^9$, $-CN$, $-C(O)NR^5R^6$, $-NR^5C(O)R^9$, $-NR^5S(O)_nR^8$, $-NO_2$, or $-S(O)_nNR^5R^6$, or (ii) selected from $C_{1-6}$ alkyl, cycloalkyl, heterocyclyl, heteroaryl, and aryl, wherein each of (ii) is optionally substituted with one or more groups selected from halo, hydroxy, $-C_1$-$C_4$ alkyl, $-C_1$-$C_4$ haloalkyl, $-O-C_1$-$C_4$ alkyl, $-C_1$-$C_4$ alkyl-OH, $-NH_2$, $-N(C_1$-$C_4$ alkyl)($C_1$-$C_4$ alkyl), $-NH(C_1$-$C_4$ alkyl), $CON(C_1$-$C_4$ alkyl)($C_1$-$C_4$ alkyl), $-CONH(C_1$-$C_4$ alkyl), $-CONH_2$, $-N(C_1$-$C_4$ alkyl)$C(O)(C_1$-$C_4$ alkyl), $-C(O)C_1$-$C_4$ alkyl, $-C(O)C_1$-$C_4$ haloalkyl, $-SO_2(C_1$-$C_4$ alkyl), $-SO_2(C_1$-$C_4$ haloalkyl), $-SO_2NH_2$, $-SO_2NH(C_1$-$C_4$ alkyl), $-NHSO_2(C_1$-$C_4$ alkyl), and heterocyclyl optionally substituted by $-SO_2(C_1$-$C_4$ alkyl), $R^5$, $R^6$, $R^7$, $R^8$, and $R^9$, are independently selected from hydrogen, alkyl, cycloalkyl, aryl, heteroaryl, and heterocyclyl, each of which, except for hydrogen, is optionally substituted with one or more groups selected from halo, hydroxy, $C_{1-6}$ alkyl, cycloalkyl, amino, and amide, wherein the amino is optionally substituted by one or two $-C_1$-$C_4$ alkyl, or $R^5$ and $R^6$, $R^5$ and $R^7$, $R^5$ and $R^8$, and $R^5$ and $R^9$ together with the atom(s) to which they are attached can form a ring, which is optionally substituted with one or more groups selected from halo, hydroxy, $C_{1-6}$ alkyl, cycloalkyl, amino, and amide.

12. The compound of claim 1, and/or a pharmaceutically acceptable salt thereof, wherein $R^2$ is independently selected from phenyl, naphthyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, and quinolinyl, which is optionally substituted by one or more groups selected from halo, $-NR^5R^6$, $-OR^7$, $-S(O)_nR^8$, $-C(O)R^9$, $-C(O)OR^7$, $-CN$, $-C(O)NR^5R^6$, $-NR^5C(O)R^9$, $-NR^5S(O)_nR^8$, $-NR^5S(O)_nNR^{10}R^{11}$, $-NR^5C(O)OR^7$, $-NR^5C(O)NR^{10}R^{11}$, $-NO_2$, and $-S(O)_nR^5R^6$.

13. The compound of claim 1, and/or a pharmaceutically acceptable salt thereof, wherein $R^2$ is independently selected from

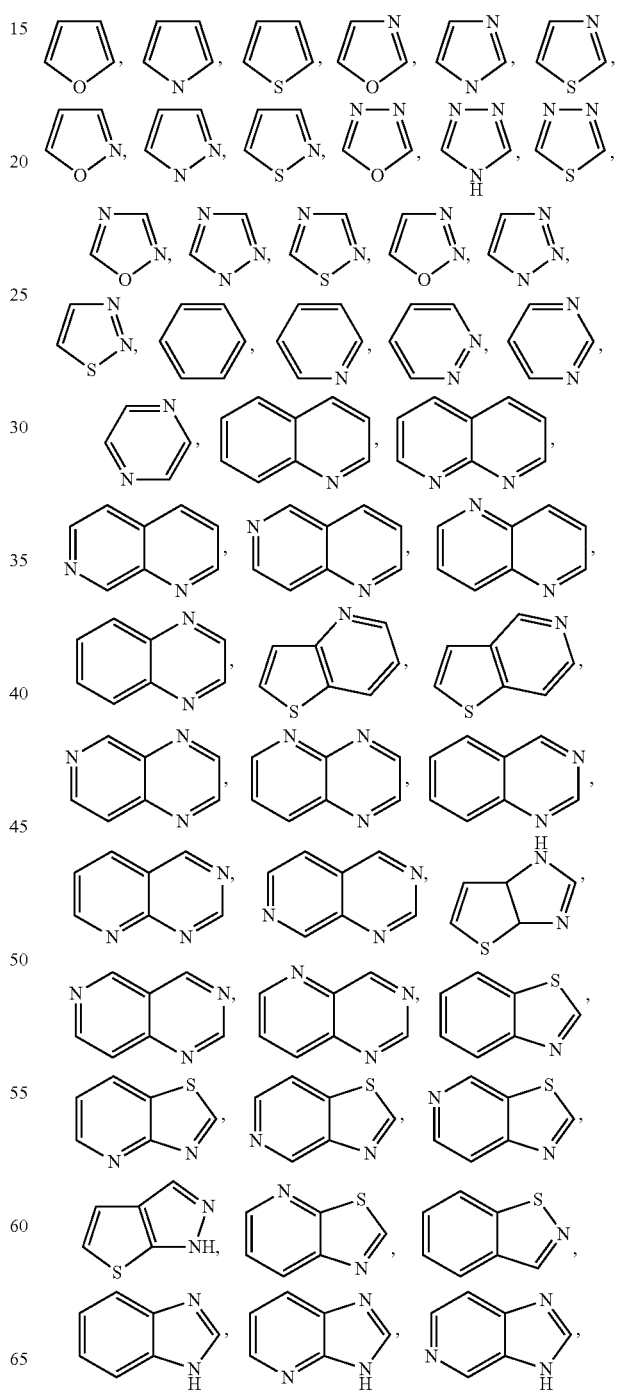

-continued

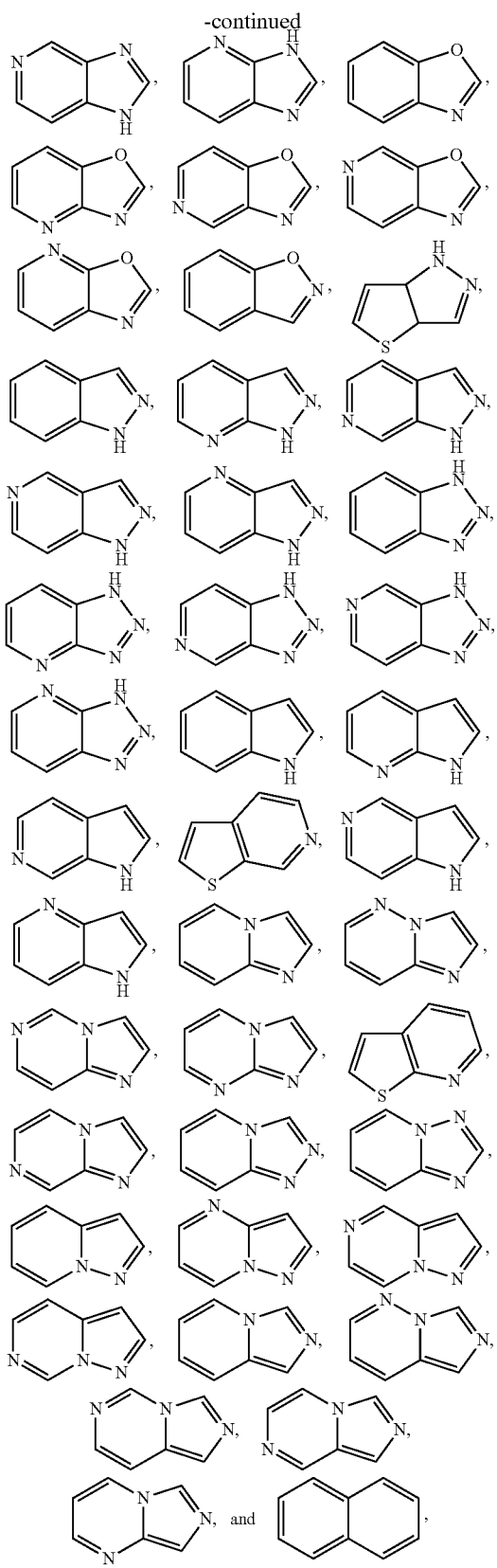

which is optionally substituted by one or more groups selected from halo, —NR⁵R⁶, —OR⁷, —S(O)ₙR⁸, —C(O)R⁹, —C(O)OR⁷, —CN, —C(O)NR⁵R⁶, —NR⁵C(O)R⁹, —NR⁵S(O)ₙR⁸, —NR⁵S(O)ₙNR¹⁰R¹¹, —NR⁵C(O)OR⁷, —NR⁵C(O)NR¹⁰R¹¹, —NO₂, and —S(O)ₙR⁵R⁶.

14. The compound of claim 1, and/or a pharmaceutically acceptable salt thereof, wherein R² is

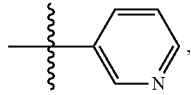 [SMILES: *c1cccnc1]

which is optionally substituted by one or more groups selected from halo, —NR⁵R⁶, —OR⁷, —S(O)ₙR⁸, —C(O)R⁹, —C(O)OR⁷, —CN, —C(O)NR⁵R⁶, —NR⁵C(O)R⁹, —NR⁵S(O)ₙR⁸, —NR⁵S(O)ₙNR¹⁰R¹¹, —NRC(O)OR⁷, —NR⁵C(O)NR¹⁰R¹¹, —NO₂, and —S(O)ₙR⁵R⁶.

15. The compound of claim 1, and/or a pharmaceutically acceptable salt thereof, wherein R² is

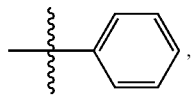

which is optionally substituted by one or more groups selected from halo, —NR⁵R⁶, —OR⁷, —S(O)ₙR⁸, —C(O)R⁹, —C(O)OR⁷, —CN, —C(O)NR₅R⁶, —NR⁵C(O)R⁹, —NR⁵S(O)ₙR⁸, —NR⁵S(O)ₙNR¹⁰R¹¹, —NR⁵C(O)OR⁷, —NR⁵C(O)NR¹⁰R¹¹, —NO₂, and —S(O)ₙR⁵R⁶.

16. The compound of claim 1, and/or a pharmaceutically acceptable salt thereof, wherein R³ and R⁴ are independently selected from hydrogen, $C_1$-$C_6$ alkyl, $C_3$-$C_8$ cycloalkyl, $C_5$-$C_{10}$aryl, 5-10 membered heteroaryl, and 3-8 membered heterocyclyl, each of which, except for hydrogen, is optionally substituted with one or more groups selected from halo, —NR⁵R⁶, —OR⁷, —C(O)OR⁷, —CN, —C(O)NR⁵R⁶, or —S(O)ₙNR⁵R⁶, $C_1$-$C_6$ alkyl, $C_3$-$C_8$ cycloalkyl, 3-8 membered heterocyclyl, 5-10 membered heteroaryl, and $C_5$-$C_{10}$aryl, wherein the 3-8 membered heterocyclyl is optionally substituted by one or more groups selected from —$C_1$-$C_4$ alkyl, —$C_1$-$C_4$ haloalkyl, —$C_1$-$C_4$ alkyl-OH, halo, hydroxy, oxo, —CON($C_1$-$C_4$ alkyl)($C_1$-$C_4$ alkyl), —CONH ($C_1$-$C_4$ alkyl), —CONH₂, —C(O)$C_1$-$C_4$ alkyl, —C(O)$C_1$-$C_4$ haloalkyl, —SO₂($C_1$-$C_4$ alkyl), —SO₂($C_1$-$C_4$ haloalkyl), —SO₂NH₂, and heteroaryl, or R³ and R⁴, together with the N atom to which they are attached, can form a 4-12 membered monocyclic, fused bicyclic or spirocyclic ring optionally containing an additional 1-3 heteroatoms chosen from N and O, which is optionally substituted with one or more groups selected from —NR⁵R⁶, —OR⁷, —C(O)OR⁷, —CN, —C(O)NR⁵R⁶, —NR⁵S(O)ₙNR¹⁰R¹¹, —NR⁵C(O) NR¹⁰R¹¹, —S(O)ₙNR⁵R⁶, $C_1$-$C_6$ alkyl, $C_3$-$C_8$ cycloalkyl, 3-8 membered heterocyclyl, 5-10 membered heteroaryl, and $C_5$-$C_{10}$ aryl, wherein the $C_1$-$C_6$ alkyl is optionally substituted by one or more groups selected from hydroxy, —NH₂, —N($C_1$-$C_4$ alkyl)($C_1$-$C_4$ alkyl), —NH($C_1$-$C_4$ alkyl), and —NHSO₂($C_1$-$C_4$ alkyl), R⁵, R⁶, R⁷, R¹⁰, and R¹¹ are independently selected from hydrogen, alkyl, and heterocyclyl, each of which, except for hydrogen, is optionally substituted with one or more groups selected from halo, hydroxy, $C_{1-6}$ alkyl, cycloalkyl, amino, and amide, or $R^5$ and $R^6$, $R^5$ and $R^7$, and $R^5$ and $R^{10}$ together with the atom(s) to which they are attached can form a ring.

17. The compound of claim 1, and/or a pharmaceutically acceptable salt thereof, wherein $R^3$ and $R^4$ are independently selected from hydrogen, methyl, ethyl, n-propyl, i-propyl, n-butyl, i-butyl, t-butyl, cyclopropyl, cyclobutyl, cyclopentyl, cyclopentenyl, cyclohexyl, cyclohexenyl, phenyl, naphthyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, pyrrolidinyl, tetrahydrofuryl, piperidinyl, piperazinyl, morpholinyl, homomorpholinyl, thiomorpholinyl, diazepanyl, and oxazepanyl, each of which, except for hydrogen, is optionally substituted with one or more groups (i) selected from halo, —$NR^5R^6$, —$OR^7$, —$C(O)OR^7$, —CN, —$C(O)NR^5R^6$, and —$S(O)_nNR^5R^6$; or (ii) selected from methyl, ethyl, n-propyl, i-propyl, n-butyl, i-butyl, t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, and naphthyl, or $R^3$ and $R^4$, together with the N atom to which they are attached, can form a 4-12 membered monocyclic, fused bicyclic or spirocyclic ring optionally containing an additional 1-3 heteroatoms chosen from N and O, which is optionally substituted with one or more groups (i) selected from halo, —$NR^5R^6$, —$OR^7$, —$C(O)OR^7$, —$C(O)NR^5R^6$, —$NR^5S(O)_nNR^{10}R^{11}$, —$NR^5C(O)NR^{10}R^{11}$, or —$S(O)_nNR^5R^6$; or (ii) selected from methyl, ethyl, n-propyl, i-propyl, n-butyl, i-butyl, t-butyl, cyclopropyl, cyclobutyl, cyclopentyl, cyclopentenyl, cyclohexyl, cyclohexenyl, pyrrolidinyl, tetrahydrofuryl, piperidinyl, piperazinyl, morpholinyl, homomorpholinyl, thiomorpholinyl, diazepanyl, oxazepanyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, phenyl, and naphthyl, $R^5$, $R^6$, $R^7$, $R^{10}$, and $R^{11}$ are independently selected from hydrogen, alkyl, and heterocyclyl, each of which, except for hydrogen, is optionally substituted with one or more groups selected from halo, hydroxy, $C_{1-6}$ alkyl, cycloalkyl, amino, and amide, or $R^5$ and $R^6$, $R^5$ and $R^7$, and $R^5$ and $R^{10}$ together with the atom(s) to which they are attached can form a ring.

18. The compound of claim 1, and/or a pharmaceutically acceptable salt thereof, wherein $R^3$ and $R^4$ are independently selected from hydrogen, alkyl, cycloalkyl, and heterocyclyl, each of which, except for hydrogen, is optionally substituted with one or more groups selected from halo, —$NR^5R^6$, —$OR^7$, —$C(O)OR^7$, —CN, —$C(O)NR^5R^6$, —$S(O)_nNR^5R^6$, $C_{1-6}$ alkyl, cycloalkyl, heterocyclyl, heteroaryl, and aryl, wherein the 3-8 membered heterocyclyl is optionally substituted by one or more groups selected from $C_1$-$C_4$ alkyl, $C_1$-$C_4$ haloalkyl, —$C_1$-$C_4$ alkyl-OH, halo, hydroxy, oxo, —$CON(C_1$-$C_4$ alkyl)($C_1$-$C_4$ alkyl), $CONH(C_1$-$C_4$ alkyl), —$CONH_2$, —$C(O)C_1$-$C_4$ alkyl, —$C(O)C_1$-$C_4$ haloalkyl, —$SO_2(C_1$-$C_4$ alkyl), —$SO_2(C_1$-$C_4$ haloalkyl), —$SO_2NH_2$, and heteroaryl, $R^5$, $R^6$, and $R^7$ are independently selected from hydrogen, alkyl, and heterocyclyl, each of which except for hydrogen, is optionally substituted with one or more group selected from halo, hydroxy, $C_{1-6}$ alkyl, cycloalkyl, amino, and amide, or $R^5$ and $R^6$, $R^5$ and $R^7$, and $R^5$ and $R^{10}$ together with the atom(s) to which they are attached can form a ring.

19. The compound of claim 1, and/or a pharmaceutically acceptable salt thereof, wherein $R^3$ and $R^4$, together with the N atom to which they are attached form a 4-7 membered monocyclic ring optionally containing an additional 1-3 heteroatoms chosen from N and O, which is optionally substituted with one or more groups selected from —$NR^5R^6$, —$OR^7$, —$C(O)OR^7$, —$C(O)NR^5R^6$, —$NR^5S(O)_n NR^{10}R^{11}$, —$NR^5C(O)NR^{10}R^{11}$, —$S(O)_nNR^5R^6$, $C_{1-6}$ alkyl, cycloalkyl, heterocyclyl, heteroaryl, and aryl, wherein the $C_{1-6}$ alkyl is optionally substituted by one or more groups selected from hydroxy, —$NH_2$, —$N(C_1$-$C_4$ alkyl)($C_1$-$C_4$ alkyl), —$NH(C_1$-$C_4$ alkyl), and —$NHSO_2(C_1$-$C_4$ alkyl), $R^5$, $R^6$, $R^7$, $R^{10}$, and $R^{11}$ are independently selected from hydrogen, alkyl, and heterocyclyl, each of which, except for hydrogen, is optionally substituted with one or more groups selected from halo, hydroxy, $C_{1-6}$ alkyl, cycloalkyl, amino, and amide, or $R^5$ and $R^6$, $R^5$ and $R^7$, $R^5$ and $R^8$, $R^5$ and $R^9$, and $R^5$ and $R^{10}$ together with the atom(s) to which they are attached can form a ring.

20. The compound of claim 1, and/or a pharmaceutically acceptable salt thereof, wherein $R^3$ and $R^4$ are independently selected from hydrogen, methyl, ethyl, n-propyl, i-propyl, n-butyl, i-butyl, t-butyl, cyclopropyl, cyclobutyl, cyclopentyl, cyclopentenyl, cyclohexyl, cyclohexenyl, phenyl, naphthyl, pyridyl, pyrimidinyl, pyrazinyl, pyridazinyl, pyrazolyl, imidazolinyl, oxazolyl, isoxazolyl, thiazolyl, thienyl, furyl, benzofuryl, benzothienyl, benzoimidazolinyl, indolyl, quinolinyl, pyrrolidinyl, tetrahydrofuryl, piperidinyl, piperazinyl, morpholinyl, homomorpholinyl, thiomorpholinyl, diazepanyl, and oxazepanyl, each of which, except for hydrogen, is optionally substituted with one or more groups selected from halo, —$NR^5R^6$, —$OR^7$, —$S(O)_nR^8$, —$C(O)R^9$, —$C(O)OR^7$, —CN, —$C(O)NR^5R^6$, —$NR^5C(O)R^9$, —$NR^5S(O)_nR^8$, —$NR^5S(O)_nNR^{10}R^{11}$, —$NR^5C(O)OR^7$, —$NR^5C(O)NR^{10}R^{11}$, —$NO_2$, and —$S(O)_nR^5R^6$.

21. The compound of claim 1, and/or a pharmaceutically acceptable salt thereof, wherein $R^4$ is hydrogen and $R^3$ is $C_{1-6}$alkyl, which is optionally substituted with one or more groups selected from alkyl, cycloalkyl, heterocyclyl and heteroaryl, wherein heterocyclyl is optionally substituted by one or more groups chosen from $C_1$-$C_4$ alkyl, $C_1$-$C_4$ haloalkyl, —$C_1$-$C_4$ alkyl-OH, halo, hydroxy, oxo, —$CON(C_1$-$C_4$ alkyl)($C_1$-$C_4$ alkyl), —$CONH(C_1$-$C_4$ alkyl), —$CONH_2$, —$C(O)C_1$-$C_4$ alkyl, —$C(O)C_1$-$C_4$ haloalkyl, —$SO_2(C_1$-$C_4$ alkyl), —$SO_2(C_1$-$C_4$ haloalkyl), —$SO_2NH_2$, and heteroaryl.

22. The compound of claim 1, and/or a pharmaceutically acceptable salt thereof, wherein $R^3$ and $R^4$, together with the N atom to which they are attached can form a 7-12 membered fused bicyclic ring optionally containing an additional 1-3 heteroatoms chosen from N and O.

23. The compound of claim 1, and/or a pharmaceutically acceptable salt thereof, wherein $R^3$ and $R^4$, together with the N atom to which they are attached can form a 7-12 membered spirocyclic ring optionally containing an additional 1-3 heteroatoms chosen from N and O.

24. The compound of claim 1, and/or a pharmaceutically acceptable salt thereof, wherein m is 1.

25. A pharmaceutical composition comprising at least one compound of claim 1, and/or a pharmaceutically acceptable salt thereof and at least one pharmaceutically acceptable carrier.

26. A method for inhibiting a spleen tyrosine kinase in a system or a subject, comprising administering to a system or a subject in need thereof a therapeutically effective amount of a compound of claim 1.

27. The method of claim 26, wherein the subject suffers from a disease chosen from the group consisting of allergic asthma, allergic rhinitis, rheumatoid arthritis, multiple sclerosis, lupus, systemic lupus erythematosus, lymphoma, B cell lymphoma, T cell lymphoma, leukemia, leucopenia, neutropenia, thrombocytopenia, granuloctopenia, pancytoia and idiopathic thrombocytopenic purpura.

28. A compound chosen from the group consisting of: 1 to 233, 236-238, 241, 246-250, 253, 256-275, 279-280, 283-288, 290, 293, 303-306, 308-310, 312-367, 372-373, 380-381, 384-391, 394-482, and 484-516

| Compound | Structure |
|---|---|
| 1 | 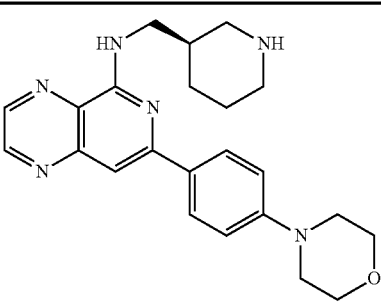 |
| 2 | 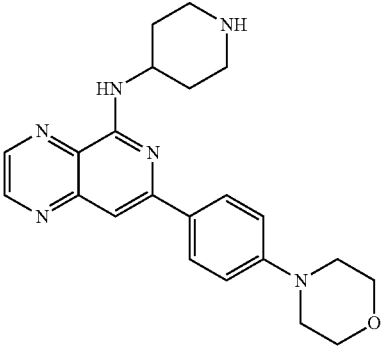 [SMILES: c1cnc2c(NC3CCNCC3)nc(-c3ccc(N4CCOCC4)cc3)cc2n1] |
| 3 | 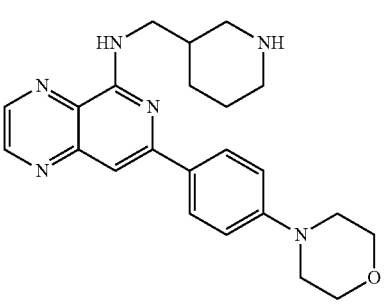 |
| 4 | 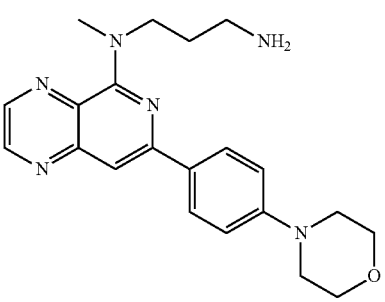 [SMILES: CN(CCCN)c1nc(-c2ccc(N3CCOCC3)cc2)cc2nccnc12] |

-continued

| Compound | Structure |
|---|---|
| 5 | *(structure)* |
| 6 | *(structure)* |
| 7 | *(structure)* |
| 8 | *(structure)* |

-continued

| Compound | Structure |
|---|---|
| 9 | (pyrido[3,4-b]pyrazine core with HN-CH2-pyrrolidine-NH at 5-position and 4-(morpholin-4-yl)phenyl at 7-position) |
| 10 | (pyrido[3,4-b]pyrazine core with HN-CH2-piperidine-NH at 5-position and 4-methoxyphenyl at 7-position) |
| 11 | (pyrido[3,4-b]pyrazine core with HN-CH2-piperidine-NH at 5-position and 3,4,5-trimethoxyphenyl at 7-position) |
| 12 | (pyrido[3,4-b]pyrazine core with HN-CH2-piperidine-NH at 5-position and 4-(dimethylamino)phenyl at 7-position) |
| 13 | (pyrido[3,4-b]pyrazine core with HN-CH2-piperidine-NH at 5-position and 3-(dimethylamino)phenyl at 7-position) |

-continued
| Compound | Structure |
|---|---|
| 14 | 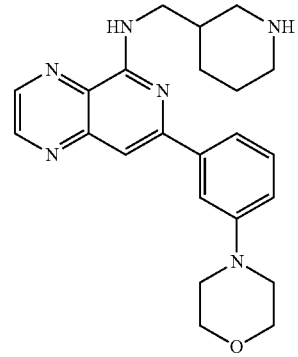 [SMILES: c1cc(-c2cc3nccnc3c(NCC3CCCNC3)n2)cc(N2CCOCC2)c1] |
| 15 | 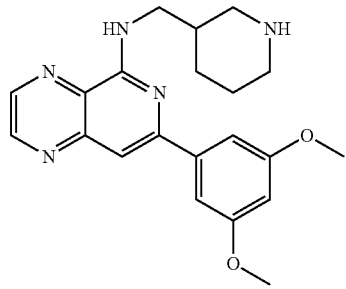 [SMILES: COc1cc(OC)cc(-c2cc3nccnc3c(NCC3CCCNC3)n2)c1] |
| 16 | 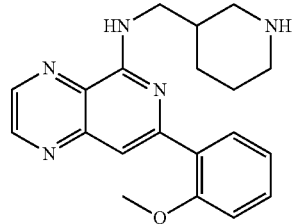 [SMILES: COc1ccccc1-c1cc2nccnc2c(NCC2CCCNC2)n1] |
| 17 | 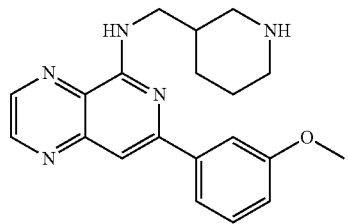 [SMILES: COc1cccc(-c2cc3nccnc3c(NCC3CCCNC3)n2)c1] |
| 18 | 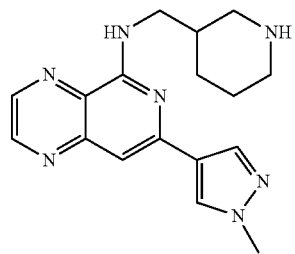 [SMILES: Cn1cc(-c2cc3nccnc3c(NCC3CCCNC3)n2)cn1] |

-continued
| Compound | Structure |
|---|---|
| 19 | 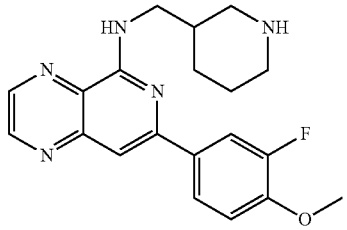 [SMILES: COc1ccc(-c2cc3nccnc3c(NCC3CCCNC3)n2)cc1F] |
| 20 | 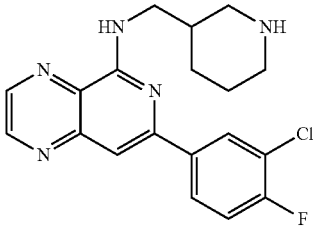 [SMILES: Fc1ccc(-c2cc3nccnc3c(NCC3CCCNC3)n2)cc1Cl] |
| 21 | 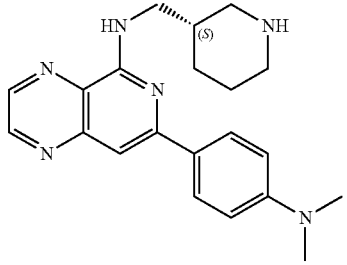 |
| 22 | 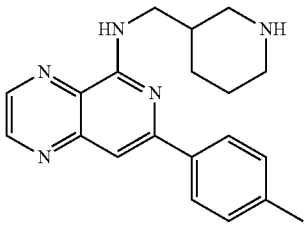 |
| 23 | 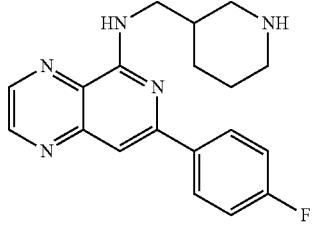 [SMILES: Fc1ccc(-c2cc3nccnc3c(NCC3CCCNC3)n2)cc1] |
| 24 | 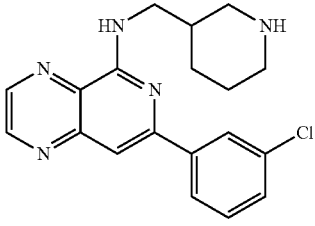 [SMILES: Clc1cccc(-c2cc3nccnc3c(NCC3CCCNC3)n2)c1] |

-continued

| Compound | Structure |
|---|---|
| 25 | 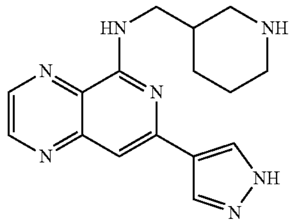 [SMILES: c1cnc2c(NCC3CCCNC3)nc(-c3cn[nH]c3)cc2n1] |
| 26 | 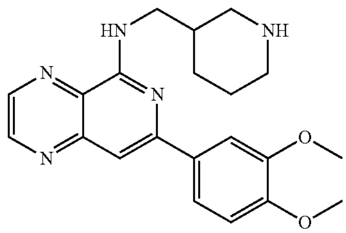 [SMILES: COc1ccc(-c2cc3nccnc3c(NCC3CCCNC3)n2)cc1OC] |
| 27 | 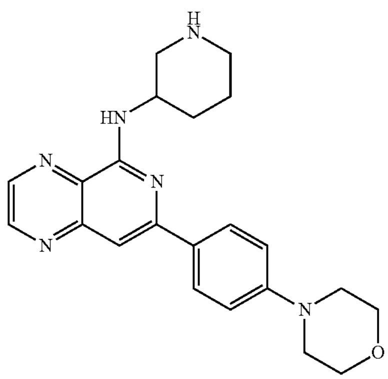 [SMILES: c1cnc2c(NC3CCCNC3)nc(-c3ccc(N4CCOCC4)cc3)cc2n1] |
| 28 | 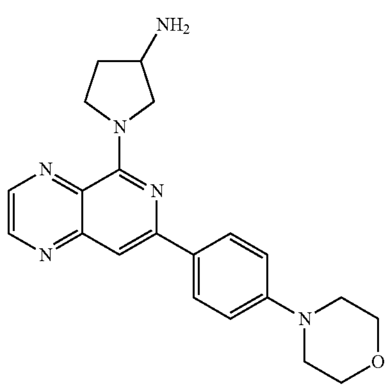 [SMILES: NC1CCN(c2nc(-c3ccc(N4CCOCC4)cc3)cc3nccnc23)C1] |
| 29 | 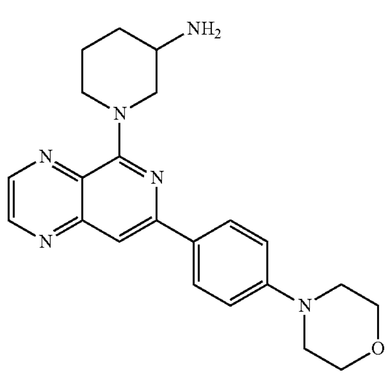 [SMILES: NC1CCCN(c2nc(-c3ccc(N4CCOCC4)cc3)cc3nccnc23)C1] |

-continued

| Compound | Structure |
|---|---|
| 30 | 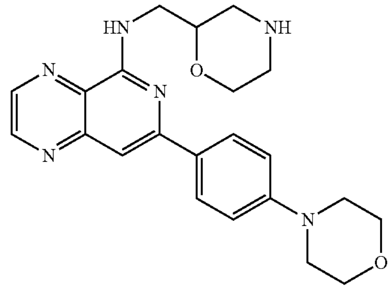 [SMILES: c1cnc2c(NCC3CNCCO3)nc(-c3ccc(N4CCOCC4)cc3)cc2n1] |
| 31 | 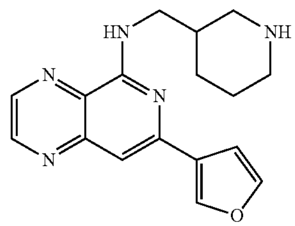 [SMILES: c1cnc2c(NCC3CCCNC3)nc(-c3ccoc3)cc2n1] |
| 32 | 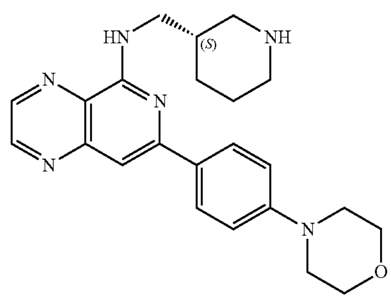 |
| 33 | 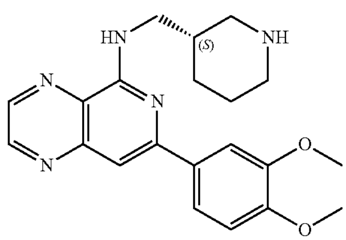 |
| 34 | 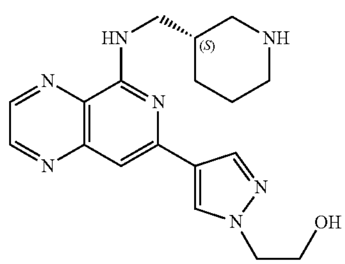 |
| 35 | 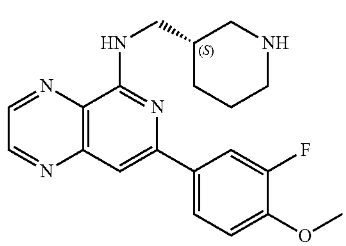 |

-continued
| Compound | Structure |
|---|---|
| 36 | 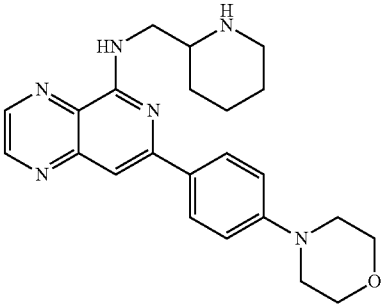 [SMILES: c1cnc2c(NCC3CCCCN3)nc(-c3ccc(N4CCOCC4)cc3)cc2n1] |
| 37 | 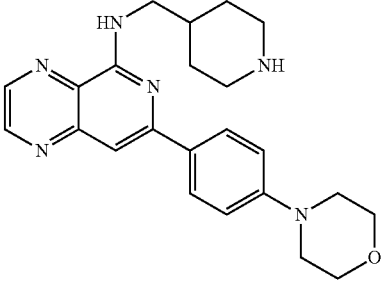 [SMILES: c1cnc2c(NCC3CCNCC3)nc(-c3ccc(N4CCOCC4)cc3)cc2n1] |
| 38 | 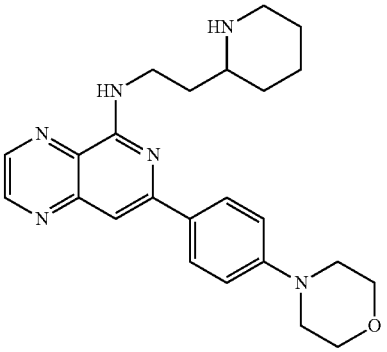 [SMILES: c1cnc2c(NCCC3CCCCN3)nc(-c3ccc(N4CCOCC4)cc3)cc2n1] |
| 39 | 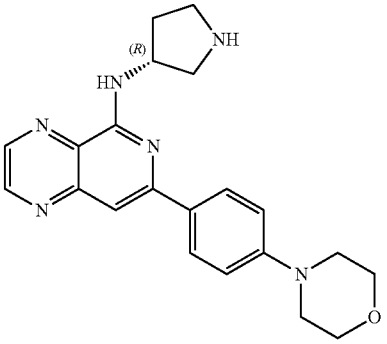 |
| 40 | 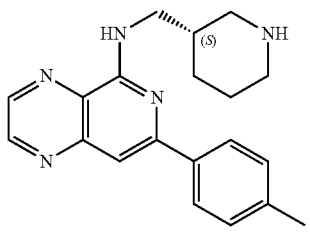 |

-continued

| Compound | Structure |
|---|---|
| 41 | (S)-N-(piperidin-3-ylmethyl)-7-(3-fluoro-4-methylphenyl)pyrido[3,4-b]pyrazin-5-amine |
| 42 | N-(piperidin-3-ylmethyl)-7-(4-isobutoxyphenyl)pyrido[3,4-b]pyrazin-5-amine |
| 43 | 4-(5-((piperidin-3-ylmethyl)amino)pyrido[3,4-b]pyrazin-7-yl)benzenesulfonamide |
| 44 | N-(piperidin-3-ylmethyl)-7-(4-(methylamino)phenyl)pyrido[3,4-b]pyrazin-5-amine |
| 45 | N-(piperidin-3-ylmethyl)-7-(4-ethylphenyl)pyrido[3,4-b]pyrazin-5-amine |
| 46 | N-(piperidin-3-ylmethyl)-7-(4-isopropylphenyl)pyrido[3,4-b]pyrazin-5-amine |

-continued

| Compound | Structure |
|---|---|
| 47 | 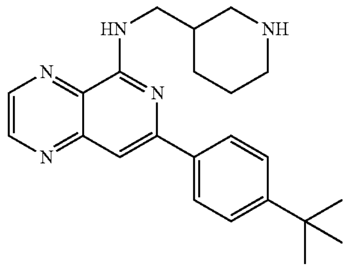 [SMILES: CC(C)(C)c1ccc(-c2cc3nccnc3c(NCC3CCCNC3)n2)cc1] |
| 48 | 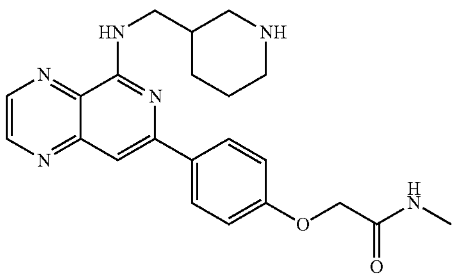 [SMILES: CNC(=O)COc1ccc(-c2cc3nccnc3c(NCC3CCCNC3)n2)cc1] |
| 49 | 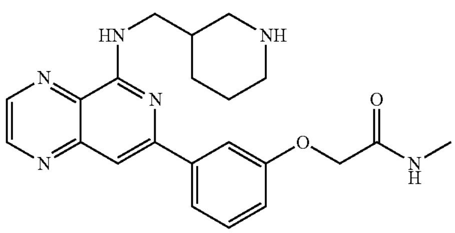 [SMILES: CNC(=O)COc1cccc(-c2cc3nccnc3c(NCC3CCCNC3)n2)c1] |
| 50 | 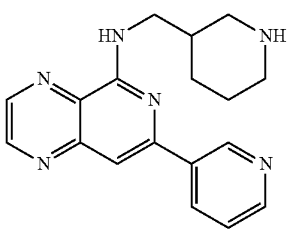 [SMILES: c1cncc(-c2cc3nccnc3c(NCC3CCCNC3)n2)c1] |
| 51 | 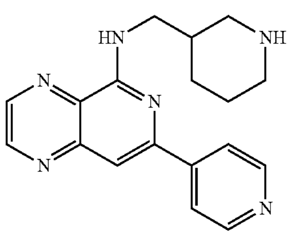 [SMILES: c1cc(-c2cc3nccnc3c(NCC3CCCNC3)n2)ccn1] |
| 52 | 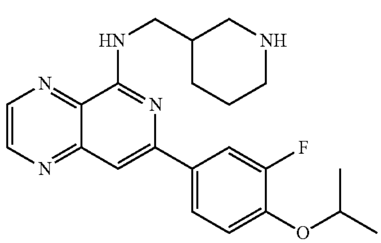 [SMILES: CC(C)Oc1ccc(-c2cc3nccnc3c(NCC3CCCNC3)n2)cc1F] |

-continued
| Compound | Structure |
|---|---|
| 53 | 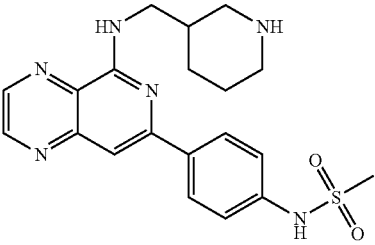 [SMILES: CS(=O)(=O)Nc1ccc(-c2cc3nccnc3c(NCC3CCCNC3)n2)cc1] |
| 54 | 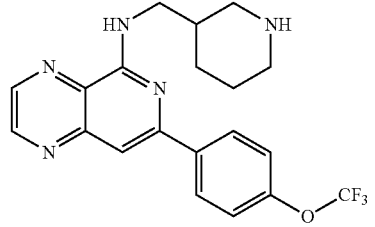 [SMILES: FC(F)(F)Oc1ccc(-c2cc3nccnc3c(NCC3CCCNC3)n2)cc1] |
| 55 | 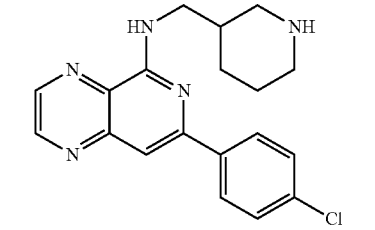 |
| 56 | 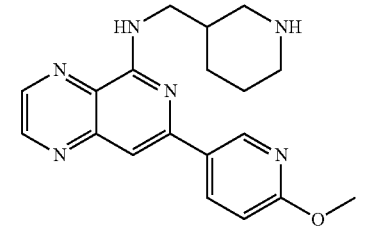 [SMILES: COc1ccc(-c2cc3nccnc3c(NCC3CCCNC3)n2)cn1] |
| 57 | 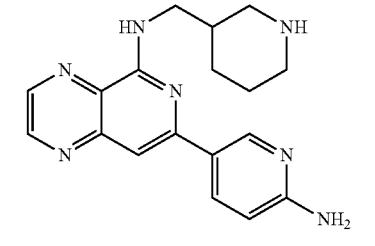 |
| 58 | 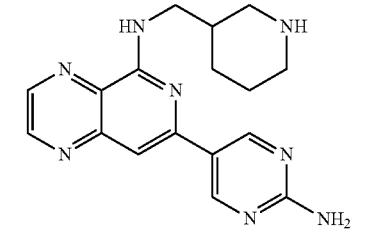 |

-continued
| Compound | Structure |
|---|---|
| 59 | 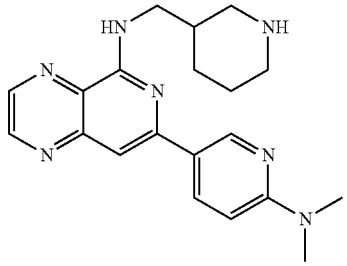 [SMILES: CN(C)c1ccc(-c2cc3nccnc3c(NCC3CCCNC3)n2)cn1] |
| 60 | 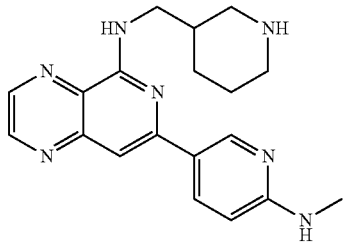 [SMILES: CNc1ccc(-c2cc3nccnc3c(NCC3CCCNC3)n2)cn1] |
| 61 | 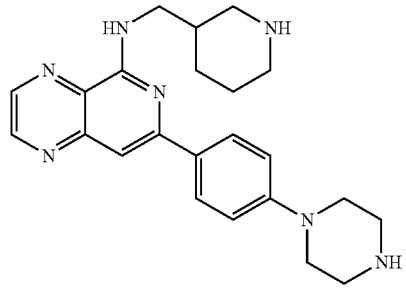 [SMILES: c1cnc2c(NCC3CCCNC3)nc(-c3ccc(N4CCNCC4)cc3)cc2n1] |
| 62 | 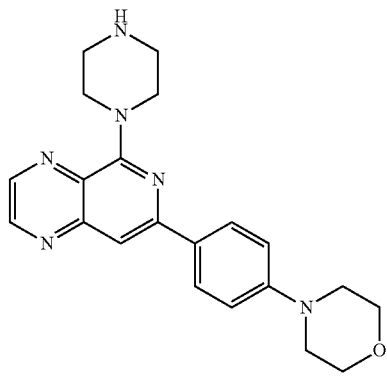 [SMILES: c1cnc2c(N3CCNCC3)nc(-c3ccc(N4CCOCC4)cc3)cc2n1] |
| 63 | 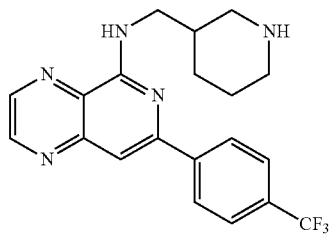 [SMILES: FC(F)(F)c1ccc(-c2cc3nccnc3c(NCC3CCCNC3)n2)cc1] |

-continued

| Compound | Structure |
|---|---|
| 64 | 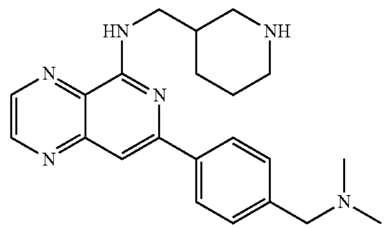 [SMILES: CN(C)Cc1ccc(-c2cc3nccnc3c(NCC3CCCNC3)n2)cc1] |
| 65 | 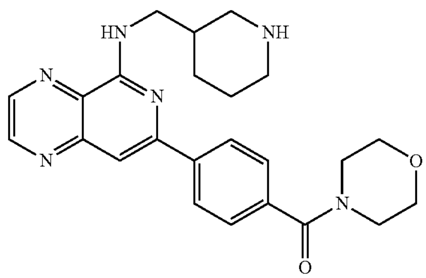 [SMILES: O=C(c1ccc(-c2cc3nccnc3c(NCC3CCCNC3)n2)cc1)N1CCOCC1] |
| 66 | 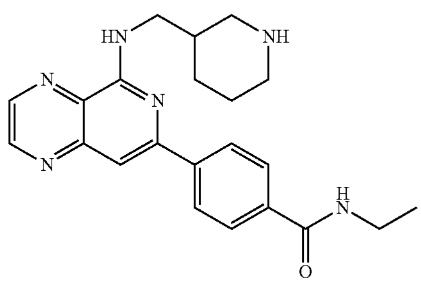 [SMILES: CCNC(=O)c1ccc(-c2cc3nccnc3c(NCC3CCCNC3)n2)cc1] |
| 67 | 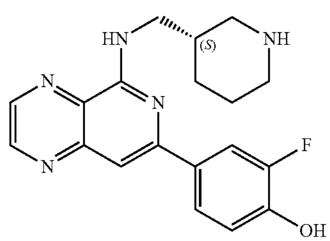 |
| 68 | 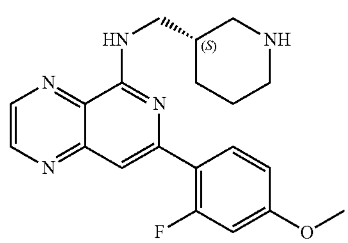 |
| 69 | 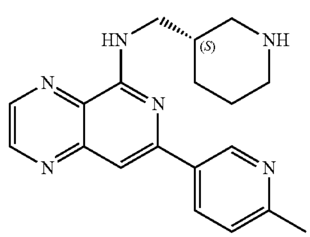 |

-continued
| Compound | Structure |
|---|---|
| 70 | 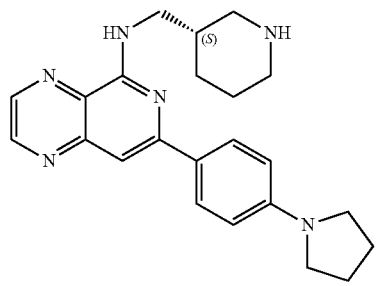 |
| 71 | 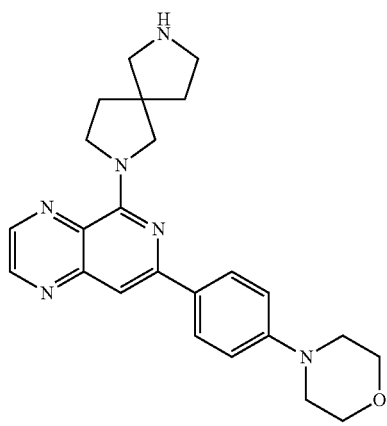 [SMILES: c1cnc2c(N3CCC4(CCNC4)C3)nc(-c3ccc(N4CCOCC4)cc3)cc2n1] |
| 72 | 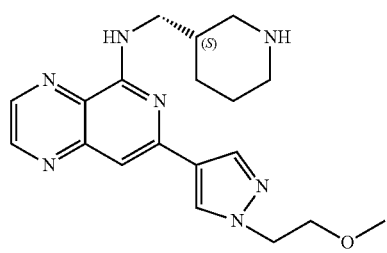 |
| 73 | 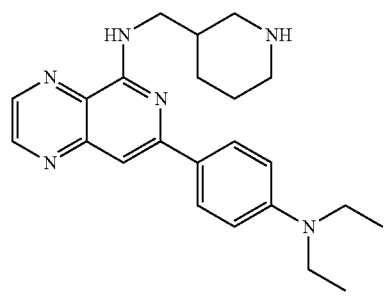 [SMILES: CCN(CC)c1ccc(-c2cc3nccnc3c(NCC3CCCNC3)n2)cc1] |
| 74 | 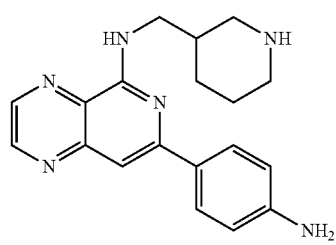 [SMILES: Nc1ccc(-c2cc3nccnc3c(NCC3CCCNC3)n2)cc1] |

-continued
| Compound | Structure |
|---|---|
| 75 | 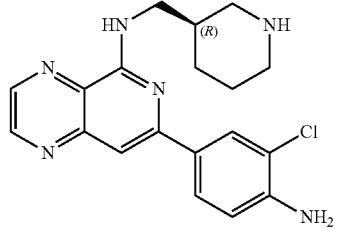 |
| 76 | 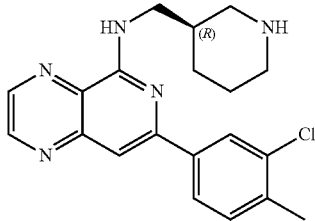 |
| 77 | 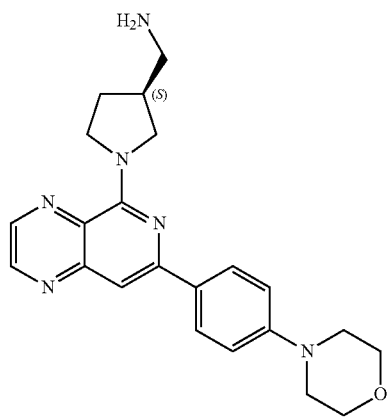 |
| 78 | 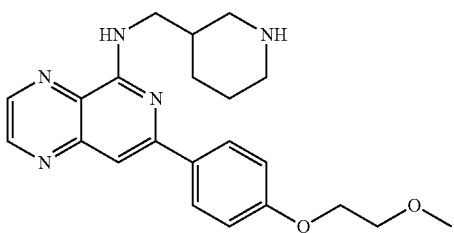 [SMILES: COCCOc1ccc(-c2cc3nccnc3c(NCC3CCCNC3)n2)cc1] |
| 79 | 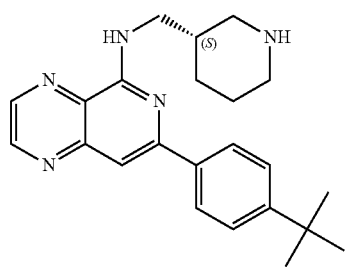 |

-continued
| Compound | Structure |
|---|---|
| 80 | 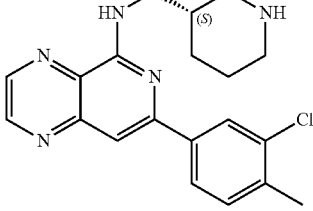 |
| 81 | 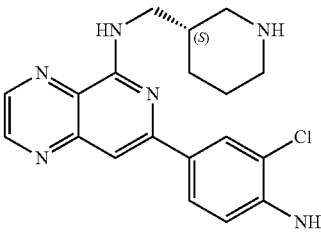 |
| 82 | 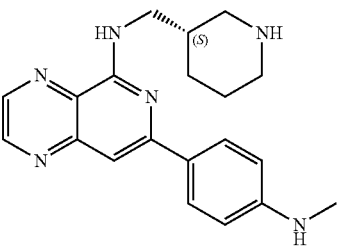 |
| 83 | 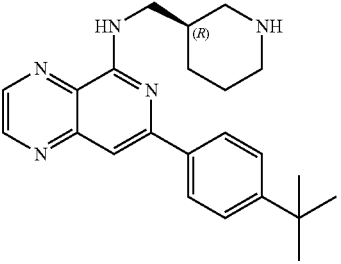 |
| 84 | 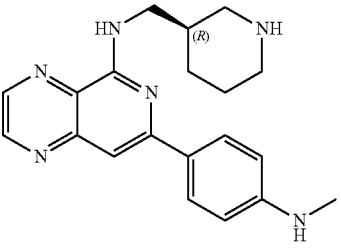 |
| 85 | 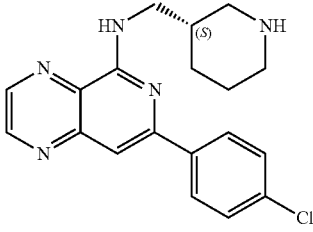 |

-continued
| Compound | Structure |
|---|---|
| 86 | 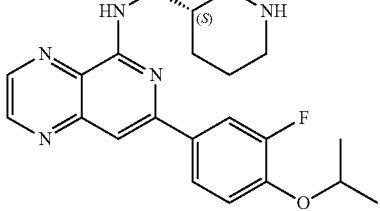 |
| 87 | 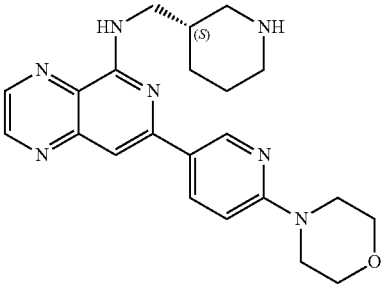 |
| 88 | 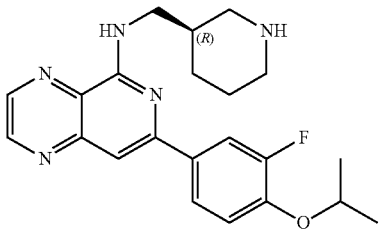 |
| 89 | 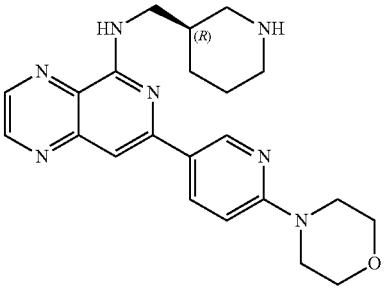 |
| 90 | 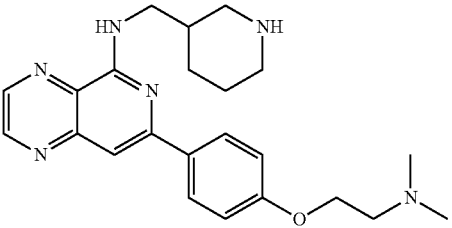 |
| 91 | 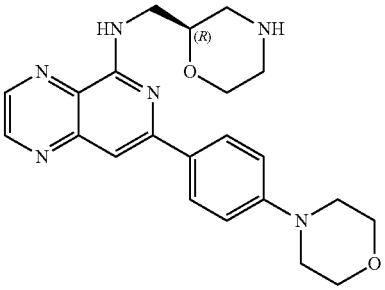 |

-continued
| Compound | Structure |
|---|---|
| 92 | 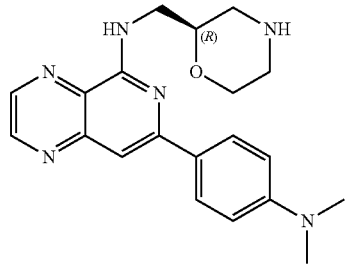 |
| 93 | 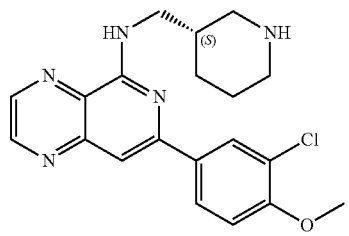 |
| 94 | 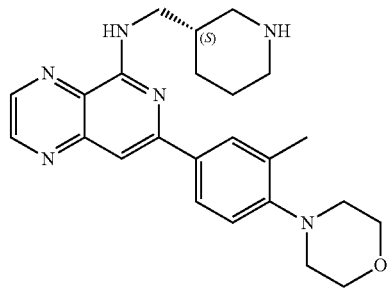 |
| 95 | 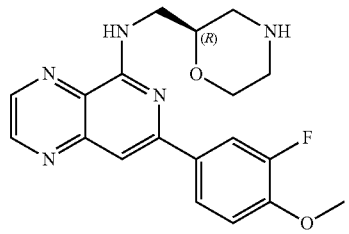 |
| 96 | 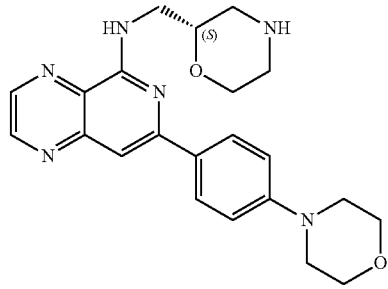 |

| Compound | Structure |
|---|---|
| 97 | 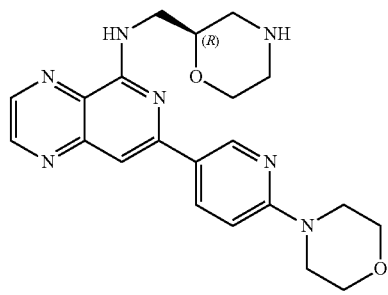 |
| 98 | 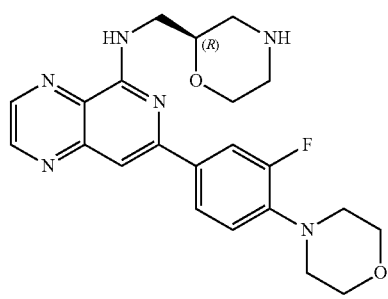 |
| 99 | 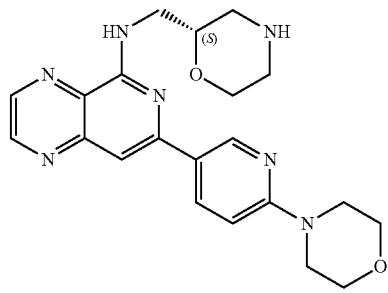 |
| 100 | 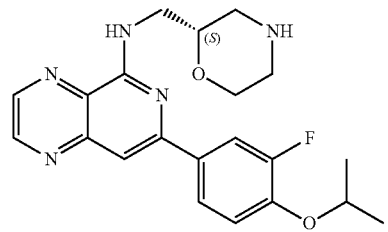 |
| 101 | 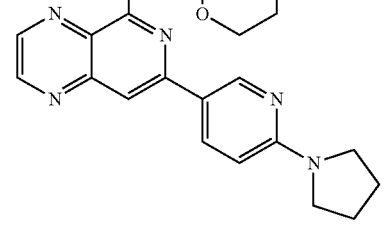 |

| Compound | Structure |
|---|---|
| 102 | 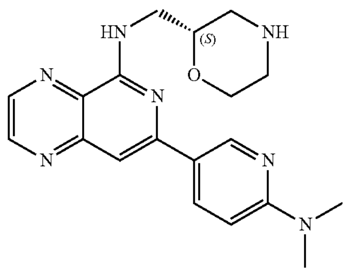 |
| 103 | 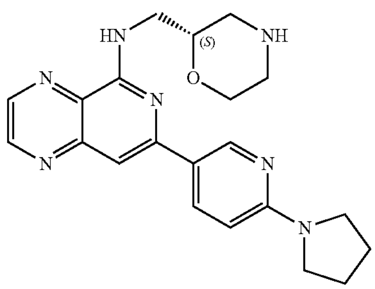 |
| 104 | 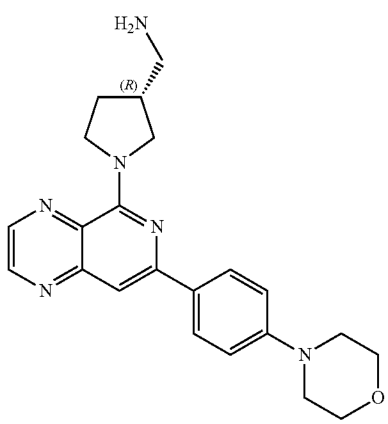 |
| 105 | 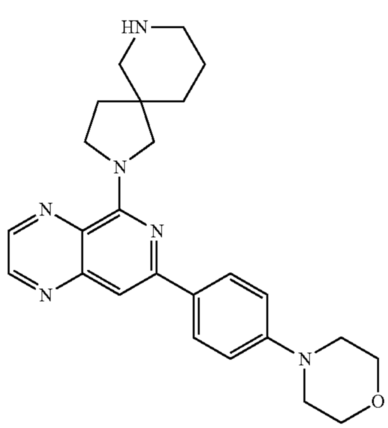 [SMILES: c1cnc2c(N3CCC4(CCCNC4)C3)nc(-c3ccc(N4CCOCC4)cc3)cc2n1] |

-continued

| Compound | Structure |
|---|---|
| 106 | 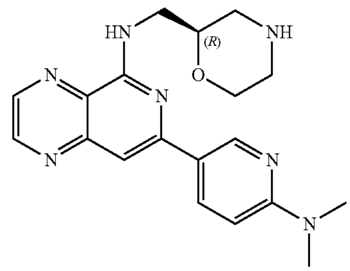 |
| 107 | 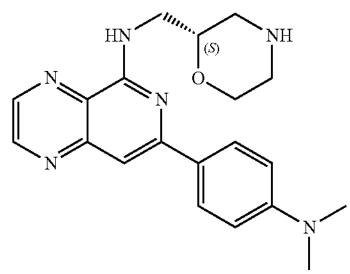 |
| 108 | 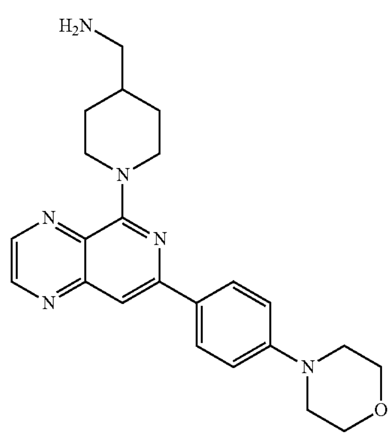 [SMILES: NCC1CCN(c2nc(-c3ccc(N4CCOCC4)cc3)cc3nccnc23)CC1] |
| 109 | 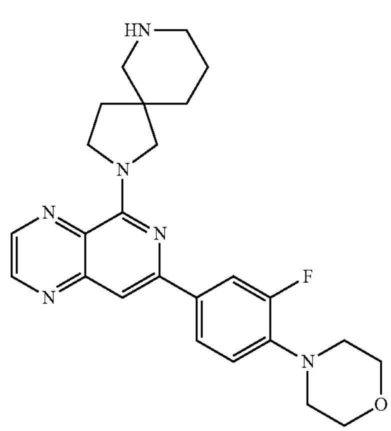 [SMILES: Fc1cc(-c2cc3nccnc3c(N3CCC4(CCCNC4)C3)n2)ccc1N1CCOCC1] |

-continued
| Compound | Structure |
|---|---|
| 110 | 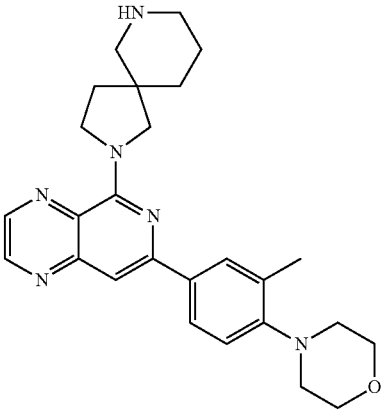 [SMILES: Cc1cc(-c2cc3nccnc3c(N3CCC4(CCCNC4)C3)n2)ccc1N1CCOCC1] |
| 111 | 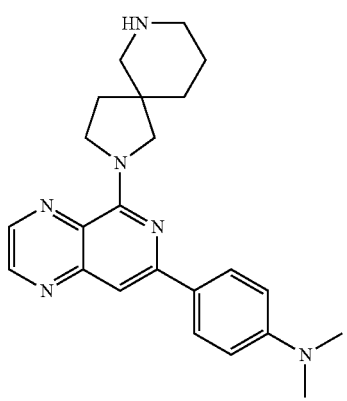 [SMILES: CN(C)c1ccc(-c2cc3nccnc3c(N3CCC4(CCCNC4)C3)n2)cc1] |
| 112 | 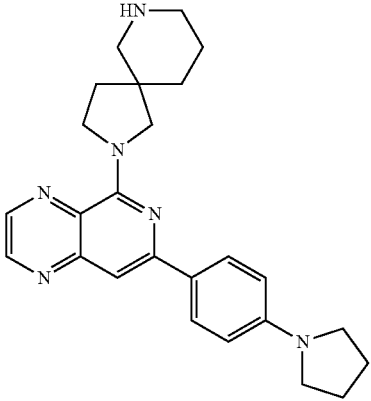 [SMILES: c1cnc2c(N3CCC4(CCCNC4)C3)nc(-c3ccc(N4CCCC4)cc3)cc2n1] |
| 113 | 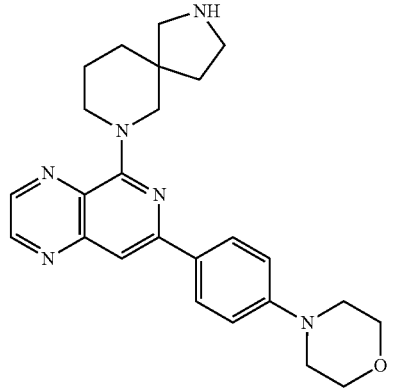 [SMILES: c1cnc2c(N3CCCC4(CCNC4)C3)nc(-c3ccc(N4CCOCC4)cc3)cc2n1] |

| Compound | Structure |
|---|---|
| 114 | 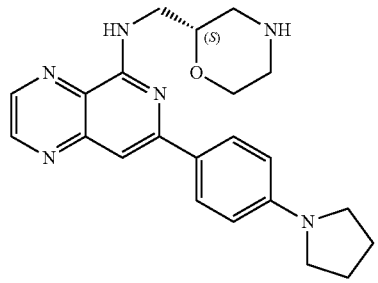 |
| 115 | 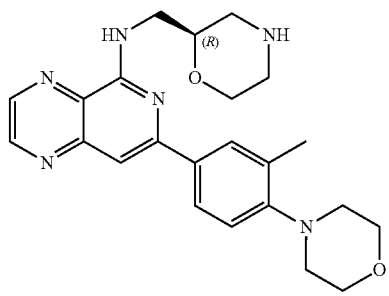 |
| 116 | 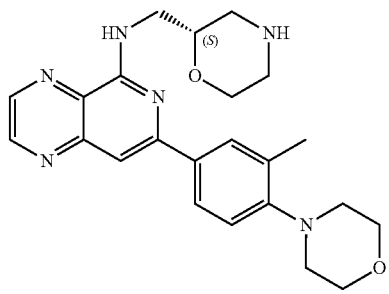 |
| 117 | 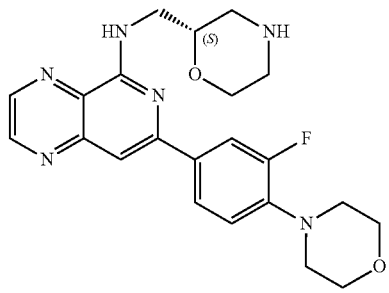 |
| 118 | 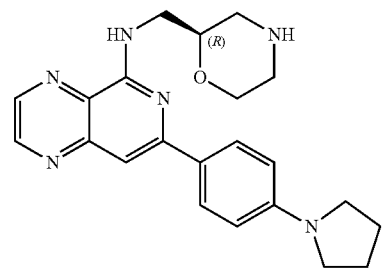 |

-continued
| Compound | Structure |
|---|---|
| 119 | 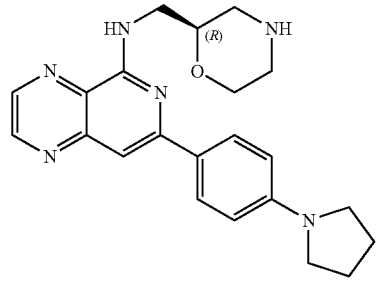 |
| 120 | 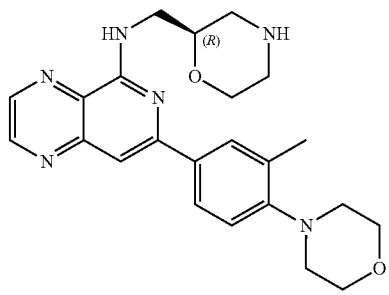 |
| 121 | 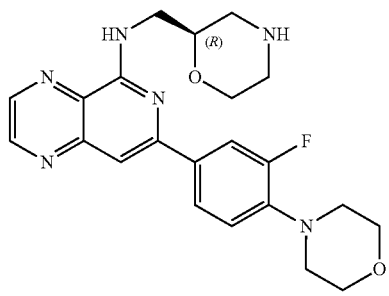 |
| 122 | 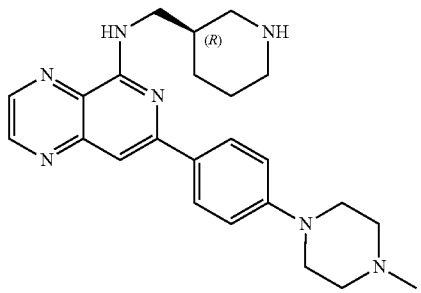 |
| 123 | 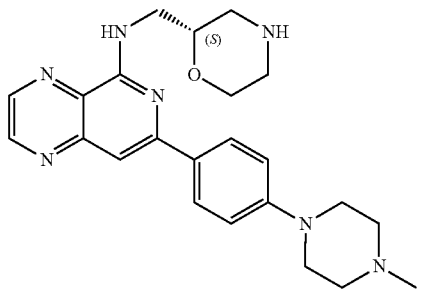 |

| Compound | Structure |
|---|---|
| 124 | 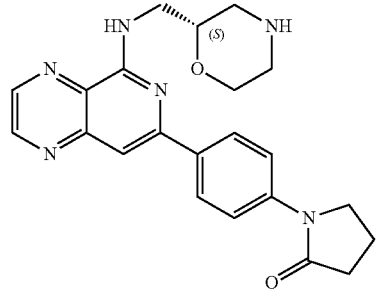 |
| 125 | 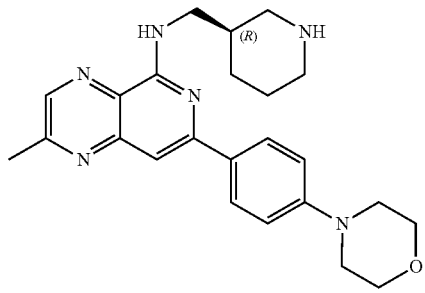 |
| 126 | 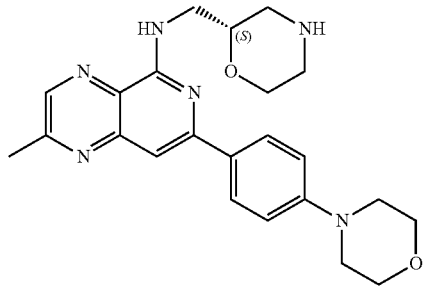 |
| 127 | 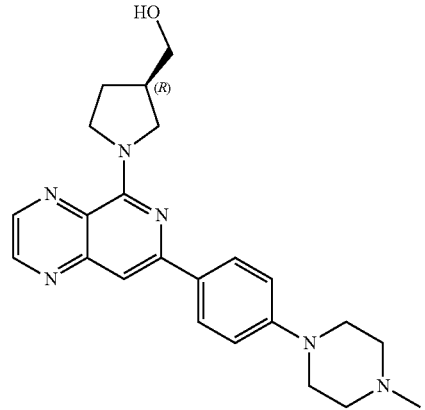 |

-continued
| Compound | Structure |
|---|---|
| 128 | 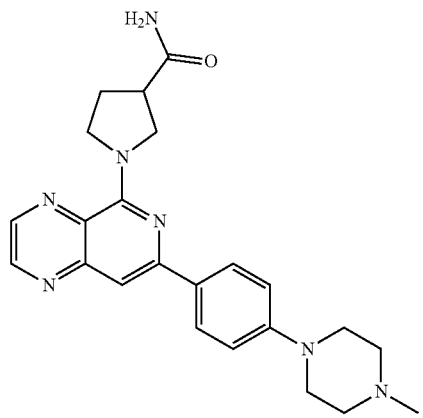 [SMILES: CN1CCN(c2ccc(-c3cc4nccnc4c(N4CCC(C(N)=O)C4)n3)cc2)CC1] |
| 129 | 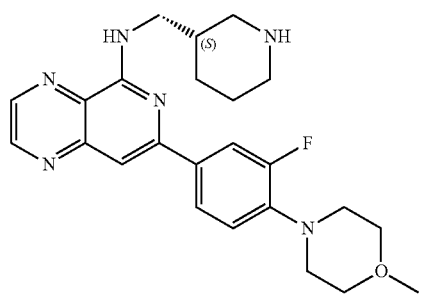 |
| 130 | 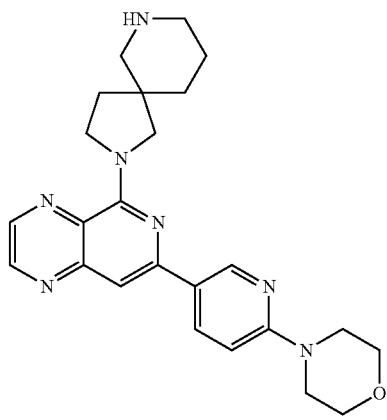 [SMILES: c1cnc2c(N3CCC4(CCCNC4)C3)nc(-c3ccc(N4CCOCC4)nc3)cc2n1] |
| 131 | 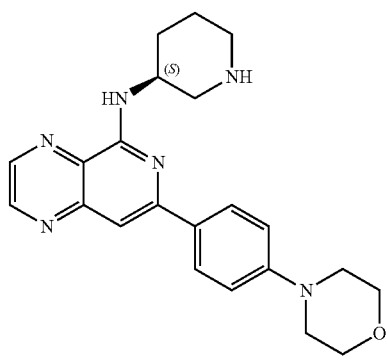 |

-continued
| Compound | Structure |
|---|---|
| 132 | 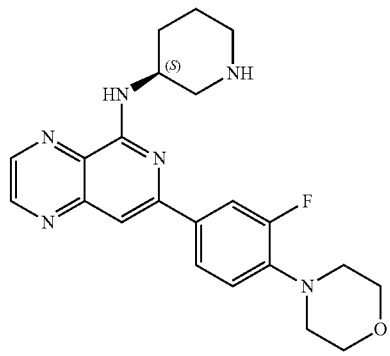 |
| 133 | 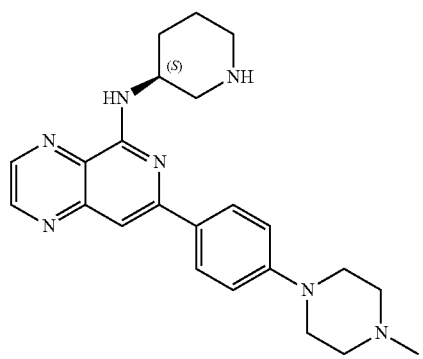 |
| 134 | 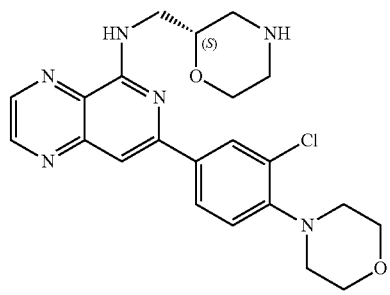 |
| 135 | 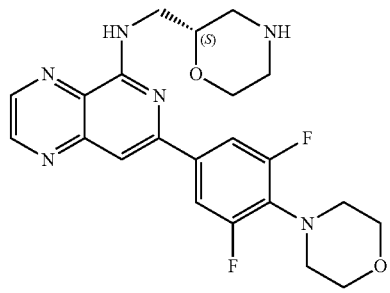 |
| 136 | 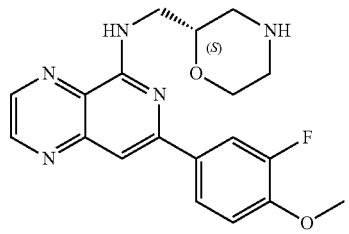 |

| Compound | Structure |
|---|---|
| 137 | 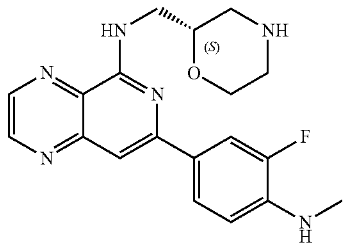 |
| 138 | 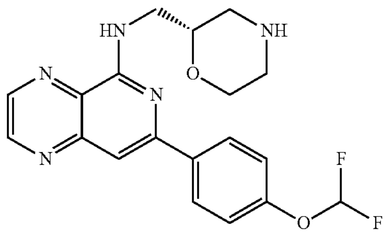 [SMILES: FC(F)Oc1ccc(-c2cc3nccnc3c(NC[C@@H]3CNCCO3)n2)cc1] |
| 139 | 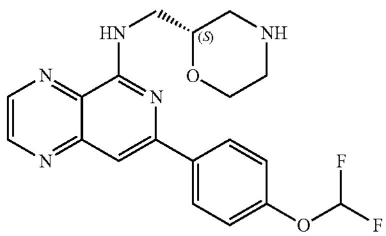 |
| 140 | 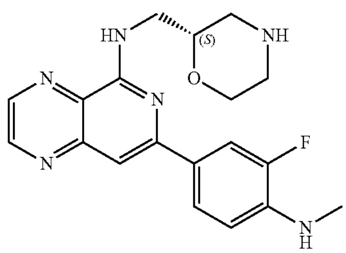 |
| 141 | 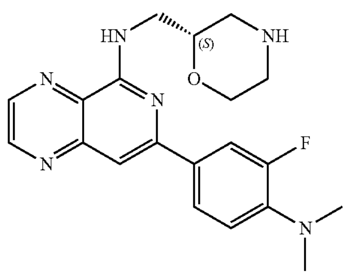 |
| 142 | 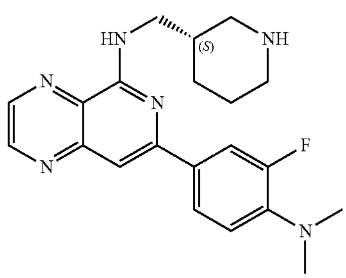 |

| Compound | Structure |
|---|---|
| 143 | 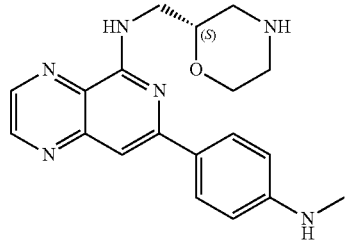 |
| 144 | 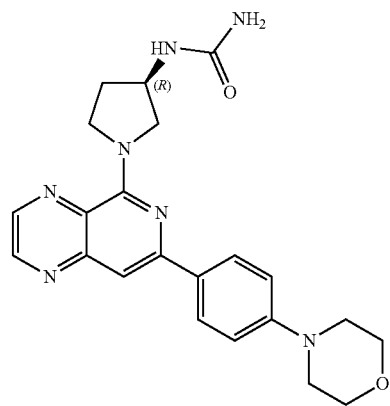 |
| 145 | 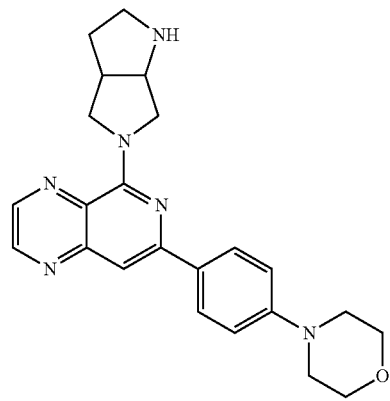 [SMILES: c1cnc2c(N3CC4CCNC4C3)nc(-c3ccc(N4CCOCC4)cc3)cc2n1] |
| 146 | 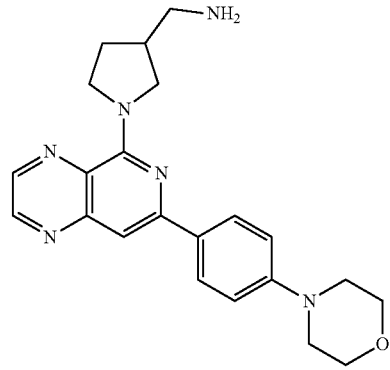 [SMILES: NCC1CCN(c2nc(-c3ccc(N4CCOCC4)cc3)cc3nccnc23)C1] |

-continued
| Compound | Structure |
|---|---|
| 147 | 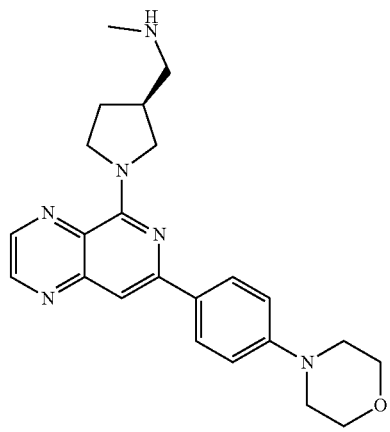 [SMILES: CNC[C@@H]1CCN(c2nc(-c3ccc(N4CCOCC4)cc3)cc3nccnc23)C1] |
| 148 | 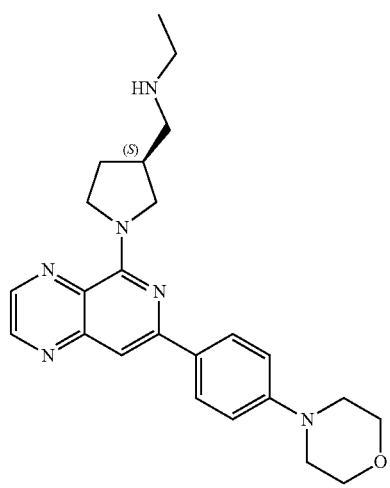 |
| 149 | 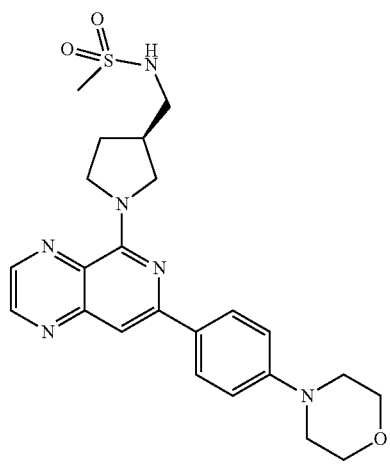 [SMILES: CS(=O)(=O)NC[C@@H]1CCN(c2nc(-c3ccc(N4CCOCC4)cc3)cc3nccnc23)C1] |

-continued
| Compound | Structure |
|---|---|
| 150 | 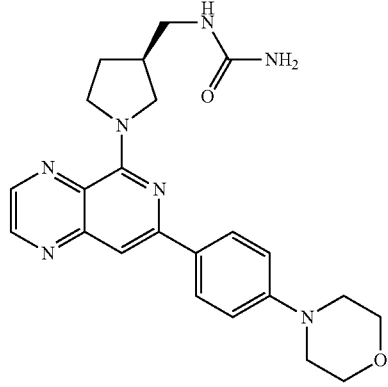 [SMILES: NC(=O)NC[C@@H]1CCN(c2nc(-c3ccc(N4CCOCC4)cc3)cc3nccnc23)C1] |
| 151 | 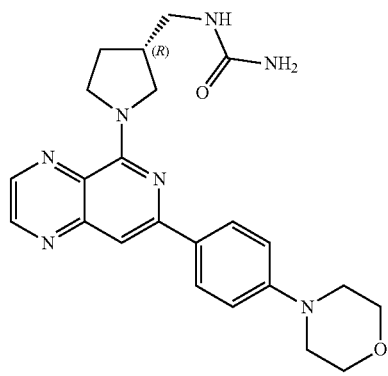 |
| 152 | 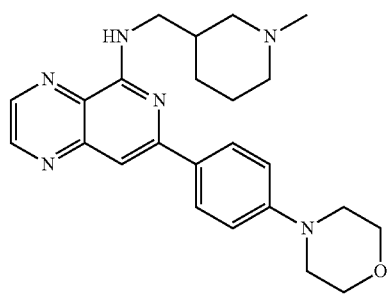 [SMILES: CN1CCCC(CNc2nc(-c3ccc(N4CCOCC4)cc3)cc3nccnc23)C1] |
| 153 | 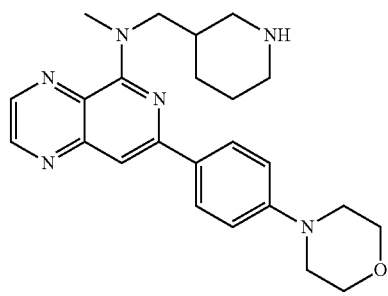 [SMILES: CN(CC1CCCNC1)c1nc(-c2ccc(N3CCOCC3)cc2)cc2nccnc12] |

-continued

| Compound | Structure |
|---|---|
| 154 | 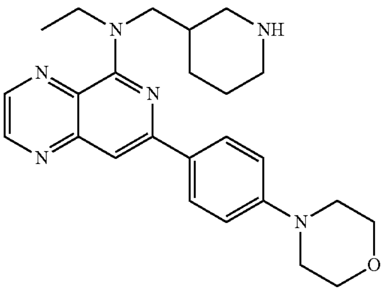 [SMILES: CCN(CC1CCCNC1)c1nc(-c2ccc(N3CCOCC3)cc2)cc2nccnc12] |
| 155 | 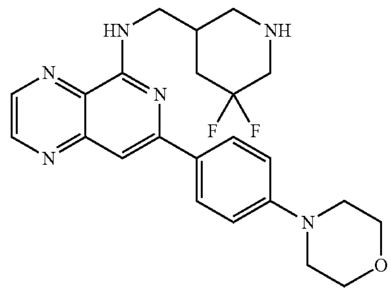 [SMILES: FC1(F)CNCC(CNc2nc(-c3ccc(N4CCOCC4)cc3)cc3nccnc23)C1] |
| 156 | 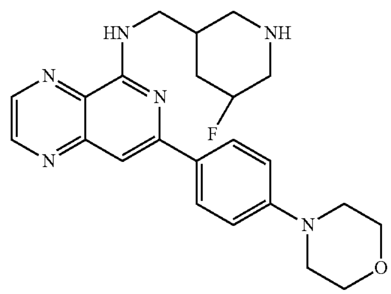 [SMILES: FC1CNCC(CNc2nc(-c3ccc(N4CCOCC4)cc3)cc3nccnc23)C1] |
| 157 | 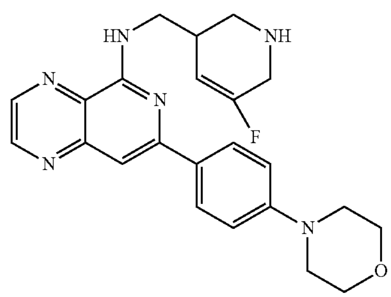 [SMILES: FC1=CC(CNc2nc(-c3ccc(N4CCOCC4)cc3)cc3nccnc23)CNC1] |
| 158 | 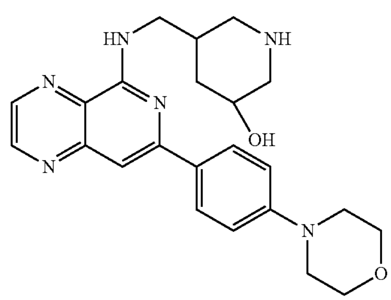 [SMILES: OC1CNCC(CNc2nc(-c3ccc(N4CCOCC4)cc3)cc3nccnc23)C1] |

| Compound | Structure |
|---|---|
| 159 | 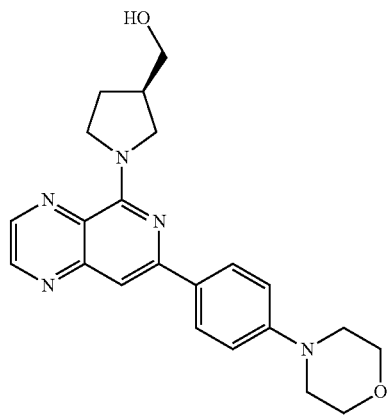 [SMILES: OC[C@@H]1CCN(c2nc(-c3ccc(N4CCOCC4)cc3)cc3nccnc23)C1] |
| 160 | 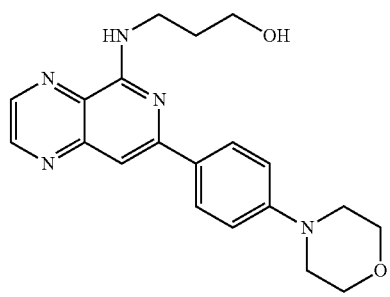 [SMILES: OCCCNc1nc(-c2ccc(N3CCOCC3)cc2)cc2nccnc12] |
| 161 | 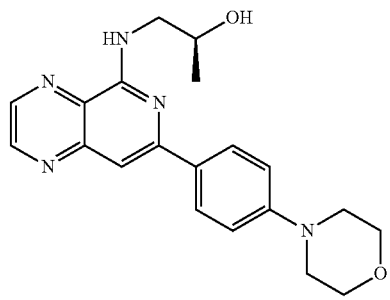 [SMILES: C[C@H](O)CNc1nc(-c2ccc(N3CCOCC3)cc2)cc2nccnc12] |
| 162 | 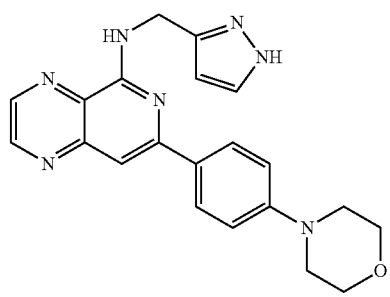 [SMILES: c1cnc2c(NCc3cc[nH]n3)nc(-c3ccc(N4CCOCC4)cc3)cc2n1] |

| Compound | Structure |
|---|---|
| 163 | 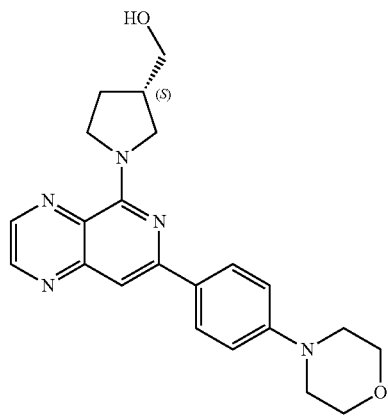 |
| 164 | 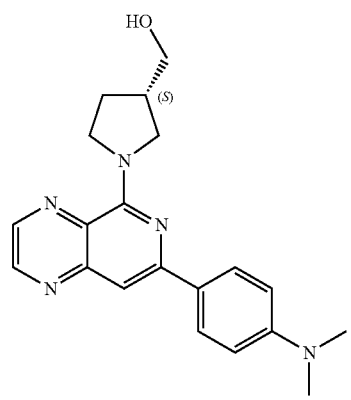 |
| 165 | 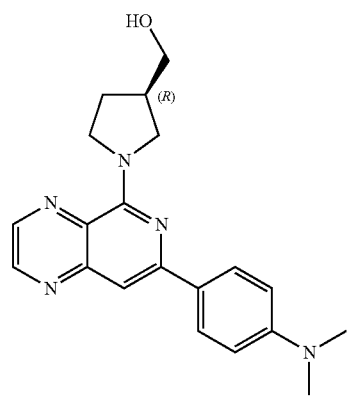 |
| 166 | 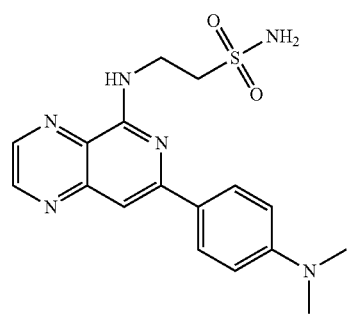 [SMILES: CN(C)c1ccc(-c2cc3nccnc3c(NCCS(N)(=O)=O)n2)cc1] |

| Compound | Structure |
|---|---|
| 167 | 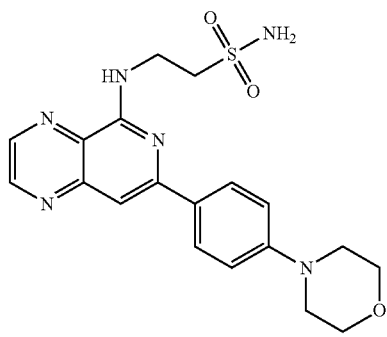 [SMILES: NS(=O)(=O)CCNc1nc(-c2ccc(N3CCOCC3)cc2)cc2nccnc12] |
| 168 | 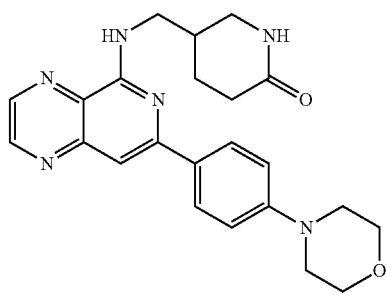 [SMILES: O=C1CCC(CNc2nc(-c3ccc(N4CCOCC4)cc3)cc3nccnc23)CN1] |
| 169 | 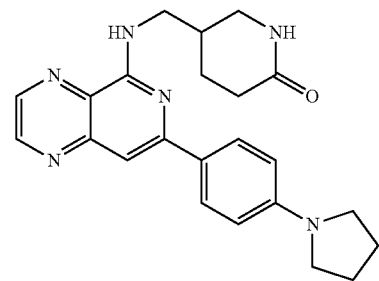 [SMILES: O=C1CCC(CNc2nc(-c3ccc(N4CCCC4)cc3)cc3nccnc23)CN1] |
| 170 | 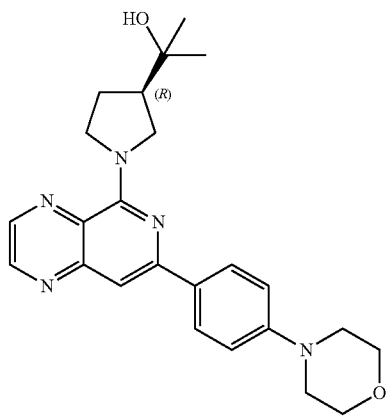 |

-continued

| Compound | Structure |
|---|---|
| 171 | 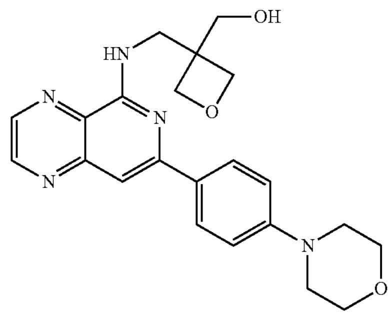 [SMILES: OCC1(CNc2nc(-c3ccc(N4CCOCC4)cc3)cc3nccnc23)COC1] |
| 172 | 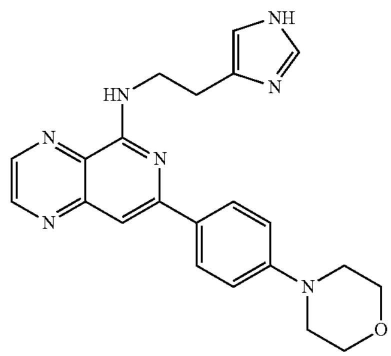 [SMILES: c1cnc2c(NCCc3c[nH]cn3)nc(-c3ccc(N4CCOCC4)cc3)cc2n1] |
| 173 | 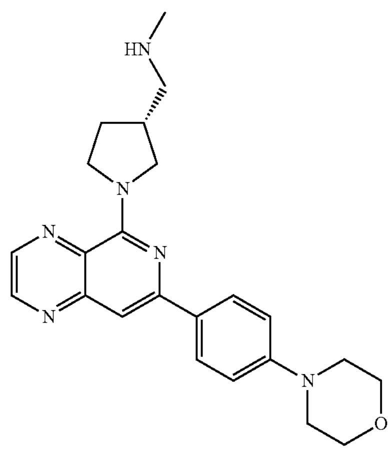 [SMILES: CNC[C@H]1CCN(c2nc(-c3ccc(N4CCOCC4)cc3)cc3nccnc23)C1] |
| 174 | 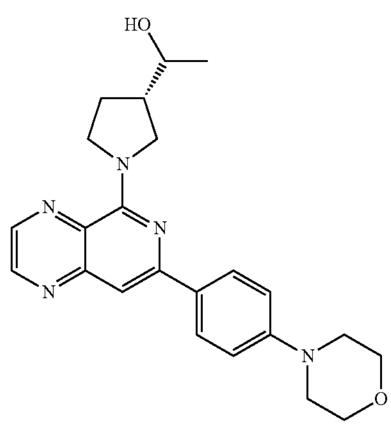 [SMILES: CC(O)[C@H]1CCN(c2nc(-c3ccc(N4CCOCC4)cc3)cc3nccnc23)C1] |

-continued
| Compound | Structure |
|---|---|
| 175 | 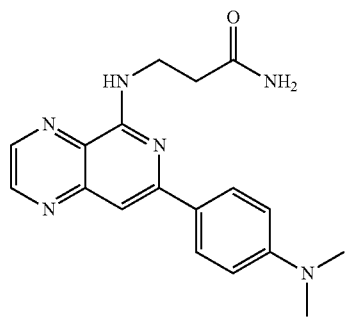 [SMILES: CN(C)c1ccc(-c2cc3nccnc3c(NCCC(N)=O)n2)cc1] |
| 176 | 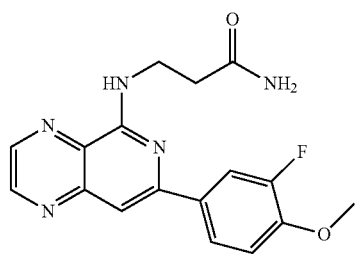 [SMILES: COc1ccc(-c2cc3nccnc3c(NCCC(N)=O)n2)cc1F] |
| 177 | 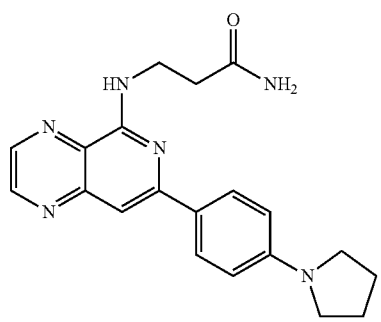 [SMILES: NC(=O)CCNc1nc(-c2ccc(N3CCCC3)cc2)cc2nccnc12] |
| 178 | 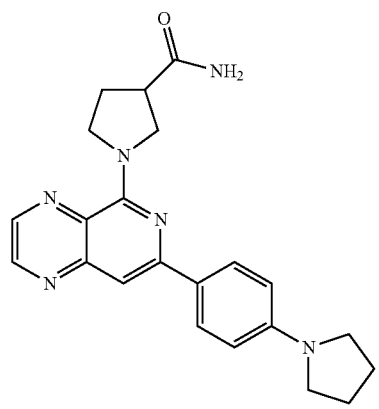 [SMILES: NC(=O)C1CCN(c2nc(-c3ccc(N4CCCC4)cc3)cc3nccnc23)C1] |

-continued
| Compound | Structure |
|---|---|
| 179 | 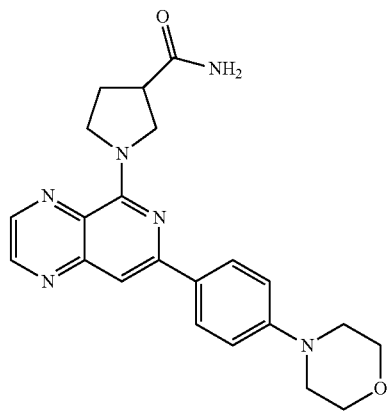 [SMILES: NC(=O)C1CCN(c2nc(-c3ccc(N4CCOCC4)cc3)cc3nccnc23)C1] |
| 180 | 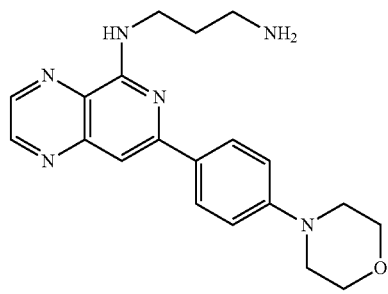 [SMILES: NCCCNc1nc(-c2ccc(N3CCOCC3)cc2)cc2nccnc12] |
| 181 | 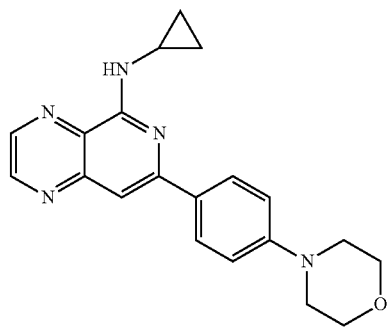 [SMILES: c1cnc2c(NC3CC3)nc(-c3ccc(N4CCOCC4)cc3)cc2n1] |
| 182 | 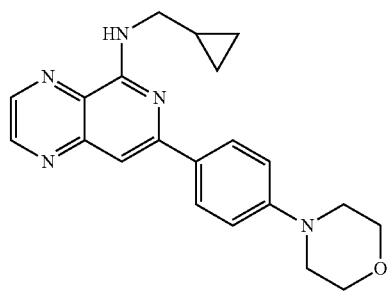 [SMILES: c1cnc2c(NCC3CC3)nc(-c3ccc(N4CCOCC4)cc3)cc2n1] |

-continued

| Compound | Structure |
|---|---|
| 183 | 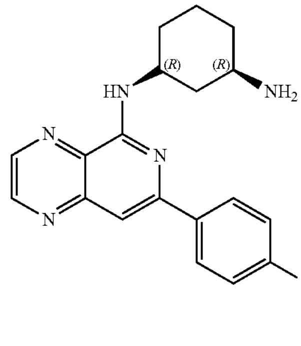 |
| 184 | 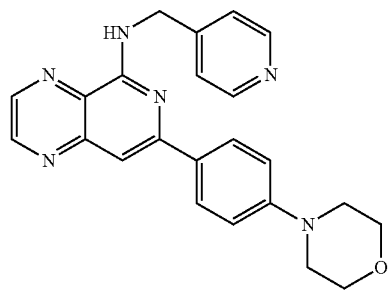 [SMILES: c1cc(CNc2nc(-c3ccc(N4CCOCC4)cc3)cc3nccnc23)ccn1] |
| 185 | 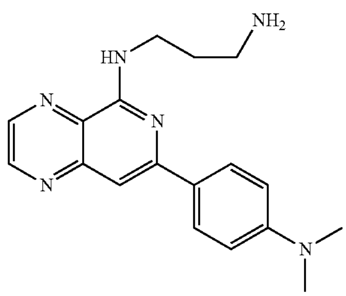 [SMILES: CN(C)c1ccc(-c2cc3nccnc3c(NCCCN)n2)cc1] |
| 186 | 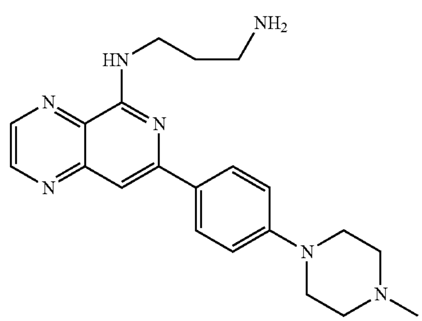 [SMILES: CN1CCN(c2ccc(-c3cc4nccnc4c(NCCCN)n3)cc2)CC1] |
| 187 | 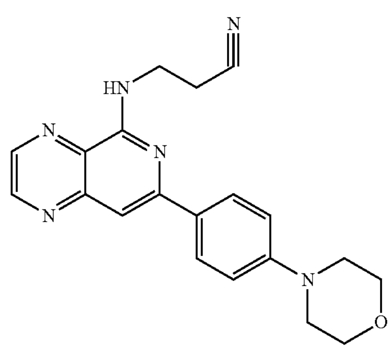 [SMILES: N#CCCNc1nc(-c2ccc(N3CCOCC3)cc2)cc2nccnc12] |

-continued
| Compound | Structure |
|---|---|
| 188 | 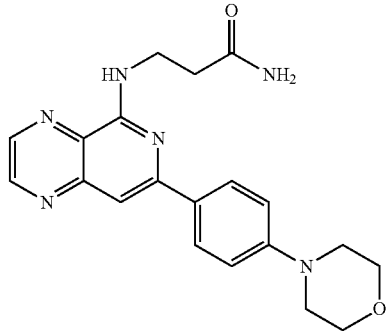 [SMILES: NC(=O)CCNc1nc(-c2ccc(N3CCOCC3)cc2)cc2nccnc12] |
| 189 | 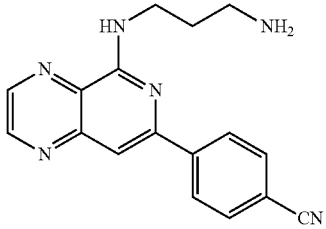 [SMILES: N#Cc1ccc(-c2cc3nccnc3c(NCCCN)n2)cc1] |
| 190 | 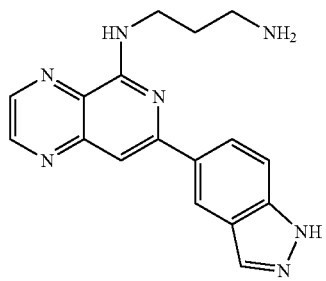 [SMILES: NCCCNc1nc(-c2ccc3[nH]ncc3c2)cc2nccnc12] |
| 191 | 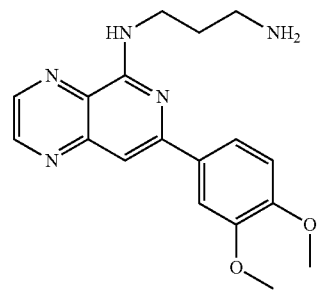 [SMILES: COc1ccc(-c2cc3nccnc3c(NCCCN)n2)cc1OC] |
| 192 | 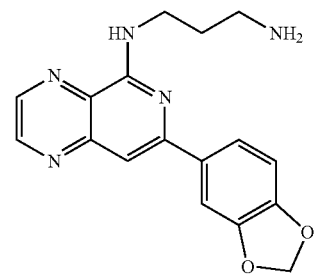 [SMILES: NCCCNc1nc(-c2ccc3c(c2)OCO3)cc2nccnc12] |

-continued
| Compound | Structure |
|---|---|
| 193 | 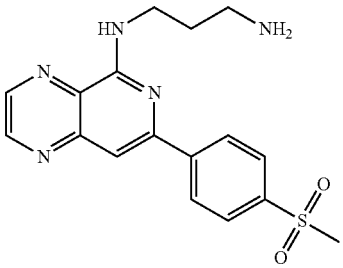 [SMILES: CS(=O)(=O)c1ccc(-c2cc3nccnc3c(NCCCN)n2)cc1] |
| 194 | 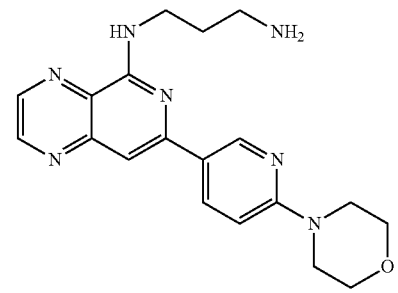 [SMILES: NCCCNc1nc(-c2ccc(N3CCOCC3)nc2)cc2nccnc12] |
| 195 | 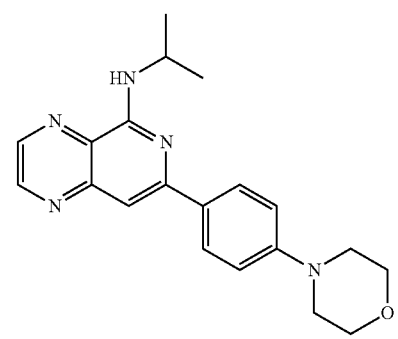 [SMILES: CC(C)Nc1nc(-c2ccc(N3CCOCC3)cc2)cc2nccnc12] |
| 196 | 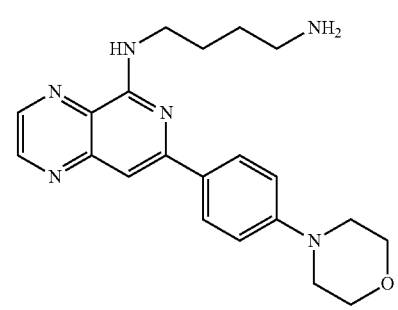 [SMILES: NCCCCNc1nc(-c2ccc(N3CCOCC3)cc2)cc2nccnc12] |
| 197 | 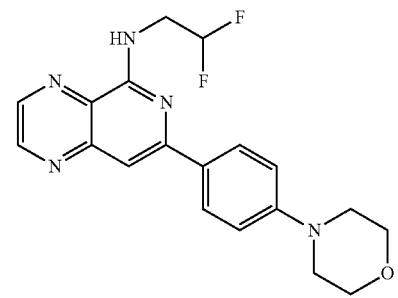 [SMILES: FC(F)CNc1nc(-c2ccc(N3CCOCC3)cc2)cc2nccnc12] |

| Compound | Structure |
|---|---|
| 198 | 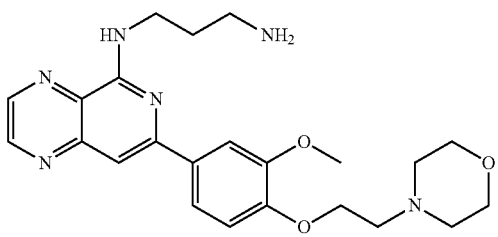 [SMILES: COc1cc(-c2cc3nccnc3c(NCCCN)n2)ccc1OCCN1CCOCC1] |
| 199 | 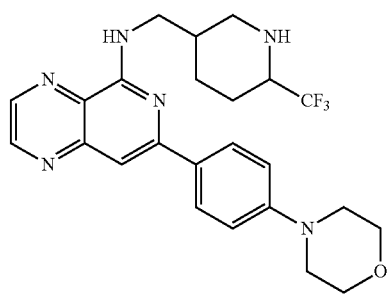 [SMILES: FC(F)(F)C1CCC(CNc2nc(-c3ccc(N4CCOCC4)cc3)cc3nccnc23)CN1] |
| 200 | 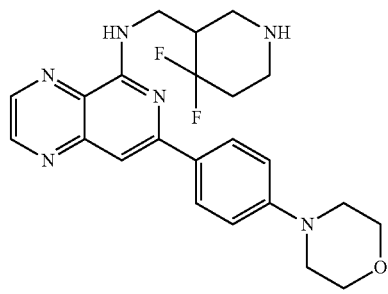 [SMILES: FC1(F)CCNCC1CNc1nc(-c2ccc(N3CCOCC3)cc2)cc2nccnc12] |
| 201 | 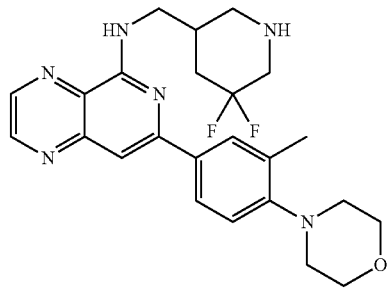 [SMILES: Cc1cc(-c2cc3nccnc3c(NCC3CNCC(F)(F)C3)n2)ccc1N1CCOCC1] |
| 202 | 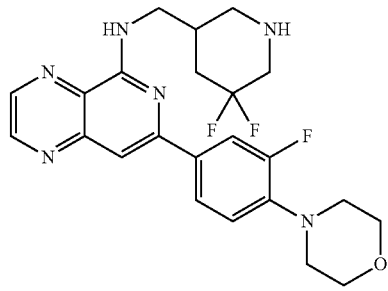 [SMILES: Fc1cc(-c2cc3nccnc3c(NCC3CNCC(F)(F)C3)n2)ccc1N1CCOCC1] |

-continued
| Compound | Structure |
|---|---|
| 203 | 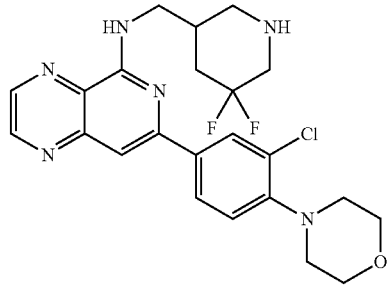 |
| 204 | 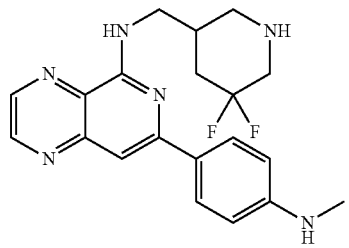 [SMILES: CNc1ccc(-c2cc3nccnc3c(NCC3CNCC(F)(F)C3)n2)cc1] |
| 205 | 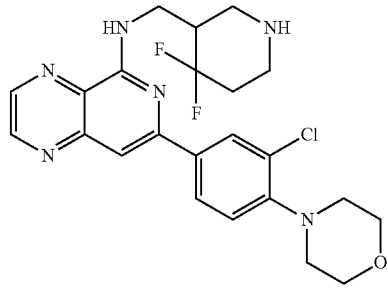 [SMILES: FC1(F)CCNCC1CNc1nc(-c2ccc(N3CCOCC3)c(Cl)c2)cc2nccnc12] |
| 206 | 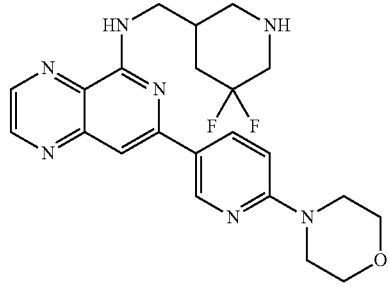 [SMILES: FC1(F)CNCC(CNc2nc(-c3ccc(N4CCOCC4)nc3)cc3nccnc23)C1] |
| 207 | 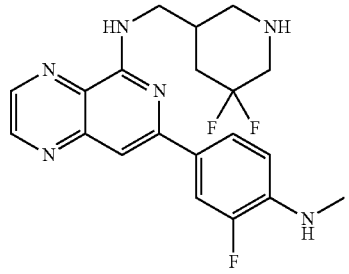 [SMILES: CNc1ccc(-c2cc3nccnc3c(NCC3CNCC(F)(F)C3)n2)cc1F] |

-continued

| Compound | Structure |
|---|---|
| 208 | 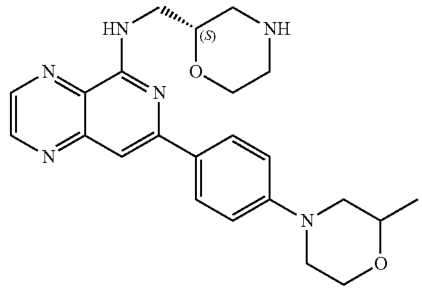 |
| 209 | 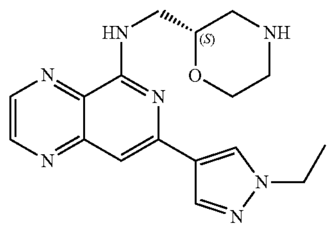 |
| 210 | 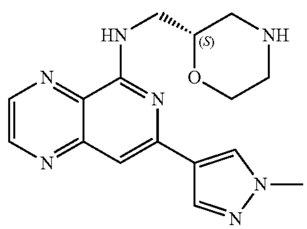 |
| 211 | 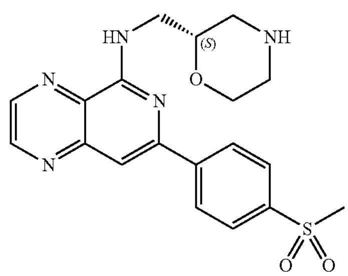 |
| 212 | 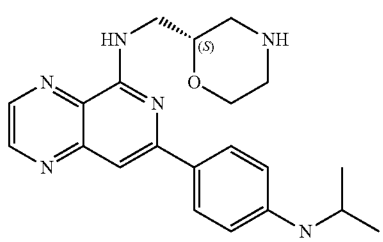 |
| 213 | 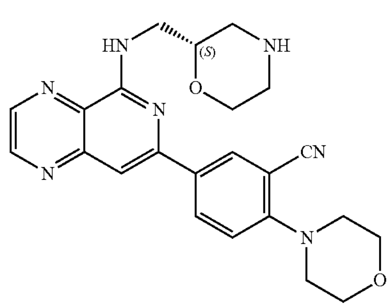 |

-continued

| Compound | Structure |
|---|---|
| 214 | 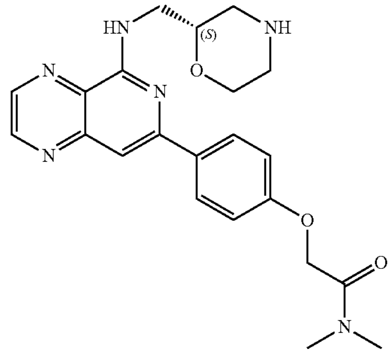 |
| 215 | 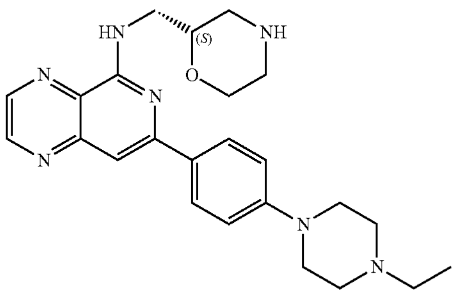 |
| 216 | 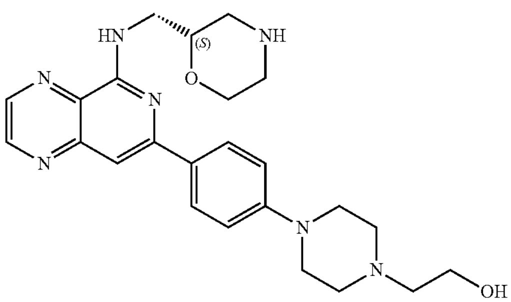 |
| 217 | 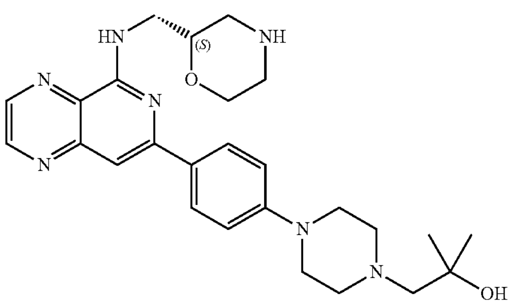 |
| 218 | 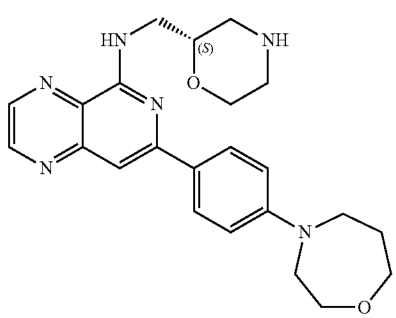 |

-continued

| Compound | Structure |
|---|---|
| 219 | 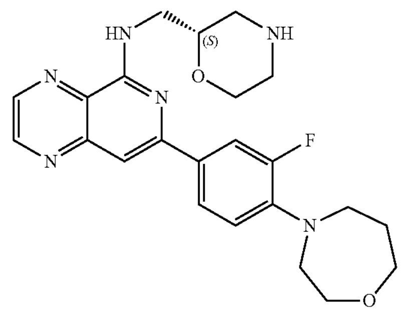 |
| 220 | 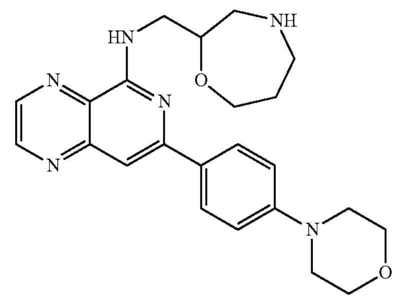 [SMILES: c1cnc2c(NCC3CNCCCO3)nc(-c3ccc(N4CCOCC4)cc3)cc2n1] |
| 221 | 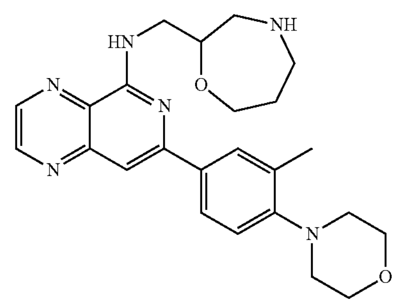 [SMILES: Cc1cc(-c2cc3nccnc3c(NCC3CNCCCO3)n2)ccc1N1CCOCC1] |
| 222 | 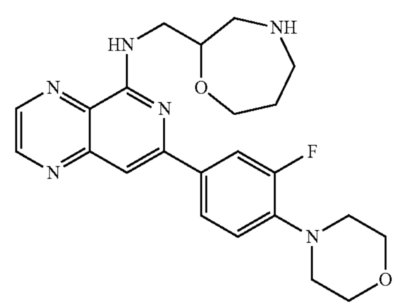 |
| 223 | 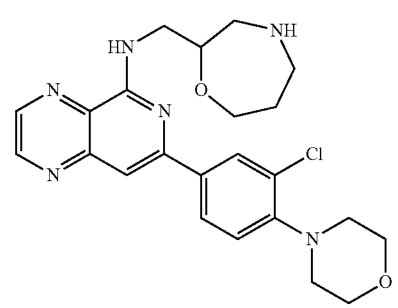 |

-continued
| Compound | Structure |
|---|---|
| 224 | 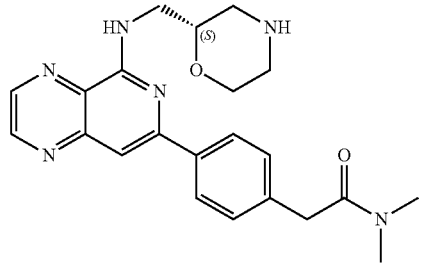 |
| 225 | 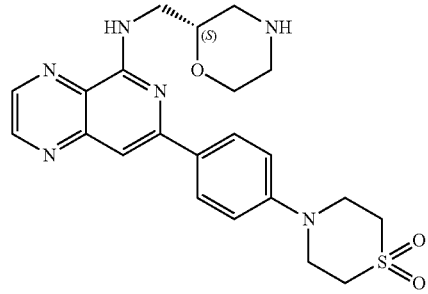 |
| 226 | 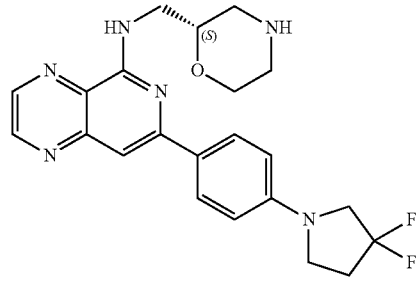 |
| 227 | 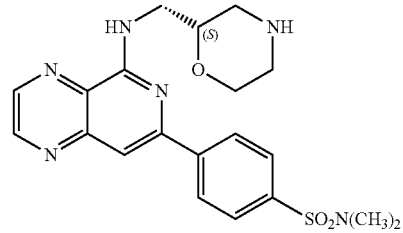 |
| 228 | 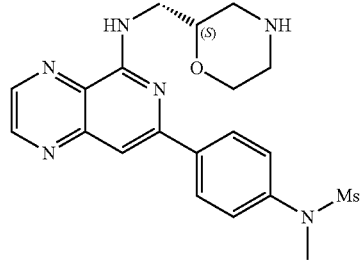 |

-continued

| Compound | Structure |
|---|---|
| 229 | 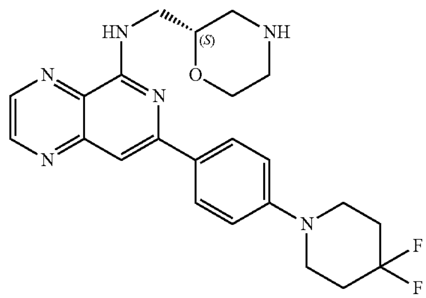 |
| 230 | 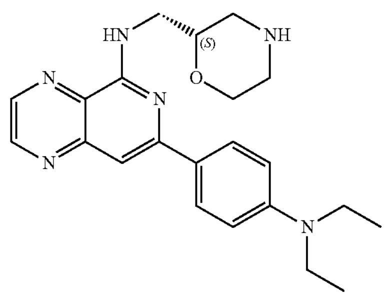 |
| 231 | 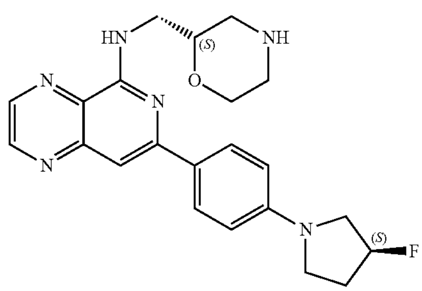 |
| 232, 233 | |

-continued

| Compound | Structure |
|---|---|
| 236 | 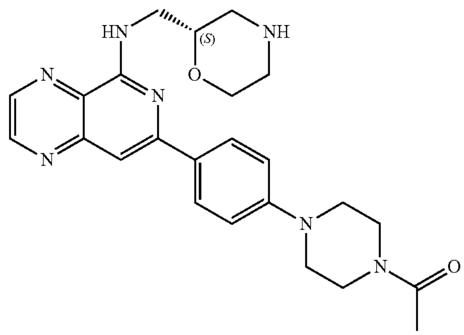 |
| 237 | 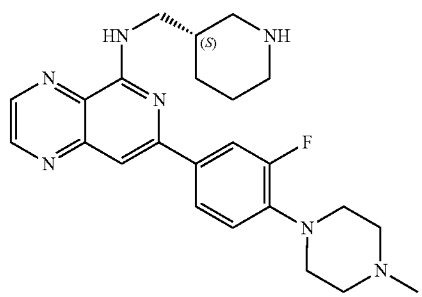 |
| 238 | 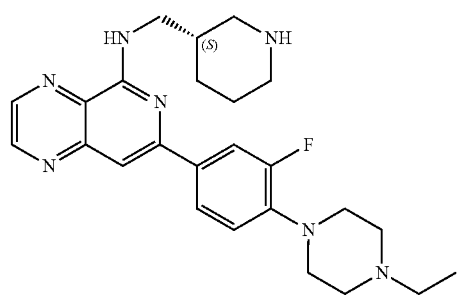 |
| 241 | 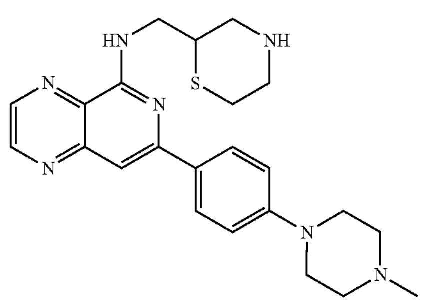 [SMILES: CN1CCN(c2ccc(-c3cc4nccnc4c(NCC4CNCCS4)n3)cc2)CC1] |
| 246 | 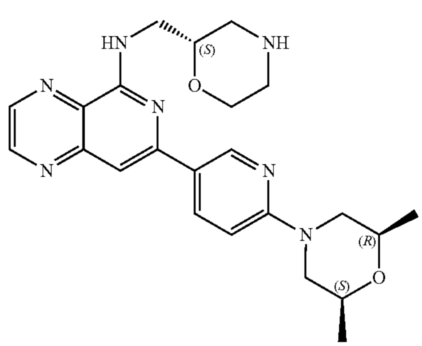 |

-continued

| Compound | Structure |
|---|---|
| 247 | 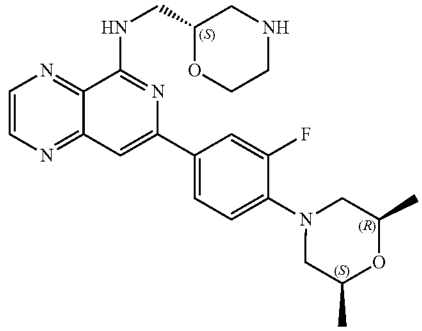 |
| 248 | 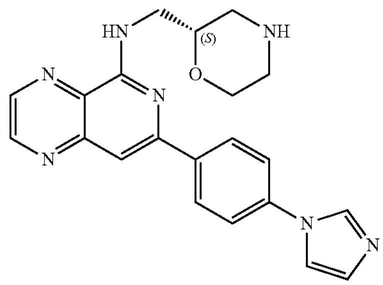 |
| 249 | 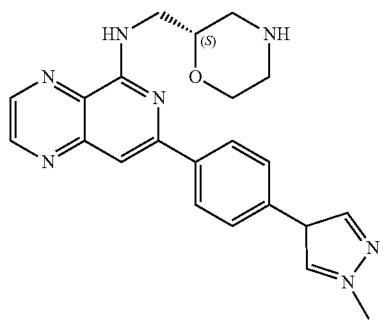 |
| 250 | 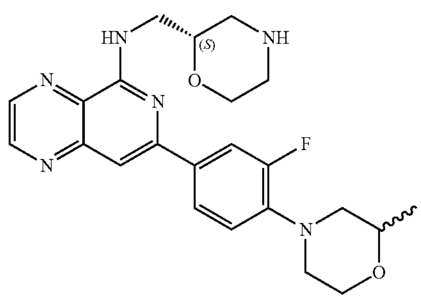 |
| 253 | 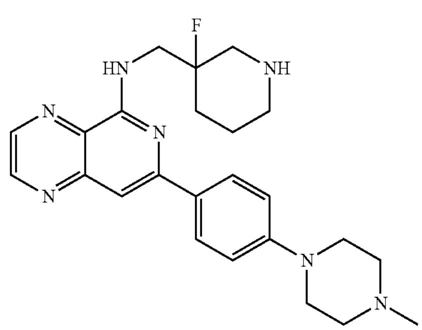 [SMILES: CN1CCN(c2ccc(-c3cc4nccnc4c(NCC4(F)CCCNC4)n3)cc2)CC1] |

-continued

| Compound | Structure |
|---|---|
| 256 | 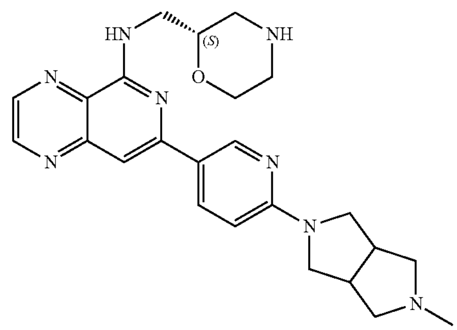 |
| 257 | 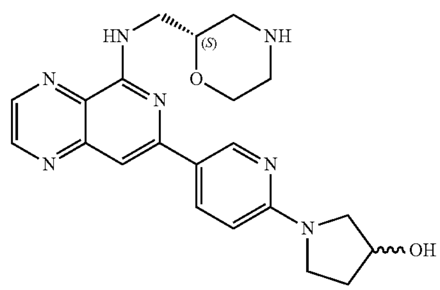 |
| 258 | 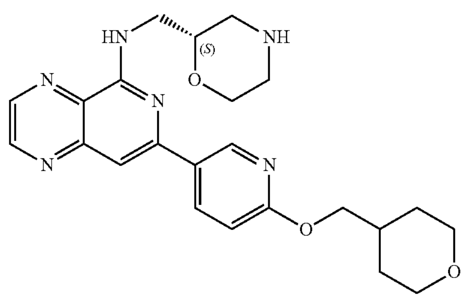 |
| 259 | 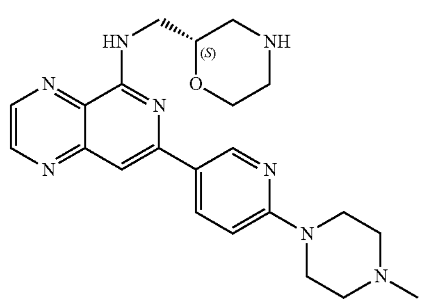 |
| 260 | 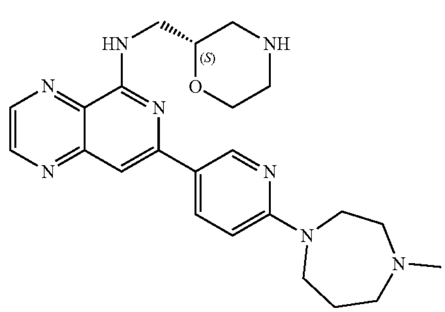 |

-continued
| Compound | Structure |
|---|---|
| 261 | 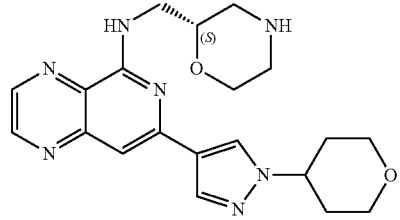 |
| 262 | 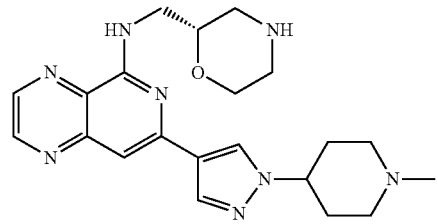 [SMILES: CN1CCC(n2cc(-c3cc4nccnc4c(NC[C@@H]4CNCCO4)n3)cn2)CC1] |
| 263 | 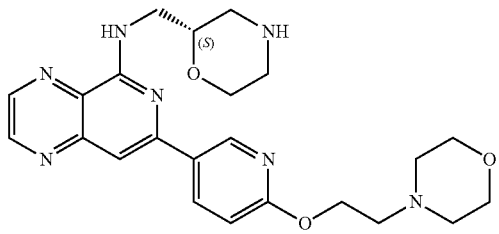 |
| 264 | 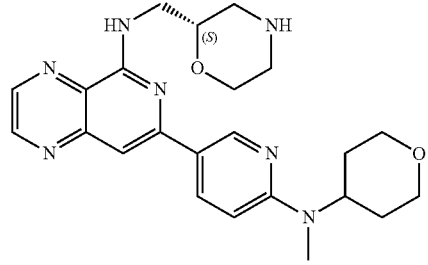 |
| 265 | 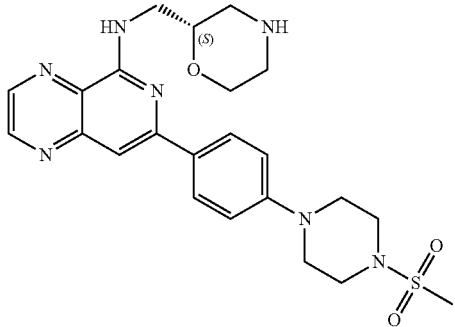 |

-continued

| Compound | Structure |
|---|---|
| 266 | 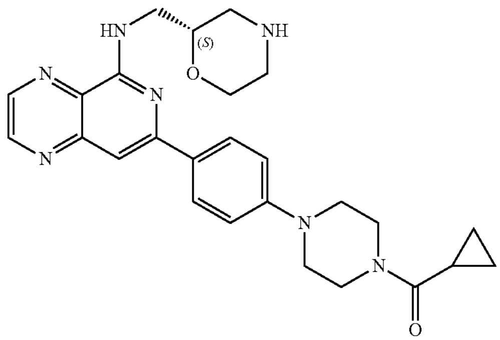 |
| 267 | 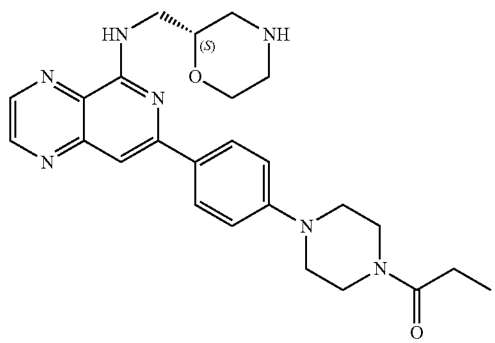 |
| 268 | 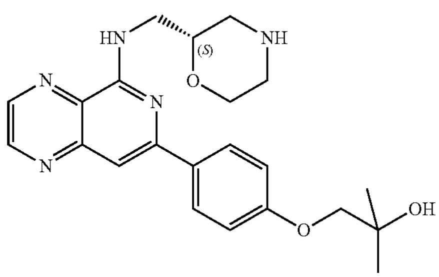 |
| 269 | 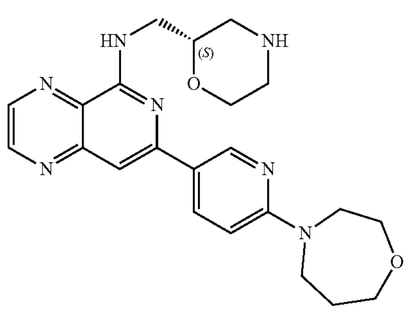 |
| 270 | 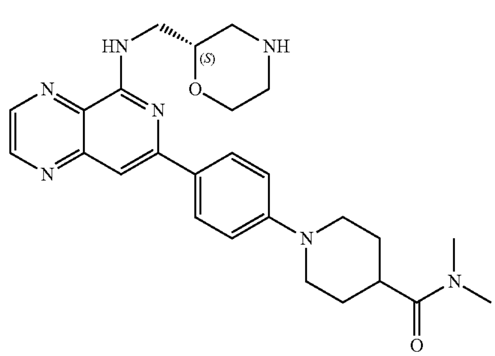 |

| Compound | Structure |
|---|---|
| 271 | 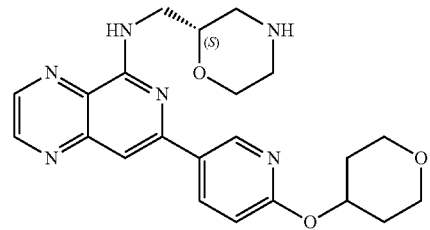 |
| 272 | 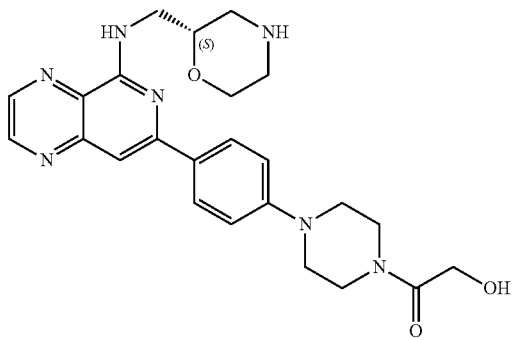 |
| 273 | 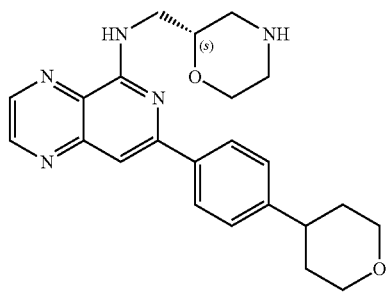 [SMILES: c1cnc2c(NC[C@@H]3CNCCO3)nc(-c3ccc(C4CCOCC4)cc3)cc2n1] |
| 274 | 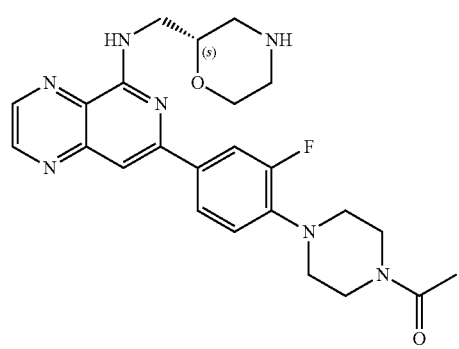 [SMILES: CC(=O)N1CCN(c2ccc(-c3cc4nccnc4c(NC[C@@H]4CNCCO4)n3)cc2F)CC1] |
| 275 | 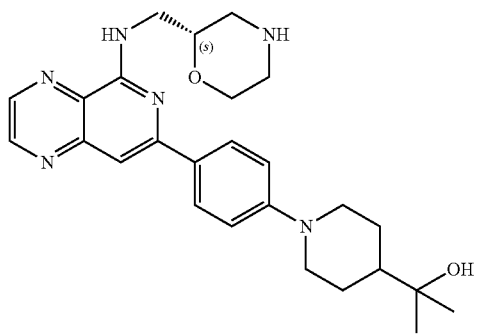 [SMILES: CC(C)(O)C1CCN(c2ccc(-c3cc4nccnc4c(NC[C@@H]4CNCCO4)n3)cc2)CC1] |

-continued

| Compound | Structure |
|---|---|
| 279 | 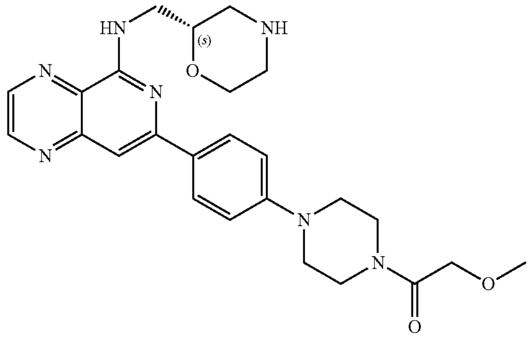 [SMILES: COCC(=O)N1CCN(c2ccc(-c3cc4nccnc4c(NC[C@@H]4CNCCO4)n3)cc2)CC1] |
| 280 | 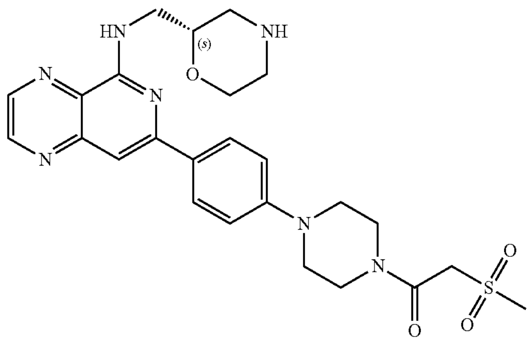 [SMILES: CS(=O)(=O)CC(=O)N1CCN(c2ccc(-c3cc4nccnc4c(NC[C@@H]4CNCCO4)n3)cc2)CC1] |
| 283 | 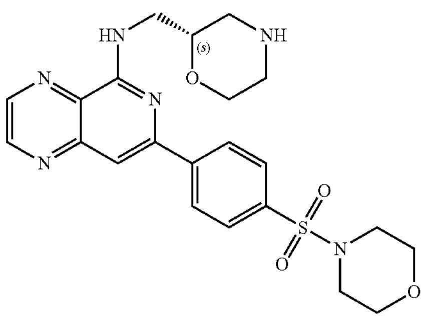 [SMILES: O=S(=O)(c1ccc(-c2cc3nccnc3c(NC[C@@H]3CNCCO3)n2)cc1)N1CCOCC1] |
| 284 | 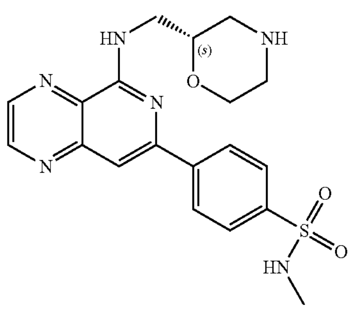 [SMILES: CNS(=O)(=O)c1ccc(-c2cc3nccnc3c(NC[C@@H]3CNCCO3)n2)cc1] |
| 285 | 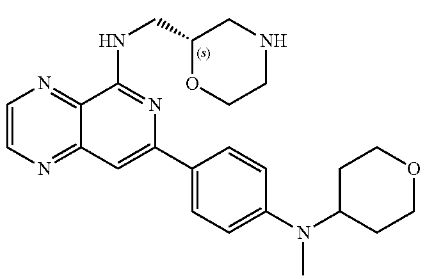 [SMILES: CN(c1ccc(-c2cc3nccnc3c(NC[C@@H]3CNCCO3)n2)cc1)C1CCOCC1] |

US 9,434,726 B2
455
456
-continued
| Compound | Structure |
|---|---|
| 286 | 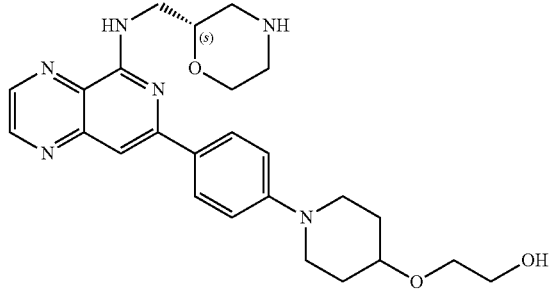 [SMILES: OCCOC1CCN(c2ccc(-c3cc4nccnc4c(NC[C@@H]4CNCCO4)n3)cc2)CC1] |
| 287 | 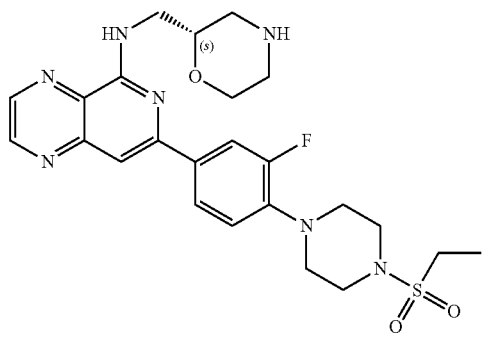 [SMILES: CCS(=O)(=O)N1CCN(c2ccc(-c3cc4nccnc4c(NC[C@@H]4CNCCO4)n3)cc2F)CC1] |
| 288 | 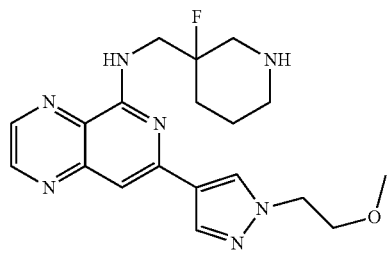 [SMILES: COCCn1cc(-c2cc3nccnc3c(NCC3(F)CCCNC3)n2)cn1] |
| 290 | 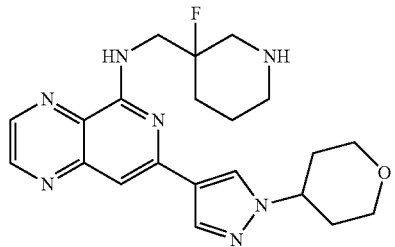 [SMILES: FC1(CNc2nc(-c3cnn(C4CCOCC4)c3)cc3nccnc23)CCCNC1] |
| 293 | 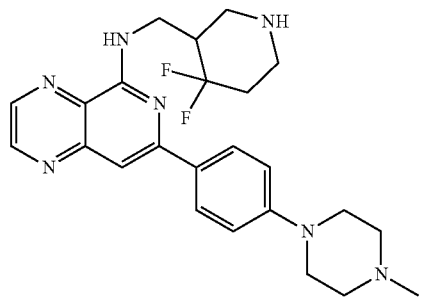 [SMILES: CN1CCN(c2ccc(-c3cc4nccnc4c(NCC4CNCCC4(F)F)n3)cc2)CC1] |

-continued
| Compound | Structure |
|---|---|
| 303 | 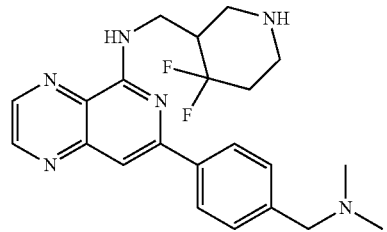 [SMILES: CN(C)Cc1ccc(-c2cc3nccnc3c(NCC3CNCCC3(F)F)n2)cc1] |
| 304 | 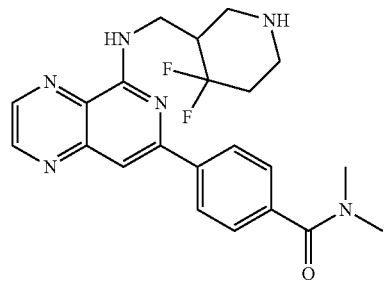 [SMILES: CN(C)C(=O)c1ccc(-c2cc3nccnc3c(NCC3CNCCC3(F)F)n2)cc1] |
| 305 | 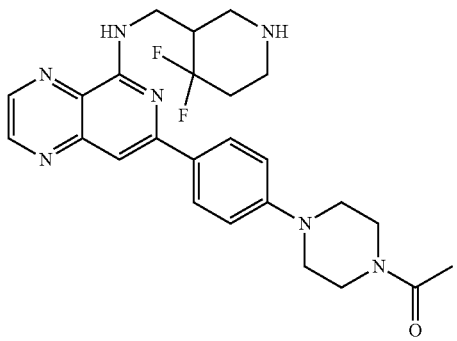 [SMILES: CC(=O)N1CCN(c2ccc(-c3cc4nccnc4c(NCC4CNCCC4(F)F)n3)cc2)CC1] |
| 306 | 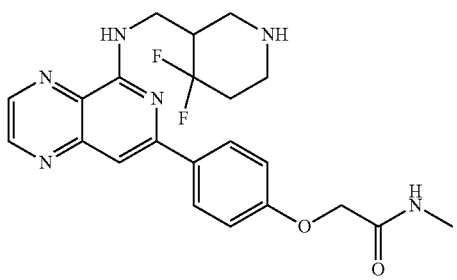 [SMILES: CNC(=O)COc1ccc(-c2cc3nccnc3c(NCC3CNCCC3(F)F)n2)cc1] |
| 308 | 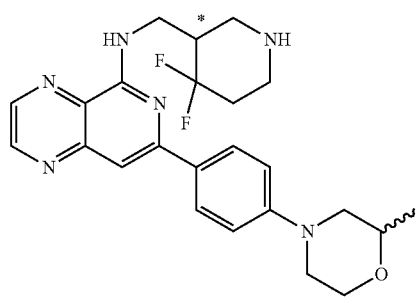 [SMILES: CC1CN(c2ccc(-c3cc4nccnc4c(NCC4CNCCC4(F)F)n3)cc2)CCO1] |

| Compound | Structure |
|---|---|
| 309 | 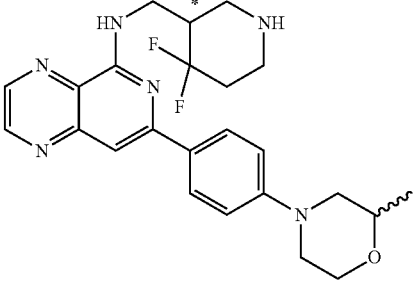 |
| 310 | 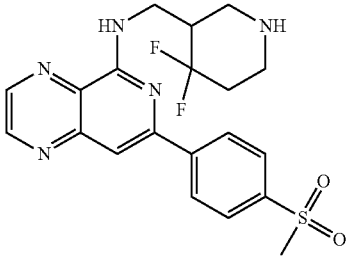 [SMILES: CS(=O)(=O)c1ccc(-c2cc3nccnc3c(NCC3CNCCC3(F)F)n2)cc1] |
| 312 | 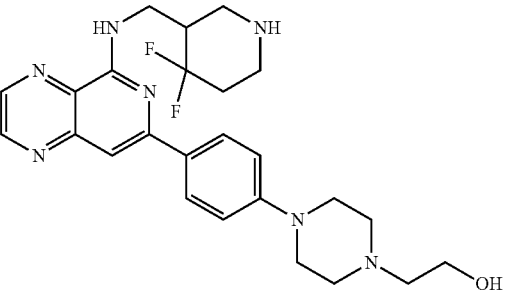 [SMILES: OCCN1CCN(c2ccc(-c3cc4nccnc4c(NCC4CNCCC4(F)F)n3)cc2)CC1] |
| 313 | 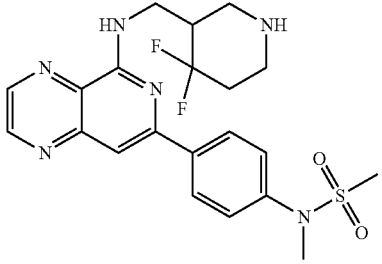 [SMILES: CN(c1ccc(-c2cc3nccnc3c(NCC3CNCCC3(F)F)n2)cc1)S(C)(=O)=O] |
| 314 | 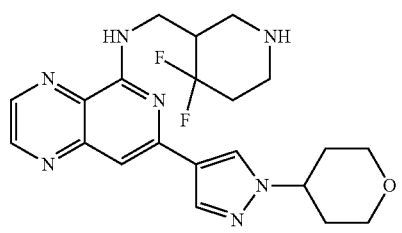 [SMILES: FC1(F)CCNCC1CNc1nc(-c2cnn(C3CCOCC3)c2)cc2nccnc12] |
| 315 | 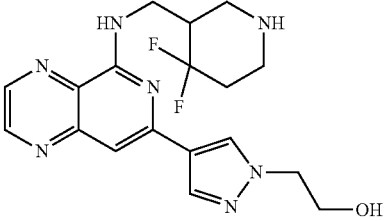 [SMILES: OCCn1cc(-c2cc3nccnc3c(NCC3CNCCC3(F)F)n2)cn1] |

-continued
| Compound | Structure |
|---|---|
| 316 | 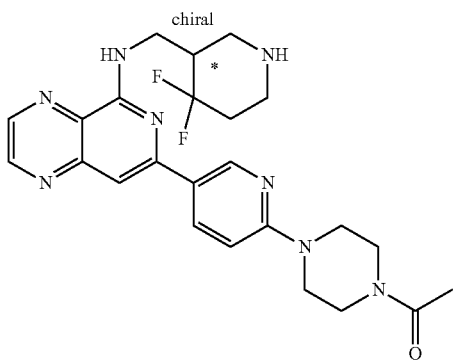 [SMILES: CC(=O)N1CCN(c2ccc(-c3cc4nccnc4c(NCC4CNCCC4(F)F)n3)cn2)CC1] |
| 317 | 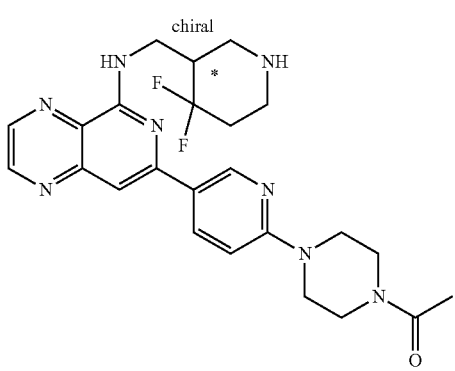 [SMILES: CC(=O)N1CCN(c2ccc(-c3cc4nccnc4c(NCC4CNCCC4(F)F)n3)cn2)CC1] |
| 318 | 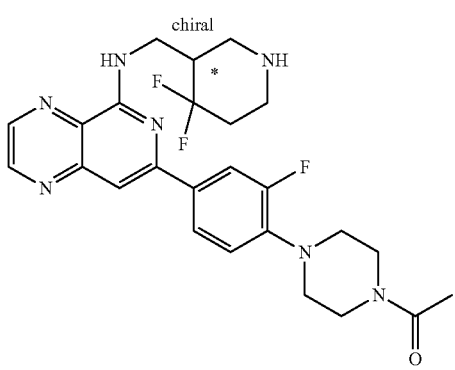 [SMILES: CC(=O)N1CCN(c2ccc(-c3cc4nccnc4c(NCC4CNCCC4(F)F)n3)cc2F)CC1] |
| 319 | 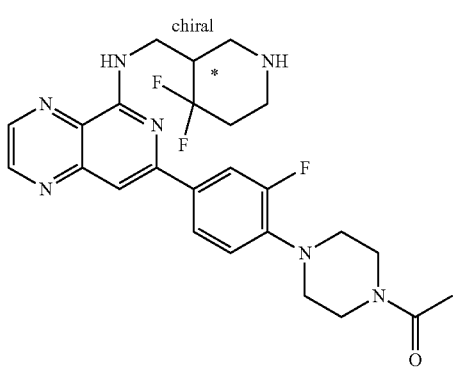 [SMILES: CC(=O)N1CCN(c2ccc(-c3cc4nccnc4c(NCC4CNCCC4(F)F)n3)cc2F)CC1] |

-continued
| Compound | Structure |
|---|---|
| 320 | 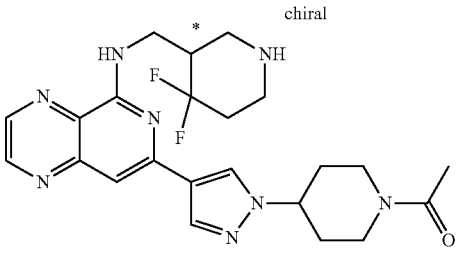 [SMILES: CC(=O)N1CCC(n2cc(-c3cc4nccnc4c(NCC4CNCCC4(F)F)n3)cn2)CC1] chiral |
| 321 | 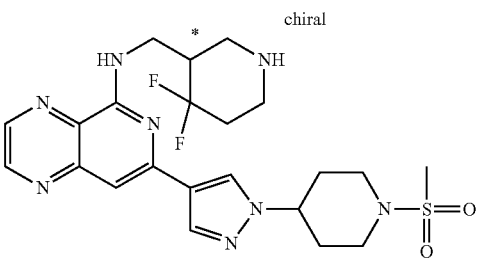 [SMILES: CS(=O)(=O)N1CCC(n2cc(-c3cc4nccnc4c(NCC4CNCCC4(F)F)n3)cn2)CC1] chiral |
| 322 | 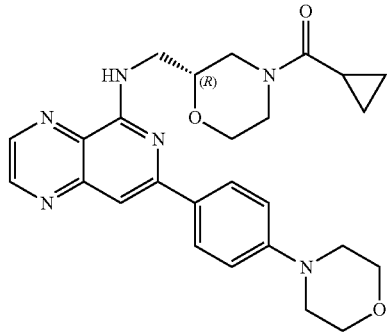 |
| 323 | 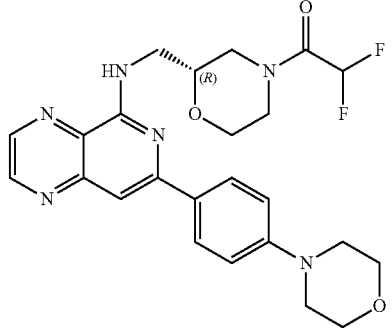 |
| 324 | 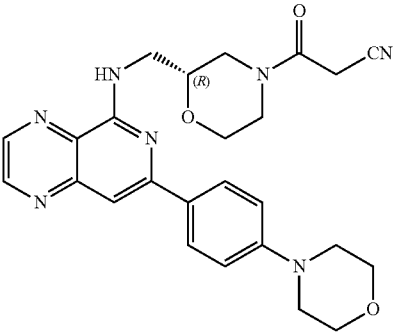 |

-continued
| Compound | Structure |
|---|---|
| 325 | 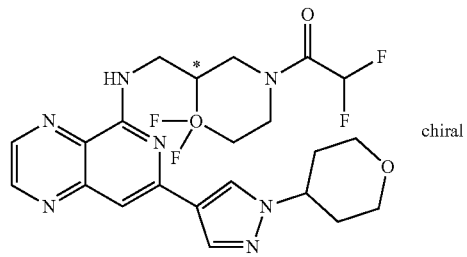 chiral |
| 326 | 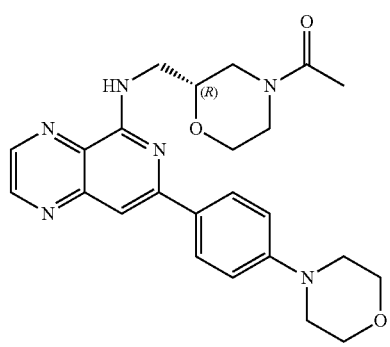 |
| 327 | 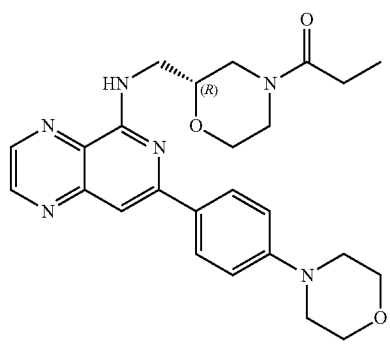 |
| 328 | 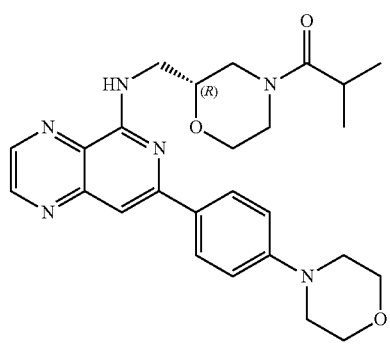 |

-continued
| Compound | Structure |
|---|---|
| 329 | 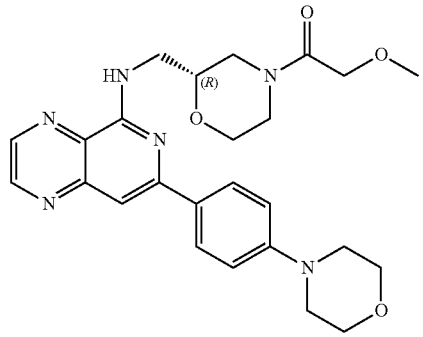 |
| 330 | 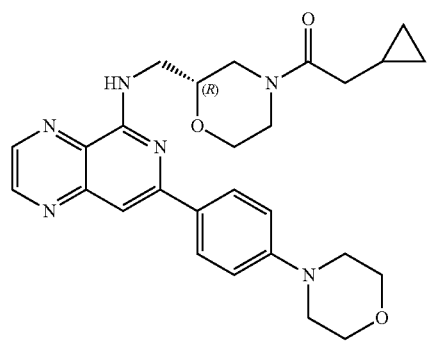 |
| 331 | 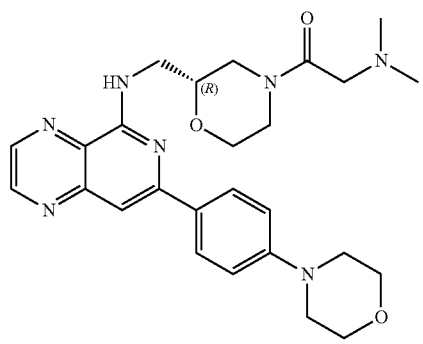 |
| 332 | 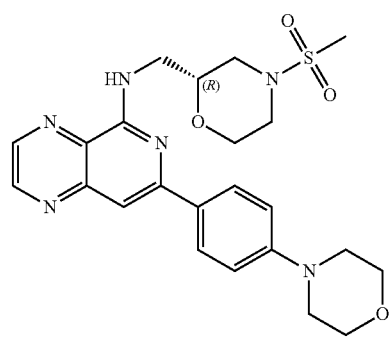 |

-continued
| Compound | Structure |
|---|---|
| 333 | 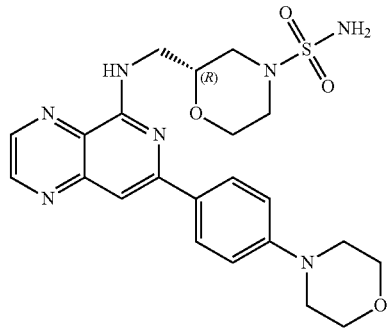 |
| 334 | 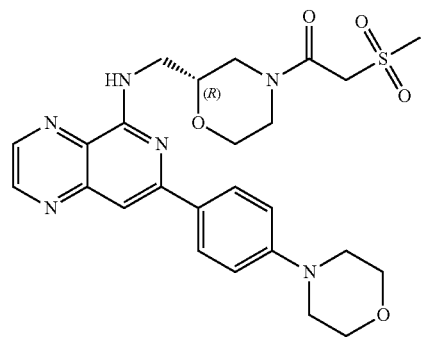 |
| 335 | 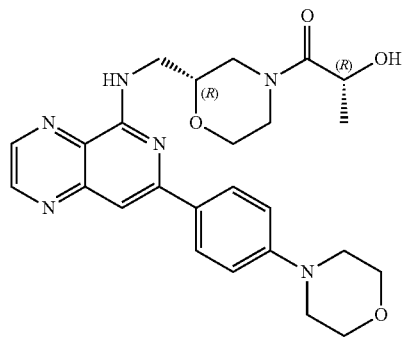 |
| 336 | 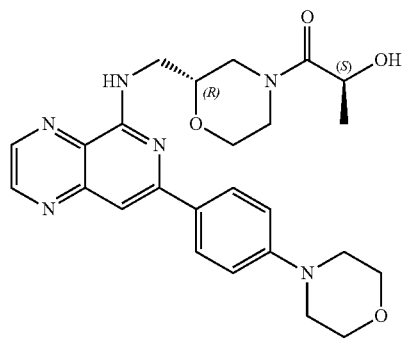 |

| Compound | Structure |
|---|---|
| 337 | 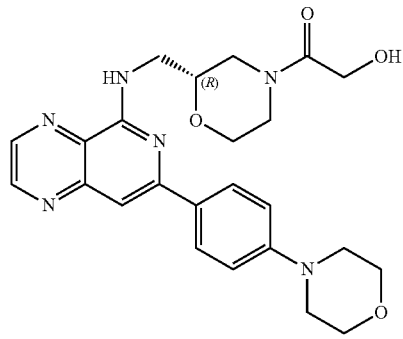 |
| 338 | 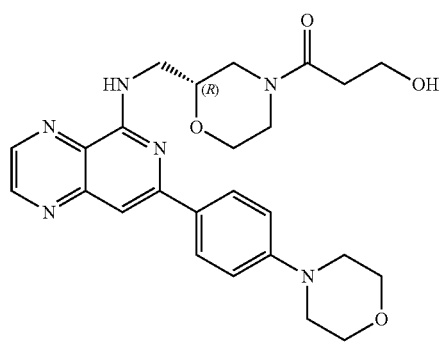 |
| 339 | 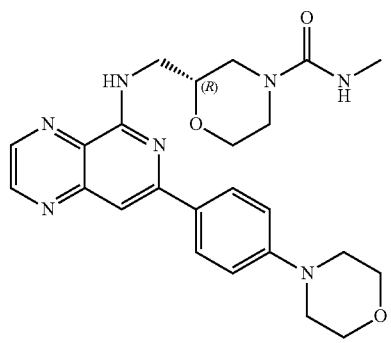 |
| 340 | 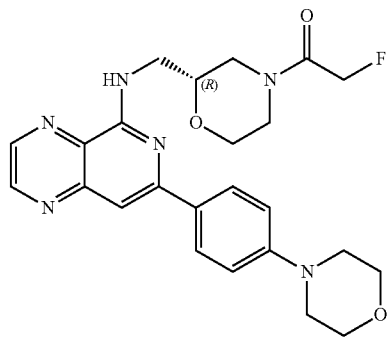 |

| Compound | Structure |
|---|---|
| 341 | 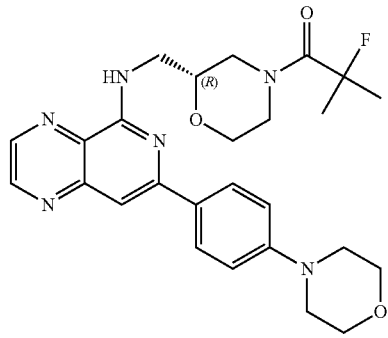 |
| 342 | 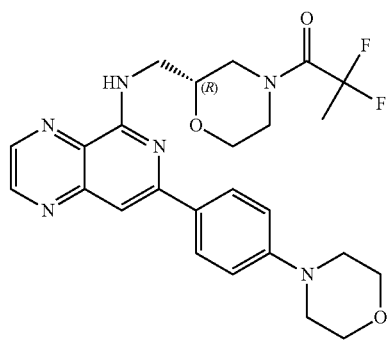 |
| 343 | 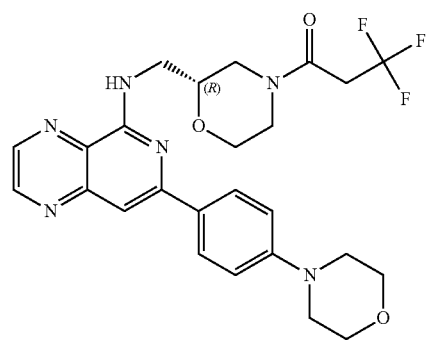 |
| 344 | 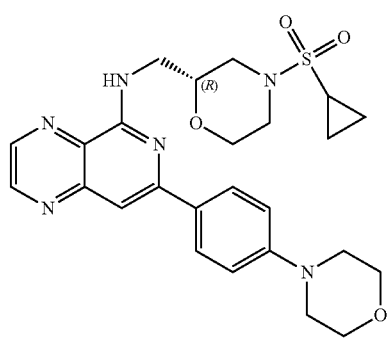 |

-continued
| Compound | Structure |
|---|---|
| 345 | 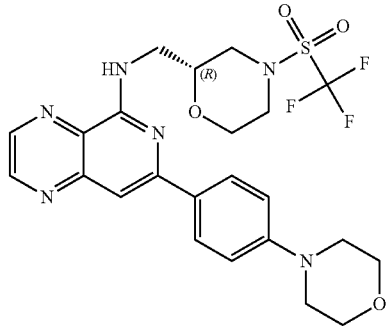 |
| 346 | 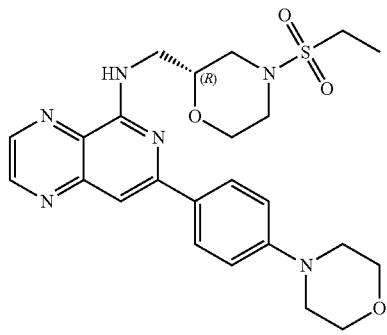 |
| 347 | 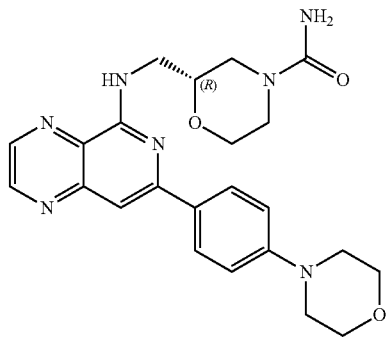 |
| 348 | 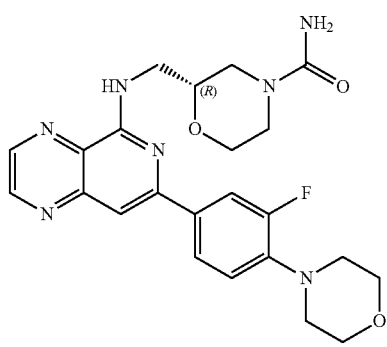 |

-continued
| Compound | Structure |
|---|---|
| 349 | 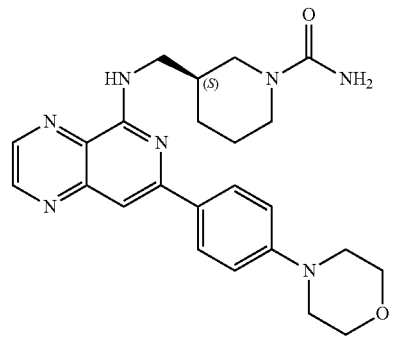 |
| 350 | 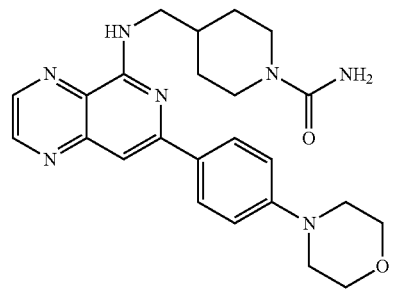 [SMILES: NC(=O)N1CCC(CNc2nc(-c3ccc(N4CCOCC4)cc3)cc3nccnc23)CC1] |
| 351 | 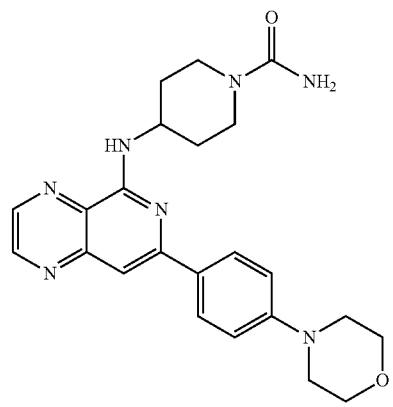 [SMILES: NC(=O)N1CCC(Nc2nc(-c3ccc(N4CCOCC4)cc3)cc3nccnc23)CC1] |
| 352 | 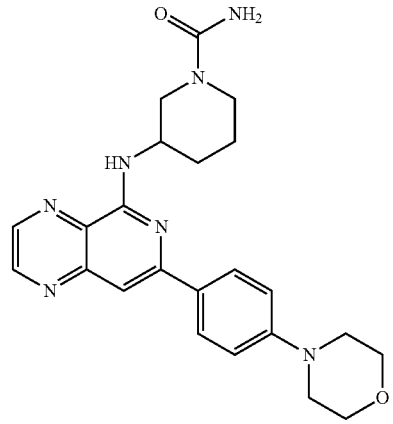 [SMILES: NC(=O)N1CCCC(Nc2nc(-c3ccc(N4CCOCC4)cc3)cc3nccnc23)C1] |

| Compound | Structure |
|---|---|
| 353 | 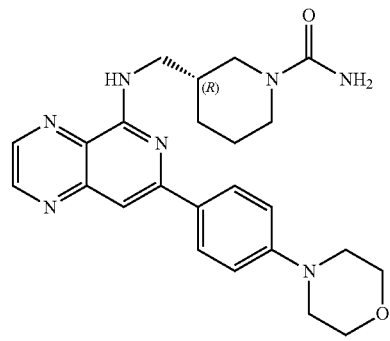 |
| 354 | 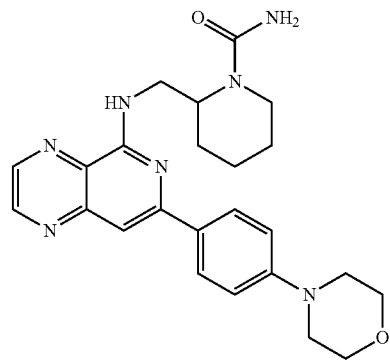 [SMILES: NC(=O)N1CCCCC1CNc1nc(-c2ccc(N3CCOCC3)cc2)cc2nccnc12] |
| 355 | 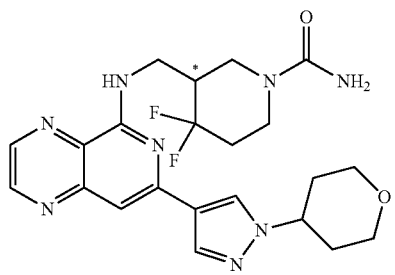 |
| 356 | 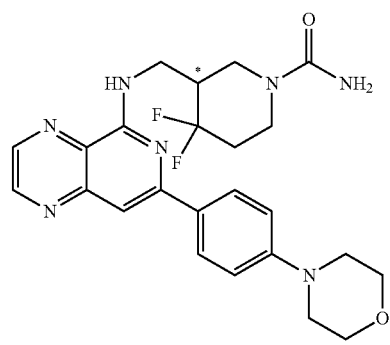 |

-continued
| Compound | Structure |
|---|---|
| 357 | 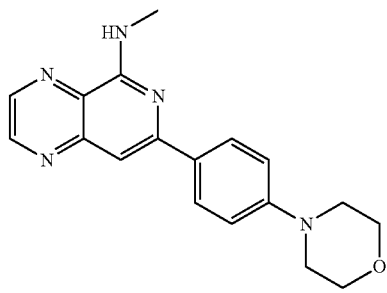 [SMILES: CNc1nc(-c2ccc(N3CCOCC3)cc2)cc2nccnc12] |
| 358 | 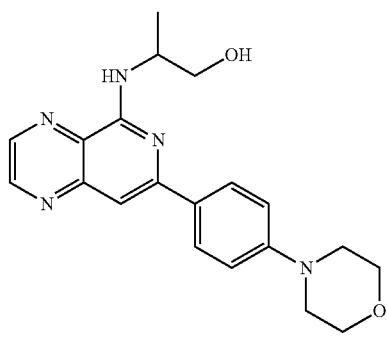 [SMILES: CC(CO)Nc1nc(-c2ccc(N3CCOCC3)cc2)cc2nccnc12] |
| 359 | 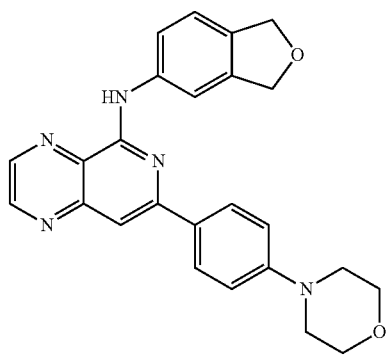 [SMILES: c1cnc2c(Nc3ccc4c(c3)COC4)nc(-c3ccc(N4CCOCC4)cc3)cc2n1] |
| 360 | 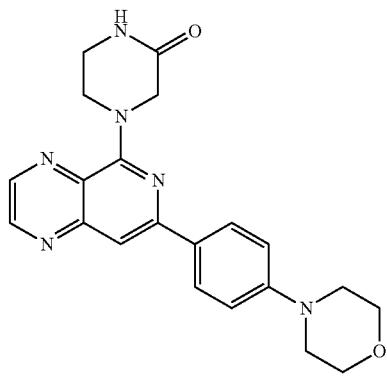 [SMILES: O=C1CN(c2nc(-c3ccc(N4CCOCC4)cc3)cc3nccnc23)CCN1] |

-continued
| Compound | Structure |
|---|---|
| 361 | 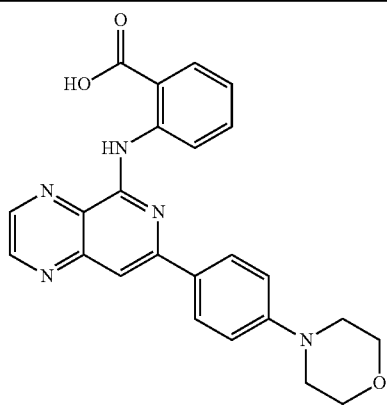 |
| 362 | 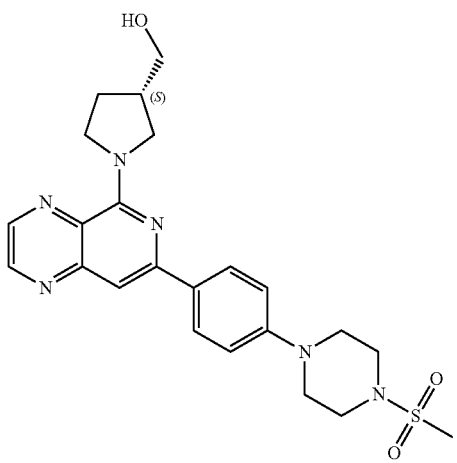 |
| 363 | 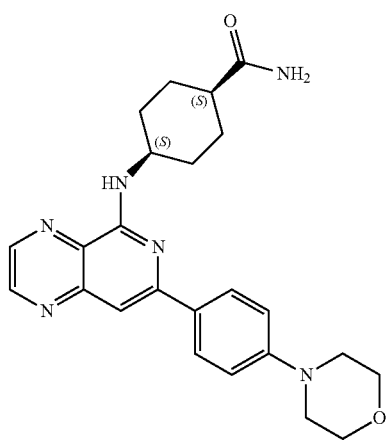 |
| 364 | 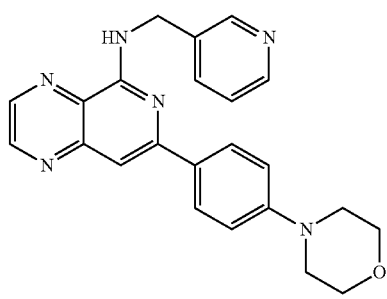 [SMILES: c1cncc(CNc2nc(-c3ccc(N4CCOCC4)cc3)cc3nccnc23)c1] |

-continued
| Compound | Structure |
|---|---|
| 365 | 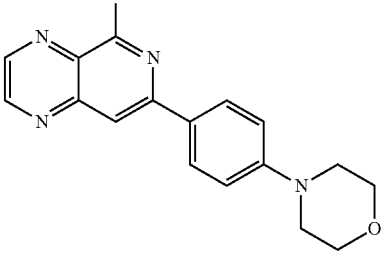 |
| 366 | 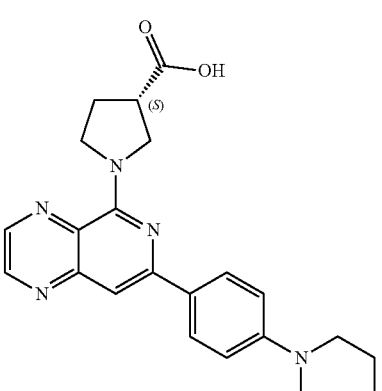 |
| 367 | 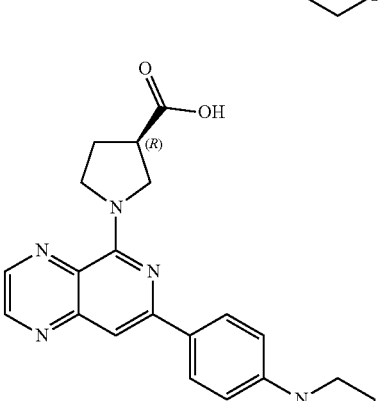 |
| 372, 373 | 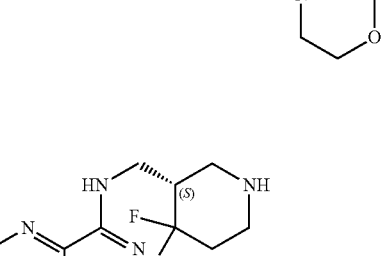 |

| Compound | Structure |
|---|---|
| | 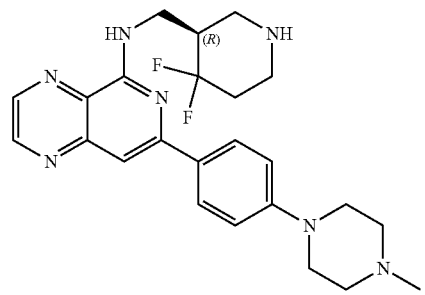 |
| 380, 381 | 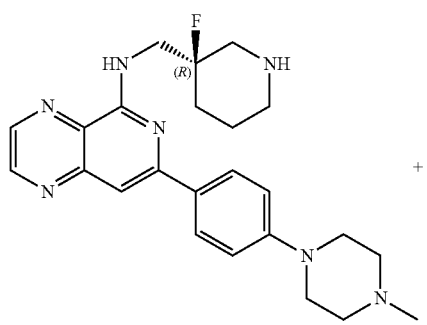 |
| | 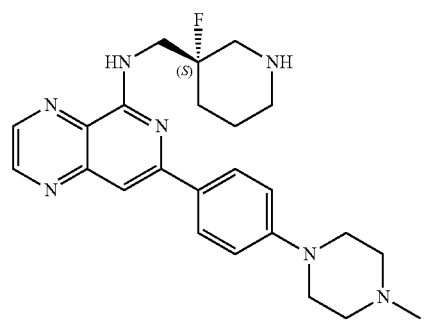 |
| 384, 385 | 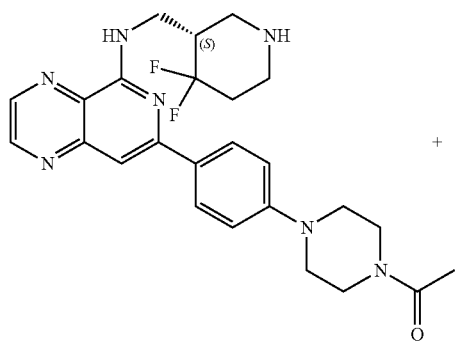 |

| Compound | Structure |
|---|---|
| | 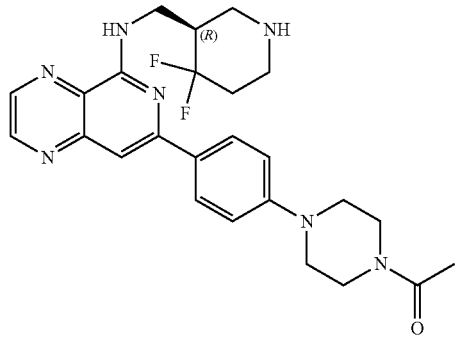 |
| 386, 387 | 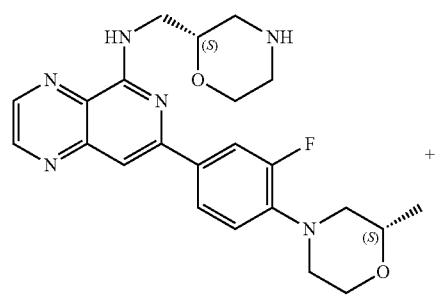 + 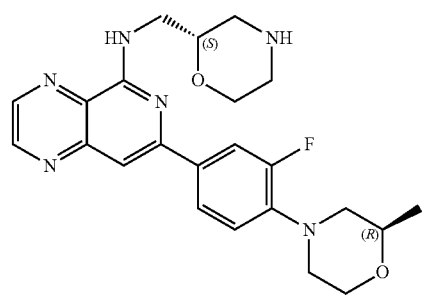 |
| 388, 389 | 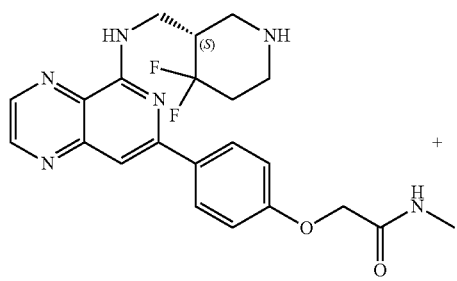 + 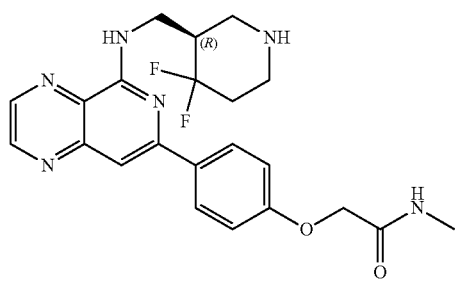 |

-continued
| Compound | Structure |
|---|---|
| 390, 391 | 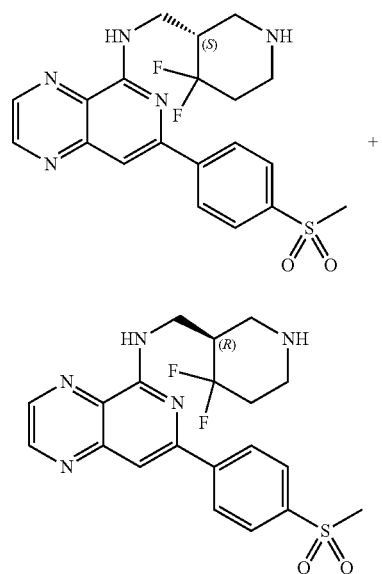 |
| 394, 395 | 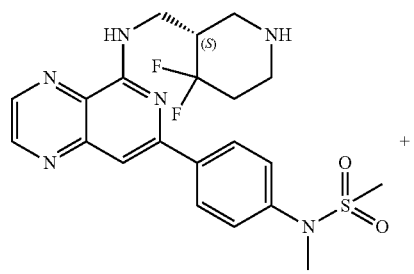 |
| 396, 397 | 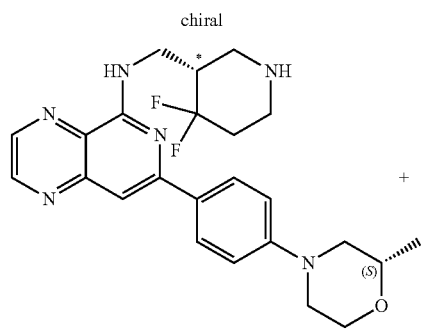 |

| Compound | Structure |
|---|---|
| 398, 399 | 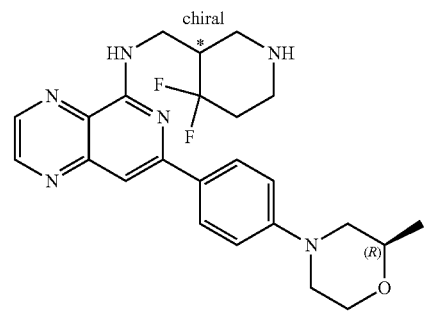 |
| | 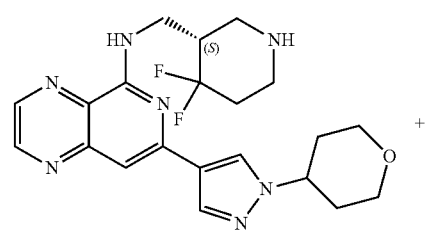 |
| | 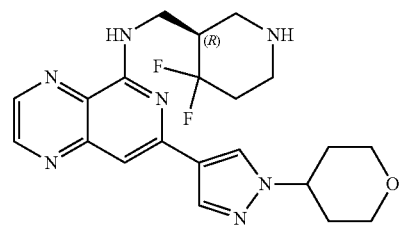 |
| 400 | 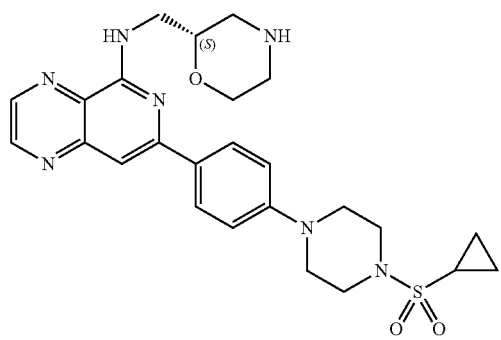 |
| 401 | 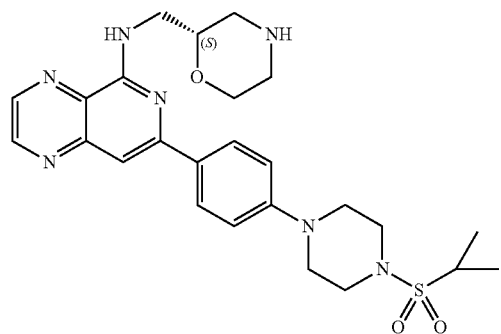 |

| Compound | Structure |
|---|---|
| 402 | 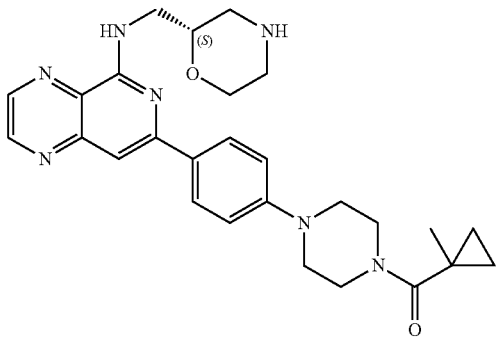 |
| 403 | 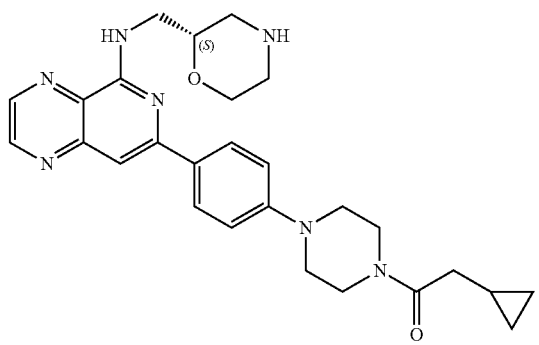 |
| 404 | 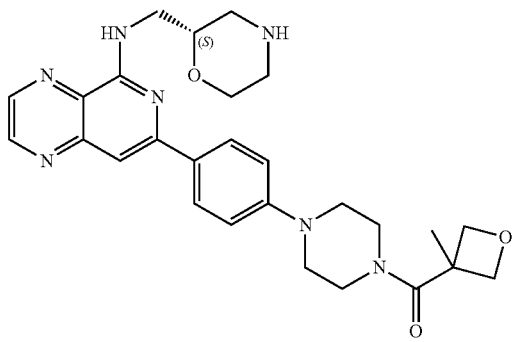 |
| 405 | 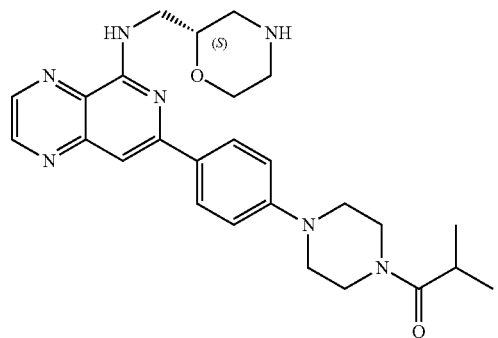 |

-continued
| Compound | Structure |
|---|---|
| 406 | 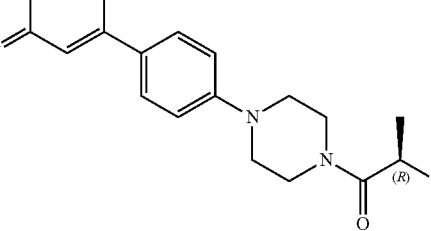 |
| 407 | 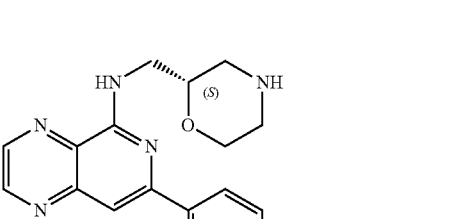 |
| 408 | 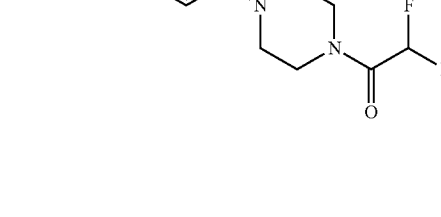 |
| 409 | 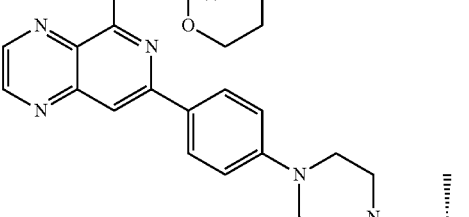 |

| Compound | Structure |
|---|---|
| 410 | 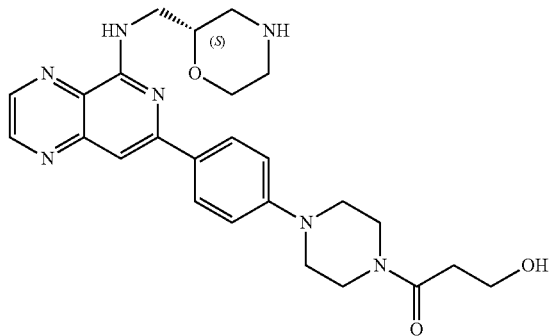 |
| 411 | 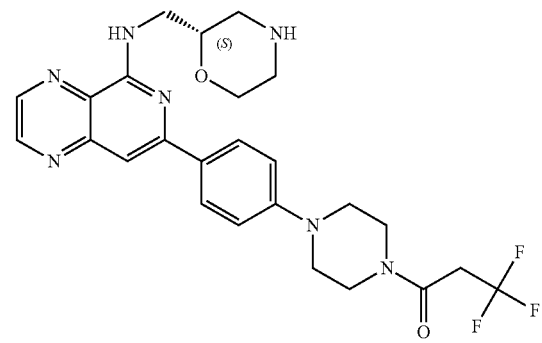 |
| 412 | 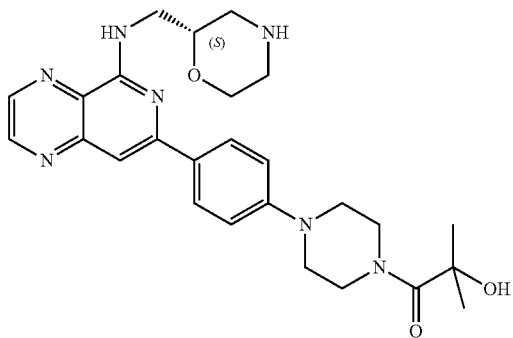 |
| 413 | 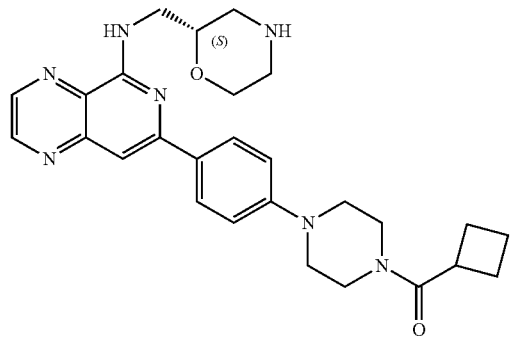 |

-continued
| Compound | Structure |
|---|---|
| 414 | 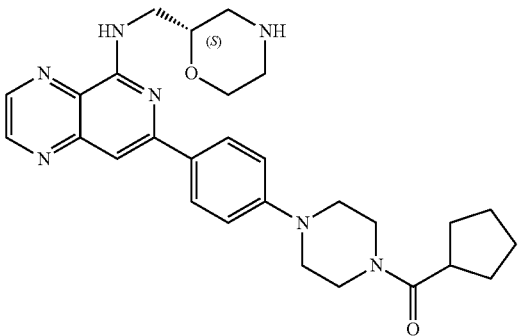 |
| 415 | 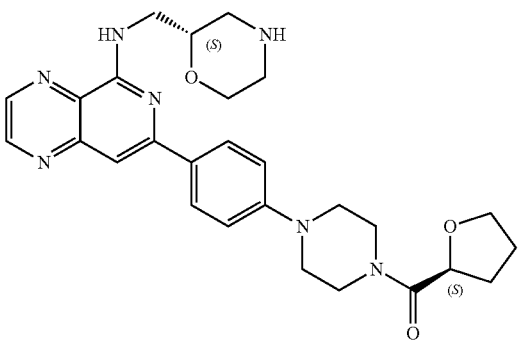 |
| 416 | 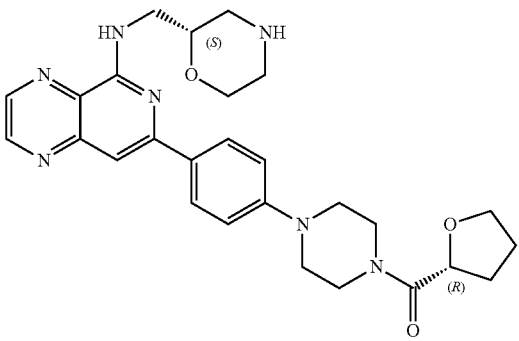 |
| 417 | 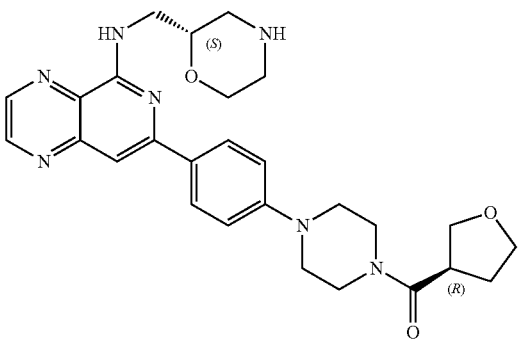 |

| Compound | Structure |
|---|---|
| 418 | 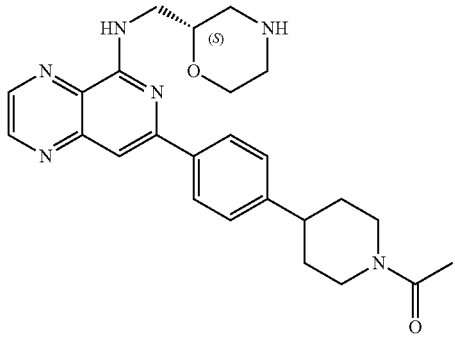 |
| 419 | 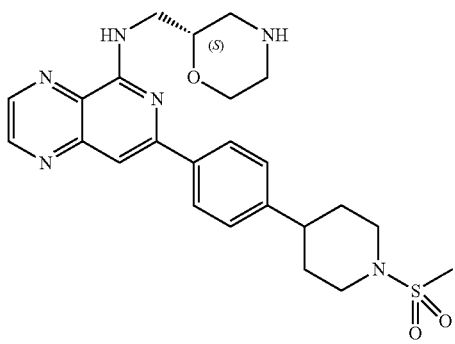 |
| 420 | 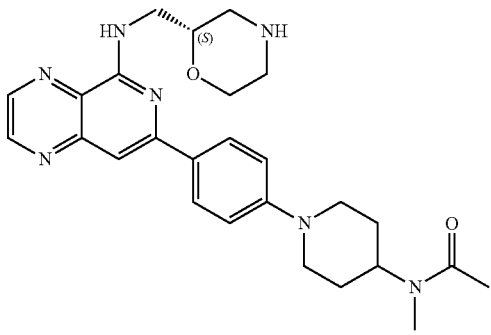 |
| 421 | 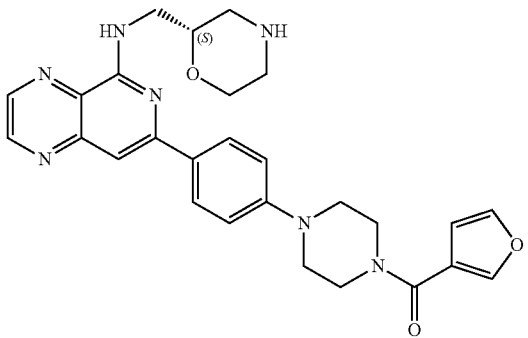 |

| Compound | Structure |
|---|---|
| 422 | 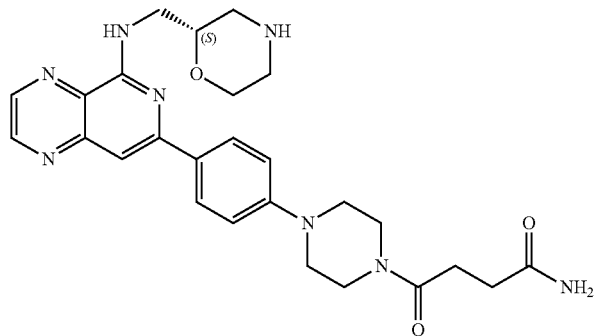 |
| 423 | 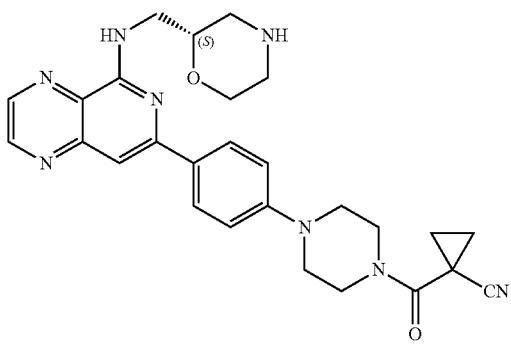 |
| 424 | 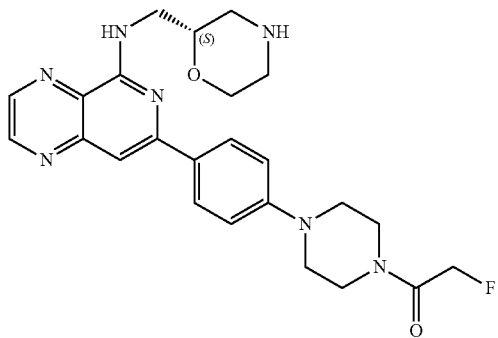 |
| 425 | 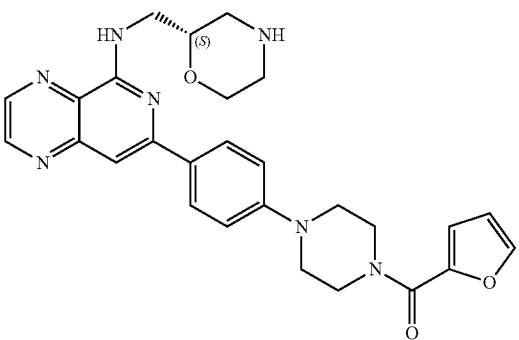 |

-continued
| Compound | Structure |
|---|---|
| 426 | 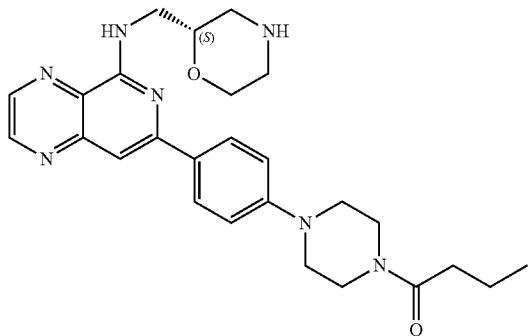 |
| 427 | 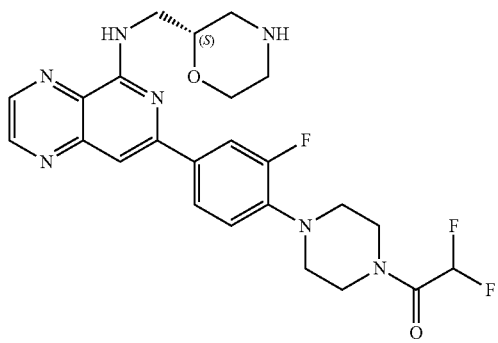 |
| 428 | 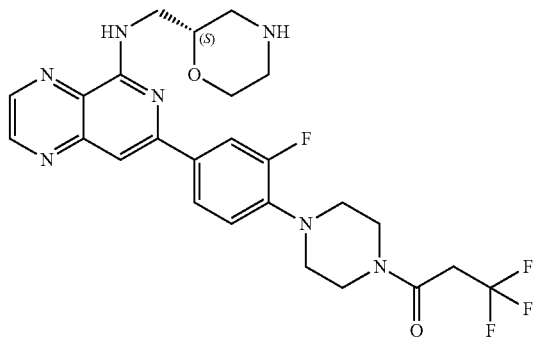 |
| 429 | 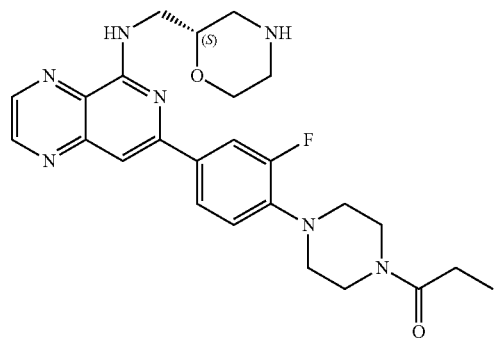 |

-continued

| Compound | Structure |
|---|---|
| 430 | 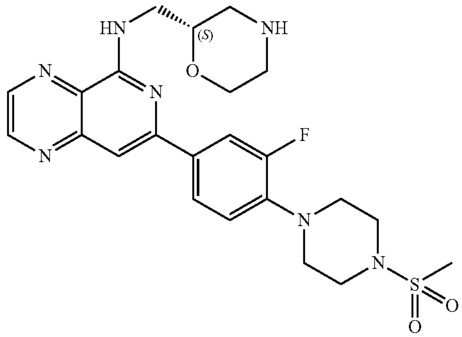 |
| 431 | 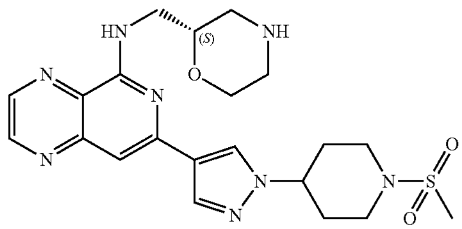 |
| 432 | 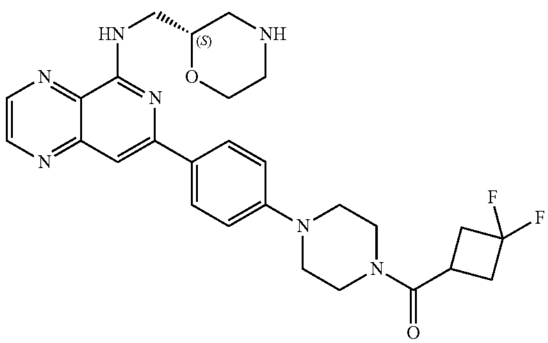 |
| 433 | 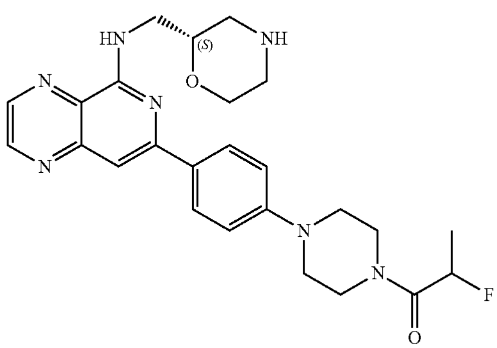 |
| 434 | 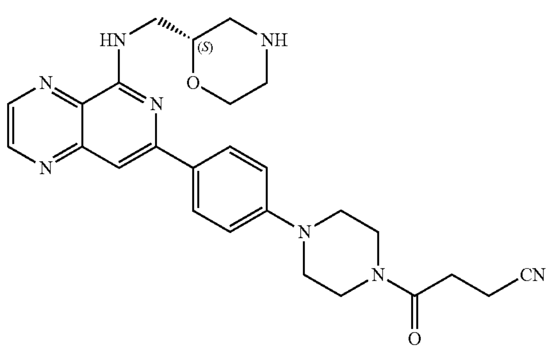 |

-continued
| Compound | Structure |
|---|---|
| 435 | 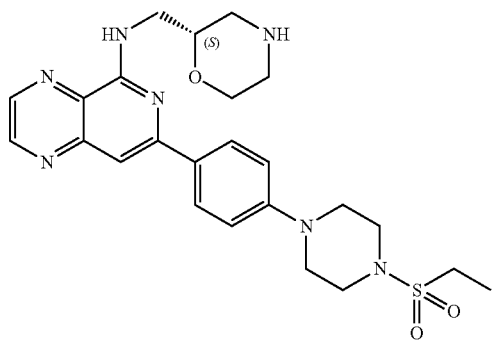 |
| 436 | 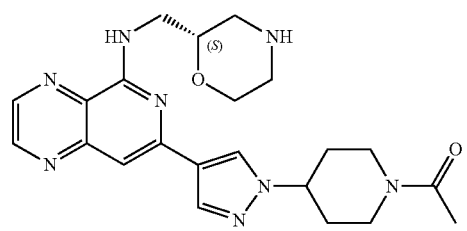 |
| 437 | 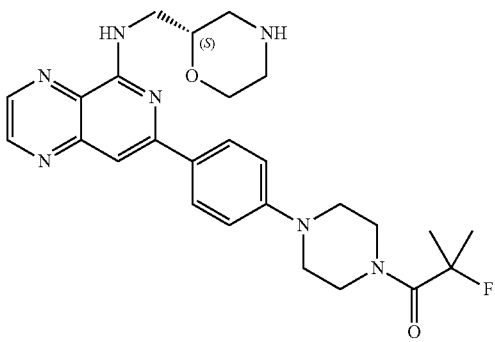 |
| 438 | 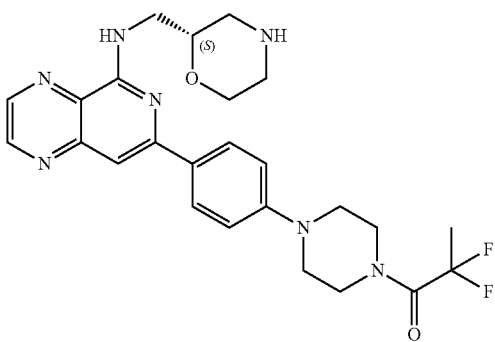 |

-continued

| Compound | Structure |
|---|---|
| 439 | 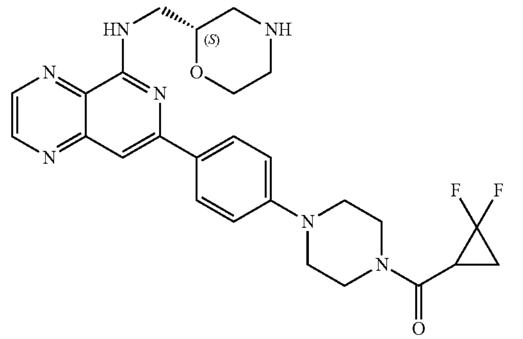 |
| 440 | 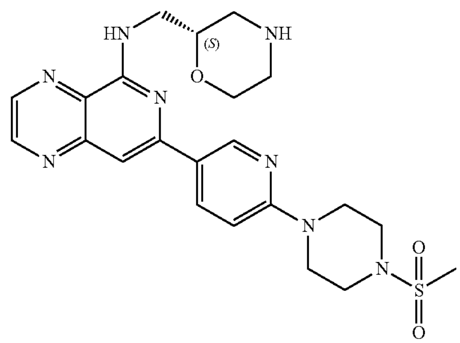 |
| 441 | 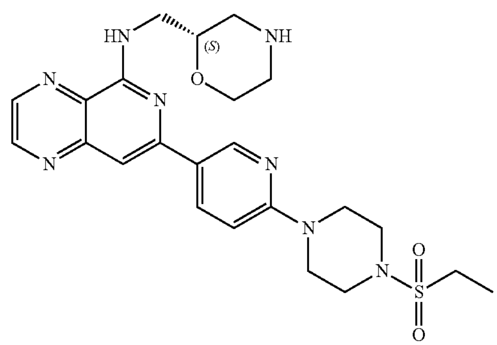 |
| 442 | chiral |

-continued
| Compound | Structure |
|---|---|
| 443 | 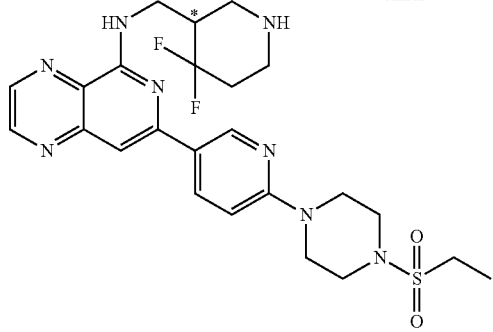 chiral |
| 444 | 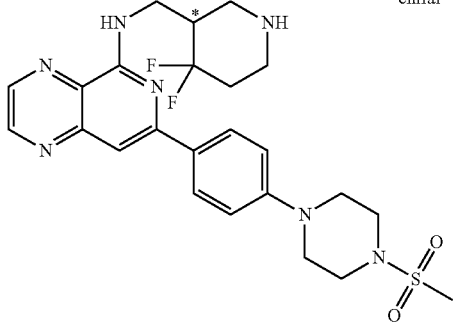 chiral |
| 445 | 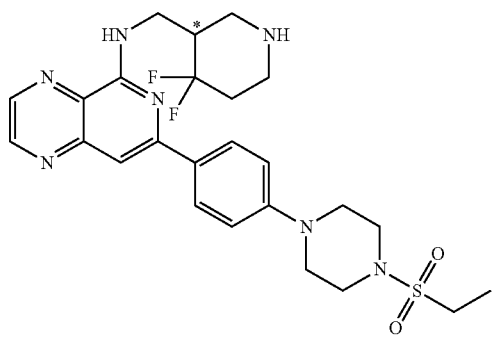 chiral |
| 446 | 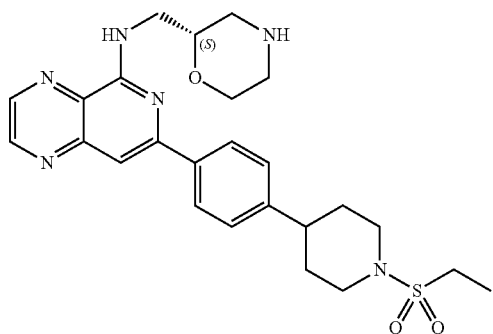 |

| Compound | Structure | |
|---|---|---|
| 447 | 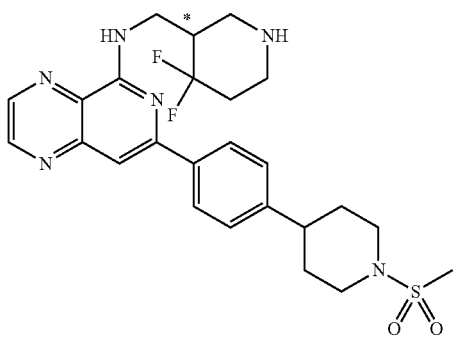 | chiral |
| 448 | 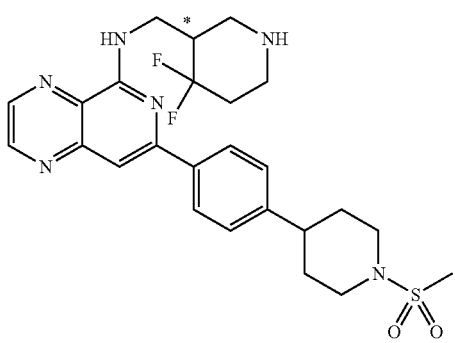 | chiral |
| 449 | 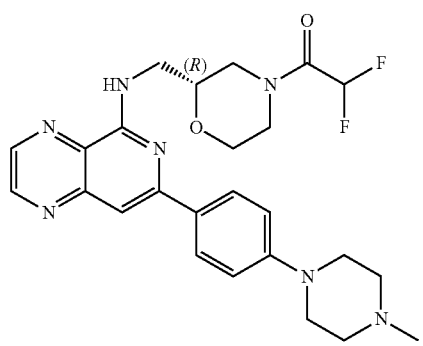 | |
| 450 | 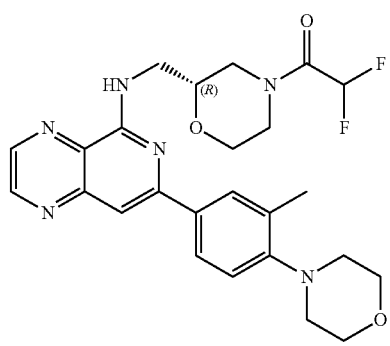 | |

-continued

| Compound | Structure |
|---|---|
| 451 | 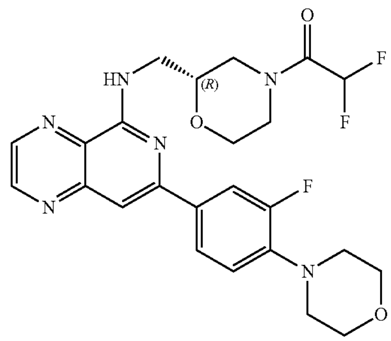 |
| 452 | 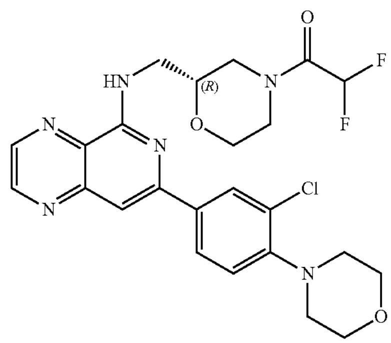 |
| 453 | 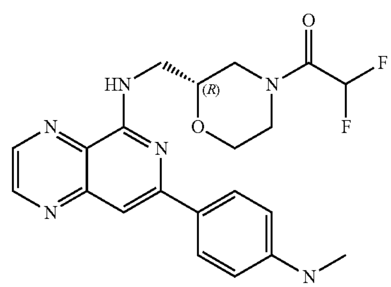 |
| 454 | 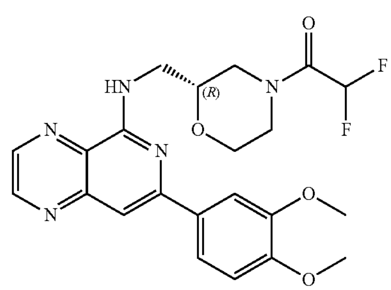 |
| 455 | 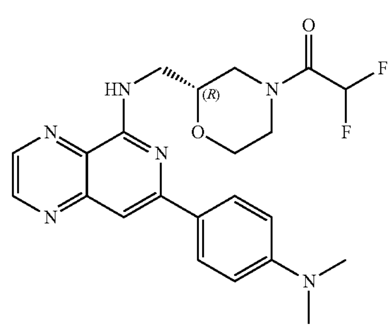 |

| Compound | Structure |
|---|---|
| 456 | 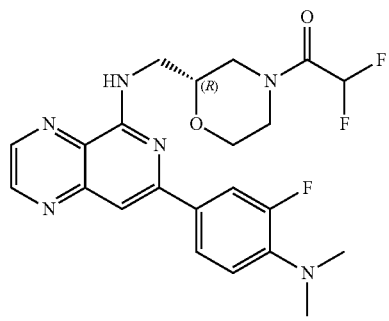 |
| 457 | 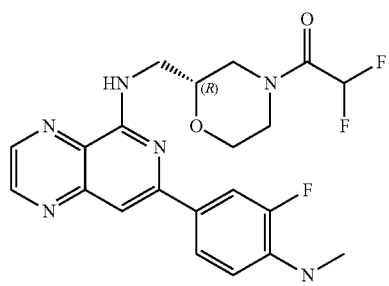 |
| 458 | 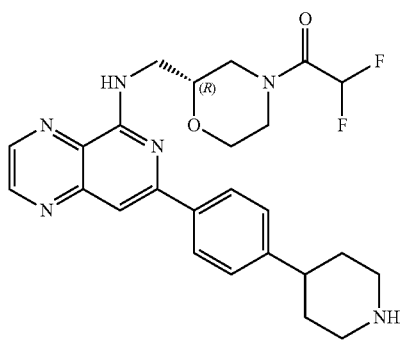 |
| 459 | 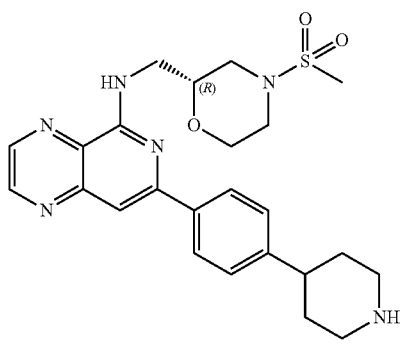 |

| Compound | Structure |
|---|---|
| 460 | 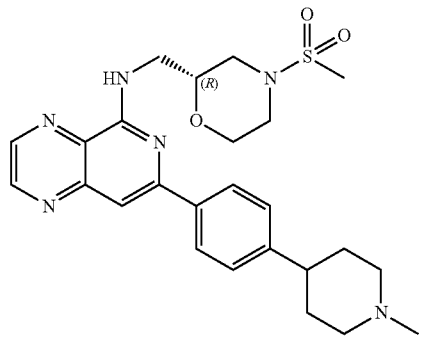 |
| 461 | 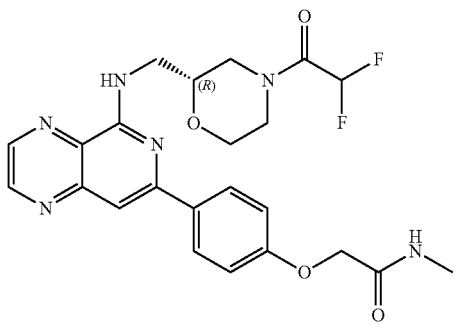 |
| 462 | 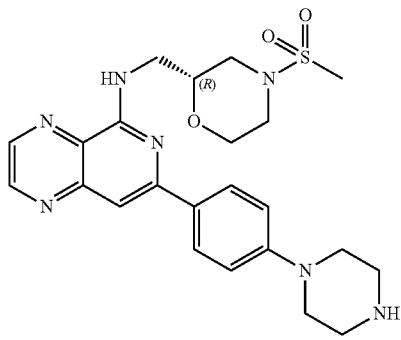 |
| 463 | 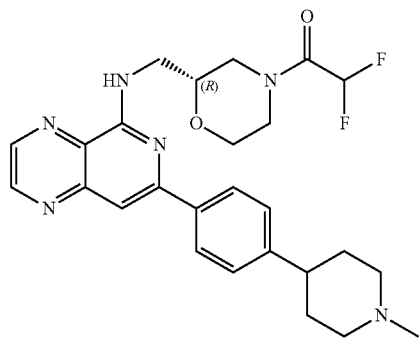 |

-continued

| Compound | Structure |
|---|---|
| 464 | 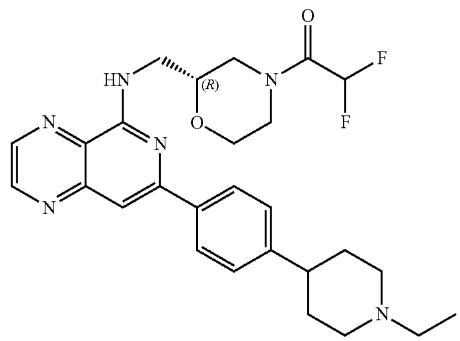 |
| 465 | 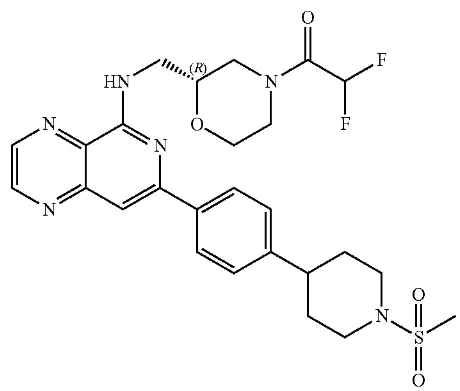 |
| 466 | 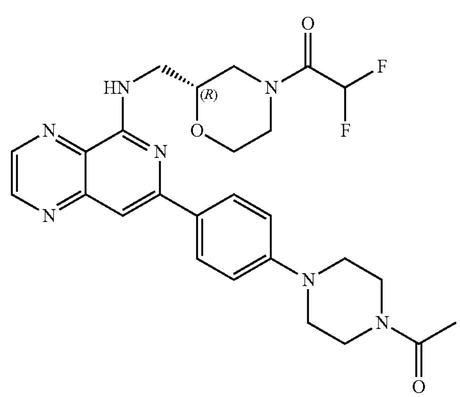 |
| 467 | 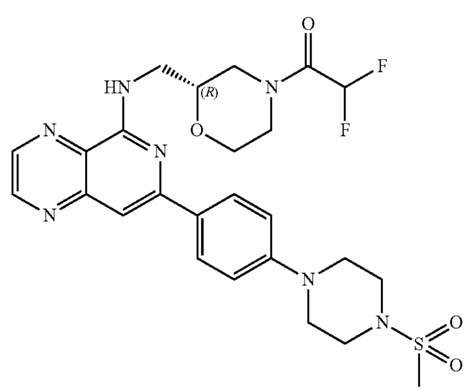 |

-continued

| Compound | Structure |
|---|---|
| 468 | 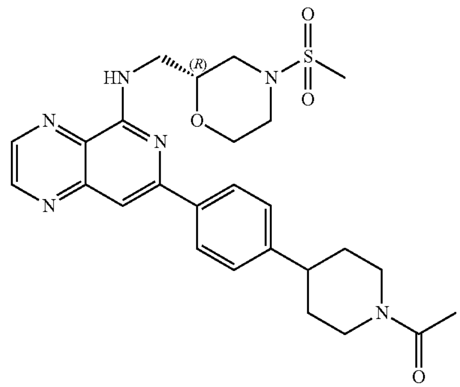 |
| 469 | 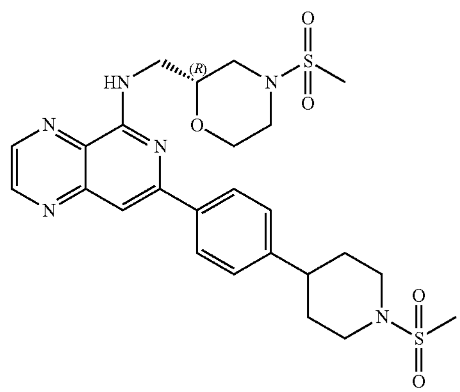 |
| 470 | 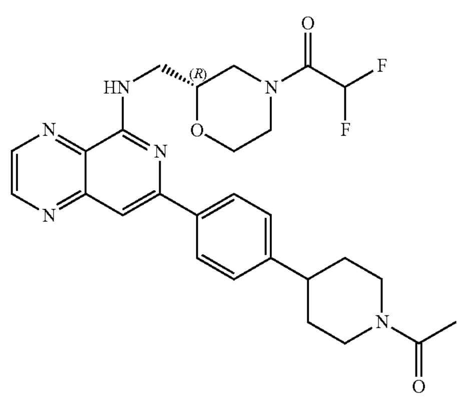 |
| 471 | 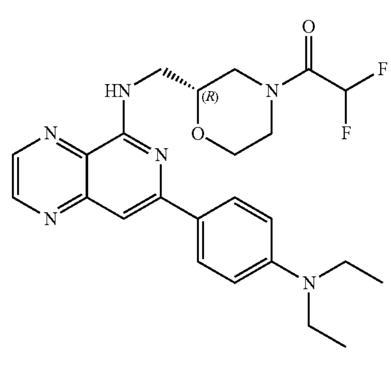 |

-continued

| Compound | Structure |
|---|---|
| 472 | (structure) |
| 473 | (structure) |
| 474 | (structure) |
| 475 | (structure) |
| 476, 477 | (structure) |

| Compound | Structure |
|---|---|
| 478 | 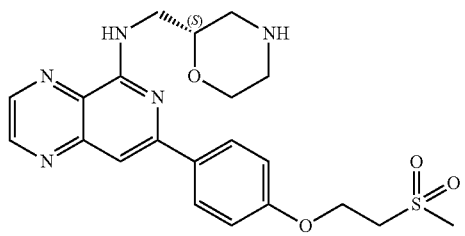 |
| 479 | 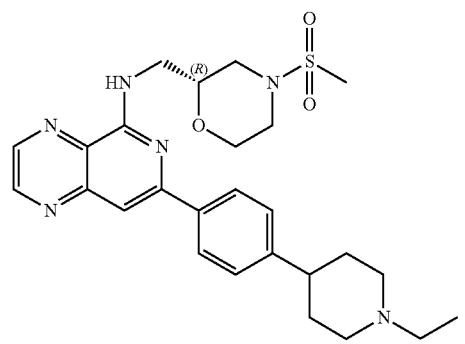 |
| 480 | 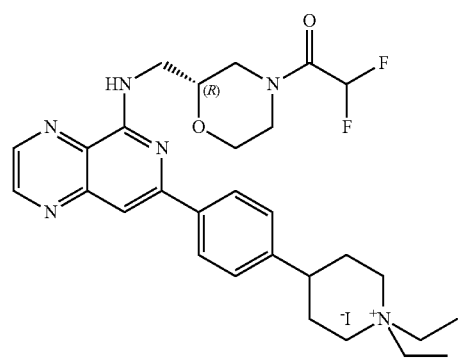 |
| 481 | 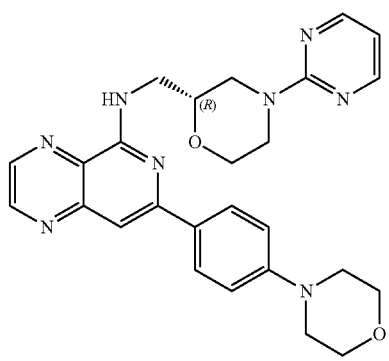 |
| 482 | 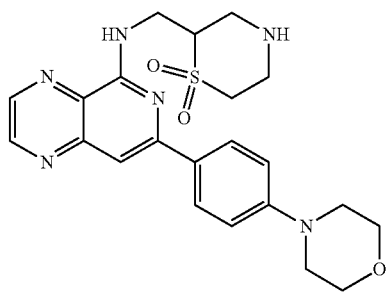 [SMILES: O=S1(=O)CCNCC1CNc1nc(-c2ccc(N3CCOCC3)cc2)cc2nccnc12] |

| Compound | Structure |
|---|---|
| 484 | 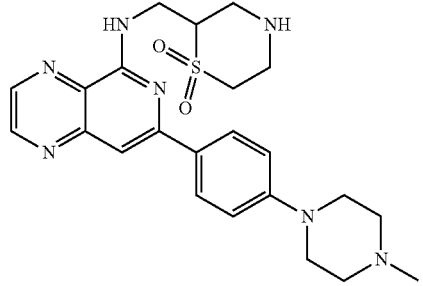 [SMILES: CN1CCN(c2ccc(-c3cc4nccnc4c(NCC4CNCCS4(=O)=O)n3)cc2)CC1] |
| 485 | 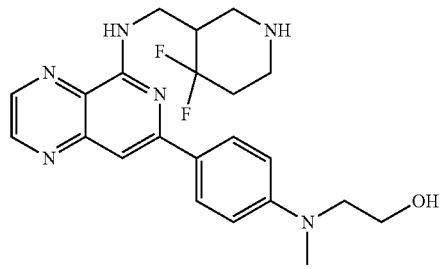 [SMILES: CN(CCO)c1ccc(-c2cc3nccnc3c(NCC3CNCCC3(F)F)n2)cc1] |
| 486 | 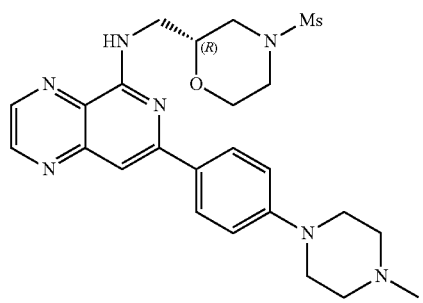 |
| 487 | 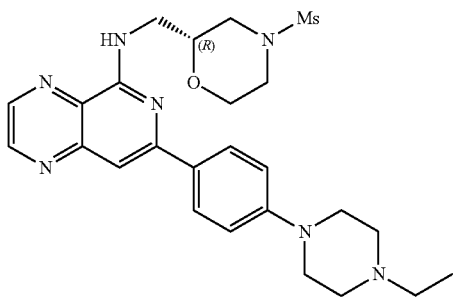 |
| 488 | 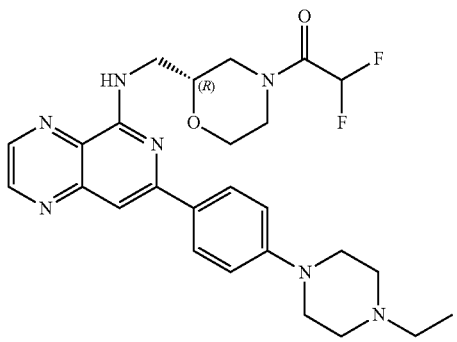 |

-continued
| Compound | Structure |
|---|---|
| 489 | 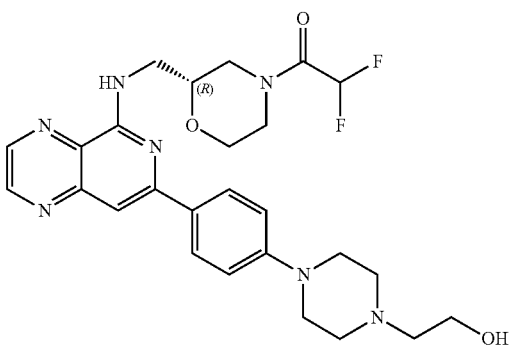 |
| 490 | 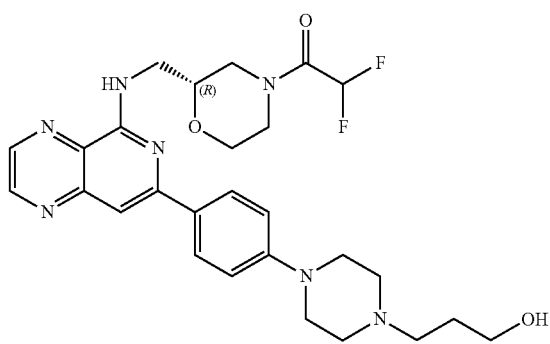 |
| 491 | 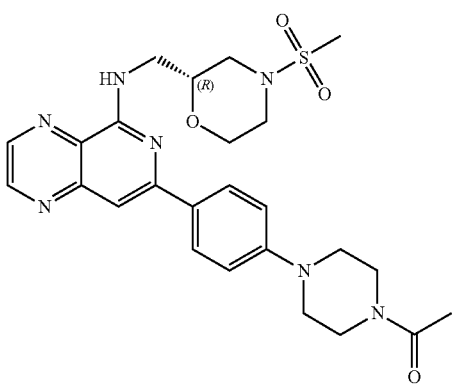 |
| 492 | 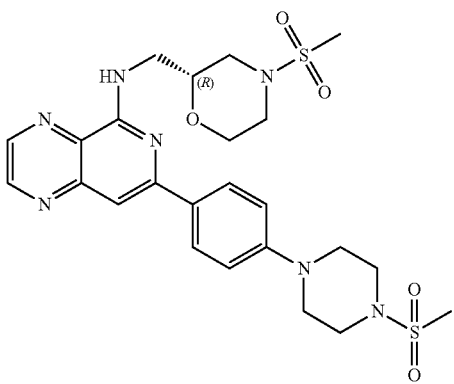 |

| Compound | Structure |
|---|---|
| 493 | 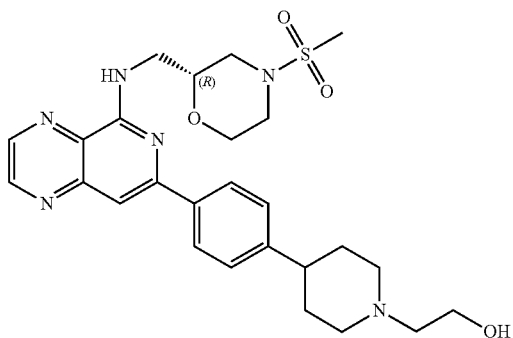 |
| 494 | 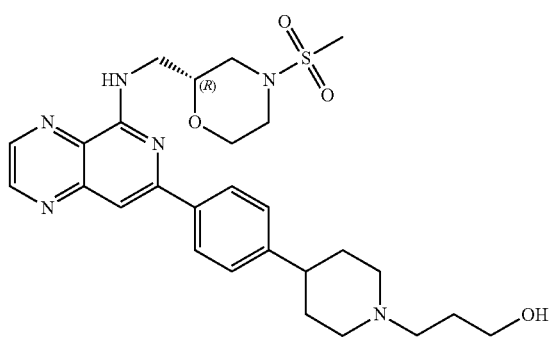 |
| 495 | 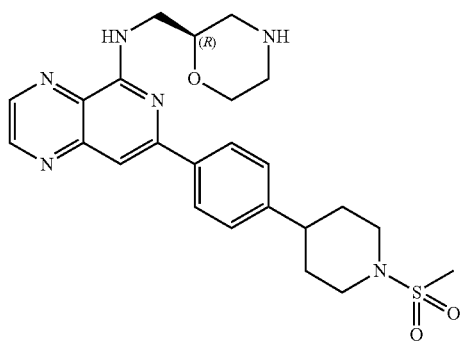 |
| 496 | 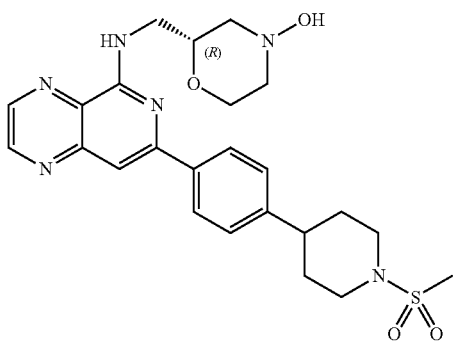 |

| Compound | Structure |
|---|---|
| 497 | 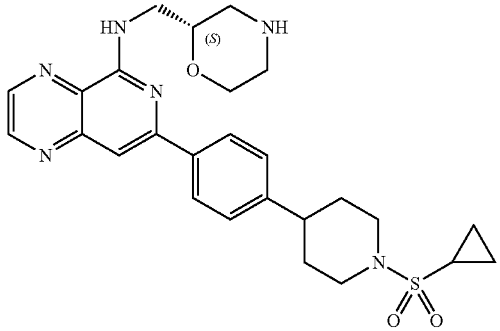 |
| 498 | 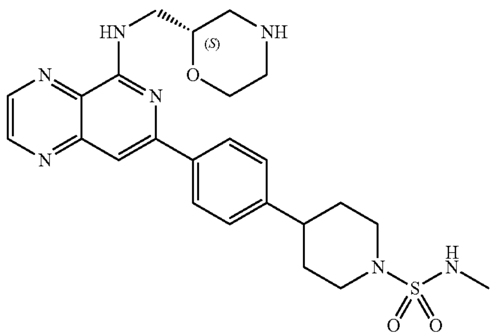 |
| 499 | 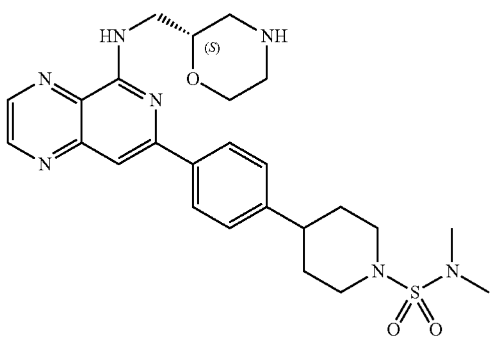 |
| 500 | 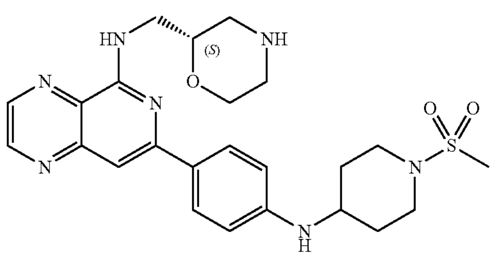 |
| 501 | 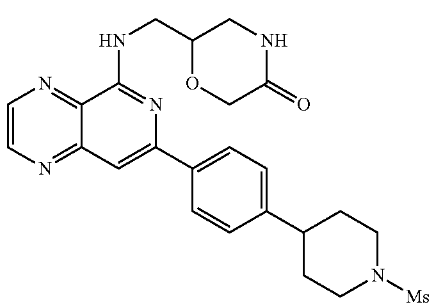 [SMILES: CS(=O)(=O)N1CCC(c2ccc(-c3cc4nccnc4c(NCC4CNC(=O)CO4)n3)cc2)CC1] |

-continued

| Compound | Structure |
|---|---|
| 502 | 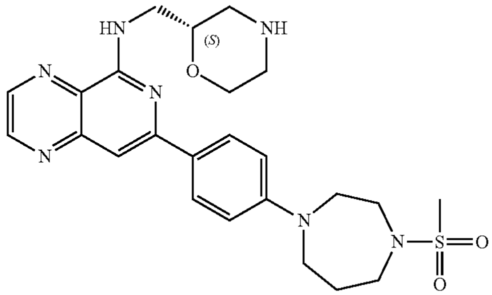 |
| 503 | 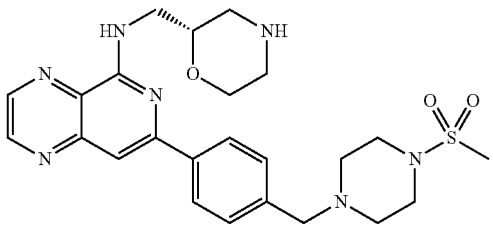 [SMILES: CS(=O)(=O)N1CCN(Cc2ccc(-c3cc4nccnc4c(NC[C@@H]4CNCCO4)n3)cc2)CC1] |
| 504 | 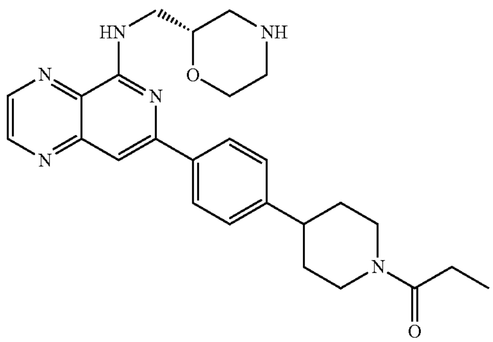 [SMILES: CCC(=O)N1CCC(c2ccc(-c3cc4nccnc4c(NC[C@@H]4CNCCO4)n3)cc2)CC1] |
| 505 | 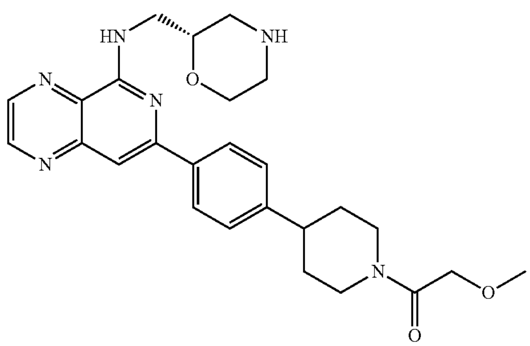 [SMILES: COCC(=O)N1CCC(c2ccc(-c3cc4nccnc4c(NC[C@@H]4CNCCO4)n3)cc2)CC1] |
| 506 | 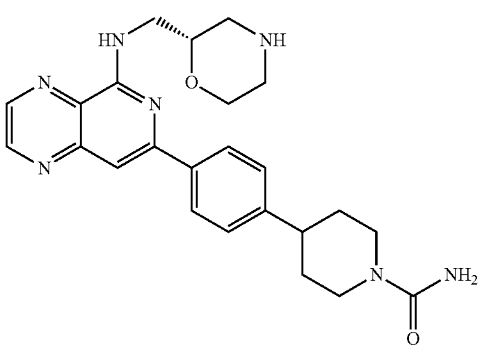 [SMILES: NC(=O)N1CCC(c2ccc(-c3cc4nccnc4c(NC[C@@H]4CNCCO4)n3)cc2)CC1] |

| Compound | Structure |
|---|---|
| 507, 508 | 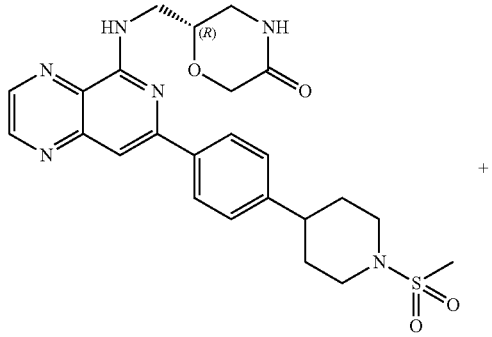 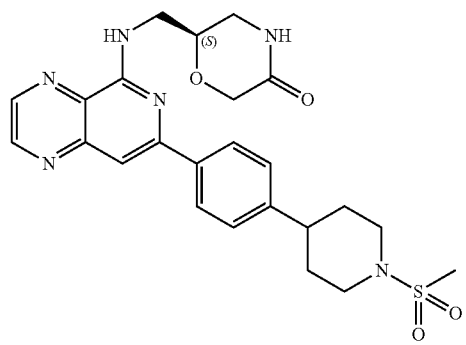 |
| 509 | 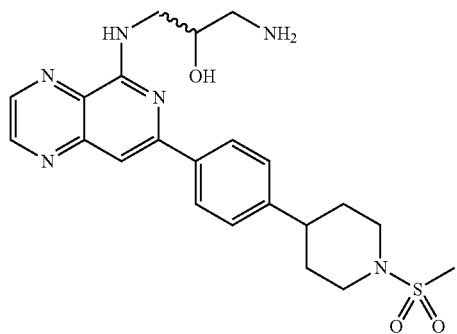 [SMILES: CS(=O)(=O)N1CCC(c2ccc(-c3cc4nccnc4c(NCC(O)CN)n3)cc2)CC1] |
| 510 | 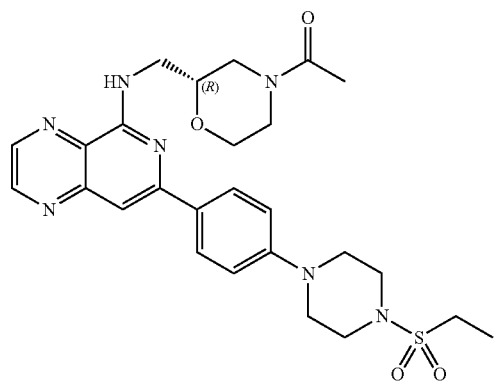 |

-continued

| Compound | Structure |
|---|---|
| 511 | 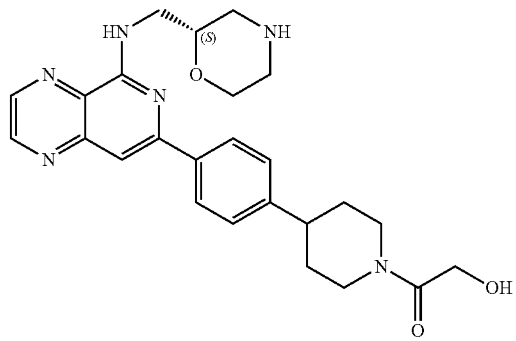 |
| 512 | 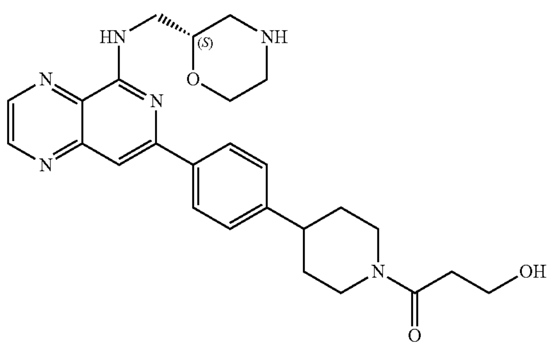 |
| 513 | 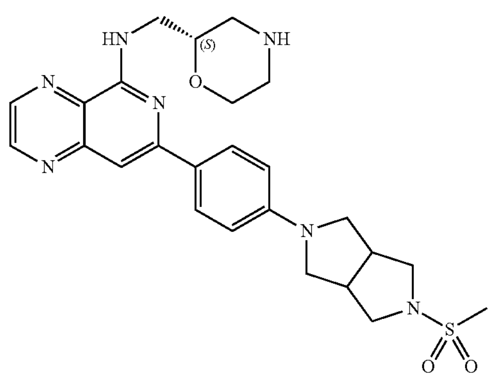 |
| 514 | 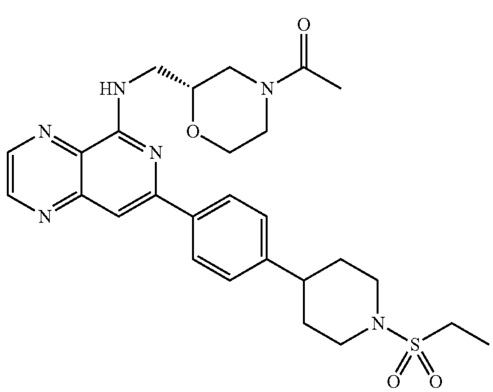 [SMILES: CCS(=O)(=O)N1CCC(c2ccc(-c3cc4nccnc4c(NC[C@@H]4CN(C(C)=O)CCO4)n3)cc2)CC1] |

| Compound | Structure |
|---|---|
| 515 | 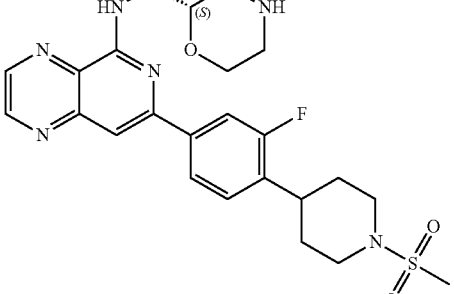 |
| and 516 | 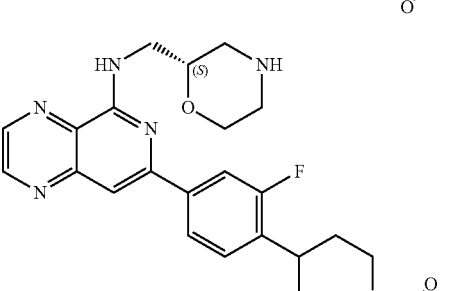 |
and/or a pharmaceutically acceptable salt thereof.
* * * * *